US010253373B2

(12) United States Patent
Sahin et al.

(10) Patent No.: US 10,253,373 B2
(45) Date of Patent: Apr. 9, 2019

(54) IDENTIFICATION OF TUMOR-ASSOCIATED MARKERS FOR DIAGNOSIS AND THERAPY

(71) Applicants: BioNTech AG, Mainz (DE); Johannes Gutenberg-Universität Mainz, Mainz (DE)

(72) Inventors: Ugur Sahin, Mainz (DE); Özlem Türeci, Mainz (DE); Michael Koslowski, Mainz (DE)

(73) Assignee: BIONTECH AG, Mainz (DE)

( * ) Notice: Subject to any disclaimer, the term of this patent is extended or adjusted under 35 U.S.C. 154(b) by 0 days.

(21) Appl. No.: 15/591,896

(22) Filed: May 10, 2017

(65) Prior Publication Data
US 2017/0314078 A1 Nov. 2, 2017

Related U.S. Application Data

(60) Division of application No. 15/003,530, filed on Jan. 21, 2016, now abandoned, which is a division of application No. 14/158,953, filed on Jan. 20, 2014, now abandoned, which is a continuation of application No. 12/765,251, filed on Apr. 22, 2010, now Pat. No. 9,175,088, which is a continuation of application No. PCT/EP2008/008924, filed on Oct. 22, 2008.

(30) Foreign Application Priority Data

Oct. 23, 2007 (EP) .................................. 07020730

(51) Int. Cl.
C12Q 1/68 (2018.01)
C12Q 1/6886 (2018.01)
C07K 14/47 (2006.01)
C07K 16/30 (2006.01)

(52) U.S. Cl.
CPC ........ *C12Q 1/6886* (2013.01); *C07K 14/4748* (2013.01); *C07K 16/30* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 5,910,480 A | * | 6/1999 | Koman | C07K 14/64 435/69.1 |
| 5,990,299 A | | 11/1999 | Ruzdijic et al. | |
| 7,371,840 B2 | | 5/2008 | Press et al. | |
| 9,175,088 B2 | | 11/2015 | Sahin et al. | |
| 2002/0086356 A1 | | 7/2002 | Tuschl | |
| 2003/0099974 A1 | | 5/2003 | Lillie et al. | |
| 2003/0148410 A1 | | 8/2003 | Berger et al. | |
| 2004/0005563 A1 | | 1/2004 | Mack et al. | |
| 2005/0181375 A1 | * | 8/2005 | Aziz | C12Q 1/6886 435/6.14 |
| 2007/0037204 A1 | | 2/2007 | Aburatani et al. | |
| 2007/0099251 A1 | | 5/2007 | Zhang | |
| 2007/0269452 A1 | | 11/2007 | Yisraeli et al. | |
| 2008/0050378 A1 | | 2/2008 | Nakamura et al. | |
| 2008/0153104 A1 | | 6/2008 | Aburatani et al. | |
| 2009/0214550 A1 | | 8/2009 | Sahin et al. | |
| 2014/0134165 A1 | | 5/2014 | Sahin et al. | |
| 2016/0215351 A1 | | 7/2016 | Sahin et al. | |

FOREIGN PATENT DOCUMENTS

| | | |
|---|---|---|
| JP | 2005/500833 A | 1/2005 |
| JP | 2007/506417 A | 3/2007 |
| JP | 2007/526759 A | 9/2007 |
| WO | 92/04381 A1 | 3/1992 |
| WO | 96/33265 A1 | 10/1996 |
| WO | 96/33739 A1 | 10/1996 |
| WO | 2001094641 A2 | 12/2001 |
| WO | 02/102235 A2 | 12/2002 |
| WO | 2003/034984 A2 | 5/2003 |
| WO | 2003/065006 A1 | 8/2003 |
| WO | 2005/113587 A2 | 12/2005 |
| WO | 2006/038212 A2 | 4/2006 |
| WO | 2006083986 A2 | 8/2006 |
| WO | 2006100089 A2 | 9/2006 |
| WO | 2007031222 A2 | 3/2007 |
| WO | 2007072042 A2 | 6/2007 |

OTHER PUBLICATIONS

Brandt et al Endocrine-Related Cancer. 12:823-837 (Year: 2005).*
Database Geneseq [Online] Dec. 2, 2004 (Dec. 2, 2004), Lilli J. et al. : "Novel isolated polypeptide associated with breast cancer", XP002518625, retrieved from EBI, Database accession No. ACN90758.
Koslowski M et al: "Frequent nonrandom activation of germ-line genes in human cancer" Cancer Research, American Association for Cancer Research, Baltimore, MD, US, vol. 64, No. 17, Sep. 1, 2004 (Sep. 1, 2004), pp. 5988-5993, XP002309835, ISSN: 0008-5472.
Tuereci Ozlem et al: "Computational dissection of tissue contamination for identification of colon cancer-specific expression profiles." The FASEB Journal : Official Publication of the Federation of American Societies for Experimental Biology Mar. 2003, vol. 17, No. 3, Mar. 2003 (Mar. 2003), pp. 376-385, XP002471061, ISSN: 1530-6860.
Prokopenko P G et al: "Antigenic structure of ovarian cancer metastases." Bulletin of Experimental Biology and Medicine Jun. 2001, vol. 131, No. 6, Jun. 2001 (Jun. 2001), pp. 561-563, XP002471062, ISSN: 0007-4888.
International Search Report for PCT/EP2008/008924, published Sep. 24, 2009, 6 pages.
Harandi, "Immunoplacental therapy, a potential multi-epitope cancer vaccine", Medical Hypotheses 2006, vol. 66, 1182-1187.
Klamp et al., "Expression profiling of autoimmun regulator AIRE mRNA in a comprehensive set of human normal and neoplasitc tissues," Immunology Letters 2006, vol. 106, 172-179.

(Continued)

*Primary Examiner* — Carla J Myers
(74) *Attorney, Agent, or Firm* — McAndrews, Held & Malloy, Ltd.

(57) ABSTRACT

The present technology relates to genetic products the expression of which is associated with cancer diseases. The present technology also relates to the therapy and diagnosis of diseases in which the genetic products are expressed or aberrantly expressed, in particular cancer diseases.

5 Claims, 28 Drawing Sheets
Specification includes a Sequence Listing.

(56) References Cited

OTHER PUBLICATIONS

Koslowski et al., "A Placenta-specific gene ectopically activated in many human cancers is essentially involved in malignant cell processes," Cancer Research 2007, vol. 67, No. 19, 9528-9534, XP002471063.
Human colon cancer antigen encoding cDNA SEQ ID No. 1454, http://www.ebu.ac.uk/cgi-bin/epo/epofetch?AAH34372, dated Feb. 29, 2008, 2 pages, XP-002471064.
Schmidt et al., Blood, 1998, 91: 22-29.
Garber et al., Proc. Natl. Acad. Sci., 2001, 98: 13784-13789.
Bhattacharjee et al., Proc. Natl. Acad. Sci., 2001, 98:13790-13794.
Ito et al., AntiCancer Research, 2002, 22(4):2385-2389.
Dermer, G.B., Bio/Technology, 1994, 12: 320.
Liu et al., Clinical Immunology, 2004, 112: 225-230.
Coleman, R., Drug Discovery Today, 2003, 8: 233-235.
Saetre et al., Molecular Brain Research, 2004, 126: 198-206.
Hanke et al., Clinical Chemistry, 2007, 53: 2070-2077.
Palmer et al., BMC Genomics, 2006, 7:115.
Min et al., BMC Genomics, 2010, 11 :96.
Goddard A et al: "Human Pro Protein #33", 1-7 Genbank, Jan. 1, 2004 (Jan. 1, 2004).
Database UniProt [Online], May 20, 2004 (May 20, 2004), Isogai T. et al.: "New polynucleotides and polypeptides useful in gene therapy, . . . ", retrieved from EBI, Database accession No. ADM02094.
Dunbar et al., Curr. Biol. 8:413-416, 1998.
Durand & Seta, 2000; Clin. Chem. 46: 795-805.
Mitsuhashi et al. Journal of Laboratory Analysis. 1996. 10: 285-293.
Gardsvoll, J. Immunol. Methods 234: 107-116, 2000.
Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner).
Greenberg, J. Immunol. 136(5):1917, 1986.
Gurchot C, Oncology 31:310-3, 1975.
Hakomori, 1996; Cancer Res. 56: 5309-18.
Hannon, GJ. 2002. RNA interference. Nature 418: 244-51.
Iles RK, Chard T, J Urol 145:453-8, 1991.
Jegstrup I. et al. 2003. Lab Anim. Jan. 2003; 37(1):1-9.
Jung et al., Mol. Cells 12: 41-49, 2001.
Kasinrerk et al., Hybrid Hybridomics 21: 287-293, 2002.
Kast et al., Cell 59:603-614, 1989.
Kayyem et al., Eur. J. Biochem. 208: 1-8, 1992.
Kessels et al., Nat Immunol. 2:957-61, 2001.
Koslowski, M. et al., Cancer Res. 62, 6750-6755 (2002).
Kreig et al., Nature 374:546-9, 1995.
Laurence DJ, Neville AM, Br J Cancer 26:335-55, 1972.
Lemoine et al., Methods Mol. Biol. 75: 441-7, 1997.
Lynch et al., Eur. J. Immunol. 21:1403-1410, 1991.
Lu et al., Clinical Cancer Research, 2004, 10:3291-3300.
Maloy et al., Proc Natl Acad Sci USA 98:3299-303, 2001.
Matsusue et al. 2003. J. Clin. Invest. 111:737-47.
Niwa H. 2001. Cell Struct. Funct. Jun. 2001; 26(3):137-48.
Ossendorp et al., Immunol Lett. 74:75-9, 2000.
Ossendorp et al., J. Exp. Med. 187:693-702, 1998.
Pardoll, Nat. Med. 4:525-31, 1998.
Peters T. et al. 2003. Hum. Mol. Genet 12:2109-20.
Riddell et al., Science 257:238, 1992.
Roitt, I. (1991), Essential Immunology, 7th Edition, Blackwell Scientific Publications, Oxford.
Sambrook, J. et al., "Molecular Cloning: A Laboratory Manual", Editors, 2nd Edition, Cold Spring Harbor Laboratory press, Cold Spring Harbor, New York, 1989.
Science 268:1432-1434, 1995, Hall et al.
Shi et al., J. Histochem. Cytochem. 39: 741-748, 1991.
Shin et al., Lab. Invest. 64: 693-702, 1991.
Simpson AJ et al., Nat Rev Cancer 5:615-25, 2005.
So et al., Mol. Cells 7:178-186, 1997.
Spiller et al., J. Immunol. Methods 224: 51-60, 1999.
Stanislawski et al., Nat Immunol. 2:962-70, 2001.
Stockton et al. 2001. Mol. Biol. Cell. 12: 1937-56.
Zambrowicz BP & Sands AT. 2003. Nat. Rev. Drug Discov. Jan. 2003; 2(1):38-51.
Tuschl T. et al., "The siRNA User Guide", revised Oct. 11, 2002.
Domcke et al., Nature Communications, pp. 1-10, 2013.
Ito Hirotaka et al: "Identification of ROBO1 as a novel heptacellular carcinoma antigen and a potential therapeutic and diagnostic target.", Clinical Cancer Research : An Official Journal of the American Association for Cancer Research, vol. 12, No. 11 Pt 1, Jun. 1, 2006 (Jun. 1, 2006), pp. 3257-3264.
Database Geneseq [Online], May 5, 2005 (May 5, 2005), Aburatani H et al: "Human TEG6 associated DNA SEQ", Database accession No. ADX83391.
Xie M-H et al: "FGF-19, A Novel Fibroblast Growth Factor With Unique Specificity for FGFR4", Cytokine, Academic Press Ltd, Phiadelphia, PA, US, vol. 11, No. 10, Oct. 1, 1999 (Oct. 1, 1999), pp. 729-735.
Database UniProt, Feb. 26, 2004, Rosen CA, 2 pages, Accession No. ADG41806.
Abate-Shen & Shen. 2002. Trends in Genetics S1-5.
Acevedo HF et al., Cancer 76:1467-75, 1995.
Adams GP, Weiner LM, Nat Biotechnol 23:1147-57, 2005.
Altman et al., Science 274:94-96, 1996.
Anderson et al., J. Immunol. 143: 1899-1904, 1989.
Azorsa et al., J. Immunol. Methods 229: 35-48, 1999.
Balling R, 2001. Ann. Rev. Genomics Hum. Genet. 2:463-92.
Beard J, Lancet 1:1758-63, 1902.
Chomczynski & Sacchi, Anal. Biochem. 162: 156-159, 1987.
Cinamon G., Alon R. J. Immunol. Methods. Feb. 2003; 273(1-2):53-62.
Clark, W.R. (1986), The Experimental Foundations of Modern Immunology, Wiley & Sons, Inc., New York.
Czauderna et al. 2003. Nucl. Acid Res. 31: 670-82.
Dabbs, David J., MD, "Diagnostic Immunohistochemistry" ISBN: 0443065667, 3 pages.
Dabbs, David J., MD, "Microscopy, Immunohistochemistry, and Antigen Retrieval Methods: for Light and Electron Microscopy" ISBN: 0306467704.
de Wildt et al., J. Immunol. Methods 207:61-67, 1997.
Dirnhofer S et al., Hum Pathol 29:377-82, 1998.
Ioannidis et al Cancer Letters. 2004. 209: 245-250.
Buck et al. Biotechniques, 1999, 27: 528-536.

* cited by examiner

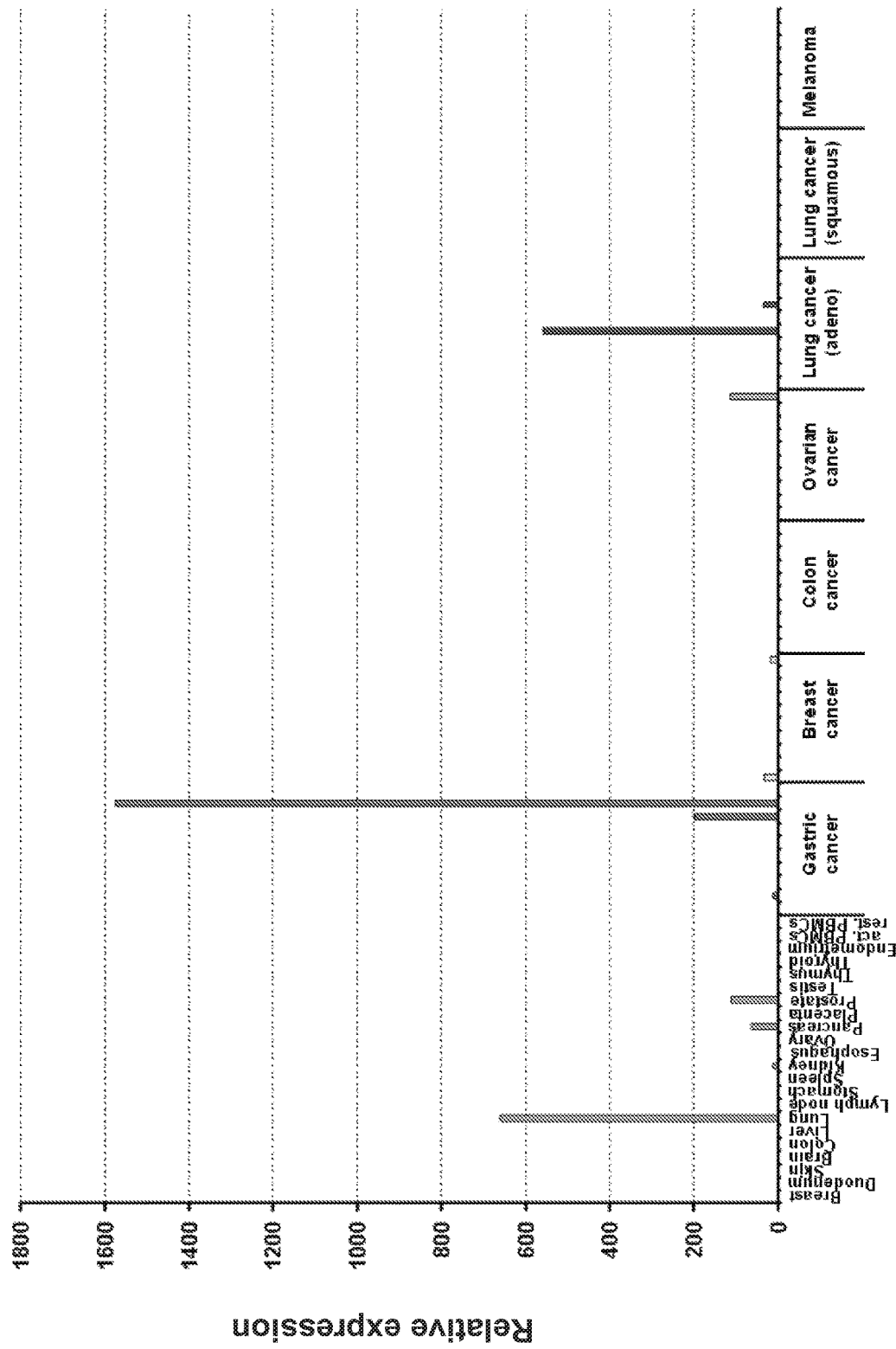

IDENTIFICATION OF TUMOR-ASSOCIATED MARKERS FOR DIAGNOSIS AND THERAPY

RELATED APPLICATIONS

The present application is a divisional application of U.S. patent application Ser. No. 15/003,530, filed Jan. 21, 2016, which is a divisional application of U.S. patent application Ser. No. 14/158,953, filed Jan. 20, 2014, now abandoned, which is a continuation application of U.S. patent application Ser. No. 12/765,251, filed Apr. 22, 2010, now U.S. Pat. No. 9,175,088, which is a continuation of International Patent Application No. PCT/EP08/08924, which was filed Oct. 22, 2008, claiming the benefit of priority to European Patent Application No. 07020730.3, which was filed on Oct. 23, 2007. The entire text of the aforementioned applications is incorporated herein by reference in its entirety.

FEDERALLY SPONSORED RESEARCH OR DEVELOPMENT

[Not Applicable]

SEQUENCE LISTING

A sequence has been submitted via EFS-Web as an as ASCII text file which is incorporated by reference into the specification. The ASCII text file named, "22939US04_SeqList.txt", was created on May 10, 2017, and is 541,212 bytes in size.

BACKGROUND OF THE INVENTION

The present technology relates to nucleic acids and encoded polypeptides which are expressed in cancers. The present technology also relates to agents which bind the polypeptides. The nucleic acids, polypeptides coded for by such nucleic acids and peptides derived therefrom, as well as related antibodies and cytolytic T lymphocytes, are useful, inter alia, in diagnostic and therapeutic contexts.

Despite interdisciplinary approaches and exhaustive use of classical therapeutic procedures, cancers are still among the leading causes of death.

More recent therapeutic concepts in cancer therapy aim at incorporating the patient's immune system into the overall therapeutic concept by using recombinant tumor vaccines and other specific measures such as antibody therapy. A prerequisite for the success of such a strategy is the recognition of tumor-specific or tumor-associated antigens or epitopes by the patient's immune system whose effector functions are to be interventionally enhanced.

Tumor cells biologically differ substantially from their nonmalignant cells of origin. These differences are due to genetic alterations acquired during tumor development and result, inter alia, also in the formation of qualitatively or quantitatively altered molecular structures in the cancer cells. Tumor-associated structures of this kind which are recognized by the specific immune system of the tumor-harboring host are referred to as tumor-associated antigens.

The specific recognition of tumor-associated antigens involves cellular and humoral mechanisms which are two functionally interconnected units: $CD4^+$ and $CD8^+$ T lymphocytes recognize the processed antigens presented on the molecules of the MHC (major histocompatibility complex) classes II and I, respectively, while B lymphocytes produce circulating antibody molecules which bind directly to unprocessed antigens. The potential clinical-therapeutical importance of tumor-associated antigens results from the fact that the recognition of antigens on neoplastic cells by the immune system leads to the initiation of cytotoxic effector mechanisms and, in the presence of T helper cells, can cause elimination of the cancer cells (Pardoll, Nat. Med. 4:525-31, 1998).

Antibody based cancer therapies have been successfully introduced into the clinic and have emerged as the most promising therapeutics in oncology over the last decade. Eight antibodies have been approved for treatment of neoplastic diseases, most of them, however in lymphoma and leukemia (Adams G P, Weiner L M, Nat Biotechnol 23:1147-57, 2005).

One of the challenges to be mastered for the advent of the next generation of upgraded antibody-based cancer therapeutics is the selection of appropriate target molecules, which is the key for a favorable toxicity/efficacy profile.

The search for genes tightly silenced in the vast majority of healthy tissues moves into the focus of attention the intriguing observation that genes of the gametogenic and/or trophoblastic lineage are frequently ectopically activated and robustly expressed in human cancer. Based on phenotypical similarities between germ cells, pregnancy trophoblast and cancer cells, John Beard proposed as much as 100 years ago a "trophoblastic theory of cancer" (Beard J, Lancet 1:1758-63, 1902; Gurchot C, Oncology 31:310-3, 1975). The discovery of the sporadic production of chorionic gonadotropin, alpha-fetoprotein, CEA and other trophoblastic hormones by cancer cells provided the first molecules shared between neoplastic and trophoblastic cells (Acevedo H F et al., Cancer 76:1467-75, 1995; Dirnhofer S et al., Hum Pathol 29:377-82, 1998; Gurchot C, Oncology 31:310-3, 1975; Iles R K, Chard T, J Urol 145:453-8, 1991; Laurence D J, Neville A M, Br J Cancer 26:335-55, 1972). The concept was reignited by the inauguration of the steadily growing so-called cancer/germline (CG) class of genes, which represents more than 100 members, each expressed in a variety of tumor types. The observation that entire trophoblastic and gametogenic programs escape transcriptional silencing and are ectopically activated in cancer cells (Koslowski M et al., Cancer Res 64:5988-93, 2004; Simpson A J et al., Nat Rev Cancer 5:615-25, 2005) indicates that within this class of genes with exquisitely selective tissue distribution, appropriate targets for mAB therapy may be found.

It was the object of the present technology to provide target structures for a diagnosis and therapy of cancers. This object is achieved by the subject matter of the claims.

BRIEF SUMMARY OF THE INVENTION

According to the present technology, placenta-specific genes are identified which are selectively or aberrantly expressed in tumor cells and thus, provide target structures for therapeutic and diagnostic approaches.

The nucleic acids identified according to the present technology to be selectively or aberrantly expressed in tumor cells are selected from the group consisting of (a) a nucleic acid which comprises a nucleic acid sequence selected from the group consisting of SEQ ID NOs: 1-540, 541, 545, 549, 553, 557, 560, 563, 566, 570, 574, 577, 580, 583, 587, 591, 595, 599, 602, 606, 610, 613, 617, 620, and 624 of the sequence listing, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). These nucleic acids are also termed "tumor-associated nucleic acids" herein.

In another aspect, the present technology relates to antigens encoded by the tumor-associated nucleic acids identified according to the present technology. Accordingly, the tumor-associated antigens identified according to the present technology have an amino acid sequence encoded by a nucleic acid which is selected from the group consisting of (a) a nucleic acid which comprises a nucleic acid sequence selected from the group consisting of SEQ ID NOs: 1-540, 541, 545, 549, 553, 557, 560, 563, 566, 570, 574, 577, 580, 583, 587, 591, 595, 599, 602, 606, 610, 613, 617, 620, and 624 of the sequence listing, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, the tumor-associated antigens identified according to the present technology comprise an amino acid sequence selected from the group consisting of SEQ ID NOs: 542, 546, 550, 554, 567, 571, 584, 588, 592, 596, 603, 607, 614, 621, and 625 of the sequence listing, a part or derivative thereof.

If, according to the present technology, reference is made to nucleic acids comprising certain nucleic acid sequences or tumor-associated antigens comprising certain amino acid sequences this also includes embodiments wherein the nucleic acids or tumor-associated antigens consist of these certain nucleic acid sequences or amino acid sequences, respectively.

The present technology generally relates to the use of tumor-associated nucleic acids and tumor-associated antigens identified according to the present technology or of parts or derivatives thereof, of nucleic acids directed against said tumor-associated nucleic acids, of antibodies or T cells directed against the tumor-associated antigens identified according to the present technology or parts or derivatives thereof and/or of host cells expressing the tumor-associated antigens identified according to the present technology or parts or derivatives thereof for therapy, prophylaxis, diagnosis and/or monitoring of neoplastic diseases.

This may also involve the use of a combination of two or more of these nucleic acids, antigens, antibodies, T cells and/or host cells.

In those embodiments of the present technology relating to the use of antibodies directed against the tumor-associated antigens identified according to the present technology or parts or derivatives thereof also T cell receptors directed against the tumor-associated antigens identified according to the present technology or parts or derivatives thereof, optionally in a complex with MHC molecules, may be used.

Especially suitable for therapy, prophylaxis, diagnosis and/or monitoring is a part of the tumor-associated antigens identified according to the present technology which corresponds to the non-transmembrane portion, in particular the extracellular portion of the tumor-associated antigens or is comprised thereof. Therefore, according to the present technology, a part of the tumor-associated antigens identified according to the present technology which corresponds to the non-transmembrane portion, in particular the extracellular portion of the tumor-associated antigens or is comprised thereof, or a corresponding part of the nucleic acids coding for the tumor-associated antigens identified according to the present technology is preferred for therapy, prophylaxis, diagnosis and/or monitoring. Similarly the use of antibodies is preferred which are directed against a part of the tumor-associated antigens identified according to the present technology which corresponds to the non-transmembrane portion, in particular the extracellular portion of the tumor-associated antigens or is comprised thereof.

Preferred diseases for a therapy, prophylaxis, diagnosis and/or monitoring are those in which one or more of the tumor-associated nucleic acids identified according to the present technology are selectively expressed or abnormally expressed. Particularly preferred diseases for a therapy, prophylaxis, diagnosis and/or monitoring are those in which one or more of the tumor-associated nucleic acids identified according to the present technology and/or one or more of the tumor-associated antigens encoded thereby are selectively expressed or abnormally expressed.

In one aspect, the present technology relates to a pharmaceutical composition comprising an agent which recognizes a tumor-associated antigen identified according to the present technology or a nucleic acid coding for the tumor-associated antigen and which is preferably selective for cells which have expression or abnormal expression of a tumor-associated antigen identified according to the present technology.

In a further aspect, the present technology relates to a pharmaceutical composition comprising an agent which (I) inhibits expression or activity of a tumor-associated antigen identified according to the present technology, and/or (II) has tumor-inhibiting or tumor-destroying activity and is selective for cells expressing or abnormally expressing a tumor-associated antigen identified according to the present technology, and/or (III) when administered, selectively increases the amount of complexes between an MHC molecule and a tumor-associated antigen identified according to the present technology or a part thereof, such as a peptide epitope. In particular embodiments, said agent may cause induction of cell death, reduction in cell growth, damage to the cell membrane or secretion of cytokines and preferably have a tumor-inhibiting activity.

In one embodiment, the agent is an antisense nucleic acid which hybridizes selectively with the nucleic acid coding for the tumor-associated antigen. In a further embodiment, the agent is a siRNA preferably comprising a sense RNA strand and an antisense RNA strand, wherein the sense and antisense RNA strands form an RNA duplex, and wherein the sense RNA strand comprises a nucleotide sequence substantially identical to a target sequence of about 19 to about 25 contiguous nucleotides in a nucleic acid coding for the tumor-associated antigen, preferably mRNA coding for the tumor-associated antigen. In a further embodiment, the agent is an antibody which binds selectively to the tumor-associated antigen, in particular a complement-activated or toxin conjugated antibody which binds selectively to the tumor-associated antigen. In a preferred embodiment, the antibody which binds selectively to the tumor-associated antigen is coupled to a therapeutically useful substance and/or recruits natural or artificial effector mechanisms to said cell expressing or abnormally expressing said tumor-associated antigen. In a further embodiment, the agent is a cytotoxic T lymphocyte which recognizes the tumor-associated antigen or a part thereof bound by an MHC molecule on a cell and lyses the cells labeled in this way. In a further embodiment, the agent is a T helper lymphocyte which recognizes the tumor-associated antigen or a part thereof bound by an MHC molecule on a cell and enhances effector functions of other cells specifically recognizing said tumor-associated antigen or a part thereof.

In a further embodiment, the agent comprises two or more agents which each recognize different tumor-associated antigens or different nucleic acids coding for tumor-associated antigens and/or inhibit expression or activity of different tumor-associated antigens, and/or have tumor-inhibiting or tumor-destroying activity and are selective for cells expressing or abnormally expressing different tumor-associated antigens, and/or when administered, selectively increase the amount of complexes between MHC molecules and different tumor-associated antigens or parts thereof, wherein at least one of said different tumor-associated antigens is a tumor-associated antigen identified according to the present technology.

Preferably, a tumor-associated antigen selectively limited to tumors serves as a label for recruiting effector mechanisms to this specific location. In this aspect, the present technology includes embodiments wherein the agent itself does not have an ability to inhibit activity of a tumor-associated antigen or a tumor-inhibiting or tumor-destroying activity but mediates such effect, in particular by recruiting effector mechanisms, in particular those having cell damaging potential, to a specific location, in particular a tumor or tumor cells.

Preferably, said cells expressing or abnormally expressing a tumor-associated antigen identified according to the present technology are non-placenta cells.

The activity of a tumor-associated antigen identified according to the present technology can be any activity of a protein or a peptide. In one embodiment this activity is an enzymatic activity.

According to the present technology the phrase "inhibit expression or activity" includes a complete or essentially complete inhibition of expression or activity and a reduction in expression or activity.

The agent which, when administered, selectively increases the amount of complexes between an MHC molecule and a tumor-associated antigen identified according to the present technology or a part thereof comprises one or more components selected from the group consisting of (i) the tumor-associated antigen or a part thereof, (ii) a nucleic acid which codes for said tumor-associated antigen or a part thereof, (iii) a host cell which expresses said tumor-associated antigen or a part thereof, and (iv) isolated complexes between peptide epitopes from said tumor-associated antigen and an MHC molecule.

The present technology furthermore relates to a pharmaceutical composition which comprises one or more components selected from the group consisting of (i) a tumor-associated antigen identified according to the present technology or a part thereof, (ii) a nucleic acid which codes for a tumor-associated antigen identified according to the present technology or a part thereof, (iii) an antibody which binds to a tumor-associated antigen identified according to the present technology or to a part thereof, (iv) an antisense nucleic acid which hybridizes specifically with a tumor-associated nucleic acid identified according to the present technology/a nucleic acid coding for a tumor-associated antigen identified according to the present technology, (v) an siRNA directed against a tumor-associated nucleic acid identified according to the present technology/a nucleic acid coding for a tumor-associated antigen identified according to the present technology, (vi) a host cell which expresses a tumor-associated antigen identified according to the present technology or a part thereof, and (vii) isolated complexes between a tumor-associated antigen identified according to the present technology or a part thereof and an MHC molecule.

In one embodiment, a nucleic acid coding for a tumor-associated antigen identified according to the present technology or a part thereof is present in the pharmaceutical composition in an expression vector and functionally linked to a promoter. In a further embodiment, a nucleic acid coding for a tumor-associated antigen identified according to the present technology or a part thereof is present in the pharmaceutical composition in a virus as further described below.

A host cell present in a pharmaceutical composition of the present technology may secrete the tumor-associated antigen or the part thereof, may express it on the surface and preferably may additionally express an MHC molecule which binds to said tumor-associated antigen or said part thereof. In one embodiment, the host cell expresses the MHC molecule endogenously. In a further embodiment, the host cell expresses the MHC molecule and/or the tumor-associated antigen or the part thereof in a recombinant manner. The host cell is preferably nonproliferative. In a preferred embodiment, the host cell is an antigen-presenting cell, in particular a dendritic cell, a monocyte or a macrophage.

In a further embodiment, an antibody present in a pharmaceutical composition of the present technology is a monoclonal antibody. In further embodiments, the antibody is a chimeric or humanized antibody, a fragment of an antibody or a synthetic antibody. The antibody may be coupled to a therapeutically or diagnostically useful agent also termed therapeutic or diagnostic agent herein.

An antisense nucleic acid present in a pharmaceutical composition of the present technology may comprise a sequence of 6-50, in particular 10-30, 15-30 and 20-30, contiguous nucleotides of the nucleic acid coding for the tumor-associated antigen identified according to the present technology.

In further embodiments, a tumor-associated antigen or a part thereof, provided by a pharmaceutical composition of the present technology either directly or via expression of a nucleic acid, binds to MHC molecules on the surface of cells, said binding preferably causing a cytolytic response and/or inducing cytokine release.

A pharmaceutical composition of the present technology may comprise a pharmaceutically compatible carrier and/or an adjuvant.

A pharmaceutical composition of the present technology is preferably used for the treatment or prevention of a disease characterized by selective expression or abnormal expression of a tumor-associated nucleic acid and/or tumor-associated antigen. In a preferred embodiment, the disease is a neoplastic disease, preferably cancer.

In a preferred embodiment, the pharmaceutical composition of the present technology is in the form of a vaccine which may be used therapeutically or prophylactically. Such vaccine preferably comprises a tumor-associated antigen identified according to the present technology or a part thereof, and/or a nucleic acid which codes for a tumor-associated antigen identified according to the present technology or a part thereof. In particular embodiments, the nucleic acid is present in a virus or host cell.

The present technology furthermore relates to methods of treating, preventing, diagnosing or monitoring, i.e. determining the regression, progression, course and/or onset of, a disease characterized by expression or abnormal expression of one of more tumor-associated nucleic acids identified according to the present technology, preferably also resulting in expression or abnormal expression of one of more tumor-associated antigens identified according to the present technology, preferably a neoplastic disease, in particular cancer. In one embodiment, the treatment or prevention comprises administering a pharmaceutical composition of the present technology.

The methods of diagnosing and/or methods of monitoring according to the present technology generally concern the detection of and/or determination of the quantity of one or more parameters selected from the group consisting of (i) a tumor-associated nucleic acid identified according to the present technology, or a part thereof, (ii) a tumor-associated antigen identified according to the present technology, or a part thereof, (iii) an antibody against a tumor-associated antigen identified according to the present technology or a part thereof, and (iv) T lymphocytes, preferably cytotoxic or T helper lymphocytes, which are specific for a tumor-associated antigen identified according to the present technology or a part thereof and/or a complex between the tumor-associated antigen or a part thereof and an MHC molecule, in a biological sample isolated from a patient, preferably from a patient having said disease, being suspected of having or falling ill with said disease or having a potential for said disease. Means for accomplishing said detection and/or determination of the quantity are described herein and will be apparent to the skilled person.

Preferably, the presence of said nucleic acid or said part thereof, said tumor-associated antigen or said part thereof, said antibody and/or said T lymphocytes and/or a quantity of said nucleic acid or said part thereof, said tumor-associated antigen or said part thereof, said antibody and/or said T lymphocytes which is increased compared to a patient without said disease is indicative for the presence of said disease or a potential for a development of said disease.

The methods of diagnosing and/or monitoring of the present technology also include embodiments wherein by detection or determination of the quantity of said nucleic acid or said part thereof, said tumor-associated antigen or said part thereof, said antibody and/or said T lymphocytes it is possible to assess and/or prognose the metastatic behavior of said disease, wherein, preferably, the presence of said nucleic acid or said part thereof, said tumor-associated antigen or said part thereof, said antibody and/or said T lymphocytes and/or a quantity of said nucleic acid or said part thereof, said tumor-associated antigen or said part thereof, said antibody and/or said T lymphocytes which is increased compared to a patient without said disease or without a metastasis of said disease is indicative for a metastatic behavior of said disease or a potential for a metastatic behavior of said disease.

In particular embodiments, said detection or determination of the quantity comprises (i) contacting a biological sample with an agent which binds specifically to said tumor-associated nucleic acid or said part thereof, to said tumor-associated antigen or said part thereof, to said antibody or to said T lymphocytes, and (ii) detecting the formation of or determining the amount of a complex between the agent and the nucleic acid or the part thereof, the tumor-associated antigen or the part thereof, the antibody, or the T lymphocytes.

In one embodiment, the disease is characterized by expression or abnormal expression of two or more different tumor-associated nucleic acids preferably also resulting in expression or abnormal expression of two or more different tumor-associated antigens and a detection or determination of the quantity comprises a detection or determination of the quantity of two or more different tumor-associated nucleic acids or of parts thereof, of two or more different tumor-associated antigens or of parts thereof, of two or more antibodies binding to said two or more different tumor-associated antigens or to parts thereof and/or of two or more T lymphocytes specific for said two or more different tumor-associated antigens or parts thereof, or complexes thereof with MHC molecules. In a further embodiment, the biological sample isolated from the patient is compared to a comparable normal biological sample.

The methods of monitoring according to the present technology preferably comprise a detection of and/or determination of the quantity of one or more of the parameters mentioned above in a first sample at a first point in time and in a further sample at a second point in time, wherein the course of the disease is determined by comparing the two samples.

Preferably, a level of said nucleic acid or said part thereof, said tumor-associated antigen or said part thereof, said antibody and/or said T lymphocytes which is increased in a sample compared to a sample taken earlier from a patient indicates that the patient has developed or is about to develop cancer and/or a metastasis of cancer and/or a relapse of cancer. Preferably, a level of said nucleic acid or said part thereof, said tumor-associated antigen or said part thereof, said antibody and/or said T lymphocytes which is decreased in a sample compared to a sample taken earlier from a patient indicates regression of cancer and/or a metastasis of cancer in said patient and thus, preferably indicates a successful cancer therapy.

According to the present technology, detection of a nucleic acid or of a part thereof or determining the quantity of a nucleic acid or of a part thereof may be carried out using a oligo- or polynucleotide probe which hybridizes specifically to said nucleic acid or said part thereof or may be carried out by selective amplification of said nucleic acid or said part thereof, e.g. by means of PCR amplification. In one embodiment, the oligo- or polynucleotide probe comprises a sequence of 6-50, in particular 10-30, 15-30 and 20-30, contiguous nucleotides of said nucleic acid.

In particular embodiments, the tumor-associated antigen or the part thereof which is to be detected or the quantity of which is to be determined in the methods of the present technology is present intracellularly, on the cell surface or in a complex with an MHC molecule.

According to the present technology, detection of a tumor-associated antigen or of a part thereof or determining the quantity of a tumor-associated antigen or of a part thereof may be carried out using an antibody binding specifically to said tumor-associated antigen or said part thereof.

According to the present technology, detection of an antibody or determining the quantity of an antibody may be carried out using a protein or peptide binding specifically to said antibody.

According to the present technology, detection of or determining the quantity of T lymphocytes which are specific for a tumor-associated antigen or a part thereof and/or a complex thereof with an MHC molecule may be carried out using a cell presenting the complex between said tumor-associated antigen or said part thereof and an MHC molecule. T lymphocytes may additionally be detected by detecting their proliferation, their cytokine production, and their cytotoxic activity triggered by specific stimulation with a complex of an MHC molecule and a tumor-associated antigen or a part thereof. T lymphocytes may also be detected with aid of a recombinant MHC molecule or a complex of two or more MHC molecules loaded with immunogenic fragments of one or more tumor-associated antigens.

An agent which is used for detection or determining the quantity in the methods of the present technology such as a oligo- or polynucleotide probe, an antibody, a protein or peptide or a cell is preferably labeled in a detectable manner, in particular by a detectable marker such as a radioactive marker or an enzymic marker.

In a particular aspect, the present technology relates to a method of treating, preventing, diagnosing or monitoring a disease characterized by expression or abnormal expression of a tumor-associated antigen identified according to the present technology, which method comprises administering an antibody which binds to said tumor-associated antigen or to a part thereof and which is coupled to a therapeutic or diagnostic agent. The antibody may be a monoclonal antibody. In further embodiments, the antibody is a chimeric or humanized antibody or a fragment of an antibody.

In certain embodiments, the methods of the present technology of diagnosing or monitoring a disease are performed with a biological sample containing or suspected of containing disseminating tumor cells or metastatic tumor cells. Such biological samples include, for example, blood, serum, bone marrow, sputum, bronchial aspirate, and/or bronchial lavage. Preferably, the methods of the present technology of diagnosing or monitoring a disease are performed with a biological sample not containing placental cells and, in particular, being a non-placenta biological sample isolated from a subject.

In one particular aspect, the present technology relates to a method of treating a patient having a disease characterized by expression or abnormal expression of a tumor-associated antigen identified according to the present technology, which method comprises (i) providing a sample containing immunoreactive cells, either obtained from said patient or from another individual of the same species, in particular a healthy individual, or an individual of a different species, (ii) contacting said sample with a host cell expressing said tumor-associated antigen or a part thereof, under conditions which favor production of cytolytic T cells against said tumor-associated antigen or a part thereof, and (iii) introducing the cytolytic T cells into the patient in an amount suitable for lysing cells expressing the tumor-associated antigen or a part thereof. In one embodiment, the method includes cloning of the T cell receptor of cytolytic T cells obtained and transferring the nucleic acid coding for the T cell receptor to T cells, either obtained from said patient or from another individual of the same species, in particular a healthy individual, or an individual of a different species, which T cells thus receive the desired specificity and, as under (iii), may be introduced into the patient.

In one embodiment, the host cell endogenously expresses an MHC molecule. In a further embodiment, the host cell recombinantly expresses an MHC molecule and/or the tumor-associated antigen or the part thereof. Preferably, the host cell presents the tumor-associated antigen or the part thereof by MHC molecules on its surface. The host cell is preferably nonproliferative. In a preferred embodiment, the host cell is an antigen-presenting cell, in particular a dendritic cell, a monocyte or a macrophage.

The present technology also relates to a method of treating a disease characterized by expression or abnormal expression of a tumor-associated antigen identified according to the present technology, which method comprises (i) identifying cells from the patient which express abnormal amounts of the tumor-associated antigen, (ii) isolating a sample of said cells, (iii) culturing said cells, and (iv) introducing said cells into the patient in an amount suitable for triggering an immune response to the cells.

The present technology furthermore relates to a nucleic acid selected from the group consisting of (a) a nucleic acid which comprises a nucleic acid sequence selected from the group consisting of SEQ ID NOs: 1-540, 541, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

In a further aspect, the present technology relates to a recombinant nucleic acid molecule, in particular DNA or RNA molecule, which comprises a nucleic acid of the present technology.

The present technology also relates to host cells which contain a nucleic acid or recombinant nucleic acid molecule of the present technology.

The host cell may also comprise a nucleic acid coding for a MHC molecule. In one embodiment, the host cell endogenously expresses the MHC molecule. In a further embodiment, the host cell recombinantly expresses the MHC molecule and/or the nucleic acid or recombinant nucleic acid molecule of the present technology or a part thereof. Preferably, the host cell is nonproliferative. In a preferred embodiment, the host cell is an antigen-presenting cell, in particular a dendritic cell, a monocyte or a macrophage.

In a further embodiment, the present technology relates to oligonucleotides which hybridize with a nucleic acid identified according to the present technology and which may be used as genetic probes or as "antisense" molecules. Nucleic acid molecules in the form of oligonucleotide primers or competent probes, which hybridize with a nucleic acid identified according to the present technology or parts thereof, may be used for detecting said nucleic acid and/or finding nucleic acids which are homologous to said nucleic acid identified according to the present technology, e.g. by PCR amplification, Southern and Northern hybridization. Hybridization may be carried out under low stringency, more preferably under medium stringency and most preferably under high stringency conditions.

In a further aspect, the present technology relates to a protein or peptide which is encoded by a nucleic acid selected from the group consisting of (a) a nucleic acid which comprises a nucleic acid sequence selected from the group consisting of SEQ ID NOs: 1-540, 541, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, the protein or peptide comprises an amino acid sequence selected from the group consisting of SEQ ID NOs: 542, 546, 550, 554, 567, 571, 584, 588, 592, 596, 603, 607, 614, 621, and 625 of the sequence listing, a part or derivative thereof.

In a further aspect, the present technology relates to an immunogenic fragment of a tumor-associated antigen identified according to the present technology. Said fragment preferably binds to a MHC molecule or an antibody, preferably to a human HLA receptor or a human antibody. According to the present technology, a part or fragment preferably comprises a sequence of at least 5, at least 6, in particular at least 8, at least 10, at least 12, at least 15, at least 20, at least 30 or at least 50, amino acids.

In a further aspect, the present technology relates to an agent which binds to a tumor-associated antigen identified according to the present technology or to a part thereof. In a preferred embodiment, the agent is a protein or peptide, in particular an antibody, a T cell receptor or an MHC molecule. In further embodiments, the antibody is a monoclonal, chimeric, or humanized antibody, an antibody produced by combinatory techniques, or a fragment of an antibody. In one preferred embodiment, the present technology relates to an antibody which binds selectively to a complex of (i) a tumor-associated antigen identified according to the present technology or a part thereof and (ii) an MHC molecule to which said tumor-associated antigen identified according to the present technology or said part thereof binds, with said antibody not binding to (i) or (ii) alone.

According to the present technology, the term "binding" preferably relates to a specific binding. "Specific binding" means that an agent such as an antibody binds stronger to a target such as an epitope for which it is specific compared to the binding to another target. An agent binds stronger to a first target compared to a second target if it binds to the first target with a dissociation constant ($K_D$) which is lower than the dissociation constant for the second target. Preferably the dissociation constant ($K_D$) for the target to which the agent binds specifically is more than 10-fold, preferably more than 20-fold, more preferably more than 50-fold, even more preferably more than 100-fold, 200-fold, 500-fold or 1000-fold lower than the dissociation constant ($K_D$) for the target to which the agent does not bind specifically.

Such specific antibodies may, for example, be obtained by immunization using the aforementioned peptides.

The present technology furthermore relates to a conjugate between an agent of the present technology which binds to a tumor-associated antigen identified according to the present technology or to a part thereof or an antibody of the present technology and a therapeutic or diagnostic agent. In one embodiment, the therapeutic or diagnostic agent is a toxin.

In a further aspect, the present technology relates to a kit for detecting a disease characterized by expression or abnormal expression of one of more tumor-associated nucleic acids identified according to the present technology, preferably also resulting in expression or abnormal expression of one of more tumor-associated antigens identified according to the present technology, preferably a neoplastic disease, in particular cancer, which kit comprises agents for detection or determining the quantity (i) of the tumor-associated nucleic acid or of a part thereof, (ii) of the tumor-associated antigen or of a part thereof, (iii) of antibodies which bind to the tumor-associated antigen or to a part thereof, and/or (iv) of T cells which are specific for the tumor-associated antigen or a part thereof or a complex thereof with an MHC molecule. Such agents are described herein above.

In one embodiment, the present technology relates to a pharmaceutical composition which comprises an agent that (I) inhibits expression or activity of a tumor-associated antigen and/or (II) has tumor-inhibiting activity, and is selective for cells expressing or abnormally expressing a tumor-associated antigen and/or (III) when administered, selectively increases the amount of complexes between an MHC molecule and a tumor-associated antigen or a part thereof, the tumor-associated antigen having a sequence encoded by a nucleic acid which is selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

In another embodiment, the present technology relates to a pharmaceutical composition which comprises one or more components selected from the group consisting of: (i) a tumor-associated antigen or a part thereof, (ii) a nucleic acid which codes for a tumor-associated antigen or a part thereof, (iii) an antibody which binds to a tumor-associated antigen or a part thereof, (iv) an antisense nucleic acid which hybridizes specifically with a nucleic acid coding for a tumor-associated antigen, (v) an siRNA directed against a nucleic acid coding for a tumor-associated antigen, (vi) a host cell which expresses a tumor-associated antigen or a part thereof, and (vii) isolated complexes between a tumor-associated antigen or a part thereof and an MHC molecule, said tumor-associated antigen having a sequence encoded by a nucleic acid which is selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

In yet another embodiment, the present technology relates to a method of diagnosing or monitoring a cancer disease which comprises detecting or determining the quantity (i) of a tumor-associated nucleic acid or of a part thereof, and/or (ii) of a tumor-associated antigen or of a part thereof, and/or (iii) of an antibody to the tumor-associated antigen or a part thereof and/or (iv) of T lymphocytes which are specific to the tumor-associated antigen or to a part thereof in a biological sample isolated from a patient, said tumor-associated nucleic acid being selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and said tumor-associated antigen having a sequence encoded by a nucleic acid which is selected from said group of nucleic acids.

In a further embodiment, the present technology relates to a method of treating or preventing a disease characterized by expression or abnormal expression of a tumor-associated antigen which comprises administration of a pharmaceutical composition of the present technology, said tumor-associated antigen having a sequence encoded by a nucleic acid which is selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

In yet another embodiment, the present technology relates to a method of treating, preventing, diagnosing or monitoring a disease characterized by expression or abnormal expression of a tumor-associated antigen which comprises administering an antibody that binds to said tumor-associated antigen or to a part thereof and is coupled to a therapeutic or diagnostic agent, said tumor-associated antigen having a sequence encoded by a nucleic acid which is selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

Another embodiment of the present technology relates to a method of treating a patient having a disease characterized by expression or abnormal expression of a tumor-associated antigen which comprises: (i) providing a sample containing immunoreactive cells, (ii) contacting said sample with a host cell expressing said tumor-associated antigen or a part thereof, under conditions which favor production of cytolytic or cytokine-releasing T cells against said tumor-associated antigen or said part thereof, and (iii) introducing the cytolytic or cytokine-releasing T cells into the patient in an amount suitable for lysing cells expressing the tumor-associated antigen or a part thereof, said tumor-associated antigen having a sequence encoded by a nucleic acid which is selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

An additional embodiment of the present technology relates to a method of inhibiting the development of cancer in a patient which comprises administering an effective amount of a pharmaceutical composition of the present technology.

In yet another embodiment, the present technology relates to an agent, which binds specifically to a protein or polypeptide or to a part thereof, said protein or polypeptide being encoded by a nucleic acid selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

In an additional embodiment, the present technology relates to an antibody, which binds selectively to a complex of: (i) a protein or polypeptide or a part thereof and (ii) an MHC molecule to which said protein or polypeptide or said part thereof binds, with said antibody not binding to (i) or (ii) alone and said protein or polypeptide being encoded by a nucleic acid selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c).

In yet another embodiment, the present technology relates to a kit for detecting cancer, which comprises agents for detecting or determining the quantity of (i) of a tumor-associated nucleic acid or of a part thereof, and/or (ii) of a tumor-associated antigen or of a part thereof, and/or (iii) of antibodies which bind to the tumor-associated antigen or to a part thereof, and/or (iv) of T cells which are specific for a complex between the tumor-associated antigen or a part thereof and an MHC molecule, said tumor-associated nucleic acid being selected from the group consisting of: (a) a nucleic acid which comprises a nucleic acid sequence selected from the group consisting of SEQ ID NOs: 541, 1-540, 545, 549, 553, 557, 560, 563, 566, 570, 574, 577, 580, 583, 587, 591, 595, 599, 602, 606, 610, 613, 617, 620, and 624, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and said tumor-associated antigen having a sequence encoded by a nucleic acid which is selected from said group of nucleic acids.

BRIEF DESCRIPTION OF SEVERAL VIEWS OF THE DRAWINGS

FIG. 28. Quantitative expression of SEQ ID NO:624 in normal tissues and cancer tissues. Real-time RT-PCR showed overexpression of the nucleic acid sequence according to SEQ ID NO:624 in gastric cancer and lung cancer.

DETAILED DESCRIPTION OF THE INVENTION

Figure 1:
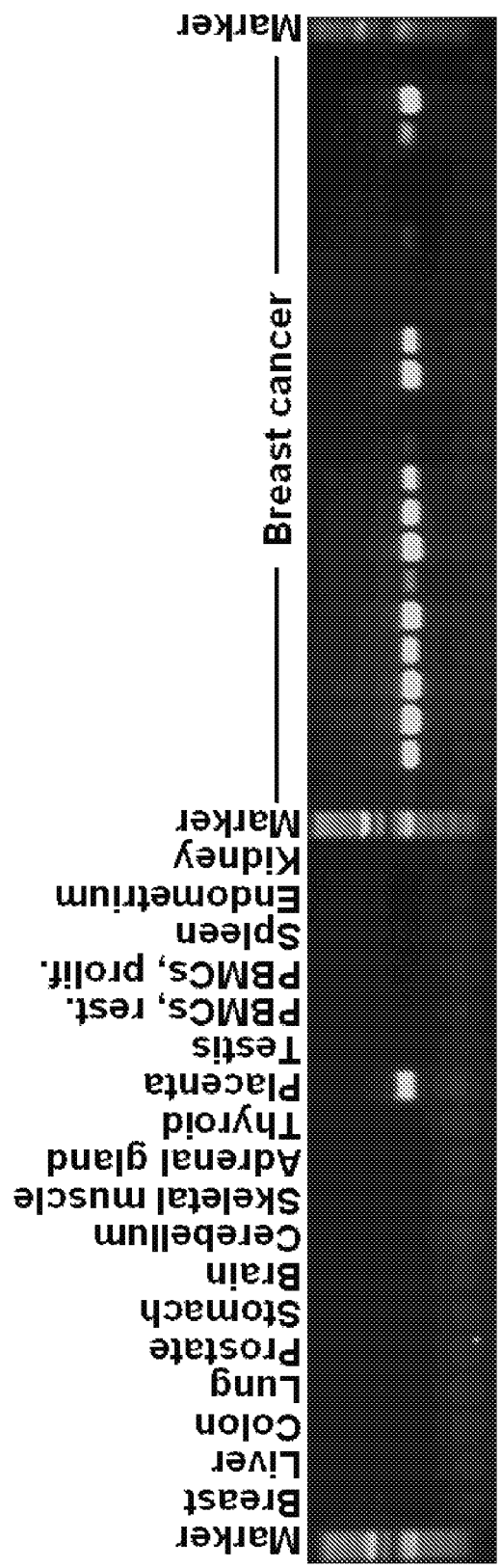
FIG. 1. Expression of a tumor-associated nucleic acid identified according to the present technology in normal tissues and cancer tissue. Significant expression of the nucleic acid sequence according to SEQ ID NO:540 was found only in placenta tissue and mamma carcinomas.

A reference herein to a range of numerical values is to be understood so as to specify and mention each of the individual numerical values comprised by said range. For example, a reference to SEQ ID NOs: 1-540 is to be understood so as to refer to each and every of the following individual SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, and 540.

According to the present technology, a "reference" such as a reference sample or reference organism may be used to correlate and compare the results obtained in the methods of the present technology from a test sample or test organism, i.e. a patient. Typically the reference organism is a healthy organism, in particular an organism which does not suffer from cancer.

A "reference value" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

According to the present technology, a nucleic acid is preferably deoxyribonucleic acid (DNA) or ribonucleic acid (RNA). Nucleic acids comprise according to the present technology genomic DNA, cDNA, mRNA, recombinantly produced and chemically synthesized molecules. According to the present technology, a nucleic acid may be present as a single-stranded or double-stranded and linear or covalently circularly closed molecule.

The terms "tumor-associated nucleic acid identified according to the present technology" and "nucleic acid encoding a tumor-associated antigen identified according to the present technology" have similar meanings. However, the different terms are used herein to account for the fact that in some embodiments only the expression of nucleic acid, in particular mRNA, is of relevance while the expression of protein is not a critical factor.

As used herein, the term "RNA" means a molecule comprising at least one ribonucleotide residue. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

If reference is made herein to the detection of or the determination of the quantity of a nucleic acid, the nucleic acid which is actually to be detected or the quantity of which is actually to be determined is preferably mRNA. However, it should be understood that this may also include embodiments wherein mRNA is detected or the quantity of mRNA is determined indirectly. For example, mRNA may be transformed into cDNA and the cDNA detected or its quantity determined. mRNA is given herein as the cDNA equivalent. One skilled in the art would understand that the cDNA sequence is equivalent to the mRNA sequence, and can be used for the same purpose herein, e.g., the generation of probes hybridizing to the nucleic acid to be detected. Thus, if reference is made herein to the sequences shown in the sequence listing this is also to include the RNA equivalents of said sequences.

The nucleic acids described according to the present technology have preferably been isolated. The term "isolated nucleic acid" means according to the present technology that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

A degenerate nucleic acid according to the present technology is a nucleic acid that differs from a reference nucleic acid in codon sequence due to the degeneracy of the genetic code.

"Derivative" of a nucleic acid means according to the present technology that single or multiple such as at least 2, at least 4, or at least 6 and preferably up to 3, up to 4, up to 5, up to 6, up to 10, up to 15, or up to 20 nucleotide substitutions, deletions and/or additions are present in said nucleic acid. Furthermore, the term "derivative" also comprises chemical derivatization of a nucleic acid on a nucleotide base, on the sugar or on the phosphate. The term "derivative" also comprises nucleic acids which contain nucleotides and nucleotide analogs not occurring naturally.

Preferably the degree of identity between a specific nucleic acid sequence described herein and a nucleic acid sequence which is a derivative of said specific nucleic acid sequence, which hybridizes with said specific nucleic acid sequence and/or which is degenerate with respect to said specific nucleic acid sequence will be at least 70%, preferably at least 75%, preferably at least 80%, more preferably at least 85%, even more preferably at least 90% or most preferably at least 95%, 96%, 97%, 98% or 99%. The degree of identity is preferably given for a region of at least about 30, at least about 50, at least about 70, at least about 90, at least about 100, at least about 150, at least about 200, at least about 250, at least about 300, or at least about 400 nucleotides. In preferred embodiments, the degree of identity is given for the entire length of the reference nucleic acid sequence, such as the nucleic acid sequences given in the sequence listing.

A nucleic acid is "complementary" to another nucleic acid if the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM NaH$_2$PO$_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1× SDS at temperatures of up to 68° C.

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or "fully complementary" means that all the contiguous residues of a nucleic acid sequence will hydrogen bond with the same number of contiguous residues in a second nucleic acid sequence. Preferably, the degree of complementarity according to the present technology is at least 70%, preferably at least 75%, preferably at least 80%, more preferably at least 85%, even more preferably at least 90% or most preferably at least 95%, 96%, 97%, 98% or 99%.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The term "percentage identity" is intended to denote a percentage of nucleotides or of amino acid residues which are identical between the two sequences to be compared, obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

In one embodiment, a nucleic acid sequence which is a derivative of a specific nucleic acid sequence, which is degenerate with respect to a specific nucleic acid sequence or which is a part of a specific nucleic acid sequence has a relevant function and/or activity of the specific nucleic acid sequence, i.e. it may encode a protein or peptide having the same activity or immunological properties as the protein or peptide encoded by the specific nucleic acid sequence and, in one embodiment, encodes the same protein or peptide.

Nucleic acids coding for tumor-associated antigens may, according to the present technology, be present alone or in combination with other nucleic acids, in particular heterologous nucleic acids. In preferred embodiments, a nucleic acid is functionally linked to expression control sequences or regulatory sequences which may be homologous or heterologous with respect to said nucleic acid. A coding sequence and a regulatory sequence are "functionally" linked to one another, if they are covalently linked to one another in such a way that expression or transcription of said coding sequence is under the control or under the influence of said regulatory sequence. If the coding sequence is to be translated into a functional protein, then, with a regulatory sequence functionally linked to said coding sequence, induction of said regulatory sequence results in transcription of said coding sequence, without causing a frame shift in the coding sequence or said coding sequence not being capable of being translated into the desired protein or peptide.

The term "expression control sequence" or "regulatory sequence" comprises according to the present technology promoters, enhancers and other control elements which regulate expression of a gene. In particular embodiments of the present technology, the expression control sequences can be regulated. The exact structure of regulatory sequences may vary as a function of the species or cell type, but generally comprises 5'untranscribed and 5'untranslated sequences which are involved in initiation of transcription and translation, respectively, such as TATA box, capping sequence, CAAT sequence, and the like. More specifically, 5'untranscribed regulatory sequences comprise a promoter region which includes a promoter sequence for transcriptional control of the functionally linked gene. Regulatory sequences may also comprise enhancer sequences or upstream activator sequences.

According to the present technology, a nucleic acid may furthermore be present in combination with another nucleic acid which codes for a peptide controlling secretion of the protein or peptide encoded by said nucleic acid from a host cell. According to the present technology, a nucleic acid may also be present in combination with another nucleic acid which codes for a peptide causing the encoded protein or peptide to be anchored on the cell membrane of the host cell or compartmentalized into particular organelles of said cell. Similarly, a combination with a nucleic acid is possible which represents a reporter gene or any "tag".

In a preferred embodiment, a recombinant nucleic acid molecule is according to the present technology a vector, where appropriate with a promoter, which controls expression of a nucleic acid, for example a nucleic acid coding for a tumor-associated antigen identified according to the present technology. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. An intermediary vehicle may be adapted, for example, to the use in electroporation, in bombardment with microprojectiles, in liposomal administration, in the transfer with the aid of agrobacteria or in insertion via DNA or RNA viruses. Vectors comprise plasmids, phagemids, bacteriophages or viral genomes.

The nucleic acids coding for a tumor-associated antigen identified according to the present technology may be used for transfection of host cells. Nucleic acids here mean both recombinant DNA and RNA. Recombinant RNA may be prepared by in-vitro transcription of a DNA template. Furthermore, it may be modified by stabilizing sequences, capping and polyadenylation prior to application.

According to the present technology, the term "host cell" relates to any cell which can be transformed or transfected with an exogenous nucleic acid. The term "host cells" comprises according to the present technology prokaryotic (e.g. *E. coli*) or eukaryotic cells (e.g. dendritic cells, B cells, CHO cells, COS cells, K562 cells, yeast cells and insect cells). Particular preference is given to mammalian cells such as cells from humans, mice, hamsters, pigs, goats, primates. The cells may be derived from a multiplicity of tissue types and comprise primary cells and cell lines. Specific examples comprise keratinocytes, peripheral blood leukocytes, stem cells of the bone marrow and embryonic stem cells. In further embodiments, the host cell is an antigen-presenting cell, in particular a dendritic cell, monocyte or a macrophage. A nucleic acid may be present in the host cell in the form of a single copy or of two or more copies and, in one embodiment, is expressed in the host cell.

According to the present technology, the term "expression" is used in its most general meaning and comprises the production of RNA or of RNA and protein. It also comprises partial expression of nucleic acids. Furthermore, expression may be carried out transiently or stably. Preferred expression systems in mammalian cells comprise pcDNA3.1 and pRc/CMV (Invitrogen, Carlsbad, Calif.), which contain a selectable marker such as a gene imparting resistance to G418 (and thus enabling stably transfected cell lines to be selected) and the enhancer-promoter sequences of cytomegalovirus (CMV).

In those cases of the present technology in which a MHC molecule presents a tumor-associated antigen or a part thereof, an expression vector may also comprise a nucleic acid sequence coding for said MHC molecule. The nucleic acid sequence coding for the MHC molecule may be present on the same expression vector as the nucleic acid coding for the tumor-associated antigen or the part thereof, or both nucleic acids may be present on different expression vectors. In the latter case, the two expression vectors may be cotransfected into a cell. If a host cell expresses neither the tumor-associated antigen or the part thereof nor the MHC molecule, both nucleic acids coding therefor may be transfected into the cell either on the same expression vector or on different expression vectors. If the cell already expresses the MHC molecule, only the nucleic acid sequence coding for the tumor-associated antigen or the part thereof can be transfected into the cell.

The present technology also comprises kits for detection and/or determination of the quantity of nucleic acids. Such kits comprise, for example, a pair of amplification primers which hybridize to the nucleic acid which is to be detected or the amount of which is to be determined. The primers preferably comprise a sequence of 6-50, in particular 10-30, 15-30 and 20-30 contiguous nucleotides of the nucleic acid and are nonoverlapping, in order to avoid the formation of primer dimers. One of the primers will hybridize to one strand of the nucleic acid, and the other primer will hybridize to the complementary strand in an arrangement which allows amplification of the nucleic acid.

"Antisense molecules" or "antisense nucleic acids" may be used for regulating, in particular reducing, expression of a nucleic acid. The term "antisense molecule" or "antisense nucleic acid" refers according to the present technology to an oligonucleotide which is an oligoribonucleotide, oligodeoxyribonucleotide, modified oligoribonucleotide or modified oligodeoxyribonucleotide and which hybridizes under physiological conditions to DNA comprising a particular gene or to mRNA of said gene, thereby inhibiting transcription of said gene and/or translation of said mRNA. According to the present technology, an "antisense molecule" also comprises a construct which contains a nucleic acid or a part thereof in reverse orientation with respect to its natural promoter. An antisense transcript of a nucleic acid or of a part thereof may form a duplex with naturally occurring mRNA and thus prevent accumulation of or translation of the mRNA. Another possibility is the use of ribozymes for inactivating a nucleic acid.

Antisense oligonucleotides preferred according to the present technology have a sequence of 6-50, in particular 10-30, 15-30 and 20-30, contiguous nucleotides of the target nucleic acid and preferably are fully complementary to the target nucleic acid or to a part thereof.

In preferred embodiments, the antisense oligonucleotide hybridizes with an N-terminal or 5' upstream site such as a translation initiation site, transcription initiation site or promoter site. In further embodiments, the antisense oligonucleotide hybridizes with a 3'untranslated region or mRNA splicing site.

In one embodiment, an oligonucleotide of the present technology consists of ribonucleotides, deoxyribonucleotides or a combination thereof, with the 5' end of one nucleotide and the 3' end of another nucleotide being linked to one another by a phosphodiester bond. These oligonucleotides may be synthesized in the conventional manner or produced recombinantly.

In preferred embodiments, an oligonucleotide of the present technology is a "modified" oligonucleotide. Here, the oligonucleotide may be modified in very different ways, without impairing its ability to bind its target, in order to increase, for example, its stability or therapeutic efficacy. According to the present technology, the term "modified oligonucleotide" means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term "modified oligonucleotide" also comprises oligonucleotides having a covalently modified base and/or sugar. "Modified oligonucleotides" comprise, for example, oligonucleotides with sugar residues which are covalently bound to low molecular weight organic groups other than a hydroxyl group at the 3' position and a phosphate group at the 5' position. Modified oligonucleotides may comprise, for example, a 2'-O-alkylated ribose residue or another sugar instead of ribose, such as arabinose.

It is to be understood that all embodiments described above with respect to oligonucleotides may also apply to polynucleotides.

By "small interfering RNA" or "siRNA" as used herein is meant an isolated RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that is used to identify a target gene or mRNA to be degraded. A range of 19-25 nucleotides is the most preferred size for siRNAs.

siRNA according to the present technology can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e. g., the use of 2'-substituted ribonucleotides or modifications to the sugar-phosphate backbone); or the substitution of one or more nucleotides in the siRNA with deoxyribonucleotides. Furthermore, siRNA may be modified to increase the stability thereof as described above for modified oligonucleotides, in particular by introducing one or more phosphorothioate linkages.

One or both strands of the siRNA can also comprise a 3'-overhang. As used herein, a "3'-overhang" refers to at least one unpaired nucleotide extending from the 3'-end of an RNA strand. Thus in one embodiment, the siRNA comprises at least one 3'-overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length. In the embodiment in which both strands of the siRNA molecule comprise a 3'-overhang, the length of the overhangs can be the same or different for each strand. In a most preferred embodiment, the 3'-overhang is present on both strands of the siRNA, and is 2 nucleotides in length. For example, each strand of the siRNA of the present technology can comprise 3'-overhangs of dideoxythymidylic acid ("TT") or diuridylic acid ("uu").

In order to enhance the stability of the siRNA, the 3'-overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3'-overhangs with 2'-deoxythymidine, is tolerated and does not affect the efficiency of RNAi degradation. In particular, the absence of a 2'-hydroxyl in the 2'-deoxythymidine significantly enhances the nuclease resistance of the 3'-overhang in tissue culture medium.

The sense and antisense strands of the siRNA can comprise two complementary, single-stranded RNA molecules or can comprise a single molecule in which two complementary portions are base-paired and are covalently linked by a single-stranded "hairpin" area. That is, the sense region and antisense region can be covalently connected via a linker molecule. The linker molecule can be a polynucleotide or non-nucleotide linker. Without wishing to be bound by any theory, it is believed that the hairpin area of the latter type of siRNA molecule is cleaved intracellularly by the "Dicer" protein (or its equivalent) to form a siRNA of two individual base-paired RNA molecules.

As used herein, "target mRNA" refers to an RNA molecule that is a target for downregulation.

siRNA can be expressed from pol III expression vectors without a change in targeting site, as expression of RNAs from pol III promoters is only believed to be efficient when the first transcribed nucleotide is a purine.

siRNA according to the present technology can be targeted to any stretch of approximately 19-25 contiguous nucleotides in any of the target mRNA sequences (the "target sequence"). Techniques for selecting target sequences for siRNA are given, for example, in Tuschl T. et al., "The siRNA User Guide", revised Oct. 11, 2002, the entire disclosure of which is herein incorporated by reference. "The siRNA User Guide" is available on the world wide web at a website maintained by Dr. Thomas Tuschl, Laboratory of RNA Molecular Biology, Rockefeller University, New York, USA, and can be found by accessing the website of the Rockefeller University and searching with the keyword "siRNA". Thus, the sense strand of the present siRNA comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3'-direction) from the start codon. The target sequence can, however, be located in the 5'- or 3'-untranslated regions, or in the region nearby the start codon.

siRNA can be obtained using a number of techniques known to those of skill in the art. For example, siRNA can be chemically synthesized or recombinantly produced using methods known in the art, such as the Drosophila in vitro system described in U.S. published application 2002/0086356 of Tuschl et al., the entire disclosure of which is herein incorporated by reference.

Preferably, siRNA is chemically synthesized using appropriately protected ribonucleoside phosphoramidites and a conventional DNA/RNA synthesizer. siRNA can be synthesized as two separate, complementary RNA molecules, or as a single RNA molecule with two complementary regions.

Alternatively, siRNA can also be expressed from recombinant circular or linear DNA plasmids using any suitable promoter. Such embodiments are included according to the present technology when reference is made herein to the administration of siRNA or the incorporation of siRNA into pharmaceutical compositions. Suitable promoters for expressing siRNA of the present technology from a plasmid include, for example, the U6 or H1 RNA pol III promoter sequences and the cytomegalovirus promoter.

Selection of other suitable promoters is within the skill in the art. The recombinant plasmids of the present technology can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly. The use of recombinant plasmids to deliver siRNA to cells in vivo is discussed in more detail below. siRNA can be expressed from a recombinant plasmid either as two separate, complementary RNA molecules, or as a single RNA molecule with two complementary regions.

Selection of plasmids suitable for expressing siRNA, methods for inserting nucleic acid sequences for expressing the siRNA into the plasmid, and methods of delivering the recombinant plasmid to the cells of interest are within the skill in the art.

siRNA can also be expressed from recombinant viral vectors intracellularly in vivo. The recombinant viral vectors comprise sequences encoding the siRNA and any suitable promoter for expressing the siRNA sequences. The recombinant viral vectors can also comprise inducible or regulatable promoters for expression of the siRNA in a particular tissue or in a particular intracellular environment. siRNA can be expressed from a recombinant viral vector either as two separate, complementary RNA molecules, or as a single RNA molecule with two complementary regions.

The term "peptide" comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

Preferably, the proteins and peptides described according to the present technology have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo.

Such proteins and peptides may be used, for example, in producing antibodies and in an immunological or diagnostic assay or as therapeutics. Proteins and peptides described according to the present technology may be isolated from biological samples such as tissue or cell homogenates and may also be expressed recombinantly in a multiplicity of pro- or eukaryotic expression systems.

For the purposes of the present technology, "derivatives" of a protein or peptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid deletion variants are characterized by the removal of one or more amino acids from the sequence.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties.

"Conservative substitutions" may be made, for instance, on the basis of similarity in polarity, charge, solubility, hydrophobicity, hydrophilicity, and/or the amphipathic nature of the residues involved. For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Preferably the degree of similarity, preferably identity between a specific amino acid sequence described herein and an amino acid sequence which is a derivative of said specific amino acid sequence will be at least 70%, preferably at least 80%, preferably at least 85%, even more preferably at least 90% or most preferably at least 95%, 96%, 97%, 98% or 99%. The degree of similarity or identity is given preferably for a region of at least about 20, at least about 40, at least about 60, at least about 80, at least about 100, at least about 120, at least about 140, at least about 160, at least about 200 or 250 amino acids. In preferred embodiments, the degree of similarity or identity is given for the entire length of the reference amino acid sequence.

In one embodiment, a protein or peptide which is a derivative of a specific protein or peptide or which is a part of a specific protein or peptide has a relevant function and/or activity of the specific protein or peptide, i.e. it may have the same activity or immunological properties as the specific protein or peptide.

The amino acid variants described above may be readily prepared with the aid of known peptide synthesis techniques such as, for example, by solid phase synthesis (Merrifield, 1964) and similar methods or by recombinant DNA manipulation. The manipulation of DNA sequences for preparing proteins and peptides having substitutions, insertions or deletions, is described in detail in Sambrook et al. (1989), for example.

According to the present technology, "derivatives" of proteins and peptides also comprise single or multiple substitutions, deletions and/or additions of any molecules associated with the protein or peptide, such as carbohydrates, lipids and/or proteins or peptides. The term "derivative" also extends to all functional chemical equivalents of said proteins and peptides.

According to the present technology, a part or fragment of a tumor-associated antigen preferably has a functional property of the protein or peptide from which it has been derived. Such functional properties comprise the interaction with antibodies, the interaction with other peptides or proteins, the selective binding of nucleic acids and an enzymatic activity. A particular property is the ability to form a complex with MHC molecules and, where appropriate, generate an immune response, preferably by stimulating cytotoxic or T helper cells. A part or fragment of a tumor-associated antigen preferably comprises a sequence of at least 6, in particular at least 8, at least 10, at least 12, at least 15, at least 20, at least 30 or at least 50, consecutive amino acids of the tumor-associated antigen. A part or fragment of a tumor-associated antigen preferably comprises a sequence of up to 8, in particular up to 10, up to 12, up to 15, up to 20, up to 30 or up to 55, consecutive amino acids of the tumor-associated antigen. A part or fragment of a tumor-associated antigen is preferably a part of the tumor-associated antigen which corresponds to the non-transmembrane portion, in particular the extracellular portion of the antigen, or is comprised thereof.

Preferred parts or fragments of a tumor-associated antigen are in particular suitable for the stimulation of cytotoxic T-lymphocytes in vivo but also for the production of expanded and stimulated T-lymphocytes for the therapeutic adoptive transfer ex vivo.

A part or a fragment of a nucleic acid coding for a tumor-associated antigen relates according to the present technology to the part of the nucleic acid, which codes at least for the tumor-associated antigen and/or for a part or a fragment of said tumor-associated antigen, as defined above. A part or fragment of a nucleic acid coding for a tumor-associated antigen is preferably that part of the nucleic acid corresponding to the open reading frame.

According to the present technology, particular embodiments ought to involve providing "dominant negative" proteins or peptides derived from tumor-associated antigens. A dominant negative protein or peptide is an inactive protein or peptide variant which, by way of interacting with the cellular machinery, displaces an active protein or peptide from its interaction with the cellular machinery or which competes with the active protein or peptide, thereby reducing the effect of said active protein.

Antisera which contain specific antibodies specifically binding to the target protein can be prepared by various standard processes; see, for example, "Monoclonal Antibodies: A Practical Approach" by Philip Shepherd, Christopher Dean ISBN 0-19-963722-9; "Antibodies: A Laboratory Manual" by Ed Harlow, David Lane, ISBN: 0879693142 and "Using Antibodies: A Laboratory Manual: Portable Protocol NO" by Edward Harlow, David Lane, Ed Harlow ISBN 0879695447. Thereby it is also possible to generate affine and specific antibodies which recognize complex membrane proteins in their native form (Azorsa et al., J. Immunol. Methods 229: 35-48, 1999; Anderson et al., J. Immunol. 143: 1899-1904, 1989; Gardsvoll, J. Immunol. Methods 234: 107-116, 2000). This is in particular relevant for the preparation of antibodies which are to be used therapeutically, but also for many diagnostic applications. In this respect, it is possible to immunize with the whole protein, with extracellular partial sequences as well as with cells which express the target molecule in physiologically folded form.

Monoclonal antibodies are traditionally prepared using the hybridoma technology. (for technical details see: "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142; "Using Antibodies: A Laboratory Manual: Portable Protocol NO" by Edward Harlow, David Lane, Ed Harlow ISBN: 0879695447).

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), *Essential Immunology,* 7th Edition, Blackwell Scientific Publications, Oxford). The pFc' and Fc regions are, for example, effectors of the complement cascade but are not involved in antigen binding. An antibody from which the pFc' region has been enzymatically removed or which has been produced without the pFc' region, referred to as F(ab')$_2$ fragment, carries both antigen binding sites of a complete antibody. Similarly, an antibody from which the Fc region has been enzymatically removed or which has been produced without said Fc region, referred to as Fab fragment, carries one antigen binding site of an intact antibody molecule. Furthermore, Fab fragments consist of a covalently bound light chain of an antibody and part of the heavy chain of said antibody, referred to as Fd. The Fd fragments are the main determinants of antibody specificity (a single Fd fragment can be associated with up to ten different light chains, without altering the specificity of the antibody) and Fd fragments, when isolated, retain the ability to bind to an epitope.

Located within the antigen-binding part of an antibody are complementary-determining regions (CDRs) which interact directly with the antigen epitope and framework regions (FRs) which maintain the tertiary structure of the paratope. Both the Fd fragment of the heavy chain and the light chain of IgG immunoglobulins contain four framework regions (FR1 to FR4) which are separated in each case by three complementary-determining regions (CDR1 to CDR3). The CDRs and, in particular, the CDR3 regions and, still more particularly, the CDR3 region of the heavy chain are responsible to a large extent for antibody specificity.

Non-CDR regions of a mammalian antibody are known to be able to be replaced by similar regions of antibodies with the same or a different specificity, with the specificity for the epitope of the original antibody being retained. This made possible the development of "humanized" antibodies in which nonhuman CDRs are covalently linked to human FR and/or Fc/pFc' regions to produce a functional antibody.

As another example, WO 92/04381 describes the production and use of humanized murine RSV antibodies in which at least part of the murine FR regions have been replaced with FR regions of a human origin. Antibodies of this kind, including fragments of intact antibodies with antigen-binding capability, are often referred to as "chimeric" antibodies.

According to the present technology, the term "antibody" also includes F(ab')$_2$, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric F(ab')$_2$-fragment antibodies in which the FR and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The term "antibody" also comprises "single-chain" antibodies.

The present technology also comprises proteins and peptides which bind specifically to tumor-associated antigens. Binding substances of this kind may be provided, for example, by degenerate peptide libraries which may be prepared simply in solution in an immobilized form or as phage-display libraries. It is likewise possible to prepare combinatorial libraries of peptides with one or more amino acids. Libraries of peptoids and nonpeptidic synthetic residues may also be prepared.

Antibodies may also be coupled to specific diagnostic substances for displaying cells and tissues expressing tumor-associated antigens. They may also be coupled to therapeutically useful substances.

Diagnostic substances or agents include any label that functions to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Diagnostic substances comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium.

According to the present technology, the terms "therapeutically useful substance", "therapeutic substance" or "therapeutic agent" means any molecule which may exert a therapeutic effect. According to the present technology, a therapeutically useful substance is preferably selectively guided to a cell which expresses one or more tumor-associated antigens and includes anticancer agents, radioactive iodine-labeled compounds, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

The term "major histocompatibility complex" or "MHC" relates to a complex of genes present in all vertebrates. MHC proteins or molecules are involved in signaling between lymphocytes and antigen presenting cells in normal immune reactions by binding peptides and presenting them for recognition by T cell receptors (TCR). MHC molecules bind peptides within an intracellular processing compartment and present these peptides on the surface of antigen presenting cells for recognition by T cells. The human MHC region also termed HLA is located on chromosome 6 and includes the class I and class II region. In one preferred embodiment of all aspects of the present technology an MHC molecule is an HLA molecule.

"Reduce" or "inhibit" as used herein means the ability to cause an overall decrease, preferably of 20% or greater, more preferably of 50% or greater, and most preferably of 75% or greater, in the level, e.g. in the level of protein or mRNA as compared to a reference sample (e.g., a sample not treated with siRNA). This reduction or inhibition of RNA or protein expression can occur through targeted mRNA cleavage or degradation. Assays for protein expression or nucleic acid expression are known in the art and include, for example, ELISA, western blot analysis for protein expression, and northern blotting or RNase protection assays for RNA.

The term "patient" means according to the present technology a human being, a nonhuman primate or another animal, in particular a mammal such as a cow, horse, pig, sheep, goat, dog, cat or a rodent such as a mouse and rat. In a particularly preferred embodiment, the patient is a human being.

According to the present technology the term "increased" or "increased amount" preferably refers to an increase by at least 10%, in particular at least 20%, at least 50% or at least 100%. The amount of a substance is also increased in a test sample such as a biological sample compared to a reference sample if it is detectable in the test sample but absent or not detectable in the reference sample.

According to the present technology, the term "disease" refers to any pathological state in which tumor-associated nucleic acids and/or tumor-associated antigens are expressed or abnormally expressed. "Abnormal expression" means according to the present technology that expression is altered, preferably increased, compared to the state in a healthy individual. An increase in expression refers to an increase by at least 10%, in particular at least 20%, at least 50% or at least 100%. In one embodiment, expression is only found in tissue of a diseased individual, while expression in a healthy individual is repressed or is repressed in a healthy individual except for placenta. One example of such a disease is cancer, wherein the term "cancer" according to the present technology comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the present technology also comprises cancer metastases.

By "tumor" is meant an abnormal group of cells or tissue that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the present technology relates to "distant metastasis" which relates to a metastasis which is remote from the primary tumor and the regional lymph node system.

According to the present technology, a biological sample may be a tissue sample, including bodily fluids, and/or a cellular sample and may be obtained in the conventional manner such as by tissue biopsy, including punch biopsy, and by taking blood, bronchial aspirate, sputum, urine, feces or other body fluids. According to the present technology, the term "biological sample" also includes fractions of biological samples. Preferably, the term "biological sample" according to the present technology does not include samples derived from placental tissue.

According to the present technology, the term "immunoreactive cell" means a cell which can mature into an immune cell (such as B cell, T helper cell, or cytolytic T cell) with suitable stimulation. Immunoreactive cells comprise CD34$^+$ hematopoietic stem cells, immature and mature T cells and immature and mature B cells. If production of cytolytic or T helper cells recognizing a tumor-associated antigen is desired, the immunoreactive cell is contacted with a cell expressing a tumor-associated antigen under conditions which favor production, differentiation and/or selection of cytolytic T cells and of T helper cells. The differentiation of T cell precursors into a cytolytic T cell, when exposed to an antigen, is similar to clonal selection of the immune system.

The terms "T cell" and "T lymphocyte" are used interchangeably herein and include T helper cells and cytotoxic T cells which comprise cytolytic T cells.

Some therapeutic methods are based on a reaction of the immune system of a patient, which results in a lysis of antigen-presenting cells such as cancer cells which present one or more tumor-associated antigens. In this connection, for example autologous cytotoxic T lymphocytes specific for a complex of a tumor-associated antigen and an MHC molecule are administered to a patient having a cellular abnormality. The production of such cytotoxic T lymphocytes in vitro is known. An example of a method of differentiating T cells can be found in WO-A-9633265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting antigen-specific cytotoxic T lymphocytes, fluorogenic tetramers of MHC class I molecule/peptide complexes are used for obtaining specific clones of cytotoxic T lymphocytes (Altman et al., *Science* 274:94-96, 1996; Dunbar et al., *Curr. Biol.* 8:413-416, 1998).

The present technology also includes therapeutic methods referred to as adoptive transfer (Greenberg, *J. Immunol.* 136(5):1917, 1986; Riddel et al., *Science* 257:238, 1992; Lynch et al., *Eur. J. Immunol.* 21:1403-1410, 1991; Kast et al., *Cell* 59:603-614, 1989), wherein cells presenting the desired complex (e.g. dendritic cells) are combined with cytotoxic T lymphocytes of the patient to be treated, resulting in a propagation of specific cytotoxic T lymphocytes. The propagated cytotoxic T lymphocytes are then administered to a patient having a cellular anomaly characterized by particular abnormal cells presenting the specific complex. The cytotoxic T lymphocytes then lyse the abnormal cells, thereby achieving a desired therapeutic effect.

Furthermore, cells presenting the desired complex (e.g. dendritic cells) may be combined with cytotoxic T lymphocytes of healthy individuals or another species (e.g. mouse) which may result in propagation of specific cytotoxic T lymphocytes with high affinity. The high affinity T cell receptor of these propagated specific T lymphocytes may be cloned and optionally humanized to a different extent, and the T cell receptors thus obtained then transduced via gene transfer, for example using retroviral vectors, into T cells of patients. Adoptive transfer may then be carried out using these genetically altered T lymphocytes (Stanislawski et al., *Nat Immunol.* 2:962-70, 2001; Kessels et al., *Nat Immunol.* 2:957-61, 2001).

Adoptive transfer is not the only form of therapy which can be applied according to the present technology. Cytotoxic T lymphocytes may also be generated in vivo in a manner known per se. One method uses nonproliferative cells expressing the complex. The cells used here will be those which usually express the complex, such as irradiated tumor cells or cells transfected with one or both genes necessary for presentation of the complex (i.e. the antigenic peptide and the presenting MHC molecule). Another preferred form is the introduction of the tumor-associated antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining the tumor-associated antigen or a fragment thereof with an adjuvant in order to make incorporation into antigen-presenting cells in vivo possible. The tumor-associated antigen or a fragment thereof may be represented as protein, as DNA (e.g. within a vector) or as RNA. The tumor-associated antigen is processed to produce a peptide partner for the MHC molecule, while a fragment thereof may be presented without the need for further processing. The latter is the case in particular, if these can bind to MHC molecules. Preference is given to administration forms in which the complete antigen is processed in vivo by a dendritic cell, since this may also produce T helper cell responses which are needed for an effective immune response (Ossendorp et al., *Immunol Lett.* 74:75-9, 2000; Ossendorp et al., *J. Exp. Med.* 187:693-702, 1998). In general, it is possible to administer an effective amount of the tumor-associated antigen to a patient by intradermal injection, for example. However, injection may also be carried out intranodally into a lymph node (Maloy et al., *Proc Natl Acad Sci USA* 98:3299-303, 2001).

The pharmaceutical compositions and methods of treatment described according to the present technology may also be used for immunization or vaccination to therapeutically treat or prevent a disease described herein. According to the present technology, the terms "immunization" or "vaccination" preferably relate to an increase in or activation of an immune response to an antigen. It is possible to use animal models for testing an immunizing effect on cancer by using a tumor-associated antigen or a nucleic acid coding therefor. For example, human cancer cells may be introduced into a mouse to generate a tumor, and one or more nucleic acids coding for tumor-associated antigens may be administered. The effect on the cancer cells (for example reduction in tumor size) may be measured as a measure for the effectiveness of an immunization by the nucleic acid.

As part of the composition for an immunization or a vaccination, preferably one or more tumor-associated antigens or stimulating fragments thereof are administered together with one or more adjuvants for inducing an immune response or for increasing an immune response. An adjuvant is a substance which is incorporated into the antigen or administered together with the latter and which enhances the immune response. Adjuvants may enhance the immune response by providing an antigen reservoir (extracellularly or in macrophages), activating macrophages and/or stimulating particular lymphocytes. Adjuvants are known and comprise in a nonlimiting way monophosphoryl lipid A (MPL, SmithKline Beecham), saponins such as QS21 (SmithKline Beecham), DQS21 (SmithKline Beecham; WO 96/33739), QS7, QS17, QS18 and QS-L1 (So et al., *Mol. Cells* 7:178-186, 1997), incomplete Freund's adjuvant, complete Freund's adjuvant, vitamin E, montanide, alum, CpG oligonucleotides (cf. Kreig et al., *Nature* 374:546-9, 1995) and various water-in-oil emulsions prepared from biologically degradable oils such as squalene and/or tocopherol. Preferably, the peptides are administered in a mixture with DQS21/MPL. The ratio of DQS21 to MPL is typically about 1:10 to 10:1, preferably about 1:5 to 5:1 and in particular about 1:1. For administration to humans, a vaccine formulation typically contains DQS21 and MPL in a range from about 1 µg to about 100 µg.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise costimulating molecules provided in the form of proteins or nucleic acids such as B7-1 and B7-2 (CD80 and CD86, respectively).

The present technology also provides for administration of nucleic acids, proteins or peptides. Proteins and peptides may be administered in a manner known per se. In one embodiment, nucleic acids are administered by ex vivo methods, i.e. by removing cells from a patient, genetic modification of said cells in order to incorporate a tumor-associated antigen and reintroduction of the altered cells into the patient. This generally comprises introducing a functional copy of a gene into the cells of a patient in vitro and reintroducing the genetically altered cells into the patient. The functional copy of the gene is under the functional control of regulatory elements which allow the gene to be expressed in the genetically altered cells. Transfection and transduction methods are known to the skilled worker. The present technology also provides for administering nucleic acids in vivo by using vectors such as viruses and target-controlled liposomes. If according to the present technology reference is made to the administration or incorporation into pharmaceutical compositions of nucleic acids this includes embodiments wherein the nucleic acid is present in such vectors.

In a preferred embodiment, a virus or viral vector for administering a nucleic acid coding for a tumor-associated antigen is selected from the group consisting of adenoviruses, adeno-associated viruses, pox viruses, including vaccinia virus and attenuated pox viruses, Semliki Forest virus, retroviruses, Sindbis virus and Ty virus-like particles. Particular preference is given to adenoviruses and retroviruses. The retroviruses are typically replication-deficient (i.e. they are incapable of generating infectious particles).

Methods of introducing nucleic acids into cells in vitro or in vivo comprise transfection of nucleic acid calcium phosphate precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor-associated antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The therapeutic compositions of the present technology may be administered in pharmaceutically compatible preparations. Such preparations may usually contain pharmaceutically compatible concentrations of salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds.

The therapeutically active compounds of the present technology may be administered via any conventional route, including by injection or infusion. The administration may be carried out, for example, orally, intravenously, intraperitoneally, intramuscularly, subcutaneously or transdermally. Preferably, antibodies are therapeutically administered by way of a lung aerosol. Antisense nucleic acids are preferably administered by slow intravenous administration.

The compositions of the present technology are administered in effective amounts. An "effective amount" refers to the amount which achieves a desired reaction or a desired effect alone or together with further doses. In the case of treatment of a particular disease or of a particular condition characterized by expression of one or more tumor-associated antigens, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. According to the present technology, a diagnosis or treatment of cancer may also include the diagnosis or treatment of cancer metastases which have already formed or will form. According to the present technology, the term "treatment" comprises therapeutic and prophylactic treatment, i.e. prevention.

An effective amount of a composition of the present technology will depend on the condition to be treated, the severeness of the disease, the individual parameters of the patient, including age, physiological condition, size and weight, the duration of treatment, the type of an accompanying therapy (if present), the specific route of administration and similar factors.

The pharmaceutical compositions of the present technology are preferably sterile and contain an effective amount of the therapeutically active substance to generate the desired reaction or the desired effect.

The doses administered of the compositions of the present technology may depend on various parameters such as the type of administration, the condition of the patient, the desired period of administration, etc. In the case that a reaction in a patient is insufficient with an initial dose, higher doses (or effectively higher doses achieved by a different, more localized route of administration) may be used.

Generally, doses of the tumor-associated antigen of from 1 ng to 1 mg, preferably from 10 ng to 100 µg, are formulated and administered for a treatment or for generating or increasing an immune response. If the administration of nucleic acids (DNA and RNA) coding for tumor-associated antigens is desired, doses of from 1 ng to 0.1 mg are formulated and administered.

The pharmaceutical compositions of the present technology are generally administered in pharmaceutically compatible amounts and in pharmaceutically compatible compositions. The term "pharmaceutically compatible" refers to a nontoxic material which does not interact with the action of the active component of the pharmaceutical composition. Preparations of this kind may usually contain salts, buffer substances, preservatives, carriers and, where appropriate, other therapeutically active compounds. When used in medicine, the salts should be pharmaceutically compatible. However, salts which are not pharmaceutically compatible may used for preparing pharmaceutically compatible salts and are included in the present technology. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the present technology may comprise a pharmaceutically compatible carrier. According to the present technology, the term "pharmaceutically compatible carrier" refers to one or more compatible solid or liquid fillers, diluents or encapsulating substances, which are suitable for administration to humans. The term "carrier" refers to an organic or inorganic component, of a natural or synthetic nature, in which the active component is combined in order to facilitate application. The components of the pharmaceutical composition of the present technology are usually such that no interaction occurs which substantially impairs the desired pharmaceutical efficacy.

The pharmaceutical compositions of the present technology may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the present technology may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present technology is described in detail by the figures and examples below, which are used only for illustration purposes and are not meant to be limiting. Owing to the description and the examples, further embodiments which are likewise included in the present technology are accessible to the skilled worker.

EXAMPLES

The techniques and methods mentioned herein are carried out in a manner known per se and are described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information unless specifically indicated.

Example 1: Screening for Placenta-Specific Genes Aberrantly Activated in Tumors

Tissues and Cell Lines

Tissues were obtained as human surplus materials during routine diagnostic or therapeutic procedures and were stored at −80° C. until use. Cell lines were purchased from the American Type Culture Collection (ATCC) and the German Resource Collection of Microorganisms and Cell Culture (DSMZ).

RNA isolation and Microarray Hybridization

Total RNA was isolated using the RNeasy Mini Kit protocol (Qiagen). Quantification of isolated RNA was performed using UV-spectroscopy and the quality was determined both by $A_{260}/A_{280}$ ratio and Agilent bioanalyzer (Agilent Technologies). Five micrograms total RNA were used for cDNA synthesis with 5 pmol $\mu l^{-1}$ T7-oligo(dT)$_{24}$ primer and was performed at 43° C. for 90 minutes with the "Superscript First-Strand Synthesis-System" for RT-PCR (Invitrogen). Second-strand synthesis was performed with complete cDNA. The cDNA solution was incubated at 16° C. for 2 hours followed by an incubation step for 20 min with 6 U T4-DNA polymerase at 16° C. and the reaction was stopped using 10 µl of 0.5 M EDTA. After purification of the double stranded cDNA using the GeneChip Sample Cleanup Module (Affymetrix) labeled cRNA was generated from the cDNA sample by an in vitro transcription reaction that was supplemented with biotin-11-CTP and biotin-16-UTP (Enzo Diagnostics) according to the manufacturer's instructions. The cRNA was quantified by $A_{260}$, and the quality was determined using the labchip bioanalyzer (Agilent). Only cRNA specimens with a high quality were selected for further analyses. Fragmented cRNA (15 µg) was used to prepare 300 µl hybridization cocktail (100 mM MES, 1 M NaCl, 20 mM EDTA, 0.01% Tween-20) containing 0.1 mg ml$^{-1}$ of herring sperm DNA, and 0.5 mg ml$^{-1}$ acetylated bovine serum albumin. Control cRNA was used in order to compare hybridization efficiencies between arrays and to standardize the quantification of measured transcript levels and was included as component of the 'Eukaryotic Hybridization Control kit' (Affymetrix, Santa Clara, Calif., USA). The cocktails were heated to 95° C. for 5 minutes, equilibrated at 45° C. for 5 minutes, and clarified by centrifugation. The cocktail was hybridized to HG U133 Plus 2.0 arrays (Affymetrix) at 45° C. for 16 hours. The arrays were washed and stained with a streptavidin-conjugated fluor using the GeneChip fluidics station protocol EukGE-WS2 (Affymetrix) according to the manufacturer's instructions. Arrays were scanned with an argon-ion laser confocal scanner (Hewlett-Packard, Santa Clara, Calif.) with detection at 570 nm. Data were extracted using Microarray Suite version 5.0 (Affymetrix) and linearly scaled to achieve an average intensity of 2,500 per gene. Text files were exported to determine the intensity of each interrogating oligonucleotide perfect match probe cells or mismatch probe cells. In addition, the ratios of 5'- and 3'-ends of mRNA were analyzed of six randomly selected specimens (two of each group) using microarray test-chips (Test3 Array) containing 24 human housekeeping/maintenance genes (Affymetrix) and RNA degradation was not observed.

Bioinformatic Analysis

The GeneChip® Operating Software 1.4 (Affymetrix) and ArrayAssist software package 5.2 (Stratagene) were used for statistical analyses.

Results

Screening of samples from the 18 normal tissues shown below in table 1 and 30 tumor cell lines of different entities shown below in table 2 resulted in the sequences described herein which are expressed in placenta among the normal tissues investigated and in tumor cell lines.

TABLE 1

Tissues used for microarray expression analysis

| Tissue | Number |
|---|---|
| Placenta | 2 |
| Testis | 2 |
| Mammary gland | 2 |
| Thymus | 2 |
| Skin | 2 |
| Liver | 2 |
| Colon | 2 |
| Esophagus | 2 |
| Stomach | 2 |
| Lung | 2 |
| Kidney | 2 |
| Lymph node | 2 |
| Skeletal muscle | 2 |
| Myocard | 1 |
| Brain | 1 |
| Cerebellum | 1 |
| resting PBMCs | 2 |
| activ. PBMCs | 2 |

TABLE 2

Cell lines used for microarray expression analysis

| Cell line | Tissue |
|---|---|
| BT-549 | Breast cancer |
| MDA-MB-231 metastasizing | Breast cancer |
| MDA-MB-231 non-metastasizing | Breast cancer |
| MDA-MB-435S | Breast cancer |
| MDA-MB-468 | Breast cancer |
| SK-BR-3 | Breast cancer |
| Caov-3 | Ovarian cancer |
| FU-OV | Ovarian cancer |
| NIH-OVCAR-3 | Ovarian cancer |
| COLO-205 | Colorectal cancer |
| HCT-116 | Colorectal cancer |
| HCT-116 DKO | Colorectal cancer |
| HCT-15 | Colorectal cancer |
| HT-29 | Colorectal cancer |
| LOVO | Colorectal cancer |
| SW-480 | Colorectal cancer |
| CPC-N | Lung cancer |
| LOU-NH-91 | Lung cancer |
| SHP-77 | Lung cancer |
| SK-MES-1 | Lung cancer |
| NCI-H-187 | Lung cancer |
| NCI-H-209 | Lung cancer |
| NCI-H-522 | Lung cancer |
| DU-145 | Prostate cancer |
| Uncap | Prostate cancer |
| PC-3 | Prostate cancer |
| MEL-JUSO | Melanoma |
| Murkowski | Melanoma |
| SK-MEL-37 | Melanoma |
| HELA | Cervical cancer |

Example 2: Validation of the Identified Tumor-Associated Markers

1. Examination of RNA Expression

The identified tumor-associated markers are first validated with the aid of RNA which is obtained from various tissues or from tissue-specific cell lines. Since the differential expression pattern of healthy tissue in comparison with tumor tissue is of decisive importance for the subsequent therapeutic application, the target genes are preferably characterized with the aid of these tissue samples.

Total RNA is isolated from native tissue samples or from tumor cell lines by standard methods of molecular biology. Said isolation may be carried out, for example, with the aid of the RNeasy Maxi kit (Qiagen, Cat. No. 75162) according to the manufacturer's instructions. This isolation method is based on the use of chaotropic reagent guanidinium isothiocyanate. Alternatively, acidic phenol can be used for isolation (Chomczynski & Sacchi, Anal. Biochem. 162: 156-159, 1987). After the tissue has been worked up by means of guanidinium isothiocyanate, RNA is extracted with acidic phenol, subsequently precipitated with isopropanol and taken up in DEPC-treated water.

2-4 µg of the RNA isolated in this way are subsequently transcribed into cDNA, for example by means of Superscript II (Invitrogen) according to the manufacturer's protocol. cDNA synthesis is primed with the aid of random hexamers (e.g. Roche Diagnostics) according to standard protocols of the relevant manufacturer. For quality control, the cDNAs are amplified over 30 cycles, using primers specific for the p53 gene which is expressed only lowly. Only p53-positive cDNA samples will be used for the subsequent reaction steps.

The targets are analyzed in detail by carrying out an expression analysis by means of PCR or quantitative PCR (qPCR) on the basis of a cDNA archive which has been isolated from various normal and tumor tissues and from tumor cell lines. For this purpose, 0.5 µl of cDNA of the above reaction mixture is amplified by a DNA polymerase (e.g. 1 U of HotStarTaq DNA polymerase, Qiagen) according to the protocols of the particular manufacturer (total volume of the reaction mixture: 25-50 µl). Aside from said polymerase, the amplification mixture comprises 0.3 mM dNTPs, reaction buffer (final concentration 1×, depending on the manufacturer of the DNA polymerase) and in each case 0.3 mM gene-specific "sense" and "antisense" primers.

The specific primers of the target gene are, as far as possible, selected in such a way that they are located in two different exons so that genomic contaminations do not lead to false-positive results. In a non-quantitative end point PCR, the cDNA is typically incubated at 95° C. for 15 minutes in order to denature the DNA and to activate the Hot-Start enzyme. Subsequently the DNA is amplified over 35 cycles (1 min at 95° C., 1 min at the primer-specific hybridization temperature (approx. 55-65° C.), 1 min at 72° C. to elongate the amplicons). Subsequently, 10 µl of the PCR mixture are applied to agarose gels and fractionated in the electric field. The DNA is made visible in the gels by staining with ethidium bromide and the PCR result is documented by way of a photograph.

As an alternative to conventional PCR, expression of a target gene may also be analyzed by quantitative real time PCR. Meanwhile various analytical systems are available for this analysis, of which the best known ones are the ABI PRISM sequence detection system (TaqMan, Applied Biosystems), the iCycler (Biorad) and the Light cycler (Roche Diagnostics). As described above, a specific PCR mixture is subjected to a run in the real time instruments. By adding a DNA-intercalating dye (e.g. ethidium bromide, CybrGreen), the newly synthesized DNA is made visible by specific light excitation (according to the dye manufacturers' information). A multiplicity of points measured during amplification enables the entire process to be monitored and the nucleic acid concentration of the target gene to be determined quantitatively. The PCR mixture is normalized by measuring a housekeeping gene (e.g. 18S RNA, β-actin). Alternative strategies via fluorescently labeled DNA probes likewise allow quantitative determination of the target gene of a specific tissue sample (see TaqMan applications from Applied Biosystems).

As shown in FIG. 1, placenta was confirmed in RT-PCR analyses as the only healthy tissue expressing the nucleic acid sequence according to SEQ ID NO:540. No significant expression was found in any other normal tissue. However, high and significant levels of expression were found in breast cancer.

Figure 2:
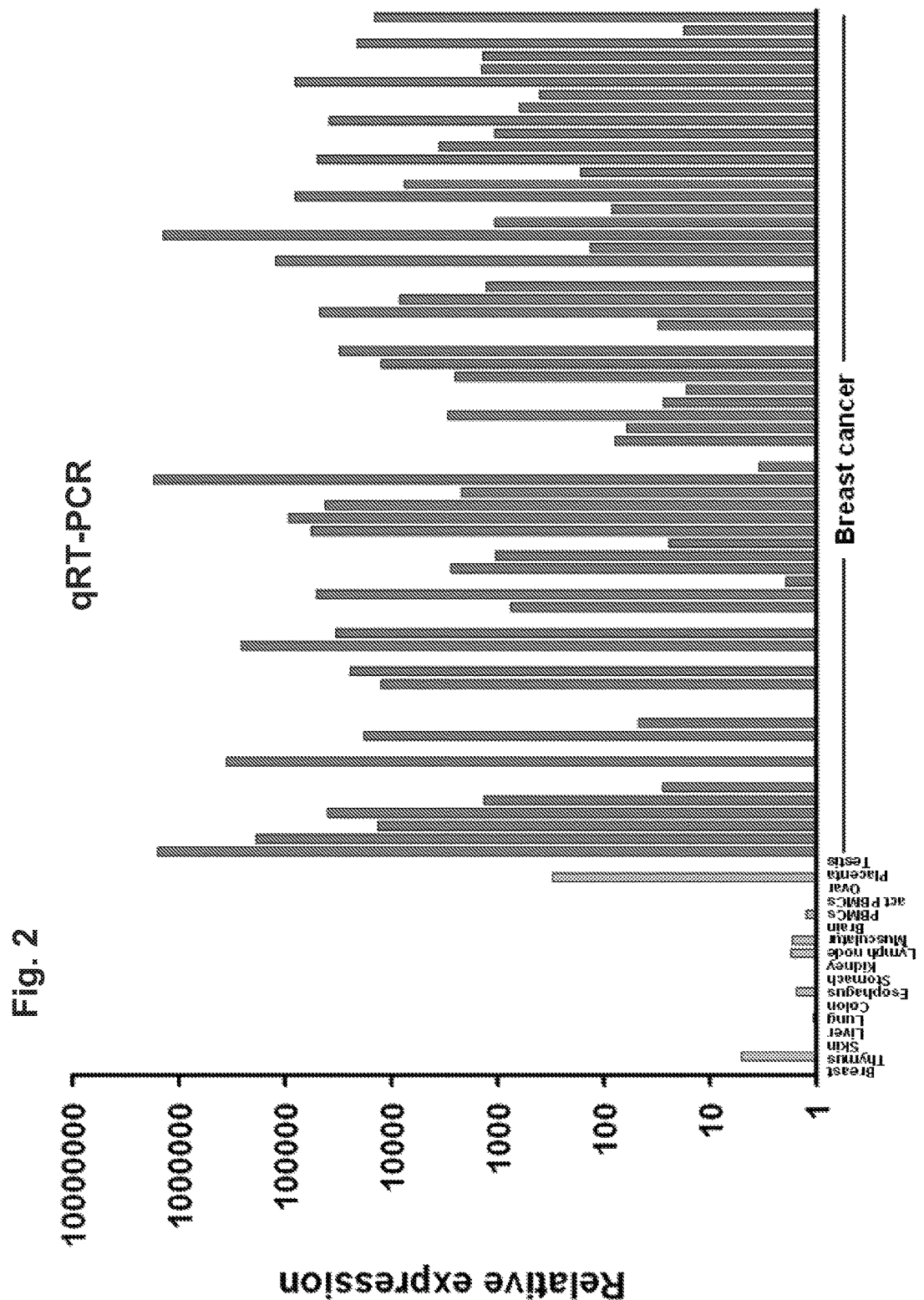
FIG. 2. Quantitative expression of a tumor-associated nucleic acid identified according to the present technology in normal tissues and cancer tissue. Quantitative RT-PCR showed selective expression of the nucleic acid sequence according to SEQ ID NO:540 in placenta tissue and mamma carcinomas.

Quantitative real-time RT-PCR analyses revealed that the nucleic acid sequence according to SEQ ID NO:540 was expressed in significant levels in the majority of breast cancer samples analyzed; cf. FIG. 2.

2. Cloning

The complete target gene which is required for further characterization of the tumor-associated marker is cloned according to common molecular-biological methods (e.g. in "Current Protocols in Molecular Biology", John Wiley & Sons Ltd., Wiley InterScience). In order to clone the target gene or to analyze its sequence, said gene is first amplified by a DNA polymerase having a proof reading function (e.g. pfu, Roche Diagnostics). The amplicon is then ligated by standard methods into a cloning vector. Positive clones are identified by sequence analysis and subsequently characterized with the aid of prediction programs and known algorithms.

3. Prediction of the Protein

Genes found according to the present technology (in particular those from the RefSeq XM domain) may require cloning of the full-length gene, determination of the open reading frame and deduction and analysis of the protein sequence.

In order to clone the full-length sequence, common protocols for the rapid amplification of cDNA ends and the screening of cDNA expression libraries with gene-specific probes may be used (Sambrook et al., *Molecular Cloning: A Laboratory Manual*, 2nd edition (1989), Cold Spring Harbor Laboratory Press, Cold Spring Harbor, N.Y.).

After assembling the fragments found in this way, potential open reading frames (ORF) can be predicted using common prediction programs. Since the position of the PolyA tail and of polyadenylation motifs predetermines the orientation of the potential gene product, only the 3 reading frames of that particular orientation remain out of a possible 6 reading frames. The former often yield only one sufficiently large open reading frame which may code for a protein, while the other reading frames have too many stop codons and would not code for any realistic protein. In the case of alternative open reading frames, identification of the authentic ORF is assisted by taking into account the Kozak criteria for optimal transcription initiation and by analyzing the deduced protein sequences which may arise. Said ORF is further verified by generating immune sera against proteins deduced from the potential ORFs and analyzing said immune sera for recognition of a real protein in tissues and cell lines.

4. Production of Antibodies

The tumor-associated antigens identified according to the present technology are characterized, for example, by using antibodies. The present technology further comprises the diagnostic or therapeutic use of antibodies. Antibodies may recognize proteins in the native and/or denatured state (Anderson et al., *J. Immunol*. 143: 1899-1904, 1989; Gardsvoll, *J. Immunol. Methods* 234: 107-116, 2000; Kayyem et al., *Eur. J. Biochem*. 208: 1-8, 1992; Spiller et al., *J. Immunol. Methods* 224: 51-60, 1999).

Antisera comprising specific antibodies which specifically bind to the target protein may be prepared by various standard methods; cf., for example, "Monoclonal Antibodies: A Practical Approach" by Phillip Shepherd, Christopher Dean ISBN 0-19-963722-9, "Antibodies: A Laboratory Manual" by Ed Harlow, David Lane ISBN: 0879693142 and "Using Antibodies: A Laboratory Manual: Portable Protocol NO" by Edward Harlow, David Lane, Ed Harlow ISBN: 0879695447. It is also possible here to generate affine and specific antibodies which recognize complex membrane proteins in their native form (Azorsa et al., *J. Immunol. Methods* 229: 35-48, 1999; Anderson et al., *J. Immunol*. 143: 1899-1904, 1989; Gardsvoll, *J. Immunol. Methods*. 234: 107-116, 2000). This is especially important in the preparation of antibodies which are intended to be used therapeutically but also for many diagnostic applications. For this purpose, both the complete protein and extracellular partial sequences may be used for immunization.

Immunization and Production of Polyclonal Antibodies

Various immunization protocols are published. A species (e.g. rabbits, mice) is immunized by a first injection of the desired target protein. The immune response of the animal to the immunogen can be enhanced by a second or third immunization within a defined period of time (approx. 2-4 weeks after the previous immunization). Blood is taken from said animals and immune sera obtained, again after various defined time intervals (1st bleeding after 4 weeks, then every 2-3 weeks, up to 5 takings). The immune sera taken in this way comprise polyclonal antibodies which may be used to detect and characterize the target protein in Western blotting, by flow cytometry, immunofluorescence or immunohistochemistry.

The animals are usually immunized by any of four well-established methods, with other methods also in existence. The immunization may be carried out using peptides specific for the target protein, using the complete protein, or using extracellular partial sequences of a protein which can be identified experimentally or via prediction programs. Since the prediction programs do not always work perfectly, it is also possible to employ two domains separated from one another by a transmembrane domain. In this case, one of the two domains has to be extracellular, which may then be proved experimentally (see below). Immunization is offered commercially by different service providers.

(1) In the first case, peptides (length: 8-12 amino acids) are synthesized by in vitro methods (possibly carried out by a commercial service), and said peptides are used for immunization. Normally 3 immunizations are carried out (e.g. with a concentration of 5-100 µg/immunization).

(2) Alternatively, immunization may be carried out using recombinant proteins. For this purpose, the cloned DNA of the target gene is cloned into an expression vector and the target protein is synthesized, for example, cell-free in vitro, in bacteria (e.g. *E. coli*), in yeast (e.g. *S. pombe*), in insect cells or in mammalian cells, according to the conditions of the particular manufacturer (e.g. Roche Diagnostics, Invitrogen, Clontech, Qiagen). It is also possible to synthesize the target protein with the aid of viral expression systems (e.g. baculovirus, vacciniavirus, adenovirus). After it has been synthesized in one of said systems, the target protein is purified, normally by employing chromatographic methods. In this context, it is also possible to use for immunization proteins which have a molecular anchor as an aid for purification (e.g. His tag, Qiagen; FLAG tag, Roche Diagnostics; GST fusion proteins). A multiplicity of protocols can be found, for example, in "Current Protocols in Molecular Biology", John Wiley & Sons Ltd., Wiley InterScience. After the target protein has been purified, an immunization is carried out as described above.

(3) If a cell line is available which synthesizes the desired protein endogenously, it is also possible to use this cell line directly for preparing the specific antiserum. In this case, immunization is carried out by 1-3 injections with in each case approx. $1-5\times10^7$ cells.

(4) The immunization may also be carried out by injecting DNA (DNA immunization). For this purpose, the target gene is first cloned into an expression vector so that the target sequence is under the control of a strong eukaryotic promoter (e.g. CMV promoter). Subsequently, DNA (e.g. 1-10 µg per injection) is transferred as immunogen using a gene gun into capillary regions with a strong blood flow in an organism (e.g. mouse, rabbit). The transferred DNA is taken up by the animal's cells, the target gene is expressed, and the animal finally develops an immune response to the target protein (Jung et al., *Mol. Cells* 12: 41-49, 2001; Kasinrerk et al., *Hybrid Hybridomics* 21: 287-293, 2002).

Production of Monoclonal Antibodies

Monoclonal antibodies are traditionally produced with the aid of the hybridoma technology (technical details: see "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142, "Using Antibodies: A Laboratory Manual: Portable Protocol NO" by Edward Harlow, David Lane, Ed Harlow ISBN: 0879695447). A new method which is also used is the "SLAM" technology. Here, B cells are isolated from whole blood and the cells are made monoclonal. Subsequently the supernatant of the isolated B cell is analyzed for its antibody specificity. In contrast to the hybridoma technology, the variable region of the antibody gene is then amplified by single-cell PCR and cloned into a suitable vector. In this manner production of monoclonal antibodies is accelerated (de Wildt et al., *J. Immunol. Methods* 207:61-67, 1997).

5. Validation of the Targets by Protein-Chemical Methods Using Antibodies

The antibodies which can be produced as described above can be used to further analyze the target protein as follows:

Specificity of the Antibody

Assays based on cell culture with subsequent Western blotting are most suitable for demonstrating the fact that an antibody binds specifically only to the desired target protein (various variations are described, for example, in "Current Protocols in Protein Chemistry", John Wiley & Sons Ltd., Wiley InterScience). For the demonstration, cells are transfected with a cDNA for the target protein, which is under the control of a strong eukaryotic promoter (e.g. cytomegalovirus promoter; CMV). A wide variety of methods (e.g. electroporation, liposome-based transfection, calcium phosphate precipitation) are well established for transfecting cell lines with DNA (e.g. Lemoine et al., *Methods Mol. Biol.* 75: 441-7, 1997). As an alternative, it is also possible to use cell lines which express the target gene endogenously (detection via target gene-specific RT-PCR). As a control, in the ideal case, homologous genes are cotransfected in the experiment, in order to be able to demonstrate in the following Western blot the specificity of the analyzed antibody.

In the subsequent Western blotting, cells from cell culture or tissue samples which might contain the target protein are lysed in a 1% strength SDS solution, and the proteins are denatured in the process. The lysates are fractionated according to size by electrophoresis on 8-15% strength denaturing polyacrylamide gels (contain 1% SDS) (SDS polyacrylamide gel electrophoresis, SDS-PAGE). The proteins are then transferred by one of a plurality of blotting methods (e.g. semi-dry electroblot; Biorad) to a specific membrane (e.g. nitrocellulose, Schleicher & SchUll). The desired protein can be visualized on this membrane. For this purpose, the membrane is first incubated with the antibody which recognizes the target protein (dilution approx. 1:20-1:200, depending on the specificity of said antibody), for 60 minutes. After a washing step, the membrane is incubated with a second antibody which is coupled to a marker (e.g. enzymes such as peroxidase or alkaline phosphatase) and which recognizes the first antibody. It is then possible to make the target protein visible on the membrane in a color or chemi-luminescent reaction (e.g. ECL, Amersham Bioscience). An antibody with a high specificity for the target protein should in the ideal case only recognize the desired protein itself.

Localization of the Target Protein

Various methods are used to confirm the membrane localization, identified in the in silico approach, of the target protein. An important and well-established method using the antibodies described above is immunofluorescence (IF). For this purpose, cells of established cell lines which either synthesize the target protein (detection of the RNA by RT-PCR or of the protein by Western blotting) or else have been transfected with plasmid DNA are utilized. A wide variety of methods (e.g. electroporation, liposome-based transfection, calcium phosphate precipitation) are well established for transfection of cell lines with DNA (e.g. Lemoine et al., *Methods Mol. Biol.* 75: 441-7, 1997). The plasmid transfected into the cells, in immunofluorescence, may encode the unmodified protein or else couple different amino acid markers to the target protein. The principle markers are, for example, the fluorescent green fluorescent protein (GFP) in various differentially fluorescent forms, short peptide sequences of 6-12 amino acids for which high-affinity and specific antibodies are available, or the short amino acid sequence Cys-Cys-X-X-Cys-Cys (SEQ ID NO: 636) which can bind via its cysteines specific fluorescent substances (Invitrogen). Cells which synthesize the target protein are fixed, for example, with paraformaldehyde or methanol. The cells may then, if required, be permeabilized by incubation with detergents (e.g. 0.2% Triton X-100). The cells are then incubated with a primary antibody which is directed against the target protein or against one of the coupled markers. After a washing step, the mixture is incubated with a second antibody coupled to a fluorescent marker (e.g. fluorescein, Texas Red, Dako), which binds to the first antibody. The cells labeled in this way are then overlaid with glycerol and analyzed with the aid of a fluorescence microscope according to the manufacturer's information. Specific fluorescence emissions are achieved in this case by specific excitation depending on the substances employed. The analysis usually permits reliable localization of the target protein, the antibody quality and the target protein being confirmed in double stainings with, in addition to the target protein, also the coupled amino acid markers or other marker proteins whose localization has already been described in the literature being stained. GFP and its derivatives represent a special case, being excitable directly and themselves fluorescing. The membrane permeability which may be controlled through the use of detergents, in immunofluorescence, allows demonstration of whether an immunogenic epitope is located inside or outside the cell. The prediction of the selected proteins can thus be supported experimentally. An alternative possibility is to detect extracellular domains by means of flow cytometry. For this purpose, cells are fixed under non-permeabilizing conditions (e.g. with PBS/Na azide/2% FCS/5 mM EDTA) and analyzed in a flow cytometer in accordance with the manufacturer's instructions. Only extracellular epitopes can be recognized by the antibody to be analyzed in this method. A difference from immunofluorescence is that it is possible to distinguish between dead and living cells by using, for example, propidium iodide or trypan blue, and thus avoid false-positive results.

Another important detection is by immunohistochemistry (IHC) on specific tissue samples. The aim of this method is to identify the localization of a protein in a functionally intact tissue aggregate. IHC serves specifically for (1) being able to estimate the amount of target protein in tumor and normal tissues, (2) analyzing how many cells in tumor and healthy tissues synthesize the target gene, and (3) defining the cell type in a tissue (tumor, healthy cells) in which the target protein is detectable. Alternatively, the amounts of protein of a target gene may be quantified by tissue immunofluorescence using a digital camera and suitable software (e.g. Tillvision, Till-photonics, Germany). The technology has frequently been published, and details of staining and microscopy can therefore be found, for example, in "Diagnostic Immunohistochemistry" by David J., MD Dabbs ISBN: 0443065667 or in "Microscopy, Immunohistochemistry, and Antigen Retrieval Methods: For Light and Electron Microscopy" ISBN: 0306467704. It should be noted that, owing to the properties of antibodies, different protocols have to be used (an example is described below) in order to obtain a meaningful result.

Normally, histologically defined tumor tissues and, as reference, comparable healthy tissues are employed in IHC. It is also possible to use as positive and negative controls cell lines in which the presence of the target gene is known through RT-PCR analyses. A background control must always be included.

Formalin-fixed (another fixation method, for example with methanol, is also possible) and paraffin-embedded tissue pieces with a thickness of 4 μm are applied to a glass support and deparaffinated with xylene, for example. The samples are washed with TBS-T and blocked in serum. This is followed by incubation with the first antibody (dilution: 1:2 to 1:2000) for 1-18 hours, with affinity-purified antibodies normally being used. A washing step is followed by incubation with a second antibody which is coupled to an alkaline phosphatase (alternative: for example peroxidase) and directed against the first antibody, for approx. 30-60 minutes. This is followed by a color reaction using alkaline phosphatase (cf., for example, Shi et al., *J. Histochem. Cytochem.* 39: 741-748, 1991; Shin et al., Lab. Invest. 64: 693-702, 1991). To demonstrate antibody specificity, the reaction can be blocked by previous addition of the immunogen.

Analysis of Protein Modifications

Secondary protein modifications such as, for example, N- or O-glycosylations or myristilations may impair or even completely prevent the accessibility of immunogenic epitopes and thus call into question the efficacy of antibody therapies. Moreover, it has frequently been demonstrated that the type and amount of secondary modifications differ in normal and tumor tissues (e.g. Durand & Seta, 2000; Clin. Chem. 46: 795-805; Hakomori, 1996; Cancer Res. 56: 5309-18). The analysis of these modifications is therefore essential to the therapeutic success of an antibody. Potential binding sites can be predicted by specific algorithms.

Analysis of protein modifications usually takes place by Western blotting (see above). Glycosylations which usually have a size of several kDa, especially lead to a larger total mass of the target protein, which can be fractionated in SDS-PAGE. To detect specific O- and N-glycosidic bonds, protein lysates are incubated prior to denaturation by SDS with O- or N-glycosylases (in accordance with their respective manufacturer's instructions, e.g. PNgase, endoglycosidase F, endoglycosidase H, Roche Diagnostics). This is followed by Western blotting as described above. Thus, if there is a reduction in the size of a target protein after incubation with a glycosidase, it is possible to detect a specific glycosylation and, in this way, also analyze the tumor specificity of a modification.

Functional Analysis of the Target Gene

The function of the target molecule may be crucial for its therapeutic usefulness, so that functional analyses are an important component in the characterization of therapeutically utilizable molecules. The functional analysis may take place either in cells in cell culture experiments or else in vivo with the aid of animal models. This involves either switching off the gene of the target molecule by mutation (knockout) or inserting the target sequence into the cell or the organism (knockin). Thus it is possible to analyze functional modifications in a cellular context firstly by way of the loss of function of the gene to be analyzed (loss of function). In the second case, modifications caused by addition of the analyzed gene can be analyzed (gain of function).

a. Functional Analysis in Cells

Transfection. In order to analyze the gain of function, the gene of the target molecule must be transferred into the cell. For this purpose, cells which allow synthesis of the target molecule are transfected with a DNA. Normally, the gene of the target molecule here is under the control of a strong eukaryotic promoter (e.g. cytomegalovirus promoter; CMV). A wide variety of methods (e.g. electroporation, liposome-based transfection, calcium phosphate precipitation) are well established for transfecting cell lines with DNA (e.g. Lemoine et al., *Methods Mol. Biol.* 75: 441-7, 1997). The gene may be synthesized either transiently, without genomic integration, or else stably, with genomic integration after selection with neomycin, for example.

RNA interference (siRNA). An inhibition of expression of the target gene, which may induce a complete loss of function of the target molecule in cells, may be generated by the RNA interference (siRNA) technology in cells (Hannon, G J. 2002. RNA interference. Nature 418: 244-51; Czauderna et al. 2003. Nucl. Acid Res. 31: 670-82). For this purpose, cells are transfected with short, double-stranded RNA molecules of approx. 20-25 nucleotides in length, which are specific for the target molecule. An enzymic process then results in degradation of the specific RNA of the target gene and thus in reduced expression of the target protein and consequently enables the target gene to be functionally analyzed.

Cell lines which have been modified by means of transfection or siRNA may subsequently be analyzed in different ways. The most common examples are listed below.

1. Proliferation and Cell Cycle Behavior

A multiplicity of methods for analyzing cell proliferation are established and are commercially supplied by various companies (e.g. Roche Diagnostics, Invitrogen; details of the assay methods are described in the numerous application protocols). The number of cells in cell culture experiments can be determined by simple counting or by colorimetric assays which measure the metabolic activity of the cells (e.g.

wst-1, Roche Diagnostics). Metabolic assay methods measure the number of cells in an experiment indirectly via enzymic markers. Cell proliferation may be measured directly by analyzing the rate of DNA synthesis, for example by adding bromodeoxyuridine (BrdU), with the integrated BrdU being detected colorimetrically via specific antibodies.

2. Apoptosis and Cytotoxicity

A large number of assay systems for detecting cellular apoptosis and cytotoxicity are available. A decisive characteristic is the specific, enzyme-dependent fragmentation of genomic DNA, which is irreversible and in any case results in death of the cell. Methods for detecting these specific DNA fragments are commercially obtainable. An additional method available is the TUNEL assay which can detect DNA single-strand breaks also in tissue sections. Cytotoxicity is mainly detected via an altered cell permeability which serves as marker of the vitality state of cells. This involves on the one hand the analysis of markers which can typically be found intracellularly in the cell culture supernatant. On the other hand, it is also possible to analyze the absorbability of dye markers which are not absorbed by intact cells. The best-known examples of dye markers are Trypan blue and propidium iodide, a common intracellular marker is lactate dehydrogenase which can be detected enzymatically in the supernatant. Different assay systems of various commercial suppliers (e.g. Roche Diagnostics, Invitrogen) are available.

3. Migration Assay

The ability of cells to migrate is analyzed in a specific migration assay, preferably with the aid of a Boyden chamber (Corning Costar) (Cinamon G., Alon R. J. Immunol. Methods. 2003 February; 273(1-2):53-62; Stockton et al. 2001. Mol. Biol. Cell. 12: 1937-56). For this purpose, cells are cultured on a filter with a specific pore size. Cells which can migrate are capable of migrating through this filter into another culture vessel below. Subsequent microscopic analysis then permits determination of a possibly altered migration behavior induced by the gain of function or loss of function of the target molecule.

b. Functional Analysis in Animal Models

A possible alternative of cell culture experiments for the analysis of target gene function are complicated in vivo experiments in animal models. Compared to the cell-based methods, these models have the advantage of being able to detect faulty developments or diseases which are detectable only in the context of the whole organism. A multiplicity of models for human disorders are available by now (Abate-Shen & Shen. 2002. Trends in Genetics S1-5; Matsusue et al. 2003. J. Clin. Invest. 111:737-47). Various animal models such as, for example, yeast, nematodes or zebra fish have since been characterized intensively. However, models which are preferred over other species are mammalian animal models such as, for example, mice (Mus musculus) because they offer the best possibility of reproducing the biological processes in a human context. For mice, on the one hand transgenic methods which integrate new genes into the mouse genome have been established in recent years (gain of function; Jegstrup I. et al. 2003. Lab Anim. 2003 January; 37(1):1-9). On the other hand, other methodical approaches switch off genes in the mouse genome and thus induce a loss of function of a desired gene (knockout models, loss of function; Zambrowicz B P & Sands A T. 2003. Nat. Rev. Drug Discov. 2003 January; 2(1):38-51; Niwa H. 2001. Cell Struct. Funct. 2001 June; 26(3):137-48); technical details have been published in large numbers.

After the mouse models have been generated, alterations induced by the transgene or by the loss of function of a gene can be analyzed in the context of the whole organism (Balling R, 2001. Ann. Rev. Genomics Hum. Genet. 2:463-92). Thus it is possible to carry out, for example, behavior tests as well as to biochemically study established blood parameters. Histological analyses, immunohistochemistry or electron microscopy enable alterations to be characterized at the cellular level. The specific expression pattern of a gene can be detected by in-situ hybridization (Peters T. et al. 2003. Hum. Mol. Genet 12:2109-20).

Example 3: Detailed Analysis of the Identified Tumor-Associated Markers

RNA-Isolation, RT-PCR and Real-Time RT-PCR

RNA extraction, first-strand cDNA synthesis, RT-PCR and real-time RT-PCR was performed as previously described (Koslowski, M. et al., Cancer Res. 62, 6750-6755 (2002), Koslowski, M. et al., Cancer Res. 64, 5988-5993 (2004)). Real-time quantitative expression analysis was performed in a 40 cycle RT-PCR. After normalization to HPRT (sense 5'-TGA CAC TGG CAA AAC AAT GCA-3' (SEQ ID NO: 628); antisense 5'-GGT CCT TTT CAC CAG CAA GCT-3' (SEQ ID NO: 629), 62° C. annealing) gene-specific transcripts in tumor samples were quantified relative to normal tissues using ΔΔCT calculation.

siRNA Duplexes

The SEQ ID NO:540 siRNA duplexes (Qiagen, Hilden, Germany) were directed against target sequences 5'-NNC CAC AGA AGG UAC CAG UUA-3' (SEQ ID NO: 634) (siRNA#1; sense (5'-CCA CAG AAG GUA CCA GUU AUU-3' (SEQ ID NO: 630)), antisense (5'-UAA CUG GUA CCU UCU GUG GUU-3' (SEQ ID NO: 631)) and 5'-NNC AGC AAG ACU CCC UCU AAA-3' (SEQ ID NO: 635) (siRNA#2; sense (5'-CAG CAA GAC UCC CUC UAA AUU-3' (SEQ ID NO: 632)), antisense (5'-UUU AGA GGG AGU CUU GCU GUU-3' (SEQ ID NO: 633)) of the SEQ ID NO:540 mRNA sequence.

Cell Proliferation Analysis 24 h after transfection with siRNA duplexes 1×10$^4$ cells were cultured for 48 h in medium supplemented with 10% FCS. Proliferation was analyzed by measuring the incorporation of BrdU into newly synthesized DNA strands using the DELFIA cell proliferation Kit (Perkin Elmer, Boston, Mass.) according to the manufacturer's instructions on a Wallac Victor$^2$ multi-label counter (Perkin Elmer, Boston, Mass.).

Figure 3:
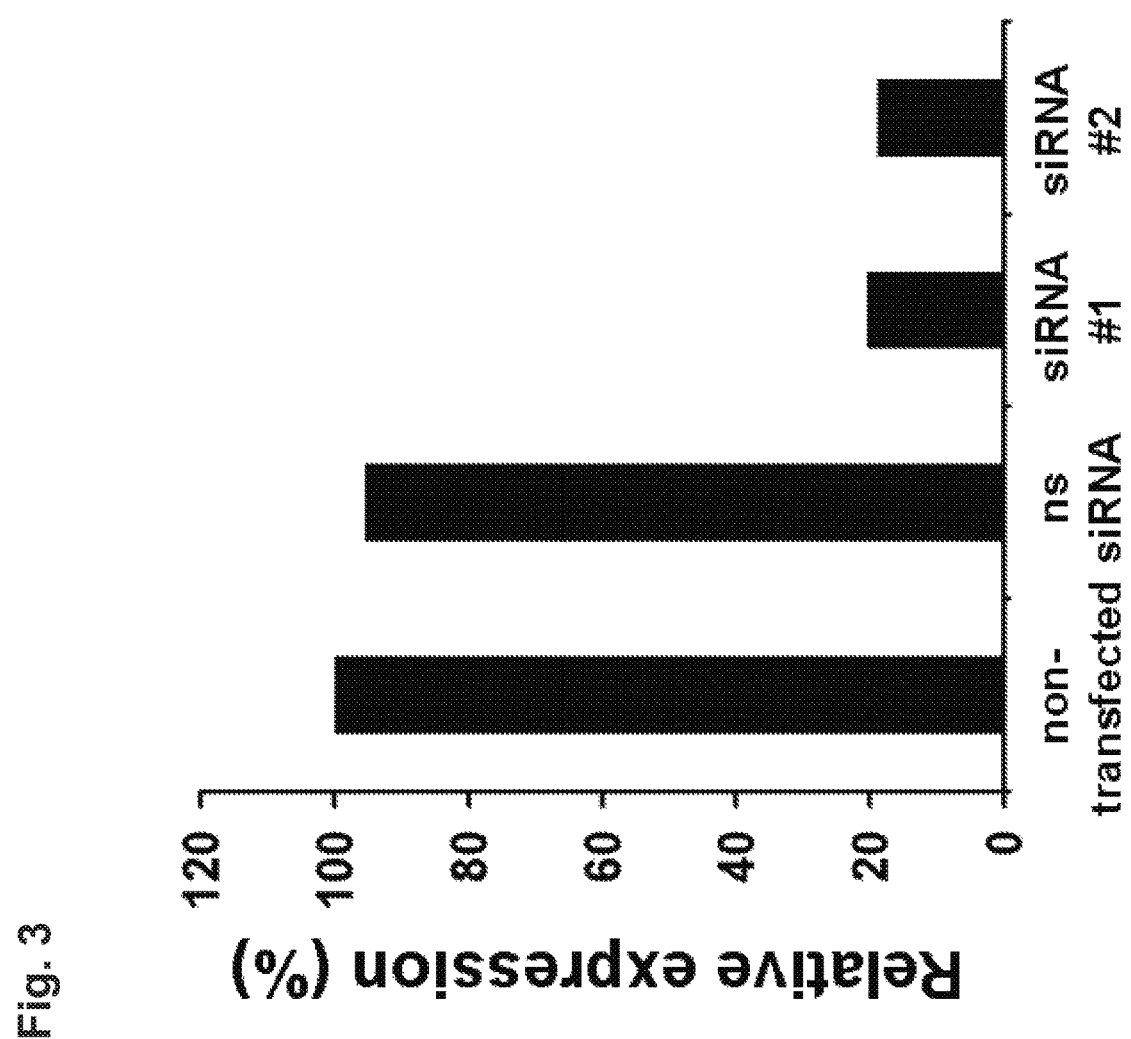
FIG. 3. Quantitative expression of SEQ ID NO:540 mRNA in MCF-7 breast cancer cells. Real-time RT-PCR 24 h after transfection with siRNA oligos showed that both SEQ ID NO:540-specific siRNAs (siRNA#1 (SEQ ID NO:630, 631), siRNA#2 (SEQ ID NO:632, 633)) induce robust silencing of SEQ ID NO:540 expression.

FIG. 3 shows the quantification of SEQ ID NO:540 mRNA expression in MCF-7 breast cancer cells by real-time RT-PCR 24 h after transfection with siRNA oligos. Compared to non-transfected cells and cells transfected with non-silencing (ns) siRNA both SEQ ID NO:540-specific siRNAs (siRNA#1 (SEQ ID NO:630, 631), siRNA#2 (SEQ ID NO:632, 633)) induce robust silencing of SEQ ID NO:540 expression.

Figure 4:
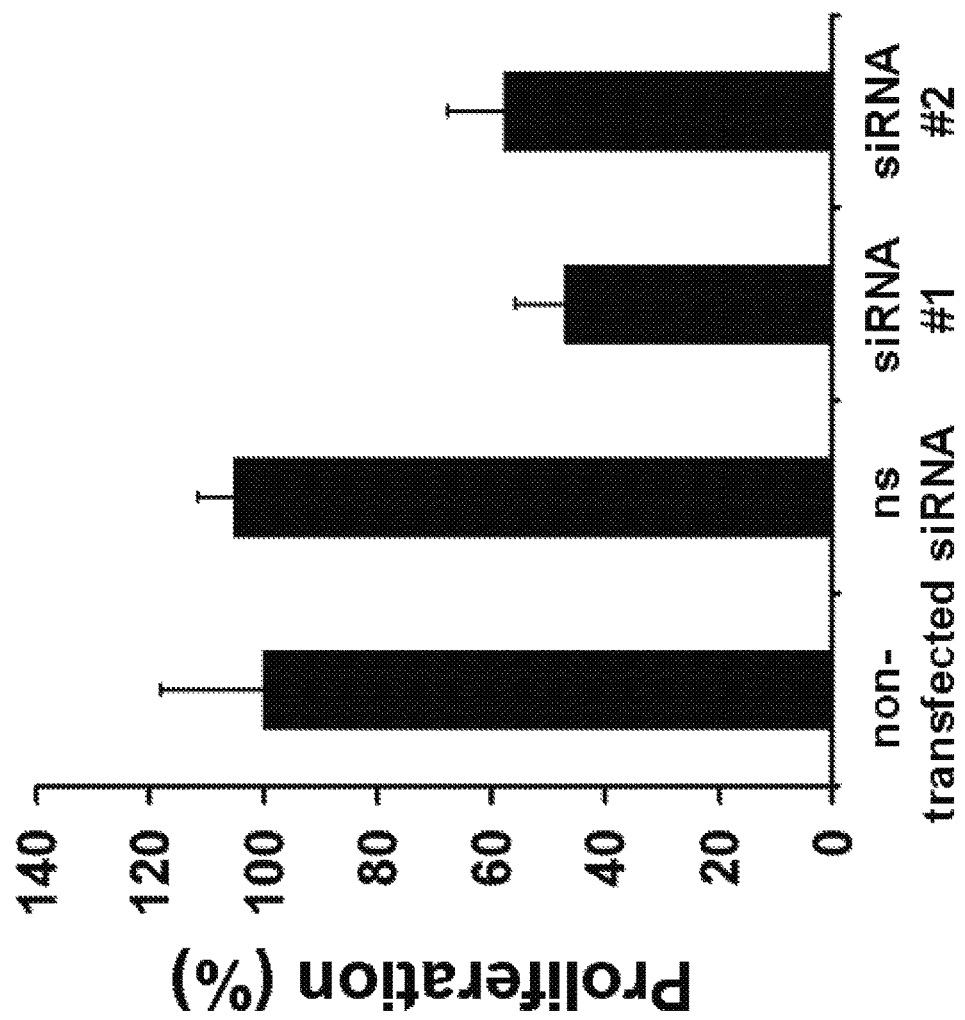
FIG. 4. Silencing of SEQ ID NO:540 expression by transfection with siRNA oligos results in impaired proliferation of MCF-7 breast cancer cells. Proliferation was quantified 96 h after transfection with siRNAs by measuring incorporation of BrdU in newly synthesized DNA strands. These results show that SEQ ID NO:540 is a positive factor for the proliferation of breast cancer cells.

FIG. 4 shows that silencing of SEQ ID NO:540 expression by transfection with siRNA oligos results in impaired proliferation of MCF-7 breast cancer cells. Proliferation was quantified 96 h after transfection with siRNAs by measuring incorporation of BrdU in newly synthesized DNA strands. These results show that SEQ ID NO:540 is a positive factor for the proliferation of breast cancer cells.

Figure 5:
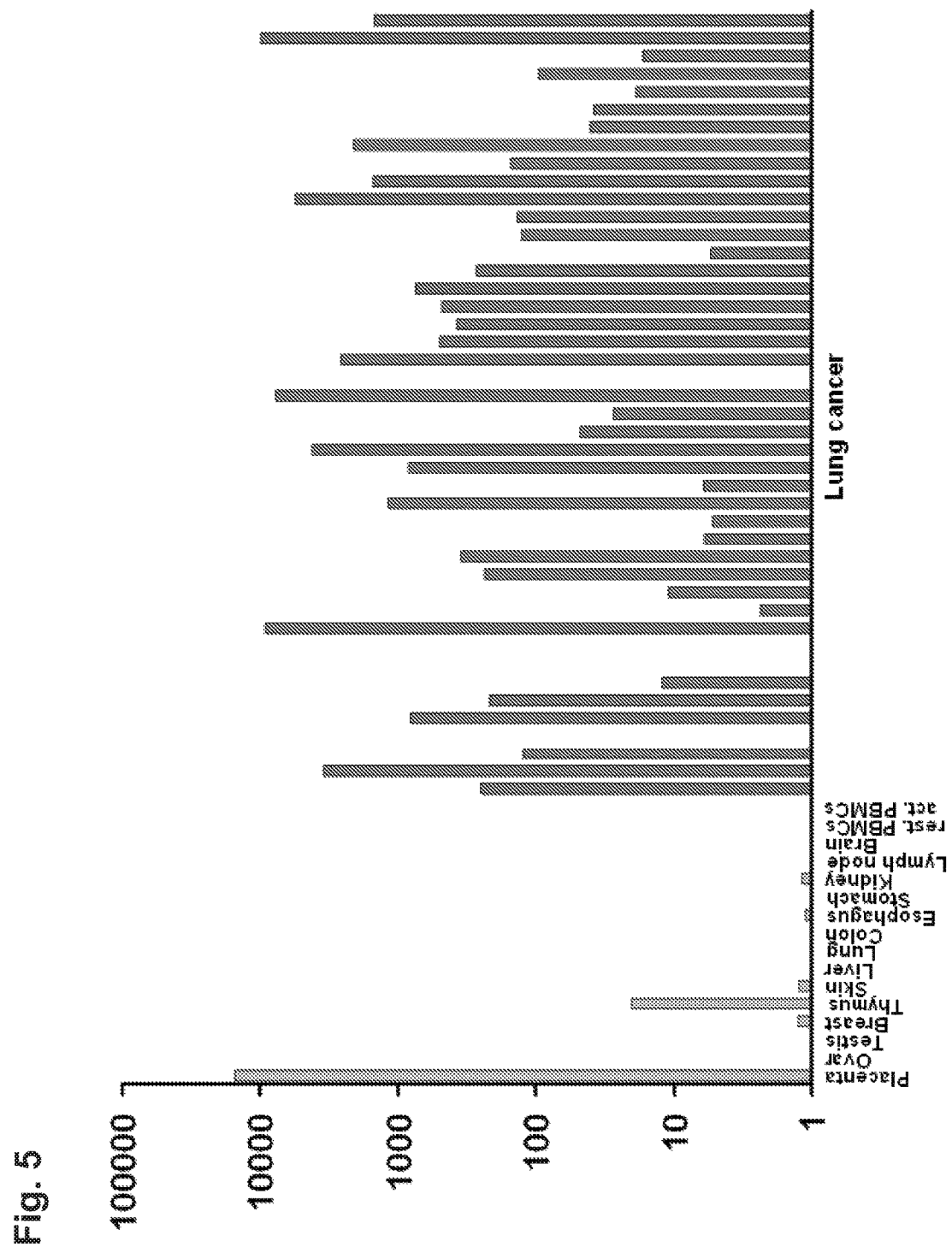
FIG. 5. Quantitative expression of SEQ ID NO:541 in normal tissues and cancer tissue. Real-time RT-PCR showed overexpression of the nucleic acid sequence according to SEQ ID NO:541 in lung cancer.

The nucleotide sequence according to SEQ ID NO:541 was deduced from SEQ ID NO:65 and codes for a 177 aa protein (SEQ ID NO:542) of unknown function. Expression of SEQ ID NO:541 in normal and cancerous tissues was quantified by real-time RT-PCR using sequence-specific oligos (SEQ ID NO:543, 544); see FIG. 5. In normal tissues SEQ ID NO:541 is highly expressed in placenta and shows only weak expression in thymus. SEQ ID NO:541 is overexpressed in lung cancer. Based on these expression results, SEQ ID NO:541 and its expression products qualify as molecular markers and/or target candidates for targeted therapies, in particular for this particular tumor type.

Figure 6:
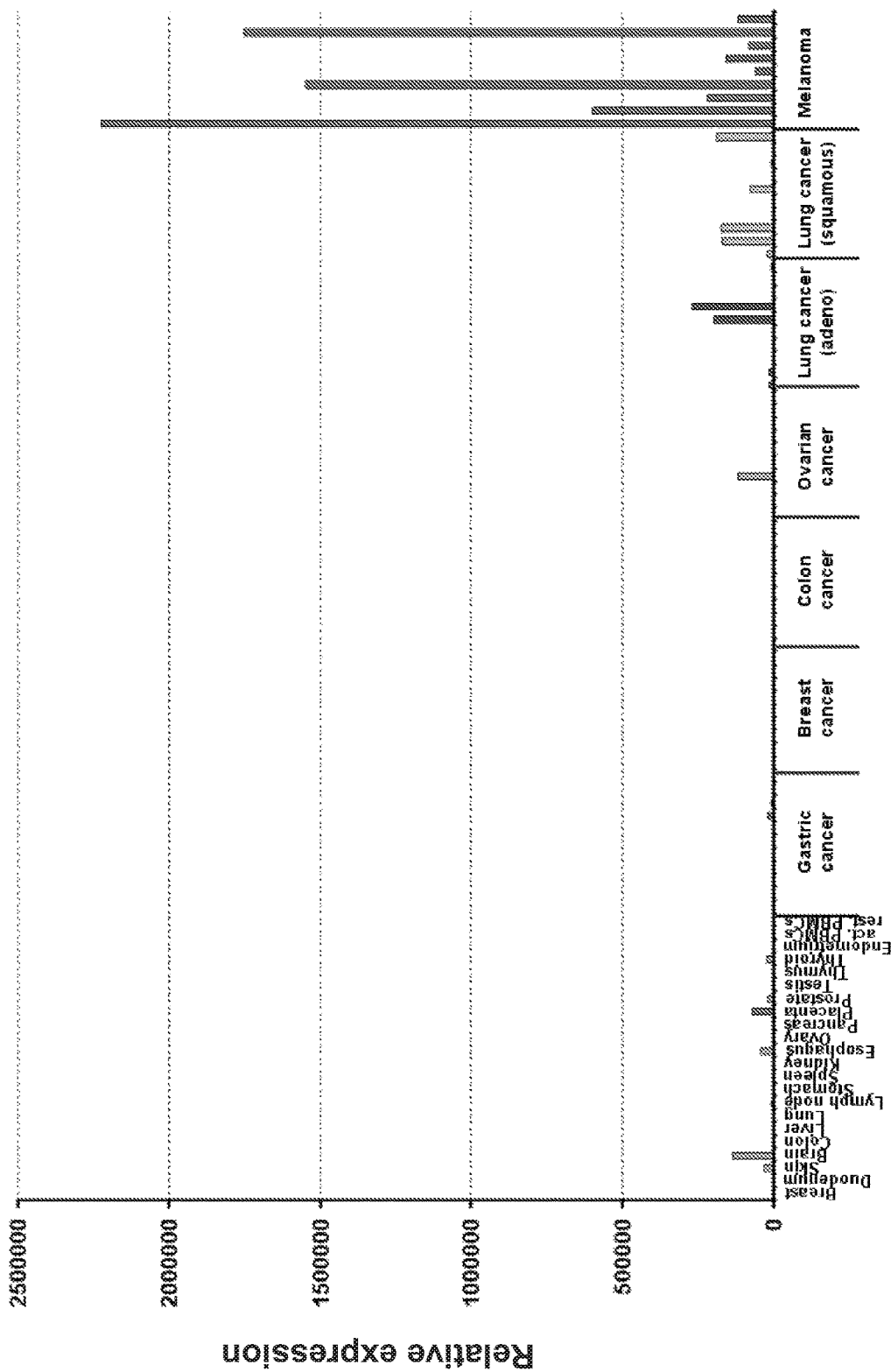
FIG. 6. Quantitative expression of SEQ ID NO:545 in normal tissues and cancer tissues. Real-time RT-PCR showed overexpression of the nucleic acid sequence according to SEQ ID NO:545 in malignant melanomas.

The nucleotide sequence according to SEQ ID NO:545 was deduced from SEQ ID NO:249 and codes for a member of the solute carrier (SLC) group of membrane proteins (SEQ ID NO:546). As is typical of integral membrane proteins, SLCs contain a number of hydrophobic transmembrane alpha helices connected to each other by hydrophilic intra- or extra-cellular loops. Depending on the SLC, these transporters are functional as either monomers or obligate homo- or hetero-oligomers. The protein encoded by SEQ ID NO:545 is a cell surface protein. Expression of SEQ ID NO:545 in normal and cancerous tissues was quantified by real-time RT-PCR using sequence-specific oligos (SEQ ID NO:547, 548); see FIG. 6. Compared to normal tissues, SEQ ID NO:545 is overexpressed in malignant melanomas. Based on these expression results, SEQ ID NO:545 and its expression products qualify as molecular markers and/or target candidates for targeted therapies, in particular for this particular tumor type.

Figure 7:
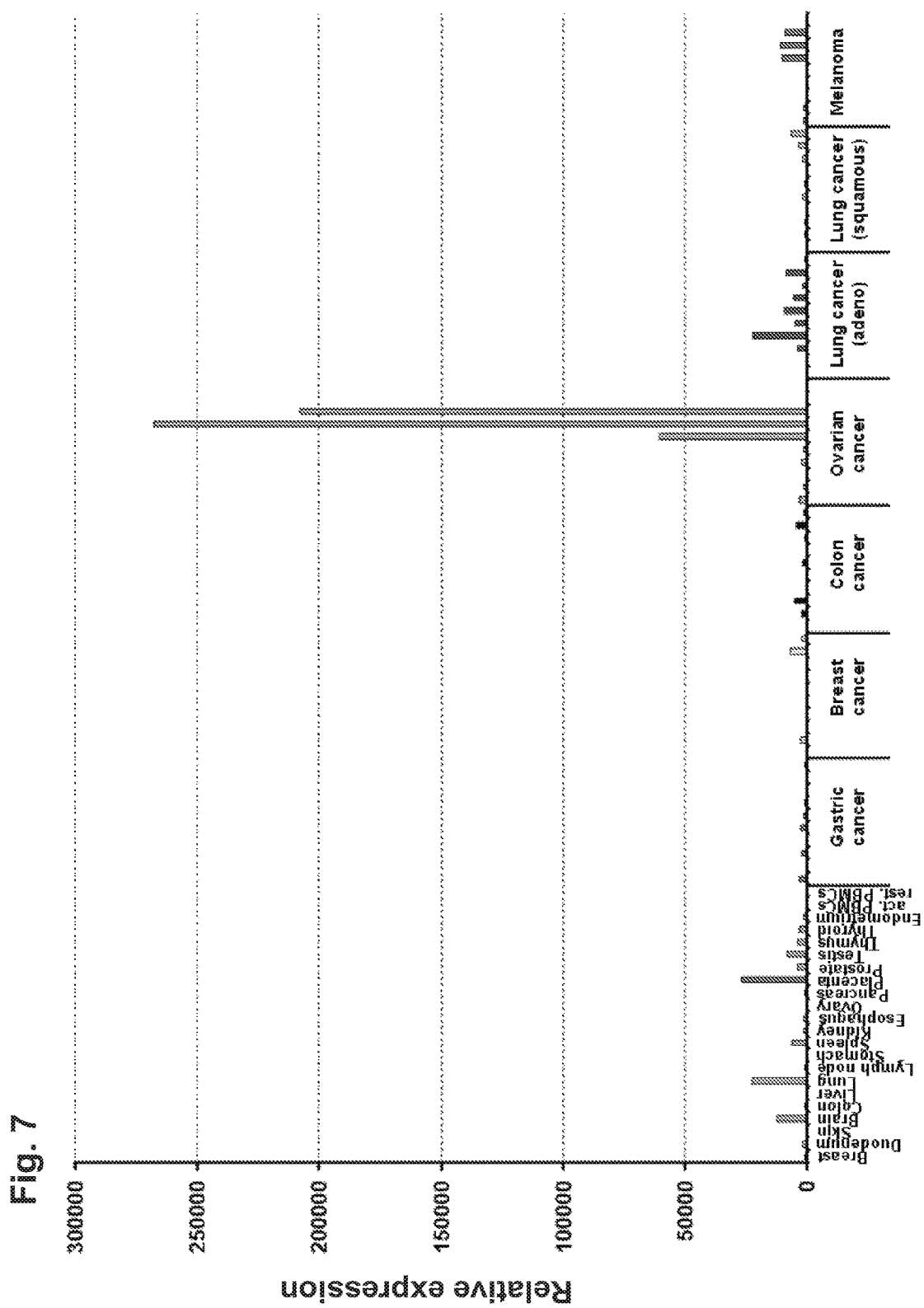
FIG. 7. Quantitative expression of SEQ ID NO:549 in normal tissues and cancer tissues. Real-time RT-PCR showed overexpression of the nucleic acid sequence according to SEQ ID NO:549 in ovarian cancer.

The nucleotide sequence according to SEQ ID NO:549 was deduced from SEQ ID NO:4 and codes for a 763 aa protein (SEQ ID NO:550) of unknown function. The protein harbors two potential transmembrane domains and a typical fibronectin type III domain. Fibronectin is a high-molecular-weight extracellular matrix glycoprotein that binds to membrane spanning receptor proteins (integrins). In addition to integrins, they also bind extracellular matrix components such as collagen, fibrin and heparan sulfate. The protein encoded by SEQ ID NO:549 might represent a hitherto unknown new fibronection-like protein. Expression of SEQ ID NO:549 in normal and cancerous tissues was quantified by real-time RT-PCR using sequence-specific oligos (SEQ ID NO:551, 552); see FIG. 7. Compared to normal tissues, SEQ ID NO:549 is overexpressed in ovarian cancer. Based on these expression results, SEQ ID NO:549 and its expression products qualify as molecular markers and/or target candidates for targeted therapies, in particular of this particular tumor type.

Figure 8:
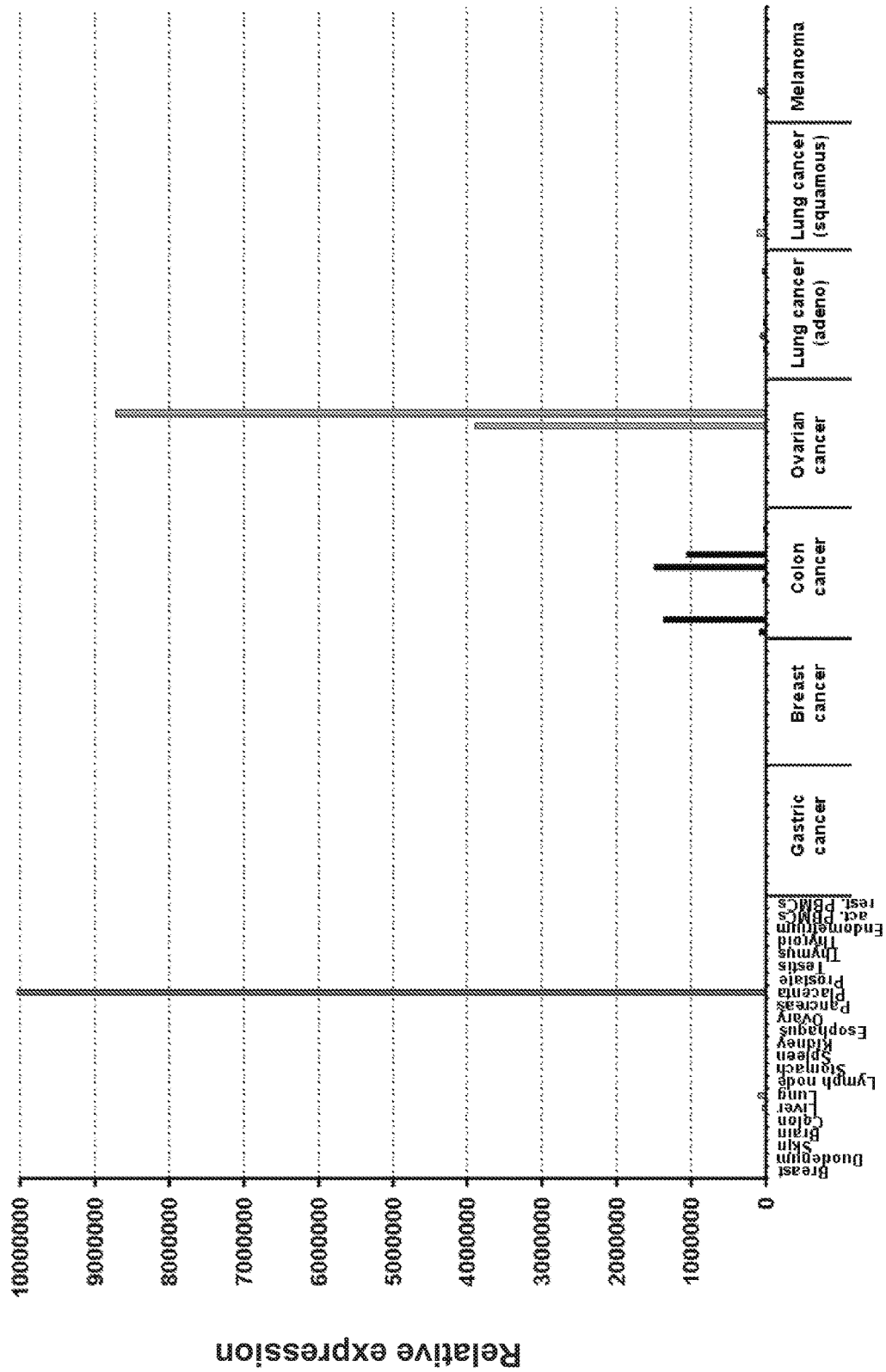
FIG. 8. Quantitative expression of SEQ ID NO:553 in normal tissues and cancer tissues. Real-time RT-PCR showed overexpression of the nucleic acid sequence according to SEQ ID NO:553 in colon cancer and ovarian cancer.

The nucleotide sequence according to SEQ ID NO:553 was deduced from SEQ ID NO:156 and codes for a 496 aa protein (SEQ ID NO:554) of unknown function. The protein harbors a potential transmembrane protein. Expression of SEQ ID NO:553 in normal and cancerous tissues was quantified by real-time RT-PCR using sequence-specific oligos (SEQ ID NO:555, 556); see FIG. 8. In normal tissues SEQ ID NO:553 is highly expressed in placenta. Compared to other normal tissues, SEQ ID NO:553 is overexpressed in colon cancer and ovarian cancer. Based on these expression results, SEQ ID NO:553 and its expression products qualify as molecular markers and/or target candidates for targeted therapies, in particular for these particular tumor types.

Figure 9:
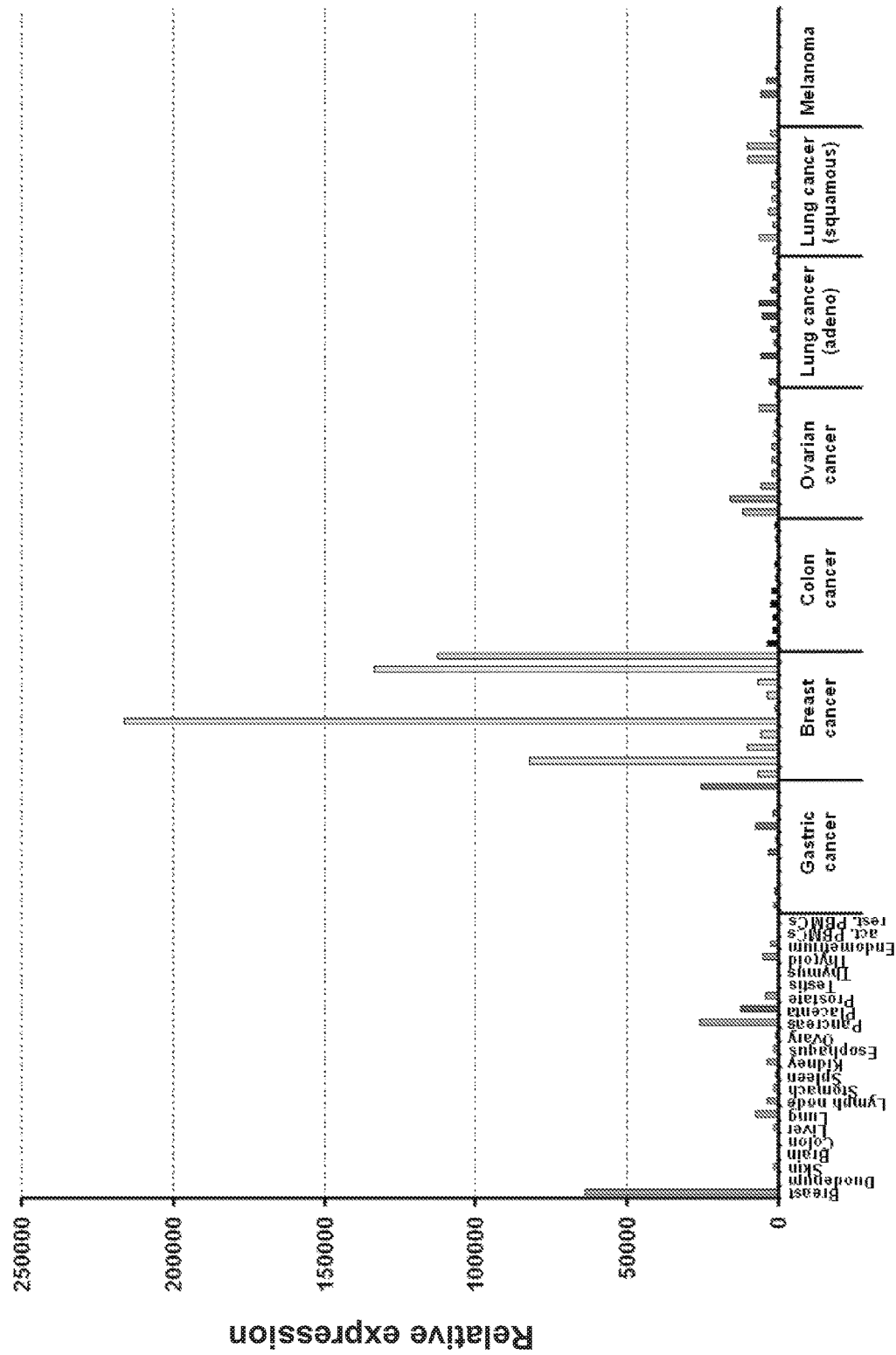
FIG. 9. Quantitative expression of SEQ ID NO:557 in normal tissues and cancer tissues. Real-time RT-PCR showed overexpression of the nucleic acid sequence according to SEQ ID NO:557 in breast cancer.

The nucleotide sequence according to SEQ ID NO:557 was deduced from SEQ ID NO:273. SEQ ID NO:557 represents a partial cDNA with no apparent open reading frame. Expression of SEQ ID NO:557 in normal and cancerous tissues was quantified by real-time RT-PCR using sequence-specific oligos (SEQ ID NO:558, 559); see FIG. 9. In normal tissues high expression of SEQ ID NO:557 is detectable in breast. Compared to normal tissues, SEQ ID NO:557 is overexpressed in breast cancer. Based on these expression results, SEQ ID NO:557 and its expression products qualify as molecular markers and/or target candidates for targeted therapies, in particular for this particular tumor type.

Figure 10:
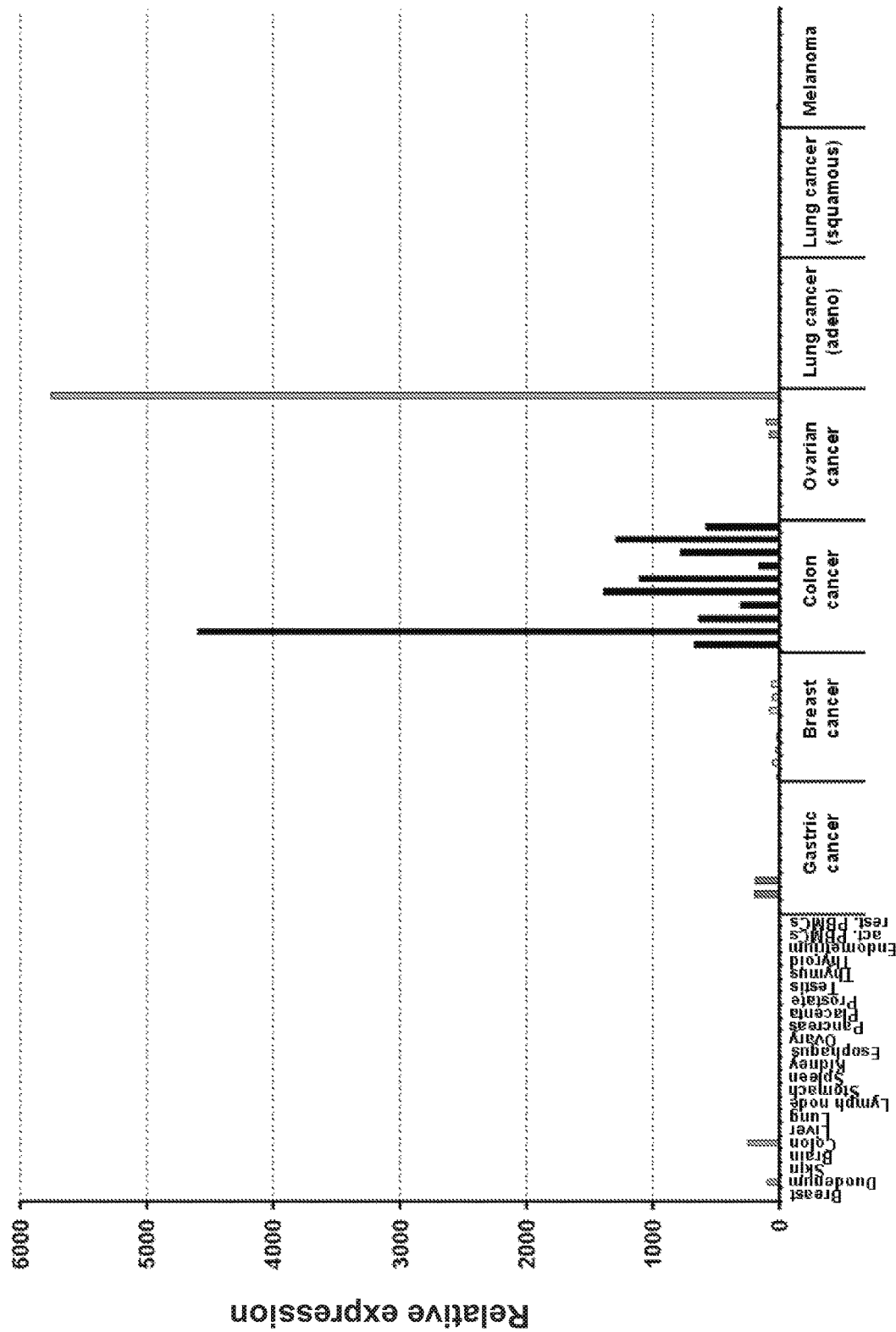
FIG. 10. Quantitative expression of SEQ ID NO:560 in normal tissues and cancer tissues. Real-time RT-PCR showed overexpression of the nucleic acid sequence according to SEQ ID NO:560 in colon cancer and ovarian cancer.

The nucleotide sequence according to SEQ ID NO:560 was deduced from SEQ ID NO:135. SEQ ID NO:560 has no apparent open reading frame. Expression of SEQ ID NO:560 in normal and cancerous tissues was quantified by real-time RT-PCR using sequence-specific oligos (SEQ ID NO:561, 562); see FIG. 10. In normal tissues expression of SEQ ID NO:560 is detectable in duodenum and colon. Compared to normal tissues, SEQ ID NO:560 is overexpressed in colon cancer and ovarian cancer. Based on these expression results, SEQ ID NO:560 and its expression products qualify as molecular markers and/or target candidates for targeted therapies, in particular for these particular tumor types.

Figure 11:
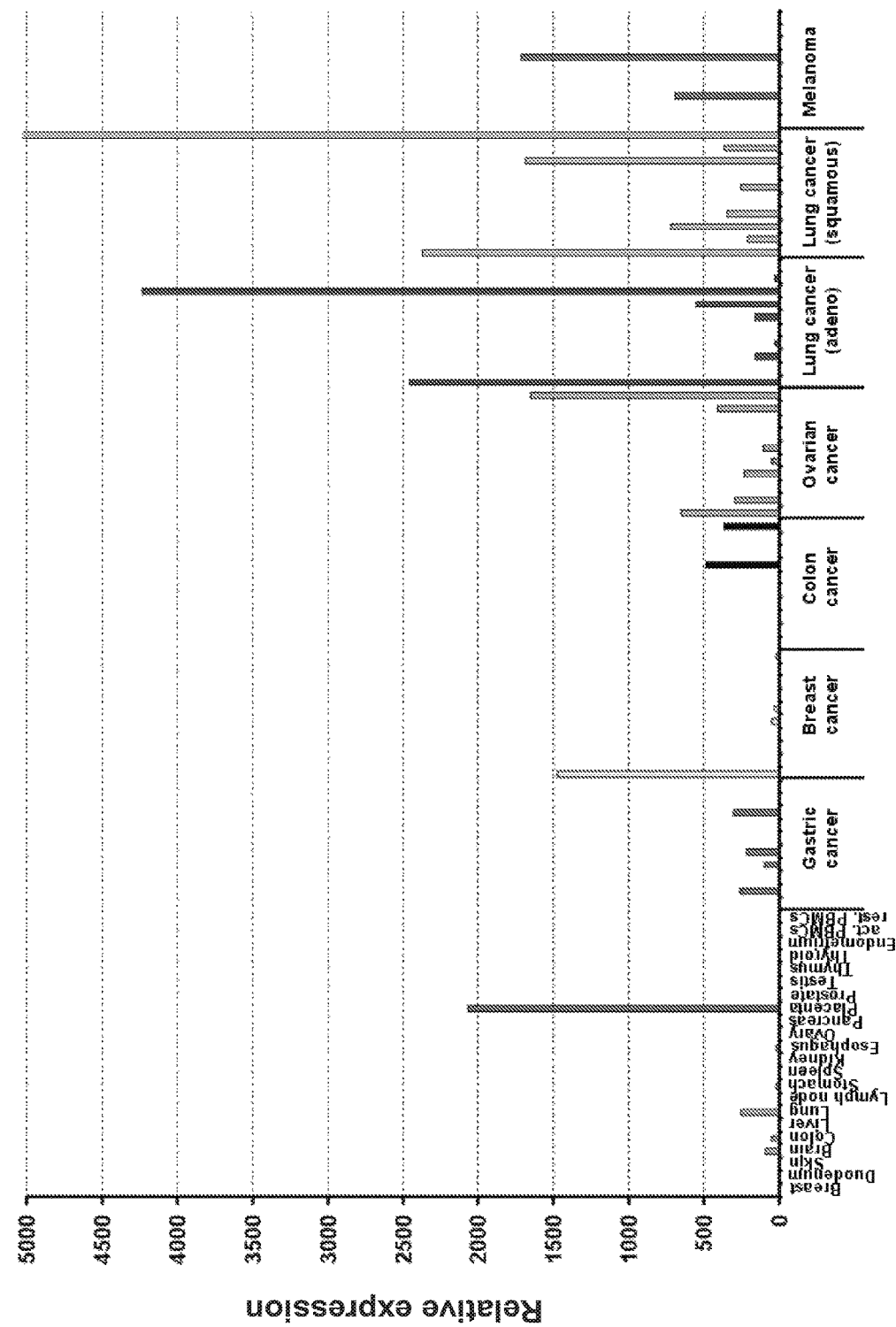
FIG. 11. Quantitative expression of SEQ ID NO:563 in normal tissues and cancer tissues. Real-time RT-PCR showed overexpression of the nucleic acid sequence according to SEQ ID NO:563 in breast cancer, colon cancer, ovarian cancer, lung cancer and melanoma.

The nucleotide sequence according to SEQ ID NO:563 was deduced from SEQ ID NO:177. SEQ ID NO:563 has no apparent open reading frame. Expression of SEQ ID NO:563 in normal and cancerous tissues was quantified by real-time RT-PCR using sequence-specific oligos (SEQ ID NO:564, 565); see FIG. 11. SEQ ID NO:563 is highly expressed in placenta. Compared to normal tissues, SEQ ID NO:563 is overexpressed in breast cancer, colon cancer, ovarian cancer, lung cancer and melanoma. Based on these expression results, SEQ ID NO:563 and its expression products qualify as molecular markers and/or target candidates for targeted therapies, in particular for these particular tumor types.

Figure 12:
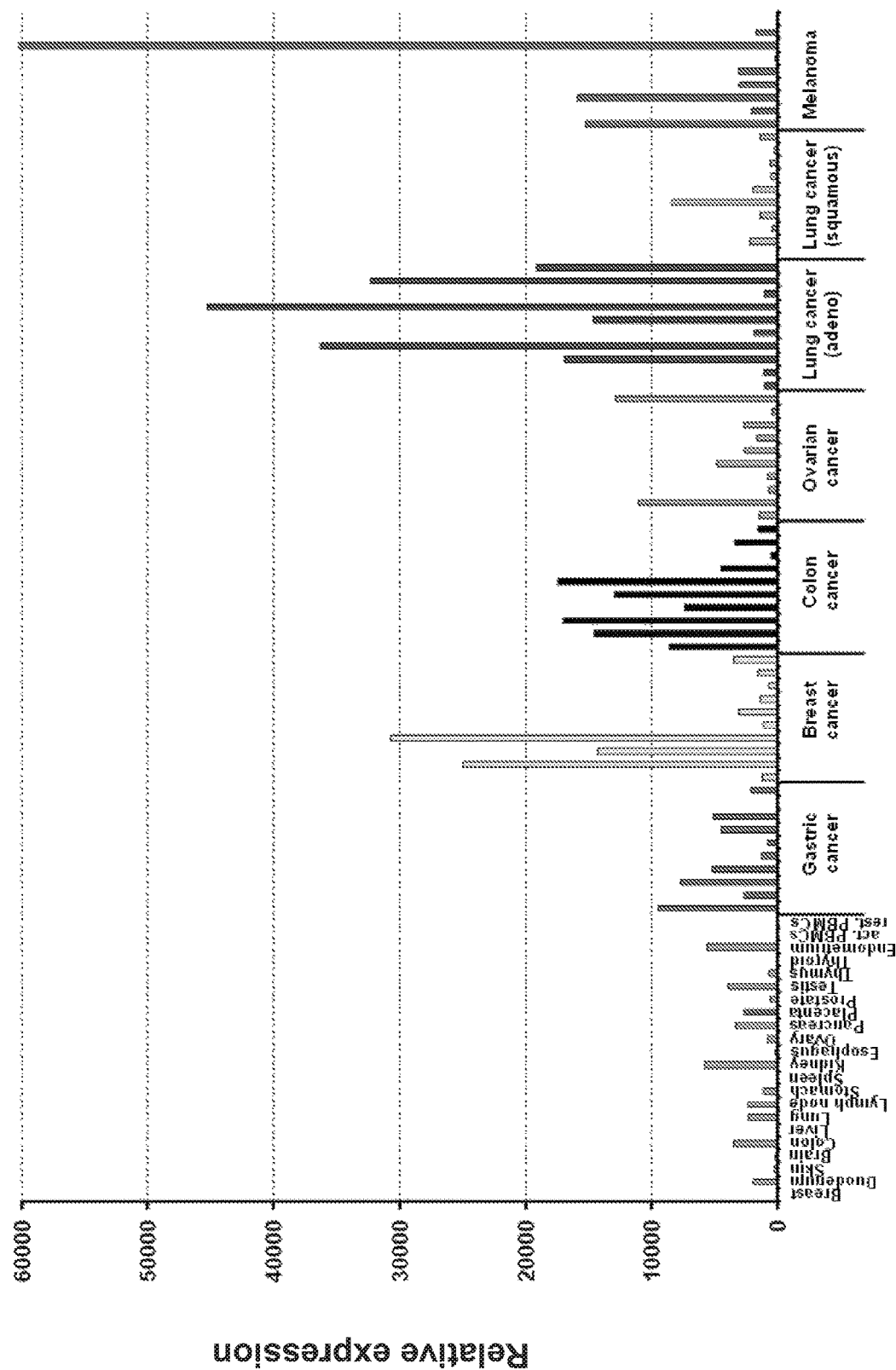
FIG. 12. Quantitative expression of SEQ ID NO:566 in normal tissues and cancer tissues. Real-time RT-PCR showed overexpression of the nucleic acid sequence according to SEQ ID NO:566 in gastric cancer, breast cancer, colon cancer, ovarian cancer, lung cancer and melanoma.

The nucleotide sequence according to SEQ ID NO:566 was deduced from SEQ ID NO:149 and codes for a 155 aa protein (SEQ ID NO:567) of unknown function. The protein sequence is partially homologous to members of the tumor necrosis factor receptor superfamily and harbors a potential transmembrane domain. The protein encoded by SEQ ID NO:566 might represent a new member of the tumor necrosis factor receptor superfamily. Expression of SEQ ID NO:566 in normal and cancerous tissues was quantified by real-time RT-PCR using sequence-specific oligos (SEQ ID NO:568, 569); see FIG. 12. Compared to normal tissues, SEQ ID NO:566 is overexpressed in gastric cancer, breast cancer, colon cancer, ovarian cancer, lung cancer and melanoma. Based on these expression results, SEQ ID NO:566 and its expression products qualify as molecular markers and/or target candidates for targeted therapies, in particular for these particular tumor types.

Figure 13:
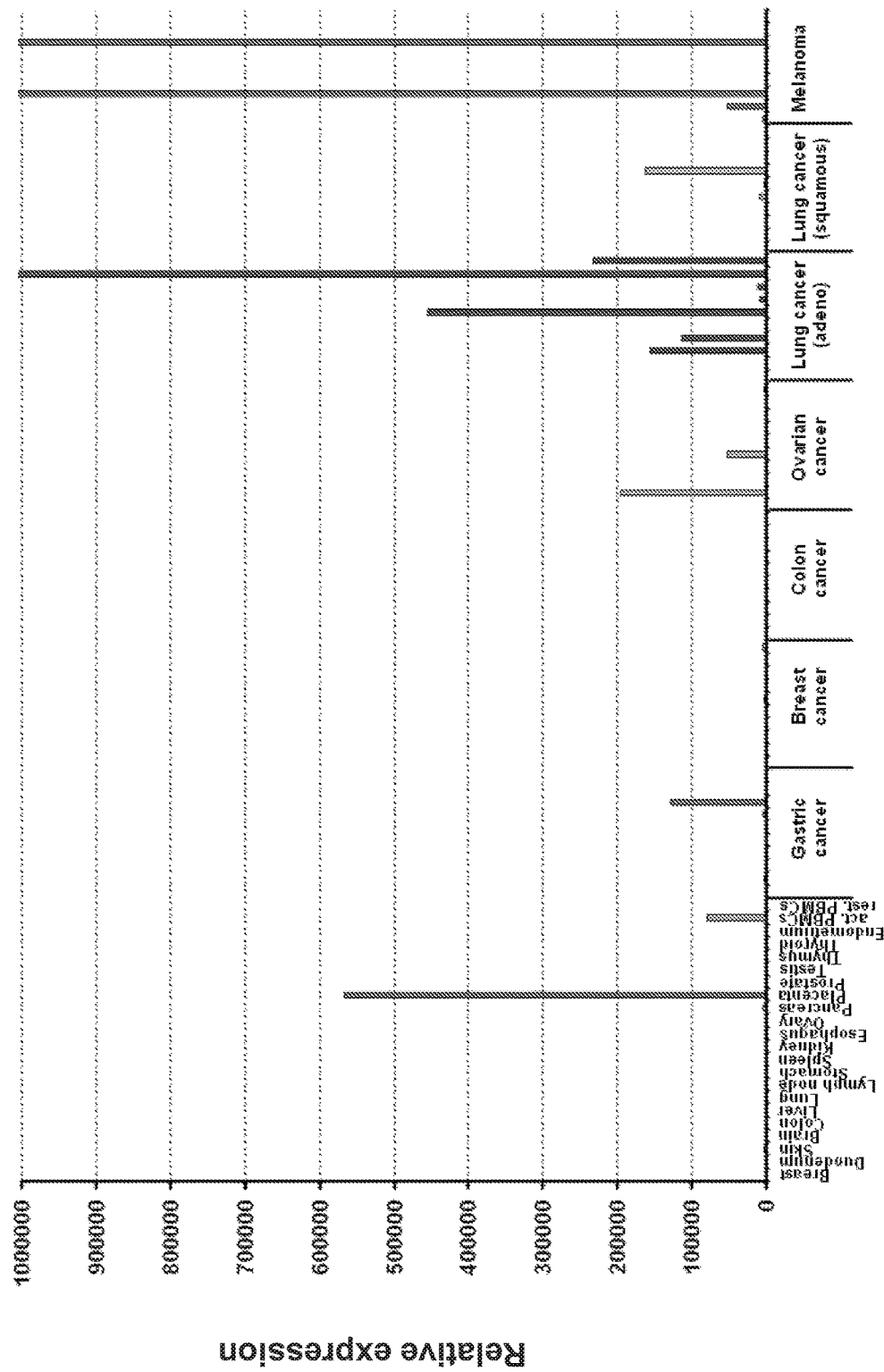
FIG. 13. Quantitative expression of SEQ ID NO:570 in normal tissues and cancer tissues. Real-time RT-PCR showed overexpression of the nucleic acid sequence according to SEQ ID NO:570 in ovarian cancer, lung cancer and melanoma.

The nucleotide sequence according to SEQ ID NO:570 was deduced from SEQ ID NO:53 and codes for a member of the kernel lipocain superfamily (SEQ ID NO:571). These secreted glycoproteins have distinct and essential roles in regulating an uterine environment suitable for pregnancy and in the timing and occurrence of the appropriate sequence of events in the fertilization process. Expression of SEQ ID NO:570 in normal and cancerous tissues was quantified by real-time RT-PCR using sequence-specific oligos (SEQ ID NO:572, 573); see FIG. 13. SEQ ID NO:570 is highly expressed in placenta. Compared to other normal tissues, SEQ ID NO:570 is overexpressed in ovarian cancer, lung cancer and melanoma. Based on these expression results, SEQ ID NO:570 and its expression products qualify as molecular markers and/or target candidates for targeted therapies, in particular for these particular tumor types.

Figure 14:
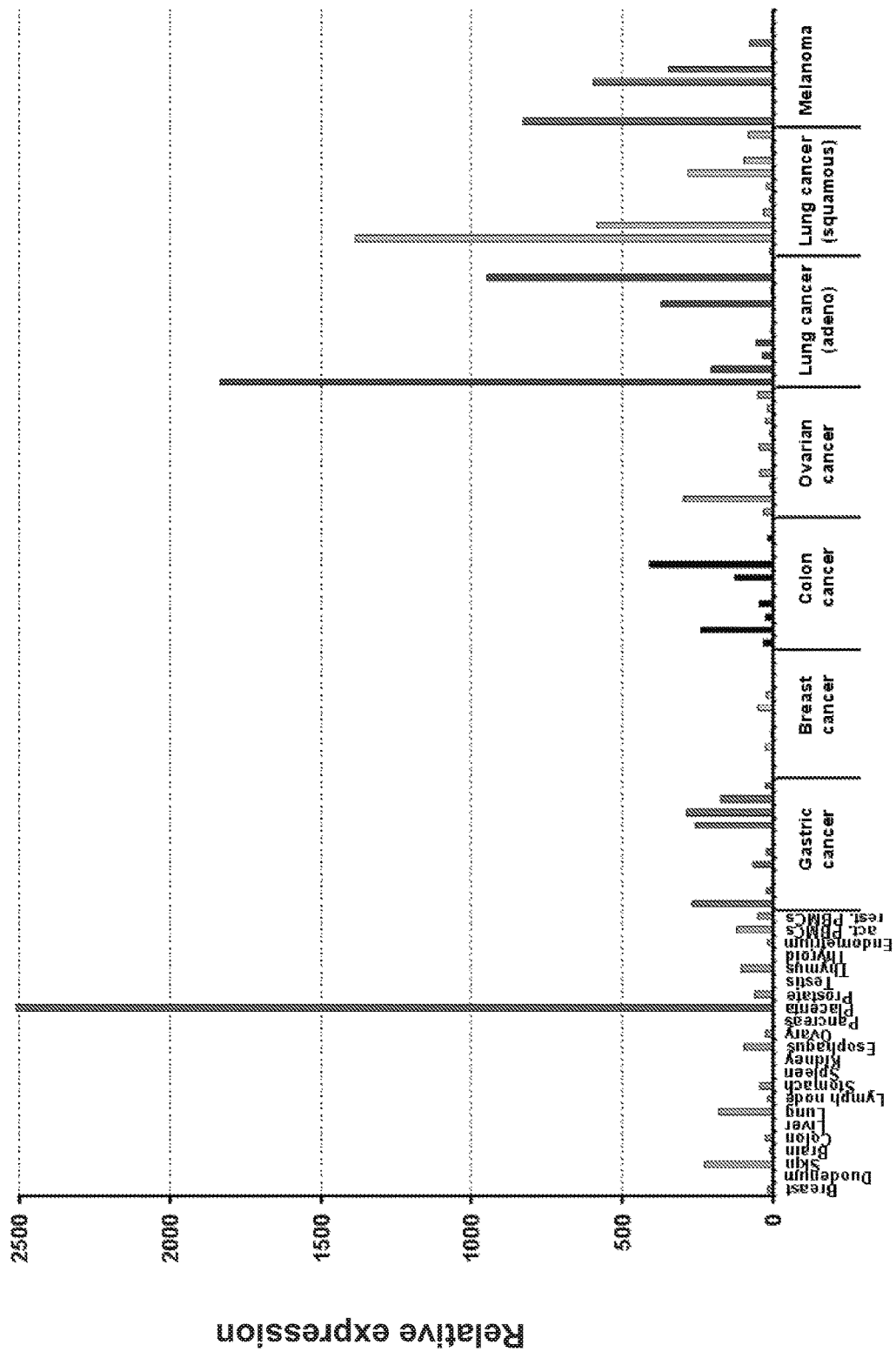
FIG. 14. Quantitative expression of SEQ ID NO:574 in normal tissues and cancer tissues. Real-time RT-PCR showed overexpression of the nucleic acid sequence according to SEQ ID NO:574 in lung cancer and melanoma.

The nucleotide sequence according to SEQ ID NO:574 has no apparent open reading frame. Expression of SEQ ID NO:574 in normal and cancerous tissues was quantified by real-time RT-PCR using sequence-specific oligos (SEQ ID NO:575, 576); see FIG. 14. SEQ ID NO:574 is highly expressed in placenta. Compared to other normal tissues, SEQ ID NO:574 is overexpressed in lung cancer and melanoma. Based on these expression results, SEQ ID NO:574 and its expression products qualify as molecular markers and/or target candidates for targeted therapies, in particular for these particular tumor types.

Figure 15:
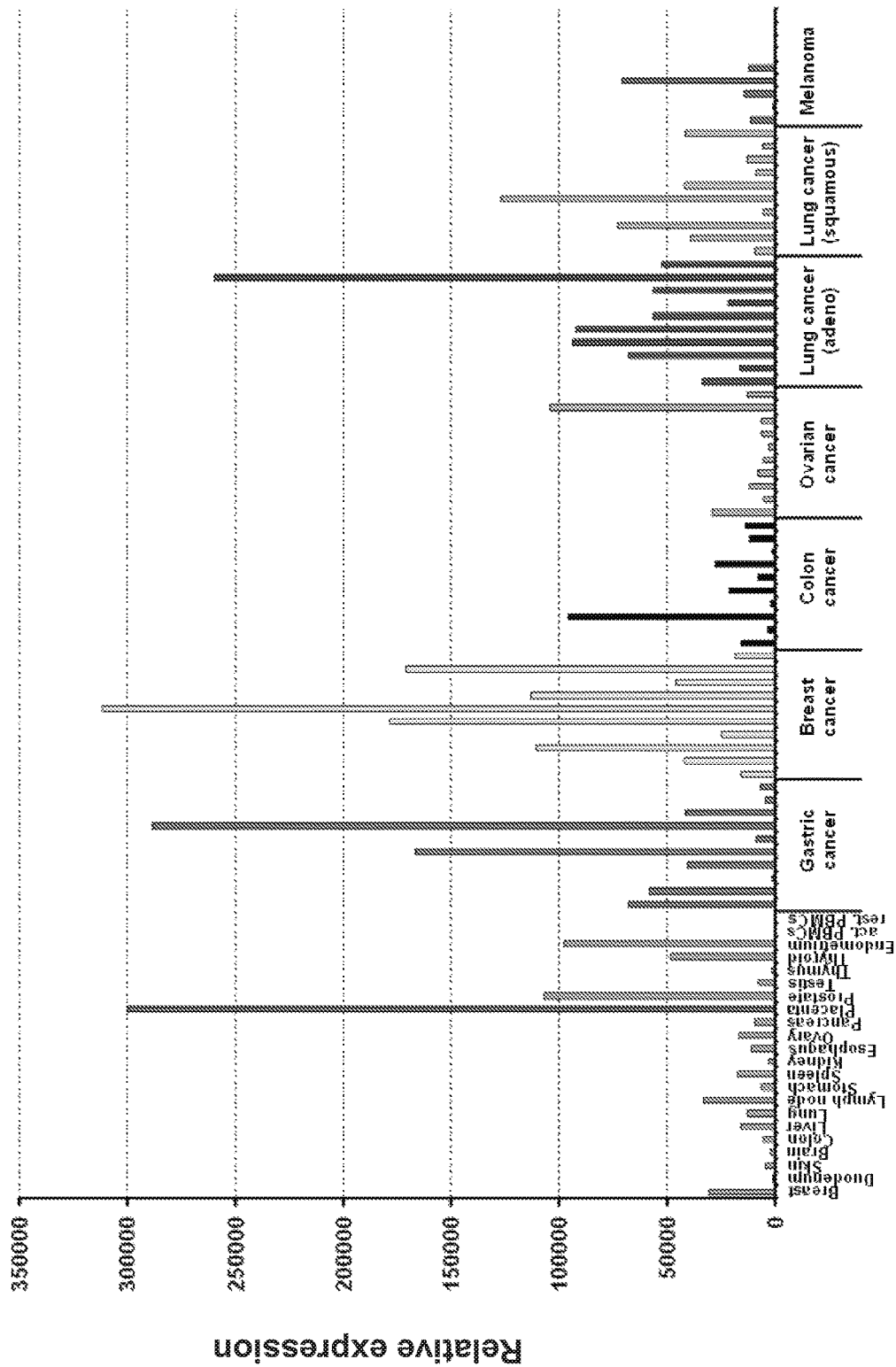
FIG. 15. Quantitative expression of SEQ ID NO:577 in normal tissues and cancer tissues. Real-time RT-PCR showed overexpression of the nucleic acid sequence according to SEQ ID NO:577 in gastric cancer, breast cancer and lung cancer.

The nucleotide sequence according to SEQ ID NO:577 was deduced from SEQ ID NO:20. SEQ ID NO:577 represents a partial cDNA with no apparent open reading frame. Expression of SEQ ID NO:577 in normal and cancerous tissues was quantified by real-time RT-PCR using sequence-specific oligos (SEQ ID NO:578, 579); see FIG. 15. SEQ ID NO:577 is highly expressed in placenta. Compared to other normal tissues, SEQ ID NO:577 is overexpressed in gastric cancer, breast cancer and lung cancer. Based on these expression results, SEQ ID NO:577 and its expression products qualify as molecular markers and/or target candidates for targeted therapies, in particular for these particular tumor types.

Figure 16:
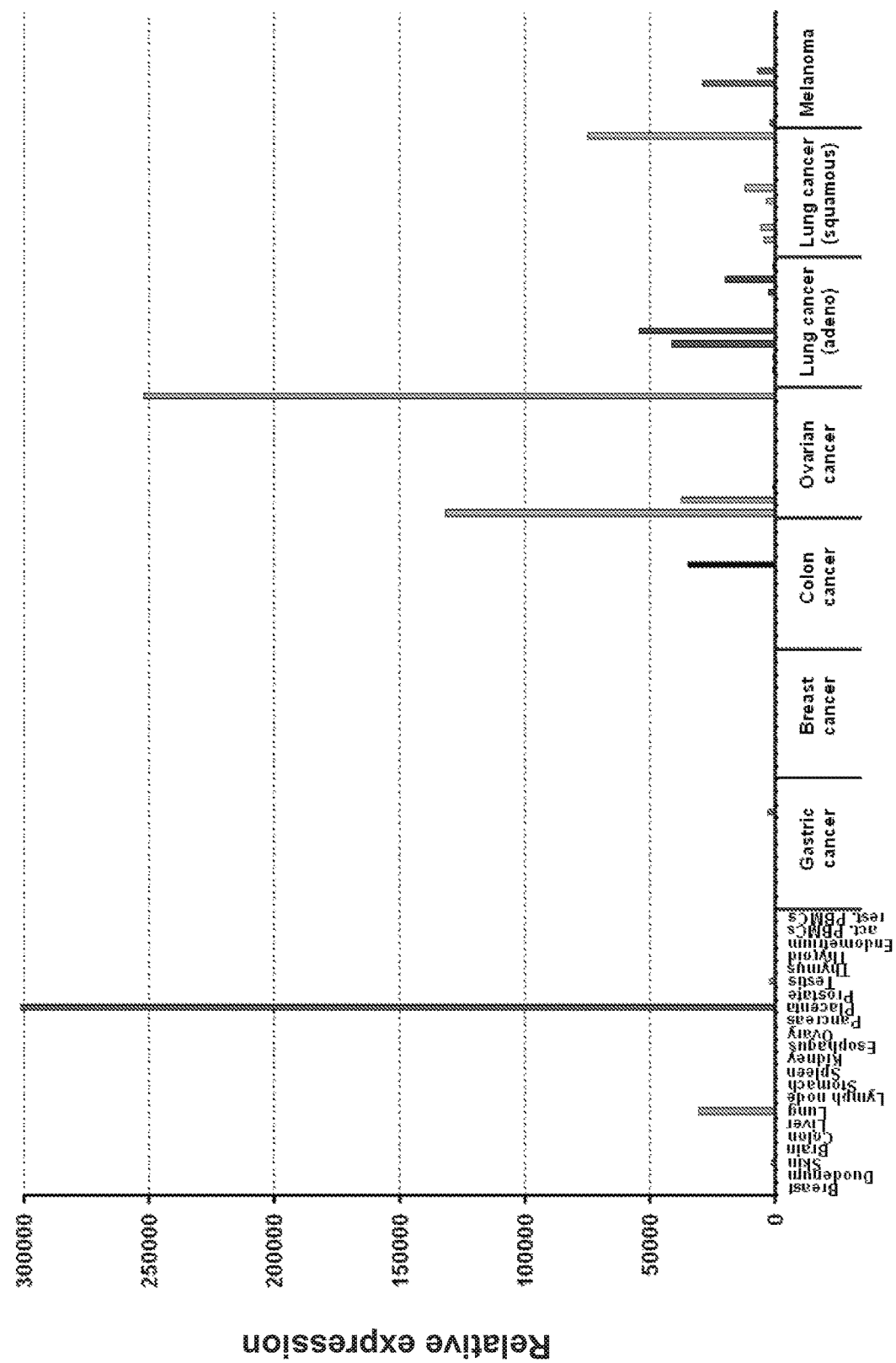
FIG. 16. Quantitative expression of SEQ ID NO:580 in normal tissues and cancer tissues. Real-time RT-PCR showed overexpression of the nucleic acid sequence according to SEQ ID NO:580 in ovarian cancer and lung cancer.

The nucleotide sequence according to SEQ ID NO:580 was deduced from SEQ ID NO:32. SEQ ID NO:580 represents a partial cDNA with no apparent open reading frame. Expression of SEQ ID NO:580 in normal and cancerous tissues was quantified by real-time RT-PCR using sequence-specific oligos (SEQ ID NO:581, 582); see FIG. 16. SEQ ID NO:580 is highly expressed in placenta. Compared to other normal tissues, SEQ ID NO:580 is overexpressed in ovarian cancer and lung cancer. Based on these expression results, SEQ ID NO:580 and its expression products qualify as molecular markers and/or target candidates for targeted therapies, in particular for these particular tumor types.

Figure 17:
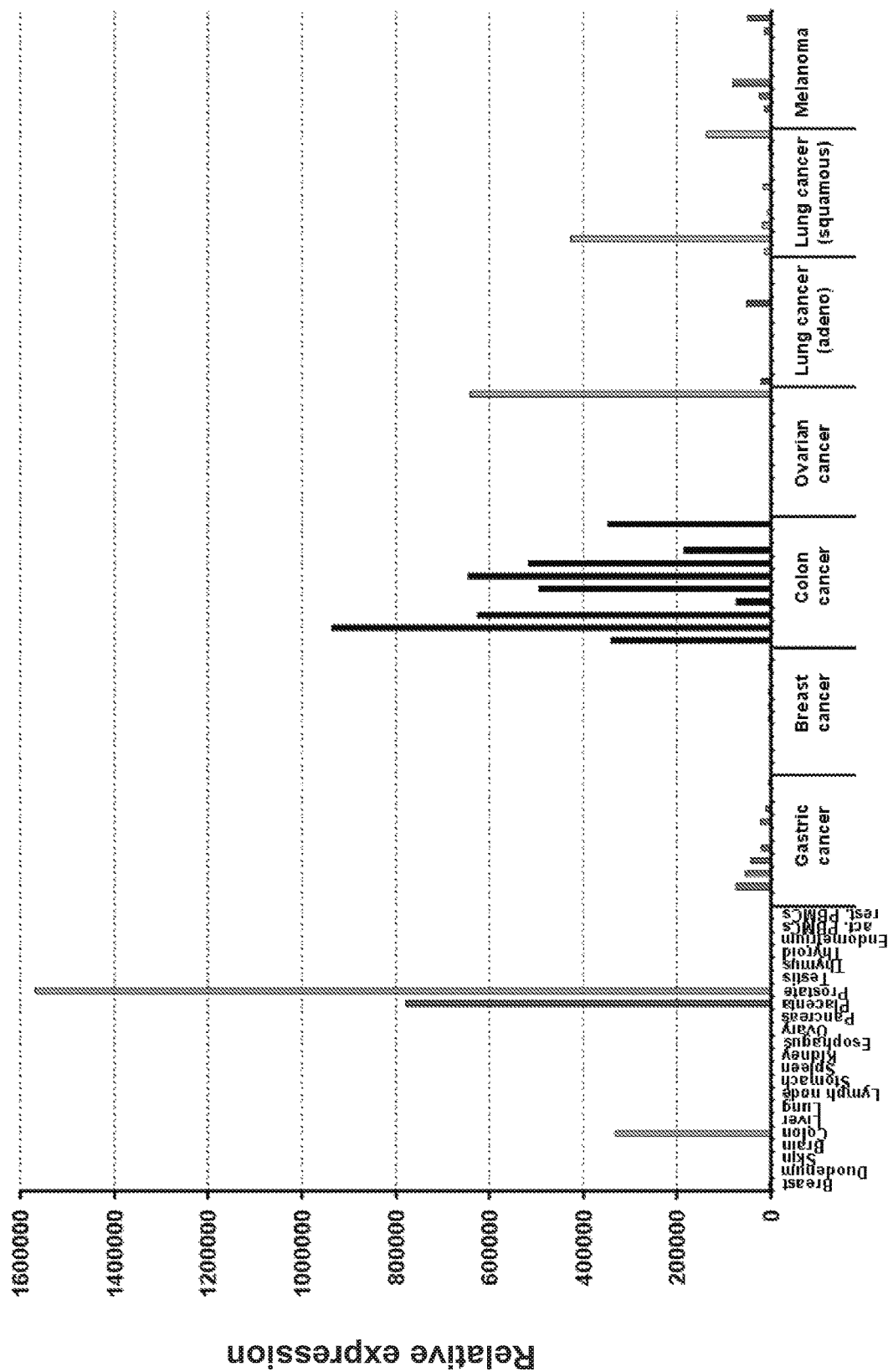
FIG. 17. Quantitative expression of SEQ ID NO:583 in normal tissues and cancer tissues. Real-time RT-PCR showed overexpression of the nucleic acid sequence according to SEQ ID NO:583 in colon cancer, ovarian cancer and lung cancer.

The nucleotide sequence according to SEQ ID NO:583 was deduced from SEQ ID NO:257 and codes for a member of the homeobox class of transcription factors (SEQ ID NO:584). Expression of these proteins is spatially and temporally regulated during embryonic development. Expression of SEQ ID NO:583 in normal and cancerous tissues was quantified by real-time RT-PCR using sequence-specific oligos (SEQ ID NO:585, 586); see FIG. 17. SEQ ID NO:583 is highly expressed in placenta and prostate. Compared to other normal tissues, SEQ ID NO:583 is overexpressed in colon cancer, ovarian cancer and lung cancer. Based on these expression results, SEQ ID NO:583 and its expression products qualify as molecular markers and/or target candidates for targeted therapies, in particular for these particular tumor types.

Figure 18:
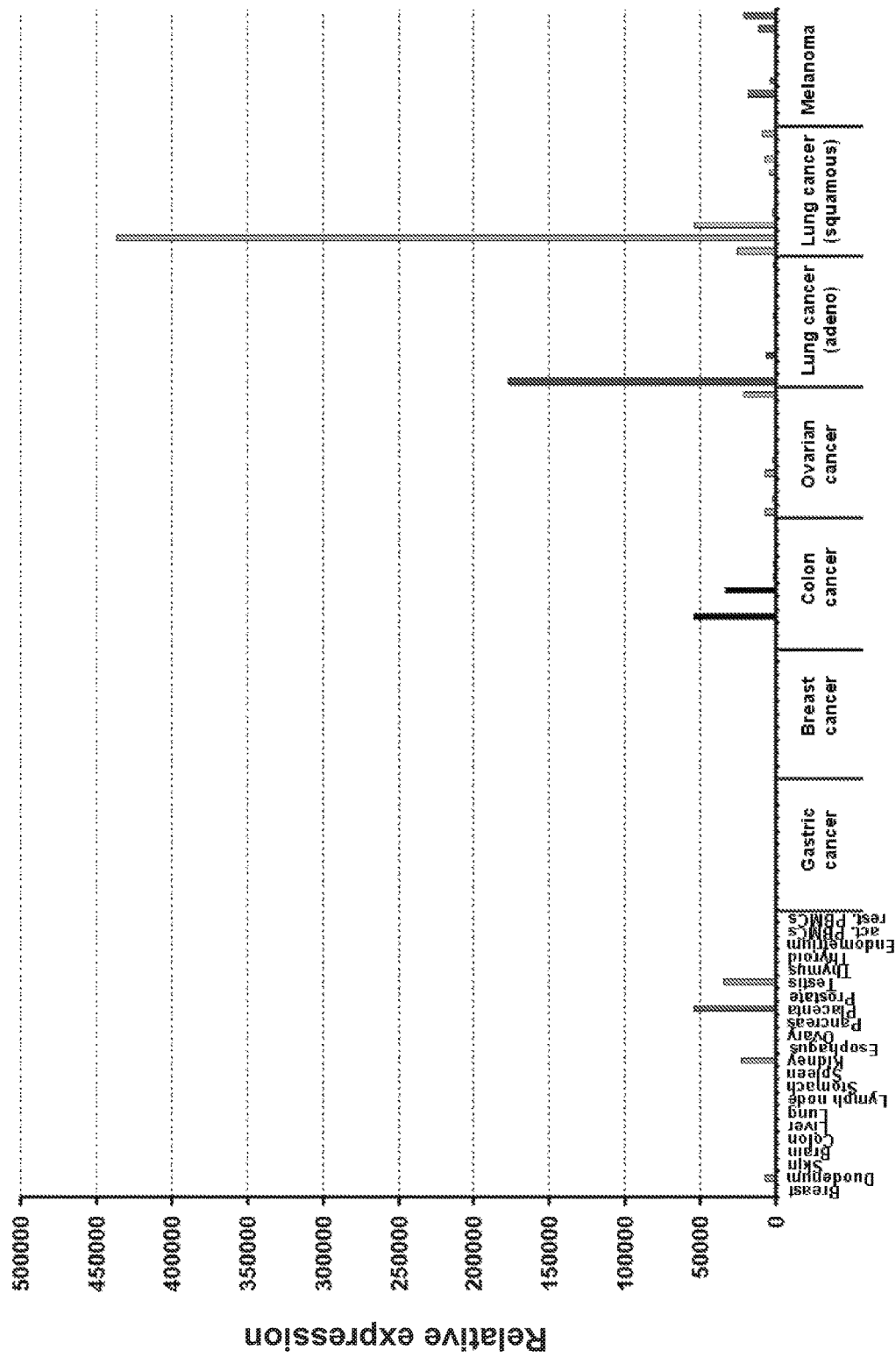
FIG. 18. Quantitative expression of SEQ ID NO:587 in normal tissues and cancer tissues. Real-time RT-PCR showed overexpression of the nucleic acid sequence according to SEQ ID NO:587 in lung cancer.

The nucleotide sequence according to SEQ ID NO:587 was deduced from SEQ ID NO:148 and codes for a member of the IGF-II mRNA-binding protein (IMP) family (SEQ ID NO:588). It functions by binding to the 5' UTR of the insulin-like growth factor 2 (IGF2) mRNA and regulating IGF2 translation. Expression of SEQ ID NO:587 in normal and cancerous tissues was quantified by real-time RT-PCR using sequence-specific oligos (SEQ ID NO:589, 590); see FIG. 18. Compared to normal tissues, SEQ ID NO:587 is overexpressed in lung cancer. Based on these expression results, SEQ ID NO:587 and its expression products qualify as molecular markers and/or target candidates for targeted therapies, in particular for this particular tumor type.

Figure 19:
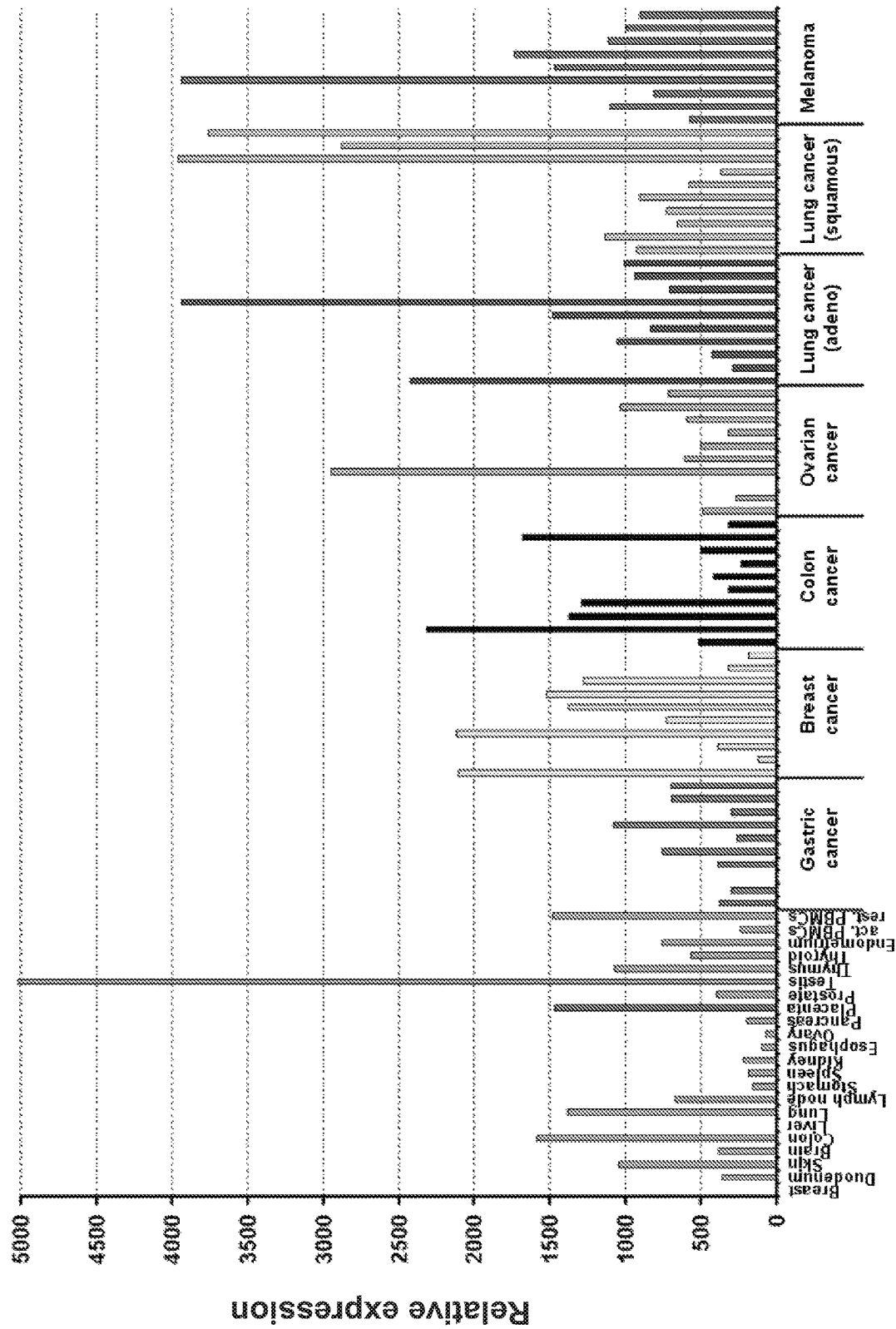
FIG. 19. Quantitative expression of SEQ ID NO:591 in normal tissues and cancer tissues. Real-time RT-PCR showed overexpression of the nucleic acid sequence according to SEQ ID NO:591 in breast cancer, colon cancer, ovarian cancer, lung cancer and melanoma.

The nucleotide sequence according to SEQ ID NO:591 was deduced from SEQ ID NO:194 and codes for a 372 aa protein (SEQ ID NO:592) of unknown function. Expression of SEQ ID NO:591 in normal and cancerous tissues was quantified by real-time RT-PCR using sequence-specific oligos (SEQ ID NO:593, 594); see FIG. 19. SEQ ID NO:591 is highly expressed in testis. Compared to other normal tissues, SEQ ID NO:591 is overexpressed in breast cancer, colon cancer, ovarian cancer, lung cancer and melanoma. Based on these expression results, SEQ ID NO:591 and its expression products qualify as molecular markers and/or target candidates for targeted therapies, in particular for these particular tumor types.

Figure 20:
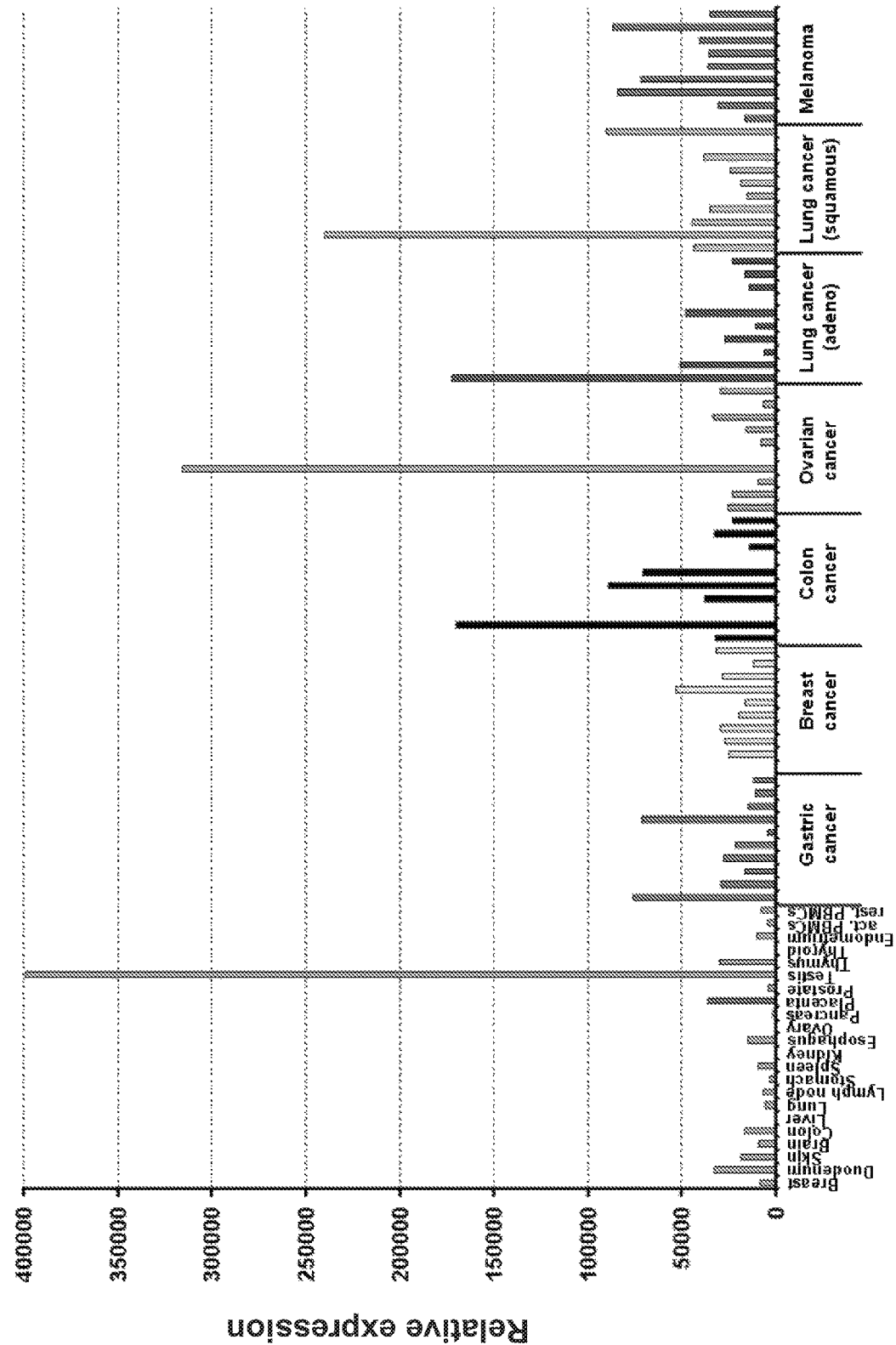
FIG. 20. Quantitative expression of SEQ ID NO:595 in normal tissues and cancer tissues. Real-time RT-PCR showed overexpression of the nucleic acid sequence according to SEQ ID NO:595 in gastric cancer, colon cancer, ovarian cancer, lung cancer and melanoma.

The nucleotide sequence according to SEQ ID NO:595 was deduced from SEQ ID NO:191 and codes for a 357 aa protein (SEQ ID NO:596) of unknown function. Expression of SEQ ID NO:595 in normal and cancerous tissues was quantified by real-time RT-PCR using sequence-specific oligos (SEQ ID NO:597, 598); see FIG. 20. SEQ ID NO:595 is highly expressed in testis. Compared to other normal tissues, SEQ ID NO:595 is overexpressed in gastric cancer, colon cancer, ovarian cancer, lung cancer and melanoma. Based on these expression results, SEQ ID NO:595 and its expression products qualify as molecular markers and/or target candidates for targeted therapies, in particular for these particular tumor types.

Figure 21:
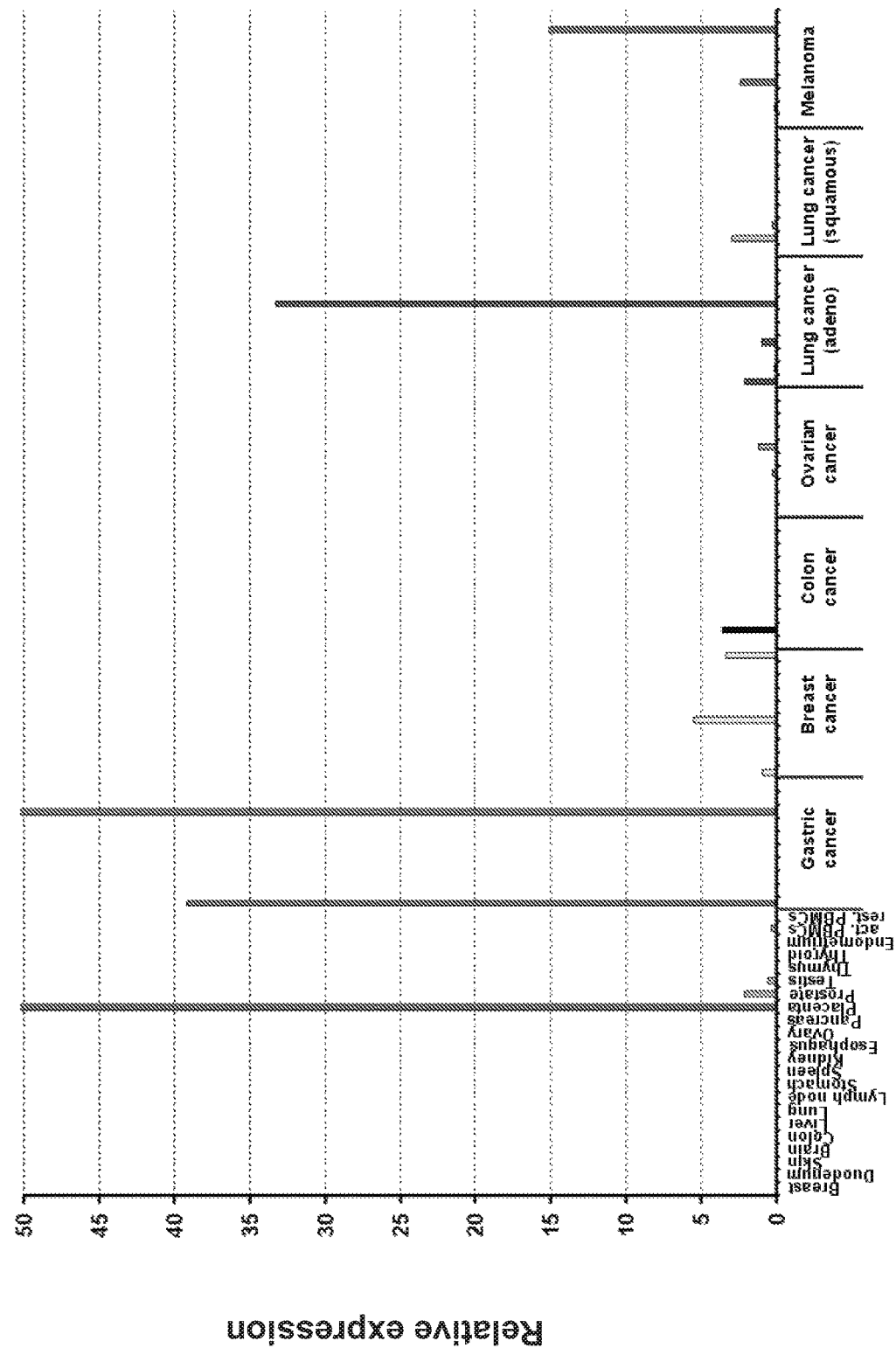
FIG. 21. Quantitative expression of SEQ ID NO:599 in normal tissues and cancer tissues. Real-time RT-PCR showed overexpression of the nucleic acid sequence according to SEQ ID NO:599 in gastric cancer, breast cancer, lung cancer and melanoma.

The nucleotide sequence according to SEQ ID NO:599 was deduced from SEQ ID NO:18 and has no apparent open reading frame. Expression of SEQ ID NO:599 in normal and cancerous tissues was quantified by real-time RT-PCR using sequence-specific oligos (SEQ ID NO:600, 601); see FIG. 21. SEQ ID NO:599 is highly expressed in placenta. Compared to other normal tissues, SEQ ID NO:599 is overexpressed in gastric cancer, breast cancer, lung cancer and melanoma. Based on these expression results, SEQ ID NO:599 and its expression products qualify as molecular markers and/or target candidates for targeted therapies, in particular for these particular tumor types.

Figure 22:
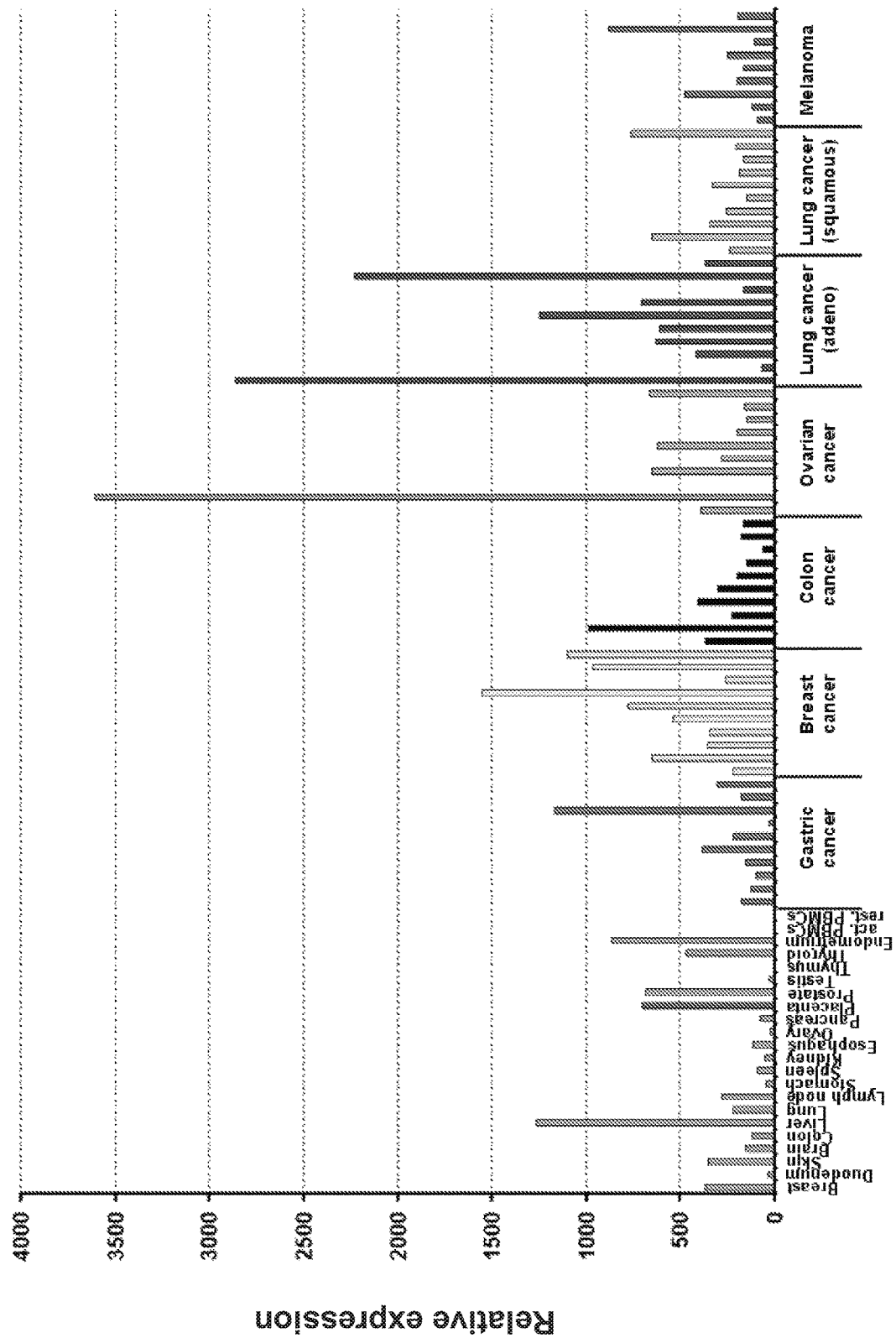
FIG. 22. Quantitative expression of SEQ ID NO:602 in normal tissues and cancer tissues. Real-time RT-PCR showed overexpression of the nucleic acid sequence according to SEQ ID NO:602 in ovarian cancer and lung cancer.

The nucleotide sequence according to SEQ ID NO:602 was deduced from SEQ ID NO:133 and codes for a member of the von Willebrand factor domain superfamily of extracellular matrix proteins (SEQ ID NO:603). Expression of SEQ ID NO:602 in normal and cancerous tissues was quantified by real-time RT-PCR using sequence-specific oligos (SEQ ID NO:604, 605); see FIG. 22. Compared to normal tissues, SEQ ID NO:602 is overexpressed in ovarian cancer and lung cancer. Based on these expression results, SEQ ID NO:602 and its expression products qualify as molecular markers and/or target candidates for targeted therapies, in particular for these particular tumor types.

Figure 23:
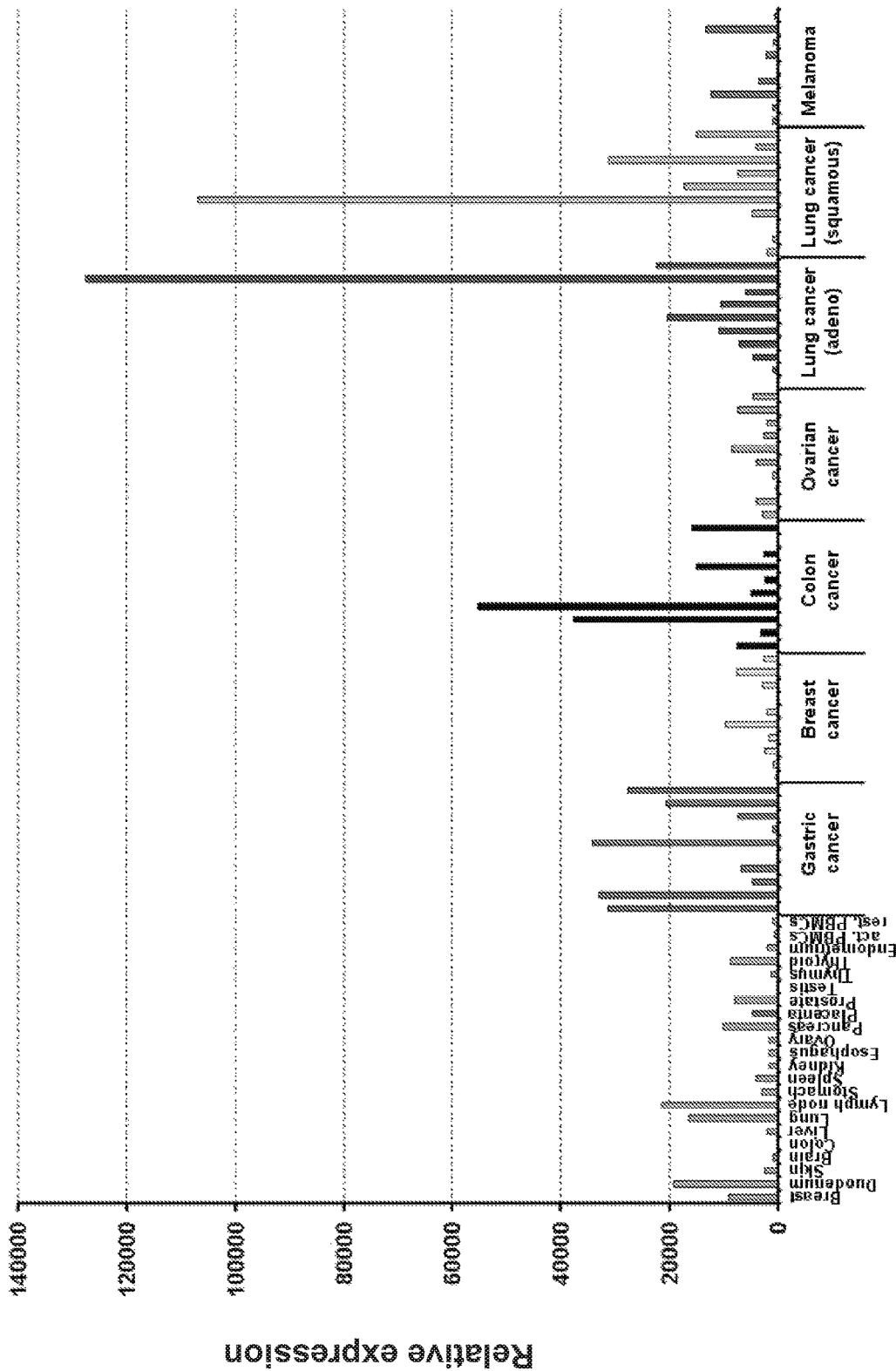
FIG. 23. Quantitative expression of SEQ ID NO:606 in normal tissues and cancer tissues. Real-time RT-PCR showed overexpression of the nucleic acid sequence according to SEQ ID NO:606 in gastric cancer, colon cancer and lung cancer.

The nucleotide sequence according to SEQ ID NO:606 was deduced from SEQ ID NO:128 and codes for a member of the Borg family of CDC42 effector proteins (SEQ ID NO:607). Borg family proteins contain a CRIB (Cdc42/Rac interactive-binding) domain. They bind to, and negatively regulate the function of CDC42. CDC42, a small Rho GTPase, regulates the formation of F-actin-containing structures through its interaction with the downstream effector proteins. Expression of SEQ ID NO:606 in normal and cancerous tissues was quantified by real-time RT-PCR using sequence-specific oligos (SEQ ID NO:608, 609); see FIG. 23. Compared to normal tissues, SEQ ID NO:606 is overexpressed in gastric cancer, colon cancer and lung cancer. Based on these expression results, SEQ ID NO:606 and its expression products qualify as molecular markers and/or target candidates for targeted therapies, in particular for these particular tumor types.

Figure 24:
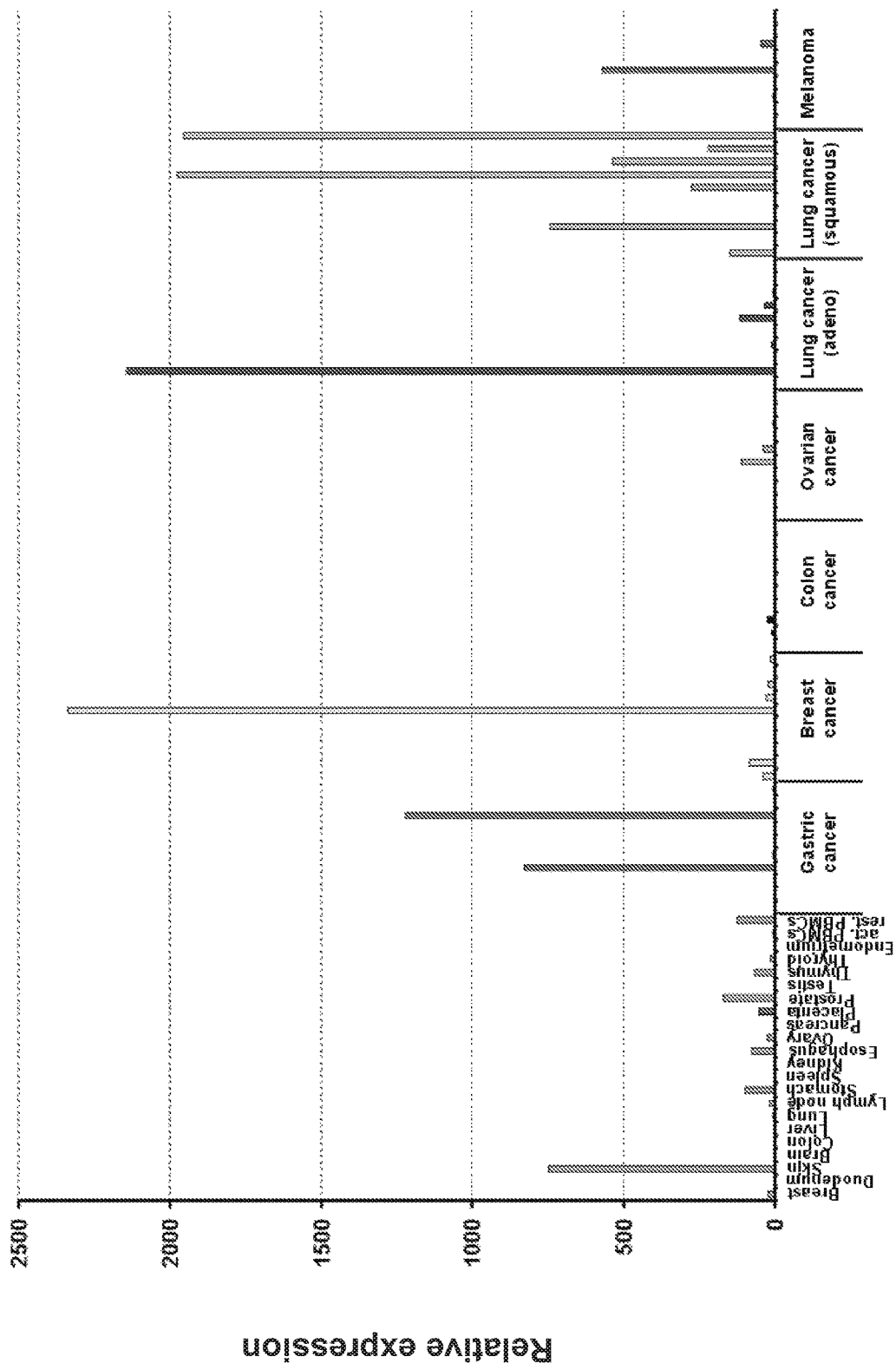
FIG. 24. Quantitative expression of SEQ ID NO:610 in normal tissues and cancer tissues. Real-time RT-PCR showed overexpression of the nucleic acid sequence according to SEQ ID NO:610 in gastric cancer, breast cancer and lung cancer.

The nucleotide sequence according to SEQ ID NO:610 was deduced from SEQ ID NO:118 and has no apparent open reading frame. Expression of SEQ ID NO:610 in normal and cancerous tissues was quantified by real-time RT-PCR using sequence-specific oligos (SEQ ID NO:611, 612); see FIG. 24. Compared to normal tissues, SEQ ID NO:610 is overexpressed in gastric cancer, breast cancer and lung cancer. Based on these expression results, SEQ ID NO:610 and its expression products qualify as molecular markers and/or target candidates for targeted therapies, in particular for these particular tumor types.

Figure 25:
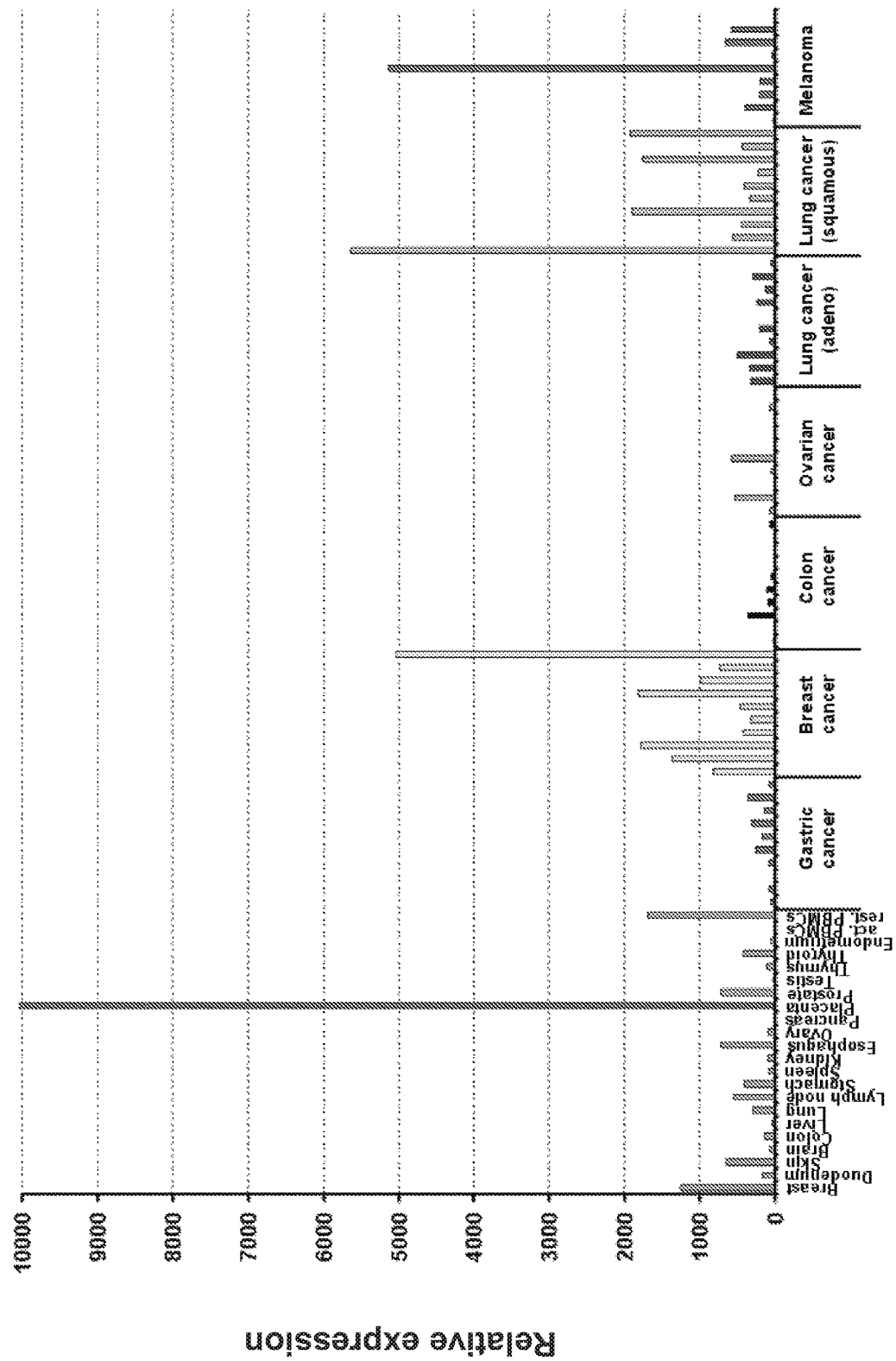
FIG. 25. Quantitative expression of SEQ ID NO:613 in normal tissues and cancer tissues. Real-time RT-PCR showed overexpression of the nucleic acid sequence according to SEQ ID NO:613 in breast cancer, lung cancer and melanoma.

The nucleotide sequence according to SEQ ID NO:613 was deduced from SEQ ID NO:116 and codes for a 76 aa protein (SEQ ID NO:614) of unknown function. Expression of SEQ ID NO:613 in normal and cancerous tissues was quantified by real-time RT-PCR using sequence-specific oligos (SEQ ID NO:615, 616); see FIG. 25. SEQ ID NO:613 is highly expressed in placenta. Compared to other normal tissues, SEQ ID NO:613 is overexpressed in breast cancer, lung cancer and melanoma. Based on these expression results, SEQ ID NO:613 and its expression products qualify as molecular markers and/or target candidates for targeted therapies, in particular for these particular tumor types.

Figure 26:
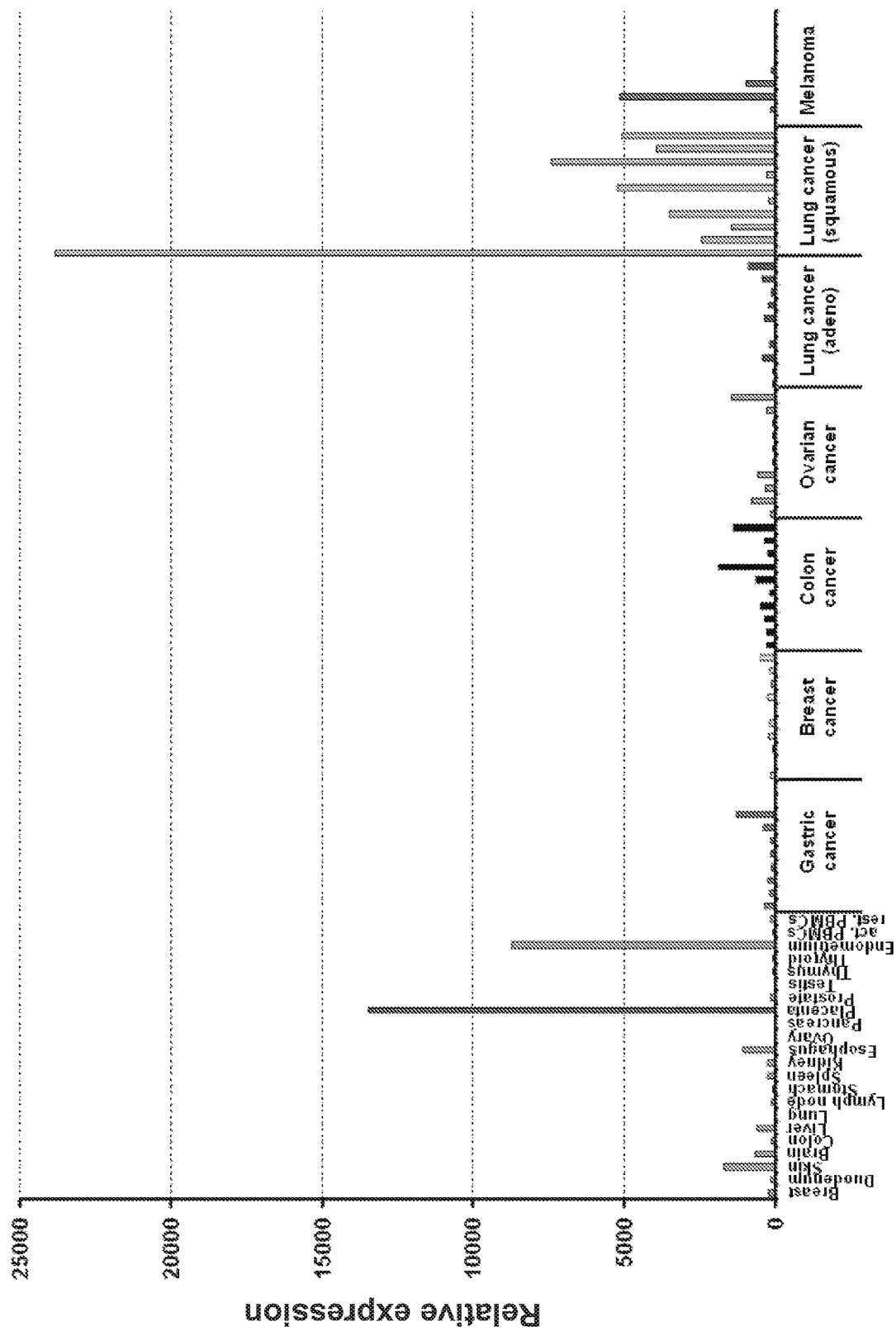
FIG. 26. Quantitative expression of SEQ ID NO:617 in normal tissues and cancer tissues. Real-time RT-PCR showed overexpression of the nucleic acid sequence according to SEQ ID NO:617 in lung cancer and melanoma.

The nucleotide sequence according to SEQ ID NO:617 was deduced from SEQ ID NO:267. SEQ ID NO:617 represents a partial cDNA with no apparent open reading frame. Expression of SEQ ID NO:617 in normal and cancerous tissues was quantified by real-time RT-PCR using sequence-specific oligos (SEQ ID NO:618, 619); see FIG. 26. SEQ ID NO:617 is highly expressed in placenta and endometrium. Compared to other normal tissues, SEQ ID NO:617 is overexpressed in lung cancer and melanoma. Based on these expression results, SEQ ID NO:617 and its expression products qualify as molecular markers and/or target candidates for targeted therapies, in particular for these particular tumor types.

Figure 27:
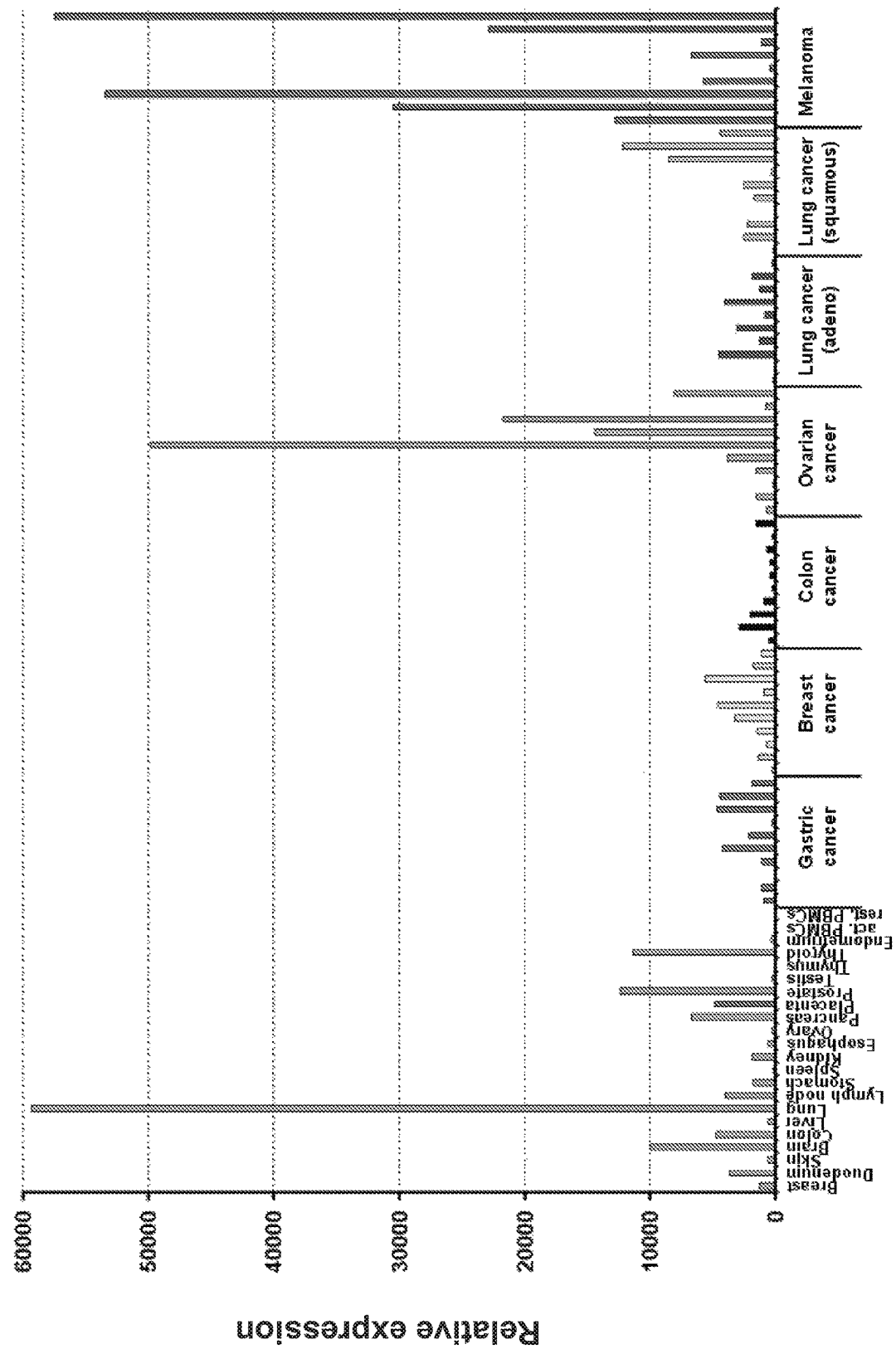
FIG. 27. Quantitative expression of SEQ ID NO:620 in normal tissues and cancer tissues. Real-time RT-PCR showed overexpression of the nucleic acid sequence according to SEQ ID NO:620 in ovarian cancer and melanoma.

The nucleotide sequence according to SEQ ID NO:620 was deduced from SEQ ID NO:182 and codes for a 829 aa protein (SEQ ID NO:621) harboring multiple putative transmembrane domains and a patched family domain. The transmembrane protein Patched is a receptor for the morphogene Sonic Hedgehog. This protein associates with the smoothened protein to transduce hedgehog signals. SEQ ID NO:620 might represent a novel member of the Patched family. Expression of SEQ ID NO:620 in normal and cancerous tissues was quantified by real-time RT-PCR using sequence-specific oligos (SEQ ID NO:622, 623); see FIG. 27. SEQ ID NO:620 is highly expressed in lung. Compared to other normal tissues, SEQ ID NO:620 is overexpressed in ovarian cancer and melanoma. Based on these expression results, SEQ ID NO:620 and its expression products qualify as molecular markers and/or target candidates for targeted therapies, in particular for these particular tumor types.

The nucleotide sequence according to SEQ ID NO:624 was deduced from SEQ ID NO:184 and codes for a 323 aa protein (SEQ ID NO:625) similar to TWIK-related acid-sensitive $K^+$ channel, a member of the superfamily of potassium channel proteins that contain two pore-forming P domains. Expression of SEQ ID NO:624 in normal and cancerous tissues was quantified by real-time RT-PCR using sequence-specific oligos (SEQ ID NO:626, 627); see FIG. 28. SEQ ID NO:624 is highly expressed in lung. Compared to other normal tissues, SEQ ID NO:624 is overexpressed in gastric cancer and lung cancer. Based on these expression results, SEQ ID NO:624 and its expression products qualify as molecular markers and/or target candidates for targeted therapies, in particular for these particular tumor types.

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

---

The invention claimed is:

1. A method of detecting a nucleic acid sequence consisting of SEQ ID NO: 44 in a cancer cell, wherein the method comprises the steps of:
   detecting the presence of or determining the quantity of the nucleic acid sequence consisting of SEQ ID NO: 44 expressed in the cancer cell in a biological sample comprising tissue isolated from a patient, wherein
      the detecting or determining comprises (i) contacting the biological sample with an agent that binds specifically to the nucleic acid, and (ii) detecting the formation of or determining the quantity of a complex between the agent and the nucleic acid, wherein said agent is an oligonucleotide or polynucleotide that hybridizes specifically to the nucleic acid or to the complementary nucleic acid sequence;
      and
   wherein said cancer cell is from a cancer or tumor selected from the group consisting of ovarian cancer, colorectal cancer, lung cancer, prostate cancer, melanoma, and cervical cancer.

2. The method of claim 1, wherein the method comprises detection of the presence of or determination of the quantity of nucleic acid in a first sample at a first point in time and in a further sample at a second point in time.

3. The method of claim 1, wherein the agent is labeled in a detectable manner.

4. The method of claim 1, wherein tissue is from a tissue biopsy.

5. The method of claim 1, wherein the detecting or determining comprises real-time reverse-transcription polymerase chain reaction (RT-PCR).

* * * * *

SEQUENCE LISTING

```
<160> NUMBER OF SEQ ID NOS: 636

<210> SEQ ID NO 1
<211> LENGTH: 398
<212> TYPE: DNA
<213> ORGANISM: Homo sapiens
<220> FEATURE:
<221> NAME/KEY: misc_feature
<222> LOCATION: (272)..(272)
<223> OTHER INFORMATION: n is a, c, g, t or u
<220> FEATURE:
<221> NAME/KEY: misc_feature
<222> LOCATION: (274)..(274)
<223> OTHER INFORMATION: n is a, c, g, t or u
<220> FEATURE:
<221> NAME/KEY: misc_feature
<222> LOCATION: (284)..(284)
<223> OTHER INFORMATION: n is a, c, g, t or u

<400> SEQUENCE: 1
aacataggtg gaccgctgct gagtccaggc ttacttgcag agatctatgc tggccaggcc      60
ctgtgctagg cagcagagga catggaataa aatcaaataa ggtcactgtg tgcaggcacc     120
tcacggtgtg gtaaaggagc agccccatcc acaggttcta ttaattccag cctgtgagaa     180
ttggaaccac agggtgaatt ttggaggaca ggcacttaca ctaatctgga agcataatat     240
ataaagagta cctacaaatc aataaaaaaa ananaaaaaa aaanagcaaa gtatatgaac     300
agaaaattca atgaaaagga aatagaaatg gctcttaaat gaatgaaaac atactctcac     360
tcagagaaat gaaaatttaa cccatgtcaa gatacttg                              398
```

<210> SEQ ID NO 2
<211> LENGTH: 99
<212> TYPE: DNA
<213> ORGANISM: Homo sapiens

<400> SEQUENCE: 2

```
atgcacagag catcacgtac aatggctcca tggacagccc agtgcccttg taccctaccg    60 attgccccc ttcttatgag gcagtcatgg gactacgag                            99
```

<210> SEQ ID NO 3
<211> LENGTH: 266
<212> TYPE: DNA
<213> ORGANISM: Homo sapiens

<400> SEQUENCE: 3

```
aggagaaaac ctctacttgt cctgcttcgc ggaatctaac ccaccggcag agtattttg     60 gacaattaat gggaagtttc agcaatcagg acaaaagctc tctatccccc aaattactac   120
aaagcataga gggctctata cttgctctgt tcgtaactca gccactggca aggaaagctc   180
caaatccatg acagtcgaag tctctgctcc ttcaggaata ggacgtcttc ctctccttaa   240
tccaatatag cagccgtgaa gtcatt                                        266
```

<210> SEQ ID NO 4
<211> LENGTH: 492
<212> TYPE: DNA
<213> ORGANISM: Homo sapiens
<220> FEATURE:
<221> NAME/KEY: misc_feature
<222> LOCATION: (369)..(369)
<223> OTHER INFORMATION: n is a, c, g, t or u
<220> FEATURE:
<221> NAME/KEY: misc_feature
<222> LOCATION: (372)..(372)
<223> OTHER INFORMATION: n is a, c, g, t or u
<220> FEATURE:
<221> NAME/KEY: misc_feature
<222> LOCATION: (418)..(419)
<223> OTHER INFORMATION: n is a, c, g, t or u
<220> FEATURE:
<221> NAME/KEY: misc_feature
<222> LOCATION: (424)..(424)
<223> OTHER INFORMATION: n is a, c, g, t or u
<220> FEATURE:
<221> NAME/KEY: misc_feature
<222> LOCATION: (443)..(443)
<223> OTHER INFORMATION: n is a, c, g, t or u

<400> SEQUENCE: 4

```
aaaggagtca tcagcgtctc tttcctggat tatatctggg ttacctaaag ctctgtagct    60
ctgtggatca aatcaaagtt cttgttaccc aaaagttgcc caacattctc tgccacgtga   120
agatccgtga aaacaataat atttctagag aggaatggga atggatccaa aagctttctg   180
gctctgaatc tatggaaagt gtggatcata cttctgactg ccccatgcaa ttgttcttct   240
acgagctcca gatggcagtg aaagctctcc ttcagcagat caatatacct ctacaccagg   300
caaggaactt ccgcctctac acacaggagg tgttggaaat gggtcacaat gtgtcctttc   360
ttctcctgnt cnctgcctca gacgacgtct gtacagcccc aggacagaat aatccttnna   420
cccnacactc agggtttctt aanctccctc ttcagatgtt tgaacttggt atagtagctt   480
gtttcaccta ga                                                       492
```

<210> SEQ ID NO 5
<211> LENGTH: 133
<212> TYPE: DNA
<213> ORGANISM: Homo sapiens

<400> SEQUENCE: 5

```
ttcaaaaact gctggtgagc ctatggaaga ggagccagcc ttgtgaagtg ccaagtcccc      60
ctctgatatt tcctgtgtgt gacatcattg tgtatccccc caccccagta ccctcagaca     120
tgtcttgtct gct                                                        133
```

<210> SEQ ID NO 6
<211> LENGTH: 371
<212> TYPE: DNA
<213> ORGANISM: Homo sapiens
<220> FEATURE:
<221> NAME/KEY: misc_feature
<222> LOCATION: (178)..(178)
<223> OTHER INFORMATION: n is a, c, g, t or u

<400> SEQUENCE: 6

```
ggtttcggcc tctgcgaaag tgaaatgccc aagcctccgg ccaaagccca gaccagtaca      60
gtatgaattg tcctatgaga ctgaggggtt cggcttcatt cctacctgcc cgcaaagctc     120
gcccccagcc tcgaaaacaa agcgactggt ctgacgtggg gtccctgcgc ccctcctnta     180
gcgcgacagg accccccag ggaagagcca gtacccgtgg gatgtcaccc cgtccccatc      240
taccggggtg gggggcctga aggagaacg atttaaaata atcttcagaa agaaaaggga      300
ggagggagcg ggtgacacat cgttcacata aacccaattt ctggtttcga gtgaagtcaa     360
gatctccgcc c                                                          371
```

<210> SEQ ID NO 7
<211> LENGTH: 215
<212> TYPE: DNA
<213> ORGANISM: Homo sapiens
<220> FEATURE:
<221> NAME/KEY: misc_feature
<222> LOCATION: (153)..(153)
<223> OTHER INFORMATION: n is a, c, g, t or u

<400> SEQUENCE: 7

```
ccatttaaca tgtatagtag gtcaacattg gtgcatccag aaaatgaagc atttaggaaa      60
tctgtttcag tgtcttttca atgtgtgtaa cttttacttg caaaccaatg gaaccaagaa     120
agtcatcatt tgcctaaaat gcagtcatca ccncaaatga ttcatttata ctatgtgagt     180
taattgcctt catctcatta atggccaagg aggga                                215
```

<210> SEQ ID NO 8
<211> LENGTH: 322
<212> TYPE: DNA
<213> ORGANISM: Homo sapiens

<400> SEQUENCE: 8

```
actgttcagt actgcaaccc caggatacac aatggcatct ggctctgttt attcaccacc      60
tactcggcca ctacctagaa acaccctatc aagaagtgct tttaaattca agaagtcttc     120
aaagtactgt agctggaaat gcactgcact gtgtgccgta ggggtctcgg tgctcctggc     180
aatactcctg tcttatttta tagcaatgca tctctttggc ctcaactggc agctacagca     240
gactgaaaat gacacatttg agaatggaaa agtgaattct gataccatgc caacaaacac     300
tgtgtcatta ccttctggag ac                                              322
```

<210> SEQ ID NO 9
<211> LENGTH: 547
<212> TYPE: DNA
<213> ORGANISM: Homo sapiens

<400> SEQUENCE: 9

```
ttacccttca ttcacctatt acggttcagg agaaaacctc gacttgtcct gcttcacgga      60
atctaaccca ccggcagagt attttttggac aattaatggg aagtttcagc aatcaggaca     120
aaagctcttt atcccccaaa ttactagaaa tcatagcggg ctctatgttt gctctgttca     180
taactcagcc actggcaagg aaatctccaa atccatgaca gtcaaagtct ctggtccctg     240
ccatggagac ctgacagagt ttcagtcatg actgcaacaa ctgagacact gagaaaaaga     300
acaggctgat accttcatga aattcaagac aaagaagaaa aaaactcaat gttattggac     360
taaataatca aaggataat gttttcataa ttttttattg gaaaatgtgc tgattctttg      420
aatgttttat tctccagatt tatgaacttt ttttcttcag caattggtaa agtatacttt    480
tgtaaacaaa aattgaaata tttgcttttg ctgtctatct gaatgcccca gaattgtgaa    540
actactc                                                              547
```

<210> SEQ ID NO 10
<211> LENGTH: 396
<212> TYPE: DNA
<213> ORGANISM: Homo sapiens

<400> SEQUENCE: 10

```
gcaggggacg caccaaggat ggagatgttc caggggctgc tgctgttgct gctgctgagc      60
atgggcggga catgggcatc caaggagccg cttcggccac ggtgccgccc catcaatgcc    120
accctggctg tggagaagga gggctgcccc gtgtgcatca ccgtcaacac caccatctgt    180
gccggctact gccccaccat gacccgcgtg ctgcagggg tcctgccggc cctgcctcag    240
gtggtgtgca actaccgcga tgtgcgcttc gagtccatcc ggctccctgg ctgcccgcgc    300
ggcgtgaacc ccgtggtctc ctacgccgtg gctctcagct gtcaatgtgc actctgccgc    360
cgcagcacca ctgactgcgg gggtcccaag gaccac                              396
```

<210> SEQ ID NO 11
<211> LENGTH: 311
<212> TYPE: DNA
<213> ORGANISM: Homo sapiens

<400> SEQUENCE: 11

```
aaatggtggt gtttgactgg tatatgacct tcctctggag gtgatcaacc agtaagggaa      60
atcgctcca agtgagcatg cacacaacct cagtaaacac actgtgcatg tggcttctcc    120
caagtactag caggccactg cacatgtcac aactgagcaa cagcccaccc caatggaggg    180
atcaagggag gagaagaaaa accccggaac caaaagccag tttataaaaa tcctgagcca    240
aaggctgagg ggggcacttg atctctcaag ttccctactt ggccctcttc caagtgtgat    300
ttgcttcttt t                                                          311
```

<210> SEQ ID NO 12
<211> LENGTH: 246
<212> TYPE: DNA
<213> ORGANISM: Homo sapiens
<220> FEATURE:
<221> NAME/KEY: misc_feature
<222> LOCATION: (184)..(184)
<223> OTHER INFORMATION: n is a, c, g, t or u

<400> SEQUENCE: 12

```
gccttagccc ccgggattta gagcatcctc gcgaccaccc ggaggcttct gggggccact      60
ctgcggatga ggaagctgac gcctgggtgc agaaccccgg accccggat tcagagccca      120
ggtccagccg cgcttccgca caaacttgcg ctcggagcaa gtcccctcct tcccagcact     180
catntgagac cagaggtgtc cccaccgtcc ccgctagcag cgctggttat attgtgggcc     240
aacctt                                                                246
```

<210> SEQ ID NO 13
<211> LENGTH: 516
<212> TYPE: DNA
<213> ORGANISM: Homo sapiens
<220> FEATURE:
<221> NAME/KEY: misc_feature
<222> LOCATION: (149)..(150)
<223> OTHER INFORMATION: n is a, c, g, t or u
<220> FEATURE:
<221> NAME/KEY: misc_feature
<222> LOCATION: (153)..(159)
<223> OTHER INFORMATION: n is a, c, g, t or u
<220> FEATURE:
<221> NAME/KEY: misc_feature
<222> LOCATION: (161)..(163)
<223> OTHER INFORMATION: n is a, c, g, t or u
<220> FEATURE:
<221> NAME/KEY: misc_feature
<222> LOCATION: (165)..(165)
<223> OTHER INFORMATION: n is a, c, g, t or u
<220> FEATURE:
<221> NAME/KEY: misc_feature
<222> LOCATION: (168)..(184)
<223> OTHER INFORMATION: n is a, c, g, t or u

<400> SEQUENCE: 13

```
cctttttgctt gagcagggtt cccaggaggg agaaagagaa gacaagagcc tgatgcccaa     60
ctttgtgtgt gtggggacgg gggagtcagg gccccccaag tcccacaata gccccaatgt     120
ttgcctatcc acctccccca agccccttnn ccnnnnnnnc nnntnacnnn nnnnnnnnn      180
nnnnctgctg ctgctgctgc tgctgcttaa aggctcatgc ttggagtggg gactggtcgg    240
tgcccagaaa gtctcttctg ccactgacgc ccccatcagg gattgggcct tctttccccc    300
ttccttctg tgtctcctgc ctcatcggcc tgccatgacc tgcagccaag cccagccccg     360
tggggaaggg gagaaagtgg gggatggcta agaaagctgg gagataggga acagaagagg    420
gtagtgggtg ggctagggg gctgccttat ttaaagtggt tgtttatgat tcttatacta     480
atttatacaa agatattaag gccctgttca ttaaga                               516
```

<210> SEQ ID NO 14
<211> LENGTH: 162
<212> TYPE: DNA
<213> ORGANISM: Homo sapiens
<220> FEATURE:
<221> NAME/KEY: misc_feature
<222> LOCATION: (92)..(92)
<223> OTHER INFORMATION: n is a, c, g, t or u

<400> SEQUENCE: 14

```
gagcctagag agtaaggaac gttatatagt tttccccaaa ggttcacttg aaagaacttt      60
tcattggttg tcatggtagt aatgtcctga tnttgaaatc tcccagaacc tagtagctct     120
taaacatgct ttcatcttgg ttcctttggt ctgacggaaa ct                        162
```

<210> SEQ ID NO 15

```
<211> LENGTH: 523
<212> TYPE: DNA
<213> ORGANISM: Homo sapiens
<220> FEATURE:
<221> NAME/KEY: misc_feature
<222> LOCATION: (49)..(49)
<223> OTHER INFORMATION: n is a, c, g, t or u

<400> SEQUENCE: 15
tttgcaaaag gtttccggga cactggaaat ggccgaagag aaaaaagana acagctcacc    60
ctgcagtcca tgagggtgtt tgatgaaaga cacaaaaagg agaatgggac ctctgatgag   120
tcctccagtg aacaagcagc tttcaactgc ttcgcccagg cttcttctcc agccgcctcc   180
actgtaggga catcgaacct caaagattta tgtcccagcg agggtgagag cgacgccgag   240
gccgagagca aagaggagca tggccccgag gcctgcgacg cggccaagat ctccaccacc   300
acgtcggagg agccctgccg tgacaagggc agccccgcgg tcaaggctca ccttttcgct   360
gctgagcggc cccgggacag cgggcggctg acaaagcgt cgcccgactc acgccatagc   420
cccgccacca tctcgtccag cactcgcggc ctggcgcgg aggagcgcag gagcccggtt   480
cgcgagggca gcgccggc caaggtggaa gaggcgcgcg cgc                      523

<210> SEQ ID NO 16
<211> LENGTH: 424
<212> TYPE: DNA
<213> ORGANISM: Homo sapiens

<400> SEQUENCE: 16
actcggtcac actcagtaag tccttgcaga gtccatgggt ttcttcgaca agtggcttca    60
aggaagggaa ttcccaccct tgtcttccag caaggccaca cacatgaaac cagcagaaaa   120
gagtcttatt tgctggaaag accccagca agggcatagt gagcccttac agtggttcca   180
gtcagaaaag gcaccacttg ggtgggcaca gccccatggg tgtccaactt ggtaagcaga   240
gcaaggctgg acttgagtcc ccgtcctcca caaaacacag agccacaagc ccagccctg   300 cagcagccct ccggaagcag cggggcactg gtttccttgt cccctgccat ctaccgagtg   360
gctcactctc aggtgggagt gctggtgatg gttaattagg actgcagaaa catgagcctc   420
ctta                                                                424

<210> SEQ ID NO 17
<211> LENGTH: 524
<212> TYPE: DNA
<213> ORGANISM: Homo sapiens

<400> SEQUENCE: 17
ctatctttct ggtcacattg tcggtgtttc tgcatgttct ccattccgct cctgatgtgc    60
aggattgccc agaatgcacg ctacaggaaa acccattctt ctcccagccg ggtgccccaa   120
tacttcagtg catgggctgc tgcttctcta gagcatatcc cactccacta aggtccaaga   180
agacgatgtt ggtccaaaag aacgtcacct cagagtccac ttgctgtgta gctaaatcat   240
ataacagggt cacagtaatg gggggtttca aagtggagaa ccacacggcg tgccactgca   300
gtacttgtta ttatcacaaa tcttaaatgt tttaccaagt gctgtcttga tgactgctga   360
ttttctggaa tggaaaatta agttgtttag tgtttatggc tttgtgagat aaaactctcc   420
ttttccttac cataccactt tgacacgctt caaggatata ctgcagcttt actgccttcc   480
tccttatcct acagtacaat cagcagtcta gttcttttca tttg                    524
```

<210> SEQ ID NO 18
<211> LENGTH: 538
<212> TYPE: DNA
<213> ORGANISM: Homo sapiens

<400> SEQUENCE: 18

```
gtagggcgaa ctctgctata cagtttatga tgtcagagtg aatactttct ttgagttgca      60
gtcagaaact gtagattttt aaaaatttaa aattcattat tctctgtcag tattccaaag     120
tgtatacaga aagctattgc actgttcagg agatggcgct taacattttg gaaattcaag     180
gtgatgaatg tccagataag actatctctc ctggtacaaa gtttgacaat gctgaacatt     240
tttaaaggtt cttttttgata tacaaagtgc accaatgagt gcttttttaat tcttacaata     300 attctgggtg aggtaggtat ttttccaatt cccattttat gcttcggtag cccttttgtat     360 ttatacttca aaacacttgg ctctcttgta attatttaag aaattagttg tgattatttg     420
tttaatgtgc aggagttaca aaaggcaagc tttagaacaa dacagacctg gttatgattc     480
ctggctctga aagctgtaca ccctgtgacc ctagacaggt gttttaatgc ctcgctgc      538
```

<210> SEQ ID NO 19
<211> LENGTH: 324
<212> TYPE: DNA
<213> ORGANISM: Homo sapiens
<220> FEATURE:
<221> NAME/KEY: misc_feature
<222> LOCATION: (294)..(295)
<223> OTHER INFORMATION: n is a, c, g, t or u

<400> SEQUENCE: 19

```
tcttggtctt ctgctcatgg atgacgcacc agtcgtgcat gttcttggtg aagtcggcca      60
gcctgagcaa gcggaggacc tacgccggcc tggcattcca cgcctacggg aaggcaggca     120
agatgctggt ggagaccagc atgatcgggc tgatgctggg cacctgcatc gccttctacg     180
tcgtgatcgg cgacttgggg tccaacttct ttgcccggct gttcgggttt caggtgggcg     240
gcaccttccg catgttcctg ctgttcgccg tgtcgctgtg catcgtgctc ccgnncagcc     300
tgcagcggaa catgatggcc tcca                                            324
```

<210> SEQ ID NO 20
<211> LENGTH: 414
<212> TYPE: DNA
<213> ORGANISM: Homo sapiens

<400> SEQUENCE: 20

```
agaaagcaga gcagcctcct ggaagaaggc cttgtcagct ttgtctgtgc ctcgcaaatc      60
agaggcaagg gagaggttgt taccagggga cactgagaat gtacatttga tctgccccag     120
ccacggaagt cagagtagga tgcacagtac aaaggagggg ggagtggagg cctgagaggg     180
aagtttctgg agttcagata ctctctgttg ggaacaggac atctcaacag tctcaggttc     240
gatcagtggg tcttttggca ctttgaacct tgaccacagg gaccaagaag tggcaatgag     300
gacacctgca ggaggggcta gcctgactcc cagaacttta agactttctc cccactgcct     360
tctgctgcag cccaagcagg gagtgtcccc ctcccagaag catatcccag atga           414
```

<210> SEQ ID NO 21
<211> LENGTH: 531
<212> TYPE: DNA
<213> ORGANISM: Homo sapiens

<400> SEQUENCE: 21

```
caaagtcatc tgaacttccg tttccccagg gcctccagct gccctcagac actgatgtct    60
gtccccaggt gctctctgcc cctcatgccc ctctcaccgg cccagtgccc cgactctcca   120
ggctttatca aggtgctaag gcccgggtgg gcagctcctc gtctcagagc cctcctccgg   180
cctggtgctg cctttacaaa cacctgcagg agaagggcca cggaagcccc aggctttaga   240
gccctcagca ggtctgggga gctagagcaa aggagggacc tcaggccttc cgtttcttct   300
tccagggtgg ggtggcctgg tgttcccta gccttccaaa cccaggtggc ctgcccttct    360
ccccagaggg aggcggcctc cgcccattgg tgctcatgca gactctgggg ctgaggtgcc   420 ccgggggtg atctctggtg ctcacagccg agggagccgt ggctccatgg ccagatgacg    480
gaaacagggt ctgaccaagt gccaggaaga cctgtgctat aaaccaccct g            531
```

<210> SEQ ID NO 22
<211> LENGTH: 522
<212> TYPE: DNA
<213> ORGANISM: Homo sapiens

<400> SEQUENCE: 22

```
atgtcctgcc atttggtcat aagacagttg catttactct gctaccattg cttcagttga    60
tatgaagaga gaaagctgtg ttgtgattta cactggatat ggaaatagag aggaacaaat   120
ctgtctgatc tactttcttc aacctctgta gtagctaata atataggaca gaatgctcca   180
aagaatgaaa atgaaagtca agattcaatg gatgaaagtg agaactcctc caggtcctgg   240
aaacaaacca tttagcatca ggtcagaagc tactccatgg aattctgaga ccacgaaagc   300
caggtcaggt ctcaaattca gtagcccacc acccacacca ccaccacac ccctgctt      360 cccctcatgc ttgctgcctc catttccttc tggaccacca ataattcccc caccacctcc   420
cacaggtcta gattttcttg atgatgttaa tgttttatga agtatgctaa tctcttggta   480
cattaagtgg ctatcatact ggctattata cagggctcaa gc                      522
```

<210> SEQ ID NO 23
<211> LENGTH: 520
<212> TYPE: DNA
<213> ORGANISM: Homo sapiens
<220> FEATURE:
<221> NAME/KEY: misc_feature
<222> LOCATION: (98)..(98)
<223> OTHER INFORMATION: n is a, c, g, t or u
<220> FEATURE:
<221> NAME/KEY: misc_feature
<222> LOCATION: (142)..(142)
<223> OTHER INFORMATION: n is a, c, g, t or u

<400> SEQUENCE: 23

```
gaaaggcctg caattgtgtc ttcacgatgc ttttccaaga cagccaaggc aggtataatt    60
ttcctcagca agaaagagga acctcggagg tgtgcacngc ctggctggcc acccaggtat   120
tggcaaaagt gactgtcggg cntgctggcc cggcccccgc ccgccgtccc tggagcactc   180
acgatgcggt ccggcggcgg cgtgctccgg atgaagcact tgatctggcc cttctcgccg   240
tggagggcgt gctgggtctg ggtgctggag atgatggggg gtcctgttga gaaacagcgt   300
cccattaggc acccgggaag ggcacgtccc tgctggcgcc ctcttgggtg ggttcagaag   360
tgtattcatt aatccaagca ttcagcaaac atttgccgaa ggcctgtatg tgcaaggtaa   420
agtgcaaggt agaggactca gagataaatt aggcattcag tcataaacct ctcaagggat   480
catgagcgaa tgcttctaag tcagaacccc cagaagatac                         520
```

```
<210> SEQ ID NO 24
<211> LENGTH: 488
<212> TYPE: DNA
<213> ORGANISM: Homo sapiens

<400> SEQUENCE: 24
agcagaacct cctagggttt ctccttccac tccttgccat gatcttcttc tactcccgta    60
ttggttgtgt cttggtgagg ctgaggcccg caggccaggg ccgggcttta aaaatagctg   120
cagccttggt ggtggccttc ttcgtgctat ggttcccata caatctcacc ttgtttctgc   180
atacgctgtt ggacctgcaa gtattcggga actgtgaggt cagccagcat ctagactacg   240
cactccaggt aacagagagc atcgccttcc ttcactgctg cttttccccc atcctgtatg   300
ccttctccag tcaccgcttc cgccagtacc tgaaggcttt cctggctgcc gtgcttggat   360
ggcacctggc acctggcact gcccaggcct cattatccag ctgttctgag agcagcatac   420
ttactgccct tgaggaaatg actggcatga atgaccttgg agagaggcag tctgagaact   480
accctaac                                                            488

<210> SEQ ID NO 25
<211> LENGTH: 552
<212> TYPE: DNA
<213> ORGANISM: Homo sapiens

<400> SEQUENCE: 25
gaggagagac ctgcgtggga taatcaacag gggtctggag gacggggaga gctgggaata    60
tcagatctga ctgcgtgttc tcacttcgct cctggaact tgctctcatt ttcctgggtg    120
catcaaacaa acaaaaaacc aaacacccag aggtctcatc tcccaggccc cagggagaa   180 agaggagtag catgaacgcc aaggaatgta cgttgagaat cactgctcca ggcctgcatt   240
actccttcag ctctggggca gaggaagccc agcccaagca cggggctggc agggcgtgag   300
gaactctcct gtggcctgct catcaccctt ccgacaggag cactgcatgt cagagcactt   360
taaaaacagg ccagcctgct tgggcgctcg gtctccaccc cagggtcata agtggggaga   420
gagcccttcc cagggcaccc aggcaggtgc agggaagtgc agagcttgtg gaaagcgtgt   480
gagtgaggga gacaggaacg gctctggggg tgggaagtgg ggctaggtct tgccaactcc   540
atcttcaata aa                                                        552

<210> SEQ ID NO 26
<211> LENGTH: 511
<212> TYPE: DNA
<213> ORGANISM: Homo sapiens

<400> SEQUENCE: 26
aagcctcaag gcacttctag gacctggctc ttctcaccaa gatgaactca ctggtttctt    60
ggcagctact gcttttcctc tgtgccaccc actttgggga gccattagaa aaggtggcct   120
ctgtggggaa ttctagaccc acaggccagc agctagaatc cctgggcctc ctggcccccg   180
gggagcagag cctgccgtgc accgagagga agccagctgc tactgccagg ctgagccgtc   240 ggggggacctc gctgtccccg ccccccgaga gctccgggag ccgccagcag ccgggcctgt   300
ccgcccccca cagccgccag atcccgcac cccaggcgc ggtgctggtg cagcgggaga   360
aggacctgcc gaactacaac tggaactcct tcggcctgcg cttcggcaag cgggaggcgg   420
caccagggaa ccacgcaga agcgctgggc ggggctgggg cgcaggtgcg gggcagtgaa   480
cttcagaccc caaaggagtc agagcatgcg g                                 511
```

<210> SEQ ID NO 27
<211> LENGTH: 131
<212> TYPE: DNA
<213> ORGANISM: Homo sapiens

<400> SEQUENCE: 27
ctcctccagc aagacagatg cctagcccgt cctcaggaat ctgccgccag ggagaatggc      60
aaccctggcc agatagctgg aagcacaggg ttgctcttca acctgcctcc cggctcagtt     120
cactataaga a                                                          131

<210> SEQ ID NO 28
<211> LENGTH: 304
<212> TYPE: DNA
<213> ORGANISM: Homo sapiens
<220> FEATURE:
<221> NAME/KEY: misc_feature
<222> LOCATION: (41)..(41)
<223> OTHER INFORMATION: n is a, c, g, t or u
<220> FEATURE:
<221> NAME/KEY: misc_feature
<222> LOCATION: (84)..(84)
<223> OTHER INFORMATION: n is a, c, g, t or u

<400> SEQUENCE: 28
tttcctctga gagaacagcg gtcttctgtc tgctgtggca nagcaagtca cttcttcttg      60
tagtgagaac tgaaaccaga accnatcatg tgccacttcc tggacacctc ctattaaata    120
ttaaagtcct ctcaccacag aagccggagt ttagtggtta ggggcacagg ttcttagata    180
tgaacatcag ttgcaaccta ccaactgcat gctcttggac aatttacatt tctgtgtatc    240
agctttcctt tttctttaga atgagatatt aatagtagca acccagaatt gtcatgaagc    300
ctaa                                                                 304

<210> SEQ ID NO 29
<211> LENGTH: 226
<212> TYPE: DNA
<213> ORGANISM: Homo sapiens

<400> SEQUENCE: 29
catggcaaag gcttgcccca aatctcaact tctcagacgt tccataccccc cacatgccaa     60 tttcagcacc caactgagat ccgaggagct cctgggaagc cctgggtgca ggacactggt    120
cgagagccaa aggtccctcc ccagacatct ggacactggg catagatttc tcaagaagga    180
agactcccct gcctcccag ggcctctgct ctcctgggag acaaag                    226

<210> SEQ ID NO 30
<211> LENGTH: 567
<212> TYPE: DNA
<213> ORGANISM: Homo sapiens
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (216)..(216)
<223> OTHER INFORMATION: n is a, c, g, t or u
<220> FEATURE:
<221> NAME/KEY: misc_feature
<222> LOCATION: (226)..(226)
<223> OTHER INFORMATION: n is a, c, g, t or u
<220> FEATURE:
<221> NAME/KEY: misc_feature
<222> LOCATION: (255)..(256)
<223> OTHER INFORMATION: n is a, c, g, t or u

```
<220> FEATURE:
<221> NAME/KEY: misc_feature
<222> LOCATION: (261)..(261)
<223> OTHER INFORMATION: n is a, c, g, t or u
<220> FEATURE:
<221> NAME/KEY: misc_feature
<222> LOCATION: (284)..(284)
<223> OTHER INFORMATION: n is a, c, g, t or u
<220> FEATURE:
<221> NAME/KEY: misc_feature
<222> LOCATION: (313)..(313)
<223> OTHER INFORMATION: n is a, c, g, t or u
<220> FEATURE:
<221> NAME/KEY: misc_feature
<222> LOCATION: (328)..(328)
<223> OTHER INFORMATION: n is a, c, g, t or u
<220> FEATURE:
<221> NAME/KEY: misc_feature
<222> LOCATION: (333)..(334)
<223> OTHER INFORMATION: n is a, c, g, t or u
<220> FEATURE:
<221> NAME/KEY: misc_feature
<222> LOCATION: (356)..(356)
<223> OTHER INFORMATION: n is a, c, g, t or u
<220> FEATURE:
<221> NAME/KEY: misc_feature
<222> LOCATION: (411)..(411)
<223> OTHER INFORMATION: n is a, c, g, t or u
<220> FEATURE:
<221> NAME/KEY: misc_feature
<222> LOCATION: (471)..(471)
<223> OTHER INFORMATION: n is a, c, g, t or u
<220> FEATURE:
<221> NAME/KEY: misc_feature
<222> LOCATION: (473)..(473)
<223> OTHER INFORMATION: n is a, c, g, t or u
<220> FEATURE:
<221> NAME/KEY: misc_feature
<222> LOCATION: (492)..(492)
<223> OTHER INFORMATION: n is a, c, g, t or u
<220> FEATURE:
<221> NAME/KEY: misc_feature
<222> LOCATION: (497)..(500)
<223> OTHER INFORMATION: n is a, c, g, t or u
<220> FEATURE:
<221> NAME/KEY: misc_feature
<222> LOCATION: (503)..(503)
<223> OTHER INFORMATION: n is a, c, g, t or u
<220> FEATURE:
<221> NAME/KEY: misc_feature
<222> LOCATION: (510)..(511)
<223> OTHER INFORMATION: n is a, c, g, t or u
<220> FEATURE:
<221> NAME/KEY: misc_feature
<222> LOCATION: (513)..(513)
<223> OTHER INFORMATION: n is a, c, g, t or u

<400> SEQUENCE: 30
ggccaccaga ggattctcag ggctcctttg tcctggactg tggaactggg ggcagctggt      60
ccctggggtc tctgaagtca gtgtctccct cactgctcac tgccatggtg tctctgcctc    120
tgcttctctg tgtccctcat cttcctccca cttcattctg actggcaagc cctgtcctgc    180
acagcttctt cccnacccc taggccttcc ccaganactc cctctnacta ggctggctgt    240
tctgttccct tcccnnctaa nactgtggcc tggcccacct cccnaggaaa taggaaaggt    300
gcagaaatca ccntggagtt gccactcntg ccnnggcttc atctcgagcc aatgtnccca    360
ggtcactaag agaatgagct tccactgtat tccatccag gctctttcc ntttgtgagg    420 ctgacctgtg acaagacaa tgggacaggg ataggcagtt cctccatcca ntntcataat    480
tgccaggcaa gntcttnnnn ccncctgcan nanccctcccc agtggatcag gggttagaga    540
tattcaaggg tagtttcagg agcacag                                       567
```

<210> SEQ ID NO 31
<211> LENGTH: 448
<212> TYPE: DNA
<213> ORGANISM: Homo sapiens
<220> FEATURE:
<221> NAME/KEY: misc_feature
<222> LOCATION: (82)..(82)
<223> OTHER INFORMATION: n is a, c, g, t or u
<220> FEATURE:
<221> NAME/KEY: misc_feature
<222> LOCATION: (96)..(97)
<223> OTHER INFORMATION: n is a, c, g, t or u

<400> SEQUENCE: 31

```
taatgcggac gtaccgactg ccagatcttt acactcaccc ctccacctgc cccgaggagt      60
ccggtcacaa gggcccagcc antcacaaag acaccnnggt gtcccttcca ttttttccca     120
cgaaggccca gaatccattt taggtttcca aacagacctt tcgtcccttc aaggtgtaac     180
caccgttttc cattccagcc atttttattgg ccacaccgtt accttactta taggtatttc    240
cccagaagaa gactccagag aggaagctca tctgaggaaa gctgagaggg aagagaaacc     300
caaacatact gaagcaaaaa aaagcctatc cttcagaaaa aagcaacaaa aagatttctg     360
ttttatcttt cgaaactaaa actattggat ttgaagatta agtatcctaa acatcactga     420
ctagaaactg ttctctttgt cagcagtg                                        448
```

<210> SEQ ID NO 32
<211> LENGTH: 396
<212> TYPE: DNA
<213> ORGANISM: Homo sapiens
<220> FEATURE:
<221> NAME/KEY: misc_feature
<222> LOCATION: (141)..(141)
<223> OTHER INFORMATION: n is a, c, g, t or u

<400> SEQUENCE: 32

```
agtgtgcatg ttcactgggc atcttccctt cgaccccttt gcccacgtgg tgaccgctgg      60
ggagctgtga gagtgtgagg ggcacgttcc agccgtctgg actctttctc tcctactgag     120
acgcagccta taggtccgca ngccagtcct cccaggaact gaaatagtga aatatgagtt     180
ggcgaggaag atcaacatat aggcctaggc caagaagaag tttacagcct cctgagctga     240
ttggggctat gcttgaaccc actgatgaag agcctaaaga agagaaacca cccactaaaa     300
gtcggaatcc tacacctgat cagaagagag aagatgatca gggtgcagct gagattcaag     360
tgcctgacct ggaagccgat ctccaggagc tatgtc                               396
```

<210> SEQ ID NO 33
<211> LENGTH: 484
<212> TYPE: DNA
<213> ORGANISM: Homo sapiens

<400> SEQUENCE: 33

```
cggtggcttg caacatgctc atgccagagc ccgctcaacg ctggctggtg ggcttcgtgt      60
tgtacacatt tctcatgggc ttcctgctgc ccgtgggggc tatctgcctg tgctacgtgc     120
tcatcattgc taagatgcgc atggtggccc tcaaggccgg ctggcagcag cgcaagcgct     180
cggagcgcaa gatcaccctta atggtgatga tggtggtgat ggtgtttgtc atctgctgga     240
tgcctttcta cgtggtgcag ctggttaacg tgtttgctga gcaggacgac gccacggtga     300
gtcagctgtc ggtcatcctc ggctatgcca acagctgcgc caaccccatc ctctatggct     360
ttctctcaga caacttcaag cgctcttttc aacgcatcct atgcctcagc tggatggaca     420
```

```
acgccgcgga ggagccggtt gactattacg ccaccgcgct caagagccgt gcctacagtg      480
tgga                                                                   484

<210> SEQ ID NO 34
<211> LENGTH: 393
<212> TYPE: DNA
<213> ORGANISM: Homo sapiens

<400> SEQUENCE: 34
tctgacttcc agaacctacg ataatagact ccatgaaatc tgtaatcagt ggccacagga       60
aactcatgca acagcccttc caaggggctc cccagcaaag cctccgtggt gtctgccccc      120 aaccctgtg cctcctggga cacaagacag gcccagcaag ggtggggtg ccacggaaag        180 cttggtggct gggcaggtcc ccagagggcc gccatcagtc ctcaaagaca tgctcagatg      240
cagtggctca ggcctggcac cagctggtcc caaggtgggg tggtgagggt acatctgctg     300
tgcacacgtg gctggacgcg ctggggcag gtccaggtca gcttcaagga ctctgcccag       360
gctaacccta gaggcctcta gtgccagcag tta                                   393

<210> SEQ ID NO 35
<211> LENGTH: 493
<212> TYPE: DNA
<213> ORGANISM: Homo sapiens

<400> SEQUENCE: 35
aggcccatgt gctgttttg acttcagtac ttcagattgc tgtgggaaca caggaggcag        60
cagccagatg agaaattgag tctgactctg gagtattata aagtccttat agttactggc      120
attaggtata gggtctgtat tattaaagag aaattattca ccaaacactt gttaaaatg       180 gcaagacagt ttatttaaga gcattgcaat aggtaagtgc tatggtctca atgtttgtgt     240
ctccctcaaa ttcataagtt gaaacttcac ttccaagatg aaggaattag gaggtgggca     300
ctttaaggga tgattatgtc ataggccaga gccctcatga acgagatcag tgcccttcta     360
aaagaggcat gggagagac ccctcacctt ttccatcata tgaggacaca gccaggaagc       420
atcatccacg aaccagaaaa ttggcccttta ccagacactg aatctgctga tgtcctgacc    480
atggacttct gag                                                         493

<210> SEQ ID NO 36
<211> LENGTH: 336
<212> TYPE: DNA
<213> ORGANISM: Homo sapiens

<400> SEQUENCE: 36
acgctgcagc gtcacattaa tctttgtgcc gccagtgcct atgccatgct tagtatgcat       60
caaatatttg agcagtacac aagtgagtac tctgagagct ccccccacca aaaatatgat     120
gattaaatac agttatgatc agatccccag agtgtggctc taaactgtat gggggccaag    180
tttgaatact gttgtgtctt acactgttat tacctatcca gtatctattt ccccatattc     240
cttataaata aaacctagat tttgattggg acagtaaggt gtcccactga aaactcattt     300
ctctaaccaa tgtgatgcca gtgcttgccc aaaaag                                336

<210> SEQ ID NO 37
<211> LENGTH: 507
<212> TYPE: DNA
<213> ORGANISM: Homo sapiens
```

<400> SEQUENCE: 37

```
gtgagtgaac gtgaaggcct gcagcattac tgtacactac catagatttt tatcaacact    60
gtacacttag ggacactaaa cttatttaaa catttttct tcaaaaataa attaacctca    120
gctcactgta actttataag ctttatattt aaaaaaactt tttgactctt ttgtagtaac   180
acttagctta aaacacaaac acattgtaca gttacacaaa atattttctt aaaaaatatt   240
ttattatatc ctattctata agcttttcct tgttttcac ttttttttaa cttttaaact    300
ttttataaaa actaagacac aaacacacac attagtgcag gcctgcatag catcaggatc   360
atcagtatca ctgtctccca cctccgcatc ttgtcccact gaaaggtctt cagcgggaat   420
atcatgcatg gagctgtcat ctcctgtgat aacaatgcct tcttctggat acctcctgaa   480
ggacctggtt gagcctgttt tacagtt                                       507
```

<210> SEQ ID NO 38
<211> LENGTH: 423
<212> TYPE: DNA
<213> ORGANISM: Homo sapiens

<400> SEQUENCE: 38

```
gaatccctta agcagaacaa ccgtgatgcc atggaactca agcccaacgg cggtgctgac    60
caaaaatgtc tcaaagtcaa cagcccaata agaatgaaga atggaaatgg aaaagggtgg   120
ctgcgactca agaataatat gggagcccat gaggagaaaa aggaagactg gaataatgtc   180
actaaagctg agtcaatggg gctattgtct gaggacccca agagcagtga ttcagagaac   240
agtgtgacca aaaacccact aaggaaaaca gattcttgtg acagtggaat tacaaaaagt   300
gaccttcgtt tggataaggc tggggaggcc cgaagtccgc tagagcacag tcccatccag   360
gctgatgcca agcaccctt ttatcccatc cccgagcagg ccttacagac cacactgcag   420
gaa                                                                  423
```

<210> SEQ ID NO 39
<211> LENGTH: 365
<212> TYPE: DNA
<213> ORGANISM: Homo sapiens
<220> FEATURE:
<221> NAME/KEY: misc_feature
<222> LOCATION: (244)..(244)
<223> OTHER INFORMATION: n is a, c, g, t or u
<220> FEATURE:
<221> NAME/KEY: misc_feature
<222> LOCATION: (253)..(253)
<223> OTHER INFORMATION: n is a, c, g, t or u

<400> SEQUENCE: 39

```
ttactctgtg attaacttcc ttctccctca ccccaaaata cagaagagtg aaatctctga    60
ccagaaagtt cctggcacct accttgggtt ctgtgaaaaa ataatggccc tggttttcaa   120
tgctgccaaa gttaagaaaa gttttcaccc cttcatttta aagcagccat aaagtgccat   180
gtgtttaacc gcaggaaaaa aagggtcttt ttaactattg agaagtagct tttcatatcc   240
ccancagggg aangaaagag cgggaaccag gagactcgtg aggactgcaa agatggtcct   300
ccctgggtac ttctgctgct ctcttctctc cagagctact ttgtgattgg cctgatggtc   360
agacc                                                                365
```

<210> SEQ ID NO 40
<211> LENGTH: 389
<212> TYPE: DNA
<213> ORGANISM: Homo sapiens

<400> SEQUENCE: 40

```
gatggagcat catgggttgg attattactg agttcaataa tctggtgggt tttgccagct    60
agaaacataa taaaatacat gataaaggaa tagaaaggaa atatatttat ttgaaattaa   120
attactgctt ataaattcat gtctctgatt ttacaaagtg taatgggtaa aattaccata   180
ttcttttttct tatttcaatc catacaatga gagtcatgtt cagttttttca ctgacttcat   240
```
```
gatggagcat catgggttgg attattactg agttcaataa tctggtgggt tttgccagct    60
agaaacataa taaaatacat gataaaggaa tagaaaggaa atatatttat ttgaaattaa   120
attactgctt ataaattcat gtctctgatt ttacaaagtg taatgggtaa aattaccata   180
ttctttttct tatttcaatc catacaatga gagtcatgtt cagttttca ctgacttcat    240
gctgggtaat gttcactctg cattagcggt tgccatgttc accgttttct tacaatgtct   300
atccagtgct tgttactgtc tcactgacag acagaagtct agctgttttc atccacataa   360
tggcaggcag ggctagtgtt gctgctgct                                    389
```

<210> SEQ ID NO 41
<211> LENGTH: 537
<212> TYPE: DNA
<213> ORGANISM: Homo sapiens

<400> SEQUENCE: 41

```
ttatgtccct gctggtattt ttgcttttttc ataaaaatta tcatttatttt ttctcaactg    60
catattgcca tcttcatttt ttaatttttct cacatattca tagaattgtt ctctgtaata   120
gatactgtac agtaattatt tgttgatcga ttaaccttttt caatgctact tccgacacct   180
acttcccatc ctccgtgtaa cagatactgt cagttaccta tccttaacag cctttccact   240
cccaacttct gtgaatggac aagagatgca attgtgatca ctgaacatga ggcaacatct   300
tctaggaaga catttccata gtcttcagac aaaagggaga gatatctttt cagacaatct   360
ttgaacaatc ctatatgaag cttacctgaa gttgctgtag ccgtttggca agtctgggga   420
gactaacaga cacactgagg atagcagaaa ataaagatag aaacagccca ggttttttggt  480
gaaattcatg agcttctgaa taacgaaccc cataccaccc tacctctata aagaat       537
```

<210> SEQ ID NO 42
<211> LENGTH: 351
<212> TYPE: DNA
<213> ORGANISM: Homo sapiens

<400> SEQUENCE: 42

```
tggatcccag catcgttggc aatagggttt taggtggagt ctatctggca ttcagagaag    60
agtcaggaaa acaattgtat tcccagcctg tgtccctagg gcacaagcaa atcccaaatt   120
ctcctcctga accctccaaa tttgtctaag aacttcgaaa actttaacaa acaggctgat   180
atcttcataa tattcccagc ctagaccaag caggaagaac attgatttca ttgaaataat   240
tgataataat gaagataatg ttttttatgat ttttatttga aaatttgcta attctttaaa   300
tggtttgttt tctacattga tggaattttt ctcttttaat ctatctacag c            351
```

<210> SEQ ID NO 43
<211> LENGTH: 528
<212> TYPE: DNA
<213> ORGANISM: Homo sapiens

<400> SEQUENCE: 43

```
tctgtttatc ccccaaatta ctacaaagca tagcgggctc tatgtttgct ctgttcgtaa    60
ctcagccact gggcaggaaa gctccacatc gttgacagtc aaagtctctg cttctacaag   120
aataggactt cttcctctcc ttaatccaac atagcagctg tgatgtcatt tctgtatttc   180
aggaagactg gcaggagatt tatggaaagg tctcttacaa ggactcttga atacaagctc   240
```

```
ctgataactt caagatcata ccactggact aagaactttc aaaattttaa tgaacaggct    300
gataccttca tgaaattcaa gacaaagaag aaaaatactc aatgttattg gactaaataa    360
tcaaaaggat aatgatttca taattttcta tttgaaaatg tgctgattct tggaatgttt    420
cattctccag atttatgaac attttttctt gagcaattgg taaagtatac ttttgtaaac    480
aaaaattgaa acatttcctt tgctctctcta tctgagtgcc ccagaatt               528
```

<210> SEQ ID NO 44
<211> LENGTH: 545
<212> TYPE: DNA
<213> ORGANISM: Homo sapiens

<400> SEQUENCE: 44

```
gggacacacc agcacagtct ggtaggctac agcagcaagt ctctaaagaa aggctgagaa     60
cacccagaac aggagagttc aggtccagga tggccagcct gttccggtcc tatctgccag    120
caatctggct gctgctgagc caactcctta gagaaagcct agcagcagag ctgaggggat    180
gtggtccccg atttggaaaa cacttgctgt catattgccc catgcctgag aagacattca    240
ccaccacccc aggagggtgg ctgctggaat ctggacgtcc caagaaatg gtgtcaacct    300 ccaacaacaa agatggacaa gccttaggta cgacatcaga attcattcct aatttgtcac    360
cagagctgaa gaaaccactg tctgaagggc agccatcatt gaagaaaata atactttccc    420
gcaaaaagag aagtggacgt cacagatttg atccattctg ttgtgaagta atttgtgacg    480
atggaacttc agttaaatta tgtacatagt agagtaatca tggactggac atctcatcca    540
ttctc                                                                545
```

<210> SEQ ID NO 45
<211> LENGTH: 166
<212> TYPE: DNA
<213> ORGANISM: Homo sapiens
<220> FEATURE:
<221> NAME/KEY: misc_feature
<222> LOCATION: (35)..(36)
<223> OTHER INFORMATION: n is a, c, g, t or u
<220> FEATURE:
<221> NAME/KEY: misc_feature
<222> LOCATION: (38)..(41)
<223> OTHER INFORMATION: n is a, c, g, t or u
<220> FEATURE:
<221> NAME/KEY: misc_feature
<222> LOCATION: (43)..(45)
<223> OTHER INFORMATION: n is a, c, g, t or u
<220> FEATURE:
<221> NAME/KEY: misc_feature
<222> LOCATION: (57)..(57)
<223> OTHER INFORMATION: n is a, c, g, t or u

<400> SEQUENCE: 45

```
tgctgtttgt gtgaaacctc cactgtgcca agcannannn nannngactg tgaatanttt     60
aacatttatt cacagatagc atgaaaagcc acagtccatt tgccatttag cttatttgat    120
tgagagaaaa ctgaggcaca ggaaggcaca gtgactgagc aagagt                   166
```

<210> SEQ ID NO 46
<211> LENGTH: 205
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is a, c, g, t or u

<400> SEQUENCE: 46

```
ggatcagtct taagaggagc ttttttttngg agcgagaaat catataaaat aaaatgaaat      60
aaaacaagga ggaaggcaac cagctgttag gggaaaaata aggcagataa aggagcgggg     120
agagaaatta attgccaacc aggaggagtt gggctgtatt tttcaaaggt ggggagagtg     180
gagcacacac cttgaggagg aaagc                                           205
```

<210> SEQ ID NO 47
<211> LENGTH: 294
<212> TYPE: DNA
<213> ORGANISM: Homo sapiens
<220> FEATURE:
<221> NAME/KEY: misc_feature
<222> LOCATION: (68)..(68)
<223> OTHER INFORMATION: n is a, c, g, t or u
<220> FEATURE:
<221> NAME/KEY: misc_feature
<222> LOCATION: (132)..(132)
<223> OTHER INFORMATION: n is a, c, g, t or u
<220> FEATURE:
<221> NAME/KEY: misc_feature
<222> LOCATION: (193)..(193)
<223> OTHER INFORMATION: n is a, c, g, t or u
<220> FEATURE:
<221> NAME/KEY: misc_feature
<222> LOCATION: (207)..(207)
<223> OTHER INFORMATION: n is a, c, g, t or u
<220> FEATURE:
<221> NAME/KEY: misc_feature
<222> LOCATION: (213)..(213)
<223> OTHER INFORMATION: n is a, c, g, t or u
<220> FEATURE:
<221> NAME/KEY: misc_feature
<222> LOCATION: (219)..(220)
<223> OTHER INFORMATION: n is a, c, g, t or u
<220> FEATURE:
<221> NAME/KEY: misc_feature
<222> LOCATION: (242)..(242)
<223> OTHER INFORMATION: n is a, c, g, t or u
<220> FEATURE:
<221> NAME/KEY: misc_feature
<222> LOCATION: (260)..(260)
<223> OTHER INFORMATION: n is a, c, g, t or u
<220> FEATURE:
<221> NAME/KEY: misc_feature
<222> LOCATION: (267)..(267)
<223> OTHER INFORMATION: n is a, c, g, t or u

<400> SEQUENCE: 47

```
gaaccatttg agattcaatg cctgtgtcca gctcccagga gtccaaccgt gaaatccaca      60
agtgcagncc ccaccctgtc ctgcagttct ctttcccctta tgataatgtg gttgagtcct    120
ttgtcactcc cntcctcctg ctggctgcag aaatgacctc agcccaggcc agagacccca    180
gctctggcaa ggncctcttg tggtcgncca ggnccccagnn tgaaagccaa gcagaatcag   240
gncaggatct ctagcgggan gggaaancct gataggacct ttgtcagact tttg          294
```

<210> SEQ ID NO 48
<211> LENGTH: 432
<212> TYPE: DNA
<213> ORGANISM: Homo sapiens

<400> SEQUENCE: 48

```
acatttaccg tattacctag cactttcatt ccttgttgtc tactccaaag gaaaaaaacc      60
tatgtccaca caacacatga atgtgaatat tagtagcagc tttatccata atagtccata    120
aagtagaaac acatcaaata tctatcagct gatgaaagaa taaacaaatg ggagtgatcc    180
atacaattta atagaatcta gcacctaaaa aaataaaata ttgatacgtg ctacaacaca    240
```

```
ggtgaaccac aaaagcacat taatctaagt gaaagaagac agatacaaaa aaccacatgt    300
tgtatgactc tattttatg atatccagaa aagacaaatc tgtagtgtca gtaagtcaat    360 tagggttgt ctggagctgg ggagtgggaa taaggggtgg tattgatgag catgagggat    420
ttcttaggaa tt                                                        432
```

<210> SEQ ID NO 49
<211> LENGTH: 541
<212> TYPE: DNA
<213> ORGANISM: Homo sapiens
<220> FEATURE:
<221> NAME/KEY: misc_feature
<222> LOCATION: (54)..(54)
<223> OTHER INFORMATION: n is a, c, g, t or u
<220> FEATURE:
<221> NAME/KEY: misc_feature
<222> LOCATION: (67)..(67)
<223> OTHER INFORMATION: n is a, c, g, t or u
<220> FEATURE:
<221> NAME/KEY: misc_feature
<222> LOCATION: (79)..(79)
<223> OTHER INFORMATION: n is a, c, g, t or u
<220> FEATURE:
<221> NAME/KEY: misc_feature
<222> LOCATION: (103)..(103)
<223> OTHER INFORMATION: n is a, c, g, t or u
<220> FEATURE:
<221> NAME/KEY: misc_feature
<222> LOCATION: (127)..(127)
<223> OTHER INFORMATION: n is a, c, g, t or u
<220> FEATURE:
<221> NAME/KEY: misc_feature
<222> LOCATION: (168)..(168)
<223> OTHER INFORMATION: n is a, c, g, t or u
<220> FEATURE:
<221> NAME/KEY: misc_feature
<222> LOCATION: (498)..(499)
<223> OTHER INFORMATION: n is a, c, g, t or u

<400> SEQUENCE: 49

```
gtgaatccta gagtagtttg ctatcaactt ctgatctttg cacattctgg attnggcata     60
taatgtnaca gcagtgccna ttgtaatgtt gcacaaagta gtntagcaat ttcttggttc    120
accaggntta gagataacat tgtagaaatg atccagcatc tttaacantc tgtggtttaa    180
ggtggggcac ttaggggtag aatcaataac aatgttagaa atcaaattag acaagataac    240
tgaaacagca tgatccatgt gtgactccaa gttataaagg aggacatgga ttaatgtat     300 acttctaggc tataggggta gtacaagtgg aaggacacca tcttagcatc agatcacttt    360
ctgagcaact ttggcaaatc ttttaaattc tctaatgtgt agtttttaa tatatgacac    420 aggtgtaaag aaaataaagc aagtgaatgt atgtgaaagc caatgctgac tgggcacggg    480
ggctcacgcc tgaaattnnt agcactttgg gaggcagagc cggggatatc acttgagccc    540
a                                                                    541
```

<210> SEQ ID NO 50
<211> LENGTH: 393
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, t or u
<220> FEATURE:
<221> NAME/KEY: misc_feature
<222> LOCATION: (65)..(65)
<223> OTHER INFORMATION: n is a, c, g, t or u
<220> FEATURE:
<221> NAME/KEY: misc_feature

```
<222> LOCATION: (67)..(69)
<223> OTHER INFORMATION: n is a, c, g, t or u
<220> FEATURE:
<221> NAME/KEY: misc_feature
<222> LOCATION: (86)..(86)
<223> OTHER INFORMATION: n is a, c, g, t or u
<220> FEATURE:
<221> NAME/KEY: misc_feature
<222> LOCATION: (88)..(88)
<223> OTHER INFORMATION: n is a, c, g, t or u
<220> FEATURE:
<221> NAME/KEY: misc_feature
<222> LOCATION: (191)..(191)
<223> OTHER INFORMATION: n is a, c, g, t or u
<220> FEATURE:
<221> NAME/KEY: misc_feature
<222> LOCATION: (285)..(285)
<223> OTHER INFORMATION: n is a, c, g, t or u

<400> SEQUENCE: 50
tcatctacac gctggccagc aaggagatgc ggcgggcctt cttccgtctg gtctgcaact      60
gcntngnnng gggacggggg gcccgngncc tcacccatcc agcctgcgct cgacccaagc     120
agaagtaaat caagcagcag caacaatagc agccactctc cgaaggtcaa ggaagacctg     180
ccccacacag nccctcatc ctgcatcatg gacaagaacg cagcacttca gaatgggatc      240
ttctgcaact gatcgtctcc atgcgcctg ctctgcggct gtgtncttat ttattgcatg      300
cgtcgcttcc acaggggccc ctcaagagct gtgactcggg agagctacct tactttgacc     360
aacagcctgc ccagtgtgga tgtctcttac aga                                  393

<210> SEQ ID NO 51
<211> LENGTH: 543
<212> TYPE: DNA
<213> ORGANISM: Homo sapiens

<400> SEQUENCE: 51
cctccttagc cttagaagcc agtggtgccc tgaccagagg ggaccctgtg ttcacaggca      60
tcctcaagga ttatcttcga gagttgccca ccccactcat cacccagccc ctgtataagg     120
tggtactgga ggccatggcc cggaccccc caaacagagt tccccccacc actgagggca      180
cccgagggct cctcagctgc ctgccagatg tggaaagggc cacgctgacg cttctcctgg     240
accacctgcg cctcgtctcc tccttccatg cctacaaccg catgacccca cagaacttgg     300
ccgtgtgctt cgggcctgtg ctgctgccgg cacgccaggc gcccacaagg cctcgtgccc     360
gcagctccgg cccaggcctt gccagtgcag tggacttcaa gcaccacatc gaggtgctgc     420
actacctgct gcagtcttgg ccaggtgagt tcatgcccag ggcctgcacc accaatctga     480
gccaggctgc tacaatcccc gcctgccccg acaatctcca gatgtcgcgc cttacttgcg     540
acc                                                                   543

<210> SEQ ID NO 52
<211> LENGTH: 367
<212> TYPE: DNA
<213> ORGANISM: Homo sapiens

<400> SEQUENCE: 52
tcgcctgtac cagctggcat atgacaccta tcaggagttt aaccccagaa cctccctctg      60
cttctcagag tctattccaa caccttccaa cagggtgaaa acgcagcaga aatctaacct     120
agagctgctc cgcatctccc tgctgctcat ccagtcatgg ctggagcccg tgcagctcct     180
caggagcgtc ttcgccaaca gcctggtgta tggcgcctcg gacagcaacg tctatcgcca     240
```

| | |
|---|---|
| cctgaaggac ctagaggaag gcatccaaac gctgatgtgg aggctggaag atggcagccc | 300 |
| ccggactggg cagatcttca atcagtccta cagcaagttt gacacaaaat cgcacaacga | 360 |
| tgacgca | 367 |

```
<210> SEQ ID NO 53
<211> LENGTH: 470
<212> TYPE: DNA
<213> ORGANISM: Homo sapiens

<400> SEQUENCE: 53
```

| | |
|---|---|
| cccccgagga caacctggag atcgttctgc acagatggga gaacaacagc tgtgttgaga | 60 |
| agaaggtcct tggagagaag actgggaatc caaagaagtt caagatcaac tatacggtgg | 120 |
| cgaacgaggc cacgctgctc gatactgact acgacaattt cctgtttctc tgcctacagg | 180 |
| acaccaccac ccccatccag agcatgatgt gccagtacct ggccagagtc ctggtggagg | 240 |
| acgatgagat catgcaggga ttcatcaggg ctttcaggcc cctgcccagg cacctatggt | 300 |
| acttgctgga cttgaaacag atggaagagc cgtgccgttt ctagctcacc tccgcctcca | 360 |
| ggaagaccag actcccaccc ttccacacct ccagagcagt gggacttcct cctgcccttt | 420 |
| caaagaataa ccacagctca gaagacgatg acgtggtcat ctgtgtcgcc | 470 |

```
<210> SEQ ID NO 54
<211> LENGTH: 504
<212> TYPE: DNA
<213> ORGANISM: Homo sapiens

<400> SEQUENCE: 54
```

| | |
|---|---|
| gtgtgtggat tcaacagtcg accccagctg tcgcagagcg cgaggaagct gcgcagtaaa | 60 |
| ccccttacat atcaacctct gaggaccggt ttttctgcac ctggtggtcc ttctagacgt | 120 |
| ctaggaggat cgtgttctca ggagagggtt cttcagcatc tgtgctgaag aacactgccc | 180 |
| cagcgggtca catgcaagat tccaccttcg agcaacatag ctgacactct gcagcccagt | 240 |
| tgtcacttgt aacaaacccc agtgggtcac atagtgaggg gaggcaaggc agcgtaaggc | 300 |
| agtggctgaa ctatcccaga aaacaaggat cacaggcccc cagtgacacc aatgttgcag | 360 |
| aaacacctgc agtggcaagt cagatgtcct ccaggaccag gcagataaca aggagtaggg | 420 |
| gtctgcagag gcctcgggag ggtctgcacc atccaaagaa atcaattgtt ctgcacagtg | 480 |
| gtaaggatcc agtgttccca gcac | 504 |

```
<210> SEQ ID NO 55
<211> LENGTH: 382
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (65)..(66)
<223> OTHER INFORMATION: n is a, c, g, t or u
<220> FEATURE:
<221> NAME/KEY: misc_feature
<222> LOCATION: (70)..(70)
<223> OTHER INFORMATION: n is a, c, g, t or u
<220> FEATURE:
<221> NAME/KEY: misc_feature
<222> LOCATION: (72)..(72)
<223> OTHER INFORMATION: n is a, c, g, t or u
<220> FEATURE:
<221> NAME/KEY: misc_feature
```

<222> LOCATION: (345)..(345)
<223> OTHER INFORMATION: n is a, c, g, t or u

<400> SEQUENCE: 55

| | | | | | |
|---|---|---|---|---|---|
| gaacaccatt | gtcttcaata | acctgtnggg | catatccagg | aggcacatag | ataggaggca | 60
| caganncatn | tnggacatc | attggaacct | gagcaggacc | tgtaatgcac | tgaaactgtc | 120
| catcttctct | tcttattgta | aatgcttctc | ctgggttaac | ttgtaccaga | ataacctgtt | 180
| gtgttccatc | tgcacttaca | ataggggcag | acaaaagaga | aatatcacta | cttaagatct | 240
| gagttgtatc | cagtagtggt | ggatgttctg | ccattatcaa | taagacatta | atatactgaa | 300
| taacgctcca | attctccgag | tcacgccgtt | ctgaggcaga | aggcngctcc | tctggcgcct | 360
| cttcttaggg | ttcctgatcg | tt | | | 382

<210> SEQ ID NO 56
<211> LENGTH: 440
<212> TYPE: DNA
<213> ORGANISM: Homo sapiens
<220> FEATURE:
<221> NAME/KEY: misc_feature
<222> LOCATION: (83)..(83)
<223> OTHER INFORMATION: n is a, c, g, t or u
<220> FEATURE:
<221> NAME/KEY: misc_feature
<222> LOCATION: (141)..(141)
<223> OTHER INFORMATION: n is a, c, g, t or u
<220> FEATURE:
<221> NAME/KEY: misc_feature
<222> LOCATION: (262)..(262)
<223> OTHER INFORMATION: n is a, c, g, t or u
<220> FEATURE:
<221> NAME/KEY: misc_feature
<222> LOCATION: (373)..(373)
<223> OTHER INFORMATION: n is a, c, g, t or u

<400> SEQUENCE: 56

| | | | | | |
|---|---|---|---|---|---|
| gaagtgggag | cggctcagca | taggatgggc | acgccatcag | ccgtcaccag | gcgcccggtg | 60
| gtgggtcgt | aggtgcccgc | cangtagtag | aggtcctgcc | ggtcctggca | cttgcggctc | 120
| cgggccatct | gctcatactg | ntcgcgcgcc | acgacctggc | acttgtggga | gatggtctgc | 180
| acgtcgttct | catcctcgtg | gcaggactgg | tacagcgcat | tcttgccgtc | gcactgcctc | 240
| ttgcccagct | tggtctcctc | angggtggta | gaaccacttg | accttgacca | ccatgttgct | 300
| gccccacgac | tcccacatgc | tctcgatgcg | gccgatgtag | gggaggttgg | gccgcccagc | 360
| tgacaggaag | acngcacagt | ccccgacacg | cagggtctcc | tcgccccgca | cgatggcctt | 420
| gtagaacagc | ttccgggcct | | | | 440

<210> SEQ ID NO 57
<211> LENGTH: 265
<212> TYPE: DNA
<213> ORGANISM: Homo sapiens

<400> SEQUENCE: 57

| | | | | | |
|---|---|---|---|---|---|
| catcgcccac | caaggcctgg | gtgggtgaga | acagtgccca | caaggagacc | ctgagtaaca | 60
| gagactcaca | gcccatccag | gtctctgggc | aggaaattga | aggaatcatc | acattttaca | 120
| gaggaggaga | ctgcagctca | gagtggggga | agtgtgtgca | ccaggccaca | ggcaagtctg | 180
| tccagagcac | tggtaggaat | gagggaaact | aggaatgacc | actttaaaaa | gttagatgag | 240
| aagaatttca | aggccgggcg | cggtg | | | 265

<210> SEQ ID NO 58

```
<211> LENGTH: 355
<212> TYPE: DNA
<213> ORGANISM: Homo sapiens
<220> FEATURE:
<221> NAME/KEY: misc_feature
<222> LOCATION: (229)..(229)
<223> OTHER INFORMATION: n is a, c, g, t or u

<400> SEQUENCE: 58
gctttatgca gtttgtcctt tcagttttca ggaatgagac ctcttgaccc ctcccctcca      60
atgcagcccc tactaagggg gagtttaagg agccatacat agttctataa ttcaaatcaa     120
gtaaacatgc ttcttgtccc aggttaactt gtgctgcctc agtcgctgtt taaacatttt     180
tatacgcact gttaacctgc ctgcccatta ccctattact tttaatggnt aaactactgt     240
tccctgggca gttgtctctt ttaacgtccc accctaaact tgccaaccct catatgaagg     300
cctcaggctt gttattggca aaggtcagaa gtcttaagct agtgaccttg caggc          355

<210> SEQ ID NO 59
<211> LENGTH: 443
<212> TYPE: DNA
<213> ORGANISM: Homo sapiens

<400> SEQUENCE: 59
ccctgacggc agaagagccc agcttcctgc agccctgag gcgacaggct ttcctgagga       60
gtgtgagtat gccagccgag acagcccaca tctcttcacc ccaccatgag ctccggcggc     120
cggtgctgca acgccagacg tccatcacac agaccatccg caggggggacc gccgactggt    180
ttggagtgag caaggacagt gacagcaccc agaaatggca gcgcaagagc atccgtcact    240
gcagccagcg ctacgggaag ctgaagcccc aggtcctccg ggagctggac ctgcccagcc    300
aggacaacgt gtcgctgacc agcaccgaga cgccaccccc actctacgtg gggccatgcc    360
agctgggcat gcagaagatc atagaccccc tggcccgtgg ccgtgccttc cgtgtggcag    420
atgacactgc ggaaggcctg agt                                            443

<210> SEQ ID NO 60
<211> LENGTH: 552
<212> TYPE: DNA
<213> ORGANISM: Homo sapiens

<400> SEQUENCE: 60
gtctcgaggc agggctgaca catggtgcca tagccagcgg agggcgctca gtgagtgccc      60
cgggccttct agacaacagg caggaaggat gaacctcagg gcaccccag gtggtgcgga     120
aagccaggca gttgggacag aggtgcccac gagggcagag gccggtgcta aggggatggg    180
gaagaaggga caagattccc agagaggaga ggaggctgtt ggtaggaaag tggcagggct    240
gggggagacc cagccccaag ggtccggggc ggaggatgct tgttctttt ctggttttgg     300
ttcctctttc gcgggggtg ggggaggtca acagggactg agtggggcag aggcccagaa    360
gtgccagcct ggggagccgt ttgggggcag ccccttctgc ccaccccatc cttcttcctc    420
tccagagatg ccaggggggc gtgtatgctc tgcccctccc ctcagacagg gctgggtgg    480
ggaggctctt taggctcagg agaagcattt taaagaaacc cccaccctgc cgcccgcatt    540
ataaacacag ga                                                       552

<210> SEQ ID NO 61
<211> LENGTH: 361
<212> TYPE: DNA
<213> ORGANISM: Homo sapiens
```

<400> SEQUENCE: 61

```
ctctttatcc ctcagattac tccaaagcat aatgggctct atgcttgctc tgctcgtaac    60
tcagccactg gcgaggaaag ctccacatcc ttgacaatca gagtcattgc tcctccagga   120
ttaggaactt tttgctttca ataatccaag tagcagccct gatgtcattt ttgtatttca   180
ggaagactgg caggagattt atggaaaaga ctatgaaaag gactcttgaa tacaagttcc   240
tgataacttc aagatcatac cactggacta agaactttca aaattttgat gaacaggctg   300
ataccttcat gaaattcaag acaaagaaga aagaactcc atttcattgg actaaataac    360
a                                                                   361
```

<210> SEQ ID NO 62
<211> LENGTH: 238
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, t or u
<220> FEATURE:
<221> NAME/KEY: misc_feature
<222> LOCATION: (33)..(33)
<223> OTHER INFORMATION: n is a, c, g, t or u
<220> FEATURE:
<221> NAME/KEY: misc_feature
<222> LOCATION: (38)..(38)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u
<220> FEATURE:
<221> NAME/KEY: misc_feature
<222> LOCATION: (77)..(77)
<223> OTHER INFORMATION: n is a, c, g, t or u
<220> FEATURE:
<221> NAME/KEY: misc_feature
<222> LOCATION: (91)..(91)
<223> OTHER INFORMATION: n is a, c, g, t or u

<400> SEQUENCE: 62

```
caaagtggga ggattacaag tgttatccna ccnatgcntg gacaggaata tttttaaata    60
atgaaaccna gttccnttt cgctttgtaa ngttaatgca tgtattgatg gtgagtagag   120
aacaatgaca caatctctag agagacatag gtgttcggcc tggctcaatc actagcctta   180
tagtctcaca ggaaaatatg aacttcatca aaatagctaa ttattaccac atcatgga     238
```

<210> SEQ ID NO 63
<211> LENGTH: 355
<212> TYPE: DNA
<213> ORGANISM: Homo sapiens

<400> SEQUENCE: 63

```
atgcagatga cgttgtggcc accgcactgg ccgtggagcc catgaagttt gtctacagag    60
gcaggatcgc tgtgttctct gtgaccgtgc tgcacgacga ccggattgtc ctggtggctg   120
agcagcggcc ggatgcctcg gaggaggaca gcttccagtg gatgagccgt gtgctgcagg   180
tgggcgcccc ggcacggcct atggttcggt gaatctccca agctggcacc cccactccac   240
tccaagtgcc aagtggttgg cttgtcccgc ccggtcctcc ctggctccag ctttgtttat   300
ctgtattttt cattgcaaat tgacaaatta cagctgtatg tatttacggg ataca         355
```

<210> SEQ ID NO 64

<211> LENGTH: 230
<212> TYPE: DNA
<213> ORGANISM: Homo sapiens

<400> SEQUENCE: 64

```
cctccctcaa agctactaaa catgaaaaca ttgtgcctat atgataaaaa tgtcaatatt      60
gctggtgata ctgatgctga tggaaatgac gatattagct gccattaacg tagtatctaa     120
tgtgtgccaa acaatattaa aaattgctgt atatacatgt ttgccattta ttatttataa    180
ccttaacaag atgtctcact cataagacta ctttccgcac tatgatacag                230
```

<210> SEQ ID NO 65
<211> LENGTH: 552
<212> TYPE: DNA
<213> ORGANISM: Homo sapiens

<400> SEQUENCE: 65

```
agtggcctta gacataactg ctgcccaagg agccacctgt gccctttag gaacacaatg       60
ttgtaccttta tccctgacaa tcagcagaac ataacagcag ccctgcaaag gggtcttcca   120
ggagattaag gtgactgaga gcctcactgt caacccctg cagagatggt gagcatccct     180
aggttctggc gtacattggg ccctaatagt cataagtatc atagctgaga tcctagtagt    240
gagctgttgc tctctgtatt gttgttgtgg gttatggact cagggctccg ccatataggc    300
atgtgtccct gcctggagga cgccctcagc ctaggggtg tagtgtaagg gaaatggctg     360
tgctttagtc aggagtaggc tgaggcagcc ttctggtgca gcatgactca gtgggtttgg    420
agtgcaagca cacaaccttg ctcgttatgt aaccacacca catgaggccc attaggtaac    480
aactcacatg agctcgtgtt tggctcagag ccactattgt ctgtaaaagg tataccttgc    540
tgatgctgca ca                                                         552
```

<210> SEQ ID NO 66
<211> LENGTH: 508
<212> TYPE: DNA
<213> ORGANISM: Homo sapiens
<220> FEATURE:
<221> NAME/KEY: misc_feature
<222> LOCATION: (48)..(48)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u
<220> FEATURE:
<221> NAME/KEY: misc_feature
<222> LOCATION: (125)..(125)
<223> OTHER INFORMATION: n is a, c, g, t or u
<220> FEATURE:
<221> NAME/KEY: misc_feature
<222> LOCATION: (127)..(129)
<223> OTHER INFORMATION: n is a, c, g, t or u
<220> FEATURE:
<221> NAME/KEY: misc_feature
<222> LOCATION: (132)..(137)
<223> OTHER INFORMATION: n is a, c, g, t or u
<220> FEATURE:
<221> NAME/KEY: misc_feature
<222> LOCATION: (139)..(139)
<223> OTHER INFORMATION: n is a, c, g, t or u
<220> FEATURE:
<221> NAME/KEY: misc_feature
<222> LOCATION: (378)..(378)
<223> OTHER INFORMATION: n is a, c, g, t or u
<220> FEATURE:
<221> NAME/KEY: misc_feature
<222> LOCATION: (421)..(421)
<223> OTHER INFORMATION: n is a, c, g, t or u

```
<220> FEATURE:
<221> NAME/KEY: misc_feature
<222> LOCATION: (474)..(474)
<223> OTHER INFORMATION: n is a, c, g, t or u

<400> SEQUENCE: 66
gggtgactgg tctaagtgct caattacctg tggcaaagga atgcagtncc gtgtnatcca      60
atgcatgcat aagatcacag gaagacatgg aaatgaatgt ttttcctcag aaaaacctgc     120
agcanannng cnnnnnnanc ttcaaccctg caatgagaaa attaatgtaa ataccataac     180
atcacccaga ctggctgctc tgactttcaa gtgcctggga gatcagtggc cagtgtactg     240
ccgagtgata cgtgaaaaga acctatgtca ggacatgcgg tggtatcagc gctgctgtga     300
aacatgcagg gacttctatg cccaaaagct gcagcagaag agttgacctc tagcaggctg     360
gctggatcac agctcttngc aattacatta tttataaaca cacacactag catgtttttc     420
nagaccaaat attatcagat tacatataat ttaatcaaat taatttattt tttntgcctg     480
ccaaacatcc aatgtggtgc ttgttttg                                        508

<210> SEQ ID NO 67
<211> LENGTH: 410
<212> TYPE: DNA
<213> ORGANISM: Homo sapiens

<400> SEQUENCE: 67
gcatgtgtaa aaagtccttc agccacaaaa ccaacctgcg gtctcatgag agaatccaca      60
caggagaaaa gccttataca tgtccctttt gtaagacaag ctaccgccag tcatccacat     120
accaccgcca tatgaggact catgagaaaa ttaccctgcc aagtgttccc tccacaccag     180
aagcttccta agctgctggt ctgataatgt gtataaatat gtatgcaagt atgtatattc     240
ctatagtatt tatctactta ggatataaga tataatctcc tgattatgct ttcaatttat     300
tgtcttgctt cattaaaatg taaggctaag gagagcatgg aatttgtcag ttttgttcac     360
taaagtattc caagtggttg ggaaagtgga acatttccaa gaaccaataa                410

<210> SEQ ID NO 68
<211> LENGTH: 291
<212> TYPE: DNA
<213> ORGANISM: Homo sapiens

<400> SEQUENCE: 68
cacaggatgt ggtctctacc gtgattcctg agcatgcatg cacccttct cctgccaata       60 gaggggagga agtcggaggg gtgtctttat gcctataaac ttgccttgga atccagcctc     120
actccctttc ctcctggagt tgagaagccc ccacagagac tggctatggg ggagtgactg     180
tctataggtt ccttggatgt cctgcctatc tgcaaaatga gaatgagatc gatacccttca   240 tgaggctgta agatggcaga tataaaagtg ctgtgttatc tcaaaagggt g              291

<210> SEQ ID NO 69
<211> LENGTH: 326
<212> TYPE: DNA
<213> ORGANISM: Homo sapiens
<220> FEATURE:
<221> NAME/KEY: misc_feature
<222> LOCATION: (47)..(47)
<223> OTHER INFORMATION: n is a, c, g, t or u
<220> FEATURE:
<221> NAME/KEY: misc_feature
<222> LOCATION: (58)..(58)
<223> OTHER INFORMATION: n is a, c, g, t or u
<220> FEATURE:
```

<220> FEATURE:
<221> NAME/KEY: misc_feature
<222> LOCATION: (60)..(60)
<223> OTHER INFORMATION: n is a, c, g, t or u
<220> FEATURE:
<221> NAME/KEY: misc_feature
<222> LOCATION: (65)..(65)
<223> OTHER INFORMATION: n is a, c, g, t or u
<220> FEATURE:
<221> NAME/KEY: misc_feature
<222> LOCATION: (218)..(219)
<223> OTHER INFORMATION: n is a, c, g, t or u

<400> SEQUENCE: 69

```
actgtgtgca gcatattgca ggctttcact catttaatat ctacaangtc ctcaatangn    60
atatnaatta cttatgattt ccctgttttt tcttcctata aggaagctga ggcacaagtt   120
aatcaaagtc tcttggccta gggtgacaca gctaagattt gtacctagag atttctgagt   180
gttgacttct ctcctgcccc cacctatctc cccccccnna aaaaaaaaca caacaacaac   240
aacaacagaa cataccaggg attcatggct tgcccaatgt tggaggggga gaagagagga   300
gagggatgag ataagctcct cccacc                                        326
```

<210> SEQ ID NO 70
<211> LENGTH: 352
<212> TYPE: DNA
<213> ORGANISM: Homo sapiens
<220> FEATURE:
<221> NAME/KEY: misc_feature
<222> LOCATION: (61)..(61)
<223> OTHER INFORMATION: n is a, c, g, t or u
<220> FEATURE:
<221> NAME/KEY: misc_feature
<222> LOCATION: (120)..(120)
<223> OTHER INFORMATION: n is a, c, g, t or u
<220> FEATURE:
<221> NAME/KEY: misc_feature
<222> LOCATION: (152)..(152)
<223> OTHER INFORMATION: n is a, c, g, t or u

<400> SEQUENCE: 70

```
ttctgttttc ttcttaaagt catttatatt atgtattact cttaaagaat gttttagtct    60
ncattttagt agtctgtgca taaggtagta atacatgtac acaaagaaaa attcacaagn   120
cccattcagg tgtcttttag aacattattt anccactaaa tatttataca gttgacataa   180
tgcttattat gcccttgaat aatagaattt gttttgtttt tacttcttat ccataagcat   240
tggccttaca ttgcctcaag aggaacagaa tttattatta aacaggattc ttaaatccat   300
aactcatatt gtgacttcat acattttgta accctagtag tgaatatacc ct           352
```

<210> SEQ ID NO 71
<211> LENGTH: 414
<212> TYPE: DNA
<213> ORGANISM: Homo sapiens

<400> SEQUENCE: 71

```
gcccaaatcg cgcaggtctg ggacctgatt gcgggccacg aggcgcaatt cggggcggag    60
ctgctgctca ggctcttcac ggtgtacccc agcaccaagg tctacttccc gcacctgagc   120
gcctgccagg acgcgacgca gctgctgagc cacgggcagc gcatgctggc ggctgtgggc   180
gcggcggtgc agcacgtgga caacctgcgc gccgcgctga gcccgctggc ggacctgcac   240
gcgctcgtgc tgcgcgtgga cccagccaac tttccgctgc taatccagtg tttccacgtc   300
gtgctggcct cccacctgca ggacgagttc accgtgcaaa tgcaagcggc gtgggacaag   360
ttcctgactg gtgtggccgt ggtgctgacc gaaaaatacc gctgagccct gtgc         414
```

```
<210> SEQ ID NO 72
<211> LENGTH: 533
<212> TYPE: DNA
<213> ORGANISM: Homo sapiens
<220> FEATURE:
<221> NAME/KEY: misc_feature
<222> LOCATION: (51)..(51)
<223> OTHER INFORMATION: n is a, c, g, t or u
<220> FEATURE:
<221> NAME/KEY: misc_feature
<222> LOCATION: (68)..(68)
<223> OTHER INFORMATION: n is a, c, g, t or u
<220> FEATURE:
<221> NAME/KEY: misc_feature
<222> LOCATION: (124)..(124)
<223> OTHER INFORMATION: n is a, c, g, t or u
<220> FEATURE:
<221> NAME/KEY: misc_feature
<222> LOCATION: (138)..(138)
<223> OTHER INFORMATION: n is a, c, g, t or u
<220> FEATURE:
<221> NAME/KEY: misc_feature
<222> LOCATION: (208)..(208)
<223> OTHER INFORMATION: n is a, c, g, t or u
<220> FEATURE:
<221> NAME/KEY: misc_feature
<222> LOCATION: (213)..(213)
<223> OTHER INFORMATION: n is a, c, g, t or u
<220> FEATURE:
<221> NAME/KEY: misc_feature
<222> LOCATION: (220)..(220)
<223> OTHER INFORMATION: n is a, c, g, t or u
<220> FEATURE:
<221> NAME/KEY: misc_feature
<222> LOCATION: (242)..(242)
<223> OTHER INFORMATION: n is a, c, g, t or u
<220> FEATURE:
<221> NAME/KEY: misc_feature
<222> LOCATION: (251)..(251)
<223> OTHER INFORMATION: n is a, c, g, t or u
<220> FEATURE:
<221> NAME/KEY: misc_feature
<222> LOCATION: (258)..(258)
<223> OTHER INFORMATION: n is a, c, g, t or u
<220> FEATURE:
<221> NAME/KEY: misc_feature
<222> LOCATION: (281)..(281)
<223> OTHER INFORMATION: n is a, c, g, t or u
<220> FEATURE:
<221> NAME/KEY: misc_feature
<222> LOCATION: (286)..(286)
<223> OTHER INFORMATION: n is a, c, g, t or u
<220> FEATURE:
<221> NAME/KEY: misc_feature
<222> LOCATION: (357)..(357)
<223> OTHER INFORMATION: n is a, c, g, t or u

<400> SEQUENCE: 72
tgccagctac aggtgctcac ctgaaaagca agccagacca tattaaccct nggcattgct      60
ggtacctngg aagactttct gattcaatgc tttccacctc ctcctacccc tcaccacccc     120
cgtnggcatg aaatcctngg gggctgcttt agaaattgtt ttctttggct gctggtgggg     180
gtgctgctgg tggggttttg cacagctngg canactgcan ccagtctggt gggggtttgc     240
anagctggca nactgcancc agtctcctgc ctgctgccaa naaggnccat ttcccaagca     300
ctggcttttg agaagttggg gctctgaagt gggaacacaa ggctgccttt tgcaggncca     360
ggtgtaaatt ctccccctgc cactttcagc ctagcgtgaa acagatggag tgtgcattcc     420
cacttccctt tatggtaccc tggaatgatg gagctgccca gggcatcgcc acgttactct     480
ctagacagtc tctttgtctt cctgcaatgg cagcgccgag gttgtatatt tct            533
```

<210> SEQ ID NO 73
<211> LENGTH: 492
<212> TYPE: DNA
<213> ORGANISM: Homo sapiens
<220> FEATURE:
<221> NAME/KEY: misc_feature
<222> LOCATION: (226)..(226)
<223> OTHER INFORMATION: n is a, c, g, t or u
<220> FEATURE:
<221> NAME/KEY: misc_feature
<222> LOCATION: (234)..(235)
<223> OTHER INFORMATION: n is a, c, g, t or u
<220> FEATURE:
<221> NAME/KEY: misc_feature
<222> LOCATION: (253)..(253)
<223> OTHER INFORMATION: n is a, c, g, t or u
<220> FEATURE:
<221> NAME/KEY: misc_feature
<222> LOCATION: (272)..(272)
<223> OTHER INFORMATION: n is a, c, g, t or u

<400> SEQUENCE: 73
gaagggctgc cttattttag agcacagatt ttctgaatat ctattttgac aggttcgatc      60 ctctccccctt cctgccttcc ttctgtcgat tttcaatgtc ttgatggtgt cccacctgag    120
tggcctttag agatgtgagt tgtgaggcac tggggaggca ggcacacgtc ctccagccca    180
agactgccta atttaacagg gatttctgca ttctggaaca agcctnccat tttnnccccca   240 agcaggatta ctnccagagg gcaaaacaca gncccaatag tatcacattt cctttctgct    300
ttagcaaaaa taaccactgt ctcattcatg ggaaaaggcc gccaaacaaa tttgttactg    360
gaaccatttg taacaacttc tagttttgcac tgccttggag caagcacact ttgtagagga   420
gggatttgca gttacttggg caacaaggta accactgatc attacaggaa gcttcagaaa   480
ccgtgggacc ag                                                        492

<210> SEQ ID NO 74
<211> LENGTH: 354
<212> TYPE: DNA
<213> ORGANISM: Homo sapiens
<220> FEATURE:
<221> NAME/KEY: misc_feature
<222> LOCATION: (90)..(90)
<223> OTHER INFORMATION: n is a, c, g, t or u
<220> FEATURE:
<221> NAME/KEY: misc_feature
<222> LOCATION: (108)..(108)
<223> OTHER INFORMATION: n is a, c, g, t or u
<220> FEATURE:
<221> NAME/KEY: misc_feature
<222> LOCATION: (261)..(261)
<223> OTHER INFORMATION: n is a, c, g, t or u

<400> SEQUENCE: 74
ctgttgctgc tgctgagcat gggcggggca tgggcatcca gggagccgct tcggccatgg      60
tgccacccca tcaatgccat cctggctgtn gagaaggagg ctgcccngt gtgcatcacc      120 gtcaacacca ccatctgtgc cggctactgc cccaccatga tgcgcgtgct gcaggcggtc    180
ctgccgcccc tgcctcaggt ggtgtgcacc taccgtgatg tgcgcttcga gtccatccgg    240
ctccctggct gccgcgtgg ngtggacccc gtggtctcct tccctgtggc tctcagctgt    300
cgctgtggac cctgccgccg cagcacctct gactgtgggg gtcccaaaga ccac          354

<210> SEQ ID NO 75
<211> LENGTH: 275
<212> TYPE: DNA
<213> ORGANISM: Homo sapiens

<400> SEQUENCE: 75
agttccagaa atccagtgac gaatgtggta tacaaaaaaa tatataaatt ctttcaactt      60
agaataatta agtcataaaa tacatagggt acaaatacca cattccgttc taaaatgata     120
tcttaggatc atcaaaagaa aaagaggatt tggattatgc aaaaaatgat tcctatatat     180
ataatcaatt atctaactga cattttttgca aatctaccac aacttcgcct tttattgcat     240
atgctaaaca agcagatgct aagtctgtaa actgt                                 275

<210> SEQ ID NO 76
<211> LENGTH: 62
<212> TYPE: DNA
<213> ORGANISM: Homo sapiens

<400> SEQUENCE: 76
ttgcttaatc atgcgctttg ttttttatgc attcacttcc tgtctttatc tctattttct      60
tt                                                                     62

<210> SEQ ID NO 77
<211> LENGTH: 471
<212> TYPE: DNA
<213> ORGANISM: Homo sapiens

<400> SEQUENCE: 77
ttaacctaag tatcagccct ggcatgctta tactggtcca agcaagcatt acgtcacagc      60
ctgttcctct tctttatcta aaagtgcttt ttcctttctc agcattccac aagttacttc     120
ctccttcctt tgttctcctc tgcctttgcc tcttttaaat agttccaagg tgctggccaa     180
tcgggacaaa tacagaatgt gaggtcccat tccagccctg gaaactggac acagcagtag     240
ggcggacgca tcaagtgata aatgaccctg tcccctttgt tcgctgtact ctcctggcaa     300
aactgctgga gagtgtaccc tttctgcaga aagtaaaaaa aaatggcctt gctgaggaaa     360
ttaatgttca agtgctattt ctttatggca ctggggaaca agcatttcaa acagacctga     420
ggtttacccg atttctgctg gaaaagaaac ctcaggtctg ctgccttaga a              471

<210> SEQ ID NO 78
<211> LENGTH: 373
<212> TYPE: DNA
<213> ORGANISM: Homo sapiens

<400> SEQUENCE: 78
tctgtaggag atcttccaaa ttactgctta tatacatgta tattctatta caaaaattac      60
accactcaat gtagtctaaa ttattgagag taaattgtag ccattctttt acatgttttc     120
tgaacttagt tgccaataat cataatcatt agcttttcaa ggtttgctct gaaacttaca     180
aaccatgcaa aagtgaaaac ttaggcttaa catatttggc aatttaaatc aactaaattg     240
aatcaatcta aatactgctt tgcaaagtaa aaaaggaatc aaaatgacac ataagacaat     300
cactaatccc tatattttta gggtctatttt caagaaattt actactactt cttaccagcc     360
taaggactgt gta                                                         373

<210> SEQ ID NO 79
<211> LENGTH: 505
<212> TYPE: DNA
<213> ORGANISM: Homo sapiens
<220> FEATURE:
<221> NAME/KEY: misc_feature
<222> LOCATION: (334)..(334)

-continued

<223> OTHER INFORMATION: n is a, c, g, t or u
<220> FEATURE:
<221> NAME/KEY: misc_feature
<222> LOCATION: (471)..(471)
<223> OTHER INFORMATION: n is a, c, g, t or u

<400> SEQUENCE: 79

```
aggccaggtg ctatgctcag agttcacacc tgcctgatac tgtgaggatt gggctacaga      60
ttctaaacca cactctccat agaggacatg gcaggtgagc ggctggcttc tgtgggtctg     120
ggcctggtgg gttagtgtgg gctgcatggc cccaaggctg ggagctgtgt tgggatctgg     180
tggcaggggg tttatctgac aacctcacta ttccatgtct cctctctgtg tggaggaatg     240
ggatgcagcg aggaggccag gctggagttc tgtagagtgt aaaatcctgg atgtcctctc     300
agcctgtctc cttgagagga cctgctgcct gccnttctgg agcacgtcat tctcttcttg     360
gatgaccaaa taaatcattc aagaatgaaa tgaaaactcc ttatctcctt ataggatctg     420
agctcagtga tgagaagtgg aaggacaata attgaccaat cacacattta natgaataaa     480
ttaggccgtt ggtgttcagc agcaa                                           505
```

<210> SEQ ID NO 80
<211> LENGTH: 366
<212> TYPE: DNA
<213> ORGANISM: Homo sapiens

<400> SEQUENCE: 80

```
tgtttccttt ccacttgcta gaagttattt tgccaatcac atatgattat tttatcattt      60
tttaattacc atcagtgcat gaaattatct ttattattca cttgttttta ttataatctt     120
ataatttcaa ataaaatgta aatctactgt cccttgcttt acctccgtgt cttcagtgcc     180
tagaacagga ctgtcataca cagtgactca atacacattt acttatgggt gattccctgc     240
ctgactgtta caggaagaag gaccaggaat atcagaatct gaagtgtcct ctaaagtcat     300
aaagactaga aggcattgaa taatgtttct taactatgca aggacttcag aattagatct     360
cacata                                                                366
```

<210> SEQ ID NO 81
<211> LENGTH: 455
<212> TYPE: DNA
<213> ORGANISM: Homo sapiens

<400> SEQUENCE: 81

```
agatctcatt ttctggaggt gcatgtctcc cgtgaccccc tctttggatt gcccgcagag      60
cccgtgaaga tggtgttatc actcctgtga ttactttact gatcaggtga ctttgagtca     120
atcaaaaggt agattatcca ggtgtgcctg atttgatcag gtggtccctt aaggaggctt     180
aaaatgaccc tttctgaagt agagtaattg gaaaagtaag agggtctatg ggtggggtca     240
cctggcaagg aactgaactc agcctccatg agctctggcc accagctgac ctttagcaag     300
aaagcaaatc tttctttggt cagtctccac aacaggacga agctggctga gcccttgcct     360
ttggccctgt gagatgctga cccgagtatc cagcgaacac gtgccagagt cctgacccat     420
ggaaactgag atgatgagtc tgtgttgctt taagc                                455
```

<210> SEQ ID NO 82
<211> LENGTH: 119
<212> TYPE: DNA
<213> ORGANISM: Homo sapiens

<400> SEQUENCE: 82 ccgatttct gtttgaagca gttcccttct atgttgcagt ctccttgaag gcaaaggttg        60
tgcactgtca tgttttgaag cccagtatcg ctgagaacaa tgacagacac atgcagtgg        119

<210> SEQ ID NO 83
<211> LENGTH: 137
<212> TYPE: DNA
<213> ORGANISM: Homo sapiens

<400> SEQUENCE: 83
tggctctcag agaaaccgta tttgatcaga gagctaaagg aagtgaggtt gtgagccaca        60
gggttatctt gaagaagagc attccaagga caggggaaac ttcctcaaag accagtaagc       120
cagagtgttc ttggtgc                                                      137

<210> SEQ ID NO 84
<211> LENGTH: 345
<212> TYPE: DNA
<213> ORGANISM: Homo sapiens

<400> SEQUENCE: 84
agcttacaca gcattcttag agaggacaca gaatttggag tttgagtctt gccaagttat        60
agggccttga gaaacattta gggctttcca tggatccacc ctaacgaagc ataaaattaa       120
gcctaggatt ttagggtcat cagccaaaaa tggaactgcc ttctagaaca aaaaatgaca       180
tccttttgag gaagacagtc atccagagtc tttacaatct tttacccaca ttgcctagta       240
cataattaaa catttctaga tatgaatagg aacaggaaaa tgtgacccat aatcaagaca       300
acaagcaata aatggaaacc taccctaag tagctaaact gttgc                        345

<210> SEQ ID NO 85
<211> LENGTH: 459
<212> TYPE: DNA
<213> ORGANISM: Homo sapiens

<400> SEQUENCE: 85
tatgtttatt cagggctctg gaacataaaa aggctttgcc acactcttca catctataag        60
gtttctctcc agtatgaatt ttcttatgtt tactcaggta tgcagaccat ccaaaggctt       120
tgccacactc ttcacatttg taaggtttct ctccagtatg aattatctta tgtttattca       180
ggtctgtgga ccatccaaag gctttgccac actcttcaca tttgtggggc ctctctccag       240
tatgaattct cttatgttca ttaagggttg tgaaccgact aaaggctttt ccacattctt       300
cacatgtgta gggtttctct ccagtatgaa tactcttatg tttattaagg gttgcggatt       360
gtctaaaggc tttgccacat tgttcacatt tgtagggctt ctctccagta tgaattctct       420
tatgttcatt cagaactgag gacctactaa aggctttgc                              459

<210> SEQ ID NO 86
<211> LENGTH: 229
<212> TYPE: DNA
<213> ORGANISM: Homo sapiens
<220> FEATURE:
<221> NAME/KEY: misc_feature
<222> LOCATION: (78)..(78)
<223> OTHER INFORMATION: n is a, c, g, t or u
<220> FEATURE:
<221> NAME/KEY: misc_feature
<222> LOCATION: (81)..(81)
<223> OTHER INFORMATION: n is a, c, g, t or u

<400> SEQUENCE: 86

```
gggagtggac ctgcattagc aagcagagaa tgtccagagc ctagagacag ccagcccatg    60
cagagggtag ggcataancc naggcagtgg agagggtgag gagtggtgta tagaagagag   120
catggagttt aagggttat tatggctgag atccagacca tgagcagaga aaagttcagt    180
ttatctcacg gaaaacttta atgttaggct taatcctctg ttccttcct               229

<210> SEQ ID NO 87
<211> LENGTH: 351
<212> TYPE: DNA
<213> ORGANISM: Homo sapiens
<220> FEATURE:
<221> NAME/KEY: misc_feature
<222> LOCATION: (80)..(80)
<223> OTHER INFORMATION: n is a, c, g, t or u

<400> SEQUENCE: 87
ggttgatggt aatttatgta ccctgacagg ggtttggttt acatagctgt attcatttgt    60
caaaacttat attaaatggn tgcaattaat attgatgcat ttcattgtat gtaaatttta   120
ccctaaaata attttagaca aattgtaaaa cctagttaaa gacatatatg ctgatatttt   180
cagggttacc tctcttgatg tctgcaactt actttgaaat gcttcaaaag gaaaatagga   240
taatggatgg aaatagggag agagaaatgg atcgatgtgt aaataaaaca aatctatcta   300
aatgttaaag cttaattgta gatgatgaat gtaggagtgt tgaatgttaa a            351

<210> SEQ ID NO 88
<211> LENGTH: 482
<212> TYPE: DNA
<213> ORGANISM: Homo sapiens

<400> SEQUENCE: 88
aagagtctat gaagaaccca acggaagttt gtggcacatc cctaccctca aattcacagt    60
gagggtggaa tgacagtaac caaatctgtg aaaatattca catgagacag gaaagaagtc   120
agaatatcca gtgtacaatg agagtgaaag aggatgtcta aaaggggaca gcccattcac   180
aacccacaca caacccacgc acaaatattt ttgggggggc ctcccatggg catttataat   240
cttctaagtg ctccgaagaa catgtgtcac aaaagatgaa gagaatattt tccagaacat   300
agcccaacaa agaacttctt tgacattttt tagtgtaaag gtaactgacg gtatctacca   360
aattagcaat ttgtaaaact ggaatttcta aaagcaaata cttggagctg agattacctc   420
ccacttccca aattcgagtt atatgatctc aagtataata ccctttggta tagacctagc   480
ca                                                                 482

<210> SEQ ID NO 89
<211> LENGTH: 37
<212> TYPE: DNA
<213> ORGANISM: Homo sapiens

<400> SEQUENCE: 89
tctgagtggg cctgctctct gtagactgaa ttcagca                             37

<210> SEQ ID NO 90
<211> LENGTH: 394
<212> TYPE: DNA
<213> ORGANISM: Homo sapiens
<220> FEATURE:
<221> NAME/KEY: misc_feature
<222> LOCATION: (130)..(130)
<223> OTHER INFORMATION: n is a, c, g, t or u
<220> FEATURE:
<221> NAME/KEY: misc_feature
```

<222> LOCATION: (135)..(135)
<223> OTHER INFORMATION: n is a, c, g, t or u

<400> SEQUENCE: 90

| | | | | | |
|---|---|---|---|---|---|
| tgcactcaat | ggcttctgtt | cgaagtccct | attaaatgtt | tctttcttaa | atactgtatt | 60 |
| tgtcagcttc | ttccttcagc | atcccaactt | cctcagactt | tggggtactt | ttgcacagac | 120 |
| ctagccaccn | caaancactg | tcatagatgc | agcaatccac | tttcacaaaa | ccccatggac | 180 |
| aatgcagagg | gggagaacag | ggactgatta | aagaaaggga | cagaaatggc | atcactatcc | 240 |
| aagactgaaa | aacaggctga | atggattatc | actctgaccc | aactgcacat | ttctaatgtc | 300 |
| ttcatgtttt | caattactcc | atgaattccc | ttatctgatg | ctgattatgc | acaggactgt | 360 |
| gtaagagtta | aacaacacct | gacactggtg | actc | | | 394 |

<210> SEQ ID NO 91
<211> LENGTH: 300
<212> TYPE: DNA
<213> ORGANISM: Homo sapiens
<220> FEATURE:
<221> NAME/KEY: misc_feature
<222> LOCATION: (175)..(175)
<223> OTHER INFORMATION: n is a, c, g, t or u

<400> SEQUENCE: 91

| | | | | | |
|---|---|---|---|---|---|
| cctcatcact | atgtcaccaa | agtgttttgg | aacttggtat | tccagagact | tctggaacgc | 60 |
| cgtgcaaggc | ctgcccccag | caagccacaa | ccaggaaggt | gcaggcacgc | cccactagc | 120 |
| tcctccccta | tttattgcct | cctggaaaac | ccaggaccct | cttccccatc | tccanccct | 180 |
| accccctgggg | gcagcccagg | gagagccagg | cacaatgagg | gctcccaaca | gctgcaagga | 240 |
| tttatctgaa | cctttgagaa | agaggaggag | ccatctaagt | ttctggaaac | ctgagcccca | 300 |

<210> SEQ ID NO 92
<211> LENGTH: 490
<212> TYPE: DNA
<213> ORGANISM: Homo sapiens
<220> FEATURE:
<221> NAME/KEY: misc_feature
<222> LOCATION: (49)..(49)
<223> OTHER INFORMATION: n is a, c, g, t or u
<220> FEATURE:
<221> NAME/KEY: misc_feature
<222> LOCATION: (69)..(69)
<223> OTHER INFORMATION: n is a, c, g, t or u

<400> SEQUENCE: 92

| | | | | | |
|---|---|---|---|---|---|
| cccattgcga | tctggctctg | ggggaccctg | ggatgatatc | cctaccccna | gggacaggac | 60 |
| ccaaccccng | gggacctgga | gagactctgt | gccctgcagg | accgatgggg | gactcctccc | 120 |
| tgtatgtacg | tgtgcgtggc | cctgccttgt | tcttgccccg | gacctggcct | ggtgaaggag | 180 |
| gcacgaggaa | gattgcagtc | agggacgctc | agcctgggag | ctgaccctca | ggtgaggccc | 240 |
| taaggaagtt | cccagacctc | cctgaacctc | agtatgctca | tctgtccagc | agcaaccctg | 300 |
| ggccttaagt | gagaacatct | atgcggaaga | ggcaggtgcc | aatcaagccc | tctgtaaagt | 360 |
| tacctcccct | tttcccttct | tctcctctca | cagagctgaa | gaatattttg | caaagttcat | 420 |
| tgtaaacatt | aaaataatct | tgggtgttta | tcattcgtta | aacctgttgg | gctgacttta | 480 |
| ggtctaccgc | | | | | | 490 |

<210> SEQ ID NO 93
<211> LENGTH: 317
<212> TYPE: DNA

<213> ORGANISM: Homo sapiens

<400> SEQUENCE: 93

```
gagaaaagta gactccccaa tgcctcgcag taaatgagga cgcctggcgc ctgcggcgag    60
gtcaactgag gtcagacgag cttatctctc ctgtcccggg aattaagggc atcctgggga   120
cagctgcaga gcaggaggct ccccgtgccc tcctcttcct aagcaagtca ggatcccaag   180
aggcgcgtgc ggggaggccc ctccgaaggg ctgctggctt gtgtcttcca ccagcgcaaa   240
gggaagctat cggttgcttc tgcagtgagg caagctcagc cggacgccca aagagagac    300
gaggtgtcgc tgtcggg                                                  317
```

<210> SEQ ID NO 94
<211> LENGTH: 208
<212> TYPE: DNA
<213> ORGANISM: Homo sapiens
<220> FEATURE:
<221> NAME/KEY: misc_feature
<222> LOCATION: (37)..(37)
<223> OTHER INFORMATION: n is a, c, g, t or u

<400> SEQUENCE: 94

```
atagatattt tttagtccac ttggctggat aataaantct taataacagg gggaaaaaaa    60
gaaagaaaaa ggaggaaaag atttaggaaa gaaaacaaca actttagtat ggaatgtgaa   120
gaactggcag gatattcacg ttgagctgtg cagtaagtag cttactggac atgtgaggct   180
gaagatacag ttgttcatat ggaagcaa                                      208
```

<210> SEQ ID NO 95
<211> LENGTH: 361
<212> TYPE: DNA
<213> ORGANISM: Homo sapiens

<400> SEQUENCE: 95

```
tccctcgtgt atcttatctt tattattgaa ttttccctca caatccactg ttaaaagaag    60
aaagtatcac acacgtgggt tcttttggct atggaagtgt ccttgagatc acttttttgca  120
cgtgactcag ctgaagtgtt caaagcacat ggaaatcact tgccagtgac aggtggacgt   180
tgtatgtgtt ttctctctcc taaggatgcc taaactttct tttcttcaca ggtaaagtca   240
gtgataaatc ttttgtttgc tgcatatact ggagatgtgt ctgcacttcg aaggtatgtt   300
tacaggatgg attagcatgc actttacaga tatttatgaa gttgcttctg ggcgagcagc   360
c                                                                   361
```

<210> SEQ ID NO 96
<211> LENGTH: 377
<212> TYPE: DNA
<213> ORGANISM: Homo sapiens
<220> FEATURE:
<221> NAME/KEY: misc_feature
<222> LOCATION: (32)..(32)
<223> OTHER INFORMATION: n is a, c, g, t or u
<220> FEATURE:
<221> NAME/KEY: misc_feature
<222> LOCATION: (49)..(49)
<223> OTHER INFORMATION: n is a, c, g, t or u
<220> FEATURE:
<221> NAME/KEY: misc_feature
<222> LOCATION: (170)..(170)
<223> OTHER INFORMATION: n is a, c, g, t or u
<220> FEATURE:
<221> NAME/KEY: misc_feature
<222> LOCATION: (270)..(270)
<223> OTHER INFORMATION: n is a, c, g, t or u

<400> SEQUENCE: 96

```
gaaacgccat ggaatgtatt gtatttctct antctatccc ttaaaatgnc cattgataat      60
tattggcaat ggttattgat agtctcaacg taatttcagt agaatttgtt ttgagatttt     120
ttttatgcac ataaaagatt tctttaggga ttattgtaca gagttctagn aaaatatata     180
atttttttt ctgggcttat aactttcttt tctaaaaatt tatttggcag cctgattaga     240
aatgtggtaa aatctgaaca ataaaatagn aaatagacta gttgcataga atgtttcaaa     300
aacaggcatt agattggcgg ctactcggga ggctgaggcg ggagaatcgc ttgagcctga     360
gaggtggagg ttgcggt                                                     377
```

<210> SEQ ID NO 97
<211> LENGTH: 525
<212> TYPE: DNA
<213> ORGANISM: Homo sapiens
<220> FEATURE:
<221> NAME/KEY: misc_feature
<222> LOCATION: (72)..(72)
<223> OTHER INFORMATION: n is a, c, g, t or u
<220> FEATURE:
<221> NAME/KEY: misc_feature
<222> LOCATION: (203)..(203)
<223> OTHER INFORMATION: n is a, c, g, t or u
<220> FEATURE:
<221> NAME/KEY: misc_feature
<222> LOCATION: (207)..(207)
<223> OTHER INFORMATION: n is a, c, g, t or u

<400> SEQUENCE: 97

```
cacctttctg ttctgtgacg ggctgtccct gcttgtcctg ctttaggagg taggtaccca      60
gtggctcccc gnccctcag cggctcattc ctctcgctct ccccacgttg gtctgtgtga     120
gctccgctgt gtggctgcca ttcatccgat ccatctgtgg acttgctggg gctgcgccgt     180
gcacggtgtg gtgaatgcta canccanccc caggggcggg gctgagagtg gctgggacct     240
ggagcacatg gggatgctgt gtgggaacca acttgccccc caccctgtgt ctctaggggt     300
ccgcagcagt agagaagcag acagccagcc ctgtccctgc ggcgtcaccc tccaccccat     360
actaacccag cagcgcatgg agagatttcg ggagtgctct aaaggccttt ggagcaattt     420
agggcaatta cggcagtttt tagaaatgct gaggggttgt tttgcctgcg ggcggggat     480
ggttgcctta tgcccacagt gaagcgggcg agatgcggta gctgg                     525
```

<210> SEQ ID NO 98
<211> LENGTH: 434
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a, c, g, t or u

<400> SEQUENCE: 98

```
gaagttcaac tcaggaaggt gcaatataan caaatgtgct atattataat gaggaatggt      60
actaccgttc cagattttct gtaattgctt ctgcaaagta ataggcttct tgtcccttt     120
ttttctggca tgttatggaa tgatcattgt aaatcaggac catttatcaa gcagtacacc     180
aactcataag atcaaatttc attgaatggt ttgaggttgt agctctataa atagtagttt     240
ttaacatgcc tgtagtattg ctaactgcaa aacatactc tttgtacaag aagtgcttct     300
aagaatttca ttgacattaa tgacactgta tacaataaat gtgtagtttc ttaatcgcac     360
```

```
tacctatgca acactgtgta ttaggtttat catcctcatg tatttttatg tgacctgtat      420
gtatattcta atct                                                        434

<210> SEQ ID NO 99
<211> LENGTH: 412
<212> TYPE: DNA
<213> ORGANISM: Homo sapiens
<220> FEATURE:
<221> NAME/KEY: misc_feature
<222> LOCATION: (47)..(47)
<223> OTHER INFORMATION: n is a, c, g, t or u
<220> FEATURE:
<221> NAME/KEY: misc_feature
<222> LOCATION: (202)..(202)
<223> OTHER INFORMATION: n is a, c, g, t or u
<220> FEATURE:
<221> NAME/KEY: misc_feature
<222> LOCATION: (386)..(386)
<223> OTHER INFORMATION: n is a, c, g, t or u

<400> SEQUENCE: 99
gggagacaga tcacaatcag atccataagg aaaagtgtgt ctgtgtntat cttcctctct       60
agggaaaaat acagcagggt gaggggattg agtgggagtg caatcaggga agacttcctg      120
aaggcagtga ctggtgactg aatgaagca tgagaatgag ccatgcaggt tgcccagaga       180
gagcatccag gcagagggag cngaaagttc catcctcacc cagctctgcc ggcccaggta      240 cttttctcctc tgccttctac tcccagtctc actccagtgc aacacacttc agttttctgg     300
gaactcctga tggaaagtgg ctgtatttgt tcatccctat agccttgggg cacagccagc      360
agcccctgga ggaagccccg caggtnggta aagagacaca gggctcccag cc              412

<210> SEQ ID NO 100
<211> LENGTH: 493
<212> TYPE: DNA
<213> ORGANISM: Homo sapiens

<400> SEQUENCE: 100
actgttttca gacctaacct tggcaaggtc agtcctactt tgatgttctt gtttcatcac       60
acttcttggc atttgtagat ttggaagaat tgggcctttg gtacctctga tctcttcgtt      120
tagcaactta ctgtgcaccc atatgcttag cttttgctgt tttagctttt ttttttttt       180 tttttaacct gccacctagt ggccgaaatg ttgctatact attgataagg tactcctaat      240
tttggcaaaa tagtaagagg caaagcacca agattatgt tctctccctt ctccaaatct       300
ctcttggtga gaatgatctt taaaacatac cactcagatt attagcaatc ttggtatgga      360
acgtttttaa aaataataat aatgtacttt atgtggtgat ttatgttatt atttaggccc      420
aaagttttga tttaattgtt ccttttagc ttattttga gatatgcagt ctgttaggaa        480
gctgtctctg tct                                                         493

<210> SEQ ID NO 101
<211> LENGTH: 415
<212> TYPE: DNA
<213> ORGANISM: Homo sapiens

<400> SEQUENCE: 101
gccctcttgt gtagttttca ttgtgtctag tgcaatgccg taaaccttaa caccatgaga       60
cccatatgaa gtgccaacag tgatgatgga agcgctttca agaaagaag tcatagacat       120 tataagaata aagcgacttg cttgatatgt acagtagata ggtacagctg tagctgctgg      180
ccatttcaga cagatgcttc atcttgtaaa cagcaacata aatgtatggt accaataaat      240
```

```
acagtacagt actgtaaatg tgttttctct tccttatgat tttcttggta catgttcttt      300
tctctagttt actttattgt taagaatata ctatataata cacatacaaa atatgtgtta      360
ttgcctgttt atgttgtggg tagggcttct ggtcaacagt gggctacatt atcga          415
```

<210> SEQ ID NO 102
<211> LENGTH: 530
<212> TYPE: DNA
<213> ORGANISM: Homo sapiens

<400> SEQUENCE: 102

```
ggactagcag tcttcttctt cagacgccat gggaccccca ggcgactgct ctactgccag       60
cgttccctgc tggacaaggt ctgacgccca ccgccggccc gcccactcct accacaagga      120
ctttgcctct gaagaccagt gtcagcaagg tggtggtggg tgggctgctc ccatccgtcc      180
ggagccccct ccccgcagcc tccttgcttc tctcagtccc ctggctggcc tccttcaccc      240
tcaccgcctg tagcttgtgt ctgtccagcc ccatctgaat gtgttggggg ctctgcactt      300
gaaggcagga ccctcagacc tcgctggtaa aggtcaaatg gggtcatctg ctccttttcc      360
atcccctgac ataccttaac ctctgaactc tgacctcagg aggctctggg cactccagcc      420
ctgaaagccc caagtgtacc cagttggcag cctcccgtca ctctgactaa aaagaatctt      480
cagagtgcat atttggaggt ggaaagattg ttcagttacc ctaaagactt                  530
```

<210> SEQ ID NO 103
<211> LENGTH: 509
<212> TYPE: DNA
<213> ORGANISM: Homo sapiens
<220> FEATURE:
<221> NAME/KEY: misc_feature
<222> LOCATION: (47)..(48)
<223> OTHER INFORMATION: n is a, c, g, t or u
<220> FEATURE:
<221> NAME/KEY: misc_feature
<222> LOCATION: (50)..(53)
<223> OTHER INFORMATION: n is a, c, g, t or u
<220> FEATURE:
<221> NAME/KEY: misc_feature
<222> LOCATION: (56)..(59)
<223> OTHER INFORMATION: n is a, c, g, t or u
<220> FEATURE:
<221> NAME/KEY: misc_feature
<222> LOCATION: (85)..(85)
<223> OTHER INFORMATION: n is a, c, g, t or u
<220> FEATURE:
<221> NAME/KEY: misc_feature
<222> LOCATION: (112)..(112)
<223> OTHER INFORMATION: n is a, c, g, t or u
<220> FEATURE:
<221> NAME/KEY: misc_feature
<222> LOCATION: (117)..(117)
<223> OTHER INFORMATION: n is a, c, g, t or u
<220> FEATURE:
<221> NAME/KEY: misc_feature
<222> LOCATION: (121)..(122)
<223> OTHER INFORMATION: n is a, c, g, t or u
<220> FEATURE:
<221> NAME/KEY: misc_feature
<222> LOCATION: (125)..(125)
<223> OTHER INFORMATION: n is a, c, g, t or u
<220> FEATURE:
<221> NAME/KEY: misc_feature
<222> LOCATION: (179)..(179)
<223> OTHER INFORMATION: n is a, c, g, t or u
<220> FEATURE:
<221> NAME/KEY: misc_feature
<222> LOCATION: (266)..(266)
<223> OTHER INFORMATION: n is a, c, g, t or u
<220> FEATURE:

```
<221> NAME/KEY: misc_feature
<222> LOCATION: (272)..(272)
<223> OTHER INFORMATION: n is a, c, g, t or u
<220> FEATURE:
<221> NAME/KEY: misc_feature
<222> LOCATION: (277)..(277)
<223> OTHER INFORMATION: n is a, c, g, t or u
<220> FEATURE:
<221> NAME/KEY: misc_feature
<222> LOCATION: (285)..(285)
<223> OTHER INFORMATION: n is a, c, g, t or u
<220> FEATURE:
<221> NAME/KEY: misc_feature
<222> LOCATION: (359)..(359)
<223> OTHER INFORMATION: n is a, c, g, t or u
<220> FEATURE:
<221> NAME/KEY: misc_feature
<222> LOCATION: (467)..(467)
<223> OTHER INFORMATION: n is a, c, g, t or u

<400> SEQUENCE: 103
taattttagc tccaatccat ctttctcttc tccaaaaccc tacctcnntn nnntcnnnnc      60
caccccttaa gtacttagtc atgcntagcc ttatattctt gtttgaattc tnatgtnctg     120
nnccncccaa acagattata catttcttgg gtcccatact ttgcatttac catagcagnt     180
ttcatagccc atacaaacat taggccttca aaatatttgt caagtatttc ttcaataaaa     240
atgaaaacat cccaaatctt gatccnccta anatgtnaaa tgggnactta gttaagcaaa     300
ctaacatcat gatatactgg aaacaggtat ctctttcctt taccettgtg cctgctgang     360 atcttattct cagccttgct gttttaaact caggggtgtg tgtacaacat atttaagcaa     420
attctggaat accaaagcca agcagtcttc caggggcttc atcctgncac acagcagctt     480
acctggtggg tgttgggtag cacacagta                                      509

<210> SEQ ID NO 104
<211> LENGTH: 338
<212> TYPE: DNA
<213> ORGANISM: Homo sapiens

<400> SEQUENCE: 104
catgatcagt gtattttagg gggactaata tggcaactaa agctactttg gaagagaaag      60
agtggagata catagattgc tattatagtt caggccaata gagaggaatt gggtttaaga     120
gatacattat ggaggcagaa gtgttcattc aacaagcgtt tgttaaatat ctactatgta     180
atcatgatta tacaactaga gagaatatga aaaaaatgaa ttacgtatgt tagcttatag     240
atggatgctc tcagtaccca tccctattaa tcgtcatttc cctttgttta gtgaaccttc     300
tgatatattg gatatcaaat atcctttcca agtattgt                             338

<210> SEQ ID NO 105
<211> LENGTH: 279
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, t or u
<220> FEATURE:
<221> NAME/KEY: misc_feature
<222> LOCATION: (34)..(35)
<223> OTHER INFORMATION: n is a, c, g, t or u
<220> FEATURE:
<221> NAME/KEY: misc_feature
<222> LOCATION: (41)..(41)
<223> OTHER INFORMATION: n is a, c, g, t or u
<220> FEATURE:
<221> NAME/KEY: misc_feature
```

<222> LOCATION: (238)..(238)
<223> OTHER INFORMATION: n is a, c, g, t or u
<220> FEATURE:
<221> NAME/KEY: misc_feature
<222> LOCATION: (241)..(241)
<223> OTHER INFORMATION: n is a, c, g, t or u

<400> SEQUENCE: 105

```
gttccaggtc ccggatagcg agggcngccg cgcnngctcc nagggccatg aagcccccag    60
gaggagaatc gagcaatctt tttggaagtc cagaagaagc tactccttcc agcaggccta   120
ataggatggc atctaatatt tttggaccaa cagaagaacc tcagaacata cccaagagga   180
caaatccccc aggatcatgt tttcttatgt gaaggagaag aaccaaaatc ggatcttnaa   240
ngcttgcaag gagcatcccg gctgggagca gagccaggg                          279
```

<210> SEQ ID NO 106
<211> LENGTH: 395
<212> TYPE: DNA
<213> ORGANISM: Homo sapiens

<400> SEQUENCE: 106

```
ccaggctact gctaagactc gtacttccca gtttggtgtg ggcagctttc agactccatc    60
ctccttcagc tccatgtccc tccctggtgc cccaactgca tcgcctggtg ctgctgccta   120
ccctagtctc accaatcgtg gatctaactt tgctcctgag actggacaga ctgcaggaca   180
attccagaca cggacagcag agggtgtggg tgtctggcca cagtggcagg gccagcagcc   240
tcatcatcgt tcaagttcta gtgagcaaca tgttcaacaa ccgccagcac agcaacctgg   300
ccagcctgag gtcttccagg agatgctgtc catgctggga gatcagagca acagctacaa   360
caatgaagaa ttccctgatc taactatgtt tcccc                              395
```

<210> SEQ ID NO 107
<211> LENGTH: 412
<212> TYPE: DNA
<213> ORGANISM: Homo sapiens

<400> SEQUENCE: 107

```
acatagagag gtgactcatt cttttttaaag gttacattaa gtttgtagta tgtcagaatg    60
gcaatactat aattgtttta accagtgacg tttaagttgt ttccagattt tttgatctaa   120
caaataatgt gtcatgagta tagaatttt atgttcatgt actagtatag ttataggatg   180
actcatattt gaagcaaagt acaaaacgca tgctttctgt agctactcat aaattctggt   240
atgagcaaaa tgtcaagatg cttgcttatc accgaccaag tgatgattaa gctcttgcta   300
aactgtatca aggagaaaa agggaaatac aggcttatcc taacaatttc acagtgaaca   360
gtaatctctg gcattcagtt aaagctagac ttgttctaat tactttgatt tt           412
```

<210> SEQ ID NO 108
<211> LENGTH: 531
<212> TYPE: DNA
<213> ORGANISM: Homo sapiens
<220> FEATURE:
<221> NAME/KEY: misc_feature
<222> LOCATION: (121)..(121)
<223> OTHER INFORMATION: n is a, c, g, t or u
<220> FEATURE:
<221> NAME/KEY: misc_feature
<222> LOCATION: (248)..(248)
<223> OTHER INFORMATION: n is a, c, g, t or u

<400> SEQUENCE: 108

| | |
|---|---|
| gtaagtggta ccagccacaa ctgaatatcc atctgggata aaataaaatt gcactcgtct | 60 |
| tagagatcca aatcaacttc agatggatta aaactttgaa tgtaaaaaac ataaatgact | 120 |
| nacagtcctg caaaatatct tggagacaac ctgtgccatc tggagagtgg aagagcaca | 180 |
| tgcaaaggcc aaggggtgga gcagcccagc atgttctgga aaaggtaggg ctccccaagg | 240 |
| ctgggatnat ggtggagacc tgggtgtgtg ggagcacagg ggtgggggcc cgtgggccag | 300 |
| gaatgcacag agaggggctg gtgctctgcc gcaggcccaa gccccaaag cccggtcatt | 360 |
| cccagcacca tcttcacggg tttctgccca ggtctttctg ctgcatctct tcctcccccg | 420 |
| attccttaat cattttttt aaaatcagtt catgtctttg taaaccaaat tatttctaaa | 480 |
| aggcaaattt atattactgc cgaaatcaag ggtcagtgag ctagttgtgt a | 531 |

<210> SEQ ID NO 109
<211> LENGTH: 541
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n is a, c, g, t or u
<220> FEATURE:
<221> NAME/KEY: misc_feature
<222> LOCATION: (98)..(98)
<223> OTHER INFORMATION: n is a, c, g, t or u

<400> SEQUENCE: 109

| | |
|---|---|
| gacttgggat tccggagcag tcgcccctat cgctgctcct gcagttgcgg acnccaccga | 60 |
| ccccgccgcc ggaggactgg gcactgaaag gcctctangc ctaggcgcgg cccgcggagc | 120 |
| cagacgtgtt gctgccgtga gtaaaacgag cgccctctcc gcactcgttt acaaattaaa | 180 |
| atggaggaaa tttcgttggc caacctggat actaacaagc tagaggccat cgctcaggag | 240 |
| atttacgtag acctgataga ggattcttgt ttgggattct gctttgaggt gcaccgggca | 300 |
| gtcaagtgtg gctacttcta cctggagttc gcagagactg gtagcgtgaa ggattttggc | 360 |
| attcagccag tggaagacaa aggagcgtgc cgcctcccgc tttgctccct tcccggagaa | 420 |
| cctgggaatg ggcctgatca gcagctccag cgctcacctc cggaattcca gtagctgcaa | 480 |
| aatgagagtc tgaaagtggc caggacaata acatagactg gtcctgtggc ttcgaggagt | 540 |
| a | 541 |

<210> SEQ ID NO 110
<211> LENGTH: 359
<212> TYPE: DNA
<213> ORGANISM: Homo sapiens

<400> SEQUENCE: 110

| | |
|---|---|
| ctccctgcaa atgcacatgt caatcaatga ttaatgcacc caggttatgt acaaggcact | 60 |
| gggcttagca ccacagggaa cttccttcca gaggctcgct ttctagttgt gtagacaaga | 120 |
| atacatgcat gagaagatac aagacaattc acccatgcca aatgattcat acaggctgtt | 180 |
| taagtactgc agaaaataaa agaaggaaag gctaccagac ttttcaataa ggtctacagc | 240 |
| ttcccaagag catgtctttg ttaaatcagg aaatataaaa attatgtgtg tatgtgtatg | 300 |
| tatatatata taccacccta ttaactattt taaaatcgta ttctattttg ggggttgtg | 359 |

<210> SEQ ID NO 111
<211> LENGTH: 491
<212> TYPE: DNA
<213> ORGANISM: Homo sapiens
<220> FEATURE:
<221> NAME/KEY: misc_feature
<222> LOCATION: (56)..(56)
<223> OTHER INFORMATION: n is a, c, g, t or u
<220> FEATURE:
<221> NAME/KEY: misc_feature
<222> LOCATION: (151)..(151)
<223> OTHER INFORMATION: n is a, c, g, t or u

<400> SEQUENCE: 111

```
cagagtggac tgttccctga ggtgggagat gtggaaaagc caagaggctg cagccnaggc    60
cactggcccc tgagatctct gcaggaaatg gctgtggagt gtggcagttt ggcaaactct   120
ccaccacacg taatgaaact tggatttgct ncagtgtctg gctgcagagc agtgggcctg   180
gccagcaggt ccccagcttt ggctatgagg gccttgagtc ccccaaaaca ccgggttcca   240
gcaccacact cagccctcat tggctcttga actgagcttg gaagcttctg gtgaccttcc   300
aagagcctga gagtgaggtg gaattatttt aaaagataaa tattatatta tatatatata   360
tatttccctg aaggaaccaa agcgaatttt aaagatgca atgtagaggg gaaaagagat    420
gatgaaaata tttaaaggcc ctatctgttt acagtgttcc gtggttaaac tcgctcactg    480
ctaagaatat t                                                        491
```

<210> SEQ ID NO 112
<211> LENGTH: 287
<212> TYPE: DNA
<213> ORGANISM: Homo sapiens

<400> SEQUENCE: 112

```
gtgatcatga gaatgctgcc tttaaagatg tggccctggt cctgactgtt ctgctagagg    60
aggaaacatt agaagcaagt gtaggcccaa gggaaacgga agaaaaagtg agagacttac   120
tctgggccaa gtttaccaac tctgacactc ccacctcctt caaccacatg gactcagaca   180
aattgagtgg gctgtggagc cgaatttcac acctggtact gccagtccag ccaatcttag   240
atgctagcgt tacatccaca aaaccagtgt tgccttgtat aactatt                287
```

<210> SEQ ID NO 113
<211> LENGTH: 389
<212> TYPE: DNA
<213> ORGANISM: Homo sapiens

<400> SEQUENCE: 113

```
tagccgatcg ttacctcaag ggagtgggaa ttgggcccag ctccggcccc tcctggtcac    60 cttggccat gatggccggg gccatgcctt gacccgacgc cggagggcca agcgtagccc   120
taagcatcac tcacagcggg ccaggaagaa gaataagaac tgccggcgcc actcgctcta   180
tgtggacttc agcgatgtgg gctggaatga ctggattgtg gccccaccag gctaccaggc   240
cttctactgc catggggact gccccttcc actggctgac cacctcaact caaccaacca   300
tgccattgtg cagaccctgg tcaattctgt caattccagt atccccaaag cctgttgtgt   360
gcccactgaa ctgagtgcca tctccatgc                                    389
```

<210> SEQ ID NO 114
<211> LENGTH: 499
<212> TYPE: DNA
<213> ORGANISM: Homo sapiens

<400> SEQUENCE: 114

```
gtacctcgct ggacctggag ttagacctgc aggcgacaag aacctggcac agccaactga    60
```

| | |
|---|---:|
| cccaggagat ctcggtgctg aaggagctca aggagcagct ggaacaagcc aagagccacg | 120 |
| gggagaagga gctgccacag tggttgcgtg aggacgagcg tttccgcctg ctgctgagga | 180 |
| tgctggagaa gcggatggac cgagcggagc acaagggtga gcttcagaca gacaagatga | 240 |
| tgagggcagc tgccaaggat gtgcacaggc tccgaggcca gagctgtaag gaacccccag | 300 |
| aagttcagtc tttcagggag aagatggcat ttttcacccg gcctcggatg aatatcccag | 360 |
| ctctctctgc agatgacgtc taatcgccag aaaagtattt cctttgttcc actgaccagg | 420 |
| ctgtgaacat tgactgtggc taaagttatt tatgtggtgt tatatgaagg tactgagtca | 480 |
| caagtcctct agtgctctt | 499 |

<210> SEQ ID NO 115
<211> LENGTH: 504
<212> TYPE: DNA
<213> ORGANISM: Homo sapiens

<400> SEQUENCE: 115

| | |
|---|---:|
| gagtttcagg accaggcagc ttgattacag catcaagggc ccctgtgttc tctgttttct | 60 |
| gcagccatag tattggcttc ttcccaagac ttattttttcc catcagtgtc acctgtgcta | 120 |
| caagctcctt cagtcacatc tatttttgat atttgtgggt acctaggagg tgcatatatt | 180 |
| tgtgggatac atgagatact ctgacacaga tgtgcagtgt gcacggatca cagggaaatg | 240 |
| gggcagccat ccatcccttc aagcattcat gatttctttg tgttgtgaac attcccgttg | 300 |
| tgctctctta gttattctga atgtacaaga aattattgct gactatagtc accctgtcgt | 360 |
| gctatcaaat actagacctc attcgtggta tctaactata ttttgtaccc attaaccatc | 420 |
| cccatctccc acccctacc tttcccacta tccatcccag cctctggtaa ccatccttcg | 480 |
| tctatctcca cgagttcaat tgaa | 504 |

<210> SEQ ID NO 116
<211> LENGTH: 476
<212> TYPE: DNA
<213> ORGANISM: Homo sapiens
<220> FEATURE:
<221> NAME/KEY: misc_feature
<222> LOCATION: (423)..(423)
<223> OTHER INFORMATION: n is a, c, g, t or u

<400> SEQUENCE: 116

| | |
|---|---:|
| agcacagtct ggctggatga gacagggtcg tgcccagatg atggagaaat cgacccagaa | 60 |
| gcctgaggag gtgtcctggg tttggctggc tggctcctgc tccagcggcc ggcttcagg | 120 |
| tgtccggggg cgtggctgcc tggagcaggt gtgctgaata ccctggatgg gaactgagcg | 180 |
| aacccgggcc tccgctcaga gagacgtggc aggaccagcg aggaatccag cctgtccact | 240 |
| tccagaacag tgtttcccag gccccgctga gtggaccgga cctctgacac ctccaggttc | 300 |
| ttgctgactc cggcctggtg aaagggagcg ccatggtcct ggctgttggg gtcccaggga | 360 |
| gaggctctct tctggacaaa cacaccctcc cagcccccag ggctgtgcaa acacatgccc | 420 |
| ctnccataag caccaacaag aacttcttgc aggtggagtg gctgtttttt ataagt | 476 |

<210> SEQ ID NO 117
<211> LENGTH: 494
<212> TYPE: DNA
<213> ORGANISM: Homo sapiens

<400> SEQUENCE: 117

| | |
|---|---:|
| atccttgtac ctgatgtctg agccactcag aactcaccaa aatgttcaac accataacaa | 60 |

```
cagctgctca aactgtaaac aaggaaaaca agttgatgac ttcacactgt ggacagtttt      120
tcccaagatg tcagaataag actccccatc atgatgaggc tctcacccct cttagctgtc      180
cttgcttgtg cctgcctctt tcacttggca ggataatgca gtcattagaa tttcacatgt      240
agtataggag cttctgaggg taacaacaga gtgtcagata tgtcatctca acctcaaact      300
tttacataac atctcaggag gaaatgtggc tctctccatc ttgcatacag ggctcccaat      360
agaaatgaac acagagatat tgcctgtgtg tttgcagaga agatggtttc tataaagagt      420
aggaaagctg aaattatagt agagtcccct ttaaatgcac attgtgtgga tggctctcac      480
catttcctaa gaga                                                       494
```

<210> SEQ ID NO 118
<211> LENGTH: 553
<212> TYPE: DNA
<213> ORGANISM: Homo sapiens
<220> FEATURE:
<221> NAME/KEY: misc_feature
<222> LOCATION: (191)..(191)
<223> OTHER INFORMATION: n is a, c, g, t or u
<220> FEATURE:
<221> NAME/KEY: misc_feature
<222> LOCATION: (235)..(235)
<223> OTHER INFORMATION: n is a, c, g, t or u

<400> SEQUENCE: 118

```
gataacccca atctacgaag actagctatg gaacttccta cactgagaca actccagtgg       60
aactctgata attatcctaa aataaggagg cttcttcagt agccctcgaa atatgttcaa      120
atacatgatt acatttatgt ccttaatatt gctattagtt tctgatgtta atgtaaaagt      180
tggggaaaaa ngtggaaaag ttaaagcagt gcaggttaat tcaatgccag agtancttct      240
cagagggtgt atattcagtg tgaacaattt tcaacagaga aatgtcaact tctggccaca      300
acggcaacca gtaaaatgac tattttttact gtcttatcta ttaatgaaga ggagattgca      360
taatatagat gaaggagcat agtatttgca ggtggaacgc ctagcagggc ttgagtctca      420
actctgctgc ttttactcta attgaccgag acaagtcatt taaactaata gagcttcaat      480
tttctcatat ctaatgtaac ataacaattc acagcctttt actttgtagt tatcgtgaag      540
atctaatcgc agt                                                        553
```

<210> SEQ ID NO 119
<211> LENGTH: 462
<212> TYPE: DNA
<213> ORGANISM: Homo sapiens

<400> SEQUENCE: 119

```
ctcctgttca tcctgttcac agagtggctc ggctgatggt agctcgacca atggctgcaa       60
ccatgagagg gctcccctga aacttctctg tgacaatatg aagtaccaga tcctctccag      120
agccttctat ggatggctgg cctactgcag acacctgtcc accgtgagaa cccacctatc      180
agccctggtc aatcacatga tcgtgtctcc agacttgccc tgcgatgctg acagggact       240 gacagccagg atctgggagc agtaccttca cgacagcaca agttacgagg agcaggagct      300
gctgcgcctc atctactacg ggggcatcca gcctgagatc cgcaaggccg tgtggccctt      360
cctcctgggc cactaccagt tcgggatgac ggaaacagaa aggaaagagg tggacgagca      420
gattcatgcc tgctatgcac agaccatggc tgagtggctg gg                        462
```

<210> SEQ ID NO 120

```
<211> LENGTH: 524
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is a, c, g, t or u
<220> FEATURE:
<221> NAME/KEY: misc_feature
<222> LOCATION: (47)..(47)
<223> OTHER INFORMATION: n is a, c, g, t or u
<220> FEATURE:
<221> NAME/KEY: misc_feature
<222> LOCATION: (56)..(56)
<223> OTHER INFORMATION: n is a, c, g, t or u

<400> SEQUENCE: 120
tctgctgctg aaggcctgtg attttgtngg ggaagggcct gttctangca actggnaaag      60
gcactgccac ctgccgttgg atgccaggac tcaagagctg gccccagtca ctgtgcgcag     120
agctgtctga aatgtgtga gtggactggg tccttcggca ctgcctgcat tggctcaggg     180
cagtcaaccg tcgcagagga tgaggggcac actcaggcag cctccccggc cctggaggca     240
gaaaggccca ggcagaacca ctgactggga ggaaacagaa aaagcagagg agagccaggc     300
tgcaggcgtg tggatgggac cagctcaggc agacgctgtc tcatacccac tctcccctct     360
cttgccaggg cctggcctgg tgtctctcag gagcctgggc atgagacaaa agcagagatt     420
gttctcttgt ggtaccacag gctgtaacca gtccacccag tgttgtttta gaaatttaaa     480
tcggttgccc atctttttaa attggcaaca tcgtttacca catt                      524

<210> SEQ ID NO 121
<211> LENGTH: 326
<212> TYPE: DNA
<213> ORGANISM: Homo sapiens

<400> SEQUENCE: 121
ccccaagttg gcgggcctga ttgggcggca cgggccccag aacaagcagc ccttcatggt      60
ggctttcttc aaggccacgg aggtccactt ccgcagcatc cggtccacgg ggagcaaaca     120
gcgcagccag aaccgctcca agacgcccaa gaaccaggaa gccctgcgga tggccaacgt     180
ggcagagaac agcagcagcg accagaggca ggcctgtaag aagcacgagc tgtatgtcag     240
cttccgagac ctgggctggc aggactggat catcgcgcct gaaggctacg ccgcctacta     300
ctgtgagggg gagtgtgcct ccctc                                           326

<210> SEQ ID NO 122
<211> LENGTH: 372
<212> TYPE: DNA
<213> ORGANISM: Homo sapiens

<400> SEQUENCE: 122
atgcggagtg agaaaagcct gttgcagaag actacataca acaggatttg acacttgtaa      60
ggctccaaaa caaagaaaat taaatgatat tgtttaggtt ttcatacata ggtgataaaa     120
gtgtgtttct ttgttttttaa tgagaaaatt agtcacagaa tttaagatct tagttacttc     180
tatagggaag gcaggggaat gggacaagga ggaagcccac agcattggtc atgctctcat     240
gttgaagttg ggttcaaagg tgttcattat taaaatgctt cataatgatg accatacatt     300
tggtatttct aggacaatct tggtttacat ctattgtctc aacataatta ttcagtgcaa     360
gccttttcctt tc                                                        372
```

```
<210> SEQ ID NO 123
<211> LENGTH: 197
<212> TYPE: DNA
<213> ORGANISM: Homo sapiens

<400> SEQUENCE: 123
ctaccttgcc tgctgagaca tagggctcca cgggtctctc tcctggggcc gggctgactg      60
tggcctgcga ggggcagtca tcgtgttggg ttttcctgcc agaggcagaa accacaaaat     120
tacctggaac atacacgccc caagtgacag attcaattca attccacaaa tattgacctc     180
gcgtctaatc cactcgt                                                    197

<210> SEQ ID NO 124
<211> LENGTH: 379
<212> TYPE: DNA
<213> ORGANISM: Homo sapiens

<400> SEQUENCE: 124
ctctgagcct tgcttggttg tcagaggcca tgagaggtgc cagttatagg tggatgtgcc      60
aagatgctgg tgaacttggt cttcagctat acccaggctc agaaagggca agagccatgc     120
tgcagcgtag gtgactttgg aggtgcactt ggggcccagg gctttgagtg ttgcgggtgt     180
gcctgtccct ccagatagtg ctctgtttct ctctgttgtc ccctgcctg tcctctggg       240 gccactgtgc tttctgctgt gtgcatttat aaatgatgtg tatttatat agacctgctt      300 gcattggctg atgctcctct aattccctga gtttgattca accaccttg ggttgttttg      360 ctatggcctt agcctttga                                                  379

<210> SEQ ID NO 125
<211> LENGTH: 495
<212> TYPE: DNA
<213> ORGANISM: Homo sapiens

<400> SEQUENCE: 125
gaaccagaat ccttggaagc tctaggtcct acctcagaaa atctcatcgt catggttctg      60
cttcaagaac agaatttggg aattaggtat aagttcaatg ttcccatcac tcgaactggc     120
agtggagata atgaagttgg ctttacatgg aatcatcagc cttggtcaga atgctcagct     180
acttgtgctg gaggtaagat gcccactagg cagcccaccc agagggcaag atggagaaca     240
aaacacattc tgagctatgc tttgtgtttg ttaaaaaagc taattggaaa catttcttgc     300
aggtttgctt caagctgtaa tttagcaaaa gaaactttgc tttaattata ttatattcca     360
tttgttttca acctcatgta atttgtgcag atttgttggt aaaatacatc ttggcacaat     420
gagtgtctct gctggtgctt ctcccaagac tatcttgaag gtgggctgtt tgcctttcgt     480
gaacacattc ttggt                                                      495

<210> SEQ ID NO 126
<211> LENGTH: 491
<212> TYPE: DNA
<213> ORGANISM: Homo sapiens

<400> SEQUENCE: 126
atacctcatg cagccttcag gttcagttct gacaccaggg atggaccatc ccatttctct      60
ccagcctgcc tccatgatgg gaccccttac ccagcaactg ggccatctct ccctcagcag     120
cacaggcacg tatatgccga cggctgcagc tatgcaagga gcttacatct cccagtacac     180
ccctgtgcct tcttccagtg tttcagtcga ggagagcagc ggccaacaga accaagtggc     240
```

```
agtggacgca ccctcagagc atggggtcta ttctttccag ttcaacaagt aacagtggga    300
ttcccctccc catctttact gaatagaaat gaattcttgg agatactcat gctcccagat    360
tccagagggt taaccaggaa tggagaccat ccgtcggccc tgctaaggac taacacttag    420
ccatcgtttt tcacaggcct gggcctggaa aagaaatct ctacgttcct gccctttact     480
attgctgatg g                                                         491

<210> SEQ ID NO 127
<211> LENGTH: 391
<212> TYPE: DNA
<213> ORGANISM: Homo sapiens

<400> SEQUENCE: 127
ggtgctgccc tgtgtacata taaatgaatc tggtgttggg gaaaccttca tctgaaaccc    60
acagatgtct ctggggcaga tccccactgt cctaccagtt gccctagccc agactctgag   120
ctgctcaccg gagtcattgg gaaggaaaag tggagaaatg gcaagtctag agtctcagaa   180
actcccctgg gggtttcacc tgggccctgg aggaattcag ctcagcttct tcctaggtcc   240 aagccccca cacctttttcc ccaaccacag agaacaagag tttgttctgt ctgggggac    300 agagaaggcg cttcccaact tcatactggc aggagggtga ggaggttcac tgagctcccc   360
agatctccca ctgcggggag acagaagcct g                                   391

<210> SEQ ID NO 128
<211> LENGTH: 458
<212> TYPE: DNA
<213> ORGANISM: Homo sapiens

<400> SEQUENCE: 128
tgtatggtcg ctggccagtg attctccttc tgagccgtgt ttcccctctc cctccctctc    60
cacgtgggca gggcaggccc catcgctttc tctgataaac cacatggaca catcctgaag   120
tcagcccagg cgccctgagc atcttggggc acctggaccc catcacaata ctccttcttc   180
cttcaggtcc ctgggtgaag gctttgctga aaccgacccc ccttttcacg tcccttctgc   240
ctctgccccg ttggatgccc tgactggggg caggggaaga cagggcac agctggccac     300 agggctcagc cactgagcag gctgttccgg gcctttggct ttgcatcctg gacggggagt   360
gtcctgtcag ggaccagatg tgtcctgcct catccctagc tccaatccct tccccacgtg   420
accggggatt ctggttgcaa taaaacatgc tgctgctg                             458

<210> SEQ ID NO 129
<211> LENGTH: 496
<212> TYPE: DNA
<213> ORGANISM: Homo sapiens

<400> SEQUENCE: 129
gcagtctcgt ccaatttcta tagcaccgtg ggcaggaacg gcgtcctgcc acaggctttc    60
gaccagtttt tcgagacagc ctacggcacc ccggaaaacc tcgcctcctc cgactacccc   120
ggggacaaga gcgccgagaa ggggcccccg gcggccacgg cgacctccgc ggcggcggcg   180
gcggctgcaa cggcgcgcc ggcaacttca agttcggaca gcggcggcgg cggcggctgc    240
cgggagacgg cggcggcagc agaggagaaa gagcggcggc ggcgcccga gagcagcagc    300 agccccgagt cgtcttccgg ccacactgag gacaaggccg gcggctccag tggccaacgc   360
acccgcaaaa agcgctgccc ctataccaag taccagatcc gagagctgga acgggagttc   420
ttcttcagcg tctacattaa caagagaag cgcctgcaac tgtcccgcat gctcaacctc    480
```
actgatcgtc aagtca                                                            496

<210> SEQ ID NO 130
<211> LENGTH: 538
<212> TYPE: DNA
<213> ORGANISM: Homo sapiens
<220> FEATURE:
<221> NAME/KEY: misc_feature
<222> LOCATION: (475)..(475)
<223> OTHER INFORMATION: n is a, c, g, t or u

<400> SEQUENCE: 130
aggtcaccca gctgtgaatg aacgtggtca gaacacagaa tctgagttgg tcacacttcc     60
cactgatcca tggggccttt aagccctctg gaagcttcca ttaaagatga ttatttgagg    120
ataattgtat tgggatgcct atgatcttat ctagggtttt cctacccatc cccaacattc    180
agctcagctg cctctttctt gaggacaccc tcactgatca ccccagccca gccagagtgg    240
ttgctcctgc tcctgcccct gaacctatga catacccaag tcccaatact ttcgagccat    300
ctgccactgc cttttgacat ctctgccttg gctagattca aatggtgttt cataataaaa    360
gtctgagttt aagcagcttt accgaaaacg caagggaagt ttcattccat ttatacttct    420
ccagaccccc tgccatcctc tgctgctacc cacacaggca gaataaaagg cttanatgtg    480
taagtcccat gaaggcaaag attggtctct tgtgttcact gctgtctgta gtacttag     538

<210> SEQ ID NO 131
<211> LENGTH: 414
<212> TYPE: DNA
<213> ORGANISM: Homo sapiens

<400> SEQUENCE: 131
gtggcaaaag gggattcggc agctgtgatt aagaaccttg tgatggggag ggattcctgg     60
attacccagg tgagtttaat gtaaccacaa agatcctttc aagagggagg caggaaggtc    120
tgaggcagac gaaagagctg tgccaaggga agcaggcggc agtgggatgc aggtggcctc    180
tagaagctgg aaaaggcaag tccatgggtt cttttcctgga gccttcagaa ggagcacggc    240
cttgctgacc catcttagaa cggcaggata atcaatgtgt gttgtttgag gccactaagt    300
ttgtggcaat ttgttacagc agcaatagga aactactaca ctgtgtctga ttagatcagg    360
ccaatgaatg gagaaagtat tggatttcag ttgagtgcta aaacctggtc tgtt          414

<210> SEQ ID NO 132
<211> LENGTH: 408
<212> TYPE: DNA
<213> ORGANISM: Homo sapiens

<400> SEQUENCE: 132
ccagcttcac atggtctctc aagtgcttat gcttttcttc tctctgccac ccacattccc     60
acatcccgcc cacccccaa ctttcctccc ttcaccttcc catggagact ttttgcctgg    120
gctaaatctg atcctcagcc cactctcaga atcgataaat gccctaggt gattgtaagc    180 tcacctaaga tatctttttt ctcctctaga atttagtttt attagatttt tctagttgtc    240
tttgcaaaag cgttaacagg ctctgacttc tgacattcaa ctagatgtgg aatatccaac    300
ccctagcatt tcatggaatg tactgaccaa gataaaatgt gttcttatta aacaatgcca    360
tttcttgacc acttctgttt ttaggaattg tggtatctga gtcatggt                408

<210> SEQ ID NO 133

```
<211> LENGTH: 483
<212> TYPE: DNA
<213> ORGANISM: Homo sapiens
<220> FEATURE:
<221> NAME/KEY: misc_feature
<222> LOCATION: (94)..(94)
<223> OTHER INFORMATION: n is a, c, g, t or u
<220> FEATURE:
<221> NAME/KEY: misc_feature
<222> LOCATION: (96)..(96)
<223> OTHER INFORMATION: n is a, c, g, t or u
<220> FEATURE:
<221> NAME/KEY: misc_feature
<222> LOCATION: (425)..(425)
<223> OTHER INFORMATION: n is a, c, g, t or u

<400> SEQUENCE: 133
gcgacaaggt tgtgatccac gtggcaggtg ttcagaaggc tgggggcggg cagcgctggg      60
gagagccctg ggtacttcga ggagaccccg aagngnggct gctcccacac ctgcgccagt     120
ttccaccctc tctgtgagca gggctgcggt cacctcccac atctgaagag aaccaacctg     180
aggatttcac gctggctgcg tgccagacca gtccctgaca ggttgtgcga ggcccttcgc     240
tggacagccc attgctggcc actggacgga gaggcagagg gggctgaaat tcgggcccat     300
gcctctgtga gcgatgacgg agcaacagct ctccagcacg tgaagctctc cagacagctg     360
ttcgtgagaa gccagacaga ggcctggggt ctcagtccag atttctgggg agtggggtgt     420
ccaancgtgg gccacgctgc tgggagccac ctagggaagc aggtcgcctg tttctatagt     480
gac                                                                   483

<210> SEQ ID NO 134
<211> LENGTH: 496
<212> TYPE: DNA
<213> ORGANISM: Homo sapiens

<400> SEQUENCE: 134
gggaaaaccc ttgtacctga agcatgagcc actcagaact caccaaaata ttcgacacca      60
taacaacaga tgctcaaact gtaaaccagg acaacaagtg gatgacttca cactgtggac     120
agttttcccc aagatgtcag aacaagactc cccatcatga tgaggctctc cccctctta     180
actgtccttg ctcatgcctg cctctttcac ttggcaggat aatgcagtca ttagaatttc     240
acatgtagta gcttctgaga gtaacaacag agtgtcagat atgtcatctc aacctcaaac     300
ttttacataa catctcaggg ggaaatgtgg ctctctccac cttgcataca gggctcccaa     360
tagaaatgaa cacagagata ttgcctgtgt gtttgcagag aagatggttt gtatgaagac     420
gtaggaaagc tgaaattata atagagtccc ctttaaatcc acattgtgtg gatggctctt     480
gccgtttcct aagaga                                                     496

<210> SEQ ID NO 135
<211> LENGTH: 479
<212> TYPE: DNA
<213> ORGANISM: Homo sapiens
<220> FEATURE:
<221> NAME/KEY: misc_feature
<222> LOCATION: (305)..(305)
<223> OTHER INFORMATION: n is a, c, g, t or u

<400> SEQUENCE: 135
gagtccgagg atttcagggg cagctgggcg caggagctgg tgggctgttg ggagtgcccc      60
tttactgggc aggcttcctt cctcctggtg atgggggtt cctcagcaca aaagtgaagg     120
ggtggagggg ctggaggagc aggaatctct cttgttgata ggtatgaggc cttgaagtcc     180
```

```
ttttctttgt cccaggattc atggacgctt cggggctgat ctttgagttt tcaagcatgg    240
ggtgcagaga cgtttaggta aactcttacc gtcctctctc ttcgtcaggg cttcccagga    300
atcancaatg cccaagaagg aagggattgt agaaatagct taacccttc atttaccaac    360
```
(Note: corrected reading where possible)

```
atcancaatg cccaagaagg aagggattgt agaaatagct taacccttc atttaccaac    360 gtggaaattg aagcccaggg aagggaaggg accggtcgtg gaaggagag ccatcagcag    420 aaagagaccc tgagatcttc gcctgggatt cccaggaagt ccagcccgag ctgattcac     479
```

<210> SEQ ID NO 136
<211> LENGTH: 393
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is a, c, g, t or u

<400> SEQUENCE: 136

```
tcccaagccc ttagggaccg cagaggactt ggggaccagc aagcaacccc cagggcacga     60
gaagagctct tgctgtctgc cctgcctcac cctgccccac nccaggcccg gtggccccca    120
gctgcatcaa gtggaggcgg aggaggaggc ggaggagggt ggaccatgg gcccgggcgg    180 tgccctccat gcccggggga tgaagacact gctgccatgg acagcccgtg ccagccgcag    240
cccctaagtc aggctctccc tcagttacca gggtcttcgt cagagccctt ggagcctgag    300
cctggccggg ccaggatggg agtggagagt tacctgccct gtccctgct ccctcctac    360 cactgtccag gagtgcctag tgaggcctcg gca                                 393
```

<210> SEQ ID NO 137
<211> LENGTH: 377
<212> TYPE: DNA
<213> ORGANISM: Homo sapiens

<400> SEQUENCE: 137

```
aacctatcgc tgacttagca accaaagcct ccatcgttag gcaaggaata aaataaaacc     60
agcacgcttt ttccactgtg attttaaaa gtcattaaaa aatatctttt cccttatgta    120
cagaaaaatt ggaacagaaa aatatctaac ttgctgagca tttgatggga aaagtaaaa    180 gataacttcc atttggtaca caacttattg tacatagagc tatgatttga ggaggcatct    240
aatttctgaa caaattcacc aagaaatacc atcacttaaa gtcattatcg caatcatgct    300
gcagtgaaca ctctatacaa aatggccagg tcattaaaca tcaaagatgg aaaacaagcc    360
agcaatctct tctgttc                                                   377
```

<210> SEQ ID NO 138
<211> LENGTH: 483
<212> TYPE: DNA
<213> ORGANISM: Homo sapiens

<400> SEQUENCE: 138

```
tgggcctcac ctatgatggg atgctgagtg atgtccagag catgcccaag actggcattc     60
tcatacttat cctaagcata atcttcatag agggctactg cacccctgag gaggtcatct    120
gggaagcact gaatatgatg gggctgtatg atggatgga gcacctcatt tatggggagc    180
ccaggaagct gctcacccaa gattgggtgc aggaaaacta cctggagtac cggcaggtgc    240
ctggcagtga tcctgcacgg tatgagtttc tgtggggtcc aagggctcat gctgaaatta    300
ggaagatgag tctcctgaaa ttttttggcca aggtaaatgg gagtgatcca agatcctccc    360
```

```
cactgtggta tgaggaggct ttgaaagatg aggaagagag agcccaggac agaattgcca    420
ccacagatga tactactgcc atggccagtg caagttctag cgctacaggt agcttctcct    480
acc                                                                 483

<210> SEQ ID NO 139
<211> LENGTH: 200
<212> TYPE: DNA
<213> ORGANISM: Homo sapiens

<400> SEQUENCE: 139
ttttgcttgt cttattggcc cagcaaccag cttgacactg gggactatca ggctccaaat     60
aataaccaat gtctcactcc aaacagacag gatactacgg agccagggtc agcaaacatt    120
ttctgtaaag ggccagatag taaatatttt gggctttgtg ggccctatgg tctctgtcac    180
aacgattcaa ctctgctgtt                                                200

<210> SEQ ID NO 140
<211> LENGTH: 243
<212> TYPE: DNA
<213> ORGANISM: Homo sapiens

<400> SEQUENCE: 140
gagcgcctcc agtctagaag gcataagcca ataggataat atattcaggg tgcagggtgg     60
gtaggttgct ctggggatgg gtttatttaa gggagattgc aaggaagcta tttaacatgg    120
tgctgagcta gccaggactg atggagcccc tgggggtgtg ggatggagga gggtctgcag    180
ccagttcatt cccagggccc catcttgatg ggccaagggc taaacatgca tgtgtcagtg    240
gct                                                                  243

<210> SEQ ID NO 141
<211> LENGTH: 554
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, t or u
<220> FEATURE:
<221> NAME/KEY: misc_feature
<222> LOCATION: (185)..(185)
<223> OTHER INFORMATION: n is a, c, g, t or u
<220> FEATURE:
<221> NAME/KEY: misc_feature
<222> LOCATION: (187)..(187)
<223> OTHER INFORMATION: n is a, c, g, t or u
<220> FEATURE:
<221> NAME/KEY: misc_feature
<222> LOCATION: (189)..(189)
<223> OTHER INFORMATION: n is a, c, g, t or u
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (199)..(199)
<223> OTHER INFORMATION: n is a, c, g, t or u
<220> FEATURE:
<221> NAME/KEY: misc_feature
<222> LOCATION: (204)..(204)
<223> OTHER INFORMATION: n is a, c, g, t or u
<220> FEATURE:
<221> NAME/KEY: misc_feature
<222> LOCATION: (206)..(206)
<223> OTHER INFORMATION: n is a, c, g, t or u
<220> FEATURE:
<221> NAME/KEY: misc_feature
```

```
<222> LOCATION: (211)..(211)
<223> OTHER INFORMATION: n is a, c, g, t or u
<220> FEATURE:
<221> NAME/KEY: misc_feature
<222> LOCATION: (219)..(219)
<223> OTHER INFORMATION: n is a, c, g, t or u
<220> FEATURE:
<221> NAME/KEY: misc_feature
<222> LOCATION: (223)..(223)
<223> OTHER INFORMATION: n is a, c, g, t or u
<220> FEATURE:
<221> NAME/KEY: misc_feature
<222> LOCATION: (237)..(237)
<223> OTHER INFORMATION: n is a, c, g, t or u
<220> FEATURE:
<221> NAME/KEY: misc_feature
<222> LOCATION: (246)..(246)
<223> OTHER INFORMATION: n is a, c, g, t or u
<220> FEATURE:
<221> NAME/KEY: misc_feature
<222> LOCATION: (265)..(265)
<223> OTHER INFORMATION: n is a, c, g, t or u
<220> FEATURE:
<221> NAME/KEY: misc_feature
<222> LOCATION: (269)..(269)
<223> OTHER INFORMATION: n is a, c, g, t or u
<220> FEATURE:
<221> NAME/KEY: misc_feature
<222> LOCATION: (275)..(275)
<223> OTHER INFORMATION: n is a, c, g, t or u
<220> FEATURE:
<221> NAME/KEY: misc_feature
<222> LOCATION: (278)..(279)
<223> OTHER INFORMATION: n is a, c, g, t or u
<220> FEATURE:
<221> NAME/KEY: misc_feature
<222> LOCATION: (407)..(407)
<223> OTHER INFORMATION: n is a, c, g, t or u

<400> SEQUENCE: 141
tgagtgggct ttgagagagg gggaagagtg agtctgagca cgagttgcag ccagggccag    60
tgnggagggg gtttgggcca gtgcaccttc cggggcccca tcccttagtt tccactgcct   120
cctgtgacgt gaggcccatt cttcactctt tgaagcgagc agtcagcatt cttagtagtg   180
ggttncngnt ctgtnggang actntngaga ntattcttng ttncctgttg gagttgntca   240
aatgtnsctt ttaacggatg gttgnatgng cgtcngcnnc caggtttatg aatgacagta   300
gtcacacata gtgctgttta tatagtttag gagtaagagt cttgtttttt attcagattg   360
ggaaatccat tccattttgt gaattgtgac ataataatag cagtggnaaa agtatttgct   420
taaaattgtg agcgaattag caataacata catgagataa ctcaagaaat caaaagatag   480
ttgattcttg ccttgtacct caatctattc tgtaaaatta acaaatatg caaaccagga   540 tttccttgac ttct                                                    554

<210> SEQ ID NO 142
<211> LENGTH: 479
<212> TYPE: DNA
<213> ORGANISM: Homo sapiens

<400> SEQUENCE: 142
ggacatggtt atctacagca ctgagataca ctactcttct aagggcacgc catctaagtt    60
tgtgatccca gtgtcatgtg ctgccccca aaagtcccca tggctcacca agccctgctc   120
catgagagta gccagcaaga gcagggccac agcccagaag gatgagaaat gctacgaggt   180
gttcagcttg tcacagtcca gtcaaaggcc caactgcgat tgtccacctt gtgtcttcag   240
tgaagaagag cataccagg tcccttgtca ccaagcaggg gctcaggagg ctcaacctct   300
```

```
gcagccatct cactttcttg atatttctga ggattggtct cttcacacag atgatatgat     360
tgggtccatg tgatcctcag gtttggggtc tcctgaagat gctatttcta gaattagtat     420
atagtgtaca aatgtctgac aaataagtgc tcttgtgacc ctcatgtgag cactttga      479

<210> SEQ ID NO 143
<211> LENGTH: 514
<212> TYPE: DNA
<213> ORGANISM: Homo sapiens

<400> SEQUENCE: 143
cagttgctgc cctacatgga gaacaggagg ggtgctgtca tcctggtctc ttccattgca      60
gcttataatc cagtagtggc gctgggtgtc tacaatgtca gcaagacagc gctgctgggt     120
ctcactagaa cactggcatt ggagctggcc cccaaggaca tccgggtaaa ctgcgtggtt     180
ccaggaatta taaaaactga cttcagcaaa gtgtttcatg ggaatgagtc tctctggaag     240
aacttcaagg aacatcatca gctgcagagg attggggagt cagaggactg tgcaggaatc     300
gtgtccttcc tgtgctctcc agatgccagc tacgtcaacg gggagaacat tgcggtggca     360
ggctactcca ctcggctctg agaggagtgg gggcggctgc gtagctgtgg tcccagccca     420
ggagcctgag ggggtgtcta ggtgatcatt tggatctgga gcagagtctg ccattctgcc     480
agactagcaa tttgggggct tactcatgct aggc                                514

<210> SEQ ID NO 144
<211> LENGTH: 265
<212> TYPE: DNA
<213> ORGANISM: Homo sapiens
<220> FEATURE:
<221> NAME/KEY: misc_feature
<222> LOCATION: (74)..(75)
<223> OTHER INFORMATION: n is a, c, g, t or u
<220> FEATURE:
<221> NAME/KEY: misc_feature
<222> LOCATION: (79)..(79)
<223> OTHER INFORMATION: n is a, c, g, t or u
<220> FEATURE:
<221> NAME/KEY: misc_feature
<222> LOCATION: (126)..(126)
<223> OTHER INFORMATION: n is a, c, g, t or u

<400> SEQUENCE: 144
gtgtggtgtt tgtgtcttaa ctatgcactg ggcccttgtc tgcgtcggct tgcatacaga      60
gggcccctgg ggtnngccnt ccggcctggc ctcagccagt gggatggaca gggccaggca     120
ggcctntgaa cttccacctc ctggggcctc ccagacctcc tgtgccccca cctgtgtggg     180
caggtgggcc agtcttcggg tgatgggacc aaaccccttc agttcagtag agaaaggcta     240
ggtcctctac aaagagctgc aagac                                          265

<210> SEQ ID NO 145
<211> LENGTH: 419
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n is a, c, g, t or u
<220> FEATURE:
<221> NAME/KEY: misc_feature
<222> LOCATION: (57)..(57)
<223> OTHER INFORMATION: n is a, c, g, t or u
<220> FEATURE:
<221> NAME/KEY: misc_feature
<222> LOCATION: (61)..(61)
<223> OTHER INFORMATION: n is a, c, g, t or u
```

```
<220> FEATURE:
<221> NAME/KEY: misc_feature
<222> LOCATION: (73)..(73)
<223> OTHER INFORMATION: n is a, c, g, t or u
<220> FEATURE:
<221> NAME/KEY: misc_feature
<222> LOCATION: (78)..(78)
<223> OTHER INFORMATION: n is a, c, g, t or u
<220> FEATURE:
<221> NAME/KEY: misc_feature
<222> LOCATION: (82)..(82)
<223> OTHER INFORMATION: n is a, c, g, t or u
<220> FEATURE:
<221> NAME/KEY: misc_feature
<222> LOCATION: (114)..(115)
<223> OTHER INFORMATION: n is a, c, g, t or u
<220> FEATURE:
<221> NAME/KEY: misc_feature
<222> LOCATION: (130)..(130)
<223> OTHER INFORMATION: n is a, c, g, t or u
<220> FEATURE:
<221> NAME/KEY: misc_feature
<222> LOCATION: (144)..(144)
<223> OTHER INFORMATION: n is a, c, g, t or u
<220> FEATURE:
<221> NAME/KEY: misc_feature
<222> LOCATION: (165)..(165)
<223> OTHER INFORMATION: n is a, c, g, t or u
<220> FEATURE:
<221> NAME/KEY: misc_feature
<222> LOCATION: (177)..(177)
<223> OTHER INFORMATION: n is a, c, g, t or u
<220> FEATURE:
<221> NAME/KEY: misc_feature
<222> LOCATION: (189)..(190)
<223> OTHER INFORMATION: n is a, c, g, t or u
<220> FEATURE:
<221> NAME/KEY: misc_feature
<222> LOCATION: (192)..(192)
<223> OTHER INFORMATION: n is a, c, g, t or u
<220> FEATURE:
<221> NAME/KEY: misc_feature
<222> LOCATION: (218)..(218)
<223> OTHER INFORMATION: n is a, c, g, t or u
<220> FEATURE:
<221> NAME/KEY: misc_feature
<222> LOCATION: (225)..(225)
<223> OTHER INFORMATION: n is a, c, g, t or u

<400> SEQUENCE: 145
ggaggcgcag aagattgatc gcatgatgga ggctttcgct tctcgctact gcntgtncaa      60
ncccggggtc ttncagtnca cnaggtcagt gcagagccca cagcctggcc cctnnccagg     120
cacagcctcn agctctggag gggncggccc ctgtgggcac agccnagcgt gtgttcntgg     180
ggacctgcnn tnccctgagc gaggacgacc tgtgggcngg gcacntcttg caggcgggcc     240
cccagcacgc ggggtcccac tgtccactgg aggttctggc tgagcccagc accccggact     300
cgttgcagac acgtgctacg tgctgtcatt cgccatcatc atgctcaaca ccagcctcca     360
caaccacaac gtgcgtgaca agcccacggc agaacggttc atcgccatga accgcggca      419

<210> SEQ ID NO 146
<211> LENGTH: 492
<212> TYPE: DNA
<213> ORGANISM: Homo sapiens
<220> FEATURE:
<221> NAME/KEY: misc_feature
<222> LOCATION: (411)..(411)
<223> OTHER INFORMATION: n is a, c, g, t or u

<400> SEQUENCE: 146
tatgagaaac ctctgcgacc attcccagat gatgtctgcg ttgtccctga gaaatttgaa      60
```

```
ggagacatca agcaggaagg ggtcggtgca tttcgagagg ggccgcccta ccagcgccgg      120
ggtgccctgc agctgtggca atttctggtg gccttgctgg atgacccaac aaatgcccat      180
ttcattgcct ggacgggccg gggaatggag ttcaagctca ttgagcctga ggaggtcgcc      240
aggctctggg gcatccagaa gaaccggcca gccatgaatt acgacaagct gagccgctcg      300
ctccgatact attatgagaa aggcatcatg cagaaggtgg ctggtgagcg ttacgtgtac      360
aagtttgtgt gtgagcccga ggccctcttc tctttggcct tcccggacaa ntcagcgtcc      420
agctctcaag gctgagtttg accggcctgt cagtgaggag gacacagtcc ctttgtccca      480
cttggatgag ag                                                         492

<210> SEQ ID NO 147
<211> LENGTH: 527
<212> TYPE: DNA
<213> ORGANISM: Homo sapiens

<400> SEQUENCE: 147
aatattgtct cataagcatc tttctatatt tgttcacatc gtacataatc atgttttgc       60 acagatacat taatattatc atagtttgtt taactacttg ctttttcta acagtttttt     120 tttttgagat ggtcttgctc tgttgcccag gctggagtgc agtgacgtga tctcggctca     180
ctgcagcctt gacttcctgg gctcaagtga tcatcccacc tcagcctcct gagtagctgg     240
gactacaggt atgcaccacg accagctaat ttttgtatt tttttttgt agagagggta      300 ttttgccatg ttgcccaggc tagtcttgaa ctcctgggct caagcgatct gcctgcttca     360
gcctcccaga gtgctaggat tacaggcatg agccactgca cccagcctct taacaaattt     420
tgaatataac tcctgtctta aaatctgcag aatattgaat ttttccagct attttttact      480
tttgcttagc ttatagatgc taaaggatac tgtcatttgc attttta                   527

<210> SEQ ID NO 148
<211> LENGTH: 476
<212> TYPE: DNA
<213> ORGANISM: Homo sapiens
<220> FEATURE:
<221> NAME/KEY: misc_feature
<222> LOCATION: (50)..(50)
<223> OTHER INFORMATION: n is a, c, g, t or u
<220> FEATURE:
<221> NAME/KEY: misc_feature
<222> LOCATION: (92)..(92)
<223> OTHER INFORMATION: n is a, c, g, t or u
<220> FEATURE:
<221> NAME/KEY: misc_feature
<222> LOCATION: (105)..(105)
<223> OTHER INFORMATION: n is a, c, g, t or u

<400> SEQUENCE: 148
ctctctcact ttctatagct tgttggacc agatggtgag gaaaggaatn ggcctcttcc        60
cttctagagg gggctggctg gagtgagacc tnggggcttg gcctnggaac ccaccacaca     120
gccccaaagt caggaagcct ggggaaacca gagctgagac ctcttcaaca gggtttcttt     180
gagatcctac acctccattg ggccttttt cagtcttcaa tgggggccca gttggctcta      240
gaaggagaag aggtgaagca ggatcctttg ccctggggga gtctgagggc gcggtccttg     300
gactcattca ggccgtcttt gtagttgggg gagttccact gggcgatccc agcccctccc    360
cacccaccct ctaatggacc tcctcataga agccccattt cacttttgtt ttatctacct    420
cttagcaaaa caatagataa attaggtagt ggcagctcca cttgcttagg ttaggg         476
```

<210> SEQ ID NO 149
<211> LENGTH: 177
<212> TYPE: DNA
<213> ORGANISM: Homo sapiens

<400> SEQUENCE: 149

```
gggagtttga ccagagatgc aagggggtgaa ggagcgcttc ctaccgttag ggaactctgg    60
ggacagagcg ccccggccgc ctgatggccg aggcagggtg cgacccagga cccaggacgg   120
cgtcgggaac cataccatgg cccggatccc caagacccta aagttcgtcg tcgtcat      177
```

<210> SEQ ID NO 150
<211> LENGTH: 497
<212> TYPE: DNA
<213> ORGANISM: Homo sapiens
<220> FEATURE:
<221> NAME/KEY: misc_feature
<222> LOCATION: (109)..(109)
<223> OTHER INFORMATION: n is a, c, g, t or u
<220> FEATURE:
<221> NAME/KEY: misc_feature
<222> LOCATION: (113)..(113)
<223> OTHER INFORMATION: n is a, c, g, t or u
<220> FEATURE:
<221> NAME/KEY: misc_feature
<222> LOCATION: (146)..(147)
<223> OTHER INFORMATION: n is a, c, g, t or u

<400> SEQUENCE: 150

```
ctaaccactg aggctctcta atcttcctct ggagttttag tgaaaggatt tattgagcag    60
cttctggaat ataatgtgca tgtccaaaat gaactcagcg cttcaaaang acnaagtctg   120
tagcctggag gggcttgagt ggatgnnagc tgatgctgtg attttgagct gtggttacat   180
gcagtcagta aacctgtgag actgctggag gaaatgtagc agacagcatg gaggctggga   240
cccagcagct actttgggtc atgtctttac tgtcctgcct ccaaccctttt agtctcgtag   300
acttttgttc ttgtggaaat tcttctgta ttccagttgt gtaaatatgt atggaaaact   360
gatattacta ggttttacgt tgcatctcca gtattgatct ttggaaactg atgttacatt   420
aggttccaat tcgcaatagt agcagagact gacatgcttt tattgagctg ctaagccccg   480
tggatgatgg agcgaga                                                  497
```

<210> SEQ ID NO 151
<211> LENGTH: 529
<212> TYPE: DNA
<213> ORGANISM: Homo sapiens
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (393)..(393)
<223> OTHER INFORMATION: n is a, c, g, t or u
<220> FEATURE:
<221> NAME/KEY: misc_feature
<222> LOCATION: (403)..(403)
<223> OTHER INFORMATION: n is a, c, g, t or u
<220> FEATURE:
<221> NAME/KEY: misc_feature
<222> LOCATION: (417)..(417)
<223> OTHER INFORMATION: n is a, c, g, t or u
<220> FEATURE:
<221> NAME/KEY: misc_feature
<222> LOCATION: (431)..(433)
<223> OTHER INFORMATION: n is a, c, g, t or u
<220> FEATURE:
<221> NAME/KEY: misc_feature
<222> LOCATION: (435)..(435)

<223> OTHER INFORMATION: n is a, c, g, t or u
<220> FEATURE:
<221> NAME/KEY: misc_feature
<222> LOCATION: (440)..(440)
<223> OTHER INFORMATION: n is a, c, g, t or u
<220> FEATURE:
<221> NAME/KEY: misc_feature
<222> LOCATION: (442)..(443)
<223> OTHER INFORMATION: n is a, c, g, t or u

<400> SEQUENCE: 151

```
gccgacagct cctttaattt catggcgttt ttcttcatct tcggagccca gtttgtcctg      60
accgtcatcc aggcgattgg cttctccggc tggggcgcgt gcggctggct gtcggcaatt     120
ggattcttcc agtacagccc gggcgctgcc gtggtcatgc tgcttccagc catcatgttc     180
tccgtgtcgg ctgcnatgat ggccatcgcg atcatgaagg tgcacaggat ctaccgaggg     240
gctggcggaa gcttccagaa ggcacagacg gagtggaaca cgggcacttg gcggaaccca     300
ccgtcgaggg aggcccagta caacaacttc tcaggcaaca gcctgcccga gtaccccact     360
gtgcccagct acccgggcag tggccagtgg ccnttagagg gangcctgcc ctgcccncac     420
cgcccaccac nnncnccccn tnnttcctgc tgctaccccct gtgtcccgag ggctgggagt     480
acctggggcc ccatccccc agctgtgatg gtggaagccg gtggtggcc                  529
```

<210> SEQ ID NO 152
<211> LENGTH: 437
<212> TYPE: DNA
<213> ORGANISM: Homo sapiens
<220> FEATURE:
<221> NAME/KEY: misc_feature
<222> LOCATION: (145)..(146)
<223> OTHER INFORMATION: n is a, c, g, t or u

<400> SEQUENCE: 152

```
agatgaagcc cttcaagcgc tacgtgaaga agaaagccaa gcccaagaaa tgtgcccggc      60
gtttcaccga ctactgtgac ctgaacaaag acaaggtcat ttcactgcct gagctgaagg     120
gctgcctggg tgttagcaaa gaagnngacg cctcgtctaa ggagcagaaa acccaagggc     180
aggtggagag tccagggagg caggatggat caccagacac ctaaccttca gcgttgccca     240
tggccctgcc acatcccgtg taacataagt ggtgcccacc atgtttgcac ttttaataac     300
tcttacttgc gtgttttgtt tttggtttca ttttaaaaca ccaatatcta ataccacagt     360
gggaaaagga aagggaagaa agactttatt ctctctctta ttgtaagttt ttggatctgc     420
tactgacaac tttttaga                                                   437
```

<210> SEQ ID NO 153
<211> LENGTH: 87
<212> TYPE: DNA
<213> ORGANISM: Homo sapiens

<400> SEQUENCE: 153

```
ttctttcaca ccctgtcggg agaatgtgtg ccctgcgact gtaatggcaa ttccaacgag      60
tgtttggacg gctcaggata ctgtgtg                                          87
```

<210> SEQ ID NO 154
<211> LENGTH: 417
<212> TYPE: DNA
<213> ORGANISM: Homo sapiens

<400> SEQUENCE: 154

```
cccgctggtg cagtggaaga gcccggcggc cgccgccgca gccttctcgg cccgcgcccc      60
```

```
cgccgcctgc accccatct gctcttcccc gcggggccg cgcggcgcgg gctgggggcc      120
cgggcagccg cgctcgggca gcggggggcgc ggggctgccg cctgcgctcg cagctggtgc   180
cggtgcgcgc gctcggcctg ggccaccgct ccgacgagct ggtgcgtttc cgcttctgca    240
gcggctcctg ccgccgcgcg cgctctccac acgacctcag cctggccagc ctactgggcg    300
ccggggccct gcgaccgccc ccgggctccc ggcccgtcag ccagccctgc tgccgaccca    360
cgcgctacga agcggtctcc ttcatggacg tcaacagcac ctggagaacc gtggacc       417
```

<210> SEQ ID NO 155
<211> LENGTH: 407
<212> TYPE: DNA
<213> ORGANISM: Homo sapiens

<400> SEQUENCE: 155

```
taagagactg agccgctagc agcgcctggg gaccagacag acgcatgtgg caaagctcac    60
catcttcact acaaacacgc ctgagagtgg cactggggaa acataactcc atctacacct   120
tggatttgga ctgattctcc attttatcac ctgaaggctt gggccagagc tcaacagcta   180
ctcaactgga ggggtgaggg ggataaggtc tgtagtatac agacaggaag atggtaggtt   240
tatgccttct gtggccagag tcttggactc atggaaatag aatgaataga ggggcattca   300
caaggcacac cagtgcaagc agatgacaaa aaggtgcaga aggcaatctt aaaacagaaa   360
ggtgcaggag gtaccttaac tcacccctca gcaaatacct atgtcaa                 407
```

<210> SEQ ID NO 156
<211> LENGTH: 399
<212> TYPE: DNA
<213> ORGANISM: Homo sapiens

<400> SEQUENCE: 156

```
gagaccagtt cacggggcaa gagatgaacg tgggcccagtt cctcatgcac atgggcttcg   60
acatgcagac ggtggcccag ccgcagggac tggagcccag tgagctgctg gggatgctga   120
gcaacggaag ctaggcagac tgtctggagg aggagccggc actgaggggc ccagacaccc   180
gctgccccag tgccacctca ccccccacca gcaggccctc ccgtctcttc gggacagggc   240
cccagccgtc cccctgtct gggtctgccc actgccctcc tgccccggct ttccctgccc    300
ctctcccaca gcccagccag agacaaggga cctgctgtca tccccatctg tggcctgggg   360
gtccttcctg acaacgaggg ggtagccaga agagaagca                          399
```

<210> SEQ ID NO 157
<211> LENGTH: 422
<212> TYPE: DNA
<213> ORGANISM: Homo sapiens

<400> SEQUENCE: 157

```
gtgaccagta ccgcaagggg atcatctcgg gctccgtctg ccaggacctg tgtgagctgc    60
atatggtgga gtggaggacc tgcctctcgg tggccccggg ccagcaggtg tacagcgggc   120
tctggcggga caaggatgta accatcaagt gtggcattga ggagaccctc gactccaagg   180 cccgtcgga tgcggccccc cggcgggagc tggtactgtt tgacaagccc acccggggca   240
cctccatcaa ggaattccgg gagatgaccc tcggcttcct caaggcgaac ctgggagacc   300
tgccttccct gccggcgctg gttgccagg tcctgctcat ggctgacttc aacaaggaca   360
accgggtgtc cctggcggaa gccaagtccg tgtgggccct gctgcagcgt aacgagttcc   420
```

```
tg                                                                       422

<210> SEQ ID NO 158
<211> LENGTH: 414
<212> TYPE: DNA
<213> ORGANISM: Homo sapiens
<220> FEATURE:
<221> NAME/KEY: misc_feature
<222> LOCATION: (364)..(364)
<223> OTHER INFORMATION: n is a, c, g, t or u
<220> FEATURE:
<221> NAME/KEY: misc_feature
<222> LOCATION: (373)..(373)
<223> OTHER INFORMATION: n is a, c, g, t or u
<220> FEATURE:
<221> NAME/KEY: misc_feature
<222> LOCATION: (375)..(376)
<223> OTHER INFORMATION: n is a, c, g, t or u
<220> FEATURE:
<221> NAME/KEY: misc_feature
<222> LOCATION: (378)..(380)
<223> OTHER INFORMATION: n is a, c, g, t or u
<220> FEATURE:
<221> NAME/KEY: misc_feature
<222> LOCATION: (383)..(384)
<223> OTHER INFORMATION: n is a, c, g, t or u

<400> SEQUENCE: 158
acgcagcccg cgacaacaaa aagacccgca tcatcccgcg ccacttgcag ctggccatcc    60
gcaacgacga ggagctcaac aagctgcttg gtaaagttac catcgctcag ggcggtgttc   120
tgcctaacat ccaggccgta ctgctcccca agaagactga gagccaccac aaagctaagg   180
gcaagtaagg gctgaacttt aaaaatgtaa acttacaaga caaaaggctc ttttcagagc   240
cacccaccat ttctacggaa gaactgagca ctctgttctc caaacctatc agaaatttgt   300
ggccgagttc aagcactgag gccattactt tcctattggg taaaataaaa gtattgaatc   360
aggnctagta aanannannn aanngctacc ttataacatg aaggaacctc ctta         414

<210> SEQ ID NO 159
<211> LENGTH: 470
<212> TYPE: DNA
<213> ORGANISM: Homo sapiens

<400> SEQUENCE: 159
tatcaagatt gccctgcgg aaggcccaga cgtcagcgaa aggatggtca tcatcaccgg     60
gccaccggaa gcccagttca aggcccaggg acggatcttt gggaaactga agaggaaaa    120 cttctttaac cccaaagaag aagtgaagct ggaagcgcat atcagagtgc cctcttccac   180
agctggccgg gtgattggca aaggtggcaa gaccgtgaac gaactgcaga acttaaccag   240
tgcagaagtc atcgtgcctc gtgaccaaac gccagatgaa aatgaggaag tgatcgtcag   300
aattatcggg cacttctttg ctagccagac tgcacagcgc aagatcaggg aaattgtaca   360
acaggtgaag cagcaggagc agaaataccc tcagggagtc gcctcacagc gcagcaagtg   420
aggctcccac aggcaccagc aaaacaacgg atgaatgtag cccttccaac              470

<210> SEQ ID NO 160
<211> LENGTH: 383
<212> TYPE: DNA
<213> ORGANISM: Homo sapiens

<400> SEQUENCE: 160
agagagactc agagacccgg gagggccttc ctctgaaagg ccaagccaag ccatgcttgg    60
cagggtgagg ggccagttga gttctgggag ctgggcacta ctctgccagt ccagagttgt   120
```

```
acagcagaag cctctctcct agactgaaaa tgaatgtgaa actaggaaat aaaatgtgcc    180
cctcccagtc tgggaggagg atgttgcaga gccctctccc atagtttatt atgttgcatc    240
gtttattatt attattgata atattattat tactattttt ttgtgtcatg tgagtcctct    300
ctccttttct ctttctgaca ttccaaaacc aggccccttc ctacctctgg ggctgcttga    360
gtctagaacc cttcgtatgt gtg                                            383
```

<210> SEQ ID NO 161
<211> LENGTH: 474
<212> TYPE: DNA
<213> ORGANISM: Homo sapiens

<400> SEQUENCE: 161

```
aggatgcccc tttgagaaat gctgttccac agaaccctgc ctttcaggcc ttggagacgt     60
gggcagggga gaagcagcgt ccctcagagc caggcctggc agtggtgcta gcagggccca    120
aggccaggga gcagggtctc ctgtcggagg acctgggca agcccctcca cgcgccagcg    180
ggtttctcag caggggaggt ccacaccaca ccgcttggga acctgggtgc ctaaacgcaa    240
caggagccaa ggcacaaatt taaccaaaca ccaaggttgc gtgaggcccc atttcatgag    300
ccgggctcca aggacgtgtc cttaggcggc tctggaaggc ccagcgccag ccccgtcct     360
ctgttaaagg gagccagccc cggcgtccgc ccaggcatgg tagcctgagc gcgccccag    420
ggtagtaggg ggcacctgag gagcagggtc tgccctggca tgagcagagc ccag          474
```

<210> SEQ ID NO 162
<211> LENGTH: 371
<212> TYPE: DNA
<213> ORGANISM: Homo sapiens
<220> FEATURE:
<221> NAME/KEY: misc_feature
<222> LOCATION: (134)..(134)
<223> OTHER INFORMATION: n is a, c, g, t or u

<400> SEQUENCE: 162

```
gatacttgga tgcttttcct ctgactgatg aagatcctga ataccaaaga gggccgctga     60
caggtctagg agtacacttc tagcacctag cagagagagg cttcactaca tcatgcttcc    120
tgacatctct cccnttgaag agcagtcaga ctcctgcttt gctcttcaga cttaatttgg    180
gggtttaaca ggtgaggttg ctgggggaac tcttttacaa catctctctg aaagaatccg    240
ggctgccagt ttcatttggt ttgggtgtca gtagcatgat ggaaagacaa aaaaacacaa    300
cttgacatct gcagaaatgg gttcaaattt tacctgcaac tcaccaattc tgtggccttg    360
gttcagcaat t                                                         371
```

<210> SEQ ID NO 163
<211> LENGTH: 445
<212> TYPE: DNA
<213> ORGANISM: Homo sapiens

<400> SEQUENCE: 163

```
caacaagacg gacctggctg ataagaggca gataaccatc gaggaggggg agcagcgcgc     60
caaagaactg agcgtcatgt tcattgagac cagtgcgaag actggctaca acgtgaagca    120
gcttttttcga cgtgtggcgt cggctctacc cggaatggag aatgtccagg agaaaagcaa    180
agaagggatg attgacatca agctggacaa accccaggag ccccccggcca gcagggcgg    240
ctgctcctgc taatgcagag ccgacctgtg gcttcccatg acactccttg cttgttgtgt    300
```

```
tgcttcctat tggctagctt cctaaggggg agggaaccg agttatcaag atgggaggat      360 tttcttttc tctctgtctt taggagtagg gtgggatggg gagggaggct gggcatcagg      420
gatcacatca ctcttaacgg ctgtt                                           445

<210> SEQ ID NO 164
<211> LENGTH: 313
<212> TYPE: DNA
<213> ORGANISM: Homo sapiens

<400> SEQUENCE: 164
ggtggcctct ggatcctccg tggaccgaac cgtcccccca ggaacacacc ttcaggtaga     60
ccccgaagcc tcaaggccgg ggctggagcg agacccag ggcctctcag gagacagtga      120
ggctgcccct cctaccacct acctcattct gcctactcac cccaggggcc acagccacag    180
cctgctggac tcaggactgt cctgtcaact ccagacaact gaataaacag gccgggtaca    240
gtggctcgca cctgtaatcc tagcactttg ggaggccgaa gcgggtggac cacttgacgt    300
ccgtagttcg aga                                                       313

<210> SEQ ID NO 165
<211> LENGTH: 344
<212> TYPE: DNA
<213> ORGANISM: Homo sapiens

<400> SEQUENCE: 165
aatgtcatgt ttattcaggc tgggaactgt attcacagta gaagtttcag tggtcaacat    60
atctatgact ctttaggctg ctgtagtttt acagtcaatt attaaaagt gagtagttac     120 atttataaga gcctgagaat acttagactc agtcatttgt tagtattttt accaaaatct    180
cttagtttca gacatgtcag aagcagctat atagcatatc ttattctatg atatacatca    240
ggctatctca agttcctgtc tcacagttaa ttcaaagaag gattaggatt tctgtatttt    300
ttctcatttg aatctttatg tgcatttggt ttgtgtacat gctt                     344

<210> SEQ ID NO 166
<211> LENGTH: 448
<212> TYPE: DNA
<213> ORGANISM: Homo sapiens

<400> SEQUENCE: 166
tcttacccca ctgaaaccaa cagggatcgg gccaggctcc cagattcttg aggacaggga    60
cttcggcatt tactaatggg ggactactgt ggggtaaggg ggcgcctgct tgcctgatac    120
aggatggggt caagggacag tggcaggtc ctcactcagg agtgggggt gtaggctggc      180 cagcccccag ggcttgtcca ccagtcttct ccccgcaagg ccctcagagc agcgcctgtg    240
ggtgtcagta ttacctgagc ctaggccaaa gctagcccaa ggctggggaa ggggaggaga    300
ctccaggtca gaatgtgagg tctcagtctg tgatttaagg tgttgcatgt ggactcttaa    360
ctgtacgtgt agtttctagt ggagaaatca aggctctgat cattttgttt ttagtatgaa    420
aatgtgattt cctttctgtt tgtaactc                                       448

<210> SEQ ID NO 167
<211> LENGTH: 334
<212> TYPE: DNA
<213> ORGANISM: Homo sapiens

<400> SEQUENCE: 167
agatgccagt aatcaatatt gaggacctga cagaaaagga caaattgaag atggaagttg    60
```

```
accagctcaa gaaagaagtg acactggaaa gaatgctagt ttccaaatgt tgtgaagaag      120
taagagatta cgttgaagaa cgatctggcg aggatccact ggtaaagggc atcccagagg      180
acaaaaatcc cttcaaggag ctcaaaggag gctgtgtgat ttcataatac aaacaaaaag      240
aaaaaaaatt aaacaaattc ttggaaatat ctcaaatgtt aataacaata tgaattttc       300 tcatgcatac tattactact aagcatgtac gtga                                  334
```

<210> SEQ ID NO 168
<211> LENGTH: 561
<212> TYPE: DNA
<213> ORGANISM: Homo sapiens

<400> SEQUENCE: 168

```
gcccccgact gaggcggaga cgaaggtgct gcaggcgcga cgggagcggc aagatcgcat       60
ctcccggctc atgggcgact atctgctgcg cggttaccgc atgctgggcg agacgtgtgc      120
ggactgcggg acgatcctcc tccaagacaa acagcggaaa atctactgcg tggcttgtca      180
ggaactcgac tcagacgtgg ataaagataa tcccgctctg aatgcccagg ctgccctctc      240
ccaagctcgg gagcaccagc tggcctcagc ctcagagctc cccctgggct tcgacctgc       300 gccccagccc ccagtacctc gtccggagca ctgtgaggga gctgcagcag gactcaaggc      360
agcccagggg ccacctgctc ctgctgtgcc tccaaataca gatgtcatgg cctgcacaca      420
gacagccctc ttgcagaagc tgacctgggc ctctgctgaa ctgggctcca gcacctccct      480
ggagactagc atccagctgt gtggccttat ccgcgcatgt gcggaggccc tgcgcagcct      540
gcagcagcta cagcactaag a                                                561
```

<210> SEQ ID NO 169
<211> LENGTH: 244
<212> TYPE: DNA
<213> ORGANISM: Homo sapiens
<220> FEATURE:
<221> NAME/KEY: misc_feature
<222> LOCATION: (94)..(94)
<223> OTHER INFORMATION: n is a, c, g, t or u
<220> FEATURE:
<221> NAME/KEY: misc_feature
<222> LOCATION: (128)..(128)
<223> OTHER INFORMATION: n is a, c, g, t or u

<400> SEQUENCE: 169

```
aatgtgtatg tctgggtaag tgtatagatt ttacaactat tttgaaggcg acctttttaa       60
ctttaaacag accactctgg aggagacgcc tganccagag cgctttacct aaagttcggt      120
gcctaaantg caccttcct ctggctggtg tctcccttct gccaagctat gcctcctgca       180
gaggtaggct ccgtggtgtc tcccactccg ccccaactgg agaacggtgt aaagaactgt      240
cagc                                                                   244
```

<210> SEQ ID NO 170
<211> LENGTH: 408
<212> TYPE: DNA
<213> ORGANISM: Homo sapiens
<220> FEATURE:
<221> NAME/KEY: misc_feature
<222> LOCATION: (262)..(262)
<223> OTHER INFORMATION: n is a, c, g, t or u
<220> FEATURE:
<221> NAME/KEY: misc_feature
<222> LOCATION: (268)..(268)
<223> OTHER INFORMATION: n is a, c, g, t or u

```
<400> SEQUENCE: 170
caggatggca ttagctctgt gtctgcaggt gctgtgcagc ctgtgtggct ggctctcgct    60
ctatatttct ttctgccacc tgaataagca ccgaagctat gagtggagct gccgcctggt   120
caccttcacc catggagtcc tctctatagg cctctccgct tatattggct tcattgatgg   180
cccatggcct tttacccacc caggctcacc caatacacct ctccaagttc atgtcctgtg   240
tctcaccttg ggctacttca tnttcganct tgggctgcat ctggcgcttt gcatggagga   300
agagcatcaa gaagtaccat gcttggagaa gcaggcggag tgaggaacgg cagctgaaac   360
acaacggaca tctcaaaata cactagccaa ggcttgctcc agattatg                408

<210> SEQ ID NO 171
<211> LENGTH: 359
<212> TYPE: DNA
<213> ORGANISM: Homo sapiens

<400> SEQUENCE: 171
aggacatcga ggctgcggtg aaccatgatt gtaccactgt attccagcct ggacgactga    60
gtgagaccct gtctcaaaca aaacaaaaca aacaaaaaa aagtacaaga ggaaaaaaat   120
tgatttctga ttgcctcact caagataagg tcaacattga aggtggaggt ggaagatgca   180
gtttatgtag gggtctgaag attttaccat tctggggact gtctttaaga aagagaatcc   240
aaaattaggt agaaaagtga acgtctgacc gggcgcggtg gctcatccct gtaatcccag   300
cacttaagga gtacgagacg ggaggatcac gaggtcaaga gatcgacagc atgctggcc    359

<210> SEQ ID NO 172
<211> LENGTH: 386
<212> TYPE: DNA
<213> ORGANISM: Homo sapiens
<220> FEATURE:
<221> NAME/KEY: misc_feature
<222> LOCATION: (182)..(182)
<223> OTHER INFORMATION: n is a, c, g, t or u

<400> SEQUENCE: 172
gtttctgcct ttgaacgtgg ctgtgggaag acatgatgct tagtgttgct gcagctatct    60
catgaccttg ggcaaaacat cccaacacac aggagggcca aacaagcagt cagaagaagc   120
ctgagtcttg tgggtgttgt tgagcagctg aacaaaccct aggatggctt ccttccagac   180
tncttaggat tgcgaacaat gaagctctat tgtttaagca aggtatcgat ggctattttc   240
acttgccact gaaagcacca ggacagagaa tcgtctttct aggaatacag ccacaaaagc   300
cttcattatg gtatatgcac ataaagaata taaaagtttc ctttatgttt ctctttaaaa   360
tatagctgaa gtctgcctca ggcaaa                                       386

<210> SEQ ID NO 173
<211> LENGTH: 408
<212> TYPE: DNA
<213> ORGANISM: Homo sapiens

<400> SEQUENCE: 173
ggttccaggc tttgcatctg gagcctttac cggttgactg ttgccttcca cacaaacagc    60
ctctgaaaag cactttctcc atacataatt ctggagaaga tgagggatct tgccctccag   120
gagccttcct tcctccccca atgaggaaat cagtcactgc actggtgcaa aggcaagcag   180
attggaattt ctgctcttca ccgatttttct cagggaaaga ccccttcccc ttgccagcag   240
aggaacctgt agtttttttcc atttcttttct tcagaaccaa agtatgtatc actcctcatg   300
```

```
ctcacaggga ttgacaggag agaattcacc aggatcttag ctcaaaagac acagcctcag    360
aatggccaga tggattgcac gaaacctgac ttggattcac catcttcc                 408
```

<210> SEQ ID NO 174
<211> LENGTH: 331
<212> TYPE: DNA
<213> ORGANISM: Homo sapiens
<220> FEATURE:
<221> NAME/KEY: misc_feature
<222> LOCATION: (227)..(227)
<223> OTHER INFORMATION: n is a, c, g, t or u
<220> FEATURE:
<221> NAME/KEY: misc_feature
<222> LOCATION: (229)..(229)
<223> OTHER INFORMATION: n is a, c, g, t or u
<220> FEATURE:
<221> NAME/KEY: misc_feature
<222> LOCATION: (264)..(264)
<223> OTHER INFORMATION: n is a, c, g, t or u

<400> SEQUENCE: 174

```
gtggacgagt gactgtccct ggtttgggct ggtgccattt agagggcaac cagagtgcag     60
ggaagggagg agcttgggca agagggacat tgctgtcgct ggttgatggt gagatggcac    120
ttaatgagaa cctggtcatt gggaaagccc caagcctgcg tcttgctgtg atgccttccc    180
cattatgaag ggtccattgg catgggagtg gggagacctg gactcanana agctacaagg    240
gcaagggtgg aaaggcatag cttntgcaag ttgatgctga aaaagatcca agactcatat    300
tcagcagaca gcccataacc aagagccaag g                                   331
```

<210> SEQ ID NO 175
<211> LENGTH: 260
<212> TYPE: DNA
<213> ORGANISM: Homo sapiens

<400> SEQUENCE: 175

```
aggtcttcaa agaattggcc agtcttacag ctcaccttgg ggtgtagatg actctccact     60
gtggtgctag gcaattttat tgaacaggtg gccactggtg gtgatggctg aaccactcat    120
taaacaaatt gctctaaatg gcctcagtat caaggtgtgc tttctgtacc cttaatctga    180
ctttaatcct gcagaacctc agtcttacca tgtttaacag cattgccatg tacgatatgc    240
ctttatccta cactgtatat                                                260
```

<210> SEQ ID NO 176
<211> LENGTH: 528
<212> TYPE: DNA
<213> ORGANISM: Homo sapiens

<400> SEQUENCE: 176

```
gctggctatg tacatggtcc cattccctac ctgcacttct ttatgcctgt cttcaccctg     60
ctgaccatcc acagcagcca gcactaccag gccctcatag tgcctgagct cacccagcag    120
atggttgatg ccaagaacat gatggttccc tgagacccct gccatggcca ctacctaaag    180
gtggccacag tgttcacgga ctacatgtcc atgaaggagt tggatgagca aatgcttaat    240
gtccaaaaca agaacagcag ctactttgtt gagtgaatcc ccaactatgt gaaaacagct    300
gtctgtgaca tcccactctt ggggctataa atgtctgcca ccttcaacat caacagcgtg    360
gccatccagg agctgttcaa gcacatctct gagtggtcat gtttcggtgc aaagcctttc    420
tgcactggca catgggcaag agcatggact agatggagtt caccaaggct gagagcaaca    480
```
tgaacaacct ggtgtcccgg taccagtaat accaggacac ctcagcca        528

<210> SEQ ID NO 177
<211> LENGTH: 540
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a, c, g, t or u
<220> FEATURE:
<221> NAME/KEY: misc_feature
<222> LOCATION: (34)..(34)
<223> OTHER INFORMATION: n is a, c, g, t or u
<220> FEATURE:
<221> NAME/KEY: misc_feature
<222> LOCATION: (48)..(49)
<223> OTHER INFORMATION: n is a, c, g, t or u
<220> FEATURE:
<221> NAME/KEY: misc_feature
<222> LOCATION: (52)..(52)
<223> OTHER INFORMATION: n is a, c, g, t or u
<220> FEATURE:
<221> NAME/KEY: misc_feature
<222> LOCATION: (54)..(54)
<223> OTHER INFORMATION: n is a, c, g, t or u
<220> FEATURE:
<221> NAME/KEY: misc_feature
<222> LOCATION: (64)..(64)
<223> OTHER INFORMATION: n is a, c, g, t or u
<220> FEATURE:
<221> NAME/KEY: misc_feature
<222> LOCATION: (66)..(66)
<223> OTHER INFORMATION: n is a, c, g, t or u
<220> FEATURE:
<221> NAME/KEY: misc_feature
<222> LOCATION: (76)..(76)
<223> OTHER INFORMATION: n is a, c, g, t or u
<220> FEATURE:
<221> NAME/KEY: misc_feature
<222> LOCATION: (78)..(78)
<223> OTHER INFORMATION: n is a, c, g, t or u
<220> FEATURE:
<221> NAME/KEY: misc_feature
<222> LOCATION: (122)..(122)
<223> OTHER INFORMATION: n is a, c, g, t or u

<400> SEQUENCE: 177
acttatctgt gctgtaacta ttgaaatgaa nccncttcaa atatgtannc cncntttctt        60
tttnanattt ctagananngg tttcaatata gactttctga cttttatggt atacatatag      120
gncaatattc tattcttctt cccttttaaa tacttactgt ttcaatttca ataaaaaat       180 cagcattcta gtttgtacat tttagcacag aaatgtttac aaccttcagc acaattgctt      240
ttgtaattta ctgacttggc attttgaggc gtttttaaca aattatgaga aataacacct      300
tcagaaagca tgtgactact ttgatgcaac tatttacaat gtattcataa gaagtcatta      360
acctgtagag ttcttagaca tgtggaacct ttaacaatta tactaaagag tacatacaaa      420
atacagagct atgtaataat aactaatttt aaatcctgac aaattagaag ttaagcctac      480
tatctgtaaa aatatgtcct gattcatttt tttaagtata tacctgagcc tttaaaaagt      540

<210> SEQ ID NO 178
<211> LENGTH: 560
<212> TYPE: DNA
<213> ORGANISM: Homo sapiens
<220> FEATURE:
<221> NAME/KEY: misc_feature
<222> LOCATION: (460)..(460)
<223> OTHER INFORMATION: n is a, c, g, t or u
<220> FEATURE:
<221> NAME/KEY: misc_feature

```
<222> LOCATION: (462)..(466)
<223> OTHER INFORMATION: n is a, c, g, t or u
<220> FEATURE:
<221> NAME/KEY: misc_feature
<222> LOCATION: (468)..(469)
<223> OTHER INFORMATION: n is a, c, g, t or u
<220> FEATURE:
<221> NAME/KEY: misc_feature
<222> LOCATION: (471)..(472)
<223> OTHER INFORMATION: n is a, c, g, t or u
<220> FEATURE:
<221> NAME/KEY: misc_feature
<222> LOCATION: (475)..(481)
<223> OTHER INFORMATION: n is a, c, g, t or u
<220> FEATURE:
<221> NAME/KEY: misc_feature
<222> LOCATION: (483)..(487)
<223> OTHER INFORMATION: n is a, c, g, t or u
<220> FEATURE:
<221> NAME/KEY: misc_feature
<222> LOCATION: (489)..(493)
<223> OTHER INFORMATION: n is a, c, g, t or u
<220> FEATURE:
<221> NAME/KEY: misc_feature
<222> LOCATION: (496)..(503)
<223> OTHER INFORMATION: n is a, c, g, t or u
<220> FEATURE:
<221> NAME/KEY: misc_feature
<222> LOCATION: (505)..(510)
<223> OTHER INFORMATION: n is a, c, g, t or u
<220> FEATURE:
<221> NAME/KEY: misc_feature
<222> LOCATION: (512)..(535)
<223> OTHER INFORMATION: n is a, c, g, t or u

<400> SEQUENCE: 178
gccattttga gtgccagatc tagttatttt gctgcaatgc tgagtggctg ttgggctgaa      60
agctcccaag agtacgttac tcttcaaggt ataagccatg tagaactgaa tgttatgatg     120
cattttatat atggaggaac tctggacatt ccagacaaaa ctaatgttgg tcagatactc     180
aatatggctg atatgtatgg actagaagga ttaaaagaag tagcaatcta tattttaaga     240
agagattact gtaatttctt tcagaagcct gttcccagaa cattgacgtc tatactagaa     300
tgcctgatta ttgctcattc agttggagtg gaaagtcttt ttgctgactg catgaagtgg     360
attgtaaagc attttgcaag gttttggtct gagagaagct ttgcaaatat acctcctgag     420
attcagaaaa gttgtcttaa tatgttgatt cagtccttan tnnnnntnnc nngannnnnn     480
ntnnnnntnn nnnccnnnnn nnngnnnnnn cnnnnnnnnn nnnnnnnnnn nnnnncaggg     540
tgcactcaca gcacagaaca                                                 560

<210> SEQ ID NO 179
<211> LENGTH: 385
<212> TYPE: DNA
<213> ORGANISM: Homo sapiens

<400> SEQUENCE: 179
gggttcacgt catttcctg tctcagcctc cccagtagct gggactccag gcacccacca       60
ccactcccgg ctaattttt gtattttag tacagacagg gtttcactgt gttggccagg       120
atggtcttga tctcctgacc ttgtgatcca cccacctcgg cctcccaaag tgctgggatt      180
gcaggcatga atgaccgcgc ccagccgcag gcgcaacttt tttgagtttt cctgccagg      240 cgcggtggct caggcctgta gtcccagcat tgggagg cgaggtgggc ggatcacttg       300
aggtcaggag ttagaaacca gcctggccaa cgtggtgaaa ccccgtctcc agtaaacata     360
caaagccatt acagggcatg gtggg                                           385
```

<210> SEQ ID NO 180
<211> LENGTH: 173
<212> TYPE: DNA
<213> ORGANISM: Homo sapiens

<400> SEQUENCE: 180

```
gacaaccttc gttcacttgg gtattcccat aatccttgtc tttcagggtt gacctgttac    60
agctgcttaa acacatcact gtatgctagg tattgcctac cttcacttac ttttctaacc   120
ttgccgatgt gctgccttca taaactgggt atatctccgc cacacttcta cgt          173
```

<210> SEQ ID NO 181
<211> LENGTH: 340
<212> TYPE: DNA
<213> ORGANISM: Homo sapiens
<220> FEATURE:
<221> NAME/KEY: misc_feature
<222> LOCATION: (167)..(167)
<223> OTHER INFORMATION: n is a, c, g, t or u

<400> SEQUENCE: 181

```
ggtaactttg gccaagactt ttcagtagga aatgcttcaa aatacaaagc aagagctatt    60
ttcaagaaag accttctaaa tttatattag gacatagtga gaagaaagcc atctgaaaac   120
caggaagaga gccctcacca gaatctgacc atgctggtgc cctgatnctt ggactttcag   180
cctccagaac tgcaaaattc tggtgtggtg tgaatgctgt ggctcagtcc gaacatgttt   240
ttttctgtaa ttttatcatt attacacgat tgcaatatca gttttgtttt taaattggaa   300
agcaacattt tctactgttg aaagacgttt tttgacaaat                         340
```

<210> SEQ ID NO 182
<211> LENGTH: 416
<212> TYPE: DNA
<213> ORGANISM: Homo sapiens

<400> SEQUENCE: 182

```
acagcttgtc tgtcacagtg cctgttctga ttgcaggctt tggtgttctc ctggtgttaa    60
tcctgacttt tttcctagtg atccaccctc tgggaaactt ctggctaatt cttagcgtca   120
cctcaattga gctgggcgtt ctgggcttaa tgacattatg gaacgtcgac atggattgca   180
tttctatctt gtgccttatc tacaccttga atttcgccat tgaccactgt gcaccactgc   240
ttttcacatt tgtattagca actgagcaca cccgaacaca atgtataaaa agctccttgc   300
aagaccatgg gacagccatt ttgcaaaatg ttacttcttt tcttattggg ttagtccccc   360
ttctatttgt gccttcgaac ctgaccttca cactgttcaa atgcttgctg ctcact        416
```

<210> SEQ ID NO 183
<211> LENGTH: 503
<212> TYPE: DNA
<213> ORGANISM: Homo sapiens
<220> FEATURE:
<221> NAME/KEY: misc_feature
<222> LOCATION: (78)..(78)
<223> OTHER INFORMATION: n is a, c, g, t or u
<220> FEATURE:
<221> NAME/KEY: misc_feature
<222> LOCATION: (84)..(84)
<223> OTHER INFORMATION: n is a, c, g, t or u
<220> FEATURE:
<221> NAME/KEY: misc_feature
<222> LOCATION: (210)..(210)
<223> OTHER INFORMATION: n is a, c, g, t or u
<220> FEATURE:
<221> NAME/KEY: misc_feature

```
<222> LOCATION: (247)..(247)
<223> OTHER INFORMATION: n is a, c, g, t or u
<220> FEATURE:
<221> NAME/KEY: misc_feature
<222> LOCATION: (371)..(371)
<223> OTHER INFORMATION: n is a, c, g, t or u

<400> SEQUENCE: 183
aggccgggct cagaggcgga aagcctgcc tggtgcccac agccgtctgg ctcagggact      60
ccaccctggc cccgagtngc cgtntgctgg gcctttcctt cctggctctg caccccatgc    120
tggctgcccg gtctggcttc ccttcttgtc tctgtcttgg gcgaggcagc tgtgagcatt    180
gcacagaggc aaagaccctc ctgcagcctn tgcgctgggc cgtagaaaca agagcctttg    240
taatacngaa cctcattcaa ggattaggag tggtggttag gtcagggcca cccccagtgc    300
tgcaggaacg gcctccaccc agctctgttg gtcagagcct gggtcatgca cctggagttg    360
ggagatcaag ntgggtctca gggcagtgag gtggccatat ccaccacatc gcatttcgtg    420
ggggaagagg tgacctcttt gttttaaact taaggtgtct gcttatccag ccagaaataa    480
aaatctgcca gtggtgttcc caa                                            503

<210> SEQ ID NO 184
<211> LENGTH: 377
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, t or u
<220> FEATURE:
<221> NAME/KEY: misc_feature
<222> LOCATION: (294)..(294)
<223> OTHER INFORMATION: n is a, c, g, t or u

<400> SEQUENCE: 184
gagtcccgtc tcagtgtgga ggaacnggct gcacatggga cctgaaggtg ccctctgtgt    60
ttatgttggg ggtgggggggg cagtgctggc tgcctctgtc ctgtgtgtga ccctacccte   120 gaagggtcct gtcctgtcag tcccgaggga gccacaacca aagctgcgga gagaaggtgg   180
ggaagggtgc ggaatggccg tggggcacag cgtggcagac tgttcagtct ctgctgggtc   240
tttcctaggg acctggaagg ccagtgttgc ttcccccctca ctcccttca ctgnaggcag    300 cctctctgct tccccaatgc cttatgcctg ggcacactgc cacagaatat gcaatatgtg    360
tgggtgacca tgccctc                                                   377

<210> SEQ ID NO 185
<211> LENGTH: 390
<212> TYPE: DNA
<213> ORGANISM: Homo sapiens

<400> SEQUENCE: 185
gtcatcctgt gctcagttag cagctcatcc agctgggtca ggaaagcctt ttggaagcgt    60
aggaccttgc cagccagcgc tgggatatgc aggaggacgg ggacagcatt cagcacctcg   120
cgcagaaagc ccgactcctc cttcagtccc tcctgagcta ggtccagcag cctgaggaag   180
cgagggtcgt cgtactcgaa gcggcgcccg caggtgaggg aggcgatcac gttgctcacg   240
gctttgtcca agagaccgtt ggggcgaaag gggcgtcgga gtggttggcg aaggcggcac   300
aaaggcaggc ggcctcctcg gtcacccact gctccagcga cttcttgccc aggcccaagt   360
tgcgcaaggt ggagacggag aagcgcctct                                     390
```

<210> SEQ ID NO 186
<211> LENGTH: 188
<212> TYPE: DNA
<213> ORGANISM: Homo sapiens

<400> SEQUENCE: 186

| | | | | | |
|---|---|---|---|---|---|
| ggctggcaac | ccagaaagat | tggatttcag | tgccatggtg | ctggctgcgg | agagcttcac | 60 |
| ctcagggagg | cactactggg | aggtggacgt | ggaaaaggca | accaggtggc | aagtgggcat | 120 |
| ataccacggc | tctgcagacg | cgaagggcag | cacggccaga | gcttccggag | agaaagtctt | 180 |
| gctcacgg | | | | | | 188 |

<210> SEQ ID NO 187
<211> LENGTH: 549
<212> TYPE: DNA
<213> ORGANISM: Homo sapiens
<220> FEATURE:
<221> NAME/KEY: misc_feature
<222> LOCATION: (213)..(213)
<223> OTHER INFORMATION: n is a, c, g, t or u

<400> SEQUENCE: 187

| | | | | | |
|---|---|---|---|---|---|
| taggaatgga | gcccgagcag | tctcgctctc | agggccctgt | gtggagtcac | tgtgctgtcc | 60 |
| cagctctgga | gacgcagaat | tccacatgag | gaatgtggaa | ttcagcatgg | ggatgacgct | 120 |
| gcttcaccca | gacttggagg | agcgtggtga | attgcccgtg | cccatgctct | gatgtgcctc | 180 |
| tctggccgct | gcgttcctcc | tttctccctg | ccntgggtca | gtgcctgtaa | acactgccct | 240 |
| aaatcagcag | ggccccgtc | acttctgctt | tatgcacctt | tttcctcaga | cacattaata | 300 |
| caggggagtt | ttgtttccaa | gggaccacat | ccagatggag | gggctgtttt | tggtgatctg | 360 |
| cactgccaaa | tgcccgagtg | tccctgacag | tcggagctga | tgaggccaag | gctgtgtgtg | 420 |
| gttcctctgg | atggccagaa | gaggaaccaa | acactgaat | tctgggcctt | cttaagagtg | 480 |
| gtgatcagca | cattgtgata | gaagcatatc | tgggaatgaa | cttggcctca | agcttttggc | 540 |
| cttttaatt | | | | | | 549 |

<210> SEQ ID NO 188
<211> LENGTH: 459
<212> TYPE: DNA
<213> ORGANISM: Homo sapiens
<220> FEATURE:
<221> NAME/KEY: misc_feature
<222> LOCATION: (120)..(120)
<223> OTHER INFORMATION: n is a, c, g, t or u

<400> SEQUENCE: 188

| | | | | | |
|---|---|---|---|---|---|
| ctactctctg | tctccataaa | ctggtctatt | ttggacattt | cacataagcc | tccctggatc | 60 |
| ccagtttaag | catcctgggg | tttgtctgcc | tgccagagcc | atggtgccac | tggggctacn | 120 |
| tgtcctgtgg | gatgacaagg | caggtccaaa | cctttgcctg | ctctcccatc | cattcctttt | 180 |
| gtgttagtcc | atgtgtctcc | cgactgttct | ctccaacaac | aacacagact | gacaaaacct | 240 |
| actgacttgg | agtcaggaac | agactttgct | attttctggc | tgtgtgatcc | tgatgagtcc | 300 |
| cttgaacctc | ctggacttgt | tcctcagcct | aaaaaccaag | actaataaat | caagtctatc | 360 |
| tcacagcctt | acgtggggat | caaaaaacat | ggagcatgtg | aacacacatt | gtacatcacg | 420 |
| aagctgtgtg | caaataaata | tcgtgtaact | ccagcccctt | | | 459 |

<210> SEQ ID NO 189
<211> LENGTH: 430

```
<212> TYPE: DNA
<213> ORGANISM: Homo sapiens
<220> FEATURE:
<221> NAME/KEY: misc_feature
<222> LOCATION: (112)..(112)
<223> OTHER INFORMATION: n is a, c, g, t or u

<400> SEQUENCE: 189
gcccgaggcc tgctgagaag catgggggcc ttgggatagt tccagaatga ggatgtgcgt    60
ttctagctgc tttgcgccct cctcccccaa aaatctgcta ccacaattcc anccggcgg    120
cacgccccca agactccttt gtcgcccag gggcgggacc tgagctgtcg gtttcaggag    180
cccttcgtga cttcaaaagt cctgggcact gttgctcatg agtgctgcac aactgtcgcc    240
ctctaaagcc acctccatcc ctcactgggc tggcctcctg agccttcggt gaggaaacgg    300
ggttccgagt tgcccgcctg agagcttaac agtctgacta gaaaagggct aattcgcttt    360
ctgtgcaaat ctcttgagct aattatttaa tctgaaacat ggacaggtaa aggaccattg    420
gcgggcgtgg                                                          430

<210> SEQ ID NO 190
<211> LENGTH: 406
<212> TYPE: DNA
<213> ORGANISM: Homo sapiens

<400> SEQUENCE: 190
acatcaagca gctttctcgc tttgctggag cttcaagtaa gattgctcca gtggaagcac    60
cagatgctaa ggtgaggatg gtgatgatcg ctggatcacc agaggctcgg ttcaaggctc    120
agggaagaat tatggaaaaa tgaaagaaga aaacttcgtt agtcctaaag aagaggtgaa    180
acttgaagct catatcagag tgccatcctt tgctgctggc agttactgga aaggaggca    240
aaacggtgaa tgaacttcag aatttgtcaa gtgcagaagt tgttgtccct tgtgaccaga    300
cacctgatga gaatgaccaa gtggttgtca aaataactgg tcacttctat gcttgccagg    360
ttgcccagag aaaaattcag gaaattctga ctcaggtaaa gcagca                  406

<210> SEQ ID NO 191
<211> LENGTH: 555
<212> TYPE: DNA
<213> ORGANISM: Homo sapiens

<400> SEQUENCE: 191
aatgctgtca gcccttaggc aagactaaat tggaaagaaa ggtgtctgcc aaagaaaaca    60
ggcaggcccc tgtcctcctt caaacataca gggaatcctg gaatggagaa acatagaat    120
cagtgaaaca aagccgtagt ccagtttctg tgttttcctg ggacaatgaa aagaatgaca    180
aggactcctg gagtcaactt ttcactgaag attctcaagg ccagcgggtc attgccaca    240
acactagagc tccttttcaa gatgtaacca ataactggaa ttgggactta gggccgtttc    300
ctaacagtcc ttgggctcag tgccaggagg atggccaac tcaaaatctg aagcctgatt    360
tgctctttac ccaggactct gaaggtaatc aagttatcag acaccaattc taaatgtttg    420
aagctttgtt tctaaaagta ccttgaaatg atagagatgt aggaaaatat agttgtgggt    480
ggagagagga gtgagtttgt ttaggtggga aggtggcatg ggatgaagtt gtcattactg    540
agcatcttct ctgtg                                                    555

<210> SEQ ID NO 192
<211> LENGTH: 554
<212> TYPE: DNA
```

<213> ORGANISM: Homo sapiens

<400> SEQUENCE: 192

| | |
|---|---|
| gccctgctca gaggtcagag ggtctgggca gaggagggac cacattcccc tgccttgccc | 60 |
| ctgagcactt ctggagactg cgtcctgtcc tatctgctca ccatcaccct tcctgcccga | 120 |
| cggagctgct tctgctccct ggggcatatg gactgaccca cctcctgctg agaaccttcc | 180 |
| cctaggccct gtgcagaagg gctactgccc cttaggcctc agctggggga aaggcagttc | 240 |
| tggtgctgta gaggccctgg tgcagaaagt gggacgtctt ttttcctaag gtgtttaagc | 300 |
| acaggcttga taagtttggt ttttaaaaaa taatctagga aatgaataat tctaaatcta | 360 |
| gtaatgagga aactgagcat ttcttttgcc ctccagggtg ccaagaccct acatatgaca | 420 |
| gaacccttgg cccttctcca tgcctgtggg atctgtttct ttaaagcact ttgtactgtt | 480 |
| attcaggagg ttgataatct ccttgaccca tgtctttcta ccctaatccc cacttccctg | 540 |
| cagaatcaat ctga | 554 |

<210> SEQ ID NO 193
<211> LENGTH: 319
<212> TYPE: DNA
<213> ORGANISM: Homo sapiens

<400> SEQUENCE: 193

| | |
|---|---|
| acgcgtccaa catctcaaac ttgatctcca tctttggctc cggcttctcg gggctggtga | 60 |
| gccgacagcc ggactcctcg gagcagccgc cgccgctcaa cgggcagctg tgcgccaagc | 120 |
| aggcgctcgc cagcctcggc gcctggactc gagccattgt cgccttctag gaccccccga | 180 |
| gggcacaggg acccggggcc ccgcgggggct ggggccagac aaagactcgg caaaggggcg | 240 |
| agaggaggga acgagcgggc gccgggccac tcggggctga gctgggggcg agcggggca | 300 |
| ggcggctgat gttttataa | 319 |

<210> SEQ ID NO 194
<211> LENGTH: 218
<212> TYPE: DNA
<213> ORGANISM: Homo sapiens

<400> SEQUENCE: 194

| | |
|---|---|
| gaagactttc taaataatga taatcagagc tgtactctct ctggaggcaa acatcatggt | 60 |
| cctgttgaag ccctgaaaca aatgttattt aaccttcaag cagtacaaga acgttttaat | 120 |
| caaaataaga ccacagatcc aaaagaagag attaaacaag tttcagaaga tgatttctct | 180 |
| aaattacagt tgaaggaaag tatgattcct attactag | 218 |

<210> SEQ ID NO 195
<211> LENGTH: 246
<212> TYPE: DNA
<213> ORGANISM: Homo sapiens

<400> SEQUENCE: 195

| | |
|---|---|
| ccccacccaa atacaagtcc cagtggaaag gaaaggtagt acctattctt ctccatgggg | 60 |
| ttcctaacac cctccattac tctttcagtc tccaagcact tgaatccat ttttaaacat | 120 |
| tcaggttgcc agacctgtca cacagtgggc tctgataggg ttacggaggg ggcctggctc | 180 |
| tcagtctcta ctctcctatg tcccatcagt tggttggagg ccaccttcca gggggtatgg | 240 |
| gagaca | 246 |

<210> SEQ ID NO 196
<211> LENGTH: 283
<212> TYPE: DNA
<213> ORGANISM: Homo sapiens

<400> SEQUENCE: 196
caccttgacg gttccagtgt ctgtatttat gttgaaagtc caggtgaatg acatcatcag      60
tcgtcagtac ctgagccaag cagttgtaga agtgtttgta aactacacga agacaaattc     120
cacagtaact aaaagcaatg gagcagtgct gataaaagta ccctacaaat taggacttag     180
tttaactatt attgcttaca aagatggcta cgtgttgacc cctctgcctt ggaaaaccag     240
aagaatgcca atatattcat cagttacact ttcactgttc ccg                      283

<210> SEQ ID NO 197
<211> LENGTH: 391
<212> TYPE: DNA
<213> ORGANISM: Homo sapiens

<400> SEQUENCE: 197
cgtccgagtg tgagtcagtc agcgacaagg ctcccagccc tgccaccctg ccagccacct      60
cctcctccct gcccagccca gccaccccat cccatggctc tcccagttcc catgggcctc     120
cagccaccca ccctacctcc cccactcccc cttcgacagc cagtggggcc accacagctg     180
ccaacggggg tagcttgaac tgcctgcaga caccatcctc caccagcagg gggcgcaaga     240
tgactgtcaa cggcgctccc gtgccccct taacttgagg ccagggaccc tctcccttct     300
tccagccaag cctctccact ccttccactt tttctgggcc cttttttcca cctcttctac     360
tttccccagc tcttcccacc ttgggggtgg g                                   391

<210> SEQ ID NO 198
<211> LENGTH: 563
<212> TYPE: DNA
<213> ORGANISM: Homo sapiens
<220> FEATURE:
<221> NAME/KEY: misc_feature
<222> LOCATION: (116)..(116)
<223> OTHER INFORMATION: n is a, c, g, t or u
<220> FEATURE:
<221> NAME/KEY: misc_feature
<222> LOCATION: (165)..(165)
<223> OTHER INFORMATION: n is a, c, g, t or u
<220> FEATURE:
<221> NAME/KEY: misc_feature
<222> LOCATION: (168)..(168)
<223> OTHER INFORMATION: n is a, c, g, t or u
<220> FEATURE:
<221> NAME/KEY: misc_feature
<222> LOCATION: (175)..(175)
<223> OTHER INFORMATION: n is a, c, g, t or u
<220> FEATURE:
<221> NAME/KEY: misc_feature
<222> LOCATION: (225)..(225)
<223> OTHER INFORMATION: n is a, c, g, t or u

<400> SEQUENCE: 198
agaggcaggc atagaggctt ctccgccagc ctcctctgga cggcaggctc actgccaggc      60
cagcctccga gagggagaga gagagagaga ggacagcttg agccgggccc ctgggnttgg     120
cctgctgtga ttccactaca cctggctgag gttcctctgc ctgcnccngc cccnagtcc     180 ccacccctgc ccccagcccc ggggtgagtc cattctccca ggtanccagc tgcgcttgct     240
tttctgtatt ttatttagac aagagatggg aatgaggtgg gaggtggaag aagggagaag     300
aaaggtgagt ttgagctgcc ttccctagct ttagaccctg ggtgggctct gtgcagtcac     360

```
tggaggttga agccaagtgg ggtgctggga ggagggagag ggaggtcact ggaaagggga      420
gagcctgctg gcacccaccg tggaggagga aggcaagagg gggtggaggg gtgtggcagt      480
ggttttggca aacgctaaag agcccttgcc tccccatttc ccatctgcac cccttctctc      540
ctccccaaat caatacacta gtt                                              563
```

<210> SEQ ID NO 199
<211> LENGTH: 591
<212> TYPE: DNA
<213> ORGANISM: Homo sapiens
<220> FEATURE:
<221> NAME/KEY: misc_feature
<222> LOCATION: (60)..(84)
<223> OTHER INFORMATION: n is a, c, g, t or u
<220> FEATURE:
<221> NAME/KEY: misc_feature
<222> LOCATION: (122)..(146)
<223> OTHER INFORMATION: n is a, c, g, t or u
<220> FEATURE:
<221> NAME/KEY: misc_feature
<222> LOCATION: (182)..(200)
<223> OTHER INFORMATION: n is a, c, g, t or u
<220> FEATURE:
<221> NAME/KEY: misc_feature
<222> LOCATION: (453)..(478)
<223> OTHER INFORMATION: n is a, c, g, t or u
<220> FEATURE:
<221> NAME/KEY: misc_feature
<222> LOCATION: (495)..(536)
<223> OTHER INFORMATION: n is a, c, g, t or u
<220> FEATURE:
<221> NAME/KEY: misc_feature
<222> LOCATION: (540)..(554)
<223> OTHER INFORMATION: n is a, c, g, t or u

<400> SEQUENCE: 199

```
ctggagagcc agtgcccatg gcccgctgcg tctccacagg gggtcgcccg ccagcccaan      60
nnnnnnnnnn nnnnnnnnnn nnnnggatgc ccaatacgag ccaggtgcca gggttcctgt     120
cnnnnnnnnn nnnnnnnnnn nnnnnntgga tattggtgcc ctcaagccag gtggacggca     180
annnnnnnnn nnnnnnnnnn gagcacgaga gctttgagaa gcctcagctg ctgactgtga     240
acctcaccgt gtactacccc ccagaggtat ccatctctgg ctatgataac aactggtacc     300
ttggccagaa tgaggccacc ctgacctgcg atgctcgcag caacccagag cccacaggct     360
ataattggag cacgaccatg ggtcccctgc caccctttgc tgtggcccag ggcgcccagc     420
tcctgatccg tcctgtggac aaaccaatca acnnnnnnnn nnnnnnnnnn nnnnnnnntg     480
ccctaggagc tcgcnnnnnn nnnnnnnnnn nnnnnnnnnn nnnnnnnnnn nnnnnnagcn     540
nnnnnnnnnn nnnncatgtc tcctattcag ctgtgagcag agagaacagc t              591
```

<210> SEQ ID NO 200
<211> LENGTH: 485
<212> TYPE: DNA
<213> ORGANISM: Homo sapiens

<400> SEQUENCE: 200

```
catcagattt ctgcagatct gctttaaagc tgtacatttt tgttacagtc taagatgtgt      60
tcttaaatca ccattccttc ctggtcctca ccctccaggg tggtctcaca ctgtaattag     120
agctattgag gagtctttac agcaaattaa gattcagatg ccttgctaag tctagagttc     180
tagagttatg tttcagaaag tctaagaaac ccacctcttg agaggtcagt aaagaggact     240
taatatttca tatctacaaa atgaccacag gattggatac agaacgagag ttatcctgga     300
taactcagag ctgagtactg ctccaggggtg gtgtgcaatc ttatattgat gcttgtgaat     360
```

```
ctgccatttg atttgtagga taaataaata tgtttaatat taacaacttc catcaaaact    420
ataataataa tattatatct actgttgacc tctaacaaca atcaggtgct gtattcagag    480
tcata                                                                485
```

<210> SEQ ID NO 201
<211> LENGTH: 432
<212> TYPE: DNA
<213> ORGANISM: Homo sapiens

<400> SEQUENCE: 201

```
gccctgactg actgtattct ctggccacat tcaagtcccc cattggtggg ggcagagaag     60
taggaccagg ccatccttgg ctccagagct cgaagacccc aagacagccc tctgctctca    120
gcggcgccac agagagcctg ggctcagcct tctgcatcag acatggcct cgtccactga    180 gggcacgatt taaacatttg acatcagaag ctttatttgt aaacctcaca cagataagga    240
ccaagggctg gcggtgtggc cagaggacag gggaagctga aggccccgtg cttgagctcg    300
gcagtcctgc tccttgcagt gaagccacca tgggtgaccg tccagcctca cccggtggcc    360
tgcacagtga gggaagggct tcagggccat ctgctcccag gcaggggac aggccaccaa    420 ggacctttgg ca                                                        432
```

<210> SEQ ID NO 202
<211> LENGTH: 499
<212> TYPE: DNA
<213> ORGANISM: Homo sapiens
<220> FEATURE:
<221> NAME/KEY: misc_feature
<222> LOCATION: (425)..(425)
<223> OTHER INFORMATION: n is a, c, g, t or u

<400> SEQUENCE: 202

```
ggtggagaag ctggcgcgtg agaacagcag catgcggctg gagctggacg ccctgcgctc     60
caagtacgag gcgctgcaga ccttcgcgcg caccgtggcc cggggacctg tggcgccctc    120
caaggtggcc accaccagcg tcatcaccat cgtcaagtcc accgagctct cctccacctc    180
cgtgcccttc tcggctgcat cctagtgccg gccgggggcg ggggtggcg gcggcgggc     240 ggcgggcagg cgggtggggg cacaccccctc gtacctgtca ctgggatgca gactctcgac    300
atccgagtcc aagcgcaggc ccctcgggcg caggcagctc acaccaggaa gagactgtat    360
tgcagggtga agagtgggct cccgtgggcc cagagctgca cgccggtcca cagacacact    420
cacgnccgcc acctgctccc cgcagatgtg tctgtgtgtg ggaattggta tcttgcaccc    480
gtgggagtcg ggacatata                                                 499
```

<210> SEQ ID NO 203
<211> LENGTH: 569
<212> TYPE: DNA
<213> ORGANISM: Homo sapiens
<220> FEATURE:
<221> NAME/KEY: misc_feature
<222> LOCATION: (107)..(107)
<223> OTHER INFORMATION: n is a, c, g, t or u

<400> SEQUENCE: 203

```
ttccagcacc attcttttcc tattaaatta cactggcaaa tttgattaaa aaaaacaact     60
gactatatat gcttgtaaac atttccagat tatgttattc ttttaancta aatatgtgtc    120
cttatgccaa taccccactc catctattac tgcagtgtat gataagtctt gaatctagt    180
```

```
agtgtaagtt cttcaacgtt gcccttaatt tttaaaatca ctcttgctat ttaaaattgt    240
ttgtattaca tggaaatttt ataatcagct tgccaatttc tacaaaagtc ctgctgagat    300
tttaattggt attttgcttg ttctgcagct taatgcaaga aaattatctt aacaatattg    360 aattttcaa tctattaaca tgttatatat tactgtttac ttaggatttt ttcacttttc    420
ctgccttgtt ttgaactgat attgtggttt taagtaattt ttttatttc tactattggc     480 ttagtaacta tgccccactt tttgattttg tagcacagtt gaccattgaa caacacaagt    540
ttgaattgtg catgtccaat tgtctatgg                                      569

<210> SEQ ID NO 204
<211> LENGTH: 266
<212> TYPE: DNA
<213> ORGANISM: Homo sapiens

<400> SEQUENCE: 204
ggagcagaga cagagcgacc catacctggc ccaggccccg gccccgcagg cagctgaatt     60
cctgagccca gtgacaaccc cttcccctg cactctgtcg tccgcccaag cctcaggccc    120
tgaggctgca gatgagactt gtccccagct ggctgtccat cctcctggtg tcagcaagct    180
gggtttgcag tgtcttccaa gcgacggtgt tcagaatgtg aaccagtgac tctcgggcgc    240
ccctgtggta actttgcagg cggccc                                         266

<210> SEQ ID NO 205
<211> LENGTH: 506
<212> TYPE: DNA
<213> ORGANISM: Homo sapiens
<220> FEATURE:
<221> NAME/KEY: misc_feature
<222> LOCATION: (41)..(41)
<223> OTHER INFORMATION: n is a, c, g, t or u
<220> FEATURE:
<221> NAME/KEY: misc_feature
<222> LOCATION: (99)..(99)
<223> OTHER INFORMATION: n is a, c, g, t or u
<220> FEATURE:
<221> NAME/KEY: misc_feature
<222> LOCATION: (103)..(103)
<223> OTHER INFORMATION: n is a, c, g, t or u

<400> SEQUENCE: 205
gcaagagctt tatccagagc tcccacctga tccgccaccg nccgcatcca cacgggcaac     60
aagccgcaca agtgtgcggg ctgcggcaaa ggcttccgnt atnaaaacgc acctcgcgca    120
gcaccagaag ctgcacctgt gttaggggct gggtccgcgg gaggctgccg tctgggagc     180 ctgtgggggg tagatatcct gggactgacc caggggaagg aagtggggaa ggggcgggag    240
ggacaatctg agagtgactg gggagccttt ggtgtttggg gtttcctgaa gtgggaggag    300
tgttgagtaa gttggtcttt cccggtgcta tacttgcctc ctctccacgg aagaattgtt    360
caggagatgc gcttggggtg atgacttcct taaatacacg ctgtaggggg tgaagagctt    420
ggaggaccag gcactttgag gaagggcagt tcgtgggctg ggtgggaac aggatggcgg     480 gcaatagact agggtaggcc gcgatg                                         506

<210> SEQ ID NO 206
<211> LENGTH: 439
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n is a, c, g, t or u
```

```
<220> FEATURE:
<221> NAME/KEY: misc_feature
<222> LOCATION: (56)..(57)
<223> OTHER INFORMATION: n is a, c, g, t or u
<220> FEATURE:
<221> NAME/KEY: misc_feature
<222> LOCATION: (60)..(62)
<223> OTHER INFORMATION: n is a, c, g, t or u
<220> FEATURE:
<221> NAME/KEY: misc_feature
<222> LOCATION: (64)..(64)
<223> OTHER INFORMATION: n is a, c, g, t or u

<400> SEQUENCE: 206
```

| | | | | | |
|---|---|---|---|---|---|
| tcatttagcc | ggtgtccact | aactcagtgt | tgtgggccat | ttgtaaaccc | ttntgnngtn | 60 |
| nncnccaggc | agacgtaggg | aaagaaagag | aggatctgta | tagacaagaa | agctggccat | 120 |
| gtgggaagtc | cagagctcaa | accatgtgcc | ccagaggact | ggtgctggca | ttaagcctgt | 180 |
| aaatcaaagg | cttctttggc | aggaccctgg | gctgttagaa | tcaccctagg | gagcagagcc | 240 |
| aggggacatt | ttggcccctg | actagcaagg | cacaacccta | taatggcaga | agcccttctt | 300 |
| tcccctcccc | gtttcccacc | agacccactt | ccttgatggg | cctctagcac | ccttccaagc | 360 |
| tgatggggtc | gggaatgtga | gctggtaaaa | tgggcagtgg | aaggggctgt | actgtttctt | 420 |
| tacatctcac | ggggactag  |            |            |            |            | 439 |

```
<210> SEQ ID NO 207
<211> LENGTH: 375
<212> TYPE: DNA
<213> ORGANISM: Homo sapiens

<400> SEQUENCE: 207
```

| | | | | | |
|---|---|---|---|---|---|
| aagaaatgct | acctcggtgc | catgttctgg | actccgcaga | acaaggactt | tttggagaac | 60 |
| tccagcctat | accctctatt | gccatgacca | gtacttcagc | cactctggtg | tcatctcagg | 120 |
| ctgatctccc | tgaattccac | ccttcagatt | caatgcaaat | caggcactgt | tgcagaggtt | 180 |
| ataaacatga | gataccagcc | acgaccttgc | cagtaccttc | cttaggcaac | caccatactt | 240 |
| attgtaacct | gcctctgacg | ctactcaacg | gacagctacc | ccttaataac | accctgaaag | 300 |
| atacccagga | atttcacagg | aacagttctt | tgctgccttt | atcctccaaa | gagcttagct | 360 |
| ttaccagtga | tattt      |            |            |            |            | 375 |

```
<210> SEQ ID NO 208
<211> LENGTH: 502
<212> TYPE: DNA
<213> ORGANISM: Homo sapiens

<400> SEQUENCE: 208
```

| | | | | | |
|---|---|---|---|---|---|
| gttcttgagt | acatagccaa | tgccaatggg | agggatccca | cttcttaccc | atccctgtat | 60 |
| gaagatgctt | tgagagagga | gggagaggga | gtctgagcat | gagatgcaac | cagggccagc | 120 |
| gggcagggaa | atgggccaat | gcatgcttca | gggccacacc | cagcagtttc | cctgtcctgt | 180 |
| gtgaaatcag | gcccattctt | ccctctgtgt | ttgatgagag | aagtcagtgt | tctcagtagt | 240 |
| agaaggcaca | gtgaatggaa | gggaacacat | tgtatactgc | ctttaggttt | ctcttccatc | 300 |
| gggtgacttg | gagatttctt | tttgtttccc | tttggtaatt | ttcaaatatt | gttcctgtaa | 360 |
| taaaagtttt | agttagcttc | aacatctaag | tgtatggatg | atactgacca | cacatgttgt | 420 |
| tttgcttatc | catttcaagt | gcaagtgttt | gccattttgt | aaaacatttt | gggaaatctt | 480 |
| ccatcttgct | gtgatttgca | at         |            |            |            | 502 |

<210> SEQ ID NO 209
<211> LENGTH: 250
<212> TYPE: DNA
<213> ORGANISM: Homo sapiens
<220> FEATURE:
<221> NAME/KEY: misc_feature
<222> LOCATION: (110)..(110)
<223> OTHER INFORMATION: n is a, c, g, t or u
<220> FEATURE:
<221> NAME/KEY: misc_feature
<222> LOCATION: (112)..(112)
<223> OTHER INFORMATION: n is a, c, g, t or u
<220> FEATURE:
<221> NAME/KEY: misc_feature
<222> LOCATION: (114)..(116)
<223> OTHER INFORMATION: n is a, c, g, t or u
<220> FEATURE:
<221> NAME/KEY: misc_feature
<222> LOCATION: (118)..(119)
<223> OTHER INFORMATION: n is a, c, g, t or u
<220> FEATURE:
<221> NAME/KEY: misc_feature
<222> LOCATION: (121)..(122)
<223> OTHER INFORMATION: n is a, c, g, t or u
<220> FEATURE:
<221> NAME/KEY: misc_feature
<222> LOCATION: (124)..(124)
<223> OTHER INFORMATION: n is a, c, g, t or u
<220> FEATURE:
<221> NAME/KEY: misc_feature
<222> LOCATION: (127)..(127)
<223> OTHER INFORMATION: n is a, c, g, t or u
<220> FEATURE:
<221> NAME/KEY: misc_feature
<222> LOCATION: (129)..(129)
<223> OTHER INFORMATION: n is a, c, g, t or u
<220> FEATURE:
<221> NAME/KEY: misc_feature
<222> LOCATION: (131)..(132)
<223> OTHER INFORMATION: n is a, c, g, t or u
<220> FEATURE:
<221> NAME/KEY: misc_feature
<222> LOCATION: (135)..(135)
<223> OTHER INFORMATION: n is a, c, g, t or u
<220> FEATURE:
<221> NAME/KEY: misc_feature
<222> LOCATION: (145)..(145)
<223> OTHER INFORMATION: n is a, c, g, t or u
<220> FEATURE:
<221> NAME/KEY: misc_feature
<222> LOCATION: (152)..(152)
<223> OTHER INFORMATION: n is a, c, g, t or u
<220> FEATURE:
<221> NAME/KEY: misc_feature
<222> LOCATION: (154)..(154)
<223> OTHER INFORMATION: n is a, c, g, t or u

<400> SEQUENCE: 209
tcccctagct tggggtccag acagcccagt ggacccaggc gcctgagcag gagggtaacc      60
caggccaccc ggcccctccg gccctctcgg ccccaccccc tgcagccggn gncnnncnnc     120
nncnacnana nngcngcgag aagangacag angngactga gcaaaggggg gtgggctcca     180
ggcgacccct agcccaattc tgcccctcca tcccaagggg cagagaaatt gtctttcttt     240
gctgactcct                                                            250

<210> SEQ ID NO 210
<211> LENGTH: 440
<212> TYPE: DNA
<213> ORGANISM: Homo sapiens
<220> FEATURE:
<221> NAME/KEY: misc_feature
<222> LOCATION: (142)..(144)
<223> OTHER INFORMATION: n is a, c, g, t or u

<400> SEQUENCE: 210

```
tttggacatg tccattttgg aagaaacttt tgtgttaaaa taaactaata tattatgggc      60
tagaacataa aattcaccaa gaatttcaag ataaaaatac taatgttttg cttgtttggg     120
ttatttcaaa caataacttt gnnntctata attttttcac caccgaccct ctacctcctt     180
gcatgctcat tctcctgtgt ggctagatgc atttcgggtg ttttgaatat tatttcagag     240
caagtatcat tccagaaaat aagtttaaag tttgaaatgt ttattttttg taacccatga     300
atcttcagct taagtatctt ctgacataaa agcattttca taattataaa agtgctgata     360
ttactctcca cagtattata tctgatcctg caaagtagtt cagataccag agaatactct     420
taaacatttt gactcacgca                                                 440
```

<210> SEQ ID NO 211
<211> LENGTH: 573
<212> TYPE: DNA
<213> ORGANISM: Homo sapiens

<400> SEQUENCE: 211

```
ggactcaggg agtacacact taccagtgcc cttaaagata gccgttttcc cccaatgaca      60
agggatgagc tgccacggct tttctgctca gtgtctctgc tcactaactt tgaagatgtc     120
tgtgattatt tggactggga ggtgggtgta catggcatta gaatagaatt catcaatgaa     180
aaaggatcaa aacgcaccgc cacctaccta ccggaggttg caaggagca aggatgggac      240
catatacaga ccatagactc cttattgagg aaaggaggat acaaagctcc gattactaat     300
gaattcagga aaaccataaa actgaccagg tatcgtagtg aaaagatgac cctgagctat     360
gctgaatacc ttgctcatcg ccagcatcat catttccaaa atggcattgg catccccttt     420
ccgccataca accattattc ctgacactga gccgcacaac cagtcactgg gcctctctgc     480
agacctcttc ccaggagacc ctacaccttc ttggtctagc tatctctttt actgtaccat     540
tttatgatga tagtttccgt tgccatggtg aag                                  573
```

<210> SEQ ID NO 212
<211> LENGTH: 514
<212> TYPE: DNA
<213> ORGANISM: Homo sapiens

<400> SEQUENCE: 212

```
cgtccttgtc atatcctttt aactaggcat ctcagagaag cagagacagg gcagccttcg      60
tcctgggggga aaagggaccc tcaggatggc atgagaggtc ctcaatccca agtgtggaac    120
tgtcccccctc aacttgttaa aatgcagatt tctgggtctt gccaatgggg cctgggactc    180
catgtgacaa ctggcccagg agcttctgat gtcacacaga attctgcagt cccaagctcc    240
agccccgacc tgctctgctg ttcctaggtg actgccctca cactgctgac cacagtggat    300
ttctcccccct gctgctcggg ctcagctggg gtcagccctg cttataaggt caactgtgca   360
aaaccttata ctggccaaga acaaactagt gctgggggag gagggctggg tgccccggcc    420
actggtggag tccccaggaa atcctcagag ctgttgcgag gatgagacac atttgtggac    480
acgtccacct gtcctcctga ccgtctggag agaa                                514
```

<210> SEQ ID NO 213
<211> LENGTH: 504
<212> TYPE: DNA
<213> ORGANISM: Homo sapiens

<400> SEQUENCE: 213

```
ccggctatgg gctcgagccg agttccttca acatgcactg cgcgcccttt gagcagaacc      60
tctccggggt gtgtcccggc gactccgcca aggcggcggg cgccaaggag cagagggact     120
cggacttggc ggccgagagt aacttccgga tctacccctg gatgcgaagc tcaggaactg     180
accgcaaacg aggccgccag acctacaccc gctaccagac cctggagctg agaaagaat      240
ttcactacaa tcgctacctg acgcggcggc ggcgcatcga gatcgcgcac acgtctctgcc    300
tcacggaaag acagatcaag atttggtttc agaaccggcg catgaagtgg aaaaaggaga    360
acaagaccgc gggcccgggg accaccggcc aagacagggc tgaagcagag gaggaagagg    420
aagagtgagg gatggagaaa gggcagagga agagacatga gaaagggaga ggaagagaag    480
cccagctctg ggaactgaat cagg                                            504
```

<210> SEQ ID NO 214
<211> LENGTH: 529
<212> TYPE: DNA
<213> ORGANISM: Homo sapiens

<400> SEQUENCE: 214

```
gaaattattc actccgtata ctgaaacaga aataaacgag gaagaactta caaagccaag      60
actcttgtgg gctctttatt ttaatatgag agattcctcg ggaatcagca gaagctcgta    120
taatggcttg ccttccaatg tttatgtctg ctctgggcct gactgtggcc tgggaaatga    180
gcatgctgtc aagcaagctg aaacactttt ccaggagatc tttccaactg aagaattctg    240
ccctccacct ccaaatccag aagacattat ctttgatggt gatgataagc agccagaggc    300
tcctggaacc aataatgtag taatggccaa actagaatcc tctgaggaaa gcaaaaaccct   360
agaaagccca gagaagcacc ttcaaaatta gaaaagagca atctcgaaat gctgttttgg    420
acctccttca tggcatcaga attttctcat ttaaaggaca gtttcccata tgagtaatta    480
gaagtggtta tatatgatga atgctatgca gatgttgtct ttaactctc                 529
```

<210> SEQ ID NO 215
<211> LENGTH: 480
<212> TYPE: DNA
<213> ORGANISM: Homo sapiens

<400> SEQUENCE: 215

```
tctttgctct agtattccac ggtgcctctg acatgagaac aggatggaga ctggcttctg      60
atttgacatg cattttgtag gtatgatcca aaatagcttg gaaactatcc cagtcttcaa    120
ccatcccatt ttttagaggt gaaatggcct ccatattctc cctcggaaca cgcagagcat    180
tagtatctat gtagtaggtg ggaccgcctt gtttgccttt atcgccatct atttccatta    240
atgtgcttcc gtcatctctt tctaccacca taccaatagc tgtaggaaaa tccaccttgg    300
ggcagtcctc accagcataa ccagctctca cagtatagga tccaatgtca aaacaaggg    360
ctccaacttc atctcccccg taccacgccg ccgctcatgg ctgctgccgg cgcgactcct    420
accctaaggg ctaactggcg aagtgactgc agtggccgcg actgcgagtc tcgaggagcg    480
```

<210> SEQ ID NO 216
<211> LENGTH: 282
<212> TYPE: DNA
<213> ORGANISM: Homo sapiens

<400> SEQUENCE: 216

```
tggaagcatt tgttgcctcg atcttccact ttagaaaaat gaagtttctc cttttctttg      60
```

```
ggagaggata tatctgaata cttgccttct tggcatttat acattcaaag ctcagtgcta      120
gattagagct attatttgca tagtcttttg gtattgccca cttttggcat taccatatta      180
tttgacaatt agaaggaata gggaaggaat attacatgac tgtaaaagag ttggttatat      240
tttatgttga cttcaagggt tccatttgaa ctattatggg ca                          282
```

<210> SEQ ID NO 217
<211> LENGTH: 563
<212> TYPE: DNA
<213> ORGANISM: Homo sapiens

<400> SEQUENCE: 217

```
gcaggaccac cttgaattct gccctgacac actggattgg agagcagcag aacccagggc      60
ctggcccacc aagctggagt gggaaaggca caagattcgg gccaggcaga acagggccta     120
cctggagagg gactgccctg cacagctgca gcagttgctg gagctgggga gaggtgtttt     180
ggaccaacaa gtgaccactc tacggtgtcg ggccttgaac tactacccc agaacatcac      240 catgaagtgg ctgaaggata agcagccaat ggatgccaag gagttcgaac ctaaagacgt     300
attgcccaat gggatgggaa cctaccaggg ctggataacc ttggctgtac cccctgggga     360
agagcagaga tatacgtgcc aggtggagca cccaggcctg gatcagcccc tcattgtgat     420
ctgggagccc tcaccgtctg gcaccctagt cattggagtc atcagtggaa ttgctgtttt     480
tgtcgtcatc ttgttcattg gaattttgtt cataatatta aggaagaggc agggttcaag     540
aggagccatg gggcactacg tct                                              563
```

<210> SEQ ID NO 218
<211> LENGTH: 391
<212> TYPE: DNA
<213> ORGANISM: Homo sapiens
<220> FEATURE:
<221> NAME/KEY: misc_feature
<222> LOCATION: (100)..(100)
<223> OTHER INFORMATION: n is a, c, g, t or u
<220> FEATURE:
<221> NAME/KEY: misc_feature
<222> LOCATION: (112)..(112)
<223> OTHER INFORMATION: n is a, c, g, t or u

<400> SEQUENCE: 218

```
gccagacaac ctgagtgtga atccagcttc accacttcat tcattcactc acccattcat      60
tcaacaacat atttgaagca catactttgt accagggacn tttccaggca cnggactaca     120
gctatgaaca agacaaacag tccctagcct cccaagagcc gtcacttcag aagggcagac     180
atgacacgca aacaaaatga tgccaggtgg taccaagtgc cttggggaaa cagtgccacc     240
tttctgagac cgtttctcca tccgtccatg gagctgataa caccagtccc tcagggtgga     300
ggtgaagact aagaggttgc tttgagaggg ggaacttggt ggcttttttt caccacctag     360
aacctggcac atactaagct ctcaataaaa g                                     391
```

<210> SEQ ID NO 219
<211> LENGTH: 474
<212> TYPE: DNA
<213> ORGANISM: Homo sapiens
<220> FEATURE:
<221> NAME/KEY: misc_feature
<222> LOCATION: (417)..(417)
<223> OTHER INFORMATION: n is a, c, g, t or u

<400> SEQUENCE: 219

```
aactacgcct ggtacaagct ggcagaggag gtttctgggc gcacagaagt cactgtgaaa    60
cagccagaca gccgcctgag gctcagccaa gcccagggga acctgtcggt tctggagacc   120
cggcaggtac agctggagtg tgtggttctc aaccgcacca gcataacctc ccagctcatg   180
gtggaatggt ttgtatggaa gcccaaccac cctgagcggg agactgtggc ccgcttgagc   240
cgtgacgcca ccttccacta tggagagcag gcagccaaga acaatctgaa ggggcggctg   300
catttggaga gtccttcccc cggcgtgtac cgtctcttca tccagaacgt ggctgtgcag   360
gacagcggga cctacagctg ccatgtggag gagtggctgc ccagcccag tggcatntgg    420 tataagcggg cagaggacac cgctgggcag acagctctga cagtcatgcg acca         474
```

<210> SEQ ID NO 220
<211> LENGTH: 471
<212> TYPE: DNA
<213> ORGANISM: Homo sapiens
<220> FEATURE:
<221> NAME/KEY: misc_feature
<222> LOCATION: (125)..(125)
<223> OTHER INFORMATION: n is a, c, g, t or u
<220> FEATURE:
<221> NAME/KEY: misc_feature
<222> LOCATION: (133)..(133)
<223> OTHER INFORMATION: n is a, c, g, t or u

<400> SEQUENCE: 220

```
gggaccttgt aacttccttg caagttaagt gagctatcct gtcacggttt tatgttgagt    60
gagtgggaag ctgggactct gttttacagc catctgtact ggagcctgga caaaccactg   120
gtctntatgg gangcccag cctcacattt ccctggcaag gagagagagg tttagccatg    180
tcctgggtct aggattacag cccagagatg ggcacttaag aagacctggt cattggtcca   240
gacttgggcc aaggctctcc tctgtgaggg atgggtttta ctggtgaatt acctgtgtgg   300
agaagctatc agggccatgt ttagcacact gaagggacca gtctccacca agcactttaa   360
catccctcca gccagcatag attgatctcg tgttacagag agggcaaggt ttttggcccc   420
tgtttgcaga ctccatgtct taatcagaga ccacagtttt ctctttgttc c             471
```

<210> SEQ ID NO 221
<211> LENGTH: 527
<212> TYPE: DNA
<213> ORGANISM: Homo sapiens
<220> FEATURE:
<221> NAME/KEY: misc_feature
<222> LOCATION: (408)..(408)
<223> OTHER INFORMATION: n is a, c, g, t or u
<220> FEATURE:
<221> NAME/KEY: misc_feature
<222> LOCATION: (439)..(439)
<223> OTHER INFORMATION: n is a, c, g, t or u

<400> SEQUENCE: 221

```
taaataatgt cctctacgtg ccggtgtgga agtagcccgg atgcaattga atgaacaaca    60
gacggtgctt tccaggacgg cgctgtgctt tccaggatgg tgctgtgctt tcattcattt   120
gggtagctcc tctgtgagcc tcccagcgcc gactgcagag cccccactct ccagcctgca   180
agaccccgaa attcaagcca cacaaagaaa ggaggagggg gccgttggca tttactgaac   240
cttataaaac tgtcagcaaa acagccctta ggcttggact ccctgctagc cgggttttac   300
ggtgctgaag tcagcatctt gattcagctg cataaataat ctcctgcagt cctgcaaggc   360
ctggggtagg agagggtatg gggaccaggg cactctgtaa gggctggnat aggaacccca   420
gggaataaga cagaccaant gcgggacttc agactccact gcagccggga tcgggttgtt   480
```

```
gttaatttct taagcaattt ctaaattctg tattgactct ctcatgc                  527
```

<210> SEQ ID NO 222
<211> LENGTH: 310
<212> TYPE: DNA
<213> ORGANISM: Homo sapiens
<220> FEATURE:
<221> NAME/KEY: misc_feature
<222> LOCATION: (43)..(43)
<223> OTHER INFORMATION: n is a, c, g, t or u
<220> FEATURE:
<221> NAME/KEY: misc_feature
<222> LOCATION: (110)..(110)
<223> OTHER INFORMATION: n is a, c, g, t or u
<220> FEATURE:
<221> NAME/KEY: misc_feature
<222> LOCATION: (115)..(115)
<223> OTHER INFORMATION: n is a, c, g, t or u
<220> FEATURE:
<221> NAME/KEY: misc_feature
<222> LOCATION: (189)..(189)
<223> OTHER INFORMATION: n is a, c, g, t or u
<220> FEATURE:
<221> NAME/KEY: misc_feature
<222> LOCATION: (236)..(236)
<223> OTHER INFORMATION: n is a, c, g, t or u
<220> FEATURE:
<221> NAME/KEY: misc_feature
<222> LOCATION: (252)..(252)
<223> OTHER INFORMATION: n is a, c, g, t or u

<400> SEQUENCE: 222

```
atacatgtgg ttatcttttg ccctgttgtg atggataatt tgnaaagaag tgggtttatg   60
tcaccttctc accttcttat aagaaagctc tgagaatggg cattttgtn ttttnttgtt  120 gttgttgaga tggagtctgc cacccaggct ggagtccagt ggcgtgatca tacctcactg  180
cagcttcanc ttcctgggct caagtaatcc tcccacccca gcctcccagg tagctngtac  240
tataggtgtg cnccaccacg cccagcaaat ttttaaattt attatagagt gggaggcagg  300
gtgcggtggc                                                        310
```

<210> SEQ ID NO 223
<211> LENGTH: 283
<212> TYPE: DNA
<213> ORGANISM: Homo sapiens
<220> FEATURE:
<221> NAME/KEY: misc_feature
<222> LOCATION: (169)..(169)
<223> OTHER INFORMATION: n is a, c, g, t or u

<400> SEQUENCE: 223

```
cactgtctgt gtgagtccat tcacttcaat accagagcca cctctttgtt tcctatttac   60
taagaagcca taccagcatg agatctcctt gatagtgtta aatcccactg tggaaagatt  120
gaaaaatatc tcccagcctt accagaggtt acgatctagt gtggaggcna agacattga  180 gaagaaaaaa gcaggtgcct cctcctggct ctcctgttag gttaacataa tcataattcc  240
cctttgaaat gtctcccaca tttgcccttt aacttcctat tgc                    283
```

<210> SEQ ID NO 224
<211> LENGTH: 499
<212> TYPE: DNA
<213> ORGANISM: Homo sapiens

<400> SEQUENCE: 224

```
gacgactacg gtctggacaa ctttgacaca cagttcacca gcgagcccgt gcagctgacc   60
```

```
ccagacgatg aggatgccat aaagaggatc gaccagtcag agttcgaagg ctttgagtat      120
atcaacccat tattgctgtc caccgaggag tcggtgtgag gccgcgtgcg tctctgtcgt      180
ggacacgcgt gattgaccct ttaactgtat ccttaaccac cgcatatgca tgccaggctg      240
ggcacggctc cgagggcggc cagggacaga cgcttgcgcc gagaccgcag agggaagcgt      300
cagcgggcgc tgctgggagc agaacagtcc ctcacacctg gcccggcagg cagcttcgtg      360
ctggaggaac ttgctgctgt gcctgcgtcg cggcggatcc gcggggaccc tgccgagggg      420
gctgtcatgc ggtttccaag gtgcacattt tccacggaaa cagaactcga tgcactgacc      480
tgctccgcca ggaaagtga                                                   499
```

<210> SEQ ID NO 225
<211> LENGTH: 562
<212> TYPE: DNA
<213> ORGANISM: Homo sapiens

<400> SEQUENCE: 225

```
tcttctgtgg aggaatggca tcccaggcct tcacccctcc aggtcagccg tggctgccgg       60
ccaagatggc cgcgtgggca gcctcacatt ccttctcggc ttttggcccc atgtcctcgg      120
cactcaggtc tgcagttcag cccaagtgtt gagactcagg tatgcagctc agggcggcct      180
taattaaccc tcccatgggc ctgggcaccg cctgcgcctc atcaactctg gctgctggt       240 tttgttcctg acgctgcagc ctgacactgt gggcggggt gcagtttgcg atggaaggct       300
gcctccgaat cgaggaagcc ttgaccttgg aggggcctg ccttttcgct gggcttgcct       360
ttctctgggc agcgttcgct cagcacttca gtgcggccga ttcccctggg actgaattca      420
caccagccac gacgacttcc cggctacttc acgttctcta tgtttgcagc tgttctttgg      480
tggcagaaaa agatgatttt cttcccccc actcccattc cttttgtta gtttctctcc        540 ctgaaccaca ttttgagctg ag                                               562
```

<210> SEQ ID NO 226
<211> LENGTH: 47
<212> TYPE: DNA
<213> ORGANISM: Homo sapiens

<400> SEQUENCE: 226

```
ttccagaatt tcttccgagg tagtatggtt ttcttcatag gataaag                    47
```

<210> SEQ ID NO 227
<211> LENGTH: 523
<212> TYPE: DNA
<213> ORGANISM: Homo sapiens
<220> FEATURE:
<221> NAME/KEY: misc_feature
<222> LOCATION: (476)..(476)
<223> OTHER INFORMATION: n is a, c, g, t or u

<400> SEQUENCE: 227

```
aggcagcgct gcggagagga gcggcagagt gggttgtctg ccgcaggcaa ccaggcaagt       60 gtgtcgggc tggggtgtga atgccagcct gtgagtcccg gaactatgtg ggtaccccta      120
cccctcacag aagccaaggg catggaggag gtccctccac agtgacaacg gtgtggggta      180
ggggaggtgc attcaggaca ccacccaggg acagtgccta tgtgatcacc tcttaaaggc      240
taagcttagg ggcatttccc aaagtgggga cagagggcag gacgcccagg ctggggctc       300 tcctcgcccg ccctggtgtc tgacagcctc aaggaaggag cagtgcctgt gtcagccatg      360
gggcccttgg agctgccgct ggtgcctagg gggcctgggt ttctgcccag gcagccagtg      420
```

```
gctgttggga gcctctgttt cccctgtgct gggggccttg agtgctatgc tagcangggc    480
ctggccccaa gtgtgagtga tgagcaataa acgtaccgtc ccc                      523

<210> SEQ ID NO 228
<211> LENGTH: 138
<212> TYPE: DNA
<213> ORGANISM: Homo sapiens

<400> SEQUENCE: 228
aagtgcgaag tcaggatgg tctaagaggg ctgagaggag aattccggaa cctcaggacc      60
ttgctcactg gctgctggct ggggctgtga agctgtccag tctagaactc aaagagtgat    120
ggtacaggct ttagagcc                                                  138

<210> SEQ ID NO 229
<211> LENGTH: 396
<212> TYPE: DNA
<213> ORGANISM: Homo sapiens
<220> FEATURE:
<221> NAME/KEY: misc_feature
<222> LOCATION: (198)..(198)
<223> OTHER INFORMATION: n is a, c, g, t or u

<400> SEQUENCE: 229
gggctgggta cctcttctgg ttgctgagtg gagtgcacca gcagcccac cccagagaag      60 ccctgttgga agcgctgtgg gaatccccca aggtagggga gtggacacca taaggaaggg    120
gaggagtgcc agctccatat gcggtctccc ccatcagtca ggccagcagc gggttcagct    180
gcctctgggc agccctancc catacagaca gggagacctc cctcccgatc ttctgtgaat    240
agtcccttat acccctgctt atgcctcagg ggctcctcca ccctttttgtc ttcatactgc    300 atatgaaaac tgcccttgta tatgtggata tctgaatgtg tcagtgaagg cctatatgaa    360
tgtgcacatg tgggtatgtt ctcagccatg tgtata                              396

<210> SEQ ID NO 230
<211> LENGTH: 432
<212> TYPE: DNA
<213> ORGANISM: Homo sapiens
<220> FEATURE:
<221> NAME/KEY: misc_feature
<222> LOCATION: (39)..(39)
<223> OTHER INFORMATION: n is a, c, g, t or u

<400> SEQUENCE: 230
gaactaaagg agccatctct ctcccctctc ctccgttcnc gagaggaggg gtgggtctca     60 gacgttttc ctatggactt atttcttcca tgtccaggac tttgcacaac tttggtttta    120
aaagctgttg aaaatagga aaacaagggg cattgttcac agatagggcc aagtctcccc    180
ttgcaagggt gcctctgttc tgtccctgcc cccacctcac cttctctact cctccagtaa    240
gttggcagtt ttggtgccaa accccaaatc tccaaagaga catgccaggc aagacaaacc    300
cccaaacacc tcctttccgg tggccttgga aacagattgc tccgagctgg agaatgtcgg    360
gtgaggtgta tgggagagga ggggagagtt agaacttgtg cctttgggag taagggtaa    420 ctgcctggag gg                                                        432

<210> SEQ ID NO 231
<211> LENGTH: 549
<212> TYPE: DNA
<213> ORGANISM: Homo sapiens
```

<400> SEQUENCE: 231

```
atcagtgcca gaaattcctt acctaaagtg gcatatgcga cggccatgga ctggttcata      60
gccgtctgtt atgcctttgt attttctgca ctgattgaat ttgccactgt caactatttc     120
accaagcgga gttgggcttg ggaaggcaag aaggtgccag aggccctgga gatgaagaag     180
aaaacaccag cagccccagc aaagaaaacc agcactacct tcaacatcgt ggggaccacc     240
tatcccatca acctggccaa ggacactgaa ttttccacca tctccaaggg cgctgctccc     300
agtgcctcct caaccccaac aatcattgct tcacccaagg ccacctacgt gcaggacagc     360
ccgactgaga ccaagaccta acagtgtgtc agcaaggttg acaaaatttc ccgcatcatc     420
tttcctgtgc tctttgccat attcaatctg gtctattggg ccacatatgt caaccgggag     480
tcagctatca agggcatgat ccgcaaacag tagatagtgg cagtgcagca accagagcac     540
tgtataccc                                                             549
```

<210> SEQ ID NO 232
<211> LENGTH: 554
<212> TYPE: DNA
<213> ORGANISM: Homo sapiens

<400> SEQUENCE: 232

```
gatgagtcca tctcacttgc tcagaacttt gcctggtgag agcggttaca agcgaacaag      60
gtggaaatga agaaacccct gactttccca ctaggaagga agagactgtt ccttcttgtg     120
atgtactctg aagaaaaatt ctaggatttg gacagatttc ttgggttata aacatgatt     180
ttcttctctg tttcttgggc ttttataatg ggtactgttg ttttcttgca aagctttaat     240
gattccataa ggacttgtat aaagtttatg ggagaatttt caatgtagat gtgaatggca     300
gaaacccaag aatctgtgtg aggttgaata agatcctgtg tctccagaga ggtctgatgg     360
ggagacacag atctaaattt taaggtggt ttgggccttc tcaatcatat attaaggtcc     420
ttttatgtta tagataagta aattaaggcc cagaaagatt aatagcccaa ggtcccaaga     480
cctgcttgag acctgtgccc catttctgac taatattctt catgatattg tatcactctg     540
tatcaaaacc aacc                                                       554
```

<210> SEQ ID NO 233
<211> LENGTH: 539
<212> TYPE: DNA
<213> ORGANISM: Homo sapiens

<400> SEQUENCE: 233

```
gatggtgcag tacctgctag cactttgctg cagaatgcct ctgcactcag ttctgcaaat      60
gtactgtttt agtttcattt aaacccctt tttttgtgag aagatttcaa acatcaggca     120
agtttgtaat gaattcaagc tgagttctct cgagggacaa acatgtataa ctacagttcc     180
agtgtcagtg ccagctgtca ggttttcact gtgcagctag gctgcctgc atcccagtc     240
atgtaaacca aattcactct agaatcggcc aggtcttacc aaaatgcaaa tagaatacaa     300
agcaactgga aatatatttc gtaatttcat tttatgtgtg attttaaaag ttaagctact     360
tcaaaactca tctgtctaac ttattttcac taataagtgt aacttgcctg gaatttggca     420
gatctaagct gggcttgggc tagatggttt caagcctgag tcattaagat gtgaaattta     480
cagaaacaac agaggattga ggaacaagtt aaaggacact ctaatggtgc agtctgcat     539
```

<210> SEQ ID NO 234
<211> LENGTH: 431

<212> TYPE: DNA
<213> ORGANISM: Homo sapiens
<220> FEATURE:
<221> NAME/KEY: misc_feature
<222> LOCATION: (102)..(102)
<223> OTHER INFORMATION: n is a, c, g, t or u

<400> SEQUENCE: 234
gtgagcatgg aagtagatct tccccggtca agcccccaga aggacccagc cctgcggaca      60
ccttgaccga aacctgtgag agctccggaa atagaggaac cnagcattcc ctctggaata    120
catcagcact gttgcctttg aggctggcct gcttgaatgc acacctgagc tccggattca    180
cagtggagga agccagatgc catgtcatga gggtgctcaa gcaacttttt ggagatgtat    240
gtatggagag aaactgaggc ctcctgccaa cagccagcac taacttggca agcatgtttg    300
agagccacct gggaagtgga gccttcagcc ccagttaagc cttcagatga gactgcagtc    360
ctggccacca tctggactgc aacttcacaa gagctcctaa gccagagcca tgcagatgga    420
ttcttggccc c                                                         431

<210> SEQ ID NO 235
<211> LENGTH: 403
<212> TYPE: DNA
<213> ORGANISM: Homo sapiens
<220> FEATURE:
<221> NAME/KEY: misc_feature
<222> LOCATION: (139)..(139)
<223> OTHER INFORMATION: n is a, c, g, t or u

<400> SEQUENCE: 235
gatctcattg cctttttatg ccgattaaca tgcttttagc ccctactgag cttatagtta      60
acagaagttt ccaggtcttt cttcacctga actgtgtcta aagcaagttc cctccacctt    120
ctgtatttat acgcttgant ttttaaaacc taaatgttgg gcttcacatt tgttccttgt    180
aaatttcatc ttggtgattg cagtctaccc tctggccttt aaaaattgtc tgagccttga    240
ttcgatcatg aaaccagctt acccttcccc tgtgtgctgg ccccagtttt ctaaccaggt    300
gttgaatgaa ctggatggac tctgccagat ccctccgtgc aaggctggaa tcagtccatt    360
gttcaactgt gcccttggg gctgtggttc atttggctct gat                        403

<210> SEQ ID NO 236
<211> LENGTH: 257
<212> TYPE: DNA
<213> ORGANISM: Homo sapiens

<400> SEQUENCE: 236
ctgctggaaa ggcatccttg ctgcagctgt gagtgtgatg ggacagcaga gtcactcctg      60
catgggattc tagggctggg ggtcccagag gggtggcctc cgcccctcct gggggccgag    120
gactgtcacc atgtcactac ggcactctcc agctgctgac caaagccctc gctaaccgca    180
gccctgccat actctgggtc tttcctctgg agcaaggtga agagactgca gcgaggcgtg    240
gaattgggaa gctcttc                                                   257

<210> SEQ ID NO 237
<211> LENGTH: 446
<212> TYPE: DNA
<213> ORGANISM: Homo sapiens

<400> SEQUENCE: 237
actgtgactg cgcgcaggac gagaactgca agtccaccaa gcgcgccatt gagccgtgcc      60

| | |
|---|---:|
| tgccccggac gagcggcggc ggcgcgggcg gccccggcgc gggcggggtc atgggctgca | 120 |
| ccgaggcccg gcggcgctgc gaccgcgaca gccgctgcaa cctggcgctg agccgctacc | 180 |
| tgacctactg cggcaaagtc ttcaacgggc tgcgctgcac ggacgaatgc cgcaccgtca | 240 |
| ttgaggacat gctggctatg cccaaggcgg cgctgctcaa cgactgcgtg tgcgacggcc | 300 |
| tcgagcggcc catctgcgag tcggtcaagg agaacatggc ccgcctgtgc ttcggcgccg | 360 |
| agctgggcaa cggccccggc agcagcggct cggacggggg cctggacgac tactacgatg | 420 |
| aggactacga tgacgagcag cgcacc | 446 |

<210> SEQ ID NO 238
<211> LENGTH: 340
<212> TYPE: DNA
<213> ORGANISM: Homo sapiens

<400> SEQUENCE: 238

| | |
|---|---:|
| ggaacagagg agagatgccg gctggaggac acagcaaatt tgaaccaaga ggagcttgga | 60 |
| ggaagcccga gcgacctgga ggggactggc tgaccttcct cattctttc aagtgtgaat | 120 |
| aataaccaag cccagtttgg caactccttg agggtgagga cgaagcccca ttctcctttt | 180 |
| tggaacttgg tggggctcag gaagcaggtt ctctccagtc ggtggctttc ctttctgttg | 240 |
| cgggtctctt gagggcctgc cttcatgaag gcacatgagt gactcatcat ttgtgaatta | 300 |
| attgctatat gtgaagggca tctgagaaca aattatcttc | 340 |

<210> SEQ ID NO 239
<211> LENGTH: 560
<212> TYPE: DNA
<213> ORGANISM: Homo sapiens

<400> SEQUENCE: 239

| | |
|---|---:|
| tgaccgccat gtggctgtgt ctgaccgcct gcgatactcg gccatcatgc atggagggct | 60 |
| gtgtgctagg ttggccatca catcctgggt cagtggctcc atcaactctc ttgtgcagac | 120 |
| tgctatcacc tttcagctgc ccatgtgcac taacaagttt attgatcaca tcctgtga | 180 |
| actcctagct gtggtcaggc tggcttgtgt ggacacctcc tccaatgagg ctgccatcat | 240 |
| ggtgtctagc attgttcttc tgatgacacc tttctgcctg gttctgttgt cctacatccg | 300 |
| gatcatctcc accatcctaa agatccagtc cagagaagga agaaagaaag ccttccacac | 360 |
| gtgtgcctct cacctcacgg tggttgccct gtgctacggc acaacgattt tcacttacat | 420 |
| ccagccccac tctggtccct cagtccttca agagaagctg atctctgtct tctatgccat | 480 |
| tgttatgcct ctgctgaacc ctgtgattta gtctaagg aataaagagg tgaaggggc | 540 |
| ctggcataaa ctattagaga | 560 |

<210> SEQ ID NO 240
<211> LENGTH: 524
<212> TYPE: DNA
<213> ORGANISM: Homo sapiens

<400> SEQUENCE: 240

| | |
|---|---:|
| ggaaatagtt tgttcatatg gccaaattat aaagggactt agtaaaagaa agctatgttt | 60 |
| tctgattacg aaggaaatct atgctcacag tgggaaaaca gaaaatgtg gcaaagcaca | 120 |
| ggtaagaaaa taaaaatcaa taatatcaac attatgaata ttttaggtac ttaggaattt | 180 |
| ggggtagaat gatggaaagc aaactgttaa ttatagctgt atatttcagt gtagaggcta | 240 |
| caggtgcctt gcatttgttt tcttataaaa tctgttccca tacattttac ttactttatt | 300 |

```
tgaatttagg aaactttcat taggtagcca ttttattttt ctgtttcttt aatcatttta    360
ctttgaaata attttaaatt tacagaaaat ttgcaaaaat agtgtagaaa tttcccattt    420
gcctttatcc agcttcctgt agtgttgcca ttttatgtaa ccatagtaca attattgaaa    480
ccaagacatt aactttgaga ggctgctact actctaagaa ccat                    524
```

<210> SEQ ID NO 241
<211> LENGTH: 504
<212> TYPE: DNA
<213> ORGANISM: Homo sapiens
<220> FEATURE:
<221> NAME/KEY: misc_feature
<222> LOCATION: (71)..(72)
<223> OTHER INFORMATION: n is a, c, g, t or u
<220> FEATURE:
<221> NAME/KEY: misc_feature
<222> LOCATION: (197)..(197)
<223> OTHER INFORMATION: n is a, c, g, t or u
<220> FEATURE:
<221> NAME/KEY: misc_feature
<222> LOCATION: (219)..(219)
<223> OTHER INFORMATION: n is a, c, g, t or u
<220> FEATURE:
<221> NAME/KEY: misc_feature
<222> LOCATION: (233)..(233)
<223> OTHER INFORMATION: n is a, c, g, t or u
<220> FEATURE:
<221> NAME/KEY: misc_feature
<222> LOCATION: (289)..(289)
<223> OTHER INFORMATION: n is a, c, g, t or u
<220> FEATURE:
<221> NAME/KEY: misc_feature
<222> LOCATION: (309)..(309)
<223> OTHER INFORMATION: n is a, c, g, t or u
<220> FEATURE:
<221> NAME/KEY: misc_feature
<222> LOCATION: (346)..(346)
<223> OTHER INFORMATION: n is a, c, g, t or u
<220> FEATURE:
<221> NAME/KEY: misc_feature
<222> LOCATION: (390)..(390)
<223> OTHER INFORMATION: n is a, c, g, t or u
<220> FEATURE:
<221> NAME/KEY: misc_feature
<222> LOCATION: (395)..(395)
<223> OTHER INFORMATION: n is a, c, g, t or u
<220> FEATURE:
<221> NAME/KEY: misc_feature
<222> LOCATION: (474)..(474)
<223> OTHER INFORMATION: n is a, c, g, t or u

<400> SEQUENCE: 241

```
tcctgtgtct tgacccagaa aattgtgaca tgtaaaaaga ataaattcct ggtttaagcc     60
agtaaggtta nnggtacatt gttacatctc agataattaa aaccttgaaa aactcatgag    120
agatcacaag tagaaccttg atctgaaaca tggcatgtgg cgatttatat tgagtattag    180
gttaaaaatg caagaaggga gcatagttaa tattttacnt taaagctaaa acnataattg    240
cctacttaaa attttcagtt aattaggttg tcacttttg ttcttaacna agaaatcaac    300
tagttttant ccataaacag ttagaactga tgcacacatc cgtttntcct tactcatttt    360
aaacagctat ctgaaatagg aagtgtaatn taatntttaa agaatctgaa aacatgacag    420
aaatgtttaa actataaaca tatattgtat atgttagcat attgtataca ttgnatatta    480
acataagcta gaatcattga cata                                          504
```

<210> SEQ ID NO 242
<211> LENGTH: 317
<212> TYPE: DNA

<213> ORGANISM: Homo sapiens

<400> SEQUENCE: 242

```
cgaaccactc agggtcctgt ggacgctcac ctagctgcaa tggctacaga ggctggaaga      60
tggcagcccc cggactgggc agatcttcaa gcagacctac agcaagttcg acacaaactc     120
acacaacgat gacgcactac tcaagaacta cgggctgctc tactgcttca ggaaggacat     180
ggacaaggtc gagacattcc tgcgcatcgt gcagtgccgc tctgtggagg cagctgtgg      240
cttctagctg cccgggtggc atccctgtga cccctcccca gtgcctctcc tggccttgga     300
agttgccact ccagtgc                                                    317
```

<210> SEQ ID NO 243
<211> LENGTH: 437
<212> TYPE: DNA
<213> ORGANISM: Homo sapiens

<400> SEQUENCE: 243

```
aatgccggct ggctcagtga tggctctgtg caatatccca tcacaaagcc cagagagccc      60
tgtgggggcc agaacacagt gcccggagtc aggaactacg gattttggga taaagataaa     120
agcagatatg atgttttctg ttttacatcc aatttcaatg gccgttttta ctatctgatc     180
cacccccacca aactgaccta tgatgaagcg gtgcaagctt gtctcaatga tggtgctcag     240
attgcaaaag tgggccagat atttgctgcc tggaaaattc tcggatatga ccgctgtgat     300
gcgggctggt tggcggatgg cagcgtccgc taccccatct ctaggccaag aaggcgctgc     360
agtcctactg aggctgcagt gcgcttcgtg ggttttccag ataaaaagca taagctgtat     420
ggtgtctact gcttcag                                                    437
```

<210> SEQ ID NO 244
<211> LENGTH: 389
<212> TYPE: DNA
<213> ORGANISM: Homo sapiens
<220> FEATURE:
<221> NAME/KEY: misc_feature
<222> LOCATION: (299)..(299)
<223> OTHER INFORMATION: n is a, c, g, t or u

<400> SEQUENCE: 244

```
tagatcatgc cctcattggg cttacatgct gttgaaaaga taggatataa atccatgaaa      60
attttttacaa tgctatttat taacaataca tgacaagagt actagaaatg ttacttgtga     120
ctattttgtc tattctagcc aagctggatg cctggctgtt tctcagttat actaaatgag     180
ttctgctctc agggtcttca tacttgccct tccctctgcc tgcaacactc ttcctccagt     240
ttttttttt ttttttttggc tctctccatc actttaggtc tccattaaaa ctgtcagcnt     300
tcagggaagt tgccttccct gaccacaacc acactaattc aaataccaat ccttccccgc     360
ctccgtttgg taactctcta gtctcttat                                       389
```

<210> SEQ ID NO 245
<211> LENGTH: 136
<212> TYPE: DNA
<213> ORGANISM: Homo sapiens
<220> FEATURE:
<221> NAME/KEY: misc_feature
<222> LOCATION: (68)..(69)
<223> OTHER INFORMATION: n is a, c, g, t or u
<220> FEATURE:
<221> NAME/KEY: misc_feature
<222> LOCATION: (91)..(91)
<223> OTHER INFORMATION: n is a, c, g, t or u

<400> SEQUENCE: 245

```
gccccaaggt ctttaagtat ctctgtcact tattagctca ccagagaaga cacaggaatg        60
agaggccnnt tgtttgtccc gagtgtcaaa naaggcttct tccagatatc agacctacgg       120
gtgcatcaga taattc                                                       136
```

<210> SEQ ID NO 246
<211> LENGTH: 369
<212> TYPE: DNA
<213> ORGANISM: Homo sapiens

<400> SEQUENCE: 246

```
ggccctgggc taagtcgggg atgaaggcgg gagctgctgt gctggactgc agctcagcac        60
agagacagtg agcctagatt gcagagctgc cagggaggg atgtcacctt ggggatgga       120
ggctgcaggt gctcctcaga ccttagggaa acatttggga gggagcttgt tgaggagata       180
caggcacctc agggtggctg gctggatgg actttgatga cccttccttt tttgagacct       240
gatggttctc taatttggga atcatttcca aagatgggtc taaaaatcct tgtttcattg       300
gaaataatga gtttgctatg atgcttaaga ccaagcatgt caccatttgt tattactgca       360
cttttccct                                                                369
```

<210> SEQ ID NO 247
<211> LENGTH: 444
<212> TYPE: DNA
<213> ORGANISM: Homo sapiens

<400> SEQUENCE: 247

```
gaggcttttg acacagttat tagttaaatc aaatgttcaa aaatacggag cagtgcctag        60
tatctggaga gcagcactac catttattct ttcatttata gttgggaaag ttttgacgg       120
tactaacaaa gtggtcgcag gagattttgg aacggctggt ttaaatggct tcaggagact       180
tcagtttttt gtttagctac atgattgaat gcataataaa tgctttgtgc ttctgactat       240
caatacctaa agaaagtgca tcagtgaaga gatgcaagac tttcaactga ctggcaaaaa       300
gcaagcttta gcttgtctta taggatgctt agtttgccac tacacttcag accaatggga       360
cagtcataga tggtgtgaca gtgttttaaac gcaacaaaag gctacatttc catggggcca       420
gcactgtcat gagcctcact aagc                                               444
```

<210> SEQ ID NO 248
<211> LENGTH: 394
<212> TYPE: DNA
<213> ORGANISM: Homo sapiens

<400> SEQUENCE: 248

```
ggggcggcgg aagcgagtag agtttgtgac atttgtgcca gccctccag cccagtcacc        60
tgaggagcct gtaggggccc ctgctgtgca gtccatcctt gtggcaggcg aggaggacat       120
ccgctgggtg tgtgaggaca tggggctgaa ggaccctgag gagcttcgca actacatgga       180
gaggatccgg ggcagctcct gaccctccac agccacctgg tcagccacca gctggggcaa       240
cgagggtgga ggtcccactg agcctctcgc ctgccccgc cactcgtctg gtgcttgttg       300
atccaagtcc cctgcctggt ccccacaag gactcccatc caggccccct ctgccctgcc       360
ccttgtcatg gaccatggtc gtgaggaagg gctc                                   394
```

<210> SEQ ID NO 249

<211> LENGTH: 414
<212> TYPE: DNA
<213> ORGANISM: Homo sapiens

<400> SEQUENCE: 249

```
tttgctttgg gtactgtgat aactactttt tatactttat cccatttaat tataaaaacc    60
actcttgaga agtaattttt attttcagaa ccatttttaca gatttaaaat aaacaggttt   120
gaggaattag tttaacttat ccaaagtttc gtggctatta agttctagta tttggagtca   180
aatgcaagtc tgtctaaatc tagagcccat gttctttaac tgcaacacta taatgtctca   240
ccccgtccta gtcccaccaa ttagtcaact cttttagggc agaagtctgt ctaattcatc   300
tttgcttcct gttactttat atttaattaa aaattttagt gactttttaa cttgtaaatt   360
gtagctgatt ttacatttat cttcctgaag gaaactctgt atcatttgt cttt          414
```

<210> SEQ ID NO 250
<211> LENGTH: 268
<212> TYPE: DNA
<213> ORGANISM: Homo sapiens

<400> SEQUENCE: 250

```
cttttattag aatgccatgc ctgcttatgt tatgcatgta ttttataata atttaatcta    60
ttttacaatt ttaaactcaa atatgattta gtattatgca cataatacaa acagtagtgg   120
tgagcaaacg tgtgtttccc ccacatgtgc agaaatgat ggattttatg aaaataaata   180
ttcttaactc caggaaatat gatctatatg gttccttaaa agattttcca atacactgaa   240
aatttagttc cttatgttca ttgtataa                                      268
```

<210> SEQ ID NO 251
<211> LENGTH: 443
<212> TYPE: DNA
<213> ORGANISM: Homo sapiens
<220> FEATURE:
<221> NAME/KEY: misc_feature
<222> LOCATION: (131)..(132)
<223> OTHER INFORMATION: n is a, c, g, t or u
<220> FEATURE:
<221> NAME/KEY: misc_feature
<222> LOCATION: (156)..(156)
<223> OTHER INFORMATION: n is a, c, g, t or u
<220> FEATURE:
<221> NAME/KEY: misc_feature
<222> LOCATION: (187)..(188)
<223> OTHER INFORMATION: n is a, c, g, t or u
<220> FEATURE:
<221> NAME/KEY: misc_feature
<222> LOCATION: (230)..(230)
<223> OTHER INFORMATION: n is a, c, g, t or u

<400> SEQUENCE: 251

```
cgtgcagcag atcccaggag ttggaaaagt taaagctccc cttctcctcc agaagtttcc    60
aagcatccag caactgagta atgcttccat tggggaactg gagcaggtgg tcggacaagc   120
agtggcacag nnagatccat gccttcttca cgcagncca ggtgagggct ggcctcaggg   180
ccacggnnat cttctcccga gaccacaaac accaggatct tgttttcagn tttaaaaacc   240
aagagaatgg gccgggtgca ctggctcacg cctctaatct cagcactttg ggaggccgaa   300
gacagcggat catctgaggt caggagttca agaccagcct ggccaacatg gagaaacccc   360
taaaaatagg aacaattagc caggcatggt gacaggtgcc tgtaatccca gctacttggg   420
aggccgaggc atgagaatca ctt                                           443
```

```
<210> SEQ ID NO 252
<211> LENGTH: 281
<212> TYPE: DNA
<213> ORGANISM: Homo sapiens

<400> SEQUENCE: 252
gagaaattcc cacactaaaa acactacaag tttttggaat cgtgccagat ggtacccttc      60
aactgttaaa ggaagccctt cctcatctac agattaattg ctcccatttc accaccattg     120
ccaggccaac tattggcaac aaaaagaacc aggagatatg gggcatcaaa tgccgactga     180
cactgcaaaa gcccagttgt ctatgaagta tttattgcag gatggtgtct cttctttaga     240
acagggaaaa taggcaggaa gcccaattgc tggagtactt a                          281

<210> SEQ ID NO 253
<211> LENGTH: 249
<212> TYPE: DNA
<213> ORGANISM: Homo sapiens

<400> SEQUENCE: 253
ccaaatatct agattctgat ccctttgag gtcctagacc ctttgagaaa ctgatgaagc       60
caggcacctc cttcctcagg aaaatgctgg tgtacaaata cacacaaagc tcttcaggca    120
gctgatagat ttccccaga gagctattca aggacttcct aaggtgggtg gactgcaggg    180
ttaggacacc tgctatagag gtgacatttt tccaaggaca agcagggact ttggtcttga    240
ctgttctct                                                             249

<210> SEQ ID NO 254
<211> LENGTH: 259
<212> TYPE: DNA
<213> ORGANISM: Homo sapiens

<400> SEQUENCE: 254
agaagagcct gaacctcaac atcttcctga agcaatttaa gtgctccaac gaggaggtcg     60
ctgctatgat ccgggctgga gataccacca agtttgatgt ggaggttctc aaacaactcc    120
ttaagctcct tcccgagaag cacgagattg aaaacctgcg ggcattcaca gaggagcgag    180
ccaagctggc cagcgccgac cacttctacc tcctcctgct ggccattccc tgctaccagc    240
tgcgaatcga gtgcatgct                                                  259

<210> SEQ ID NO 255
<211> LENGTH: 535
<212> TYPE: DNA
<213> ORGANISM: Homo sapiens

<400> SEQUENCE: 255
aaattctgca atgaaccta caccgaccgg acagaagaaa gggaagaatc caaagaggaa      60
gaagactggt ccctccgacc tgtcctttcg ggagctgaga agatgacga agctgagcgt    120 ctcagagaaa caacgaaga cggagaagac ccgccaggct acaccaccga catgagaaca    180
gataaagaag ctgactcaaa tggcagaggg cagcctaaag gagaaacaac tggcaattat    240
cccgggtaat atgatcttgg ctgccttgat ggtaattacc gcggcggtaa gtctccctgc    300
tgtctggact gaagaaaatt ttacatactg gcttctgttc catttcctcc tttaattagg    360
ccagttactt ggatggattc cctattgaa gtttatacaa atgatagtat tttggatgcc    420
tgggccgatt gatgatggct gtcctgcaca gcctgagaag gagggtatgt tgatgaatgt    480
aactggtatg aataccctcc aatttgttta ggaattgctc cttgatgttt accat          535
```

<210> SEQ ID NO 256
<211> LENGTH: 230
<212> TYPE: DNA
<213> ORGANISM: Homo sapiens

<400> SEQUENCE: 256

```
ggaagtaatg acttttttgc ccatttactc actgagtccc ataatgtggt aaatgtataa      60
tgctgacatt tgttccgtcc ttatagattg aggatagtac ggccctgaat tttgccttta     120
ctttagaaac ctgattcaac ttaaccgaac tctcaggaat ctgattccta agctgagtat     180
cacattttag attacttact aatttgtgca tctatccacc tagcaaatat                 230
```

<210> SEQ ID NO 257
<211> LENGTH: 532
<212> TYPE: DNA
<213> ORGANISM: Homo sapiens
<220> FEATURE:
<221> NAME/KEY: misc_feature
<222> LOCATION: (97)..(97)
<223> OTHER INFORMATION: n is a, c, g, t or u
<220> FEATURE:
<221> NAME/KEY: misc_feature
<222> LOCATION: (152)..(152)
<223> OTHER INFORMATION: n is a, c, g, t or u

<400> SEQUENCE: 257

```
taaaaccaac cagctgaacc tttcaggcta caagagaacc cgggtcggta atgtcttttt      60
aagaataatt tttaattgct tataacaagc atatttngtg gcatttgaac tatatttact     120
gctccaatat ccgttatttt ccaaaggatt tngtatcttt ttgaaaatgt ttacatcatc     180
agatgatcca cagaattcac tttatgtgag atctcccgag agtttccatc ccaacataat     240
ggactttggt ttgaacacaa ttcgtttttt catttgaatt ggcatttccc aatatttgct     300
aaacatttgc tggagaaatc attttttcttt tttcttttttt agaaaactca gaatgaaaat    360 tcattccccct gaaatattta ggtgtctata ttctatattt tgatctatta agggattagt     420
atttttccat gtttattgtg ttatcagagt gcattagaaa gattagtgat tcatcttcac     480
agcacatttt taatcaagca gttatttcaa ccagcacatt cgttttgttc at             532
```

<210> SEQ ID NO 258
<211> LENGTH: 489
<212> TYPE: DNA
<213> ORGANISM: Homo sapiens
<220> FEATURE:
<221> NAME/KEY: misc_feature
<222> LOCATION: (363)..(363)
<223> OTHER INFORMATION: n is a, c, g, t or u
<220> FEATURE:
<221> NAME/KEY: misc_feature
<222> LOCATION: (441)..(441)
<223> OTHER INFORMATION: n is a, c, g, t or u

<400> SEQUENCE: 258

```
atcaccccct gttcattatg tcaggcctca tgggagcctg gccttctcca gaagctggcc      60
ccggcgtcct cccaagctgg accacgtagg ccccagatca cacctggggg tccagatgta     120
ggggtcccgt gtgcacgccc aatcagaccg agcacttgtg acactacccc aacacctctc     180
ccagggctga atgaggaacg cgccactgga cacatgagga agaggctgcc ctgggagcta     240
ctgatgctgt gacctcacct ctctggcttt gggcggcagg tccctgcacc taggatgcct     300
gcctggaaat gtccttgcat tcgtggcctc cttcacagcc tcctcctcag agaagcctct     360
gcnagtgcac agggagtgtg tgcagccttg tgaagggctg ggaccacttg cccagactgg     420
```

```
ggcccctcag gcacaggcgt ngggtcctac tgacctgtct ccccagctcc cacacagaaa        480
gcatctaaa                                                               489

<210> SEQ ID NO 259
<211> LENGTH: 468
<212> TYPE: DNA
<213> ORGANISM: Homo sapiens

<400> SEQUENCE: 259
cagaaggaaa cggtgtctct cggctgtggc tctgagtgca aattgcatgg gcggaaaggc         60
gggggtggct gctcttcctg gcaggcctgg gccatcagcg aactgggccc cgtgaggagg        120
gcgggagtgt ggaggagggt gggcctctca cccaggcttt ctcgcccct ctcctcagct         180 tgcagagctg gccagccccc tccttagggg gtgggcgagg agcctctggg cagacccaag        240
aaccatgggg actggggtgg gttggtggca ccaatggcag ccctccccgc ccctctcctt       300
caaggagggt tcccgcagct ggggggtgtg cggaggcgca tggcctcccg ccacggggcc       360
gtgctgtgtt tatggctggc agaggcagcc agcgggtggg ggattctgct gctcgctcac       420
ctgcctggct cgctggtctc tcgaattttc ttccctctga aatcctat                   468

<210> SEQ ID NO 260
<211> LENGTH: 531
<212> TYPE: DNA
<213> ORGANISM: Homo sapiens

<400> SEQUENCE: 260
ctgcaccaac tcatgctgga ctgttggcag aaggaccgca accaccggcc caagttcggc         60
caaattgtca acacgctaga caagatgatc cgcaatccca acagcctcaa agccatggcg        120
cccctctcct ctggcatcaa cctgccgctg ctggaccgca cgatccccga ctacaccagc        180
tttaacacgg tggacgagtg gctgaaggcc atcaagatgg ggcagtacaa ggagagcttc       240
gccaatgccg gcttcaccct ctttgacgtc gtgtctcaga tgatgatgga ggacattctc       300
cgggttgggg tcactttggc tggccaccag aaaaaaatcc tgaacagtat ccaggtgatg      360
cgggcgcaga tgaaccagat tcagtctgtg gaggtttgac attcacctgc ctcggctcac      420
ctcttcctcc aagccccgcc ccctctgccc cacgtgccgg ccctcctggt gctctatcca    480
ctgcagggcc agccactcgc caggaggcca cgggcacggg aagaaccaag c               531

<210> SEQ ID NO 261
<211> LENGTH: 379
<212> TYPE: DNA
<213> ORGANISM: Homo sapiens
<220> FEATURE:
<221> NAME/KEY: misc_feature
<222> LOCATION: (210)..(210)
<223> OTHER INFORMATION: n is a, c, g, t or u
<220> FEATURE:
<221> NAME/KEY: misc_feature
<222> LOCATION: (331)..(331)
<223> OTHER INFORMATION: n is a, c, g, t or u

<400> SEQUENCE: 261
cctcggacac cagagacaat aactgagcgc ggaggacacg cctgccctgc ctgccatctg        60
tggcccgaag ccattgccat ccactgcaga cgcctggaga gggacaggcc gcttccgagt      120
gcagtcctgg cgcagcaccg actcccacgc acccggggaa ggacccctc actcccacac       180 cccgggaaga acactagaac atcagcagan gggccctgcc cctccgcctg cagccgtgaa      240
```

```
aggaagctgg gtcatcagcc cagccccgcc cacccagcc cctatgtgtg tttccctcaa        300
taaggagatg ccttgttctt ttcaccatgc naataacatg cccagcaaaa acttgcttta        360
tgggtctgcc tggagaaaa                                                    379
```

<210> SEQ ID NO 262
<211> LENGTH: 486
<212> TYPE: DNA
<213> ORGANISM: Homo sapiens

<400> SEQUENCE: 262

```
aaccacacca gaagacatcc tcaggaacaa aggctgctcc agctctacca gtgtcctcct         60 caccccttgac aacaacgtgg tgaatggttc cagccctgcc atccgcacta actacattgg       120
ccacaagaca aaggacttgc aagccatctg cggcatctcc tgtgatgagc tgtccagcat       180
ggtcctggaa ctcagggggcc tgcgcaccat tgtgaccacg ctgcaggaca gcatccgcaa      240
agtgactgaa gagaacaaag agttggccaa tgagctgagg cggcctcccc tatgctatca      300
caacggagtt cagtacagaa ataacgagga atggactgtt gatagctgca ctgagtgtca      360
ctgtcagaac tcagttacca tctgcaaaaa ggtgtcctgc cccatcatgc cctgctccaa      420
tgccacagtt cctgatggag aatgctgtcc tcgctgttgg cccagcgact ctgcggacga      480
tggctg                                                                  486
```

<210> SEQ ID NO 263
<211> LENGTH: 350
<212> TYPE: DNA
<213> ORGANISM: Homo sapiens

<400> SEQUENCE: 263

```
tctccgtgga ggctatggct tcagacaggc cccgaaggtc tgtcaccaat gtgctcggtt         60
gtgggtcaca taacgctctc tggagggctt gcctttcagc ttgggatcat gaaaagatga       120
tttgacgctg tttctcatgg tctccgacct aataaagcaa gataagagaa acaaatgtt       180 attttaaaaa aatcacccctt tggcaaaaga acatgtaaa attagaatct ggcacaaaca      240
aaacctgaat ctgggttgtg aactttcacc acccgccgca actctttgat aaaacctcaa      300
gtgatatcta ttaccattgt aaaaataaag cctgccccta tgcttagaat                 350
```

<210> SEQ ID NO 264
<211> LENGTH: 507
<212> TYPE: DNA
<213> ORGANISM: Homo sapiens

<400> SEQUENCE: 264

```
ggcaaccggg gaagtattgt ggccttggag tttgctaaat ccaaatatga aaatcaaaag         60
ctttagtatt cctcatcttc tcttctggaa gatttgcgtt agagtttttg ttgggccttc       120
aaaaagctgt gttcagagtt aggagaatat atccaataaa agatggtttc gtctaccaat       180
tggggaagtt tcaccctctc cctatctgaa gaaaaaaatc aaaaacaaat gtccccggat      240
ctttcgatgc aagtcctgga ggcagggaga tcactgcctg cctggcccac gctgctggga      300
cggctcgtcc tccctgcttt ttgttttttca aacctcctgc ttctcccacc ttgggaagga     360
gaaatgtgaa acccggcagc ggccgaccta ggcggtcttg tggcccggag ccggcccggc      420
ccgaaaacca tagacctggt tgtactgtag cttgttgttt ggggggaccaa attttctaga     480 gagaactaga gcactttgt tgtgttt                                            507
```

<210> SEQ ID NO 265
<211> LENGTH: 192
<212> TYPE: DNA
<213> ORGANISM: Homo sapiens

<400> SEQUENCE: 265

```
cacaggcctt cagaggcgat ggctgggcga cagtgacgaa agcaaagcaa agcagggctg    60
tggagacact cctcgcattt gtctcttccc tccaaggatt atctgagcaa gtcgacttgt   120
tcattcaaag gcggggtctg ccaagccctg ctctatccaa tggggatagc ttctacgtaa   180
cggattccaa tt                                                       192
```

<210> SEQ ID NO 266
<211> LENGTH: 202
<212> TYPE: DNA
<213> ORGANISM: Homo sapiens

<400> SEQUENCE: 266

```
agagcaacag ctctatatct ggatcactgc agtgcctaga agatacaaca gcacaattta    60
caaatccaaa tttccaggaa gtctctgcac atacctctag tacaaaagat gtttcagaga   120
ctagagggtc agaaggcaaa gagaggcaat attcaactcc cagttcaggt caaaagggaa   180
gaaagcctgg tgttgaaaga aa                                            202
```

<210> SEQ ID NO 267
<211> LENGTH: 278
<212> TYPE: DNA
<213> ORGANISM: Homo sapiens

<400> SEQUENCE: 267

```
gaaccacgtt ctttgtatgg gcccaatgag ctgtcaagct gccctgtgtt catttcattt    60
ggaattgccc cctctggttc ctctgtatac tactgcttca tctctaaaga cagctcatcc   120
tcctccttca cccctgaatt ccagagcac ttcatctgct ccttcatcac aagtccagtt   180
ttctgccact agtctgaatt tcatgagaag atgccgattt ggttcctgtg ggtcctcagc   240
actattcagt acagtgcttg atgcacagca ggcactca                           278
```

<210> SEQ ID NO 268
<211> LENGTH: 392
<212> TYPE: DNA
<213> ORGANISM: Homo sapiens
<220> FEATURE:
<221> NAME/KEY: misc_feature
<222> LOCATION: (302)..(302)
<223> OTHER INFORMATION: n is a, c, g, t or u

<400> SEQUENCE: 268

```
ctcctggcct gatactctag ggatgcaggt gggagaagca ggggtcctgg gggctgcctg    60
gagctctggg aggcattctg aacgggtct actactgatc tcaggtgagc tctgccctcc   120
tctgaaagtc acttttctca tcagttaaat ggggcaagg gtccgtggtc cgaccaaggt   180
cttggcttca cagacatcac caggagcctg catgcccctg atcactcctt ctccttcctc   240
caggaaactc cagcctggcc tctgacccca gttcaatccg accatgccca agcccaagcg   300
gnccttttcct ccagaactgc tccggggcct ggctgtgtga ctggagcaag gtgctaaacc   360
tctctgtgcc tcgctggtct aatctgtaaa at                                 392
```

<210> SEQ ID NO 269
<211> LENGTH: 417
<212> TYPE: DNA

```
<213> ORGANISM: Homo sapiens
<220> FEATURE:
<221> NAME/KEY: misc_feature
<222> LOCATION: (240)..(240)
<223> OTHER INFORMATION: n is a, c, g, t or u

<400> SEQUENCE: 269
taatctcatc caaaaccatg ctcacagaca cacccagcat aatgtttgac caagtatctg    60
ggcaccttgt ggttcagtca aattaacaca tattaactac cttagcaaga tgaaaagcag   120
tgaatgcagg atggtggttg aaattttaaa tacgttggtt atatagtctc attgaaaaag   180
gaacatttga gtgaagactt gaaggggtgg tggaataaac catttatttg cttattgccn   240
gtctccctct atcagaatga aagcttcatg aagcgagaga cttaattttt atctgttata   300
tccctagtgc ctggtgcagg gtaagtactc aaaaatattt gttgagtgaa taagtaatga   360
ttgaggatgg ggactggttt gtatctggtt atatctcttg tccttagcac agtacct     417

<210> SEQ ID NO 270
<211> LENGTH: 412
<212> TYPE: DNA
<213> ORGANISM: Homo sapiens

<400> SEQUENCE: 270
ggggccctag ggattatagc caggactcta atctgcctac catgccattt aacaagagat    60
cccactctcc agctgccttg tgtccctagg gtcctggcca tgtgtttagt gtgctaaact   120
ttctcctttg ttctcaggcc ttccaggtag tccccttcct ggacttaaga gtgcaaactc   180
ttctctgtgg ttctagcctt gggcagaatt atatcccaga gaccacagag caactgtcaa   240
gctgcttacc ccctcaccca gggctacagc ctgtgcccag ccctctaatt tgtgcctctc   300
ttgtgttggg ggtggtgggg gttattcctt tccctttcct gctctggcct ccttgaaagt   360
tcagagtacc cagtacaagt cagccaccat gctgacgggt attttcctc at            412

<210> SEQ ID NO 271
<211> LENGTH: 372
<212> TYPE: DNA
<213> ORGANISM: Homo sapiens
<220> FEATURE:
<221> NAME/KEY: misc_feature
<222> LOCATION: (76)..(76)
<223> OTHER INFORMATION: n is a, c, g, t or u
<220> FEATURE:
<221> NAME/KEY: misc_feature
<222> LOCATION: (270)..(270)
<223> OTHER INFORMATION: n is a, c, g, t or u
<220> FEATURE:
<221> NAME/KEY: misc_feature
<222> LOCATION: (347)..(347)
<223> OTHER INFORMATION: n is a, c, g, t or u

<400> SEQUENCE: 271
tagccaggta tagtggcagg aacctgtaat cccagctaca ggggaggctg aggcaggaga    60
atcgcttgaa cccggnaggt gtaggttgca gtgagccgag attgcaccac tgcactccag   120
cctgggcgac agagcgagac tctgtctcga aaaaaaaaaa ggtccgtgcc aagctgctcc   180
ctgcccttgc cctttccctt tccctggggt ccaaaccaca tgtgtcctgc ctctcctggc   240
cctaccacat tctggtgctg tcctcactcn ccctggccc agaggctcct gaagatgctg   300
ggcggtcctg gcacagggag gagcagctct gtaaatctgt gcacatngcc actcttggcc   360
taataaagga gg                                                      372
```

<210> SEQ ID NO 272
<211> LENGTH: 427
<212> TYPE: DNA
<213> ORGANISM: Homo sapiens

<400> SEQUENCE: 272

```
cctaccaccg tcttcgagag gatgtcatgc ggctctctcg cctagcactg ggctcagagg     60
cctggcgccg agtctggagc cgcagtctgc agctggcgag ttggccaaac cggggagggg    120
cacctggagc tccccagggt gaccctatga gggtattctc agttaggacc cggagacagg    180
acactcttcc tgaagcgggg cgcagatcag aggcagaaga ggaggaggcc aggaccatca    240
gagtgacacc tgtcaggggc cgagagaggc tcaatgagga ggagcctcca ggtgggcaag    300
acccttggaa attgctgaag gagcaagagg agcggaagaa gtgtgtcatc tgccaggacc    360
agagcaagac agtgttgctc ctgccctgcc ggcatctgtg cctgtgccag gcctgcactg    420
aaatcct                                                              427
```

<210> SEQ ID NO 273
<211> LENGTH: 526
<212> TYPE: DNA
<213> ORGANISM: Homo sapiens

<400> SEQUENCE: 273

```
gtccacattc ctgcaagcat tgattgagac atttgcacaa tctaaaatgt aagcaaagta     60
gtcattaaaa atacaccctc tacttgggct ttatactgca tacaaattta ctcatgagcc    120
ttcctttgag gaaggatgtg gatctccaaa taaagattta gtgtttattt tgagctctgc    180
atcttaacaa gatgatctga acacctctcc tttgtatcaa taaatagccc tgttattctg    240
aagtgagagg accaagtata gtaaaatgct gacatctaaa actaaataaa tagaaaacac    300
caggccagaa ctatagtcat actcacacaa agggagaaat ttaaactcga accaagcaaa    360
aggcttcacg gaaatagcat ggaaaaacaa tgcttccagt ggccacttcc taaggaggaa    420
caaccccgtc tgatctcaga attggcacca cgtgagcttg ctaagtgata atatctgttt    480
ctactacgga tttaggcaac aggacctgta cattgtcaca ttgcat                   526
```

<210> SEQ ID NO 274
<211> LENGTH: 429
<212> TYPE: DNA
<213> ORGANISM: Homo sapiens

<400> SEQUENCE: 274

```
tgtgtccact ggtttcagtc tgagttctct gcactttgag gatgcagaca gtgaagttct     60
cccatggtta tagggggaga gatcatagga atgctatgga agaggcctg aagtcagagc     120
cagctagtgg ttattattta ttaattgcct gtgaggtgcc aggcgcacat attagaccat    180
atgtgattgc agtgagccac ccggatcccc ttcaagctgc tgctgcagct gatggaagtc    240
ctattggcag acagccttct ctcatcagcc ccttcaggac ttgcctcagt tgcagagagc    300
tgccttcccc aagatcacac ccttccctgg ggactcacaa ccaatggctg atccagaaga    360
atccataaag cccgtatcat ttcagcccaa tttaggacag cttttgttgag ccattagacc    420
tacatgcag                                                            429
```

<210> SEQ ID NO 275
<211> LENGTH: 434
<212> TYPE: DNA
<213> ORGANISM: Homo sapiens
<220> FEATURE:

```
<221> NAME/KEY: misc_feature
<222> LOCATION: (376)..(390)
<223> OTHER INFORMATION: n is a, c, g, t or u

<400> SEQUENCE: 275
gaagctctac ttgcctggtg gtaattccag gatgacccag gagaggctgg aaagagcgtt      60
caaacggcag ggcagccagc ccgcacctgt caggaaaaat cagttgctgc cgtctgacaa     120
ggtggatggt gagctgggtg ccctgcggct cgaggatgtg gaggatgagt tgataaggga     180
agaggtcatc ctgtcgccag tcccatcagt gctcaagttg cagacagcat caaaaccaat     240
tgacctctca gtagcaaagg aaataaagac ccttctgttt ggttccagct tttgctgttt     300
caatgaagaa tggaaacttc agagtttttc ctttagtaac acagcctcat taaaatacgg     360
catagtgcag aacaannnnn nnnnnnnnnn agtcctggca gctgtccaag gctgtgtcct     420
acagaaactc ctgt                                                      434

<210> SEQ ID NO 276
<211> LENGTH: 189
<212> TYPE: DNA
<213> ORGANISM: Homo sapiens

<400> SEQUENCE: 276
aaaatcactg ccactgactt ttaccctctt caggaagagg ccaaggagga ggaacgcctc      60
atagctttga agaaaatcct cagctcgggg gtgttctatt tctcatggcc aaacgatggg     120
tctcgctttg acctgactgt ccgcacgcag aagcagggggg atgacagctc tgaatggggg     180
aactccttc                                                            189

<210> SEQ ID NO 277
<211> LENGTH: 542
<212> TYPE: DNA
<213> ORGANISM: Homo sapiens

<400> SEQUENCE: 277
gaggagcagg caaggctacg tgggcagctg aaggagcaaa gcgtgcgctg ccggcgcctc      60
gctcacctgc tggcctcggc ccagaaggag cctgaggcag cagccccagc cccagggacc     120
gggggtgatt ctgtgtgtgg ggagacccac cgggccctgc aggggggccat ggagaagctg     180 cagagccgct ttatggagct catgcaggag aaggcagacc tgaaggagag gccagggagg     240
gttctccccg tgacaacccc actgcacagc agatcatgca gctgcttcgt gagatgcaga     300
acccccggga gcgcccaggc ttgggcagca acccctgcat tccttttttt taccgggctg     360
acgagaatga tgaggtgaag atcactgtca tctaaaagcc ggctactgtc agcaaagcct     420
gaagaagtgg ggctggatac cctgccccca ccatatccct accatccctt ctcagtcaac     480
cctttaccct tacagtagca agcatagacc cctgtctaac gggggtagac aggtgcagat     540
ga                                                                   542

<210> SEQ ID NO 278
<211> LENGTH: 475
<212> TYPE: DNA
<213> ORGANISM: Homo sapiens

<400> SEQUENCE: 278
gacagtctac cgtcacgaga agcgggtgaa actgcagatc tgggacacag ctgggcagga      60
gcggtaccgg accatcacaa cagcctatta ccgtggggcc atgggcttca ttctgatgta     120
tgacatcacc aatgaagagt ccttcaatgc tgtccaagac tgggctactc agatcaagac     180
```

```
ctactcctgg gacaatgcac aagttattct ggtggggaac aagtgtgaca tggaggaaga    240
gagggttgtt cccactgaga agggccagct ccttgcagag cagcttgggt ttgatttctt    300
tgaagccagt gcaaaggaga acatcagtgt aaggcaggcc tttgagcgcc tggtggatgc    360
catttgtgac aagatgtctg attcgctgga cacagacccg tcgatgctgg gctcctccaa    420
gaacacgcgt ctctcggaca ccccaccgct gctgcagcag aactgctcat gctag         475
```

<210> SEQ ID NO 279
<211> LENGTH: 294
<212> TYPE: DNA
<213> ORGANISM: Homo sapiens
<220> FEATURE:
<221> NAME/KEY: misc_feature
<222> LOCATION: (225)..(228)
<223> OTHER INFORMATION: n is a, c, g, t or u
<220> FEATURE:
<221> NAME/KEY: misc_feature
<222> LOCATION: (231)..(231)
<223> OTHER INFORMATION: n is a, c, g, t or u

<400> SEQUENCE: 279

```
tttttagat ctaccctctt gttgcccagg gggagtccag tggcgtgatc ttggctcact    60
gcaaccgccg cctcccgggt tcaagcaatt ctcctgcctc agtctcccga gtgtcttctg   120
tcttttgtaa aagttttca tgcccaagtg agattaattg tttaaaaaaa aaaaaacaag    180
aagaaaacaa catagattta ccgcaagacc tattgatata ttatnnnnca nggtggtata   240
cccagggtgg gtgtgacaca gaccaaaaga ggctgtgtgt tctgttgttg ataa         294
```

<210> SEQ ID NO 280
<211> LENGTH: 421
<212> TYPE: DNA
<213> ORGANISM: Homo sapiens
<220> FEATURE:
<221> NAME/KEY: misc_feature
<222> LOCATION: (129)..(129)
<223> OTHER INFORMATION: n is a, c, g, t or u
<220> FEATURE:
<221> NAME/KEY: misc_feature
<222> LOCATION: (136)..(137)
<223> OTHER INFORMATION: n is a, c, g, t or u
<220> FEATURE:
<221> NAME/KEY: misc_feature
<222> LOCATION: (146)..(146)
<223> OTHER INFORMATION: n is a, c, g, t or u
<220> FEATURE:
<221> NAME/KEY: misc_feature
<222> LOCATION: (323)..(323)
<223> OTHER INFORMATION: n is a, c, g, t or u

<400> SEQUENCE: 280

```
ggaagcgtgt ctgctgggag tttgcgaccg atgactatga cattggcttt ggagtttatt    60
ttgactggac ccctgtaact agcactgaca taactgtgca ggtcagtgat ccagtgacg    120 atgaggatna agaagnnagg aagagnagga agagattgaa gaacccgttc cagctggaga   180
tgtggagaga ggctccagga gctccttgcg gggtcgctat ggggaggtca tgcctgtgta   240
ccggcgggac agccaccgag acgtgcaggc tggcagccat gactaccctg gtgagggcat   300
ctacctgctc aagttcgaca acnnctactc cctgctgcgc aacaagactc tctacttcca   360
catctactac accagctgaa ggactgctgt gacaggggca ggctgtattt gctggctgaa   420
g                                                                  421
```

<210> SEQ ID NO 281

<211> LENGTH: 544
<212> TYPE: DNA
<213> ORGANISM: Homo sapiens

<400> SEQUENCE: 281

```
atgagaacgg cgtcttcatg tgcgccgagg gcaccggcaa gttctgtccc ctgaggtcct   60
tcccagacac tgtctacaag aagctggtcc agagagagaa gactttaaag gttagaggag  120
tggaccgcac tccctacctg ggggatgtcg ctgttgtcgt gcaccctggg aaaaaagaga  180
tgggaacccc actcgcagac actcctaccc ggcccgtcac ccggcatggg ggcatgaggg  240
accttcacga atccagcttc agcctctctg gctctcagat cgatgaccat gttccaaagc  300
gagcttcagc tcggatcctc gctcctcccg gaggcaggtc gagtggcatt tggtaaaggc  360
attgccaagc cccccgagtg aggacgcacc gccgccacca gcccgcaact ctccagccga  420
agctgcaggg gcaggagagg ctgggctggg tggcacacca cccgaggggg gccccgggac  480
ccacggagcc ctccctatgt ctgcaaagtg attcactgtg cttcgagcca actctaacag  540
gcac                                                               544
```

<210> SEQ ID NO 282
<211> LENGTH: 430
<212> TYPE: DNA
<213> ORGANISM: Homo sapiens

<400> SEQUENCE: 282

```
ctgattctac ttctgcaggg ttccacagaa gtctccagtc ttcaaatctt cagtgtatga   60
aagcacagat tcctgaaaga atggcctcaa atgaccagga gtaggagctc tctatatccc  120
tgctcctgaa aaacaagcta actggagtct ccatcacctg ccaccagcta tacacactac  180
caactaccca actgaactcc atgactgatt tgccagctaa tcatgcccct gacccagccc  240
acatggacat gggaaggaca tcagtgaact gtgaaaagag gcagagactc actcccgttt  300
gtattatgaa aacacgccc aataggacat aaaaagaagc aagagtactg ggctttacca  360
tgagttcaaa tctcatttct ggcaattcct atgtctaaaa aaagcttcgt aatctctttt  420
gagccctcac                                                         430
```

<210> SEQ ID NO 283
<211> LENGTH: 219
<212> TYPE: DNA
<213> ORGANISM: Homo sapiens

<400> SEQUENCE: 283

```
ccagaggatg atagcacctg tcagtgccag gcgtgcgggc ctcaccaagc cgcgggtcca   60
gatcttggtt cctctaatga tggctgccct cagctgttcc aggagcggtc agtcatagtg  120
gagaactcct caggctctac cagcgcttct gagctcctca aacccatgaa gaagaggaag  180
cgcagggaat accagagccc atcagaggag gagtcggag                         219
```

<210> SEQ ID NO 284
<211> LENGTH: 232
<212> TYPE: DNA
<213> ORGANISM: Homo sapiens

<400> SEQUENCE: 284

```
tttgcctgag gttgactata catacaaata ttgagcattt cctcctggtc tccgtgataa   60
acaaggtttt tgatattgtt cggcgagatg gaaagaaaat atcaaggagt gagctgaagc  120
cactgccctt gagaaccctc tcgaggagtc tggcctcatg aagatgccag aataaacggc  180
```
agatatatcc tgaatgaatg tgagattttt accctgtgaa tttcctgtga gg            232

<210> SEQ ID NO 285
<211> LENGTH: 249
<212> TYPE: DNA
<213> ORGANISM: Homo sapiens
<220> FEATURE:
<221> NAME/KEY: misc_feature
<222> LOCATION: (208)..(208)
<223> OTHER INFORMATION: n is a, c, g, t or u

<400> SEQUENCE: 285
agtgcttcca gtggcccaaa aatgcttttt gaagtgtgtt ttgaaacagc ccccaccaac    60
atacacccca ccaggagtac tgatcctgcc tcccttcatg tctagggaa gcattcgcct   120 ttgagcactt gtttgcaaat ctggggagtt tgagacctcc tagcatctct tcccttcttt   180
ccctgcagtc tattcactcc cgcagccnaa aaatctctgg cgttcaggtt agcagtttct   240
gggttggtt                                                          249

<210> SEQ ID NO 286
<211> LENGTH: 510
<212> TYPE: DNA
<213> ORGANISM: Homo sapiens
<220> FEATURE:
<221> NAME/KEY: misc_feature
<222> LOCATION: (138)..(140)
<223> OTHER INFORMATION: n is a, c, g, t or u
<220> FEATURE:
<221> NAME/KEY: misc_feature
<222> LOCATION: (142)..(143)
<223> OTHER INFORMATION: n is a, c, g, t or u
<220> FEATURE:
<221> NAME/KEY: misc_feature
<222> LOCATION: (371)..(371)
<223> OTHER INFORMATION: n is a, c, g, t or u

<400> SEQUENCE: 286
gggaattacc ttttgtattg cttgaattta ctgctgtctg tatgaactct ttttcagata    60
aatttttaag aaatcagata agtgaagtga aagagagaga tcaaagtgtt gtggcagcac   120
aaaggagaga ctgactannn tnntgctggg gaatctgaaa gagtgctttg gtggaggtaa   180
catgagatca gggccttgaa gggtgagtca agtctgtcaa ggagacaaga gggagagaag   240
agcttgccag aggcccagag accagcgagg aggctgtggt gtcctggaat gagggcgaga   300
tacttggtgg gactggtcaa cacggcaatg aagagggata tggccgagga aaatggagag   360
gggcactgga nctgtgccag caaggactgg gatgcgtgga cttgatcctg tagataacgg   420
gaggaagaaa ggcctggatg cagcgccatg tcatgagcac atctgatcat gacagctcac   480
ctatgggagg attctccctc aacattttc                                    510

<210> SEQ ID NO 287
<211> LENGTH: 555
<212> TYPE: DNA
<213> ORGANISM: Homo sapiens
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (89)..(89)
<223> OTHER INFORMATION: n is a, c, g, t or u
<220> FEATURE:
<221> NAME/KEY: misc_feature
<222> LOCATION: (106)..(107)

<223> OTHER INFORMATION: n is a, c, g, t or u
<220> FEATURE:
<221> NAME/KEY: misc_feature
<222> LOCATION: (272)..(274)
<223> OTHER INFORMATION: n is a, c, g, t or u

<400> SEQUENCE: 287

```
aggatgtgac agtgactcgg ggcgaccagg ctatgtttnc ttgcatcgta aacttccagc    60
tgccaaagga ggagatcacc tattcctgna agttcgcagg aggagnnctc cggactcagg   120
acttgtccta tttccgagat atgccgcggg ccgaaggata cctggcgcgg atccggccgg   180
ctcagctcac gcaccgcggg acgttctcct gcgtgatcaa gcaagaccag cgccccctgg   240
cccggctcta cttctttctt aacgtgacgg gnnngccccc gcgggcggag acagagttgc   300
aggcctcgtt ccgggaagtg ctgcgctggg cgccgcggga tgccgagctg atcgagccct   360
ggaggcccag cctgggcgag ctgctggcca ggcccgaggc tctgacgccc agcaatctgt   420
tcctgcttgc agtcctcggg gccctcgcat cagcgagtgc gacagtgttg gcgtggatgt   480
tctttcgatg gtactgcagt ggcaactaac aaaggtatct ttcctccttc cctatcctat   540
ttccatcctg aaaat                                                    555
```

<210> SEQ ID NO 288
<211> LENGTH: 381
<212> TYPE: DNA
<213> ORGANISM: Homo sapiens

<400> SEQUENCE: 288

```
atgtatccgc tgtcaactac gaatttgagg atgaatactt cagtaatacc agtgccctag    60
ccaaagattt cataagaaga cttctggtca aggatccaaa gaagagaatg acaattcaag   120
atagtttgca gcatccctgg atcaagccta agatatacaca acaggcactt agtagaaaag   180
catcagcagt aaacatggag aaattcaaga agtttgcagc ccggaaaaaa tggaaacaat   240
ccgttcgctt gatatcactg tgccaaagat tatccaggtc attcctgtcc agaagtaaca   300
tgagtgttgc cagaagcgat gatactctgg atgaggaaga ctcctttgtg atgaaagcca   360
tcatccatgc catcaacgat g                                             381
```

<210> SEQ ID NO 289
<211> LENGTH: 488
<212> TYPE: DNA
<213> ORGANISM: Homo sapiens

<400> SEQUENCE: 289

```
cacgctcctg gaacgtcaga tcattattga ggcaaatgat cgccatctag aatcagcagg    60
acagactgag atcttccgaa agcacccccg caaagcctcc atcctcaaca tgccactagt   120
gacaacactt ttctactcct gcttctatca ctacacagag gctgagggga cattcagcag   180
tcccgtcaac ctgaagaaga catttaagat cccagataaa cagtatgtgc tgacagccct   240
ggctgctcgt gccaagcttc gagcctggaa tgatgtagat gccctattca ccacaaagaa   300
ctggctgggc tataccaaga agagagcacc cattggcttc catcgggttg tcgaaatttt   360
gcacaagaac aatgcccctg tgcagatatt acaggagtat gtcaatctgg tggaagatgt   420
ggacacgaag ttgaacttag ccactaagtt caagtgccat gatgtcgtca ttgatacctac  480
ccgggacc                                                            488
```

<210> SEQ ID NO 290
<211> LENGTH: 306

```
<212> TYPE: DNA
<213> ORGANISM: Homo sapiens

<400> SEQUENCE: 290
tttcatgact tctccttcac ctaagcacct caaaacagat gatagcactt caggattgac      60
gcgaagcatc ttcaaatatt tggagagcta acaccatcaa aggtgccaaa atctacattg     120
agactgcttt gagaagtttc tagcactgaa agttggaatt gacactccag ccaatgatcc     180
ttccttcttt cataatcaat gcaataagat tgcagacaga aattccagtg atttctactg     240
cacagctctg gacatctctt ttcctagtat tattccctga attggccact gatttcaatt     300
ctgcag                                                                306

<210> SEQ ID NO 291
<211> LENGTH: 348
<212> TYPE: DNA
<213> ORGANISM: Homo sapiens

<400> SEQUENCE: 291
ctcctgggtc cgcagtgtac tgcgagggag cacagatgtc catccccgc tggggtggag       60 agcggcagca ggcctgatgg atgagggatc gtggcttccc ggcccagaga catgaggtgt     120
ccagggccag gcccccacc ctcagttggg gctgttccgg gggtgactgt gagcgatccc      180
accccaaacc tgagatgggg tagcccgtcc tgtgtcctcc acaggacaa gcagtgggag      240 gagtctgaat ggtcaccagg aagcccgggc tccatcttga cctccttttt cagggacagg     300
agcaacaggc ccctcttccc tgactctaag cccttccctg taaggtga                  348

<210> SEQ ID NO 292
<211> LENGTH: 395
<212> TYPE: DNA
<213> ORGANISM: Homo sapiens
<220> FEATURE:
<221> NAME/KEY: misc_feature
<222> LOCATION: (343)..(343)
<223> OTHER INFORMATION: n is a, c, g, t or u
<220> FEATURE:
<221> NAME/KEY: misc_feature
<222> LOCATION: (361)..(361)
<223> OTHER INFORMATION: n is a, c, g, t or u

<400> SEQUENCE: 292
tctctgcttt ccctcttatg aaaatggcag atgccttttt gtgaaggtct caaagcccac      60
ttcatcctgg ctgcagcacc aaaaggacaa aggcccgctt ttgaagtgcc tgataaggca    120
ttcctttcac ccctccatga ggaaggtggc aaatcttgag actccctatt agagagcttc     180
gattttcctg aaattgtgtt aggaaaatag ggtgacttgg tttgatcttg gtttctatac    240
ctattatggc tgcctgactc tggtcatttg gcccctgcag gcctaagcca cttggttttg    300
cttcacatat tggggtttat tagaacagta cgtagggaag canatgccag aggcacccgt    360
nccttttccc tgccttctag gtgctcctgg gaaat                                395

<210> SEQ ID NO 293
<211> LENGTH: 557
<212> TYPE: DNA
<213> ORGANISM: Homo sapiens

<400> SEQUENCE: 293
accaagatct ctgcctggca caataacgtg gagaaaaccc tgccctccac caaggccacg      60
cgggtgggcg tgcttctcaa ctgtgaccac ggctttgtca tcttcttcgc tgttgccgac    120
```

```
aaggtccacc tgatgtataa gttcaggtg gactttactg aggctttgta cccggctttc    180
tgggtatttt ctgctggtgc cacactctcc atctgctccc ccaagtaggc aggctgtagg    240
cacttgggct gactgcctgc agaagtccca agaccctagt gaaaatacag caggcagaac    300
tctccttgga taattccccc aagaggtccc caaggattgg gagcatggga ggggagctgg    360
cgggagggtg ggaggtggga tttagccagg aaaggggtga gagtgattgt gttgtgggcg    420
aggaggcgtt tccaccccct ggtgcctatc agggcagggt gacctactcc ccattgttct    480
ggaaatctcc aggctgctgg gcagctgggc agctgggcag agctctggga agtgaagtca    540
tgagtgcccg attcctc                                                  557

<210> SEQ ID NO 294
<211> LENGTH: 547
<212> TYPE: DNA
<213> ORGANISM: Homo sapiens

<400> SEQUENCE: 294
ggttcgggtg agggcactct atgactacgc tggccaggaa gctgatgagc tgagcttccg     60
agcaggggag gagctgctga agatgagtga ggaggacgag cagggctggt gccaaggcca    120
gttgcagagt ggccgcattg gcctgtaccc tgccaactac gtggagtgtg tgggcgcctg    180
agtgtcctga cagcccttct gcaacgttta cccaccctgg ttcagagccc agcttctcct    240
ggagagccgg accctcaggg ccctgaaccg tcgctctctg gctgctcctc tgtcccttga    300
gggaggaagt cctgggaccc agggagggga ggggcctttg tctagggaag ggactggtag    360
ggaagggacg agtctaggct gagggcaaga tgggaggtca gaggtgacag aagcgttcag    420
gggtgcctgg gcctccccag gagctgtgga ctcagttcct gacctctgct ttggggttcc    480
tggggtgggc ttggggtgag tgtagttctg gcctagcagc accctcttgt ggcttgttct    540
agcgtgt                                                             547

<210> SEQ ID NO 295
<211> LENGTH: 147
<212> TYPE: DNA
<213> ORGANISM: Homo sapiens

<400> SEQUENCE: 295
tgtatgtgac caaaggtagg tcctgggatg acagcaatgc tgacactggc ctaaggagtt     60
actcatccat ttaataagta ttccagcaga tacagatgtg aacagtcaag tctctgccat    120
ccacaatgct tgtgttctaa tgcaaga                                       147

<210> SEQ ID NO 296
<211> LENGTH: 83
<212> TYPE: DNA
<213> ORGANISM: Homo sapiens

<400> SEQUENCE: 296
atgtgttcaa ccaagcggga aactctccgg gtagagtgaa atccgaagtt gctatgctac     60 aagataaccct gggccgtgcg ccg                                           83

<210> SEQ ID NO 297
<211> LENGTH: 545
<212> TYPE: DNA
<213> ORGANISM: Homo sapiens

<400> SEQUENCE: 297
gtctttctga gagtttcatt gccattatca acaagagaag ttgaaattta caagtcagga     60
```

```
ggttattttt ccagattgat aaccatagaa agtgaataaa cacttttaag gtcgcaaaca      120
tttgctaggt tgtccttctc aatgcatgtg caggctgcat cctgtccttg tttttaagcc      180
agggtttata aataagtaga tttataccaa tcttaataga attgtatatt ttatgcaaga      240
attaaatgct ttacaacatg aagtataact caacccattg taaactttgg tggcaatatg      300
gatttgaaac tcgacagttc tcttgtattt gcttcctagg tttctgcatg caagttatga      360
caggtaggac tgaaaaaaca ctgccttttg acttctagca tttagcaacc gagagtcgta      420
gagtcaataa agctgtaagt gtcttcactt aatctgtggt tctcctaaaa ctattatctg      480
aaacctacag catcccacca tgaaatattt ggtaaattta tgttgtgacg tgttgcagca      540
tgtaa                                                                 545
```

<210> SEQ ID NO 298
<211> LENGTH: 485
<212> TYPE: DNA
<213> ORGANISM: Homo sapiens

<400> SEQUENCE: 298

```
aatttgtctg tgacccagat gccctcttct ccatggcttt cccggataac cagcgtccgt       60
tcctgaaggc agagtccgag tgccacctca gcgaggagga caccctgccg ctgacccact      120
ttgaagacag ccccgcttac ctcctggaca tggaccgctg cagcagcctc ccctatgccg      180
aaggctttgc ttactaagtt tctgagtggc ggagtggcca aaccctagag ctagcagttc      240
ccattcaggc aaacaagggc agtggttttg tttgtgtttt tggttgttcc taaagcttgc      300
cctttgagta ttatctggag aacccaagct gtctctggat tggcaccctt aaagacagat      360
acattggctg gggagtggga acagggaggg gcagaaaacc accaaaaggc cagtgcctca      420
actcttgatt ctgatgaggt ttctgggaag agatcaaaat ggagtctcct taccatggac      480
aatac                                                                 485
```

<210> SEQ ID NO 299
<211> LENGTH: 409
<212> TYPE: DNA
<213> ORGANISM: Homo sapiens
<220> FEATURE:
<221> NAME/KEY: misc_feature
<222> LOCATION: (36)..(36)
<223> OTHER INFORMATION: n is a, c, g, t or u
<220> FEATURE:
<221> NAME/KEY: misc_feature
<222> LOCATION: (38)..(38)
<223> OTHER INFORMATION: n is a, c, g, t or u
<220> FEATURE:
<221> NAME/KEY: misc_feature
<222> LOCATION: (40)..(40)
<223> OTHER INFORMATION: n is a, c, g, t or u
<220> FEATURE:
<221> NAME/KEY: misc_feature
<222> LOCATION: (312)..(312)
<223> OTHER INFORMATION: n is a, c, g, t or u

<400> SEQUENCE: 299

```
acagcttagc gatggagaaa atggcatccc tgttgntntn tcaccagata aattgcctgg       60
atctctggga caccccgtc cccaggagaa ggatgtttgg gaagagatgg atgccaacaa      120
aaacaagata aagcttggaa tttgtaaggc tgctactgaa gaggagaaca gccatggcca      180
ggcaaatggt cttctcaatg ctccaagcct tgggtcacca attcgtgtcc gctcagagat      240
tactcagcca gacagagata ttccactggt gcgaaagtta cgttccattc acagctttga      300
```

```
gctggaaaaa cntctgaccc tggagccaaa gccagacact gacaagttcc ttgagacctg    360
gtataaaata gtgtattttt ctttttaaag cttctaaggt accattatt                409

<210> SEQ ID NO 300
<211> LENGTH: 430
<212> TYPE: DNA
<213> ORGANISM: Homo sapiens
<220> FEATURE:
<221> NAME/KEY: misc_feature
<222> LOCATION: (150)..(150)
<223> OTHER INFORMATION: n is a, c, g, t or u
<220> FEATURE:
<221> NAME/KEY: misc_feature
<222> LOCATION: (164)..(164)
<223> OTHER INFORMATION: n is a, c, g, t or u
<220> FEATURE:
<221> NAME/KEY: misc_feature
<222> LOCATION: (170)..(170)
<223> OTHER INFORMATION: n is a, c, g, t or u
<220> FEATURE:
<221> NAME/KEY: misc_feature
<222> LOCATION: (173)..(174)
<223> OTHER INFORMATION: n is a, c, g, t or u
<220> FEATURE:
<221> NAME/KEY: misc_feature
<222> LOCATION: (185)..(185)
<223> OTHER INFORMATION: n is a, c, g, t or u
<220> FEATURE:
<221> NAME/KEY: misc_feature
<222> LOCATION: (187)..(187)
<223> OTHER INFORMATION: n is a, c, g, t or u
<220> FEATURE:
<221> NAME/KEY: misc_feature
<222> LOCATION: (207)..(207)
<223> OTHER INFORMATION: n is a, c, g, t or u
<220> FEATURE:
<221> NAME/KEY: misc_feature
<222> LOCATION: (210)..(210)
<223> OTHER INFORMATION: n is a, c, g, t or u
<220> FEATURE:
<221> NAME/KEY: misc_feature
<222> LOCATION: (220)..(220)
<223> OTHER INFORMATION: n is a, c, g, t or u
<220> FEATURE:
<221> NAME/KEY: misc_feature
<222> LOCATION: (390)..(390)
<223> OTHER INFORMATION: n is a, c, g, t or u
<220> FEATURE:
<221> NAME/KEY: misc_feature
<222> LOCATION: (393)..(393)
<223> OTHER INFORMATION: n is a, c, g, t or u
<220> FEATURE:
<221> NAME/KEY: misc_feature
<222> LOCATION: (395)..(398)
<223> OTHER INFORMATION: n is a, c, g, t or u
<220> FEATURE:
<221> NAME/KEY: misc_feature
<222> LOCATION: (400)..(400)
<223> OTHER INFORMATION: n is a, c, g, t or u
<220> FEATURE:
<221> NAME/KEY: misc_feature
<222> LOCATION: (403)..(403)
<223> OTHER INFORMATION: n is a, c, g, t or u

<400> SEQUENCE: 300
gagggccaag agctagggac aggggaaga gactggccca ggtggtaggg aggaaagaac     60
tcccagagtt tcctttagcc aggaaacctg ctctactgac cccgtgactt ggacagtcag   120
acatcaccct gagagtgaca agtgtaaaan tgactcccct cctncccgn ccnncggaag    180 tatantnaga tacttgaaag cagtccnttn ctaaaatggn cttacctatg tggcctgaac   240
gattaaaaga aagaactcag agttacaagg gaaaagaaa aagagttaca agggaattgt   300 agtcttttc tgaatagaat attagtactg tggtattgca tttcatggga atggaaatgt   360
```

```
attggtaaag ctacctgatg gaagctttcn ctngnnnncn aanatggagg gtgtattatg    420
tgcagttatt                                                          430
```

<210> SEQ ID NO 301
<211> LENGTH: 536
<212> TYPE: DNA
<213> ORGANISM: Homo sapiens
<220> FEATURE:
<221> NAME/KEY: misc_feature
<222> LOCATION: (68)..(69)
<223> OTHER INFORMATION: n is a, c, g, t or u
<220> FEATURE:
<221> NAME/KEY: misc_feature
<222> LOCATION: (72)..(72)
<223> OTHER INFORMATION: n is a, c, g, t or u
<220> FEATURE:
<221> NAME/KEY: misc_feature
<222> LOCATION: (74)..(76)
<223> OTHER INFORMATION: n is a, c, g, t or u
<220> FEATURE:
<221> NAME/KEY: misc_feature
<222> LOCATION: (78)..(82)
<223> OTHER INFORMATION: n is a, c, g, t or u
<220> FEATURE:
<221> NAME/KEY: misc_feature
<222> LOCATION: (100)..(100)
<223> OTHER INFORMATION: n is a, c, g, t or u
<220> FEATURE:
<221> NAME/KEY: misc_feature
<222> LOCATION: (121)..(121)
<223> OTHER INFORMATION: n is a, c, g, t or u
<220> FEATURE:
<221> NAME/KEY: misc_feature
<222> LOCATION: (129)..(129)
<223> OTHER INFORMATION: n is a, c, g, t or u
<220> FEATURE:
<221> NAME/KEY: misc_feature
<222> LOCATION: (134)..(134)
<223> OTHER INFORMATION: n is a, c, g, t or u
<220> FEATURE:
<221> NAME/KEY: misc_feature
<222> LOCATION: (168)..(168)
<223> OTHER INFORMATION: n is a, c, g, t or u
<220> FEATURE:
<221> NAME/KEY: misc_feature
<222> LOCATION: (216)..(216)
<223> OTHER INFORMATION: n is a, c, g, t or u
<220> FEATURE:
<221> NAME/KEY: misc_feature
<222> LOCATION: (228)..(228)
<223> OTHER INFORMATION: n is a, c, g, t or u
<220> FEATURE:
<221> NAME/KEY: misc_feature
<222> LOCATION: (254)..(254)
<223> OTHER INFORMATION: n is a, c, g, t or u
<220> FEATURE:
<221> NAME/KEY: misc_feature
<222> LOCATION: (276)..(276)
<223> OTHER INFORMATION: n is a, c, g, t or u

<400> SEQUENCE: 301

```
atcgaagaac aaagagtgct ccaaaaaata ggtcattctt ttattttcat aaagtatcta    60
aactgtanna anannnannn nngtgtttca ttctaaattn gcagctgaaa taaatttatt   120
ngcgatagna gaantatctt attattcatc ctcagaaata aaggattnga agggatagag   180
attatatgat aaatttatag aagactttca gaattntgaa tgcatttngt ttagtgttat   240
gaaatgacaa tagnaaaaaa gtctcgactt caattnaaaa gttacacaaa caaacaaatc   300
tacaggcatg tctttatata ccatcaggtc taagttttca agaaaatgg tagatataac   360 tgcagataac tcattacagt cataatctct gcccatgtgt attgagaggg ggcagttgtg   420
```

```
cacgaaaaaa gaatttatgt ggccatttta ataaattcag tttaaaatag acttgtgtat    480
atgcatgaat catcagagat gaaactggtt tgagagactc atgtgaacct tacgaa        536
```

<210> SEQ ID NO 302
<211> LENGTH: 371
<212> TYPE: DNA
<213> ORGANISM: Homo sapiens

<400> SEQUENCE: 302

```
ctggtacgct gctgctgcag ttaccagaaa aactcataag caaatacaac tggatcaagc     60
aatggaaact tggactgaaa tttgatggga agaatgagga cctggttgat aaaattaaag    120
agtcccttac tctgctgagg aagaaggttt ggaacctgta gtgtcctgtc tgataagggt    180
gaagctctcg ttcttgcttg ccccagaaga ccagttttta gtcttcactc agtggatttt    240
caaatgctct tggctgattt ttaggcaaaa tggttttaaa tgaattcaaa ctcttcccac    300
gagggcttta gtaaaatggg aagtaccaac attatatatt cttagagcag atgccatgta    360
ctagggtatc a                                                        371
```

<210> SEQ ID NO 303
<211> LENGTH: 355
<212> TYPE: DNA
<213> ORGANISM: Homo sapiens
<220> FEATURE:
<221> NAME/KEY: misc_feature
<222> LOCATION: (223)..(223)
<223> OTHER INFORMATION: n is a, c, g, t or u
<220> FEATURE:
<221> NAME/KEY: misc_feature
<222> LOCATION: (227)..(227)
<223> OTHER INFORMATION: n is a, c, g, t or u

<400> SEQUENCE: 303

```
gaagctgtgt ggagtggaag atggacattg aggaagaagg gcaggtgtgg tctcacccag     60
aatggttcct gctgcttccg cggtgcccag gcttttctca cggcctctgc tgggttctcc    120
cctgggtgct gtggatgcat cctgcctgct ggaaattctg tgctctctgt ttccatccct    180
ttgtcgtggt aatgaccgta tacctctccc ctgtaccctc ctntgcntgc tctccgtgca    240
ggcccctctc cctctggttg tcccatcagc atttccccac agctcgttgt tcctccttcc    300
tcttttctgg tgacctttct actgattgca ttgtacctct ttccctgata ttaaa         355
```

<210> SEQ ID NO 304
<211> LENGTH: 362
<212> TYPE: DNA
<213> ORGANISM: Homo sapiens

<400> SEQUENCE: 304

```
gcctgtgtct tcgggctgaa tttgatctgg ccatcccagg gggtctcctc cctgagtgcc     60
cttgtgcccc tgaacatgtt cactgaactg ctgatcgagt actatgaaaa gatcttcagc    120
accccggagg cacctgggga gcacggcctg gcaccatggg aacaggggag cagggcagcc    180
cctttgcagg aggctgtgcc acggacacaa gccacgggcc tcaccaagcc taccctacct    240
ccgagtcccc tgatggcagc cagaagacgt ctctagtgtt gcgaacactc tgtatgtttc    300
gagctacctc ccacacctgt ctgtgcactt gtatgttttg taaacttggc atctgtaaaa    360
at                                                                  362
```

<210> SEQ ID NO 305
<211> LENGTH: 533

```
<212> TYPE: DNA
<213> ORGANISM: Homo sapiens

<400> SEQUENCE: 305
cgaagagcaa gacccactct gttccagaag ccctataagc tggaggtgga caactcgatg      60
taaatttcat gggaaaaccc ttgtacctga catgtgagcc actcagaact caccaaaatg     120
ttcgacacca taacaacagc tactcaaact gtaaaccagg ataagaagtt gatgacttca     180
cactgtggac agttttttcca aagatgtcag aacaagactc cccatcatga taaggctccc    240
acccctctta actgtccttg ctcatgcctg cctctttcac ttggcaggat aatgcagtca     300
ttagaatttc acatgtagta gcttctgagg gtaacaacag agtgtcagat atgtcatctc     360
aacctcaaac ttttacgtaa catctcaggg gaaatgtggc tctctccatc ttgcatacag     420
ggctcccaat agaaatgaac acagagatat tgcctgtgtg tttgcagaga agatggtttc     480
tataaagagt aggaaagctg aaattatagt agagtctcct ttaaatgcac att            533

<210> SEQ ID NO 306
<211> LENGTH: 434
<212> TYPE: DNA
<213> ORGANISM: Homo sapiens
<220> FEATURE:
<221> NAME/KEY: misc_feature
<222> LOCATION: (131)..(131)
<223> OTHER INFORMATION: n is a, c, g, t or u
<220> FEATURE:
<221> NAME/KEY: misc_feature
<222> LOCATION: (191)..(191)
<223> OTHER INFORMATION: n is a, c, g, t or u
<220> FEATURE:
<221> NAME/KEY: misc_feature
<222> LOCATION: (205)..(205)
<223> OTHER INFORMATION: n is a, c, g, t or u

<400> SEQUENCE: 306
ggaaccctcc tcttggcaag ggctttccga agttaacctg aaaaactggt tcaggccatg      60
acagcaaagg gttggatagc ctcattatcc ctcctcccct cagaactctg gaacagccag     120
cgttaacatc nacacaggcc ttcagtctga tgagaaacat ttaccatcta ttgtctcgga     180
agcctgctac ntggaggctt catcntgatg ataaagcctt ggtctccaca accccgtata     240
acccagacat tcctttctat tgataactct tgcaagcgat tgccaaccag aagatgttta     300
aatccaccta taacctggaa gcccccagtt ccagctgccc acctttctgg actaaaccaa     360
tgtatatctt caatatattt gattgatgtc tcatgtctcc ctaaaatggg taccatcaag     420
ctgtgcactg acca                                                       434

<210> SEQ ID NO 307
<211> LENGTH: 157
<212> TYPE: DNA
<213> ORGANISM: Homo sapiens

<400> SEQUENCE: 307
cctccgcaca ctggatgaga atccatcttc cattcgagct gggaatagac tttgtgaaag      60
atattatgta atggagtctc gggaaccctg agacctctcc agcgaagctg aagtgaatta     120
attaagtgct ttaaacggtc ttggtgctgt gttacgg                              157

<210> SEQ ID NO 308
<211> LENGTH: 367
<212> TYPE: DNA
<213> ORGANISM: Homo sapiens
<220> FEATURE:
```

```
<221> NAME/KEY: misc_feature
<222> LOCATION: (35)..(35)
<223> OTHER INFORMATION: n is a, c, g, t or u
<220> FEATURE:
<221> NAME/KEY: misc_feature
<222> LOCATION: (38)..(40)
<223> OTHER INFORMATION: n is a, c, g, t or u
<220> FEATURE:
<221> NAME/KEY: misc_feature
<222> LOCATION: (43)..(47)
<223> OTHER INFORMATION: n is a, c, g, t or u
<220> FEATURE:
<221> NAME/KEY: misc_feature
<222> LOCATION: (52)..(53)
<223> OTHER INFORMATION: n is a, c, g, t or u
<220> FEATURE:
<221> NAME/KEY: misc_feature
<222> LOCATION: (58)..(58)
<223> OTHER INFORMATION: n is a, c, g, t or u
<220> FEATURE:
<221> NAME/KEY: misc_feature
<222> LOCATION: (60)..(60)
<223> OTHER INFORMATION: n is a, c, g, t or u
<220> FEATURE:
<221> NAME/KEY: misc_feature
<222> LOCATION: (62)..(64)
<223> OTHER INFORMATION: n is a, c, g, t or u
<220> FEATURE:
<221> NAME/KEY: misc_feature
<222> LOCATION: (67)..(68)
<223> OTHER INFORMATION: n is a, c, g, t or u
<220> FEATURE:
<221> NAME/KEY: misc_feature
<222> LOCATION: (71)..(71)
<223> OTHER INFORMATION: n is a, c, g, t or u
<220> FEATURE:
<221> NAME/KEY: misc_feature
<222> LOCATION: (73)..(73)
<223> OTHER INFORMATION: n is a, c, g, t or u
<220> FEATURE:
<221> NAME/KEY: misc_feature
<222> LOCATION: (75)..(75)
<223> OTHER INFORMATION: n is a, c, g, t or u
<220> FEATURE:
<221> NAME/KEY: misc_feature
<222> LOCATION: (79)..(79)
<223> OTHER INFORMATION: n is a, c, g, t or u
<220> FEATURE:
<221> NAME/KEY: misc_feature
<222> LOCATION: (82)..(82)
<223> OTHER INFORMATION: n is a, c, g, t or u
<220> FEATURE:
<221> NAME/KEY: misc_feature
<222> LOCATION: (84)..(86)
<223> OTHER INFORMATION: n is a, c, g, t or u
<220> FEATURE:
<221> NAME/KEY: misc_feature
<222> LOCATION: (89)..(91)
<223> OTHER INFORMATION: n is a, c, g, t or u
<220> FEATURE:
<221> NAME/KEY: misc_feature
<222> LOCATION: (93)..(93)
<223> OTHER INFORMATION: n is a, c, g, t or u
<220> FEATURE:
<221> NAME/KEY: misc_feature
<222> LOCATION: (289)..(289)
<223> OTHER INFORMATION: n is a, c, g, t or u

<400> SEQUENCE: 308
aggtgatgca ctatgcccag tacgtcctcc tggcnctnnn ctnnnnngcg tnncctgntn      60
cnnntcnntg ncntntgcna antnnngann nanaaccgtg taaaaccatt tttatgtggc     120
ttcaacgtca actataaatt agcttggtta tcttctagga gaaatgctat ttattttgga     180
gtagtagtaa aagggctca aaggataagg aggccattca ggcctattct gaatccctga     240
tgacatcagc tcccaagggc tctgtgctgc aggaagcaaa actgtaggng ggtaccaggt     300
```

-continued

```
aatgccgtgc gcctccccgc cccctcccat atcaagtaga atgctggcgg cttacagact    360
gaagatg                                                              367
```

<210> SEQ ID NO 309
<211> LENGTH: 484
<212> TYPE: DNA
<213> ORGANISM: Homo sapiens

<400> SEQUENCE: 309

```
accccaccac gtaccagatg gatgtgaacc ccgagggcaa atacagcttt ggtgccacct     60
gcgtgaagaa gtgtccccgt aattatgtgg tgacagatca cggctcgtgc gtccgagcct    120
gtggggccga cagctatgag atggaggaag acggcgtccg caagtgtaag aagtgcgaag    180
ggccttgccg caaagtgtgt aacggaatag gtattggtga atttaaagac tcactctcca    240
taaatgctac gaatattaaa cacttcaaaa actgcacctc catcagtggc gatctccaca    300
tcctgccggt ggcatttagg ggtgactcct tcacacatac tcccccctg gatccacagg    360 aactggatat tctgaaaacc gtaaaggaaa tcacaggttt gagctgaatt atcacatgaa    420
tataaatggg aaatcagtgt tttagagaga gaacttttcg acatatttcc tgttcccttg    480
gaat                                                                 484
```

<210> SEQ ID NO 310
<211> LENGTH: 526
<212> TYPE: DNA
<213> ORGANISM: Homo sapiens

<400> SEQUENCE: 310

```
ccatggggcc atctgggcca ttcagagact ggagtgagat ttgggtgtgg aggggggaggc    60 gccaaggtgg aggagcttcc cactccagga ctgttgatga aagggacaga ttgaggagga   120
agtgggctct gaggctgcag ggctggaagt ccttgcccac ttcccactct cctgccccaa   180
tctatctagt acttcccagg caaataggcc cctttgaggc tcctgagtgc cctcagatgg   240
tcaaaaccca gttttccctc tgggagccta accaggctg catcggaggc caggacccgg   300
atcattcact gtgataccct gccctccaga gggtgcgctc agagacacgg gcaagcatgc   360
ctcttccctt ccctggagag aaagtgtgtg atttctctcc cacctccttc ccccaccag   420 acctttgctg ggcctaaagg tcttggccat ggggacgccc tcagtctagg gatctggcca   480
cagactccct cctgtgaacc aacacagaca cccaagcaga gcaatc                  526
```

<210> SEQ ID NO 311
<211> LENGTH: 319
<212> TYPE: DNA
<213> ORGANISM: Homo sapiens
<220> FEATURE:
<221> NAME/KEY: misc_feature
<222> LOCATION: (264)..(264)
<223> OTHER INFORMATION: n is a, c, g, t or u

<400> SEQUENCE: 311

```
taaattgcct ggatctctgg gacacccccg tccccaggag aaggatgttt gggaagagat     60
ggatgccaac aaaaacaaga taagcttgg aatttgtaag gctgctactg aagaggagaa    120
cagccatggc caggcaaatg gtcttctcaa tgctccaagc cttgggtcac caattcgtgt   180
ccgctcagag attactcagc cagacagaga tattccactg gtgcgaaagt tacgttccat   240
tcacagcttt gagctggaaa aacntctgac cctggagcca aagccagaca ctgacaagtt    300
```
ccttgagacc tggtataaa                                              319

<210> SEQ ID NO 312
<211> LENGTH: 234
<212> TYPE: DNA
<213> ORGANISM: Homo sapiens
<220> FEATURE:
<221> NAME/KEY: misc_feature
<222> LOCATION: (85)..(87)
<223> OTHER INFORMATION: n is a, c, g, t or u
<220> FEATURE:
<221> NAME/KEY: misc_feature
<222> LOCATION: (89)..(90)
<223> OTHER INFORMATION: n is a, c, g, t or u
<220> FEATURE:
<221> NAME/KEY: misc_feature
<222> LOCATION: (92)..(92)
<223> OTHER INFORMATION: n is a, c, g, t or u
<220> FEATURE:
<221> NAME/KEY: misc_feature
<222> LOCATION: (94)..(95)
<223> OTHER INFORMATION: n is a, c, g, t or u
<220> FEATURE:
<221> NAME/KEY: misc_feature
<222> LOCATION: (97)..(97)
<223> OTHER INFORMATION: n is a, c, g, t or u
<220> FEATURE:
<221> NAME/KEY: misc_feature
<222> LOCATION: (186)..(186)
<223> OTHER INFORMATION: n is a, c, g, t or u

<400> SEQUENCE: 312
gcgcttgcgc agtagctgaa cgcgggcgtt tctttcctcc ctttttttcg aattggtttt     60
gggggtagat tcgagttaca aaatnnncnn cngnngngtg ttcggcgcgg ttccccccagc   120 tgtctctggc tgaaccggcg ctctcgcctc cctgccgaac acagcgtgag gagccccccc   180
aggganatgg tgtttgagtc tctgggcttg ccgagcacta agtcctctga gttc         234

<210> SEQ ID NO 313
<211> LENGTH: 125
<212> TYPE: DNA
<213> ORGANISM: Homo sapiens

<400> SEQUENCE: 313
gtactgcaaa aatcaccctc ggcaagacga atgtctgacg tgccggaagg agtcatacgg     60
gtccatgctc cacttctctc caaggtgtcc atggccattc aactcaacaa tcaaaccaaa   120
gccaa                                                                125

<210> SEQ ID NO 314
<211> LENGTH: 446
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n is a, c, g, t or u
<220> FEATURE:
<221> NAME/KEY: misc_feature
<222> LOCATION: (93)..(93)
<223> OTHER INFORMATION: n is a, c, g, t or u
<220> FEATURE:
<221> NAME/KEY: misc_feature
<222> LOCATION: (130)..(130)
<223> OTHER INFORMATION: n is a, c, g, t or u
<220> FEATURE:
<221> NAME/KEY: misc_feature
<222> LOCATION: (205)..(205)
<223> OTHER INFORMATION: n is a, c, g, t or u
<220> FEATURE:
<221> NAME/KEY: misc_feature

```
<222> LOCATION: (211)..(211)
<223> OTHER INFORMATION: n is a, c, g, t or u

<400> SEQUENCE: 314
aagtcattcg tttaagcgtg gattattttg ccgaatgaat aatgatgatg gcngctttca    60
tctcttatga agttttcctg gccaagagcc agnagttgga agtttggatc attcttttt    120 cttttttaan catttcttct cttctttctc tttttttatca ctaaatgaat gacatgtgga   180
gaaactattc agcttttaaa gtatnctcca nttacttgtc tcaactacca ctatttattg   240
tgtttatcaa aatcataaaa agctcatttt tggcatttac cttcgtggtt gagactgctg   300
tctgtatgtc tgggaatgga agtcctcttc agggattcag caagggctgt acttttgctt   360
aatactagtg gttccttatt ctaagtgatg acatcatcca cctttcctag aaatgggtct   420
ttgtgcctag tatgatatct ttccaa                                         446

<210> SEQ ID NO 315
<211> LENGTH: 473
<212> TYPE: DNA
<213> ORGANISM: Homo sapiens
<220> FEATURE:
<221> NAME/KEY: misc_feature
<222> LOCATION: (207)..(207)
<223> OTHER INFORMATION: n is a, c, g, t or u
<220> FEATURE:
<221> NAME/KEY: misc_feature
<222> LOCATION: (264)..(264)
<223> OTHER INFORMATION: n is a, c, g, t or u
<220> FEATURE:
<221> NAME/KEY: misc_feature
<222> LOCATION: (375)..(375)
<223> OTHER INFORMATION: n is a, c, g, t or u
<220> FEATURE:
<221> NAME/KEY: misc_feature
<222> LOCATION: (395)..(395)
<223> OTHER INFORMATION: n is a, c, g, t or u
<220> FEATURE:
<221> NAME/KEY: misc_feature
<222> LOCATION: (405)..(405)
<223> OTHER INFORMATION: n is a, c, g, t or u

<400> SEQUENCE: 315
tgtttcaggc ccatccacag ttgaagcagt gtgtgcgtca ggcaattgaa cgggctgtcc    60
aggagctggt ccatcctgtg gtggatcgat caattaagat tgccatgact acttgtgagc   120
aaatagtcag gaaggatttt gccctggatt cggaggaatc tcgaatgcga atagcagctc   180
atcacatgat gcgtaacttg acagctngga atggctatga ttacatgcag ggaacctttg   240
ctcatgagca tatctaccaa cttnaaaaaa cagttttgcc tcagcccttc gtgtaagttg   300
gctatttcct tggtataggt acaaaacgta ttactgcttg tctgtaataa ttttttttctt   360 tgtctatata tggcnctggg cgttaccact tattnttaat aatcnccata tttgtttgat   420
gtcttccatc attttagatt gtaattctgt gaggcaaagc atcatgtctg tgt           473

<210> SEQ ID NO 316
<211> LENGTH: 576
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, t or u
<220> FEATURE:
<221> NAME/KEY: misc_feature
<222> LOCATION: (351)..(352)
<223> OTHER INFORMATION: n is a, c, g, t or u
<220> FEATURE:
```

```
<221> NAME/KEY: misc_feature
<222> LOCATION: (395)..(395)
<223> OTHER INFORMATION: n is a, c, g, t or u
<220> FEATURE:
<221> NAME/KEY: misc_feature
<222> LOCATION: (496)..(496)
<223> OTHER INFORMATION: n is a, c, g, t or u

<400> SEQUENCE: 316
aggacaccag gctggtggcc acagtgctgc tgtccgtggt cgtgctgctc cacgccctcc      60
tgnccatggg ctgtaagttg tacttcttcc agtcgctgcc tccggagaac gtggctcctc     120 cacccccaaat cacatctctg ccctcaaaca tcgcgctgtc ccctaccttg ccgcagtccc    180 tggcccccctc ctaggaaggc ccgggtccca caggcaacac ctaagtggac caacccctct   240
gcctgtcctg ccccccagac gatgactgaa ggctcctttg acaccttgag atgattctgc    300
tactttccag actttttctta caaagcaaac acttttattt tctatgcaaa nntgattcag   360
agaatttata taaaggcggg cgaggggcag ccgancaggg agctttggga cagggctggg   420
gcccccatat cccccccggg ccacctgctt tccctcctat ggctcccctg aacaggagg     480 gagagccaag ggggcngccc agcctggaca gcgcccgctc ctgcctgggt gcacacacgg    540
cgggcctgag ctccagcatc tgagtttggg ggtatg                             576

<210> SEQ ID NO 317
<211> LENGTH: 265
<212> TYPE: DNA
<213> ORGANISM: Homo sapiens

<400> SEQUENCE: 317
ccaggagcag ctgcgtgacg tcatgttcta cctggagaca cagcagaaga tcaaccatct      60
gcctgccgag accggcaga aatccaggag ggacagatca acatcgccat ggcctcggcc     120
tcgagccctg cctcttcggg gggcagtggg aagttgccct ccaggaaggg ccgcagcaag    180 agggggcaagt gaccttcaga gcaacagaca tccctgagac tgttctccct gacactgtga   240
gagtgtgctg ggaccttcag ctaaa                                          265

<210> SEQ ID NO 318
<211> LENGTH: 515
<212> TYPE: DNA
<213> ORGANISM: Homo sapiens
<220> FEATURE:
<221> NAME/KEY: misc_feature
<222> LOCATION: (108)..(108)
<223> OTHER INFORMATION: n is a, c, g, t or u
<220> FEATURE:
<221> NAME/KEY: misc_feature
<222> LOCATION: (115)..(115)
<223> OTHER INFORMATION: n is a, c, g, t or u
<220> FEATURE:
<221> NAME/KEY: misc_feature
<222> LOCATION: (203)..(203)
<223> OTHER INFORMATION: n is a, c, g, t or u
<220> FEATURE:
<221> NAME/KEY: misc_feature
<222> LOCATION: (241)..(241)
<223> OTHER INFORMATION: n is a, c, g, t or u

<400> SEQUENCE: 318
atacgtgggt agtgttgcat ttcaaatgag gctcttctgg ttgaaatgat atatttataa      60
gaccagaata tcacaaatgg gtgatgtata atgtctcttt agtttttngg tattnggcct    120
cttttaaagc ctgtcggatg tatgggagaa acaatgaac gtgctttgat ttcctatcag     180
tcactcttaa gaacatacat atngtttaag taactcggtc tttttttatct gattcttgag   240
```

```
ncactatggg tagcaagtaa ccacttacaa atttaaatgt aatatacact cctttctgt      300 gtgtcaagtc cttatttta ggtgcatatt gacatttaaa tgttaattat tgtttggcat      360
ataatatcaa aaatctatta tttattttat gctgttacag ttaaaagatg tgatttatga    420
catactgaat caacttgcct tccaatttag tgtgtaatat ggtaagcatt tatacttta     480 gatatgtctt attttattt ggatgcctgt ctacc                                 515
```

```
<210> SEQ ID NO 319
<211> LENGTH: 541
<212> TYPE: DNA
<213> ORGANISM: Homo sapiens
<220> FEATURE:
<221> NAME/KEY: misc_feature
<222> LOCATION: (136)..(136)
<223> OTHER INFORMATION: n is a, c, g, t or u
<220> FEATURE:
<221> NAME/KEY: misc_feature
<222> LOCATION: (141)..(141)
<223> OTHER INFORMATION: n is a, c, g, t or u
<220> FEATURE:
<221> NAME/KEY: misc_feature
<222> LOCATION: (147)..(147)
<223> OTHER INFORMATION: n is a, c, g, t or u
<220> FEATURE:
<221> NAME/KEY: misc_feature
<222> LOCATION: (159)..(159)
<223> OTHER INFORMATION: n is a, c, g, t or u
<220> FEATURE:
<221> NAME/KEY: misc_feature
<222> LOCATION: (161)..(161)
<223> OTHER INFORMATION: n is a, c, g, t or u
<220> FEATURE:
<221> NAME/KEY: misc_feature
<222> LOCATION: (167)..(167)
<223> OTHER INFORMATION: n is a, c, g, t or u
<220> FEATURE:
<221> NAME/KEY: misc_feature
<222> LOCATION: (172)..(172)
<223> OTHER INFORMATION: n is a, c, g, t or u
<220> FEATURE:
<221> NAME/KEY: misc_feature
<222> LOCATION: (181)..(181)
<223> OTHER INFORMATION: n is a, c, g, t or u
<220> FEATURE:
<221> NAME/KEY: misc_feature
<222> LOCATION: (188)..(188)
<223> OTHER INFORMATION: n is a, c, g, t or u
<220> FEATURE:
<221> NAME/KEY: misc_feature
<222> LOCATION: (191)..(191)
<223> OTHER INFORMATION: n is a, c, g, t or u
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (220)..(220)
<223> OTHER INFORMATION: n is a, c, g, t or u
<220> FEATURE:
<221> NAME/KEY: misc_feature
<222> LOCATION: (260)..(260)
<223> OTHER INFORMATION: n is a, c, g, t or u
<220> FEATURE:
<221> NAME/KEY: misc_feature
<222> LOCATION: (509)..(509)
<223> OTHER INFORMATION: n is a, c, g, t or u

<400> SEQUENCE: 319
gagttaatgc agcactcgtc attcagaaat attggcgaag agtcttagca cagagaaaat    60
tattaatgtt aaaaaaggaa aagctggaaa aagttcaaaa taaagcagca tcacttattc   120
```

```
agggatattg gagaanatat nccactngac aaagatttnc ngaaatngaa anattattca      180
ntcatccngc naatntagga taagaatgat aattgctgtn acatcttata aacgatatct      240
ttgggctaca gttacaattn cagaggcatt ggcgtgctta tttaagaaga aaacaagatc      300
aacaaagata tgaaatgcta aaatcatcaa ctcttataat ccaatctatg ttcagaaaat      360
ggaagcaacg taaatgcaa tcacaagtaa aagctacagt aatattgcaa agagctttta      420
gagaatggca tttaagaaaa caagctaaag aagaaaattc tgctattatc atacaatcat      480
ggtatagaat gcataaagaa ttacggaant atatttatat tagatcttgt gttgttatca      540
t                                                                     541

<210> SEQ ID NO 320
<211> LENGTH: 495
<212> TYPE: DNA
<213> ORGANISM: Homo sapiens
<220> FEATURE:
<221> NAME/KEY: misc_feature
<222> LOCATION: (144)..(145)
<223> OTHER INFORMATION: n is a, c, g, t or u

<400> SEQUENCE: 320
cttcggattt ttattgactc aaaatagtgc cattccccctt aatgaaatag attttgagtc      60 ttttttttcat tgtaaccccc aaatgagaat catctacctg attcttgtac caaaaaaaaa    120 ttttttttcag tcttttttttt tttnnagaga gggtctcttg tcaacgcaag actgggagtg    180
gcagtggcac gatcttagct cactacaact tctggcctcc caggctcaag caattctcct    240
gcctcagcct cctgagtagc tgggattac aggcatgcac caccacgccc agctaatttt     300
ggtattttta gtagagacag ggtttcacca ttgtttggcc aggctggtcc cgaactcctg    360
acctcaggtg atccacccac ctcggcctcc caaagtgctg ggattatagg tgcgagccat    420
tgcgcccagc ctcagttatt ttatttaaca gtgtaagtac ttagaaagta agaaaatggc    480
gtgattagtt ttttg                                                      495

<210> SEQ ID NO 321
<211> LENGTH: 429
<212> TYPE: DNA
<213> ORGANISM: Homo sapiens

<400> SEQUENCE: 321
ggctgaggag gctggtctga acatcactca catttgcctc cctccagata gcagtgaagc      60
cgagattata gatgaaatct aaagatcaa tgaagatacc agagtacatg gccttgccct     120
tcagatctct gagaacttgt ttagcaacaa agtcctcaat gccttgaaac cagaaaaaga    180
tgtggatgga gtaacagaca taaacctggg gaagctggtg cgaggggatg cccatgaatg    240
ttttgtttca cctgttgcca aagctgtaat tgaacttctt gaaaaatcag taggtgtcaa    300
cctagatgga aagaagattt tggtagtggg ggcccatggg tctttggaag ctgctctaca    360
atgcctgttc cagagaaaag ggtccatgac aatgagcatc cagtggaaaa cacgccagct    420
tcaaagcaa                                                             429

<210> SEQ ID NO 322
<211> LENGTH: 467
<212> TYPE: DNA
<213> ORGANISM: Homo sapiens

<400> SEQUENCE: 322
tctgagggtg ccttgatgct ggctcatcac acattgagta tcttgggcat tatcatggcc      60
```

```
cttgtgcttg gggagtctgg cacagaggtc aatgcagtcc tctttggaag tgagcttacc    120 aacccttgc tacagatgcg ctggtttctc cgggaaacag ggcactatca cagtttcact    180
ggagatgtag tggacttcct ctttgtggct ctgttcacag gagtgaggat tggtgtggga    240
gcttgcctcc ttttctgtga aatggtctcc cccacgccta agtggtttgt gaaggctggg    300
ggagtagcga tgtatgctgt gtcttggtgt tcatgtttta gcatctggcg ctttgcatgg    360
aggaagagca tcaagaagta ccatgcttgg agaagcaggc ggagtgagga acggcagctg    420
aaacacaacg gacatctcaa aatacactag ccaaggcttg ctccaga                  467
```

<210> SEQ ID NO 323
<211> LENGTH: 504
<212> TYPE: DNA
<213> ORGANISM: Homo sapiens

<400> SEQUENCE: 323

```
ttggcacttc agaagtctcc ccaatcttga caaagccctg gagaaagggc cgggcctccc    60
gttgataaga atatcactgc agataaatgg aggttttcaaa ttgaaagaaa ggaggagggc   120
ctcctgttga taagattatt gtcactgcag gtaaatggag gcttcaaata gaaatacatt   180
tcagttacag aaaaaaaaat tatctttgtt acacatttga gtttgcaggc ctaaggttac   240
tcccgctaca ctatcatctg taaccataac gcactcaaca ttttaagcta actataagga   300 tgttgcttc actcaaagat cctgaggttt tattcactaa catttttatt tggtgactat    360
agttgacaag aacaaagctg tggggaacca acaaacactg caatgcctgg cattgtcacc   420
tcactagatt gtgagttcct ctgggacagg gtccgtacat tttcttagaa tccctcactt   480
agccattagc ctgcacagtg cttg                                           504
```

<210> SEQ ID NO 324
<211> LENGTH: 163
<212> TYPE: DNA
<213> ORGANISM: Homo sapiens

<400> SEQUENCE: 324

```
catggaggag tgcatttcct tggctattcc agaagtccta cctcccttct gagattttat    60
aatggtattt cttatggtta tcccaaatat acttggcaag tcgtcttata aaccaccaat   120
aatagcctct taaaaattca aaattactc ctcttggcta aca                      163
```

<210> SEQ ID NO 325
<211> LENGTH: 441
<212> TYPE: DNA
<213> ORGANISM: Homo sapiens

<400> SEQUENCE: 325

```
cctccgcgga aggcgtggca gggaggcagt cgccctgcgg tgcaagctgc tgctccagag    60
cataccgtgg cccaggtggt atccccaagg cctcgtgccg tggctggggt cctgggaggt   120
ggtcgccctg cagtgcaagc tgctgctcca gagcgtaccg tggcccagac tgatcctcga   180
ggcctcctgc cgtggctggg gtcatggtcg gctgcgcatg tccagaagca tttccttcct   240
gcgaccatcc cggcgcccct aggggagaa gccaggacag cagcttccgc tgtctccaca    300
gcagacacgg gacggattcc acagacggga gcctcattcg taccatgcca aacgcattca   360
ctcggggcag tattaaccgt tctagaaagc cactgttta tagcaaaaca ggaaaggaaa   420
agctaccagt tttttattca g                                              441
```

<210> SEQ ID NO 326
<211> LENGTH: 457
<212> TYPE: DNA
<213> ORGANISM: Homo sapiens

<400> SEQUENCE: 326

```
tttcccctag ttgacctgtc tataagagaa ttatatattt ctaactatat aaccctagga      60
atttagacaa cctgaaattt attcacatat atcaaagtga gaaaatgcct caattcacat     120
agatttcttc tctttagtat aattgaccta ctttggtagt ggaatagtga atacttacta    180
taatttgact tgaatatgta gctcatcctt tacaccaact cctaattta aataatttct     240 actctgtctt aaatgagaag tacttggttt ttttttttctt aaatatgtat atgacattta    300
aatgtaactt attattttt ttgagaccga gtcttgctct gttacccagg ctggagtgca     360
gtgggtgatc ttggctcact gcaagctctg ccctccccgg gttcgcacca ttctcctgcc    420
tcagcctccc aattagcttg gcctacagtc atctgcc                              457
```

<210> SEQ ID NO 327
<211> LENGTH: 438
<212> TYPE: DNA
<213> ORGANISM: Homo sapiens
<220> FEATURE:
<221> NAME/KEY: misc_feature
<222> LOCATION: (65)..(65)
<223> OTHER INFORMATION: n is a, c, g, t or u
<220> FEATURE:
<221> NAME/KEY: misc_feature
<222> LOCATION: (96)..(96)
<223> OTHER INFORMATION: n is a, c, g, t or u
<220> FEATURE:
<221> NAME/KEY: misc_feature
<222> LOCATION: (112)..(112)
<223> OTHER INFORMATION: n is a, c, g, t or u
<220> FEATURE:
<221> NAME/KEY: misc_feature
<222> LOCATION: (218)..(218)
<223> OTHER INFORMATION: n is a, c, g, t or u
<220> FEATURE:
<221> NAME/KEY: misc_feature
<222> LOCATION: (229)..(229)
<223> OTHER INFORMATION: n is a, c, g, t or u

<400> SEQUENCE: 327

```
ttgtccttta tgtatcttct ttccatagtg cttactggag ccttccaaaa taatgtctcc      60
tcaangtgac agcccctcag gaatttgaag gcaatngtca caccctcacc cncttcctg     120 agttttttct ggtttattaa cgtcagtctt tacagtcagt gctcattgac ggtggttttc    180
tctggttgtt tcctgaacac gtagtgctct taaagcantg ccctgaggng aatacaattc    240
tccaggggca ttctgattgg caggtgaagc acagtgccat gttcccagca ctgatttggg    300
aagtggcttg tcacatccca cagtgaactc agtcaactgg aatgcctaac tctctttcat    360
aagacctcct gctacattat gtttctccca gactgtactc aggtccaaga acagaattta    420
ctagtctatc cttctcaa                                                   438
```

<210> SEQ ID NO 328
<211> LENGTH: 535
<212> TYPE: DNA
<213> ORGANISM: Homo sapiens
<220> FEATURE:
<221> NAME/KEY: misc_feature
<222> LOCATION: (40)..(40)
<223> OTHER INFORMATION: n is a, c, g, t or u

<400> SEQUENCE: 328

```
cccttcttgc tgccacagga tgaataaagt gttgagattn gtctatggag aaagctgtgt    60
gtctgttttt atctcccctc tcaggaccag tcagccactg gtcaatcagg ctgatcatgg   120
aacattagga attctccaat taagggagaa aaagtccagg gacttagtta tatcttcaga   180
ccagtgcagc tgggacacac aaagttctcc tgtctcacca tctgatatgg tttggatgct   240
cgtcccctcc aaatctcatg ttgaaatgta attcccagtg ttggaagtgg agcctggtgg   300
gaagtatttg gatcatgaga gaggatcctt catgaatggc tcagcaccat ctccttggtg   360
atgagtgagt tctcactcaa ttcacataga tatggttgtt taaaagagtc tgagacctct   420
cccctctttc tcgccatgtg atatgcctgc tccccctcca ccttccgcct ttactgtaag   480
cttcctgagg ccctcaccag aagctgagca atgttggtg ccatgccagt acagc        535
```

<210> SEQ ID NO 329
<211> LENGTH: 432
<212> TYPE: DNA
<213> ORGANISM: Homo sapiens

<400> SEQUENCE: 329

```
gccacagact gaactcgcag ggagtgcagc aggaaggaac aaagacaggc aaacggcaac    60
gtagcctggg ctcactgtgc tggggcatgg cgggatcctc cacagagagg aggggaccaa   120
ttctggacag acagatgttg ggaggataca gaggagatgc cacttctcac tcaccactac   180
cagccagcct ccagaaggcc ccagagagac cctgcaagac cacggaggga gccgacactt   240
gaatgtagta ataggcaggg ggccctgcca ccccatccag ccagaccoca gctgaaccat   300 gcgtcagggg cctagaggtg gagttcttag ctatccttgg ctttctgtgc cagcctggct   360
ctgcccctcc cccatgggct gtgtcctaag gcccatttga aagctgagg ctagttccaa   420 aaacctctcc tg                                                      432
```

<210> SEQ ID NO 330
<211> LENGTH: 234
<212> TYPE: DNA
<213> ORGANISM: Homo sapiens

<400> SEQUENCE: 330

```
agcaaatcta gctttcagta ttcctaattt ttacctaagc tcattgctcc aggctttgat    60
tacctaaaat aagcttggat aaaattgaac caacttcaag aatgcagcac ttcttaatct   120
ttagctcttt cttgggagaa gctagacttt attcattata ttgctatgac aacttcactc   180
tttcataata tataggataa attgtttaca tgattggacc ctcagattct gtta         234
```

<210> SEQ ID NO 331
<211> LENGTH: 317
<212> TYPE: DNA
<213> ORGANISM: Homo sapiens

<400> SEQUENCE: 331

```
acttaggagt ggtgcttttt ctcagaaaac aggccacggt gtttcataca gaatgtcttc    60
atatcatctg aaatggtatg gctgaagttc atttgtttac agggtcggga atgtcttcag   120
ttcttgagag tcaacagtaa tgattggttg taagccaagg acatttaa gctagtgaag    180 agttttttct ggaattgatt tttcccaaaa gaatatatta attgaggtta agaagtcagt   240
gggaaacaca cagaaatttg ttttaaaatc tttcaggagc tttactgaaa gacttggtta   300
tcaagtcttt tggggag                                                 317
```

<210> SEQ ID NO 332
<211> LENGTH: 415
<212> TYPE: DNA
<213> ORGANISM: Homo sapiens

<400> SEQUENCE: 332

| | | | | | | |
|---|---|---|---|---|---|---|
| gacttacttt | aacaaccagc | caatccctac | ctaagcctag | tagccatggt | ttggctaaga | 60 |
| ccgcagcgac | tgtatttagt | aaatcctttg | aacaagtcag | tggtgtcaca | gtcccacata | 120 |
| acccgtcatc | tgctgttggt | tgtggggctg | ggacagatgc | caataggttt | tccgcttgta | 180 |
| gtctccaaga | agaaaagctt | atttacgttt | cagaaagaac | tgaacttcca | atgaagcatc | 240 |
| aatcaggtca | gcagagacct | cctagtatta | gcattactct | gtccacagat | taattagtaa | 300 |
| catattttc | tcccataacc | tagtgaacct | ggaaatacaa | ctttgcttct | ttatgaaagt | 360 |
| accctgggtc | tttcatccgt | attcctgaca | ggagccctga | tgtcttaaat | tctga | 415 |

<210> SEQ ID NO 333
<211> LENGTH: 489
<212> TYPE: DNA
<213> ORGANISM: Homo sapiens

<400> SEQUENCE: 333

| | | | | | | |
|---|---|---|---|---|---|---|
| gacgggtcca | ttaacaaagc | gggctttgcc | gtcaactttt | tcaaagaggt | ggacgagtgc | 60 |
| tctcggccca | accgcggggg | ctgtgagcag | cggtgcctca | cacccctggg | cagctacaag | 120 |
| tgcagctgtg | accccgggta | cgagctggcc | ccagacaagc | gccgctgtga | ggctgcttgt | 180 |
| ggcggattcc | tcaccaagct | caacggctcc | atcaccagcc | cgggctggcc | caaggagtac | 240 |
| ccccccaaca | agaactgcat | ctggcagctg | gtggccccca | cccagtaccg | catctccctg | 300 |
| cagtttgact | tctttgagac | agagggcaat | gatgtgtgca | agtacgactt | cgtggaggtg | 360 |
| cgcagtggac | tcacagctga | ctccaagctg | catggcaagt | tctgtggttc | tgagaagccc | 420 |
| gaggtcatca | cctcccagta | caacaacatg | cgcgtggagt | tcaagtccga | caacaccgtg | 480 |
| tccaaaaag | | | | | | 489 |

<210> SEQ ID NO 334
<211> LENGTH: 239
<212> TYPE: DNA
<213> ORGANISM: Homo sapiens

<400> SEQUENCE: 334

| | | | | | | |
|---|---|---|---|---|---|---|
| cacagataga | acctgcacat | tgcccattaa | tgcacacttg | tgtatgccta | ttacagtctg | 60 |
| tgaagtttgg | tttagggtca | gatgctgggc | agagagctgt | gaagccatta | catattcctt | 120 |
| cccttgcaca | gtctgaatca | tcccgacact | tctcagactt | tgacttgaat | gcacactgtg | 180 |
| ctgtacaaca | aggaccttga | cttggactgc | actgtttccc | aggtttcagt | ttgcattttt | 239 |

<210> SEQ ID NO 335
<211> LENGTH: 432
<212> TYPE: DNA
<213> ORGANISM: Homo sapiens

<400> SEQUENCE: 335

| | | | | | | |
|---|---|---|---|---|---|---|
| gccctgactg | actgtattct | ctggccacat | tcaagtcccc | cattggtggg | ggcagagaag | 60 |
| taggaccagg | ccatccttgg | ctacagagct | cgaagacccc | aagacagccc | tctgctctca | 120 |
| gcggcgccac | agagagcctg | ggctcagcct | tctgcatcag | gacatggcct | cgtccactga | 180 |
| gggcacgatt | taaacatttg | acatcagaag | ctttatttgt | aaacctcaca | cagataagga | 240 |

```
ccaagggctg gcggtgtggc cagaggacag gggaagctga aggccccgtg cttgagctcg    300
gcagtcctgc tccttgcagt gaagccacca tgggtgaccg tccagcctca cccggtggcc    360
tgcacagtga gggaagggct tcagggccat ctgctcccag gcaggggac aggccaccaa    420 ggacctttgg ca                                                       432
```

<210> SEQ ID NO 336
<211> LENGTH: 380
<212> TYPE: DNA
<213> ORGANISM: Homo sapiens

<400> SEQUENCE: 336

```
aatgttgaca tatttcctct atctcataga tggtaaaagt gttgctttta aactggcaaa    60
tgcactcttc agaaatcctt ttctatctga tccacatgga gaggttaaag gttcaatttc    120
atgacctcta tgcaggcagc gctctcattg gatgtaagaa tattacctgc aaggatagaa    180
tgcagttgtg caacagagac acattcttat ttctttttt tcacaatttt gttttgtttt    240 taatgacccct tttattgaat attggactga aatataaatt ttaaaaaaca cgttggaaag    300
gatgtacaac agaaggctat gtatgtatat acagtatgtc aaaagccttt tattttata    360 cttcaaatgc tctaaattaa                                               380
```

<210> SEQ ID NO 337
<211> LENGTH: 544
<212> TYPE: DNA
<213> ORGANISM: Homo sapiens

<400> SEQUENCE: 337

```
gagtctctgc ttgataagtg cctctatacc aaccgctctc ctcatcctga catcttgata    60
cggacttctg gagaagtgcg gctgagtgac ttcttgctat ggcagacctc tcactcctgc    120
ctggtgttcc aacccgttct gtggccagag tatacatttt ggaacctctt cgaggccatc    180
ctgcagttcc agatgaacca tagcgtgctt cagaaggccc gagacatgta tgcagaggag    240
cggaagaggc agcagctgga gagggaccag gctacagtga cagagcagct gctgcgagag    300
gggctccaag ccagtgggga cgcccagctc cgaaggacac gcttgcacaa actctcggcc    360
agacgggaag agcgagtcca aggcttcctg caggccttgg aactcaagcg agctgactgg    420
ctggcccgtc tgggcactgc atcagcctga atgaggctgg ccacctgcca cttttgccctg    480 ccctctgcct ccagggctcc actccccttc cttttcttgg tgaaaggcac ctcctttcct    540
gata                                                                544
```

<210> SEQ ID NO 338
<211> LENGTH: 530
<212> TYPE: DNA
<213> ORGANISM: Homo sapiens

<400> SEQUENCE: 338

```
tcaaagaacg cgtactgcag accccaaatg accttctggc tgctggcttt gaggagcaca    60
agttcagaaa cttcttcaat gcttttaca gtgtggtgga actggtagag aaggacggct    120
cagtgtccag cctgctgaag gtgttcaacg accagagtgc ctcggaccac atcgtgcagt    180
tcctgcgcct gctcacgtcg gccttcatca ggaaccgagc agacttcttc cggcacttca    240
ttgatgagga gatggacatc aaaagacttct gcactcacga agtagagccc atggccacgg    300
agtgtgacca catccagatc acggcgttgt cgcaggccct gagcattgcc ctgcaagtgg    360
```

```
agtacgtgga cgagatggat accgccctga accaccacgt gttccctgag gccgccaccc    420
cttccgttta cctgctctat aaaacatccc actacaacat cctttatgca gccgataaac    480
attgattaat tttaggccat gcagtggaac ctgtcaccta atgggactgc               530
```

<210> SEQ ID NO 339
<211> LENGTH: 75
<212> TYPE: DNA
<213> ORGANISM: Homo sapiens

<400> SEQUENCE: 339

```
agtcatgcga ccaggtgagg gtccacgtcc ccaagcttcc actccctctg gtgtttccca    60
tttaagtata ctgtt                                                     75
```

<210> SEQ ID NO 340
<211> LENGTH: 376
<212> TYPE: DNA
<213> ORGANISM: Homo sapiens

<400> SEQUENCE: 340

```
gatgctcacg tcacttggtg taggtttcag gatcgcctct ttgaggaagg acttcaggac    60
caactggggc ctgcataaga aaacttatct cattattaga gtactcacag cttgtatctc   120
ccagctacat cctagaaccc cattgtcctt tattccacca aaccagctcc aggtgaccag   180
actctactca gaaagcaaat tcgtcatcaa agaacagaga ctggccacca caaggacatg   240
caggagaact gtcgggacca ggaagactca ttccaaaaag cccaggccgg gcacagtcgt   300
caagcctgta atcccaacac tttgggagac cgaggtgggg gtatcgattg agcctcggag   360
gtcgagatca gcctgg                                                   376
```

<210> SEQ ID NO 341
<211> LENGTH: 499
<212> TYPE: DNA
<213> ORGANISM: Homo sapiens

<400> SEQUENCE: 341

```
ccccgcctgt ggcattttct atgggctcag gttacacctt cccagctggt gtttctgtcc    60
caggaacctt tcttcagcct acagctcact ctccagcagg aaaccaggtg caagctggga   120
aacagtccca cattccttac agccagcaac ggccctctgg accagggcca atgaaccagg   180
gacctcaaca atcacagcca ccttcccagc aaccccttac atctttacca gctcagccaa   240
cagcacagtc tacaagccag ctgcaggttc aagctctaac tcagcaacaa caatccccta   300
caaaagctgt gccggctttg gggaaaagcc cgcctcacca ctctggattc cagcagtatc   360
aacaggcaga tgcctccaaa cagctgtgga atcccccctca ggttcaaggc ccattaggga   420
aaattatgcc tgtgaaacag ccctactacc ttcagaccca agaccccata aaactgtttg   480
agccgtcatt gcaacctcc                                                499
```

<210> SEQ ID NO 342
<211> LENGTH: 183
<212> TYPE: DNA
<213> ORGANISM: Homo sapiens
<220> FEATURE:
<221> NAME/KEY: misc_feature
<222> LOCATION: (75)..(75)
<223> OTHER INFORMATION: n is a, c, g, t or u

<400> SEQUENCE: 342

```
caccccgagac tgacacactg aactccactt cctcctctta aatttatttc tacttaatag    60
```

```
ccactcgtct ctttntttcc ccatctcatt gctccaagaa ttttttcttt cttactcgcc      120
aaagtcaggg ttccctctgc ccgtcccgta ttaatatttc cacttttgga actactggcc      180
ttt                                                                    183
```

<210> SEQ ID NO 343
<211> LENGTH: 558
<212> TYPE: DNA
<213> ORGANISM: Homo sapiens
<220> FEATURE:
<221> NAME/KEY: misc_feature
<222> LOCATION: (72)..(72)
<223> OTHER INFORMATION: n is a, c, g, t or u
<220> FEATURE:
<221> NAME/KEY: misc_feature
<222> LOCATION: (239)..(242)
<223> OTHER INFORMATION: n is a, c, g, t or u
<220> FEATURE:
<221> NAME/KEY: misc_feature
<222> LOCATION: (400)..(400)
<223> OTHER INFORMATION: n is a, c, g, t or u
<220> FEATURE:
<221> NAME/KEY: misc_feature
<222> LOCATION: (405)..(409)
<223> OTHER INFORMATION: n is a, c, g, t or u
<220> FEATURE:
<221> NAME/KEY: misc_feature
<222> LOCATION: (411)..(416)
<223> OTHER INFORMATION: n is a, c, g, t or u

<400> SEQUENCE: 343

```
tgggccttcc cttaaacatc agaacaatga gatttgtccc tattttacag gggttagaat       60
agactattaa gngacaactg agaaaggaca gagaagtgac agccagaggt tgagagggc       120 cataaaaaca tacaatcaga catatatctg ctaccacttt gtagcaagat ggttcctatc      180
ataactctgg gtcaaaaaga tagtaatttg gttataatg ttgaaagaaa gcagaaagnn       240
nnagatgggg tctcactgtc gttctggagt gtagtggttc aatcatctct cactgcagcc      300
ttgaacccct aggctcaaag gatcctccca cctcagcctc ctgaatagct gggactagag      360
gcatgagcca ctatgtcttg ctgattaaaa attgtttttn caaannnnna nnnnnnactt      420
tactgcctaa gctggtcttg aaatcctggc ttcaagcaat cctttcactt tggcctccca      480
aaatgctggg attacaggca tgagtcaata tgcccagtct cttttctttc ttagttactc      540
tagaaaatgg cttgttga                                                    558
```

<210> SEQ ID NO 344
<211> LENGTH: 526
<212> TYPE: DNA
<213> ORGANISM: Homo sapiens

<400> SEQUENCE: 344

```
aataatgttc tgtcacgtga aatatttaag tatatagtat atttatactc tagaacatgc       60
acatttatat atatatgtat atgtatatat atatagtaac tacttttat actccataca      120 taacttgata tagaaagctg tttatttatt cactgtaagt ttattttttc tacacagtaa      180
aaacttgtac tatgttaata acttgtccta tgtcaatttg tatatcatga aacacttctc      240
atcatattgt atgtaagtaa ttgcatttct gctcttccaa agctcctgcg tctgttttta      300
aagagcatgg aaaaatactg cctagaaaat gcaaatgaa ataagagaga gtagttttc       360 agctagtttg aaggaggacg gttaacttgt atattccacc attcacattt gatgtacatg      420
tgtagggaaa gttaaaagtg ttgattacat aatcaaagct acctgtggtg atgttgccac      480
```

```
ctgttaaaat gtacactgga tatgttgtta aacacgtgtc gataat          526
```

<210> SEQ ID NO 345
<211> LENGTH: 435
<212> TYPE: DNA
<213> ORGANISM: Homo sapiens
<220> FEATURE:
<221> NAME/KEY: misc_feature
<222> LOCATION: (334)..(334)
<223> OTHER INFORMATION: n is a, c, g, t or u

<400> SEQUENCE: 345

```
ttgtgtacac ataatctcat tttgagatat ataactattt ttgtctttca gaagtgaatc    60
aaaatatttc aaaatgctgt cttatgaaac tacaatattc tcacagatta gaaaagtttt   120
tctgtaaaag tcagatagta aatattttag gttttgcagt gtcttttgca actactcaac   180
tttcctactg tagcacaaga gtagctgtgg tactgtgcaa ataaattgct tgtgttccaa   240
taaagcttca tttacaaaaa catgccatgg gccatatttg gcctgtacac tgttgtttgc   300
caagtcctaa tatagttgct tagcaagtat tgtnagctat tgaggaaga catgaaagtt    360
cattgggttg ctaaaaagta tgtagaaatt caaaggaaaa ttaaaattta ggctaagtta   420
taatacactg tttta                                                    435
```

<210> SEQ ID NO 346
<211> LENGTH: 343
<212> TYPE: DNA
<213> ORGANISM: Homo sapiens
<220> FEATURE:
<221> NAME/KEY: misc_feature
<222> LOCATION: (95)..(95)
<223> OTHER INFORMATION: n is a, c, g, t or u
<220> FEATURE:
<221> NAME/KEY: misc_feature
<222> LOCATION: (227)..(227)
<223> OTHER INFORMATION: n is a, c, g, t or u

<400> SEQUENCE: 346

```
tctcatttac cttctctctt gagcaacgtc agtaattgat cttgcatctc agagagagag    60
aaagagcatg tgtgagagag aaactggttt ctatngccag cactcctgaa accccttact   120
gtaaggatat tttctcttac cccttgggat ccaggctctg agtctcttct ctttgggagt   180
atccatcaaa atgacttttt ttaaaaacag attttccccc aaccagnaga atctgcacaa   240
acttggcagc gttttttactt gtttaatgag tttaagacat tacatggtga agagaagca   300
ttttggactc ctgcattttt atttaccatt cccagactga cga                     343
```

<210> SEQ ID NO 347
<211> LENGTH: 534
<212> TYPE: DNA
<213> ORGANISM: Homo sapiens
<220> FEATURE:
<221> NAME/KEY: misc_feature
<222> LOCATION: (34)..(34)
<223> OTHER INFORMATION: n is a, c, g, t or u
<220> FEATURE:
<221> NAME/KEY: misc_feature
<222> LOCATION: (74)..(74)
<223> OTHER INFORMATION: n is a, c, g, t or u

<400> SEQUENCE: 347

```
gcctaacaat caaatctctt tcttttaaag cacnaccttc taggcaggga caggagctca    60
ttttccacac catnctttgt caactctcat agaaagtttt ccttgtatcg agctcaaatc   120
tgcctcctgg aaattcttct tcttcttccc tccctgttgg taccagctct gctgtcagag   180
```

```
acttcacagt ctgtgctccc tctgccctgt gacgtcttca gactatttga gaacaggaat      240
catgactcct gggacttgcc ttttctctag gtcaaatacc tctataattc catctgctgt      300
tcttcatagg gtcttctccc tatcctgccc ttttcctcca atccatcttt taactgctct      360
tgagcagtct aactgagaag tatgattcaa agcaaaataa atcttaaggt ggcatgactc      420
tgaaaaaatt gagaaaattg aactcagaga tcccgatccc aaccccttc tcctgggagt       480 gaaaccttag tttctaccag agagtgtggg aaaccacttc tggtggaagc ccct            534
```

<210> SEQ ID NO 348
<211> LENGTH: 580
<212> TYPE: DNA
<213> ORGANISM: Homo sapiens
<220> FEATURE:
<221> NAME/KEY: misc_feature
<222> LOCATION: (109)..(109)
<223> OTHER INFORMATION: n is a, c, g, t or u
<220> FEATURE:
<221> NAME/KEY: misc_feature
<222> LOCATION: (241)..(241)
<223> OTHER INFORMATION: n is a, c, g, t or u

<400> SEQUENCE: 348

```
aacattccct tgtcaaccaa gaatactcaa agctacttgt attggaaatg gcagaaggcc       60
taaatccaaa tttcttattt tttataattt accatagaag ttttgtgant aaattcttac      120
ttctgccagt ggaggtttat gcctgaaagg tcatggggtc ctgtctgtaa atagacctaa      180
agagaagtgc agtatttatt ctttgtaggc ataatgtgtt tgtcactgac aagcattcat      240
nttcatccca ctagtctttt attgcagtct tttattgtca ttttcagcct tatgttggag      300
agctttgctt tctcatcatg ttcacattgt cttaagtttt gtgagcttct gagaaagagc      360
ttggtaaagg tttaaagggg actttgttcc accagggagc attttatttg ggcgtctcac      420 cctttctaa tgaaagctgt tgtaagccac ctctgacttg gaaattctga agtatgaat       480 attttttata tcttaattgt aaaatgccag ttctccatta tttagatgaa tagtagaaca      540
ctgcacccct tgtgcagtgt ttttgttct ctactgcatt                            580
```

<210> SEQ ID NO 349
<211> LENGTH: 541
<212> TYPE: DNA
<213> ORGANISM: Homo sapiens

<400> SEQUENCE: 349

```
ccagtcttcc tggcaagggt aaacagatcc cctctcctca tccttcctct ttcctgtcaa       60
gtgcctcctt tggtgaaggt gacacatcat gtgacctctt cagtgaccac tctacggtgt      120
cgggccttga actactaccc ccagaacatc accatgaagt ggctgaagga taagcagcca      180
atggatgccg aggagttcga acctaaagac gtattgccca tggggatgg gacctaccag      240 ggctggataa ccttggctgt accccctggg gaagagcaga gatatacgtg ccaggtggag      300
cacccaggcc tggatcagcc cctcattgtg atctgggta tgtgactgat gagagccagg       360
agctgagaaa atctattggg ggttgagagg agtgcctgag gagagccctc accgtctggc      420
accctagtca ttggagtcat cagtggaatt gctgtttttg tcgtcatctt gttcattgga      480
attttgttca taatattaag gaagaggcag ggttcaagag gagccatggg gcactacgtc      540
t                                                                     541
```

<210> SEQ ID NO 350

```
<211> LENGTH: 415
<212> TYPE: DNA
<213> ORGANISM: Homo sapiens

<400> SEQUENCE: 350
gaataaatct ctgggaccgg gtctcaccat attgctctgg ctggtttcaa actcctgggc      60
tcaagcgatc ctcctgcctc agccttccaa aaccaggtgt ttaacttggg actaacatga    120
agcacttaga agactacgtg gaacatagca atgactatat atgtactaca acgtaaacag    180
cacctcctgg attgaataga acataactga catgaccagc agagacaggc taaagacact    240
gagctgaaaa ccctggactc tattgctaaa ttgaggctcc tgaatccgtt cgctctgagc    300
aactgttgct gtggtgctgc cttcacaagc actctgctga gcactcagat agaggggctg    360
tgctatccgt caacagacaa gctgcagcca gaactgctca gctgacaaac tggta         415

<210> SEQ ID NO 351
<211> LENGTH: 438
<212> TYPE: DNA
<213> ORGANISM: Homo sapiens

<400> SEQUENCE: 351
gtggggaagc ctgaacacag tcctataaac taaaggccac tgcagacttt tagcacaagg     60
agatccttac agggaacatg tgccatcagc tctttggagt gaacaaggaa ttagaccccc    120
atcatgccaa aaaactagga ttttaggtg gtctttccat cccttcagat ttaagtattc     180
aaagaaagag agacagacct acattccaag ggtcttctga gtgcaaggcc ttgtgttgtt    240
tgtttattta ggggagggcc tggtgctctt ctctgttttta tgctttacct tcttttattt    300
ctcagatctc atgttagcac tatgttctga attccctaat aatggctctt gagaactgat    360
ttacattttg ttggtttgtt tacttcttga gcacataaaa ggaccccaaa ttagagatac    420
tatcccttgg gcttctga                                                  438

<210> SEQ ID NO 352
<211> LENGTH: 224
<212> TYPE: DNA
<213> ORGANISM: Homo sapiens

<400> SEQUENCE: 352
gtccactgct ggaaatagaa gttttttcgc tgcagggcaa ttctgtaaat gtgcttccca     60
gctttaggag gtctgaggct actcttctcc aataaccttc cttcccactg gaccttctca    120
ctcacagcac tgctgccctc tggacaagcc acagtggaca aatatgtcaa gctgaagatg    180
cacaaataat ttcaagttca gttctcaggg attcaaagga catg                     224

<210> SEQ ID NO 353
<211> LENGTH: 415
<212> TYPE: DNA
<213> ORGANISM: Homo sapiens
<220> FEATURE:
<221> NAME/KEY: misc_feature
<222> LOCATION: (177)..(177)
<223> OTHER INFORMATION: n is a, c, g, t or u

<400> SEQUENCE: 353
tgtcctgggg atcttggagc ctgaattcat tggcacaaaa ggcagcagca tcctcactgt     60
atctgcagtc catttggact caataaaaac tttgaaagtc acatgtgtta tggaattcct    120
tctcagtgac acattcatct gtgctcagtt gtcccagcaa gggtcagccc tcatanccc     180 tgcagcatcc gctgctatga agcagagctg taaacgccct ccctgtgtat aggaaaagct    240
```

```
acatggagca aatcctcctg cctgaagaag tgcatctcag catcacttca gctgtcgggg      300
catttgtggg gagaaccaga ccacctctgc ggaaggcagc agaccctctt ccagccatgg      360
atggagttga attctctata aacggttcac cagcaaacca ccaatacatt ccatt          415
```

<210> SEQ ID NO 354
<211> LENGTH: 186
<212> TYPE: DNA
<213> ORGANISM: Homo sapiens

<400> SEQUENCE: 354

```
gccaggttaa tggtatcgat cctaatgggg attcggcaga gtttgatttg ttgtttgaaa      60
atgcttttga ccagtgggta gccagcacag cgtcagaaaa atgcaccttc ttccagatcc     120
tccaccatac ctgccagagg tacctcacgg acaggaagcc agagtttatt aactgccaat     180
ccaaaa                                                                186
```

<210> SEQ ID NO 355
<211> LENGTH: 457
<212> TYPE: DNA
<213> ORGANISM: Homo sapiens

<400> SEQUENCE: 355

```
ctttacccta ggtcagGGgt cagcaaacta ctgcctgtgg gccaaatttg cccaccacct      60
gtatctgtaa ataaggtttc attggaacac agctgtggcc atatgtttgt atattgtgtg     120
tggctgcttt tgcattagga tgacagaggt gaatagttgc aacagagact ggctggtctg     180
caaagcctaa aatatgtcct gtgtggccct ttacagaaaa agttttctaa cccctgctct     240
aggttacgga gaaaaaaaaa tggaataatg ttctctgcta cttttaacct gattttcttt     300
gtacctaaat aggcagctag aatgctgcct atattttaat aaggatttgg atctcacaag     360
acaccttagg cctacacaag ttgttcagat tctttgcccc agttctaatc tagtgacaaa     420
ggcatagaat tctcctccca caggaatgta tttctat                              457
```

<210> SEQ ID NO 356
<211> LENGTH: 373
<212> TYPE: DNA
<213> ORGANISM: Homo sapiens

<400> SEQUENCE: 356

```
cagtctcctg ctcgtttaga agtaagggat aataatgtat ccatagctaa atgcccagtc      60
gttatatttt ctagatcaag atgcttgttg tgtacagttt cacagagcct tcggatttt      120 tctttaattt tgttcatgtc tttttcattc agtagcttgg ctgatgaagc atcttgttcc     180
agttccaaaa gtcgaatcat tagatccaag ctagctctat caagatccat gttcaaacga     240
tctctactca gtatatacat gagggcagct gtacagaggg acagattctg atggtgctgg     300
gaatcatcca aggttttaaa gaccattgct accatcccat gtgctctcag gtgcattcgc     360
cagtaggcca aca                                                        373
```

<210> SEQ ID NO 357
<211> LENGTH: 116
<212> TYPE: DNA
<213> ORGANISM: Homo sapiens

<400> SEQUENCE: 357

```
tttgctccta acttgctctt ggacaggaac cagggaaaat gtgtagaggg catggtggag      60
```
aggctagaga tcctgatgat tggtctcgtc tggcgctcca tggatgcagg gagagg       116

<210> SEQ ID NO 358
<211> LENGTH: 522
<212> TYPE: DNA
<213> ORGANISM: Homo sapiens
<220> FEATURE:
<221> NAME/KEY: misc_feature
<222> LOCATION: (297)..(297)
<223> OTHER INFORMATION: n is a, c, g, t or u
<220> FEATURE:
<221> NAME/KEY: misc_feature
<222> LOCATION: (418)..(418)
<223> OTHER INFORMATION: n is a, c, g, t or u
<220> FEATURE:
<221> NAME/KEY: misc_feature
<222> LOCATION: (483)..(483)
<223> OTHER INFORMATION: n is a, c, g, t or u
<220> FEATURE:
<221> NAME/KEY: misc_feature
<222> LOCATION: (486)..(486)
<223> OTHER INFORMATION: n is a, c, g, t or u
<220> FEATURE:
<221> NAME/KEY: misc_feature
<222> LOCATION: (490)..(490)
<223> OTHER INFORMATION: n is a, c, g, t or u

<400> SEQUENCE: 358
gggcatctgg aattgacaca ccattacatt ctgtttgcag dattttttt gtaaccatga    60
aattgaacat ttccaaatta taaactatgt taatacctat aaaatatata gccaggaacc   120
atttatcatc aagaaaagtg taagaaatta ttttgagat gtaatttaag attgttttat    180
gtaaaaggaa aatcttgtat ggcatcgaat agccttaatg aatttaattc tttcacaaaa   240
atgatttcaa attatcctag agtataacat ttttatcaaa gatattattt ccggagntct   300
tctttctttc tttttttttt tttttagta atttagcaaa aacattactg ttctaatgct    360
gaagtgactt tgccagtgc catgtccagg gggggaggta taagttactt gctcttanca    420
tttgggctgg attttttggt ttgggggaca cctttgggag tattcccaaa gcatgtctca   480
agnggnggcn cccgagagca tggtttaaaa gcttggaccc ct                      522

<210> SEQ ID NO 359
<211> LENGTH: 369
<212> TYPE: DNA
<213> ORGANISM: Homo sapiens
<220> FEATURE:
<221> NAME/KEY: misc_feature
<222> LOCATION: (121)..(121)
<223> OTHER INFORMATION: n is a, c, g, t or u

<400> SEQUENCE: 359
gctgggccag tgcatctaac agccctgtgc agcagcttcc cttgcctcgt gtaacatgag    60
gcccattctt cactctgttt gaagaaaata gtcagtgttc ttagtagtgg gtttctattt   120
ngttggatga cttggagatt tatctctgtt tccttttaca attgttgaaa tgttcctttt   180
aatggatggt tgaattaact tcagcatcca agtttatgaa tcgtagttaa cgtatattgc   240
tgttaatata gtttaggagt aagagtcttg tttttttattc agattgggaa atccgttcta  300
ttttgtgaat ttgggacata ataacagcag tggagtaagt atttagaagt gtgaattcac   360
cgtgaaata                                                           369

<210> SEQ ID NO 360
<211> LENGTH: 378
<212> TYPE: DNA
<213> ORGANISM: Homo sapiens

<400> SEQUENCE: 360

```
agatactcag cactagacta acataacagg tcactacacg ggtgcagaat cactttacaa    60
aagaagactc tgttttacga aggggattca ctacagggac ttagagaaca gtctcttttc   120
tgcctttaaa atgagagttc ctccatttac caaaatttga cacgcacaca ttcttcaggg   180
gcatgccaat tgcgtaaagt gaggctcgcc tgcatagcta atcctgttaa agacaacttc   240
tcaaagcaca acgtgcttgt ttcctatcgg gctccctgcg gggctttctc tcactacaag   300
tcaagcttgg gctctcaaag ccctgcgcct gttaccacgg atgcccacag ggcctgggca   360
gttgctgtgg cgacagga                                                 378
```

<210> SEQ ID NO 361
<211> LENGTH: 291
<212> TYPE: DNA
<213> ORGANISM: Homo sapiens

<400> SEQUENCE: 361

```
acagtggatc aaatttaggc ttcttgatgc aggcatggtg tagattacta cttctgtatt    60
gtcccaggag ctcagcacat tccttgccag agatgataag gagctcaatc ttgaatactt   120
gttcaagctt ttgaataaaa aaccacagtt cctcaaagaa gaagaagaat tgcgaaatca   180
ccggaaataa ccgaaaactt cccccctgttt gactttcaac attcttgaat gcaccaagat   240
agcctctttc tgtgagatta ataaatgaat aaatgcctcc atattttca a              291
```

<210> SEQ ID NO 362
<211> LENGTH: 313
<212> TYPE: DNA
<213> ORGANISM: Homo sapiens
<220> FEATURE:
<221> NAME/KEY: misc_feature
<222> LOCATION: (200)..(200)
<223> OTHER INFORMATION: n is a, c, g, t or u

<400> SEQUENCE: 362

```
aagccggatg gcaaaagagc ccagaaccta ttggaactga caaaatcaag tcacggcgcc    60
tacaaagatg aggggcagat tctggctgcc ttttaatttc gtccttcacc tgatatctgt   120
gccagagaat gtcttccagg agttctgcta cagagaagag agtaacccc atccatcatg    180
gccaaagcac ccagtcaggn tccgctctgg atccagcccg acaaatgcaa cccttgaata   240
gggtttgtgc aagcaaactg gatgacgacc gaagaaaccc tgtcgcttct gagaagacac   300
ccaatccaag aat                                                      313
```

<210> SEQ ID NO 363
<211> LENGTH: 318
<212> TYPE: DNA
<213> ORGANISM: Homo sapiens

<400> SEQUENCE: 363

```
cctggaccca actttgttac tgtgagaaag ggtcttcatt cattcaagat ggcatttgtt    60
aagcacctac tgctggagtg cagtggttca atcacggatc actgcagcct ccacctccca   120
gttcaagaaa ttctcatgtc tcagcctcct gagcagctag gattacagac aaaccttgga   180
aatcaagaaa gttctggaat gatgaagctg ttcatgccaa gaccgaaagt gctggcccag   240
tatgagtcca ttcagttcat gccgtgacaa ttttcttgga actccttttt attgttagtt   300
ctcacttgtt tccatatt                                                 318
```

<210> SEQ ID NO 364
<211> LENGTH: 531
<212> TYPE: DNA
<213> ORGANISM: Homo sapiens
<220> FEATURE:
<221> NAME/KEY: misc_feature
<222> LOCATION: (117)..(117)
<223> OTHER INFORMATION: n is a, c, g, t or u
<220> FEATURE:
<221> NAME/KEY: misc_feature
<222> LOCATION: (119)..(119)
<223> OTHER INFORMATION: n is a, c, g, t or u
<220> FEATURE:
<221> NAME/KEY: misc_feature
<222> LOCATION: (122)..(122)
<223> OTHER INFORMATION: n is a, c, g, t or u
<220> FEATURE:
<221> NAME/KEY: misc_feature
<222> LOCATION: (153)..(153)
<223> OTHER INFORMATION: n is a, c, g, t or u
<220> FEATURE:
<221> NAME/KEY: misc_feature
<222> LOCATION: (155)..(155)
<223> OTHER INFORMATION: n is a, c, g, t or u
<220> FEATURE:
<221> NAME/KEY: misc_feature
<222> LOCATION: (241)..(241)
<223> OTHER INFORMATION: n is a, c, g, t or u

<400> SEQUENCE: 364

```
ttagcatctt ggttactgga gaactataac ttttatgtag tcatgcttgg aaaacactaa      60
aagggaaatc gagtctgttt gacaatattc tgtcttcact gttgttcact tcataangng     120
tnggaatata aagttctata cagtaatat gangntctct ttagcattta aaacatgatt      180
tgcattttca tgaggcattt tggctaattt tattgatttc cttatatttc atagtcctta    240
nccttatgag aatcttatgt ttctgtgtgt tttctatcat gtagcacaat ttctgacaca    300
caaaacatac aataaacttg tgttaatttt tctatcaaag tcagaattta ttcataagga    360
atctgaagta aggtgtacta agcttgttta tgggttaagt gatatagcca aattcaaaac    420
tttacttttt atgtcagtct agaaatatct cagattaaaa catatcactt cttagttcca    480
attagataag ggaaatcttt tataataatg ccaggattgc tataatctga t             531
```

<210> SEQ ID NO 365
<211> LENGTH: 525
<212> TYPE: DNA
<213> ORGANISM: Homo sapiens
<220> FEATURE:
<221> NAME/KEY: misc_feature
<222> LOCATION: (35)..(36)
<223> OTHER INFORMATION: n is a, c, g, t or u
<220> FEATURE:
<221> NAME/KEY: misc_feature
<222> LOCATION: (39)..(39)
<223> OTHER INFORMATION: n is a, c, g, t or u
<220> FEATURE:
<221> NAME/KEY: misc_feature
<222> LOCATION: (78)..(78)
<223> OTHER INFORMATION: n is a, c, g, t or u
<220> FEATURE:
<221> NAME/KEY: misc_feature
<222> LOCATION: (86)..(86)
<223> OTHER INFORMATION: n is a, c, g, t or u
<220> FEATURE:
<221> NAME/KEY: misc_feature
<222> LOCATION: (92)..(92)
<223> OTHER INFORMATION: n is a, c, g, t or u
<220> FEATURE:
<221> NAME/KEY: misc_feature
<222> LOCATION: (234)..(234)
<223> OTHER INFORMATION: n is a, c, g, t or u

```
<400> SEQUENCE: 365
aggccatagt aatcatcctg ctgatattgc aagtnngtng ctagaatgag gttatataat        60
atatacaaaa acattttntc aactgntaaa gntgccttag taatataggg taataccagc       120
aacattatgg atatataatt atagtctatt gggccacact taagtttgga gtctaataaa       180
gtcacaatca aattctgcaa tttcaattga agataacctt gtctttatat tatnaattag       240
aagctaaagt tgattttctt aagagttctt tatttaaatg aagtactctg ggactgacct       300
tttcggaaat ggaatcttca ttggtcaggt gattcaacat ttttatacaa tttatccatc       360
ctcatctctt caggatttgc ataccttgcc agtttctact ggccattgtt gaaaatacat       420
ttatttggag aagtccaaag ccaaggggct catgggctg tgaggtcctt cttgctgcat        480
cgtcctgtgg tagaaggtgg aggagtcaag agagtgcccc agagt                       525

<210> SEQ ID NO 366
<211> LENGTH: 267
<212> TYPE: DNA
<213> ORGANISM: Homo sapiens

<400> SEQUENCE: 366
gggccaatga aagcagggtc aaggacagga ccagcgcagg ccaaggaagg gaatatctga        60
cagcgcccac ccagccaaac cctcagccca aggacaggaa tgaggagatg ctggtgaact       120
agccatccat cagtacctgc cttcccccga ggctgcagcc ccactcccag gcgcctggcc       180 agggagttt tctaggttct gagagccacg ttgtcatccc tgggctttga agttaaacat        240
cacacagctg tctataaaca agatttt                                           267

<210> SEQ ID NO 367
<211> LENGTH: 199
<212> TYPE: DNA
<213> ORGANISM: Homo sapiens
<220> FEATURE:
<221> NAME/KEY: misc_feature
<222> LOCATION: (67)..(67)
<223> OTHER INFORMATION: n is a, c, g, t or u
<220> FEATURE:
<221> NAME/KEY: misc_feature
<222> LOCATION: (107)..(107)
<223> OTHER INFORMATION: n is a, c, g, t or u
<220> FEATURE:
<221> NAME/KEY: misc_feature
<222> LOCATION: (120)..(120)
<223> OTHER INFORMATION: n is a, c, g, t or u

<400> SEQUENCE: 367
gattcaggga ttggatgagt ctctatggtt tgttttgccc tgaagagcag aaggcttctg        60
tcccaantgg tgttgccaaa gcaacatatt aattccatgc catgatnctg ggtcaagatn       120
tgcacaatct gattgggcat gtcacctcgg atggcaaggg agtggaagtg gtcaaaatca       180
tggagtccca gctttcgga                                                    199

<210> SEQ ID NO 368
<211> LENGTH: 372
<212> TYPE: DNA
<213> ORGANISM: Homo sapiens

<400> SEQUENCE: 368
gccccatgtt gcataggtgg cctataacca gtcagacaca ggagacaaca tgaagcccca        60
tctgtgcttc cctttctgac attaccacat ttgcctgatg gagtggccag ctcccttcta       120
```
ctgctggaat gaatacaatc cagaaaacct accttctatt gctttaccta atggggtaag    180
gaaatttaag tagaaattgc taaccgaaga ctttgctaag caaacccagg tctgcttgat    240
gtcagagccc ttgctgttaa ccccatttac tgcttagcct ccaaagagaa gcaatagcat    300
cacatgggga aatgtcaaca gcataagagg actttcataa tcagaattta aactggctat    360
tatccctctg ga                                                        372

<210> SEQ ID NO 369
<211> LENGTH: 296
<212> TYPE: DNA
<213> ORGANISM: Homo sapiens

<400> SEQUENCE: 369
gaccgtgact cctgaagctt ttcagcgcag gtgtagccgg cttggcgtcg ccgcagtgag    60
gtttggagcc gctttggatt gctgagtcac tttcttcagc cacttaggga aaccgaaagt    120
ggaaactcgt ggggcttgaa atagtgtgtt ctcttgagaa ccaccgaggc agtgagattt    180
gggattccgg ggtctggaga tcgtgctttt tgtggactgc gtttgcagtt cctagggtgc    240
tgctgattca caggccttct ctgtctttaa gtgtgcagat cattgaccgc tcagtt       296

<210> SEQ ID NO 370
<211> LENGTH: 228
<212> TYPE: DNA
<213> ORGANISM: Homo sapiens

<400> SEQUENCE: 370
aaacccagag ccttctggat gtgtgaggta gtaggcttca accctcattc atgcataggt    60
cacacttctc caaagttggt atggcctgtc tccttggcat gttcccttgc ttctgcttgt    120
ccagttaatc ctttctgaca taccatgcat ctcagggtga agcggttgac atcagtaaac    180
tgtctccttc ttctagcttc atctgctaat ccagtgcatt gtacaaga                228

<210> SEQ ID NO 371
<211> LENGTH: 206
<212> TYPE: DNA
<213> ORGANISM: Homo sapiens

<400> SEQUENCE: 371
cctcctgatc accatagctt tatgcaacaa caagaaacaa atttattagc taacctaacc    60
actaatgacg caagagacaa ttctaaggac tttcaaaaca gcaaagtagg agcagctgct    120
acctctaggg atgagggatg caattgtcca attattggtg aaattgtcat ttcatgctat    180
tggctatttg aaattcctcc tctaat                                         206

<210> SEQ ID NO 372
<211> LENGTH: 463
<212> TYPE: DNA
<213> ORGANISM: Homo sapiens
<220> FEATURE:
<221> NAME/KEY: misc_feature
<222> LOCATION: (94)..(94)
<223> OTHER INFORMATION: n is a, c, g, t or u
<220> FEATURE:
<221> NAME/KEY: misc_feature
<222> LOCATION: (121)..(121)
<223> OTHER INFORMATION: n is a, c, g, t or u
<220> FEATURE:
<221> NAME/KEY: misc_feature
<222> LOCATION: (382)..(382)
<223> OTHER INFORMATION: n is a, c, g, t or u

<400> SEQUENCE: 372

```
ccctgcctgt actaatgatc caaaaattag ccaggtgtgg tggtgcgtgt ctgtagtgcc    60
agctactcgg gaggctgagg caggagaatc tcangaaccc gggaggcgga ggttgcagtg   120
ngccgaggtt gcactactgc agtccagcct ggctctgtct tggtgttcag ccatgttccc   180
atgctcactc ccaaggtgac tctgggaagg tctcagcctt tttgtcttcc cagttaggat   240
ggtcccatgc ccctgttacc atcagacttg gtaagtttcc cgaggagact ctgcaagagg   300
cactgttctg gatggtggag gagagactag ttgttctgct ctcctggcca cagtgggtgc   360
agtggacccc atcatggaga anttcaacac atccagccta cgaccagcac ctgtgggagg   420
tggatattca aggcagcaga gcctacagcc ggggcatgga gaa                     463
```

<210> SEQ ID NO 373
<211> LENGTH: 451
<212> TYPE: DNA
<213> ORGANISM: Homo sapiens
<220> FEATURE:
<221> NAME/KEY: misc_feature
<222> LOCATION: (38)..(38)
<223> OTHER INFORMATION: n is a, c, g, t or u
<220> FEATURE:
<221> NAME/KEY: misc_feature
<222> LOCATION: (87)..(88)
<223> OTHER INFORMATION: n is a, c, g, t or u
<220> FEATURE:
<221> NAME/KEY: misc_feature
<222> LOCATION: (231)..(231)
<223> OTHER INFORMATION: n is a, c, g, t or u
<220> FEATURE:
<221> NAME/KEY: misc_feature
<222> LOCATION: (406)..(408)
<223> OTHER INFORMATION: n is a, c, g, t or u
<220> FEATURE:
<221> NAME/KEY: misc_feature
<222> LOCATION: (421)..(421)
<223> OTHER INFORMATION: n is a, c, g, t or u

<400> SEQUENCE: 373

```
agggtctcaa atgaactctg agttaccatc tttggacnga cttttaatat aaagctgtaa    60
tccttaaatc tgtgtcagta gtcccannta ctatgtcact ttaattggat gaatgcgtta   120
atgaaaagtt tgttttcaaa cctcactaaa ctgctactta agatcacagt taatgtgagt   180
cctgcttaat ttggaaagca tttaaaaaat ggaaagtttt cttagggaag naaaaatttt   240
gcaactctgc ctacaaggta cagtaattgg ctaggttctt ttgaagagca gtgttgacta   300
gagttaagga aaagtcagtt gtgaaaaatg gacatttta atagcaaaat gatgtgcttt    360
actgtagaaa caggaggaag ggtgcattat cctggggaaa atgaannntt cttcagttat   420
nttttatgct gctctacttt attgcaaaac g                                   451
```

<210> SEQ ID NO 374
<211> LENGTH: 46
<212> TYPE: DNA
<213> ORGANISM: Homo sapiens

<400> SEQUENCE: 374

```
cagtcaccga ccttccctga gattgctacc tggaagctct ttctat                    46
```

<210> SEQ ID NO 375
<211> LENGTH: 519
<212> TYPE: DNA
<213> ORGANISM: Homo sapiens

<400> SEQUENCE: 375

```
gaataagtac acagagtccc caaagactag tgaggccaag atgtgtgagt cattttccat    60
cacacacaaa aaacccaatt gttctaagta tgtattttac caagcagctt tatagaaaga    120
aaaacaaaca aacaaaccaa acaacaacaa caacaaaaaa ccttggccag gcacagtggc    180
ttacacctgt aatcccagca ttttgggaga ttcaggcggg tggatccttt gagcttggga    240
gtttgagatc agcctgggta atgtggcgaa acctcatctc taccaaaaat ataaaaacta    300
gccaggtgtg gtggtgcacg cctgtagtcc cagctgctta ggaaactgag gtgggaagat    360
tgcctgagcc caagaggtag aggtttcagt gagccgtggg aagattgcct gagcccaaga    420
ggtagaggtt tcagtgagcc gtgggaagat tgcctgagcc caagaggtag aggtttcagt    480
gagccaagat tgtatcactg cacaactgtt gcctgggca                          519

<210> SEQ ID NO 376
<211> LENGTH: 222
<212> TYPE: DNA
<213> ORGANISM: Homo sapiens

<400> SEQUENCE: 376
cctgctggac agccgcgcag gatgagccgg agaccccgag ggccgtggcc ttccaggact    60
gccccgtgga cctgttcttt gtgctggaca cctctgagag cgtggccctg aggctgaagc    120
cctacggggc cctcgtggac aaagtcaagt ccttcaccaa gcgcttcatc gacaacctga    180
gggacaggta ctaccgctgt gaccgaaaacc tggtgtggaa cg                     222

<210> SEQ ID NO 377
<211> LENGTH: 460
<212> TYPE: DNA
<213> ORGANISM: Homo sapiens

<400> SEQUENCE: 377
atagtagggg caattttgtc tgtagatggc agtatgacaa ttcttgctag agaatatatt    60
gaaaaaaact tcaacacaaa gggttgtagc actgtcctca gtaccattgt gtgcatgagg    120
atcagaatag tctgggctag atacatcaca ttaaagcttt tcagaatctg ataaatagct    180
ctaaatacta atgatattga aagcctagc ttcacttggg aaaatctgtg ctgttcaca     240 gaaattcagc accaagttat tccccccata ctctaccagg ccttcaggtc tcataaaga    300 aaagtgtcgt tttcagatta ggaactcaaa attattttgg tgcatcaaat ctacagtcac    360
acaatataac aagaatggga ttagaaaaat gaaagcctac tcattctcat ctttaagcca    420
gagaatgaaa tatatatgag gtctctggat agctatttaa                        460

<210> SEQ ID NO 378
<211> LENGTH: 544
<212> TYPE: DNA
<213> ORGANISM: Homo sapiens

<400> SEQUENCE: 378
cgccgcatca agccgtggcg gagatcgacg cgctctacga cgtgtacctg gacgtgatcg    60
acaagtgggg caccgacgac atgctgttcc tgggcgactt caacgccgac tgcagctatg    120
tgcgggcgca ggactgggcc gccatccgtc tgaggagcag tgaggtcttc aagtggctca    180
tccctgacag cgccgacacc acggtgggca actcagactg cgcctacgac cgcattgtgg    240
cctgtggcgc ccgcctcgc cggagcctga gccccagtc ggccaccgtg cacgacttcc     300
aggaggaatt cggcctggac cagactcagg ctcttgccat cagcgaccac tttccagtgg    360 aggtgacccct caagttccac cgatgactcg aggcctgact ggggcatgcc acctgcagac    420
```

```
cctggctctg aggaatggcc caacagtggc cccttcaggg tggcagccac ccttcagtga    480
ggccccaagg cagagtcggc tgggcgtgga ccagggcat ggacacgtga tgtgctgctc    540
tgta                                                                 544
```

<210> SEQ ID NO 379
<211> LENGTH: 254
<212> TYPE: DNA
<213> ORGANISM: Homo sapiens

<400> SEQUENCE: 379

```
gaagtttgtc ttcctacaac cacgtgatcc tctctctggg atttccccac tcaaccaggg    60
acaagaggtc aaagttgacc tgattatgtg tccatcaagg aagtgcccct ggaaggcaaa   120
taaagaaggc accatttaca ttacagtctc ctaagtgcag gcaatgatac cccaaggtgg   180
ggctctgcag accctccagc aaagagcttt tgaaaataaa tgtgaagctg ggcttaggag   240
ctcatgcctg caat                                                    254
```

<210> SEQ ID NO 380
<211> LENGTH: 398
<212> TYPE: DNA
<213> ORGANISM: Homo sapiens
<220> FEATURE:
<221> NAME/KEY: misc_feature
<222> LOCATION: (140)..(140)
<223> OTHER INFORMATION: n is a, c, g, t or u
<220> FEATURE:
<221> NAME/KEY: misc_feature
<222> LOCATION: (295)..(295)
<223> OTHER INFORMATION: n is a, c, g, t or u

<400> SEQUENCE: 380

```
aacctgctaa ccaagaatgc tttacctggc aaagctgtcc ttcagaaatg agggagaaat    60
gaaagctttc tcagacaaac aaaaacaaag gaaacatgta aaagtgaaaa ataaatggt    120 ataagtaata tatagtcccn actcagaatt ctctaatact gttaaggtgg tgtgtgaagc   180
aatcttatta ctactaggag ggttaagaga caaaactatt aaaaacaact gcagctacag   240
tatattgtta aaggacacaa attttaagtt tacatcaaaa tcagaaaaca tgggnaagga   300
aggaatgaaa gtgcagagtt tttgtatgtg attaaaggca aattgttatc agtttaaagc   360
ctgttttaag gataaaatat tttatgtaag cctcatgg                          398
```

<210> SEQ ID NO 381
<211> LENGTH: 276
<212> TYPE: DNA
<213> ORGANISM: Homo sapiens

<400> SEQUENCE: 381

```
cccgccgcgc gagattaaag gacagaccaa gagggcgcgg gagctaccag cttggagggg    60
aggacagatg gggacccagg gctggccagg gctggtctct ggagctgttc tgccagagtg   120 atggggcgc ttggcgaggc caaggatttg gttgggtcct atctctgaga cattttgaag   180
tctcacaccc cttccatttg ttgcctattc cacttaactt tgtatttgtt tgaaatctac   240
tgttcggatg ctggactaga agagggacac ttggcc                            276
```

<210> SEQ ID NO 382
<211> LENGTH: 119
<212> TYPE: DNA
<213> ORGANISM: Homo sapiens

<400> SEQUENCE: 382
aaacataaca gaggagttgc gaattttatg aaatttctga gtcttacaaa cttctcttta     60
agactatgag gaaatgctga cttgtattat ttatatcatt aaatttgctt gtgtatggt    119

<210> SEQ ID NO 383
<211> LENGTH: 490
<212> TYPE: DNA
<213> ORGANISM: Homo sapiens

<400> SEQUENCE: 383
gtccctgctg tttagtatgc tggagtggag gttctgtgac ttcctgttta gtggtgctga     60
ttctagttgg tgtgaaacgt cagatttcat cccagtcgcg tggctgattt ttttatgtgt    120
ggttctctgt gtttccagcc tggtcctgct ggtcaggatc ctctgtggat cccggaagat    180
gccgctgacc aggctgtacg tgaccatcct gctcacagtg ctggtcttcc tcctctgcgg    240
cctgcccttc ggcattctgg gggccctaat ttacaggatg cacctgaatt tggaagtctt    300
atattgtcat gtttatctgg tttgcatgtc cctgtcctct ctaaacagta gtgccaaccc    360
catcatttac ttcttcgtgg gctcctttag gcagcgtcaa aataggcaga acctgaagct    420
ggttctccag agggctctgc aggacaagcc tgaggtggat aaaggtgaag ggcagcttcc    480
tgaggaaagc                                                          490

<210> SEQ ID NO 384
<211> LENGTH: 458
<212> TYPE: DNA
<213> ORGANISM: Homo sapiens
<220> FEATURE:
<221> NAME/KEY: misc_feature
<222> LOCATION: (72)..(73)
<223> OTHER INFORMATION: n is a, c, g, t or u
<220> FEATURE:
<221> NAME/KEY: misc_feature
<222> LOCATION: (229)..(229)
<223> OTHER INFORMATION: n is a, c, g, t or u

<400> SEQUENCE: 384
gatacctcat tatacatctt acagagagca tcattggtgt ttccaaggtc acagggctag     60
gcaagggtgg anncctgagt ctgcttgtct gtttgcccca tgacagccca ggggtggtgg    120
cctcactcca cctccaggca cccacaagaa tataaaatct tgtacaagga tgtcgatatt    180
actattgcca ttcccaagtg cacctgcacc tgtagtatca ggtggtttnc agccttggct    240
gcatagctgc atatgagaat cacctgggaa gcttttaaag atcccagtat ccccacctct    300
tccccagtta cagtggagtc ttgcgggtgg tgggggacat cattattttt gaagcttcca    360
agtaattctg gtgtgcagtg gggtgaccag ctgtcccagg gacctccttt aaaaaataat    420
atcccgggca catgacaggc caattgccct aatgcaac                           458

<210> SEQ ID NO 385
<211> LENGTH: 510
<212> TYPE: DNA
<213> ORGANISM: Homo sapiens
<220> FEATURE:
<221> NAME/KEY: misc_feature
<222> LOCATION: (343)..(343)
<223> OTHER INFORMATION: n is a, c, g, t or u
<220> FEATURE:
<221> NAME/KEY: misc_feature
<222> LOCATION: (467)..(467)
<223> OTHER INFORMATION: n is a, c, g, t or u
<220> FEATURE:
<221> NAME/KEY: misc_feature

```
<222> LOCATION: (471)..(476)
<223> OTHER INFORMATION: n is a, c, g, t or u

<400> SEQUENCE: 385
cacctctgca cttttgtagg ctcaacaagt actggggagc ctgccaccac tgtatgcctt      60
tgaggcccct gccctgcctc cctggctggc cacggagctc gccctccctg gtaggggtg     120 agtttggaag tgagaggctg gtgtgggtct gtcccatgag ctgactcaca cttgcctcac    180
cacacatacc atcagaagac ccacgtggtg gagctaccgc tgctgctccc cacagtgcac   240
ctaggcaccc tcctgtcctt cccatggcac tcggttgacc tgggggttcc tgtccaacag   300
gtgaggcctg gtgtgcacag acactctgcc attgctagaa ggnggctgtg cccctgcta    360 agatatcagt aggtccttca cagcctcacc ttgttcctcc catttgtttt taaaaattgt   420
ttcttatata tacagtttat ttagcttacg taaacatttg gtgcacntaa nnnnnntcaa   480
agatcatgat gtctcttttg tggttttata                                     510

<210> SEQ ID NO 386
<211> LENGTH: 92
<212> TYPE: DNA
<213> ORGANISM: Homo sapiens

<400> SEQUENCE: 386
cctctgccat tgcccaaaga agtacgcag gagggaaggc gccggggcg caggagtcgg      60 ggggaagtga aatctcggca ttagaaccccc cg                                 92

<210> SEQ ID NO 387
<211> LENGTH: 394
<212> TYPE: DNA
<213> ORGANISM: Homo sapiens

<400> SEQUENCE: 387
aaggcgccgt caagtcaaat aaataaatgc cctacaacac caacccagga ctgagatctg    60
catgctggaa tgacggtggt ggtggtggct ttcagtattc cccaggtttt gtccggagca   120
ccggcacgcc ctctcttgaa gtccgctctc cgcacagtgg ttagacggga agatccggag   180
ctgtccagtg tcttgggtaa tgcacggcat cgcctgatgt ctgacgctag aacaccacgt    240
aaagtcaagc agagggaagt gaatgcgccc taggcccctg caggccacca agaagagcta   300
gagggagttg gtgcaatcct agagatgccg gcaggtgcac caatctgtgg cacacgtacg    360
ctctccaatg gaagacaact caagaccaca ccaa                                394

<210> SEQ ID NO 388
<211> LENGTH: 289
<212> TYPE: DNA
<213> ORGANISM: Homo sapiens

<400> SEQUENCE: 388
actataatgc acttcgcaaa atgtaagggg ccggcttcac gccagcgggg ccttctggga    60 cttttgaattc aaccaggtga gcgctccagg tgccccgaca ggcgcactgt agccactggg   120
tgttaggggc gggagtctgg aaggtgacgg tagacggcca cttgggccct tctggggggcg   180 agcctactgg tggggtcagg gctctccgtg ctcagagcaa ggtagaggag caaggcccta   240
cttttggggg gcagggtcca gaccaaggac cctatgcgcg gagggtggc                289

<210> SEQ ID NO 389
<211> LENGTH: 139
<212> TYPE: DNA
```

<213> ORGANISM: Homo sapiens

<400> SEQUENCE: 389

```
aggcctgacc gaagagaact ttaaggaact aaagcaagac atttctagtt tccgctttga    60
agtcctggga ttactaagag gaagcaaact ttccacaata caatctgcga atgcctcgaa   120
ggagtcttca aattcggca                                                139
```

<210> SEQ ID NO 390
<211> LENGTH: 528
<212> TYPE: DNA
<213> ORGANISM: Homo sapiens

<400> SEQUENCE: 390

```
caggttcttg aagttctcca ccatgacatc tcggtacagc ttcctctggg taagatcgag    60
cagtcgcagt tcctccctgg agaagaccac agccacatcc ttgaatgtca cagcctccta   120
caatatcaaa cacatgtaac ctcaatctta caaccaacct tcactagaag aagggtggca   180
tcaagaagga aaagagcacc acaaaaaagt tgttatagat tccaagagat ctcagtcaat   240
tttcagctgt tacagttttc cctgtctcac tatctcctac gctcatcccc ataaagcctg   300
tagtttatca ctgttttttg ttttttttctt ttttgagatg gagtctcact ctgtcaccca   360
ctgcactcca gcctgggtga caggggtgag acactgtctt aaaataaata aattttaga    420
attaaaataa atagatcata aagtgtttga aaggatcaga tgaatgaata tatgtcaagc   480
acttagaagt gcctagcaca ccatacatgc tcaataaact cgaacaac                528
```

<210> SEQ ID NO 391
<211> LENGTH: 443
<212> TYPE: DNA
<213> ORGANISM: Homo sapiens

<400> SEQUENCE: 391

```
gccaggggtc gccaatcctg gaaccccact ggcttagagg gctggggag agaaacatgc    60
tgccctcttt gtagcagtca ggcgctgacc caagagaact caccttattc ttcatttcgc   120
ctggtaatcc tccaggccct tctctacacc ctgaagggga gggaggaaaa tggatgaatg   180
agagagggag ggaacagtgc ccaagcgctt ggcctctcct tctcttcctt cactttgcag   240
aggctggaag acggcagccg ccggactggg cagatcctca agcagaccta cagcaagttt   300
gacacaaact cacacaacca tgacgcactg ctcaagaact acgggctgct ctactgcttc   360
aggaaggaca tggacaaggt cgagacattc ctgcgcatgg tgcagtgccg ctctgtagag   420
ggtagctgtg gcttctaggt gcc                                           443
```

<210> SEQ ID NO 392
<211> LENGTH: 463
<212> TYPE: DNA
<213> ORGANISM: Homo sapiens

<400> SEQUENCE: 392

```
tattggcacg tagcagtaca aggatggtga ggggtgggta gggggcagac agctaggcac    60
ttgaaaggaa agctcatctg gaaagattgg atcgtctcaa atgcacatac tcgtacactc   120
gattgaagcg tactctgtgc ctactagatc ttttcacagc caaaacacc tggcaaccct    180
tggagaagta actattcctt tttttcacaa gtaagaaaat agagcctcag aaaatttaac   240
agttgtctaa gctagaaagt agcaggactg gactttgaag tagtctttag gttgtgctgt   300
acattttgtg gatatgctta aatcacagtt tagcttgtac acattttcct ttattagaat   360
```

```
tggaagtaag tattaatgtt tgaaaaaata ttttagcctg acaatattta ttctatcttc    420
atatgttttt gaaattagat attttaaact aggcacggtg gct                      463

<210> SEQ ID NO 393
<211> LENGTH: 376
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, t or u
<220> FEATURE:
<221> NAME/KEY: misc_feature
<222> LOCATION: (65)..(65)
<223> OTHER INFORMATION: n is a, c, g, t or u
<220> FEATURE:
<221> NAME/KEY: misc_feature
<222> LOCATION: (99)..(99)
<223> OTHER INFORMATION: n is a, c, g, t or u
<220> FEATURE:
<221> NAME/KEY: misc_feature
<222> LOCATION: (123)..(123)
<223> OTHER INFORMATION: n is a, c, g, t or u

<400> SEQUENCE: 393
agctcatttt agtctcattt ctctcnctcc cttcttccct gatgaataaa gtttattggg     60
atggntttca gatgctcagc ttttccatat gattaggtna gtgatccaga acccttccaa   120
agnaccctgt ggactcaacc ctctgtttga acaacataca agataatatg agacatttat   180
ttatcgagga ccctctgagc acctggcact gtgccagatt ctttcagata tataaaattt   240
cacttgctcc tgttgattct ggaaaggagc aacggcatct tatgaagctg tagcagatac   300
tgtcctggcc tcgctcatgt gtgtcagatg tgttggagtg ccctggctgc tgctctgcat   360
gtgtagctga ggtcct                                                   376

<210> SEQ ID NO 394
<211> LENGTH: 220
<212> TYPE: DNA
<213> ORGANISM: Homo sapiens

<400> SEQUENCE: 394
tggattcatg ccaaaggaaa ctgaaagcct gcctttcttt ttttcccagt gcacatctca     60
gattatttgg cctttgtccg aggactgaaa acagttctgt gtccaagtat gttttttaata   120 cctgatattt atttcacaaa aaaactgaaa ttgctttgtg tgtccaggct tgaatgttta   180
aggcatactt gattaataca tgtgtgctga gtgcttcctg                          220

<210> SEQ ID NO 395
<211> LENGTH: 553
<212> TYPE: DNA
<213> ORGANISM: Homo sapiens

<400> SEQUENCE: 395
caaccgccac atagtcacat tgtcaaatag cgtattcacc ttctcttata agaaggctca     60
gcgagatctg gcgtataagc cactctacag ctgggaggaa gccaagcaga aaacggtgga   120
gtgggttggt tcccttgtgg accggcacaa ggagaccctg aagtccaaga ctcagtgatt   180
taaggatgac agagatgtgc atgtgggtat tgttaggaga tgtcatcaag ctccacccctc  240 ctggcctcat acagaaagtg acaagggcac aagctcaggt cctgctgcct ccctttcata   300
caatggccaa cttattgtat tcctcatgtc atcaaaacct gcgcagtcat tggcccaaca   360
```

```
agaaggtttc tgtcctaatc atataccaga ggaaagacca tgtggtttgc tgttaccaaa    420
tctcagtagc tgattctgaa caatttaggg actcttttaa cttgagggtc gttttgacta    480
ctagagctcc atttctactc ttaaatgaga aaggatttcc tttcttttta atcttccatt    540
ccttcacata gtt                                                       553
```

```
<210> SEQ ID NO 396
<211> LENGTH: 357
<212> TYPE: DNA
<213> ORGANISM: Homo sapiens
<220> FEATURE:
<221> NAME/KEY: misc_feature
<222> LOCATION: (90)..(90)
<223> OTHER INFORMATION: n is a, c, g, t or u
<220> FEATURE:
<221> NAME/KEY: misc_feature
<222> LOCATION: (103)..(103)
<223> OTHER INFORMATION: n is a, c, g, t or u
<220> FEATURE:
<221> NAME/KEY: misc_feature
<222> LOCATION: (111)..(111)
<223> OTHER INFORMATION: n is a, c, g, t or u
<220> FEATURE:
<221> NAME/KEY: misc_feature
<222> LOCATION: (114)..(114)
<223> OTHER INFORMATION: n is a, c, g, t or u
<220> FEATURE:
<221> NAME/KEY: misc_feature
<222> LOCATION: (124)..(124)
<223> OTHER INFORMATION: n is a, c, g, t or u
<220> FEATURE:
<221> NAME/KEY: misc_feature
<222> LOCATION: (132)..(132)
<223> OTHER INFORMATION: n is a, c, g, t or u

<400> SEQUENCE: 396
ctagaaactc actcagtcct gtggttgcca acctttctcc atctcccgca gacgttttac     60
tgcatgccag ataccatgtg cagtaacttn tgaatcctct canccccta nctnccagaa    120 cacnggacta tnagttactt gaaagctgag gcttggtaga gggctggagc caattgcgtt    180
aaactaacta acattattgc aaaatatatt ctagggcttt tactctaata aaaatgactc    240
ctggaactgc agtactatat tcttggaacc ccaagaaacc aggtgacaac ccataaattt    300
accatcactt ttcagatgag gaaggcaaat ctggaaggcc aaattacttg tccaaag      357
```

```
<210> SEQ ID NO 397
<211> LENGTH: 423
<212> TYPE: DNA
<213> ORGANISM: Homo sapiens
<220> FEATURE:
<221> NAME/KEY: misc_feature
<222> LOCATION: (184)..(184)
<223> OTHER INFORMATION: n is a, c, g, t or u
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (350)..(350)
<223> OTHER INFORMATION: n is a, c, g, t or u

<400> SEQUENCE: 397
gttagcacat accattgaat tcactgagac acatgagaaa atatgggaaa gtcggagagt     60
ggaagtaaat gtaaagaccc ccctcctccc caaagagtac gttgtgtagt ggggtagagt    120
ggaaaatcaa tccaagaaaa gtagcaaacg gacccaaaga tgaagaggaa gaaagaaac    180 agcnacacga aacgnaaaaa aaaagccacc agatttgttg caacgttgat gtaaacctgg    240
```

```
ccgtcttcct gaaccagtga cccagggttt ccgcttccct ttgctgtcat cttgctcaag    300
tctagaagct gaaatatcat catcaactcg acatgagggg ataacctctn gatccactca    360
tcagatgctc atcagacgtt ccaattacaa aactgaacct cttcttagtg ctggggcggt    420
tag                                                                  423
```

<210> SEQ ID NO 398
<211> LENGTH: 515
<212> TYPE: DNA
<213> ORGANISM: Homo sapiens
<220> FEATURE:
<221> NAME/KEY: misc_feature
<222> LOCATION: (132)..(132)
<223> OTHER INFORMATION: n is a, c, g, t or u
<220> FEATURE:
<221> NAME/KEY: misc_feature
<222> LOCATION: (150)..(150)
<223> OTHER INFORMATION: n is a, c, g, t or u

<400> SEQUENCE: 398

```
ggacaaaaac tttcccaagt cagcttttta ctatgattac gtcctagcct cagatgtggt    60
ctaccatcac tacttcctgg acaagctgct caccaccatg gtgtaccttt cccagccagg   120
gacggtgctg cnttgggcaa acaaattcan ggttcagcac cgactatgaa ttttttagata  180 aattcaagca agttttttgac acaacactgt tggctgaata tccagagtca tcagtcaaac  240
tttttaaggg gatactaaaa tgggactaaa tccaacaaaa tgcctttcac aacgttactg  300
tgtcttttga gcaatgtgtt agaaattgct ttggtaatag acttcttca caggattgag    360 aaggtagtgc atagaaacaa cttgtatact tggaacaaat gtaacaatac tgcagaaact   420
ttctaatttc taagataatt taagattatc tggttaatct aaatatctaa aagaacaac    480 ataaaaacat gaaagtagct ttgttggttc caacg                              515
```

<210> SEQ ID NO 399
<211> LENGTH: 483
<212> TYPE: DNA
<213> ORGANISM: Homo sapiens
<220> FEATURE:
<221> NAME/KEY: misc_feature
<222> LOCATION: (55)..(60)
<223> OTHER INFORMATION: n is a, c, g, t or u
<220> FEATURE:
<221> NAME/KEY: misc_feature
<222> LOCATION: (62)..(63)
<223> OTHER INFORMATION: n is a, c, g, t or u
<220> FEATURE:
<221> NAME/KEY: misc_feature
<222> LOCATION: (65)..(65)
<223> OTHER INFORMATION: n is a, c, g, t or u
<220> FEATURE:
<221> NAME/KEY: misc_feature
<222> LOCATION: (85)..(85)
<223> OTHER INFORMATION: n is a, c, g, t or u
<220> FEATURE:
<221> NAME/KEY: misc_feature
<222> LOCATION: (88)..(88)
<223> OTHER INFORMATION: n is a, c, g, t or u
<220> FEATURE:
<221> NAME/KEY: misc_feature
<222> LOCATION: (90)..(90)
<223> OTHER INFORMATION: n is a, c, g, t or u
<220> FEATURE:
<221> NAME/KEY: misc_feature
<222> LOCATION: (93)..(93)
<223> OTHER INFORMATION: n is a, c, g, t or u
<220> FEATURE:
<221> NAME/KEY: misc_feature
<222> LOCATION: (134)..(134)

```
<223> OTHER INFORMATION: n is a, c, g, t or u
<220> FEATURE:
<221> NAME/KEY: misc_feature
<222> LOCATION: (278)..(278)
<223> OTHER INFORMATION: n is a, c, g, t or u
<220> FEATURE:
<221> NAME/KEY: misc_feature
<222> LOCATION: (304)..(304)
<223> OTHER INFORMATION: n is a, c, g, t or u

<400> SEQUENCE: 399
gactgccatc tgatcaacag ctacccttca gccaatttca cctttctgtt acttnnnnnn      60
anngngccct tgtgtggata atgtncancn cantaaggaa tgcatgttag gtactttaag     120
tcccagtaga atancagttc ataatatcac acatgtggtg aaatctaaaa aggcaatagg     180
gctaattttg gcaggagttg gaatagcccc ttgggatggc tttgcatact gtcagacagc     240
tttgagaaac tttcaaaccc ttgaaacact ggcaactnag tacaggcaga gccataaaag     300
gacntcaagc ctccctgcac tccctagcca atgctgtctt ggataacaga tttgccctgg     360
aatatcttct ggctgaacaa gggcgggtat gcacagtaat aaaccacatc tgttgttctt     420
acattaacag ttcaggattg gctaaactgc aagttcaaaa gatttaccaa gaccaggcac     480
aat                                                                   483

<210> SEQ ID NO 400
<211> LENGTH: 555
<212> TYPE: DNA
<213> ORGANISM: Homo sapiens
<220> FEATURE:
<221> NAME/KEY: misc_feature
<222> LOCATION: (483)..(483)
<223> OTHER INFORMATION: n is a, c, g, t or u

<400> SEQUENCE: 400
ggagcaaaac acttggaacc cacaagactc ccagaaggtg aagttaagag ctcccagact      60
cataaggtta ttagaacagc aaactggcac cccaaagaac tttacggaga cttgcaacct     120
atcaacaagt tggatgaggg attaaaagcc ttcaacaacc aacaacccca agcatcaaac     180
tgaaggaaac attctaacct tcacagacag actggaggct ggatggggac ctggctgaag     240
acatctggag aatgaaagtt aagtaccagc ttgcattttt gtgcccctag attattttg      300 cattttaaaa taagaagcat caaattgcgt gtctctgtgt aaaagttcta gcaatttgtt     360
ttaaggtgaa cttatttgg cttagggact acaaaaagag aaggtaattc ctagggaagg      420
aagaagagaa agaaatgaaa attagagaat aagattattt tgaatgactt caggtagcga     480
ggngtgtgtg tttgtgagtg tgtatttgag agacttggct catgcctgtg ggtcttctct     540
tctagtatca gtgag                                                      555

<210> SEQ ID NO 401
<211> LENGTH: 327
<212> TYPE: DNA
<213> ORGANISM: Homo sapiens

<400> SEQUENCE: 401
ggctgagaaa ctactggagc accagggaca gtctgtaaag ttggatggac caccaatggg      60
aaaatgagag ctgcccaccc tggccttaca ctccttcaat taatacataa acagaaagga     120
ggatatacag agagccaaag gcccatggga cgtgaccaac attccactga gtctatacga     180
tcaaacagca aactgtttat catgaataca gaatgtgggc aaactcatga ctgtgcctgc     240
cccagaaggt ttgctgaggg caattgcttc ctgacgccaa gctccttgag gttatctatt     300
```

```
gggacatcca gagaatgcag tcttgca                                         327
```

<210> SEQ ID NO 402
<211> LENGTH: 497
<212> TYPE: DNA
<213> ORGANISM: Homo sapiens

<400> SEQUENCE: 402

```
gggtggcctg gggatagtgg cttcatcttt tggggcttca agattctttg tctttaaaat     60
caggggttat atcaagatca tcaaagttcc cattccatta agaaaaccc tgcatgtatc    120
cataatgatg cttcttcctg ttaaatttac aatgaaggga aacccatcac ttaactgtag   180
gaatttccca aaatgaactg atgaccagtg atctctctat cagaaaatgg cagatttcta   240
gccttccaga actttgattt tcttggacat tcaatggttc cttttcccca aatatttttc   300
aactgatgcc aaaccttgga tttggtttaa tccacctttg gtttaggttt ggggacccct   360
ttcctggacc gtcccagttt tgggttaaac cgatttggat gaccctgtga gtcgccactg   420
gataccgaca gtctgctgtg gtgcttagaa gccactgaaa cattggtgaa tgtgaagtca   480
cttttggggt gcctgcc                                                  497
```

<210> SEQ ID NO 403
<211> LENGTH: 512
<212> TYPE: DNA
<213> ORGANISM: Homo sapiens

<400> SEQUENCE: 403

```
gaaagctcca atccatgac agtcgaagtc tctgctcctt caggaacagg acatcttcct     60
ggccttaatc cattatagca gccgtgatgt catttctgta tttcaggaag actggcagac   120
agttgctttc attcttcctc aaagtattta ccatcagcta cagtccaaaa ttgcttttg    180
ttcaaggaga tttatgaaaa gactctgaca aggactcttg aatacaagtt cctgataact   240
tcaagatcat accactggac taagaacttt caaaatttta atgaacaggc tgatacttca   300
tgaaattcaa gacaaagaaa aaacccaat tttattggac taaatagtca aaacaatgtt    360
ttcataattt tctatttgaa aatgtgctga ttcttttgaat gttttattct ccagatttat  420
gcactttttt tcttcagcaa ttggtaaagt atacttttgt aaacaaaaat tgaaacattt   480
gcttttgctc cctaagtgcc ccagaattgg ga                                 512
```

<210> SEQ ID NO 404
<211> LENGTH: 229
<212> TYPE: DNA
<213> ORGANISM: Homo sapiens

<400> SEQUENCE: 404

```
caccccattc aaactcaagc acagtatgcc tccccagtct ttatgcagcc tgtatataat     60
cctcaccaac agtactcggt ctatagtatt gtgcctcagt cttggtctcc aaatcctaca   120
ccttactttg aaacaccact ggctcccttt cccaatggta gttttgtgaa tggctttaat   180
tcgccaggat cttataaaac aaatgctgct gctatgaata tgggtcgac                229
```

<210> SEQ ID NO 405
<211> LENGTH: 495
<212> TYPE: DNA
<213> ORGANISM: Homo sapiens

<400> SEQUENCE: 405

```
acagctcagg ttttatcacc gactgggaat agacaacctc aatgctgaac cgcactggag      60
aaaaggggca aggtacccct gctgaggtgt atgggctgcc atctcaggct gtcttgagga     120
cctgggctcc ctctgctact cccaggaaat gggctcctga cacagcagtc tgccaccaca     180
gccccaggag ggtgtcaaca ccagcaaatg ctgtatttgc agcatgtcca agatgaccct     240
tctcccctac ctctacctag ccactggcag ggaggggaga cagtggtgat agcagcagca     300
ctctaggcat ggtgaacgcc tgggaccaag ccatgtggcg ttttttattt tgcctttctg     360
gaagactcaa gatatgtctc ttcattctct ctcagtattt gtttactttg gttttttttgt    420 ttttaatctc agagagaggt gtgtttagtg ggcacaagct gtaatattca gcaaaacttt     480
gtcgactggc actgt                                                      495
```

<210> SEQ ID NO 406
<211> LENGTH: 472
<212> TYPE: DNA
<213> ORGANISM: Homo sapiens
<220> FEATURE:
<221> NAME/KEY: misc_feature
<222> LOCATION: (77)..(77)
<223> OTHER INFORMATION: n is a, c, g, t or u
<220> FEATURE:
<221> NAME/KEY: misc_feature
<222> LOCATION: (79)..(79)
<223> OTHER INFORMATION: n is a, c, g, t or u

<400> SEQUENCE: 406

```
ttcctcttgc tgagaaaacc caccctgctc acctaaaccc tggccttgcc tggtaattcc      60
atccatgcgc ctggaangnc ccagacatca aggctctgag gggccaggca cggggagaac     120
ccagcagtgc cctgccctgc agtctgagct accagattcc ttgtgaagat aatttgagga     180
ccatgactca cccaaccaca tttcctgggg cctcaaattg aaaattcagg atgggctttt     240
ctatatgact ggctgatatc caactatgcc atggtcttta catgccatga acattctttc     300
ctgccagagt tctaagaatc tgtgttctct gccttagacc ttctgcagat gagcccacag     360
gaagctccac gtgtagctga gctacatgca ccaggcctca gtttgcccca agtcccctgt     420
gtactctctc atggcctgtg ccaagaaat gtattctctc actttggact ta               472
```

<210> SEQ ID NO 407
<211> LENGTH: 395
<212> TYPE: DNA
<213> ORGANISM: Homo sapiens

<400> SEQUENCE: 407

```
agcagatgga ccctactgga agtcagttgg attcagattt ctctcagcaa gatactcctt      60
gcctgataat tgaagattct cagcctgaaa gccaggttct agaggatgat tctggttctc     120
acttcagtat gctatctcga caccttccta atctccagac gcacaaagaa atcctgtgtt     180
tggatgttgt gtccaatcct gaacaaacag ctggagaaga acgaggagac ggtaatagtg     240
ggttcaatga acatttgaaa gaaaacaagg ttgcagaccc tgtggattct tctaacttgg     300
acacatgtgg ttccatcagt caggtcattg agcagttacc tcagccaaac aggacaagca     360
gtgttctggg aatgtcagtg gaatctgctc ctgct                                 395
```

<210> SEQ ID NO 408
<211> LENGTH: 397
<212> TYPE: DNA
<213> ORGANISM: Homo sapiens

<400> SEQUENCE: 408

```
attttcctca taaagcattg ctccagctaa tcttatctat tttctccag aatctccatc      60 cccttcccgt cagatacatc taaaactttt tttgtatctt tgttttcct cgtgttgtat     120 catcttccta aaacatgttc tacttgtgaa aaccctaaga aattctctct gtcttattga    180
aattctatct ccactgtgaa gcattatcat ggtgtggcca tatatgatct atccctatct    240
gaagtcactg catttattcc ctgatcctca tttgcaggtc cagtaccttg tacaagtttc    300
tttttgtgcc atattagact gtaagctcca agagggcagg gcccaagtct tatgaatttg    360
tgtctgcata gtgtctagta cttgtctgag gcccaca                             397
```

<210> SEQ ID NO 409
<211> LENGTH: 48
<212> TYPE: DNA
<213> ORGANISM: Homo sapiens

<400> SEQUENCE: 409

```
aggacgtacc ttgtgagatg cgagccggcc aacagcttgc aagcatgc                  48
```

<210> SEQ ID NO 410
<211> LENGTH: 459
<212> TYPE: DNA
<213> ORGANISM: Homo sapiens

<400> SEQUENCE: 410

```
gcaagtcgcg tgatttctac cacacctgct actgcctgag cggcctgtcc atagcccagc     60
acttcggcag cggagccatg ttgcatgatg tggtcctggg tgtgcccgaa aacgctctgc    120
agcccactca cccagtgtac aacattggac cagacaaggt gatccaggcc actacatact    180
ttctacagaa gccagtccca ggttttgagg agcttaagga tgagacatcg gcagagcctg    240
caaccgacta gaggacctgg gtcccggcag ctctttgctc acccatctcc ccagtcagac    300
aaggtttata cgtttcaata catactgcat tctgtgctac acaagcctta gcctcagtgg    360
agctgtggtt ctcttggtac tttcttgtca aacaaaacca atggctctgg gtttggagaa    420
cacagtggct ggttttaaaa ttctttccac acctgtcaa                           459
```

<210> SEQ ID NO 411
<211> LENGTH: 275
<212> TYPE: DNA
<213> ORGANISM: Homo sapiens

<400> SEQUENCE: 411

```
agagggcaag gggctggatg caggcagaga atgactttaa gaaaagattc tatgatccct     60
tcctttagta tggagctcga ttttccagct ggcgcttggt gagaaagtac ttgaagaact    120
catagacaga ccaagaaatg gcggtggagg gcatctggta gatgacacgc gcctggatgc    180
ctttgaagta gccggccagg ccgttgagct ggtacaccgt ccggaaggca ttggccatac    240
ccgacagccg gccgctgatg ttggccagcg agagg                               275
```

<210> SEQ ID NO 412
<211> LENGTH: 536
<212> TYPE: DNA
<213> ORGANISM: Homo sapiens

<400> SEQUENCE: 412

```
gcagataagc tccgtctgca gttccaggcc agccagaaac tcctgtgtcc acatagagct     60
gacgtgagaa atatctttca gcccaggaga gaggggtcct gatcttaacc ctttcctggg    120
```

```
tctcagacaa ctcagaaggt tgggggggata ccagagaggt ggtggaatag gaccgcccccc    180 tccttacttg tgggatcaaa tgctgtaatg gtggaggtgt gggcagagga gggaggcaag    240
tgtcctttga aagttgtgag agctcagagt ttctggggtc ctcattagga gcccccatcc    300
ctgtgttccc caagaattca gagaacagca ctggggctgg aatgatcttt aatgggccca    360
aggccaacag gcatatgcct cactactgcc tggagaaggg agagattcag gtcctccagc    420
agcctccctc acccagtatg ttttacagat tacgggggga ccgggtgagc cagtgacccc    480
ctgcagcccc cagcttcagg cctcagtgtc tgccagtcaa gcttcacagg cattgt        536
```

<210> SEQ ID NO 413
<211> LENGTH: 286
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, t or u
<220> FEATURE:
<221> NAME/KEY: misc_feature
<222> LOCATION: (121)..(121)
<223> OTHER INFORMATION: n is a, c, g, t or u

<400> SEQUENCE: 413

```
ttaatttctg tgaagagtgc ccctggtgtt tcatcttggc ctgttttgat gagaatgtta     60
tcntttgtgt ctggataacg cgtcagcttc ttaaagtaca tataaagata ttctgtcacc    120
nccccacatg cacacacttt taaaatctat ttttattctc ttgctaaagt tgtaattatg    180
tcaagaattt tccagctcta actgccttct tagtacatgt cttctgcct ttgaagcata     240 tgagtttgcc aaagtcattc tcccctaatg acatattgtg gactta                    286
```

<210> SEQ ID NO 414
<211> LENGTH: 166
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is a, c, g, t or u
<220> FEATURE:
<221> NAME/KEY: misc_feature
<222> LOCATION: (74)..(74)
<223> OTHER INFORMATION: n is a, c, g, t or u

<400> SEQUENCE: 414

```
gaaagacgga ggaaacaatc aaaatcncca ttctattgct ttgacacctt tactaggtga     60
attggtggca ttcncaaagc taatagggac gtttatatca agaaacattt ctgtatatat    120
tgttgaattt tagttgtaca tatactttgt atgttttgt cttctt                    166
```

<210> SEQ ID NO 415
<211> LENGTH: 552
<212> TYPE: DNA
<213> ORGANISM: Homo sapiens

<400> SEQUENCE: 415

```
tgcaggctag gggaggagcc accccgcgtt cctattgtg accaggccta tggggaggag      60
ctgtccatac gccaccgtga gacctgggcc tggctctcaa ggacagacac cgcctggcct    120
ggtgctccag gggtgaagca ggccagaatc ctgggggagc tgctcctggt ttgagctgca    180
ttcaggaagt gcgggacatg gtaggggagg caaaaagcct tggcactac cctccctgtg    240 gagctgttcg gtgtccgtcg agctagccac accctgacac catgttcaag ggtaccggaa    300
```

```
gagaagggtg tctgccccca acctcccctg tgggtgtcac tggccagatg tcatgaggga    360
agcaggcctt gtgagtggac actgaccatg agtccctggg gggagtgatc ccccaggcat    420
cgtgtgccat gttgcacttc tgcccaggca gcagggtggg tgggtaccat gggtgcccac    480
ccctccacca catggggccc caaagcactg caggccaagc agggcaaccc cacacccttg    540
acataaaagc at                                                        552

<210> SEQ ID NO 416
<211> LENGTH: 524
<212> TYPE: DNA
<213> ORGANISM: Homo sapiens

<400> SEQUENCE: 416
acgccgcgcg aaggtgatga gctcgcccgg ctgccctacc tacggacctg gttccgcacc     60
cgcagcgcca tcatcctgca cctcagcaac ggcagcgtgc agatcaactt cttccaggat    120
cacaccaagc tcatcttgtg cccactgatg gcagccgtga cctacatcga cgagaagcgg    180
gacttccgca cataccgcct gagtctcctg gaggagtacg gctgctgcaa ggagctggcc    240
agccggctcc gctacgcccg cactatggtg gacaagctgc tgagctcacg ctcggccagc    300
aaccgtctca aggcctccta atagctgccc tcccctccgg actggtgccc tcctcactcc    360
cacctgcatc tggggcccat actggttggc tcccgcggtg ccatgtctgc agtgtgcccc    420
ccagccccgg tggctgggca gagctgcatc atccttgcag gtgggggttg ctgtataagt    480 tattttgta catgttcggg tgtgggttct acagacttgt cccc                      524

<210> SEQ ID NO 417
<211> LENGTH: 378
<212> TYPE: DNA
<213> ORGANISM: Homo sapiens

<400> SEQUENCE: 417
aaatgactgc attcgtctct ttttaaagg tagagattaa actgtataga cagcataggg      60
atgaaaggaa ccaagcgttt ctgtgggatt gagactggta cgtgtacgat gaacctgctg    120
ctttgttttc tgagaagagg tttgaagaca ttttattaac agcttaattt ttctctttta    180
ctccatagga acttatttta atagtaacat taacaacaag aatactaaga ctgtttggga    240
attttaaaaa gctactagtg agaaaccaaa tgataggttg tagagcctga tgactccaaa    300
caaagccatc acccgcattc ttcctccttc ttctggtgct acagctccaa gggcccttca    360
ccttcatgtc tgaaatgg                                                  378

<210> SEQ ID NO 418
<211> LENGTH: 116
<212> TYPE: DNA
<213> ORGANISM: Homo sapiens

<400> SEQUENCE: 418
agtatggaag ctgagaagag ttattggaat cacccccacc gttgacagag gaaggcaggg     60
ggtgagaatt aactgcttga gggtaggaga gtctgagatg tgggggccct attccg        116

<210> SEQ ID NO 419
<211> LENGTH: 147
<212> TYPE: DNA
<213> ORGANISM: Homo sapiens

<400> SEQUENCE: 419
```

```
cctgagccac cacgcagaag aggcactttc caagttgttt accaagaatt tacattaaaa    60
taacaagcta ttgtttggct atacattgtt ctttgtatca catattccag gaactacagg   120
aaaataatgg gtgaggcagc tagttag                                       147
```

<210> SEQ ID NO 420
<211> LENGTH: 310
<212> TYPE: DNA
<213> ORGANISM: Homo sapiens

<400> SEQUENCE: 420

```
gaaattccat caatacatct agacagatgt ttgcttgtag ttttggtat ccaaaacctt    60 ttttccacac atcgcacaga tgcctttttt gtaggcacag ccctggcagt aatgagaacc   120
tggttggtgc acagaacttt tacaaattct acaagtggag aacttattct ttccatatgg   180
atcaaatctt gctttttttg aagtcaaagc tttatttca ttcagctttc ttccaccact   240
ttctgtggta ttcctagcac cacctttcca tgtatctgga gtgataacag taccaagttt   300
cttttcacat                                                         310
```

<210> SEQ ID NO 421
<211> LENGTH: 154
<212> TYPE: DNA
<213> ORGANISM: Homo sapiens
<220> FEATURE:
<221> NAME/KEY: misc_feature
<222> LOCATION: (68)..(68)
<223> OTHER INFORMATION: n is a, c, g, t or u

<400> SEQUENCE: 421

```
agatataact ggtagagcac gtcaaagata tacagaaata accagagaaa agtttgaggc    60
attaaaanaa gaaatatgg acctaaacaa tatgaatcaa agccttaccc ttgaactaaa   120
cacaatgaaa caagcaatga aagaactaca gtta                              154
```

<210> SEQ ID NO 422
<211> LENGTH: 444
<212> TYPE: DNA
<213> ORGANISM: Homo sapiens
<220> FEATURE:
<221> NAME/KEY: misc_feature
<222> LOCATION: (92)..(92)
<223> OTHER INFORMATION: n is a, c, g, t or u
<220> FEATURE:
<221> NAME/KEY: misc_feature
<222> LOCATION: (264)..(264)
<223> OTHER INFORMATION: n is a, c, g, t or u

<400> SEQUENCE: 422

```
tttttgtgca tgattacact ccactgacat cttccaagta ctgcatgtga ttgaataaga    60
aacaagaaag tgaccacacc aaagcctccc tnggctggtg tacagggatc aggtccacag   120
tggtgcagat tcaaccacca cccagggagt gcttgcagac tctgcataga tgttgctgca   180
tgcgtcccat gtgcctgtca gaatggcagt gtttaattct cttgaaagaa agttatttgc   240
tcactatccc cagcctcaag gagnccaagg aagagtcatt cacatggaag gtccgggact   300
ggtcagccac tctgactttt ctaccacatt aaattctcca ttacatctca ctattggtaa   360
tggcttaagt gtaaagagcc atgatgtgta tattaagcta tgtgccacat atttattttt   420
agactctcca cagcattcat gtca                                         444
```

<210> SEQ ID NO 423
<211> LENGTH: 510

```
<212> TYPE: DNA
<213> ORGANISM: Homo sapiens
<220> FEATURE:
<221> NAME/KEY: misc_feature
<222> LOCATION: (357)..(357)
<223> OTHER INFORMATION: n is a, c, g, t or u
<220> FEATURE:
<221> NAME/KEY: misc_feature
<222> LOCATION: (454)..(454)
<223> OTHER INFORMATION: n is a, c, g, t or u
<220> FEATURE:
<221> NAME/KEY: misc_feature
<222> LOCATION: (462)..(462)
<223> OTHER INFORMATION: n is a, c, g, t or u

<400> SEQUENCE: 423
gctttggact ggctcgcatg gaaaaccagg catttgatcc cgagaaaggg aacttcaaca    60
ctttgttttg caggctctgc gtgctgctgc tggtgtgtgc cgcccaggcc tggctcatgt   120
ggcgcttcat ccactcccag ctgcggcact ggcgggaata ctggaatgag cagagtgcaa   180
agcggagagt cccagccaca cccagactac cagccaggct catcaagagg gaatctggtt   240
accatgaaaa tggagtggtg aaggcagaga acggaacctc cccacggact aagaaactca   300
agtctcccta aggccaaagt gctaagaaca ggaatcctct tggtggggc cgagcanggg    360 gcaaggagcc caggccccct ccctgcctcc tccttcctgc ctgtgatgct ccgtctcaaa   420
cagccgaaac ctgtcttgca atgggggag gggngcgttt cnctttcctt cttcttggct   480
tcctcttatt cttccacaaa ccattctcaa                                    510

<210> SEQ ID NO 424
<211> LENGTH: 191
<212> TYPE: DNA
<213> ORGANISM: Homo sapiens

<400> SEQUENCE: 424
acattgtgcc tcaggatttt gataataatt ctggatattg gaacagaata gaaatgtact    60
gtcgagagct gacagaaagg tttgaagatg tttgggtggt atctgggcct ttgaccttac   120
ctcagactag aggcgatgga aagaaaatag ttagttacca ggtgattggc gaggacaacg   180
tggcagtccc c                                                        191

<210> SEQ ID NO 425
<211> LENGTH: 186
<212> TYPE: DNA
<213> ORGANISM: Homo sapiens

<400> SEQUENCE: 425
gcggtgtgga ccgaggaaca acttggaaga tctacctgca acacaacatt tgtgtcactg    60
tacagttttg tggactgagc gaggaaaaac aacaaataat ttaagttggc tagagcttct   120
gtattttcaa agactgccac gtgccttagg aatactgttt tatctccata ctttggatga   180
cttgtt                                                              186

<210> SEQ ID NO 426
<211> LENGTH: 465
<212> TYPE: DNA
<213> ORGANISM: Homo sapiens

<400> SEQUENCE: 426
gttttggacc aacaagtgcc tcctttggtg aaggtgacac atcatgtgac ctcttcagtg    60
accactctac ggtgtcgggc cttgaactac tacccccaga acatcaccat gaagtggctg   120
```

| | |
|---|---|
| aaggataagc agccaatgga tgccaaggag ttcgaaccta agacgtatt gcccaatggg | 180 |
| gatgggacct accagggctg gataaccttg gctgtacccc ctggggaaga gcagagatat | 240 |
| acgtgccagg tggagcaccc aggcctggat cagcccctca ttgtgatctg ggagccctca | 300 |
| ccgtctggca ccctagtcat tggagtcatc agtggaattg ctgttttgt cgtcatcttg | 360 |
| ttcattggaa ttttgttcat aatattaagg aagaggcagg gttcaagagg agccatgggg | 420 |
| cactacgtct tagctgaacg tgagtgacac gcagcctgca gactc | 465 |

<210> SEQ ID NO 427
<211> LENGTH: 480
<212> TYPE: DNA
<213> ORGANISM: Homo sapiens

<400> SEQUENCE: 427

| | |
|---|---|
| tcctttgtgt agcattatca gcctcggtct ggcctctggc acctcaccct tgccatggct | 60 |
| gaccccaccc attccaaggc ggggtcacgg taccagcagc acttggggtg aggcctccaa | 120 |
| agcttcctca gaattgtggc tgtgccacgc tggaccacag gtccccctc aagcatctcg | 180 |
| gggccctatt ctctctgagc acctggaggg ctggactcag gcttgtgcca gggcctgact | 240 |
| tgggcctggg ggccctagaa cactcctcct cctgagccta ctgccaaacg tcctcagtgt | 300 |
| tgtctgcacc tgctccgact ccttcagccg ccccattcag cgcccgctcc gtccagtgcc | 360 |
| cgccctgtgg ggcaaggcg gccgtgcctt actactctgt gtcttctgcc tcctctgagg | 420 |
| aatctggccc tgtctgacag tcccagaccc cccgttctct cctctttagt tgcatgagtt | 480 |

<210> SEQ ID NO 428
<211> LENGTH: 533
<212> TYPE: DNA
<213> ORGANISM: Homo sapiens

<400> SEQUENCE: 428

| | |
|---|---|
| ttcattcaca aacttccgct gtacctgcgt ctaaaaaggc ccaaacccga gagagacctg | 60 |
| atgccggagc ccctcactg ttcttctcca ggaagtggct ggggtcgggg aacagatgaa | 120 |
| tatttcatcc ggaagccgcc aagtgatttt ctcttcccca aacccaatag gttccagcct | 180 |
| gaactgtctg cccctgatct gcggcgattt atcgatggtc caaaccgggc tgtggccctg | 240 |
| cttccggagc tacgggaggt cgtctcctct atcagctaca tcgctcgaca gctgcaggaa | 300 |
| caggaggacc acgatgcgct gaaggaggac tggcagtttg tggccatggt agtggaccgc | 360 |
| ctcttcctgt ggacttcat catcttcacc agcgttggga ccctagtcat cttcctggac | 420 |
| gccacgtacc acttgccccc tccagacccc tttccttgaa gactggaggg ttgagaccag | 480 |
| gccccctgcc agttgaagtg agagagtttg tgatactgt caagccctat cct | 533 |

<210> SEQ ID NO 429
<211> LENGTH: 486
<212> TYPE: DNA
<213> ORGANISM: Homo sapiens

<400> SEQUENCE: 429

| | |
|---|---|
| gtgacctttc acgaacatgg gcatggctgc ggctccctcg tcatcaggtg catagcaagt | 60 |
| gaaagcaagt gttcacaacg gtgaaacttg agcgtcattt ttcttagtgt gccaagagtt | 120 |
| cgatgttagt gtttccattg tatttcttta cagtgtgcca ttctgttaga tactatcctt | 180 |
| ataattgatg agcaagacat actgaatgca tatttcggtt tgtgtatcca tgcacctacg | 240 |
| tcagaaaaca agtattgtca ggtattctct ccatagaaca gcactatcct catctctccc | 300 |

```
cagatgtgac tactgagggc agttctgagt gtttaatttc agactttttc ctctgcattt    360
acacacacac acacacacac acgcacacac acacaccaag taccagtata agcatctccc    420
atctgctttt cccattgcca tgcgtcctgg tcaagccccc ctcactctgt ttcctggtca    480
gcatgt                                                                486

<210> SEQ ID NO 430
<211> LENGTH: 97
<212> TYPE: DNA
<213> ORGANISM: Homo sapiens

<400> SEQUENCE: 430
tattagttaa ttagtgattt cacagtatcc tttcgcaggc cgatccccac tccaaccgtt    60
ccctcagcaa ccccaggggt gtcagacggg gcaccct                              97

<210> SEQ ID NO 431
<211> LENGTH: 241
<212> TYPE: DNA
<213> ORGANISM: Homo sapiens
<220> FEATURE:
<221> NAME/KEY: misc_feature
<222> LOCATION: (88)..(88)
<223> OTHER INFORMATION: n is a, c, g, t or u

<400> SEQUENCE: 431
gctgcctttg cactggcgaa gggaggggca ctggttatgt tgtttccatt cgacagtcct    60
tccaaaggct tccctccagc gccactancc aaatccagaa aagcgtcctc ctccagaagg    120
taccaccaaa cctttaaaac ctttaaaggc tcctccagtg tcagattcaa atccaacatt    180
tctgcgcttt gctttcttta tggctctatt cttcaagact tcctcactgg ccatggagaa    240
t                                                                     241

<210> SEQ ID NO 432
<211> LENGTH: 537
<212> TYPE: DNA
<213> ORGANISM: Homo sapiens

<400> SEQUENCE: 432
tgagcctgtg cgttttgcat actgggttgg tttgctgggg ctgcggtgac agcatatgcc    60
gcgagctggg ctttaacaga gatgtgtgct ctcacagctt tgcaggcggg ggtctgagat    120
cagggtgtcg cgggtgpgggg gtcactgctg aggccgtgag gggaatctgc tcaggcctgt    180
ccctggcttc tggggctgc tggtggtatt ttcagttcct tggtgtgtgg atacttcgcc    240
ccatctctgc cttcacctgt gtcctccctg tgtgggtgct ggtgtccaaa atttcccctt    300
ttcgtagtga caccagctgt gttggattgg ggcccaccct gctccagcat ggcctaatct    360
taactaatta catttgcaag gatcttatgt ccacaaaagt cacagtctga ggtgctgggg    420
gttaggactt caatatataa attttgcggt tacacaattc aatccatgac agaatccaaa    480
ggtttactct ggttataaaa acagtacaat aaaatattgt ttatagcctt ccctgta       537

<210> SEQ ID NO 433
<211> LENGTH: 355
<212> TYPE: DNA
<213> ORGANISM: Homo sapiens
<220> FEATURE:
<221> NAME/KEY: misc_feature
<222> LOCATION: (56)..(56)
<223> OTHER INFORMATION: n is a, c, g, t or u
<220> FEATURE:
```

```
<221> NAME/KEY: misc_feature
<222> LOCATION: (109)..(109)
<223> OTHER INFORMATION: n is a, c, g, t or u
<220> FEATURE:
<221> NAME/KEY: misc_feature
<222> LOCATION: (186)..(186)
<223> OTHER INFORMATION: n is a, c, g, t or u

<400> SEQUENCE: 433
gaaaacccgt tatgagacac aacttgaatt aaatgatgaa ctagaaaagc aaattnttta      60
tctcaaggag aaagtggaaa aaatccatgg aaactcttca gatagactnt cttctattcg     120
tgtctatgaa cgaatgccag tggaatcctt aaacacatta cttaaacagc tagaagaaga     180
aaagangact cttgaaagtc aagtgaaata ctatgcactt aaactggaac aagaatcaaa     240
ggcttaccag aagatcaaca atgaacgccg tacataccta gctgaaatgt ctcagggttc     300
tggtttacat caagtttcta aaaggcaaca ggtggatcaa ctgcctagga tgcaa         355

<210> SEQ ID NO 434
<211> LENGTH: 319
<212> TYPE: DNA
<213> ORGANISM: Homo sapiens

<400> SEQUENCE: 434
ggcaagaagc caggtaaggc atgcagtctt tctgttcccc gttgggggag tggtattaag      60
gaactgtgtc ttcaggatac agtgagctgt aaaaatagac aacaagaaca cggaaaactat    120 ggtagacgaa tgggctgagg acacagttca tgaaagagaa atatactcaa gatagaagaa    180
cctgcttcat cttagtggtg attttttgtaa aatgtaattt aaaatattcc ccgatgctgg    240
gagctaagta aaaataaat aagtaaataa aatacaaaat tacatgtaca tttaaatgtt      300
ttttctctat caagtttat                                                 319

<210> SEQ ID NO 435
<211> LENGTH: 511
<212> TYPE: DNA
<213> ORGANISM: Homo sapiens

<400> SEQUENCE: 435
cacgatgacc ccagacatga gatccatcac taataatagc tcagatcctt tcctcaatgg      60
agggccatat cattcgaggg agcagagcac tgacagtggc ctggggttag ggtgctacag     120
tgtccccaca actccggagg acttcctcag caatgtggat gagatggata caggagaaaa     180
cgcaggacaa acacccatga acatcaatcc ccaacagacc cgtttccctg atttccttga    240
ctgtcttcca ggaacaaacg ttgacttagg aactttggaa tctgaagacc tgatccccct    300
cttcaatgat gtagagtctg ctctgaacaa aagtgagccc tttctaacct ggctgtaatc    360
actaccattg taacttggat gtagccatga ccttacattt cctgggcctc ttggaaaaag    420
tgatggagca gagcaagtct gcaggtgcac cacttcccgc tccatgact cgtgctccct     480 cctttttatg ttgccagttt aatcattgcc t                                    511

<210> SEQ ID NO 436
<211> LENGTH: 515
<212> TYPE: DNA
<213> ORGANISM: Homo sapiens
<220> FEATURE:
<221> NAME/KEY: misc_feature
<222> LOCATION: (89)..(89)
<223> OTHER INFORMATION: n is a, c, g, t or u
<220> FEATURE:
<221> NAME/KEY: misc_feature
```

```
<222> LOCATION: (91)..(92)
<223> OTHER INFORMATION: n is a, c, g, t or u
<220> FEATURE:
<221> NAME/KEY: misc_feature
<222> LOCATION: (96)..(98)
<223> OTHER INFORMATION: n is a, c, g, t or u
<220> FEATURE:
<221> NAME/KEY: misc_feature
<222> LOCATION: (100)..(100)
<223> OTHER INFORMATION: n is a, c, g, t or u

<400> SEQUENCE: 436
taagatccag ggttccagga ctgccaccaa ctcctgtcca gctgctctat ccagtgtccc      60
gattcagcaa tgtcaaatcc ctccagcanc nntgcnnntn ccggatacga cagctcgtca     120
ggatagatca catcccagat ctcccactgc ctaaacctct gatctcttat atccgaaagt     180
tctactacta tgatcctcag gaagaggtat acctgtctct aaaggaagcg cagctcattt     240
ccaaacagaa gcaagaggtg gaaccctcca cgtagcgagg ggctccctgc tggtcaccac     300
caagggcatt tggttgccaa gctccagctt tgaagaacca aattaagcta ccatgaaaag     360
aagaggaaaa gtgagggaac aggaaggttg ggattctctg tgcagagact ttggttcccc     420
acgcagccct ggggcttgga agaagcacat gaccgtactc tgcgtggggc tccacctcac     480
acccacccct gggcatctta ggactggagg ggctc                                515

<210> SEQ ID NO 437
<211> LENGTH: 489
<212> TYPE: DNA
<213> ORGANISM: Homo sapiens

<400> SEQUENCE: 437
gctttgagga aaccactgtg caacttgaga tgtctgtggt tgtggggatg ttccatccct      60
ccgttcagtt gtgaagacct ctgctctgcc ctcagcaacc agagcctcgt cactctggac     120
ctgggtcaga atcccttggg gtctagtgga gtgaagatgc tgtttgaaac cttgacatgt     180
tccagtggca ccctccggac actcaggttg aaaatcgatg actttaatga tgaactcaat     240
aagctgctgg aagaaataga agaaaaaaac ccacaactga ttattgatac tgagaaacat     300
catccctggg cagaaaggcc ttcttctcat gacttcatga tctgaatccc ccgagtcat      360 tcattctcca tgaagtcatc gattttccag gtgttggtga actgcctgtg actcctctcc     420
tccccggccc ctacccctca gggataatga gttcattgct gggctagatg ttttagccat     480
gattctgcc                                                             489

<210> SEQ ID NO 438
<211> LENGTH: 580
<212> TYPE: DNA
<213> ORGANISM: Homo sapiens
<220> FEATURE:
<221> NAME/KEY: misc_feature
<222> LOCATION: (275)..(275)
<223> OTHER INFORMATION: n is a, c, g, t or u
<220> FEATURE:
<221> NAME/KEY: misc_feature
<222> LOCATION: (284)..(285)
<223> OTHER INFORMATION: n is a, c, g, t or u
<220> FEATURE:
<221> NAME/KEY: misc_feature
<222> LOCATION: (293)..(294)
<223> OTHER INFORMATION: n is a, c, g, t or u
<220> FEATURE:
<221> NAME/KEY: misc_feature
<222> LOCATION: (303)..(304)
<223> OTHER INFORMATION: n is a, c, g, t or u
<220> FEATURE:
```

<221> NAME/KEY: misc_feature
<222> LOCATION: (313)..(314)
<223> OTHER INFORMATION: n is a, c, g, t or u
<220> FEATURE:
<221> NAME/KEY: misc_feature
<222> LOCATION: (322)..(323)
<223> OTHER INFORMATION: n is a, c, g, t or u
<220> FEATURE:
<221> NAME/KEY: misc_feature
<222> LOCATION: (327)..(327)
<223> OTHER INFORMATION: n is a, c, g, t or u
<220> FEATURE:
<221> NAME/KEY: misc_feature
<222> LOCATION: (332)..(333)
<223> OTHER INFORMATION: n is a, c, g, t or u
<220> FEATURE:
<221> NAME/KEY: misc_feature
<222> LOCATION: (350)..(351)
<223> OTHER INFORMATION: n is a, c, g, t or u
<220> FEATURE:
<221> NAME/KEY: misc_feature
<222> LOCATION: (369)..(370)
<223> OTHER INFORMATION: n is a, c, g, t or u
<220> FEATURE:
<221> NAME/KEY: misc_feature
<222> LOCATION: (386)..(386)
<223> OTHER INFORMATION: n is a, c, g, t or u
<220> FEATURE:
<221> NAME/KEY: misc_feature
<222> LOCATION: (389)..(389)
<223> OTHER INFORMATION: n is a, c, g, t or u
<220> FEATURE:
<221> NAME/KEY: misc_feature
<222> LOCATION: (408)..(408)
<223> OTHER INFORMATION: n is a, c, g, t or u
<220> FEATURE:
<221> NAME/KEY: misc_feature
<222> LOCATION: (427)..(427)
<223> OTHER INFORMATION: n is a, c, g, t or u
<220> FEATURE:
<221> NAME/KEY: misc_feature
<222> LOCATION: (446)..(446)
<223> OTHER INFORMATION: n is a, c, g, t or u
<220> FEATURE:
<221> NAME/KEY: misc_feature
<222> LOCATION: (523)..(523)
<223> OTHER INFORMATION: n is a, c, g, t or u

<400> SEQUENCE: 438

```
agcgagaccc agactcgtac aacaaacacc tcttcgtgca cattgggcat gccaaccatt    60
cttacagtga cccattgctt gaatcagtgg acattcgtca gatttatgac aaatttcctg   120
aaaagaaagg tggcttaaag gaactgtttg gaaagggccc tcaaaatgcc ttcttcctcg   180
taaaattctg ggctgattta aactgcaata ttcaagatga tgctgggggct ttttatggtg   240 taaccagtca gtacgagagt tctgaaaata tgacngtcac ctgnnccacc aannttgct   300 ccnntgggaa gcnngtagta gnnaaantag anncggagta tgcaaggttn nagaatggcc   360
gatttgtann ccgaataaac cgctcnccna tgtgtgaata tatgatcnac ttcatccaca   420
agctcanaca cttaccagag aaatanatga tgaacagtgt tttggaaaac ttcacaattt   480
tattggtggt aacaaacagg gatacacaag aaactctact ctngcatggc ctgtgtgttt   540
gaagtttcaa atagtgaaca cggagcacaa catcatattt                          580
```

<210> SEQ ID NO 439
<211> LENGTH: 581
<212> TYPE: DNA
<213> ORGANISM: Homo sapiens

<400> SEQUENCE: 439

```
gcacggacac ctatgaagac cagcagtgga gaccccccaa gcccactggt gaaacagctg    60
```

```
agtgaagtat ttgaaactga agactctaaa tcaaatcttc ccccagagcc tgttctgccc      120
ccagaggcac ctttatcttc tgaattggac ttgcctctgg gtacccagtt atctgttgag      180
gaacagatgc caccttggaa ccagactgag ttccctcca aacaggtgtt ttccaaggag       240
gaagcaagac agcccacaga aaccccctgtg gccagccaga gctccgacaa gccctcaagg     300
gaccctgaga ctcccagatc ttcaggttct atgcgcaata gatggaaacc aaacagcagc     360
aaggtactag ggagatcccc cctcaccatc ctgcaggatg acaactcccc tggcaccctg      420
acactacgac agggtaagcg gccttcaccc ctaagtgaaa atgttagtga actaaaggaa      480
ggagccattc ttggaactgg acgacttctg aaaactggag gacgagcatg ggagcaaggc      540
caggaccatg acaaggaaaa tcagcacttt cccttggtgg a                         581

<210> SEQ ID NO 440
<211> LENGTH: 449
<212> TYPE: DNA
<213> ORGANISM: Homo sapiens

<400> SEQUENCE: 440
ggcgtataat tcagccctgt ttaaatatac ttgcctttca aattcttcaa gtaacatggg       60
aagtattctt gaaatgtcac attttctgcc ttccctctaa gtatgctttc tgaagaagtc      120
agggaaagtt agagtctgtg gcctgaggtg tctgctctgg gtggcgatag tgggcacctc      180
aggcaggtcg gtgacgttta gcacaggtgc cagggctcct gcctgctcct cctgtgttag      240
ctctgtgaag ttcatttagg aattttttt tcctatgcag tttaagaaat aatcctaatt       300
gttttttctt attacctaag caatatattt ttattatagc aacctcagaa agaaaaata      360 aaaggataat ttaaaaaact cattcatagt ctcagttacc cagataacct cggttgtcac      420
cttggagtat cttgttgtag tccctttac                                        449

<210> SEQ ID NO 441
<211> LENGTH: 457
<212> TYPE: DNA
<213> ORGANISM: Homo sapiens

<400> SEQUENCE: 441
agcagaggct catccgggag cagatacgcc aggagcgtga ccagaggttg agaggaaagg       60
cagaaaatac tgaaggccaa ggaaccccca aactaaagct aaaatggaag tgcaagaagg     120
aggatgagtc aaaaggtggc tactccaaag acgtcctcct acggcttttg cagaagtatg      180
gtgaggttct caacctggtg cttttccagta agaagccagg cactgctgtg gtggagtttg    240
caaccgtcaa ggcagcggag ctggctgtcc agaatgaagt tggcctggtg gataaccctc     300
tgaagatttc ctggttggag ggacagcccc aggatgccgt gggccgcagc cactcaggac      360
tgtcaaaggg ctcagtgctg tcagagaggg actacgagag cctcgtcatg atgcgcatgc     420
gccaggcggc cgagcggcaa cagctgatcg cacggat                              457

<210> SEQ ID NO 442
<211> LENGTH: 498
<212> TYPE: DNA
<213> ORGANISM: Homo sapiens

<400> SEQUENCE: 442
aaggctatta acgacgcgat ttcacaaagt cggcagagtt ctgcgggaaa tcccctggaa       60
agactcaatt aaagagcagt gaagagagtg cagatcccgt cactggaagt tcggaaaatg      120
```

```
cagtgtcatc ttcagaactg atgtcccaga ctcccagtga agttctgggt accaacgaga    180
atgagaaact gagccctaca agtaatacct catatagttt agaaaaaatc tccagtctgg    240
cccctcctag catggagtac tgcgttttac tcttctgctg ttgtatttgt ggttttgaat    300
caaccagcaa agaaaacctc ttggatcata tgaaagagca cgagggtgaa attgtaaaca    360
tcatcctgaa taaggaccac aatacagctc taaacacaaa ttaggtggaa taatgactcg    420
agcaggaaag cagtagaaga ggattccttc accacagttt cacctttacg ctgtcagaca    480
acttcctgcc acagaaga                                                  498
```

```
<210> SEQ ID NO 443
<211> LENGTH: 476
<212> TYPE: DNA
<213> ORGANISM: Homo sapiens
<220> FEATURE:
<221> NAME/KEY: misc_feature
<222> LOCATION: (73)..(73)
<223> OTHER INFORMATION: n is a, c, g, t or u
<220> FEATURE:
<221> NAME/KEY: misc_feature
<222> LOCATION: (243)..(243)
<223> OTHER INFORMATION: n is a, c, g, t or u
<220> FEATURE:
<221> NAME/KEY: misc_feature
<222> LOCATION: (245)..(245)
<223> OTHER INFORMATION: n is a, c, g, t or u
<220> FEATURE:
<221> NAME/KEY: misc_feature
<222> LOCATION: (269)..(269)
<223> OTHER INFORMATION: n is a, c, g, t or u
<220> FEATURE:
<221> NAME/KEY: misc_feature
<222> LOCATION: (320)..(320)
<223> OTHER INFORMATION: n is a, c, g, t or u
<220> FEATURE:
<221> NAME/KEY: misc_feature
<222> LOCATION: (362)..(362)
<223> OTHER INFORMATION: n is a, c, g, t or u
<220> FEATURE:
<221> NAME/KEY: misc_feature
<222> LOCATION: (370)..(370)
<223> OTHER INFORMATION: n is a, c, g, t or u
<220> FEATURE:
<221> NAME/KEY: misc_feature
<222> LOCATION: (390)..(390)
<223> OTHER INFORMATION: n is a, c, g, t or u
<220> FEATURE:
<221> NAME/KEY: misc_feature
<222> LOCATION: (398)..(398)
<223> OTHER INFORMATION: n is a, c, g, t or u
<220> FEATURE:
<221> NAME/KEY: misc_feature
<222> LOCATION: (419)..(420)
<223> OTHER INFORMATION: n is a, c, g, t or u
<220> FEATURE:
<221> NAME/KEY: misc_feature
<222> LOCATION: (429)..(429)
<223> OTHER INFORMATION: n is a, c, g, t or u
<220> FEATURE:
<221> NAME/KEY: misc_feature
<222> LOCATION: (438)..(438)
<223> OTHER INFORMATION: n is a, c, g, t or u

<400> SEQUENCE: 443
```

```
caaccgagag ggccggcagg agcttgaaat cattattgga gatgaacaca tttcttttac    60
aacatcaaaa atnggttccc ttattgatgt cagtcaatcc aaggatccag aaggcttatg   120
agtattttat tatcctgtcc aggaccctga agtgtttggt cttcagtctt actggattac   180
acttcaagat taaaccaatc taaactgaat attgatgtgg acatgggggg gtgggagtag   240
ttntnaatta ccattatcaa gaacattttg tgtcagggca gtatattttt ataaactata   300
```

-continued

```
tatgattatc tttaataaan tatgtgataa aatttaaaaa aagcaaaaca aaacttctag    360
angaataccn tcaaaacctt ggtgagggan attcttanac agcacaaaaa tcattaggnn    420
aagatcaant ttaacatngt caaattaatc aatgacttct cttcctcaaa agacat       476
```

<210> SEQ ID NO 444
<211> LENGTH: 133
<212> TYPE: DNA
<213> ORGANISM: Homo sapiens

<400> SEQUENCE: 444

```
ttccagagct acccagacca tatggtgcac ccacagatcc agctgcagct ggtcctttag    60
gtccatgggg atccatgtct tctggacctt gggcgccagg aatgggaggg cagtatccta   120
cccctaatat gcc                                                      133
```

<210> SEQ ID NO 445
<211> LENGTH: 353
<212> TYPE: DNA
<213> ORGANISM: Homo sapiens

<400> SEQUENCE: 445

```
cgccgctgcg aattctcgga caaaactgtc aacagcccgg gcgcgccttt tggctctgcg    60
ggtccctcta tttatgcaaa gccgacctat gctacagccc cccaaccccc gacctggggt   120
agggaggaag agggtgccgg ggaagggagt ccgccctgtc caggcactag aggctcsctt   180
gacgtttggc agatgaaaaa caactaagcc ttttttgaggt gtagagattc tcaggtccag   240
gcgttaaaaa ataatggtca aaagaataat acaaaaatag taaaggtctt gaagaatgcc   300
agcgaagcaa ttcttttta tttgaggaca cttgtctggt gtacttttc atg            353
```

<210> SEQ ID NO 446
<211> LENGTH: 416
<212> TYPE: DNA
<213> ORGANISM: Homo sapiens
<220> FEATURE:
<221> NAME/KEY: misc_feature
<222> LOCATION: (275)..(278)
<223> OTHER INFORMATION: n is a, c, g, t or u

<400> SEQUENCE: 446

```
gaggaagata tcctggctgg cactctttca gttgacagag agtgacctca ggctggggcg    60
gctcctcctc cgtgtggccc cggatcagca caccaggctg ctgcctttcg cttttacag    120 tcttctctcc tacttccatg aagacgcggc catcaggaa gaggccttcc tgcatgttgc    180
tgtggacatg tacttgaagc tggtccagct cttcgtggct ggggatacaa gcacagtttc   240
acctccagct ggcaggagcc tggagctcaa gggtnnnnca gggcaacccc gtggaactga   300
taacaaaagc tcgtcttttt ctgctgcagt taatacctcg gtgcccgaaa aagagcttct   360
cacacgtggc agagctgctg gctgatcgtg gggactgcga cccagaggtg agcgcc       416
```

<210> SEQ ID NO 447
<211> LENGTH: 409
<212> TYPE: DNA
<213> ORGANISM: Homo sapiens

<400> SEQUENCE: 447

```
gctcccccaca tgctggtggt gtactctgct aatggagaga tgtttaaact gagagctgct    60
gatgcaaaag agaaacaatt ctgggtgact cagcttcgag cttgtgccaa ataccacatg   120
```

| | |
|---|---|
| gaaatgaatt ctaagagtgc tccaagctcc cgaagccgaa gtctcacttt gctcccacat | 180 |
| ggaacaccca attctgcgtc tccctgtagc cagagacacc tcagtgtggg ggcccccggt | 240 |
| gttgtcacaa tcacgcatca caagtcgcct gcagccgccc gaagagccaa gagtcagtat | 300 |
| tccggccagc ttcacgaagt cagagaggta cacactctcc tgacagagga aagctgtttg | 360 |
| ctgcactggt ttactggata gattaactgg gttgaggctg tgtaattta | 409 |

<210> SEQ ID NO 448
<211> LENGTH: 316
<212> TYPE: DNA
<213> ORGANISM: Homo sapiens

<400> SEQUENCE: 448

| | |
|---|---|
| gaggggcaca tgcaagtcac caaagtggga agccttcacc aaggccacac ccaaagtcta | 60 |
| ctgattgtct gtccaaagtt cgttgattcc tggccatgaa caagcacaat agaaaaagac | 120 |
| acagggtcct agtggctaca agtcaatgtg aattggcaca tggtctagca gttttaaaat | 180 |
| ctgacagtag agtatggcaa tgggcaaggg ccaagaagtc ctgagatggg aggtcagcgc | 240 |
| tctaactggg ctcagtggag gtctgtgacc agtgtctgga cactagctac aggggaccgg | 300 |
| gcagaggatt ctgggc | 316 |

<210> SEQ ID NO 449
<211> LENGTH: 473
<212> TYPE: DNA
<213> ORGANISM: Homo sapiens
<220> FEATURE:
<221> NAME/KEY: misc_feature
<222> LOCATION: (241)..(241)
<223> OTHER INFORMATION: n is a, c, g, t or u
<220> FEATURE:
<221> NAME/KEY: misc_feature
<222> LOCATION: (341)..(341)
<223> OTHER INFORMATION: n is a, c, g, t or u
<220> FEATURE:
<221> NAME/KEY: misc_feature
<222> LOCATION: (384)..(385)
<223> OTHER INFORMATION: n is a, c, g, t or u
<220> FEATURE:
<221> NAME/KEY: misc_feature
<222> LOCATION: (417)..(417)
<223> OTHER INFORMATION: n is a, c, g, t or u
<220> FEATURE:
<221> NAME/KEY: misc_feature
<222> LOCATION: (420)..(420)
<223> OTHER INFORMATION: n is a, c, g, t or u
<220> FEATURE:
<221> NAME/KEY: misc_feature
<222> LOCATION: (427)..(427)
<223> OTHER INFORMATION: n is a, c, g, t or u
<220> FEATURE:
<221> NAME/KEY: misc_feature
<222> LOCATION: (430)..(430)
<223> OTHER INFORMATION: n is a, c, g, t or u

<400> SEQUENCE: 449

| | |
|---|---|
| gcactttagt gattgctttt attacattag ttaagatgtc ttgagagacc atctcctatc | 60 |
| ttttatttca ttcatatcct ccgcccttttt tgtcctagag tgagagtttg gaaggtgtcc | 120 |
| aaatttaatg tagacattat cttttggctc tgaagaagca acatgactaa gagacgcacc | 180 |
| ttgctgcagt gtccagaagc ggcctgtgcg ttcccttcag tactgcagcg ccacccagtg | 240 |
| naaggacact cttggctcgt ttgggctcaa ggcaccgcag cctgtcagcc aacattgcct | 300 |
| tgcatttgta ccttattgat cttgtgccat ggaagtctca nagatctttc gttggttgtt | 360 |
| tctctgagct ttgttactga aatnngcctc gtggggagca tcagagaagg ccaggangan | 420 |

```
tggtgtnttn ccctagactc tgtaaccacc tctctgtctt tgtccttcct gag        473
```

<210> SEQ ID NO 450
<211> LENGTH: 512
<212> TYPE: DNA
<213> ORGANISM: Homo sapiens
<220> FEATURE:
<221> NAME/KEY: misc_feature
<222> LOCATION: (363)..(363)
<223> OTHER INFORMATION: n is a, c, g, t or u

<400> SEQUENCE: 450

```
gggaagtagg tgatgccagc cctcaagtct gtcttcagcc agggacttga gaagttatat     60
tgggcagtgg ctccaatctg tggaccagta tttcagcttt ccctgaagat caggcagggt    120
gccattcatt gtctttctct cctagccccc tcaggaaaga aggactatat ttgtactgta    180
ccctaggggt tctggaaggg aaaacatgga atcaggattc tatagactga taggccctat    240
ccacaagggc catgactggg aaaaggtatg ggagcagaag gagaattggg attttagggt    300
gcagctacgc tcaccctaaa cttttggtgg cctggggcat gtcttgaggc ccagactgtt    360
aancaggctc tgctggcctg tttactcgtc accacctctg cacctgctgt cttgagactc    420
catccagccc caggcacgcc acctgctcct gagcctccac tatctccctg tgacgggtga    480
acttcgtgta ctgtgtctcg ggtccatata tg                                  512
```

<210> SEQ ID NO 451
<211> LENGTH: 397
<212> TYPE: DNA
<213> ORGANISM: Homo sapiens

<400> SEQUENCE: 451

```
gtgaacattt caaccagcct tatagctgtt ctcatcatca ccttctgcat tgtgaccgtg     60
cttggaaggg aggctctcac caaaggggcg ctgtgggcag tctttctgct cgcagggtct    120
gccctcctct gtgccgtggt cacgggcgtc atctggaggc agcccgagag caagaccaag    180
ctctcattta aggttccctt cctgccagtg ctccccatcc tgagcatctt cgtgaacgtc    240
tatctcatga tgcagctgga ccagggcacc tgggtccggt ttgctgtgtg gatgctgata    300
ggcttcatca tctactttgg ctatggcctg tggcacagcg aggaggcgtc cctggatgcc    360
gaccaagcaa ggactcctga cggcaacttg gaccagt                             397
```

<210> SEQ ID NO 452
<211> LENGTH: 426
<212> TYPE: DNA
<213> ORGANISM: Homo sapiens
<220> FEATURE:
<221> NAME/KEY: misc_feature
<222> LOCATION: (32)..(32)
<223> OTHER INFORMATION: n is a, c, g, t or u

<400> SEQUENCE: 452

```
gactgtaggt gcgtgggaga aactttgcag gntgggacc cggcggctgc tggccggtag      60
tgactggtgg gcgcgctcga ggactccaag gggcgcagcc cggggcaga cccttgggtc     120
gggcggggat cttacgcttc ccttacccgc cccttttgt ctttcacctc agcccgccg      180
gctgctgtgg gagcggcggc cgtccctctc ctggaggtcg tctcctggca tcctcgggc     240
cgcaggaagg aagaggaggc agcggccgga gccctggtgg gcggcctgag gtgagagccc    300
gaccggcccc tttgggaata tggcgaccgg tggctaccgg accagcagcg gcctcggcgg    360
```

| | |
|---|---|
| cagcaccaca gacttcctgg aggagtggaa ggcgaaacgc gagaagatgc gcgccaagca | 420 |
| gaaccc | 426 |

<210> SEQ ID NO 453
<211> LENGTH: 384
<212> TYPE: DNA
<213> ORGANISM: Homo sapiens

<400> SEQUENCE: 453

| | |
|---|---|
| ctaaagaaag tacacacact ctctcgctct ctctcggtct tataaaactc gttggtgtct | 60 |
| tataaaacaa acagtgataa tctcaagtta gaaacagta ggtcctgaga accataagaa | 120 |
| aaatgactgg tgtgatgttg agtaacaagt tggtacagtt actttagcta tttattaact | 180 |
| tgctcatctc atagaacatt ttaatagatt tttcacacac ctcattatta aaaaaaaaca | 240 |
| aacatgctgg tgtcttggtt acccattatt cctctgtacc tgaattcagg ttggtttttc | 300 |
| tatttggaaa agactttata aatgttggct taaaagagg ttgagcacca gaatctcaga | 360 |
| atttaccacc aaagaactca tcca | 384 |

<210> SEQ ID NO 454
<211> LENGTH: 407
<212> TYPE: DNA
<213> ORGANISM: Homo sapiens

<400> SEQUENCE: 454

| | |
|---|---|
| agcataatga agcctgcatg tgcccagctt caataattac caatatcttg ccagttttgt | 60 |
| ttcgtttctc ctttgattct ctgtattgag caagtcttag acatcatacg tttcccgcgt | 120 |
| aagtaccta ttctacatca ttaaccagta aggactttt aattaaccac aataccacta | 180 |
| tcacacctaa taatagtaat tccttatgga tcttttcttt agacctattt ttgaaggcat | 240 |
| aaaagcagtt gagtttctgg agaattttg gatggtgatt aatgacttga ctggctgctc | 300 |
| ttcccagagc tgtggcagct ctccccccgt agaagatggg gtttgtattg gcgcaccaag | 360 |
| atctccaaca gccagtgtgt gtttcccatt tcctgtaggt tccatca | 407 |

<210> SEQ ID NO 455
<211> LENGTH: 223
<212> TYPE: DNA
<213> ORGANISM: Homo sapiens

<400> SEQUENCE: 455

| | |
|---|---|
| tagtcagagt gacccatgta tctgggaaga ctctagtctg gactgtggcc cagcttgggg | 60 |
| accttgtgtg ctcagatcat cttcaggaag gaaaaggcat cctggagaca ggagtccatt | 120 |
| cactcctctg ctctctaccc actcatttgc ttgccaaact tagctttgcc agtgatagtc | 180 |
| aatattaaag tgtactttt tccccttaa tccaatatag ttg | 223 |

<210> SEQ ID NO 456
<211> LENGTH: 160
<212> TYPE: DNA
<213> ORGANISM: Homo sapiens

<400> SEQUENCE: 456

| | |
|---|---|
| tataattata accttaccgc atggacagtt ttgaatccta tgctaattgg ggtaattaag | 60 |
| tcaattattt catatgttat gttctcttca tgtgcatttt tcaatgatat attatgttcc | 120 |
| attgtgttgg aatgtgaatg ttcaattact tttcccata | 160 |

<210> SEQ ID NO 457
<211> LENGTH: 465
<212> TYPE: DNA
<213> ORGANISM: Homo sapiens

<400> SEQUENCE: 457

```
ccacatccat ggcctaggag ctactgggca ggttcccggc cacacatctg gtgggctgtt      60
ttgttttttt ttttcctctt cccccagatg tcttgacggg atcactgggg ctctttgtga     120
gtgagggtgg ccaaactacc gccggaggag atggggtctc agagcgagag ctgcggaggg     180 ggagggaag aagaaggcct cacttttgct gctgcgggc ccacacagcc gctgctactt       240 tgggggggtgg ggaaggggcc aagctgcaga cacacacagt cattcatttc tgtccacacc    300
cctgtgggtg gcgggtgtgc gtgtgtgtgc ttgtgtgtgc gcacgtgtcg gcgctcacac     360
acacatgcta gcccactgat gcacccagcc cagggctggc agtctttgca gcgtggggcc     420
gtctcaccct ggagcctgga gaggatctat gcttgtttgt ttttg                     465
```

<210> SEQ ID NO 458
<211> LENGTH: 212
<212> TYPE: DNA
<213> ORGANISM: Homo sapiens
<220> FEATURE:
<221> NAME/KEY: misc_feature
<222> LOCATION: (122)..(122)
<223> OTHER INFORMATION: n is a, c, g, t or u
<220> FEATURE:
<221> NAME/KEY: misc_feature
<222> LOCATION: (158)..(158)
<223> OTHER INFORMATION: n is a, c, g, t or u

<400> SEQUENCE: 458

```
gtgccgctgg cacccgggaa gacgctgggg gccggcgctg tagagccggg catgggctgg      60
gatgtgtttg gattccaatc cgggcctgac accagttcag tgacctcggg aagttcccca    120 anctccggg cctgtttcct ccctctgaag tggcgacnag tagtagaacc gacctcgtag     180
gctcatcggg aggtcctgat gggagaaccc at                                    212
```

<210> SEQ ID NO 459
<211> LENGTH: 342
<212> TYPE: DNA
<213> ORGANISM: Homo sapiens
<220> FEATURE:
<221> NAME/KEY: misc_feature
<222> LOCATION: (161)..(162)
<223> OTHER INFORMATION: n is a, c, g, t or u

<400> SEQUENCE: 459

```
ggttgtactc aagatgtttt cctggaaaaa ttcattctgc tttctgacca ggatttccag      60
aaactctgac ccttctaaga ggtctgggtg gaattgtgat ggtgattctg ctagtagaca    120
gtgtaacttc tgcgtctaca aaagaggat aggccgtcac nnctcacatg gctttgcgtg    180
aaagcccaat ggtactgtct ctatggcaga gatgaggaag gaacaccagc gtcctccaac    240
tttcctgttc ttcctttggg ttaatggcca ctgtaaggaa acagttttct gccacgtgtg    300
gggtgatttg aatgtaaaat gcccaactct catagcaggc tg                        342
```

<210> SEQ ID NO 460
<211> LENGTH: 519
<212> TYPE: DNA
<213> ORGANISM: Homo sapiens

<400> SEQUENCE: 460

| | |
|---|---:|
| aaggggaaga tttgctgctg ctgccgggcc aagttcccgc tgttctcgtg gccgcccagc | 60 |
| tgtctcttct gcaagagagc cgtctgcact tcctgtagca taaagatgaa gatgccttct | 120 |
| aagaaatttg gacacatccc tgtctacaca ctgggctttg agagtcctca gagggtatca | 180 |
| gctgccaaaa ccgcgccaat ccagagaaga gacatctttc agtctctgca agggccacag | 240 |
| tggcagagcg tggaggaggc gttccccac atctactccc acggctgtgt cctgaaggat | 300 |
| gtctgcagtg agtgcaccag ctttgtggca gacgtggtgc gttccagccg caagagcgtg | 360 |
| gacgtcctca acactacgcc acgacgcagt cgccagaccc aatccctcta catccctaac | 420 |
| accaggactc ttgacttcaa gtgacagccc caggtggcca ggcctccagg aggcaccagg | 480 |
| caggccctgt atcaggctag gacgctctga gctgtgcat | 519 |

<210> SEQ ID NO 461
<211> LENGTH: 208
<212> TYPE: DNA
<213> ORGANISM: Homo sapiens

<400> SEQUENCE: 461

| | |
|---|---:|
| tcccccctct gaattttact gatgaagaaa ctgaggccac agagctaaag tgacttttcc | 60 |
| caaggtcgcc cagcgaggac gtgggacttc tcagacgtca ggagagtgat gtgagggagc | 120 |
| tgtgtgacca tagaaagtga cgtgttaaaa accagcgctg ccctctttga aagccaggga | 180 |
| gcatcattca tttagcctgc tgagaaga | 208 |

<210> SEQ ID NO 462
<211> LENGTH: 532
<212> TYPE: DNA
<213> ORGANISM: Homo sapiens

<400> SEQUENCE: 462

| | |
|---|---:|
| ctcagcattt agtgaaggta attccaaaat actggtatca gtactcttat ttataagtgt | 60 |
| acggaatgca taacatgaac attagtcaaa gaacttttaa tataattcac tttttaagtg | 120 |
| ttaaaattta aaggtcaagt aaaattgtaa atttgtaata tggaaacatt aagcgtcatt | 180 |
| atcatacaaa ttattagcag ataaccttaa taaaaataaa cgtttgcggg ttttttttga | 240 |
| gacagggtct cgctttgtca cctaagctgg agtgcagtgc gcgatctcgg ctcactgcaa | 300 |
| cttccgcctc ctgggatcaa gtgattctcc tgccttagcc tcctgagtat ctgggtttac | 360 |
| aggtgtgtac cgccacaccc gtctctacta aaaatacaaa aacaaaaaa agattagctg | 420 |
| ggcgtggtgg caggtgcctg tggtcccagc tgctcgggag gctgaggcag gagaatagca | 480 |
| tggacctggg aggcggagct tgcagtgagc tgaaatggtg ccactgcact cc | 532 |

<210> SEQ ID NO 463
<211> LENGTH: 542
<212> TYPE: DNA
<213> ORGANISM: Homo sapiens

<400> SEQUENCE: 463

| | |
|---|---:|
| attatcgatc atgtctattg ctccccgtcc cttcgctgcg ttcagactgc acacaatatc | 60 |
| ttgaaaggtt tacaacaaga aaatcacttg aagatccgtg tagagcccgg cttatttgag | 120 |
| tggacaaaat gggttgctgg gagcacatta cctgcatgga tacctccatc agagttagct | 180 |
| gcagccaacc tgagtgttga tacaacctac agacctcaca ttccaatcag caaattagtt | 240 |
| gtttcagaat cctatgatac ttatatcagt agaagtttcc aagtaacaaa agaaataata | 300 |
| agtgaatgta aaagtaaagg aaataacatc ctgattgtgg cccacgcatc ttcccttgaa | 360 |

-continued

| gcgtgtacct gccaacttca gggcctgtca cctcagaact ccaaggactt cgtacaaatg | 420 |
| gtccgaaaga tcccatatct gggattttgt tcctgtgaag aattaggaga aactggaata | 480 |
| tggcagctga cagatccacc aatccttcct cttacccatg gaccaactgg gggcttcaac | 540 |
| tg | 542 |

<210> SEQ ID NO 464
<211> LENGTH: 451
<212> TYPE: DNA
<213> ORGANISM: Homo sapiens
<220> FEATURE:
<221> NAME/KEY: misc_feature
<222> LOCATION: (368)..(368)
<223> OTHER INFORMATION: n is a, c, g, t or u

<400> SEQUENCE: 464

| cagccccatg acagcgaagg gacctttctg tccccgcccc tgtccctgtg ctgggcccac | 60 |
| gtactcaccc acgtactggt gcccggctcc cctgggcacc cagagccccc cagataggcc | 120 |
| ggtggaggag gtggaggagc tgtcccccca aaactactgg cctgtggtct ggactccagg | 180 |
| gccccatttc tgatgtcgcc aggtgtgcct gagcccatcg gggccaggcc tgaggaagtg | 240 |
| tttcttggga ggatgggatg acccccctgtt cccaagagat ggcagcacag tggaggccat | 300 |
| ggtggaaaag gccctgccat ggggtccttg agggccagga cagcctgagg gagggatggt | 360 |
| ggccactncc cacaagggc ctggtgggaa cgggtcccag gacagactca tagctagacc | 420 |
| ccgttggcgg cctctgtgtt gaaccagaac t | 451 |

<210> SEQ ID NO 465
<211> LENGTH: 467
<212> TYPE: DNA
<213> ORGANISM: Homo sapiens

<400> SEQUENCE: 465

| ggccccaggc agttttatga tgacacctgt gttgtcccag aaaaattcga tggagacatc | 60 |
| aaacaagagc caggaatgta tcgggaagga cccacatacc aacggcgagg atcacttcag | 120 |
| ctctggcagt ttttggtagc tcttctggat gacccggcaa attctcattt tattgcctgg | 180 |
| actggtcgag gcatggaatt taaactgatt gagcctgaag aggtggcccg acgttggggc | 240 |
| attcagaaaa acaggccagc tatgaactat gataaactta gccgttcact ccgctattac | 300 |
| tatgagaaag gaattatgca aaaggtggct ggagagagat atgtctacaa gtttgtgtgt | 360 |
| gatccagaag ccctttctc catggccttt ccagataatc agcgtccact gctgaagaca | 420 |
| gacatggaac gtcacatcaa cgaggaggac acagtgcctc tttctca | 467 |

<210> SEQ ID NO 466
<211> LENGTH: 405
<212> TYPE: DNA
<213> ORGANISM: Homo sapiens
<220> FEATURE:
<221> NAME/KEY: misc_feature
<222> LOCATION: (162)..(162)
<223> OTHER INFORMATION: n is a, c, g, t or u
<220> FEATURE:
<221> NAME/KEY: misc_feature
<222> LOCATION: (301)..(301)
<223> OTHER INFORMATION: n is a, c, g, t or u

<400> SEQUENCE: 466

| catacaccta ttaccataca ggggaagtcc ccaagctctc cggcctcaca gactctcacc | 60 |

-continued

| | |
|---|---|
| cacgggcaga gcattcttgg ctgattgagg ggaagttcca gcaatcagca caagtgttct | 120 |
| ttatacccca aatcactaaa acatatagag gggtctatgt cngtttcatc cataactcag | 180 |
| ccactggtgg aacaaatctc ataatcaaga ggatcatagt ccctggtaag tggatccctg | 240 |
| gagcattggc accatgtttt ccagtaaagt ctatctagct gtcagggaag agccacctgc | 300 |
| nctctgcaaa gggagaggga aaatcaaaac ccaggaaagg gaatatgttt ctgctccaaa | 360 |
| accaccagct tctgcctgtc cccttcactc tttctagatc attct | 405 |

<210> SEQ ID NO 467
<211> LENGTH: 110
<212> TYPE: DNA
<213> ORGANISM: Homo sapiens

<400> SEQUENCE: 467

| | |
|---|---|
| gaaagagcga gagaagggga aagacaagtc gggagaggcc ggtaggcgtg aggcgggcct | 60 |
| gaagcggcag cgggcggcct tcgtccggcg agagctaggc cgaggacccg | 110 |

<210> SEQ ID NO 468
<211> LENGTH: 204
<212> TYPE: DNA
<213> ORGANISM: Homo sapiens

<400> SEQUENCE: 468

| | |
|---|---|
| ctgcccccca gggctagtga agtggcctct tggataccag ctcaggggac actgccccca | 60 |
| caggagttgt gagccctcta gggcaggggtg ggagccggga ccctcaggtg tagctgagct | 120 |
| gtgacattgc tggtcatcct tggtgctctt gcttttttga agatgctttt ttttttttt | 180 |
| aactgacgta gaatgaagaa ctgc | 204 |

<210> SEQ ID NO 469
<211> LENGTH: 139
<212> TYPE: DNA
<213> ORGANISM: Homo sapiens

<400> SEQUENCE: 469

| | |
|---|---|
| tcagatagga aggatggata tgtctttatc tacagcagaa gttagttacc ctttcatgag | 60 |
| gtgattagtt tacttctagg tggaaaaaga gaggactttg aacttggtgt tgtcacagga | 120 |
| gctgctctca tggacaaga | 139 |

<210> SEQ ID NO 470
<211> LENGTH: 115
<212> TYPE: DNA
<213> ORGANISM: Homo sapiens
<220> FEATURE:
<221> NAME/KEY: misc_feature
<222> LOCATION: (81)..(81)
<223> OTHER INFORMATION: n is a, c, g, t or u

<400> SEQUENCE: 470

| | |
|---|---|
| ctcagagatt actcagccag acagagatat tccactggtg cgaaagttac gttccattca | 60 |
| cagctttgag ctggaaaaac ntctgaccct ggagccaaag ccagacactg acaag | 115 |

<210> SEQ ID NO 471
<211> LENGTH: 475
<212> TYPE: DNA
<213> ORGANISM: Homo sapiens

<400> SEQUENCE: 471

| | |
|---|---|
| cagcgcctcc ggtttataagt tgaagaaata agaccagttt ccaaataaat gacaaagagc | 60 |

```
ttggtattcc tgcaggcatc agaatcacct ggaggaggag atgctgctgc tggtggtggc    120
ccagagacca cacattgaga accactgctc tagaaaacca tttgtctttg ctgatggaga    180
aacctggctc taatagaagg cttgtatgt gtccaggaag tctagtgaat tcgaccatga     240
atccagacat ggccagtggc taaatcctgt gggaagacac tgtgcttctc tctgacccat    300
gaacactctg ctagtcaagc tctctgtcac aaagacaact tgaagagaca gagtggacct    360
cacagaagat accatcgtca ctcttaccaa tgcaactgtg gtgaacagga ccactattat    420
tccttagatc aaaaggacag cacattcaac agcatcctca tggcatgcca gcaat         475
```

<210> SEQ ID NO 472
<211> LENGTH: 446
<212> TYPE: DNA
<213> ORGANISM: Homo sapiens

<400> SEQUENCE: 472

```
cggcttgttg ggaccaccaa ccaaggggac cagcgcatcc tgcgcagcag cgcccctccc    60
tccctggctg gccctgctgt tagtcacaga ggccgcaagg ccaagacgtg agtgggctgc    120
ccctccacct aggcttttcca ccgtggccac tccctccatg accaggcctg actctgttaa    180
ccactacttg aagtcttgag ggggaaagcc tccaggagaa catagggggcc ttctcccttc    240 ttcccaccaa agtagggggt aggcaactgg ttgtcatgga aatggggatc atcacagtcc    300 ccttccccctt caccccacgt ggctgggcag tgttaagggt ggcaagatag tctctgtccc    360 caccccccttg tacttgattc cccagctgtc tttcacacag ccccccaccc ttaggggaag    420
ggggaggggc ttctctacaa tgaggt                                         446
```

<210> SEQ ID NO 473
<211> LENGTH: 443
<212> TYPE: DNA
<213> ORGANISM: Homo sapiens

<400> SEQUENCE: 473

```
gagacttggt ggtctgagct gtcccaagtc ctccggttct tcctcgggat tggcgggtcc    60
acttgccagg gctctggggg cagatttgtg ggacctcag cctgcaccct cttctcctct     120
ggcttccctc tctgaaatag ccgaactcca ggctgggctg agccaaagcc agagtggcca    180
cggcccaggg agggtgagct ggtgcctgct ttgacgggcc aggccctgga gggcagagac    240
aatcacgggc ggtcctgcac agattcccag gccagggctg ggtcacagga aggaaacaac    300 atttttcttga aagggaaac gtctcccaga tcgctccctt ggctttgagg ccgaagctgc    360
tgtgactgtg tccccttact gagcgcaagc cacagcctgt cttgtcaggt ggaccctgta    420
aatacatcct ttttctgcta acc                                           443
```

<210> SEQ ID NO 474
<211> LENGTH: 465
<212> TYPE: DNA
<213> ORGANISM: Homo sapiens

<400> SEQUENCE: 474

```
cctaattcac acaaagactc cttgtggact ggctgtgccc ctgatgcagc ctgtggctgg    60
agtggccaaa taggagggag actgtggtag gggcagggag gcaacactgc tgtccacatg    120
acctccattt cccaaagtcc tctgctccag caactgccct tccaggtggg tgtgggacac    180
ctgggagaag gtctccaagg gagggtgcag ccctcttgcc cgcacccctc cctgcttgca    240
```

```
cacttcccca tctttgatcc ttctgagctc cacctctggt ggctcctcct aggaaaccag    300
ctcgtgggct gggaatgggg gagagaaggg aaaagatccc caagacccc tggggtggga     360 tctgagctcc cacctccctt cccacctact gcactttccc ccttcccgcc ttccaaaacc    420
tgcttccttc agtttgtaaa gtcggtgatt atatttttgg gggct                   465
```

<210> SEQ ID NO 475
<211> LENGTH: 443
<212> TYPE: DNA
<213> ORGANISM: Homo sapiens

<400> SEQUENCE: 475

```
agaatgcaaa gaggccgctt ccctaagagg cttggaggag ctgggctcta tcccacaccc     60 accccccaccc caccccacc cagcctccag aagctggaac catttctccc gcaggcctga    120
gttcctaagg aaaccaccct accggggtgg aagggagggt cagggaagaa acccactctt    180
gctctacgag gagcaagtgc ctgcccctc ccagcagcca gccctgccaa agttgcatta    240
tctttggcca aggctgggcc tgacggttat gatttcagcc ctgggcctgc aggagaggct    300
gagaccagcc cacccagcca gtggtcgagc actgccccgc cgccaaagtc tgcagaatgt    360
gagatgaggt tctcaaggtc acaggcccca gtcccagcct ggggggctggc agaggccccc   420 atatactctg ctacagctcc tat                                            443
```

<210> SEQ ID NO 476
<211> LENGTH: 458
<212> TYPE: DNA
<213> ORGANISM: Homo sapiens

<400> SEQUENCE: 476

```
gactcagtgg gcactagaac gcctgaggct gcagctgggc tccccggggt ccttgcagag     60
gaaactcagt ctgctggagc aggaatccca gcagcaggag ctgcagatcc agggcttcga    120
gagtgacctc gccgagatcc gcgccgacaa acagaacctg gaggccattc tgcacagcct    180
gcccgagaac tgtgccagct ggcagtgagg gctgcccaga tccccggcac acactccccc    240
acctgctgtt tacatgaccc aggggtgca cactacccca caggtgtgcc catacagaca    300
ttccccggag ccggctgctg tgaactcgac cccgtgtgga tagtcacact ccctgccgat    360
tctgtctgtg gcttcttccc tgccagcagg actgagtgtg cgtacccagt tcacctggac    420
atgagtgcac actctcaccc ctgcacatgc ataaacgg                            458
```

<210> SEQ ID NO 477
<211> LENGTH: 475
<212> TYPE: DNA
<213> ORGANISM: Homo sapiens
<220> FEATURE:
<221> NAME/KEY: misc_feature
<222> LOCATION: (342)..(342)
<223> OTHER INFORMATION: n is a, c, g, t or u

<400> SEQUENCE: 477

```
agcatcctga accagctgtg ttttattatg cacagatatc gtaaaaattt gactgccgca     60
aagaaaaatg agttggtaca aaagacaaaa tcagagttca atttcagcag caagacttat    120
caagaattta attactattt gacatcaatg gttggttgcc tgtggacgtc caaacccttt    180
gcgaaaggaa tatatattga ccctgaaatc ctagaaaaaa ctggagtggc tgaatataaa    240
aacagtttaa atgtagtcca tcatccttct ttcttgagtt acgctgtttc cttttttgcta   300 caggaaagcc cagaagaaag gacagtaaac gtgagctcta tncggggaaa gaaatggagc    360
```
tggtatttgg actatttatt ttcacagggg ttacaaggct tgaaactttt tataagaagt      420
agtgttcatc attcttccat tcccagagca gagggcataa actgcaacaa tcaat           475

<210> SEQ ID NO 478
<211> LENGTH: 490
<212> TYPE: DNA
<213> ORGANISM: Homo sapiens

<400> SEQUENCE: 478
ctcgcagagt tccgtcgatc aggactggag gaagccacgt ttcaacagat atatagtcaa      60
catgtggcac tgtgcagaat ggagggactg ccgtacccca ccatgtcaga gaccatggcc     120
gtgtgttctc acctgggctc ctgtcgcctc ctgcttgtgg agcccagcag gaacgatctg     180
ctccttcggg tgcggctcaa cgtcagccag gatgatgtgc tgtatgcgct gaaagacgag     240
taaaggggct tcacaagtta aaagactggg gtcttgctgg gttttgtttt ttgagacagg     300
gtcttgctct gtcgcccagg ctggagtgca gtggcacgat catggctcac tgcagccttg     360
acttctcagg cttaggtgac cccccaacct catcctccca ggtggctgaa actacaggca     420
catgccacca tgcccagctg attttttgta gagacagggc ttcaccatgt tgccaagcta     480
gtctacaaag                                                           490

<210> SEQ ID NO 479
<211> LENGTH: 460
<212> TYPE: DNA
<213> ORGANISM: Homo sapiens
<220> FEATURE:
<221> NAME/KEY: misc_feature
<222> LOCATION: (72)..(77)
<223> OTHER INFORMATION: n is a, c, g, t or u
<220> FEATURE:
<221> NAME/KEY: misc_feature
<222> LOCATION: (364)..(364)
<223> OTHER INFORMATION: n is a, c, g, t or u

<400> SEQUENCE: 479 tttttttaggg actctcaacc tcctggcagg gttaaaggga gagtacttta aacccatata    60
ccagctgtgc tnnnnnntct ctcactttgc cctgggtaag ctgctgtagg gtcagaagta    120 acccttctg tgccagttga gaatgagcct gtgtggtagc tgatgtcaga ggacaaagct     180
ctctgcaagg gctggacaca gagctgcaga gtcctgaaca tccctccttt caggctgcag   240
aagggagagg caatgaagac aggtgctccg gaagcagcat cagggctctt ggaggggact   300
ggtggggact caggctgggt gcagcctcca aacagagaac ggaacttagg tgtgtctcta   360
cagnctaggc ccagcctagc ccagcccaga acaaacaccc ttcagagcct aaccaaagaa   420
cataagctgc aaaatgtgca cccatatttt aagctgcttt                          460

<210> SEQ ID NO 480
<211> LENGTH: 492
<212> TYPE: DNA
<213> ORGANISM: Homo sapiens
<220> FEATURE:
<221> NAME/KEY: misc_feature
<222> LOCATION: (77)..(77)
<223> OTHER INFORMATION: n is a, c, g, t or u

<400> SEQUENCE: 480
cctgtctcct acatttagcc aatgaaaaga atctaaaact ggaaggaaca gaggacctct    60
ctgatgttct tgtgagncaa ggagattgag ttcactatgg agaagtcagc agcaggaggc   120

```
ccatcccctta ctcagttgcc gggacatccc cagtctcggg ggaagaagat gccatgggct    180
tatacccagg ctgtagccaa ctaccaacgt gcctgtttgt ttgttgctct ttccttctct    240
ccatcatagt ctgggtgcca gcgccctgaa gctccgtgct caactgatta aactttactg    300
ccctatggtg accatctagg agaggggagg gcagagggggg tgagggtact attctggatt    360
gagaaaacct atatccattc tttatatcaa tgtatagttt tagtctccta aattgatctg    420 ttatttttcca aactattctc ttgtagaaaa ttttccagtg ggcacttaat ggtgcccttg    480
aagaacttcc ta                                                          492

<210> SEQ ID NO 481
<211> LENGTH: 501
<212> TYPE: DNA
<213> ORGANISM: Homo sapiens
<220> FEATURE:
<221> NAME/KEY: misc_feature
<222> LOCATION: (197)..(197)
<223> OTHER INFORMATION: n is a, c, g, t or u
<220> FEATURE:
<221> NAME/KEY: misc_feature
<222> LOCATION: (247)..(247)
<223> OTHER INFORMATION: n is a, c, g, t or u

<400> SEQUENCE: 481
ggagggagag gtccctgcaa ggtcccttcc cgggcagggg agggatggaa atgccgtcac     60
agtagtaggg actggagcgt ctacaaggat ggaggggagc tactcaggcc taacgttagc    120
tacaaggaaa aaggacgcct tccgtgacag atccttgagg tgtctgtgtc tgccccaagt    180
ggccggcagt ggccttncct ccgggcccaa ggcctgcagc cacctgctct aactcttgag    240
tgggggngcg ggggggggacc tgcaggggct cggggacagg acagcagcaa gaggcagggg    300
ccgaggacgg aggccttccc gacagtgggg tgggttgtac attcaagtgt gaggtgaacc    360
ctttggtggg gaggggggccc ctgaagcctc ggcggggcca cccctccccg cggcgcctct    420
gagtctaggg agaggggctg ctggctcggc ccggccggcc tggcttcaca gagggtctgc    480
ggattgacac tggttctttt c                                              501

<210> SEQ ID NO 482
<211> LENGTH: 490
<212> TYPE: DNA
<213> ORGANISM: Homo sapiens
<220> FEATURE:
<221> NAME/KEY: misc_feature
<222> LOCATION: (120)..(120)
<223> OTHER INFORMATION: n is a, c, g, t or u
<220> FEATURE:
<221> NAME/KEY: misc_feature
<222> LOCATION: (122)..(122)
<223> OTHER INFORMATION: n is a, c, g, t or u
<220> FEATURE:
<221> NAME/KEY: misc_feature
<222> LOCATION: (185)..(185)
<223> OTHER INFORMATION: n is a, c, g, t or u
<220> FEATURE:
<221> NAME/KEY: misc_feature
<222> LOCATION: (271)..(271)
<223> OTHER INFORMATION: n is a, c, g, t or u
<220> FEATURE:
<221> NAME/KEY: misc_feature
<222> LOCATION: (306)..(306)
<223> OTHER INFORMATION: n is a, c, g, t or u
<220> FEATURE:
<221> NAME/KEY: misc_feature
<222> LOCATION: (313)..(313)
<223> OTHER INFORMATION: n is a, c, g, t or u
<220> FEATURE:
<221> NAME/KEY: misc_feature
```

```
<222> LOCATION: (352)..(354)
<223> OTHER INFORMATION: n is a, c, g, t or u
<220> FEATURE:
<221> NAME/KEY: misc_feature
<222> LOCATION: (357)..(357)
<223> OTHER INFORMATION: n is a, c, g, t or u
<220> FEATURE:
<221> NAME/KEY: misc_feature
<222> LOCATION: (359)..(359)
<223> OTHER INFORMATION: n is a, c, g, t or u
<220> FEATURE:
<221> NAME/KEY: misc_feature
<222> LOCATION: (361)..(362)
<223> OTHER INFORMATION: n is a, c, g, t or u
<220> FEATURE:
<221> NAME/KEY: misc_feature
<222> LOCATION: (365)..(365)
<223> OTHER INFORMATION: n is a, c, g, t or u
<220> FEATURE:
<221> NAME/KEY: misc_feature
<222> LOCATION: (367)..(367)
<223> OTHER INFORMATION: n is a, c, g, t or u
<220> FEATURE:
<221> NAME/KEY: misc_feature
<222> LOCATION: (371)..(371)
<223> OTHER INFORMATION: n is a, c, g, t or u
<220> FEATURE:
<221> NAME/KEY: misc_feature
<222> LOCATION: (373)..(374)
<223> OTHER INFORMATION: n is a, c, g, t or u
<220> FEATURE:
<221> NAME/KEY: misc_feature
<222> LOCATION: (376)..(377)
<223> OTHER INFORMATION: n is a, c, g, t or u

<400> SEQUENCE: 482
gtgaggagct gttttcatct gtgtctgttg gagatcaaga tgattgctat tccctgttag      60
atgatcagga cttcacttct tttgatttat ttcctgaggg gagtgtctgc agtgatgtcn     120
cntcttctat tagcacttac tgggattggt cagatagcga gtttgaatgg cagttaccag     180
gcagntgaca ttgccagtgg gagtgatgta cttttctgatg tcatacccag tattccaagt    240
tcaccttgcc tgcttcctaa aaagaaaaac nagcaccgga atttagatga actcccttgg     300
agtgcnatga canatgatga gcaggtggaa tatattgagt atctgagtcg gnnngtnant    360
nntgngntgg ncnncnntac tgtcctgtgg tctagtgggc agggacctgg gggccatcag    420
tggctgtagg acttttttac ccctctgttc ctggcctaaa tatgtgatgg gtatgcttca    480
ccttaagtgg                                                              490

<210> SEQ ID NO 483
<211> LENGTH: 231
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, t or u

<400> SEQUENCE: 483
ctttcacact gtggcagccc agtgaagcag actgggccat gaactctcct agccctgggg      60
ccnagcctgt tccacaggca cccctgcagg aggcgctgcc aggagagcct tccatctcgg     120
ggctctttga ggttccctcc ttctgggtgt tcttcaggct gagcagagag gctcctgtac    180
cctctctctc ggaatctgaa gagccagatt taggccgggc aaaggggctc a              231

<210> SEQ ID NO 484
<211> LENGTH: 414
<212> TYPE: DNA
```

<213> ORGANISM: Homo sapiens

<400> SEQUENCE: 484

```
ggtgctggaa aaactactat cttgtttaag ttaaaacagg atgaattcat gcagcccatt      60
ccaacaattg gttttaacgt ggaaactgta gaatataaaa atctaaaatt cactatttgg     120
gatgtaggtg gaaaacacaa attaagacca ttgtggaaac attattacct caatactcaa     180
gctgttgtgt ttgttgtaga tagcagtcat agagacagaa ttagtgaagc acacagcgaa     240
cttgcaaagt tgttaacgga aaaagaactc cgagatgctc tgctcctgat ttttgctaac     300
aaacaggatg ttgctggagc actgtcagta gaagaaatca ctgaactact cagtctccat     360
aaattatgct gtggccgtag ctggtatatt cagggctgtg atgctcgaag tgtt           414
```

<210> SEQ ID NO 485
<211> LENGTH: 508
<212> TYPE: DNA
<213> ORGANISM: Homo sapiens

<400> SEQUENCE: 485

```
tcctctgtcc tctatattca gcatgttcct tgtcagctgc tgggccggcc ctgccttgcg      60
ctagcagagc ctctcctggc agcttctcag gtctccctaa tggagacacc aggctactag     120
gacactggct ggggccaccc cctcctgcct aatgcctcac cttacagctg ggaaactga      180
ggcctggaat ggcccagagt caccaaggca agttgggc tggtcccagc ctgaggctcc       240
agctgatgcc ctcagctccc agagagggggg tgccccatct agctgggtgc aggggtcact    300
gcttgtcagc tcagggccct gtgcccgctt gcctgttccc ctacatctgt gcctgcacat    360
ccagaactgc ctccttgccg ctgcctccag gaagcccacc ttgagccaga gtcaagggct    420
gcagcactgc ccgatagaac acgcccgccc tcactgctgt tcttgcctta cagccaccat    480
gggaaagctg caacctttct gttttatt                                        508
```

<210> SEQ ID NO 486
<211> LENGTH: 555
<212> TYPE: DNA
<213> ORGANISM: Homo sapiens
<220> FEATURE:
<221> NAME/KEY: misc_feature
<222> LOCATION: (400)..(401)
<223> OTHER INFORMATION: n is a, c, g, t or u
<220> FEATURE:
<221> NAME/KEY: misc_feature
<222> LOCATION: (410)..(410)
<223> OTHER INFORMATION: n is a, c, g, t or u

<400> SEQUENCE: 486

```
tgtcaacttg tcatatacac ctccagggac caaaaacaaa agcagctcgg agtctgtgtt      60
gcctgattgg aaagtagaag ctctggtgta tgctacagca cataacacat ttttactaaa     120
ggaaaaaagc taattatgtc catgcctctc gtaaaactgg ggggaacctt aaagagaaag     180
aactaaggct taagttatct gtagtataat caattagaag taatgaatgg atgcatgtaa     240
aatggatgtg attttttttc aagcttattt tgaaatctta aaaatcaggt tacaccatag     300
ctactcaaaa gttttacaca cttaaaactc agatcagtaa gtgttggtac cttttagact     360
cataaaattg aataaaccat tgcaatgctt taaaaaaaan naaaaaaaan ggttttattg     420
ctatgatttt atggcagaca catccaagca aaaccatttt ccaaatgcag accttcctga    480
tgttatctga aatctgataa aatgaccccta ctctctgctg tggttcattc ttgctccatg    540
ctgtccatat ttatg                                                      555
```

<210> SEQ ID NO 487
<211> LENGTH: 541
<212> TYPE: DNA
<213> ORGANISM: Homo sapiens

<400> SEQUENCE: 487

| | | | | | |
|---|---|---|---|---|---|
| gtggcactta | ggcactatat | tattgatatc | tacaatggcc | tcctggatgc | acaaaagacc | 60 |
| ctgaagggct | tttttgatca | gcaaaacaaa | aacagaaaag | caaaaaacag | ttaattttg | 120 |
| tttggtcaag | tttactcaac | cagaccacct | tgataccaac | aatgctggag | agcatttggc | 180 |
| aagagcaggg | ccacaatgcc | aaattccttg | gaaaggtaga | cttcctatga | tactttcatg | 240 |
| gattggcaaa | tttgtggggt | ttttttggta | gtagcttttg | agaatgttag | tttctggctg | 300 |
| gggtagtgac | ttcatctgt | aatcccagca | cttcgggagg | cgaaggcagg | tggattgctt | 360 |
| gtgcccagga | gtttgagacc | agcctgggta | acatggtgag | accccatctc | tattttata | 420 |
| aaattaaaaa | aaaaaaaaaa | gatagagaat | gttactttcc | tataaagcca | tgataccta | 480 |
| agtactaaga | catgtctgtt | gttgtccttt | ccttcataac | atttctcata | acccgtaatt | 540 |
| t | | | | | | 541 |

<210> SEQ ID NO 488
<211> LENGTH: 523
<212> TYPE: DNA
<213> ORGANISM: Homo sapiens
<220> FEATURE:
<221> NAME/KEY: misc_feature
<222> LOCATION: (86)..(86)
<223> OTHER INFORMATION: n is a, c, g, t or u
<220> FEATURE:
<221> NAME/KEY: misc_feature
<222> LOCATION: (106)..(106)
<223> OTHER INFORMATION: n is a, c, g, t or u
<220> FEATURE:
<221> NAME/KEY: misc_feature
<222> LOCATION: (140)..(140)
<223> OTHER INFORMATION: n is a, c, g, t or u

<400> SEQUENCE: 488

| | | | | | |
|---|---|---|---|---|---|
| cagccctgac | gtgaactcat | tttattttgg | ccaggaccca | gaaaggagtc | tactgctaag | 60 |
| atttcagcat | gtcctgtggc | tgagtnaatc | agagttatga | caggnaggta | ccgggcacac | 120 |
| catcgcaatg | ctccatcaan | gctagtatgt | tgtgttcttt | ccttcatatc | aagtcaactc | 180 |
| aagcttgctc | tacttacctg | gtgtacacag | tctaagaact | gtaagaagac | tggagcaaaa | 240 |
| ccactcccct | gacagttgag | ggtcaagctg | ctcctctgac | tgaatttgtg | accaaaagag | 300 |
| agccactctt | tttcaaccaa | catctggaag | ccttcaagtg | tcctataaaa | gggatcactg | 360 |
| agtaactgaa | ccagggatgt | cacctagggc | ataagcagga | tggattgtca | ttaattttag | 420 |
| ttctgaaaaa | ggcctattac | taagataaaa | gcacttcctt | ctgatgatag | ctaattcaca | 480 |
| aatttacctg | gacagcaaat | ttgttcacta | accattccag | gat | | 523 |

<210> SEQ ID NO 489
<211> LENGTH: 306
<212> TYPE: DNA
<213> ORGANISM: Homo sapiens

<400> SEQUENCE: 489

| | | | | | |
|---|---|---|---|---|---|
| cggctgtacg | actccataat | gggcatgggg | actcaagata | aggtcctgat | cagaatcatg | 60 |
| gtctcccaca | atgaagtgga | catgttgaaa | attaggtctg | aattcaagag | aaagtatagc | 120 |

-continued

| | |
|---|---|
| aagtccctgt actactatat ccagcaagac actaagggtg ctgtacctgt gtggtggaga | 180 |
| tggctgaagt ccgacacagc acgagcgtcc agaaatggtg ctccccatgc ttccagctaa | 240 |
| caggtctaga aaacccgctt gtgactagca gtccctgtgg ctgttcctgt gaggatgacg | 300 |
| ttagca | 306 |

<210> SEQ ID NO 490
<211> LENGTH: 170
<212> TYPE: DNA
<213> ORGANISM: Homo sapiens

<400> SEQUENCE: 490

| | |
|---|---|
| agaagattcc cttgaagcct tctccttcca aaaagtttcg gtctggctca tctttctctc | 60 |
| ggcgagcagg ctccagtggc aactcctgca ttacttacca gccatcggtc tctggggaac | 120 |
| acaaggcaca agtgacaaca aaggcagaag tggagccagg cgttcacctt | 170 |

<210> SEQ ID NO 491
<211> LENGTH: 532
<212> TYPE: DNA
<213> ORGANISM: Homo sapiens

<400> SEQUENCE: 491

| | |
|---|---|
| tgggggtgac tgctgcttat taagatgatt catttcattt ccactcgtgg ttgtgatttt | 60 |
| caccttctca aaactgagtc agcaagagaa atcttgtct tagaagggcc agataacact | 120 |
| tcgctgtgag aacaggaggg ataatggatt ggagatggct atgtgtaaag cagccctgcc | 180 |
| tgctgattta acacactttc aaaatagatg tgtcagtatt catttaaagc aagactctga | 240 |
| tgacagaagg aaccttgaaa actacctgat attgaaatgg ttgtgcccctt tatagccctt | 300 |
| ttgcatctcc ttgactttcc agtcatgcct cctaaatcag aagaaaagct gcaaagaaaa | 360 |
| tgttttgtgt ggttctgggc ttatttgaat aatgttcatg accacaggct gccatagcac | 420 |
| aagtgagaat tcagaccac aagggtttaa ggagcagtgc tctcttctct caaagctcag | 480 |
| aacggtctct ggatccatgg tatcgtacac ccagtgtgga tattaacatt ct | 532 |

<210> SEQ ID NO 492
<211> LENGTH: 559
<212> TYPE: DNA
<213> ORGANISM: Homo sapiens
<220> FEATURE:
<221> NAME/KEY: misc_feature
<222> LOCATION: (232)..(232)
<223> OTHER INFORMATION: n is a, c, g, t or u
<220> FEATURE:
<221> NAME/KEY: misc_feature
<222> LOCATION: (259)..(259)
<223> OTHER INFORMATION: n is a, c, g, t or u

<400> SEQUENCE: 492

| | |
|---|---|
| aagggaagtt agcaccttcc tcttggaggt gctgaggatt aaatgagata atacgtggaa | 60 |
| agcattaggc atgtagcaca gttagcagat ggtggttggc tccctctgct tttccatcag | 120 |
| tctgtggcct agtttaaatg gtgggaggaa gggtgtgaga tttaaggctg gttgtaaggg | 180 |
| atcagtcagt gtagttggaa aaattgtaag atgaagttat aggatataga cncaaaacctt | 240 |
| cctggaaggc cagaaagtnt gcatagcttc aataaaggat ttggctgaaa gcagcgtaat | 300 |
| ccccttttacc ttgagttgat agcaatagag caaataacat gggaacgtgg gggagtttat | 360 |
| tgaatagctt gtttactcat gtggtcctaa gaccaacctt tgattatcca cgggtgcatg | 420 |
| attgctctct actcggtggt cggcaaattt aattacccac aggtgtgttg actcaaagcc | 480 | tctgtcatta aatctatgct gaataaatgc cgtcaggcca gctagtcaag gtgcacaact    540 cttttttgtgc gtggtgtgg                                                559

<210> SEQ ID NO 493
<211> LENGTH: 287
<212> TYPE: DNA
<213> ORGANISM: Homo sapiens

<400> SEQUENCE: 493
gtaagtctca gtcctttaaa actcagaaaa aggtgtgttt tccaaattta atatttcctt    60
tctgtaagtc tcagtgtctg cactatttgt cttggagact taaaattatc ccttgaaagc   120
ataagaagta caccccaaac cagctttgtc cttcctgtcc tcttctagtt tacattttat   180
gtggttagta attttgtacc taaaagtatt tgaaattcta taaatttgga cttgacgtga   240
gcaaaagaaa atttctacgt aagcgaaact aataaaacta cagtcac                 287

<210> SEQ ID NO 494
<211> LENGTH: 476
<212> TYPE: DNA
<213> ORGANISM: Homo sapiens

<400> SEQUENCE: 494
ctgtggcatc tataacctga gttcagtcac ttaataccga ggtcctgcgc tctgctgtgt    60
gcctggccct gggctgggca ctggggacat agcagtgacc gagacagaca ggctcacaag   120
gagacatacg acaaccaggt aaacatggca gacaagagca tgtcagatgc gctgtgaaga   180
acactgcggg gccctcctaa ggaggtggca tgagttacat gcagacagag acgatccggg   240
ggcagacgga gttccatgtg gggcagtggt gagggcagac gctctggggc tgggatccct   300
gggagtgttc gagaagcacc gagaaggctt ctgtggctgg agccggccag ctgggggaga   360
tggggccagg gagatggcag gggcctctcc ctgtcccagg acccagagcc aagggaggct   420
ttaagcccag gaccagggggt ctgaaaacga aaagcactca cagtccttga acattg      476

<210> SEQ ID NO 495
<211> LENGTH: 542
<212> TYPE: DNA
<213> ORGANISM: Homo sapiens

<400> SEQUENCE: 495
ggcaacctcc tggacaagga cgacctggcc atcccacccc ccgattacgg cgccgcctcc    60
cgggccttcc ccgcccagac ggccagcggc ttcaagcaga ggcccctacag tgtggccgtg   120 cccgccttct cccagggcct ggatgactat ggagcgcggt ccatgagcag tggcagcggc   180
acgctggtgt ccacagtgtg aggacgctga ccccgggcag ccgctgctct gaagagcttc   240
cgcgccttcc ccctggtctc gtccgttttc ctcctcagct ctcgctggtt tgttcttggg   300 ttgttttttct tttccacctg ccccatgcct tttggttggt gacccagac tctgtgatcc    360 cccagggtcc atggtgctgc tccatccgcc cccctcccc tgtgtttacg cgccccatcc    420
tgtgtgtccc agccttttga gcagaaactg ccaggcagga cctgctgggc cgtgcggggc   480
accctcggcc tcccctgca gtgtctgtgg cactcactgc ttttctaagg ctcgccgtga    540
gc                                                                  542

<210> SEQ ID NO 496
<211> LENGTH: 438
<212> TYPE: DNA

<213> ORGANISM: Homo sapiens

<400> SEQUENCE: 496

```
gagaggtatt atcgagacat tgcaaagatg gcatccatca gcgaccagga catggatgcc    60
tacctggtgg agcagtcccg cctccacgcc agcgacttca gcgtcctgag tgcgctcaac   120
gagctgtatt tctatgtcac caagtaccgc caggagattc tcacggctct ggaccgagat   180
gcctcttgtc ggaagcataa gttgcggcag aaactggaac agatcatcag cctcgtgtcc   240
agcgacagct aaggtggtgg aatcggtgag gaggggcttc tcagtcctg tgccgtcctc    300
ccatccaggg gagtggctgg ctcaagcctg ggtccccggg ctgagccctg gattgggtat   360
cgtggggcag gtcaccctgg ccacgatgcc cccggcacac ccaggccccc ttcattagtg   420
ccttgctttg ggccctgc                                                 438
```

<210> SEQ ID NO 497
<211> LENGTH: 419
<212> TYPE: DNA
<213> ORGANISM: Homo sapiens
<220> FEATURE:
<221> NAME/KEY: misc_feature
<222> LOCATION: (248)..(251)
<223> OTHER INFORMATION: n is a, c, g, t or u

<400> SEQUENCE: 497

```
taagttctca tccaacattt ctcctggcca tccattctcc atctttaaag gcaatcacca    60
ttgccagttt cttctgtatc cttctggaaa tacaatatat tacataaatg acagcattct   120
atattctctc ttctatatct tacctatttc tgtgaataat ttattttgga cagcatttta   180
tgtatgaata ttcacaaatg tgcttcctta tttcagaggc tgaactaata aaaattttgt   240
ttattttnnn nttgaggcaa tattttata tggtaccct atctttaata cttaacctgc     300
cagactttaa ccgtaacaca ataatgtatt gccaaatagc accattcttc ttctctcact   360
ctcttgccat gggggctctt aaaaaaaaaa gtatacatct aaggtgtaca acatgctgt    419
```

<210> SEQ ID NO 498
<211> LENGTH: 477
<212> TYPE: DNA
<213> ORGANISM: Homo sapiens

<400> SEQUENCE: 498

```
accagtttac ctaggccttg gactgccaaa tagctacaca actgcttaag ctggcctata    60
aggacagacc agagacaaag caagaagatc attggtccag actgagaaga aagttgccag   120
agggatgtct ccactaaggc ctttgagcag ggattaatgc tgtcaccacc ttggtggaga   180
acaagaaagc tcagctggtg gtgactgcac gtgacaatgg atctcataga gctagctgtc   240
ttcctgcctg ccctgcatca taaaatacaa agggaagaga agactgggat gtctagtcca   300
caggaagact tgcaccactg tcgccttcac acagattaac ttggcagaca aaggagcttt   360
ggctaagctg gtggaagcca tcagaaccaa tgacaatgac agacaggatg agatccactg   420
tcactaggga ggcaatatcc tgggtccaaa atctctggct ctcattgcca agctgga      477
```

<210> SEQ ID NO 499
<211> LENGTH: 366
<212> TYPE: DNA
<213> ORGANISM: Homo sapiens

<400> SEQUENCE: 499

```
tgagggaggg atgtgcctct ggccacgtgg ttaccttgca gtgcacagcc tgtggtcata    60
```

```
gaaggggcta cagctcacgc atcgtgggtg gaaacatgtc cttgctctcg cagtggccct    120
ggcaggccag ccttcagttc cagggctacc acctgtgcgg gggctctgtc atcacgcccc    180
tgtggatcat cactgctgca cactgtgttt atgacttgta cctccccaag tcatggacca    240
tccaggtggg tctagtttcc ctgttggaca atccagcccc atcccacttg gtggagaaga    300
ttgtctacca cagcaagtac aagccaaaga ggctgggcaa tgacatcgcc cttatgaagc    360
tggccg                                                              366

<210> SEQ ID NO 500
<211> LENGTH: 537
<212> TYPE: DNA
<213> ORGANISM: Homo sapiens
<220> FEATURE:
<221> NAME/KEY: misc_feature
<222> LOCATION: (193)..(193)
<223> OTHER INFORMATION: n is a, c, g, t or u
<220> FEATURE:
<221> NAME/KEY: misc_feature
<222> LOCATION: (210)..(210)
<223> OTHER INFORMATION: n is a, c, g, t or u
<220> FEATURE:
<221> NAME/KEY: misc_feature
<222> LOCATION: (379)..(379)
<223> OTHER INFORMATION: n is a, c, g, t or u
<220> FEATURE:
<221> NAME/KEY: misc_feature
<222> LOCATION: (443)..(444)
<223> OTHER INFORMATION: n is a, c, g, t or u
<220> FEATURE:
<221> NAME/KEY: misc_feature
<222> LOCATION: (446)..(446)
<223> OTHER INFORMATION: n is a, c, g, t or u
<220> FEATURE:
<221> NAME/KEY: misc_feature
<222> LOCATION: (448)..(451)
<223> OTHER INFORMATION: n is a, c, g, t or u

<400> SEQUENCE: 500
gaacaatcgt cttttgaact tccagtaggc ccacagttgt tggttgttcc tcaaaacagg     60
ttgtggctcc tgttgaataa gatgatccat taaaaactga acaaggttga ggagaaatag    120
tgcttacgtt gaaaaatctt taagtctttg tccccgttct ctaacttcct tacgttttcg    180
tttatttagc tcnatcccca ctatctactn gaatttctca tatttaaacc aagatgggag    240
actaggtcat taggaaaata ttaccgtcta caattttctt atactttgat ctgtcttttta   300 tttgattgta agttgctgat ggacagtgat cattagaaac tgaattttgt ataatactag    360
ttttatatga aactagatnt ttattgcgct caggttatgt tccttttacc tccttcctta    420
ataaagagac cacttgaaat aannanannn nttccaagta ctgtctgcac cttatcccac    480
ctctttccca tttatgagat agtgcaaaac cctagcacag tcttttccat ttagtaa       537

<210> SEQ ID NO 501
<211> LENGTH: 332
<212> TYPE: DNA
<213> ORGANISM: Homo sapiens

<400> SEQUENCE: 501
aagtatctcc atacaaaata cggttgaatt acaaaagaa aattgtaaca ttagcatgga      60
caaacctggc aggtactcct taactctcct aagtaataaa aactgtaaaa tgcaaataag    120
ccttcgatga catttactaa cctttactaa agtatcaatg atgacttggt tgtttaaaca    180
gctgacattt gggcaatttg agtatgtcaa actcaataat actggttttc atttgcaaga    240
```

-continued

| | |
|---|---|
| tccacttaaa acttaaggag gccaaaaaac atcatttaaa atacccata aattataatc | 300 |
| atacatatga tacgaaaaat atcctacttc ag | 332 |

<210> SEQ ID NO 502
<211> LENGTH: 375
<212> TYPE: DNA
<213> ORGANISM: Homo sapiens

<400> SEQUENCE: 502

| | |
|---|---|
| agggtaactt ccagtgtcac aatgagcagt tctgtaagtg ggtgcctctc agcacatttc | 60 |
| tatgaatata ttatgtagat aggctgtatt gattttggta gcattgacac cttcttaggc | 120 |
| aattagttga agaaaactgc aaaatatttt cttatgtaat agctgtatag agcaatagca | 180 |
| atcaaagcat gagaaggcac taacgctggg atgaaagatg agattcagag gtgactgaga | 240 |
| atcatgtgag tgatggctgt atattttgtg taaaatatat gtgtgaaaat gaactaagag | 300 |
| tgagttactc agcactctca agaattatgc agattctgca ttttctattat gccgtgtgcc | 360 |
| taaaaaccta cttga | 375 |

<210> SEQ ID NO 503
<211> LENGTH: 468
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a, c, g, t or u

<400> SEQUENCE: 503

| | |
|---|---|
| gggacaggat gaccttcccg aggaactcan tggcctgggg tagtttaaga agtaatgttc | 60 |
| tttctttctt tctcttttcc ctacctcctg ctaacccaac cagagatccc cttccttgct | 120 |
| gagagggttg ggggcaggag gagatttggc agtgcctgca ggttgcctgg ccaggtggag | 180 |
| aggggggaaag aggaagggca ccgtgggtgt aagatgcctt tctcctccac ccatcgaaac | 240 |
| cagccacccc ttccctgtgc caccaagaca gccttttcca gtggccatcc taaggggaac | 300 |
| tcccaaatgg gtgttgctgg tggacacaga tgctccccc aatggaagcc caagctctg | 360 |
| aggtatgcgg gtagaggctt tggataggtt ttcttctgct cccctctttt atagatctag | 420 |
| gctgcttggc tgcctgtctt tctaggcagt cccctagag gaaaaatg | 468 |

<210> SEQ ID NO 504
<211> LENGTH: 484
<212> TYPE: DNA
<213> ORGANISM: Homo sapiens

<400> SEQUENCE: 504

| | |
|---|---|
| accccaccac gtaccagatg gatgtgaacc ccgagggcaa atacagcttt ggtgccacct | 60 |
| gcgtgaagaa gtgtccccgt aattatgtgg tgacagatca cggctcgtgc gtccgagcct | 120 |
| gtggggccga cagctatgag atggaggaag acggcgtccg caagtgtaag aagtgcgaag | 180 |
| ggccttgccg caaagtgtgt aacggaatag gtattggtga atttaaagac tcactctcca | 240 |
| taaatgctac gaatattaaa cacttcaaaa actgcacctc catcagtggc gatctccaca | 300 |
| tcctgccggt ggcatttagg ggtgactcct tcacacatac tcctcctctg gatccacagg | 360 |
| aactggatat tctgaaaacc gtaaaggaaa tcacaggttt gagctgaatt atcacatgaa | 420 |
| tataaatggg aaatcagtgt tttagagaga gaacttttcg acatatttcc tgttcccttg | 480 |
| gaat | 484 |

<210> SEQ ID NO 505
<211> LENGTH: 277
<212> TYPE: DNA
<213> ORGANISM: Homo sapiens
<220> FEATURE:
<221> NAME/KEY: misc_feature
<222> LOCATION: (136)..(136)
<223> OTHER INFORMATION: n is a, c, g, t or u

<400> SEQUENCE: 505

```
ctgcacagtc tccagtgtgg aaagctgtgg gaaaggaagg agcaggttct aggtcttcag      60
gattttctgc atcttaaagc agctcatctc ctttgccctc ctaggagca ggggggccta     120
gctttgggat cgtccnccta gcctcagaaa taattgttca agaaataaca tttctcacac    180
aaaggataaa tgtttgaggg gatggatacc ccatcttcca tgatttgatt attacacatt    240
gcatgcctgt atcaaaaatc tcatatatac acctact                             277
```

<210> SEQ ID NO 506
<211> LENGTH: 515
<212> TYPE: DNA
<213> ORGANISM: Homo sapiens
<220> FEATURE:
<221> NAME/KEY: misc_feature
<222> LOCATION: (380)..(380)
<223> OTHER INFORMATION: n is a, c, g, t or u

<400> SEQUENCE: 506

```
gggggtgatt agtatgttgg gacaaacacg ctgttgctaa atggaaacac tgacctcaca      60
gtgcatcctc ctgccaacac acacacacac acacctctca cacatgcacg cttacacaca    120
cacacacaca cacacacaca cacacacata cacacacaca cacacacgct ctctctctct    180
ctctctctct ctctctgtca gtgtgttatc ggtgtggagc ggaggccgcg gaggctcctc    240
ggtccttcag caccccctcgg cccgacgcac ccacgcccct cacccccccga gagccgaacg   300
ctccccgcac cgccccggt cccttccctc ggccgggagc gacttctgca gctcgttctt    360
ccgaatcgca ccagcaatgn cggccagccg tagaggagg aagagcccgg ggagcccgag    420
catagcgtaa acggctctct gaccttaatt tcatcctgca tggcgaatct ctgccgtctc    480
tctgaacgca gaagggtctg agactggccg tctcc                               515
```

<210> SEQ ID NO 507
<211> LENGTH: 259
<212> TYPE: DNA
<213> ORGANISM: Homo sapiens

<400> SEQUENCE: 507

```
ttcagtttat actcaaagcc ctgcagtttc ctgacagcac agagcacacc tgtcacgcga      60
gcaggatgaa gcccagaggc tgcctggtga agtgggcggc gcgctggaaa atccacgtag    120
ctttgttccc tccacgggga gcgtgcaagg ccctctcgag cactacggga gcctcgcctt    180
ctgcacagac ttcggagcca ggtgctggag cggcagcaac tgagggggcgt ggatgtcttt   240
gcatggttcc catacgttt                                                 259
```

<210> SEQ ID NO 508
<211> LENGTH: 285
<212> TYPE: DNA
<213> ORGANISM: Homo sapiens
<220> FEATURE:
<221> NAME/KEY: misc_feature
<222> LOCATION: (189)..(189)

<223> OTHER INFORMATION: n is a, c, g, t or u

<400> SEQUENCE: 508

```
atagcagtgg actgtcactc atcagtatct gcagttctgt ttaccaaagc ctgcttgcta      60
gagacgtttc agggcctcct tccctcaaag cgtccactgt acctccatct ggatacaatt     120
agctggctcc ccacttcctg gactgacggt aaccaccttt tccaatgacc ctgaagaaaa     180
catgcaatnt aagctgcttt aagagtaacc tacaactgag acaaattttt ctatcaactc     240
ccagtacccc tctctgccgt ggctgatttg ttactggttt tcctt                     285
```

<210> SEQ ID NO 509
<211> LENGTH: 274
<212> TYPE: DNA
<213> ORGANISM: Homo sapiens

<400> SEQUENCE: 509

```
gaggtgcatg ggatcaatgg gacccaatgg ggccagactc tgaggatggg atggtagtag      60
tgaaggacat aggatggggg tagagtgtgg agacttttg aaatagtata gatgaatgcc     120
ctgaggggac tgtgaacaag ctctgccect cttaggaaat caatgggaa tcaactaaat      180
taataaaaa atgggtcaa gattaagagg cagggtcacc cagggaatgg tttaggtcct      240
ggcaactctg aaggggttgg aagggctggc agga                                 274
```

<210> SEQ ID NO 510
<211> LENGTH: 470
<212> TYPE: DNA
<213> ORGANISM: Homo sapiens

<400> SEQUENCE: 510

```
gcgtgggttt ttgtatccag agctgtttgg atacagctgc tttgagctac aggacaaagg      60
ctgacagact cactgggaag ctcccacccc actcagggga ccccactccc ctcacacacc     120
cccccccaca aggaaccctc aggccaccct ccacgaggtg tgactaacta tgcaataatc     180
caccccaggt gcagcccag ggcctgcgga ggcggtggca gactagagtt tagatgcccc      240
gagcccaggc agctatttca gcctcctgtt tggtggggtg gcacctgttt cccgggcaat     300
ttaacaatgt ctgaaaaggg actgtgagta atggctgtca cttgtcgggg gcccaagtgg     360
ggtgctctgg tctgaccgat gtgtctccca gaactattct gggggcccga caggtgggcc     420
tgggaggaaa atgtttacat ttttaaaggc acactggtat ttatatttca                470
```

<210> SEQ ID NO 511
<211> LENGTH: 193
<212> TYPE: DNA
<213> ORGANISM: Homo sapiens

<400> SEQUENCE: 511

```
gaaaatgaat tccatgttct tgaaggaaag actgtaacta tgtacattca tgatgttcct      60
ttggtgtgtg gttctgtga gtaacaggta gatgtcattt ctggaaatgg tatgtttatg     120
tctatacatt gttttataaa actccatgga gaagaaggg gtttacttgc tttgtatcac     180
atagcaataa cat                                                        193
```

<210> SEQ ID NO 512
<211> LENGTH: 452
<212> TYPE: DNA
<213> ORGANISM: Homo sapiens

<400> SEQUENCE: 512

```
ctggcccacc caggaacagt gagggcgacg agaactacat ggagttcctc gaggtgctga        60
ccgagggcct tgagcgggtg ctgttggtgc gcggtggtgg ccgtgaagtc atcaccatct       120
actcctgagc ccagtgtcat cttgtggcct ggagtcgagg tcttggccag gacataacaa       180
gctgtggtct ggggtaacag cctcttccca gcacccacct gccagccctg cttgcctggc       240
cctgtcctgg acccagcttt gctaggtctc cttggaaacc aggcctgggc tcaaaatgg        300 agatggatcc caggtcttgt gggaccctgg gatgtttggg gactttacta tctagcaccc       360
cagtaggcct gtcctggcca gagaagactg gtagggccg  agtgggttt  gaaggcagcc       420 ggcccggccc agcccaggag cgctatttat tg                                      452

<210> SEQ ID NO 513
<211> LENGTH: 411
<212> TYPE: DNA
<213> ORGANISM: Homo sapiens

<400> SEQUENCE: 513
ttggaggcct ttgcagcggc ctacaaaggc acgcggccgt ttgccagtgc caacagcgtg        60 ctggaccccca tcctcttcta cttcacccag aagaagttcc gccggcgacc acatgagctc      120
ctacagaaac tcacagccaa atggcagagg cagggtcgct gagtcctcca ggtcctgggc       180
agccttcata tttgccattg tgtccggggc accaggagcc ccaccaaccc caaaccatgc       240
ggagaattag agttcagctc agctgggcat ggagttaaga tccctcacag acccagaag        300 ctcaccaaaa actatttctt cagccccttc tctggcccag accctgtggg catggagatg       360
gacagacctg ggcctggctc ttgagaggtc ccagtcagcc atggagagct g                411

<210> SEQ ID NO 514
<211> LENGTH: 423
<212> TYPE: DNA
<213> ORGANISM: Homo sapiens
<220> FEATURE:
<221> NAME/KEY: misc_feature
<222> LOCATION: (110)..(111)
<223> OTHER INFORMATION: n is a, c, g, t or u

<400> SEQUENCE: 514
tcgtttctct gaacacacaa cacccatcgt cctcttttat gttacttgaa atatcaaaag        60
aattattaca gctgaaaaca aatctatgta aatcggatct tgaaagagan naagcttttct      120 ccagttttga aaggcgccat ttttaacttt gatcttgtaa tgacaaataa gaatgttgaa       180
tcggctggct ttttctctatc ctaggtaatg tggactgtgg agctctgtgc tggtcacttt      240
caaccctgaa cctgatgcta cttatttttgc agttctaagt gcaaagtcgg cctggtggat     300
gcttcccatt ataatattaa atttgcttct tcgtgaggtc acacctcaca tccccagtgt       360
cactttaata actagtgttt tttacatggt gggccatgac ccattagtgg actctgcatt       420
taa                                                                     423

<210> SEQ ID NO 515
<211> LENGTH: 230
<212> TYPE: DNA
<213> ORGANISM: Homo sapiens

<400> SEQUENCE: 515
ccctggcaag gcccgggaca ggaaggccta cacggtcctc ctatacggaa acggtccagg        60
ctatgtgctc aaggacggcg cccggccgga tgttaccgag agcgagagcg ggagccccga      120
```

| | |
|---|---|
| gtatcggcag cagtcagcag tgcccctgga cgaagagacc cacgcaggcg aggacgtggc | 180 |
| ggtgttcgcg cgcggcccgc aggcgcacct ggttcacggc gtgcaggagc | 230 |

<210> SEQ ID NO 516
<211> LENGTH: 426
<212> TYPE: DNA
<213> ORGANISM: Homo sapiens

<400> SEQUENCE: 516

| | |
|---|---|
| atgaccttcg aatgcatagg cctttaatgg tgcagacaga ggaccagtat gttttcctca | 60 |
| atcagtgtgt tttggatatt gtcagatccc agaaagactc aaaagtagat cttatctacc | 120 |
| agaacacaac tgcaatgaca atctatgaaa accttgcgcc cgtgaccaca tttggaaaga | 180 |
| ccaatggtta catcgcctaa ttccaaagga ataaccttc tggagtgaac cagaccgtcg | 240 |
| cacccacagc gaaggcacat gcccgatgtc gacatgtttt atatgctaat atcttaattc | 300 |
| tttgttctgt tttgtgagaa ctaatttga gggcatgaag ctgcatatca tagatgacaa | 360 |
| attggggctg tcggggctg tggatgggtg gggagcaaat catctgcatt cctgatgacc | 420 |
| aatggg | 426 |

<210> SEQ ID NO 517
<211> LENGTH: 448
<212> TYPE: DNA
<213> ORGANISM: Homo sapiens

<400> SEQUENCE: 517

| | |
|---|---|
| gagcaagttg taaattgtct cttatcggac ttaaagggt gcctggctct tacttagttg | 60 |
| attatctcct ggatctggaa agaaaggaag gaaaacaaag gcggaagggg aatctctata | 120 |
| gaatgtggat ttttcccaca agagactttg cagggcaatt tcaaggtatg gcacggaaat | 180 |
| atattttggg gttaaatatt ttttttccttg tctcataatg ttatgccaga gtcagattga | 240 |
| aaagtaaatc acaacatata gggtcaaata aaacccatct gatgagaatg tgtggtttgt | 300 |
| agggcatgac ttcctagacc tcttaggtag gaatctgggt aagacagaat atcagactta | 360 |
| gtcctcaatt cctaatgcaa agttctgaga tccaaaatgc tccaaaatct aaaacatttt | 420 |
| ttagcaccga cataatgcca caagtgga | 448 |

<210> SEQ ID NO 518
<211> LENGTH: 148
<212> TYPE: DNA
<213> ORGANISM: Homo sapiens

<400> SEQUENCE: 518

| | |
|---|---|
| aattaacacc aggaacagca ccttgaatat tccttttca agttcctctt cctcaggaga | 60 |
| tattcaaggt cgaaacacaa gccccaatgt ttctgtacag aaatccaatc ccatgaggat | 120 |
| tactgagagt catgccacca agggccac | 148 |

<210> SEQ ID NO 519
<211> LENGTH: 173
<212> TYPE: DNA
<213> ORGANISM: Homo sapiens
<220> FEATURE:
<221> NAME/KEY: misc_feature
<222> LOCATION: (141)..(141)
<223> OTHER INFORMATION: n is a, c, g, t or u

<400> SEQUENCE: 519

| | |
|---|---|
| gaaaatcaca actctaacca taatcatctg cactatatgc ctcgcatcag gtaatgtgtc | 60 |

| | |
|---|---|
| taaaataata agtaacattt agcatttctg accttatccc aaagtatttt aatagtatct | 120 |
| gttaatgttt taattaatgg nttttgtatt gcatctcctg gataacaaag tag | 173 |

```
<210> SEQ ID NO 520
<211> LENGTH: 441
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, t or u
<220> FEATURE:
<221> NAME/KEY: misc_feature
<222> LOCATION: (28)..(28)
<223> OTHER INFORMATION: n is a, c, g, t or u
<220> FEATURE:
<221> NAME/KEY: misc_feature
<222> LOCATION: (54)..(54)
<223> OTHER INFORMATION: n is a, c, g, t or u

<400> SEQUENCE: 520
```

| | |
|---|---|
| catgagtgtg agctgatttg cacccnanca ccctctgtaa gtgcctgctg tggntttggt | 60 |
| tttgattatt ccgttaatgc tgagtctgtt tcacaaacga gattagcaga attaattatt | 120 |
| gaagatgcag tatgctttat ggttttaata acactgttaa aaactaaaca aggaagttaa | 180 |
| atatgttgat gattatcggt gactgctcac cacacagcat ccctcaggcc gagtcagttg | 240 |
| gcccagtgac tcccacatca caaactgccc tttcttggtc agaagaagca gagtggagcc | 300 |
| ttctcatccc cacgcgcgca gctgtggggc cccgtggtca cctggccaca tgggagtttg | 360 |
| catactgagt ggttcatctt ttccaatgtg ttgtgtcctt aatttacat ttatatttca | 420 |
| ttgccctttc taatgatcag a | 441 |

```
<210> SEQ ID NO 521
<211> LENGTH: 488
<212> TYPE: DNA
<213> ORGANISM: Homo sapiens
<220> FEATURE:
<221> NAME/KEY: misc_feature
<222> LOCATION: (456)..(456)
<223> OTHER INFORMATION: n is a, c, g, t or u

<400> SEQUENCE: 521
```

| | |
|---|---|
| tttgagttct gctctggcca atccccaagc tccacgctgt cagccacccc gctctcctac | 60 |
| ctcccagagg agcaggctac actcctgttc cttttagaga gagaaatatt gcggccgggc | 120 |
| gcggtggctc acgtctgtaa tcccagcatt ttggcaggcc aagggttttg ccatgttcgt | 180 |
| ggggctggtc tcaaactaat tacctcagat gatccgccca cctcggcctc ccaaagtgct | 240 |
| gggattacag ccgtcctggg ccgcggaca ccccgctgg ggcgatgcc caacagtgac | 300 |
| atcgacttga gcaacctgga gcggctggag aagtaccgga gcttcgaccg ctaccggcgc | 360 |
| cgggcagagc aggaggcgca ggccccgcac tggtggcgga cctaccgaga gtatttcggg | 420 |
| gagaagacag agttccagct tctaaaatat ttgctnctaa aatcttgacc acctgacttt | 480 |
| ccggattg | 488 |

```
<210> SEQ ID NO 522
<211> LENGTH: 339
<212> TYPE: DNA
<213> ORGANISM: Homo sapiens
<220> FEATURE:
<221> NAME/KEY: misc_feature
<222> LOCATION: (117)..(119)
```

<223> OTHER INFORMATION: n is a, c, g, t or u
<220> FEATURE:
<221> NAME/KEY: misc_feature
<222> LOCATION: (228)..(228)
<223> OTHER INFORMATION: n is a, c, g, t or u

<400> SEQUENCE: 522

| | | | | | |
|---|---|---|---|---|---|
| aaaatggatc | ctgtctttct | tagccaagga | ctggtctctt | ttctccaatg | tgtccctaac | 60 |
| agagtggtga | ggctggctct | tcccaccagt | acaggaagat | cattccttaa | aagaaannnc | 120 |
| catatggctt | ataagtgttc | tttcctgtat | gaagcccaag | ctgtccactt | ggagagacat | 180 |
| ctggccagcc | ccccgttgtt | ccagccatcc | ccagttcagg | catcaganat | gtggtgaaga | 240 |
| agccatccta | gatgcccagc | cccagctacc | atctgatgca | accacactgc | tcaccccgag | 300 |
| caagaactgc | ctgcaggagc | ctagtattat | cctctctca | | | 339 |

<210> SEQ ID NO 523
<211> LENGTH: 396
<212> TYPE: DNA
<213> ORGANISM: Homo sapiens

<400> SEQUENCE: 523

| | | | | | |
|---|---|---|---|---|---|
| gcggcagcaa | ccggaaccgg | aactcgtcgc | ggccaccacc | actgagcgct | gcggggaggg | 60 |
| ggagcaagga | ccggacgaga | cgctacgcct | gaaaacaggc | ggcgggcgag | ggacgaggct | 120 |
| taccacggca | ccacgcgagt | ggaaagggtc | gtctccgcta | gcggcggccc | acaccagctc | 180 |
| accgaggggc | ggcagcgcgc | ggcccggctg | ccggaccgta | ccatcccggg | cggtggagcc | 240 |
| gccgcggagg | ggcgcgcgcg | agccgaaggc | gcacccggga | ggcccaggta | gcccgggggc | 300 |
| cggtgctggg | gcgccgggca | ggcccggctc | ccgcctcgac | ccacccggag | ccagcccct | 360 |
| ctgcggacac | gacatcccca | tggggacggt | ggcgcg | | | 396 |

<210> SEQ ID NO 524
<211> LENGTH: 194
<212> TYPE: DNA
<213> ORGANISM: Homo sapiens

<400> SEQUENCE: 524

| | | | | | |
|---|---|---|---|---|---|
| ccccacaggt | gttcctctgt | gagctggtcg | ggcggccggg | gccggggccg | ggcttcgctg | 60 |
| ctccgtgcct | tccacctccc | tggcggtgcg | gggcctcagg | gtgggcctgg | gaagctggaa | 120 |
| acacctttgg | aaacagccgc | ctgaggcagc | tgtggacaga | agaccctgcc | cagcagccaa | 180 |
| gggagctggc | ctct | | | | | 194 |

<210> SEQ ID NO 525
<211> LENGTH: 526
<212> TYPE: DNA
<213> ORGANISM: Homo sapiens
<220> FEATURE:
<221> NAME/KEY: misc_feature
<222> LOCATION: (424)..(430)
<223> OTHER INFORMATION: n is a, c, g, t or u
<220> FEATURE:
<221> NAME/KEY: misc_feature
<222> LOCATION: (443)..(443)
<223> OTHER INFORMATION: n is a, c, g, t or u
<220> FEATURE:
<221> NAME/KEY: misc_feature
<222> LOCATION: (445)..(445)
<223> OTHER INFORMATION: n is a, c, g, t or u

<400> SEQUENCE: 525

| | | | | | |
|---|---|---|---|---|---|
| caagggcacg | aggcagtacc | tttgctccat | gcctttgctt | ggactagtcc | taccaccagc | 60 |

```
aattcctgca tttctgtgtt tggcaagttt ctgctcagcc tccaaagcct taaccaagtg      120
tcaccttttc tctgcagcat tttctgccac cctcccatt tcttccaata gaaccaggga      180
tcttttactt gggatccaga agcactgtgg acatattgcc atcacaacac ctttcatgtc      240
acaatggcaa ggtttgcact gtcttggagg agaggaagga agccatattc atccctgaac      300
cctcatctcc cagcactggt tgtaaaactg aaacaaaaat ggaaaacctt gatgaaattc      360
attgttggtg tggctatggg gaaacagatt ttccatttct gatagtaaat gaaataggca      420
ccannnnnnn aaaaaaaaaa aananattat taacactgaa aatgcacaca tctttcaacc      480
cagcaatttt atttcttgct ttctagagga atgtttgccc atgtgc                    526

<210> SEQ ID NO 526
<211> LENGTH: 197
<212> TYPE: DNA
<213> ORGANISM: Homo sapiens

<400> SEQUENCE: 526
cattattaat tataccaatc ctttcatata tgtagaaaaa atgtttgagt tggtcatctg       60
tcttttattg aagatgcatt tcaaatatca aatatatttg aaagataaaa tagcatctgt      120
gaaattgaat attattttat gtgcgcttgg ctatgcccta aatgtcagt ttattgtccc      180 taaagacgta tttattg                                                    197

<210> SEQ ID NO 527
<211> LENGTH: 275
<212> TYPE: DNA
<213> ORGANISM: Homo sapiens

<400> SEQUENCE: 527
ggatgaacgg gtgggctgaa gaacagctga atccaatagc ttggcagaac atgaagacag       60
gtttgttttc cagattctta aaactccaaa cttgatatta ttacagacac aaagtaaatg      120
gcacataaca agaggaagga gatcacagtt tgcaaaactt ttatgtggac cttggtactg      180
ggatcttgag atcctttgcc atggaggtgc atcttcttga gatgtttaca cagagaacag      240
actaacagca gaaaagatat cagggttaca gtaaa                                275

<210> SEQ ID NO 528
<211> LENGTH: 496
<212> TYPE: DNA
<213> ORGANISM: Homo sapiens
<220> FEATURE:
<221> NAME/KEY: misc_feature
<222> LOCATION: (43)..(43)
<223> OTHER INFORMATION: n is a, c, g, t or u
<220> FEATURE:
<221> NAME/KEY: misc_feature
<222> LOCATION: (46)..(46)
<223> OTHER INFORMATION: n is a, c, g, t or u
<220> FEATURE:
<221> NAME/KEY: misc_feature
<222> LOCATION: (48)..(48)
<223> OTHER INFORMATION: n is a, c, g, t or u
<220> FEATURE:
<221> NAME/KEY: misc_feature
<222> LOCATION: (51)..(51)
<223> OTHER INFORMATION: n is a, c, g, t or u

<400> SEQUENCE: 528
aataaatcct gcgagttcac gcccgcgtag ttcgccccct ganttntnga ngcgactcct       60
ttcgcatggg atctacaaaa ccgaactgcc ttaaagacct ctttcacacg gacgtgaagt      120
```

```
cacagaactg acaaaatccc atcctgtcaa agtgcacggg tctttgaaat ctaacacaaa    180
aagccataga aagattctct aaacaccctg tactaagagg aacacggaca gggcactgcg    240
ttctgaagta gaggccaggg cactggccct tagacacgtc tcgctgtcac cgggctaaca    300
acattggcaa gggcggcggc agcagcactg atatttgcag cccccaaggg ctctggcgaa    360
accccctcta ttactctgta tcctgcctgc ttccaagatg aacctgttgc tgggaaagaa    420
caggctaaat tagaaaaggg agtattttgt caaagttgaa ggtgagtgat agcctgcccg    480
cctcaaatag gatggg                                                    496

<210> SEQ ID NO 529
<211> LENGTH: 524
<212> TYPE: DNA
<213> ORGANISM: Homo sapiens

<400> SEQUENCE: 529
agcgcagtgg cgaggcgagt gtggaaggac tcctgaacca gctcgtcctg gagcacctgc     60
agctggcgcc tctgcagtgg gatgtgctgg tggacggaca gccatgtgac cgcgaggctg    120
tggcggcctg ccaggtgggc gaccccgtgc gcctggaggt gcggctgacc aaccggagcc    180
cgcgcagcgt agggcccttc gccctcactg tggtccccct tccaggacca cagaacggcg    240
tgcacaacta cgacctgcac gacaccgtct ccttcgtggg ctccagcacc ttctacctcg    300
acgcggtgca gccgtccggc cagtcggcct gcctcggggc cctcctcttc ctctacacgg    360
gagacttctt cctccacatc cggttccacg aggacagcac cagcaaggag ctgccaccct    420
cttggttctg cctgcccagt gtgcacgtgt gtgccctgga ggcgcaggcc tgagcccgcc    480
tacttccgtc cctctttctg cagggccaga ggtgaccctg cctg                     524

<210> SEQ ID NO 530
<211> LENGTH: 497
<212> TYPE: DNA
<213> ORGANISM: Homo sapiens

<400> SEQUENCE: 530
aggtcaatct cgtattctct atgtgatatt gctgacaaag tcaaagtaag gaaagacata     60
tcaagggaag gcaatggaag cacctttttct ttatagtaca ttcacctacc ttaacagacc    120
aagataacat aggagagaaa ctggggctta agtccttgat agagcttctg ggggcacagt    180
agttataggg ccaggtcaga aaatgtcctc acacactaag aaggcatttt aaaatcagaa    240
aagacagtca cactcacttt ggtcaccaag tcatttagcc atcctgtctg gaaagcatgt    300
tttcctctgg ggtcttcctc tggggtatct tgggaagggg tagagttttg aggagctaga    360
gaagagaaag aggtcatgag ggagattagt cctttctgaa tagcctagga aacccctcac    420
caaatagatg cctacacttt cttaaatcga gaagtaagaa ggaaatcaaa aacagcactc    480
ctacttcaaa gcatcag                                                   497

<210> SEQ ID NO 531
<211> LENGTH: 253
<212> TYPE: DNA
<213> ORGANISM: Homo sapiens

<400> SEQUENCE: 531
gtgaaaagca accaaaggca acagagtcta gctcatggcc accagaccaa aagcatccag     60
cttctgtgca cctcctgcaa agctggcaga ggccctggaa ttccagatca cctgagggga    120
aagggttgtc tctctccttt ctgttggggg aggggatgg gggacttttg ttggtggctc    180
```

```
ccacccatat atccctcctt taccatagta ctcccaccca cttccatcac ccatccaata    240
aaatgcagcc agg                                                       253
```

<210> SEQ ID NO 532
<211> LENGTH: 567
<212> TYPE: DNA
<213> ORGANISM: Homo sapiens

<400> SEQUENCE: 532

```
cacctcggtc accagtgtga accaagccag cacatcccgc ctggagggcc tacagtcaga    60
aaaccatcgc ctgcgaatga agatcacaga gctggataaa gacttggaag aggtcaccat    120
gcagctgcag gacacaccag aaaagaccac ctacattaaa cagaaccact accaagagct    180
caatgacatc ctcaacctgg gaaacttcac tgagagcaca gatggaggaa aggccatttt    240
aaaaaatcac ctcgatcaaa atccccagct acagtggaac acaacagagc cctctcgaac    300
atgcaaagat cctatagaag atataaactc tccagaacac atccagcgtc ggctgtccct    360
ccagctcccc atcctccacc acgcctacct cccatccatc ggaggcgtgg acgccagctg    420
tgtcagcccc tgcgtcagcc ccaccgccag ccccgccac agacatgtgc cacctcctt    480 ccgagtcatg gtctcgggcc tgtaagggtg gggggcctgg gcccggggcc tccccgtga    540 cagaaccaca ctgggcagag gggtctg                                        567
```

<210> SEQ ID NO 533
<211> LENGTH: 402
<212> TYPE: DNA
<213> ORGANISM: Homo sapiens

<400> SEQUENCE: 533

```
cagtattctg taccatagcg ctgctcttat gccatttgtt tattttata tagcttgaaa     60 catagaggga gagagggaga gagcctatac cccttactta gcatgcacaa agtgtattca    120
cgtgcagcag caacacaatg ttattcgttt tgtctacgtt tagtttccgt ttccaggtgt    180
ttatagtggt gttttaaaga gaatgtagac ctgtgagaaa cgttttgttt tgaaaaagca    240
gacagaagtc actcaattgt ttttgttgtg gtctgagcca aagagaatgc cattctcttg    300
ggtgggtaag actaaatctg taagctcttt gaaacaactt tctcttgtaa acgtttcagt    360
aataaaacat ctttccagtc cttggtcagt ttggttgtgt aa                       402
```

<210> SEQ ID NO 534
<211> LENGTH: 279
<212> TYPE: DNA
<213> ORGANISM: Homo sapiens
<220> FEATURE:
<221> NAME/KEY: misc_feature
<222> LOCATION: (178)..(178)
<223> OTHER INFORMATION: n is a, c, g, t or u

<400> SEQUENCE: 534

```
tgcattgtac ctgtagccat tccattgtga ataacacaaa aagtggagga aatatttttc    60
tcgcatttgg aaattattct gtgattcagc aaagaagttg ttcatgtcat taacaagttc    120
agaaatacat gctgccaaag ccaaaaagag tcttcagttt aataaaaata attaacanga    180
aggtgagaaa tggtttacca gctgttcact tactggattt aaggttactt gttggggaaa    240
gagcagagta agatgcaact ctgtcaaatc atggctgaa                           279
```

<210> SEQ ID NO 535

```
<211> LENGTH: 354
<212> TYPE: DNA
<213> ORGANISM: Homo sapiens

<400> SEQUENCE: 535
tagcaaagga catggaagcc tggaaagatg taaccagtgg aaatgctaaa atttaccagc    60
ttccaggggg tcacttttat cttctggatc ctgcgaacga gaaattaatc aagaactaca   120
taatcaagtg tctagaagta tcatcgatat ccaattttta gatattttcc ctttcacttt   180
taaaataatc aaagtaatat catactcttc tcagttattc agatatagct cagttttatt   240
cagattggaa attacacatt ttctactgtc agggagattc gttacataaa tatatttacg   300
tatctgggga caaaggtcaa gccagtaaag aatacttctg gcagcacttt ggga         354

<210> SEQ ID NO 536
<211> LENGTH: 497
<212> TYPE: DNA
<213> ORGANISM: Homo sapiens
<220> FEATURE:
<221> NAME/KEY: misc_feature
<222> LOCATION: (302)..(302)
<223> OTHER INFORMATION: n is a, c, g, t or u
<220> FEATURE:
<221> NAME/KEY: misc_feature
<222> LOCATION: (304)..(306)
<223> OTHER INFORMATION: n is a, c, g, t or u
<220> FEATURE:
<221> NAME/KEY: misc_feature
<222> LOCATION: (308)..(309)
<223> OTHER INFORMATION: n is a, c, g, t or u
<220> FEATURE:
<221> NAME/KEY: misc_feature
<222> LOCATION: (311)..(313)
<223> OTHER INFORMATION: n is a, c, g, t or u
<220> FEATURE:
<221> NAME/KEY: misc_feature
<222> LOCATION: (315)..(317)
<223> OTHER INFORMATION: n is a, c, g, t or u
<220> FEATURE:
<221> NAME/KEY: misc_feature
<222> LOCATION: (354)..(354)
<223> OTHER INFORMATION: n is a, c, g, t or u
<220> FEATURE:
<221> NAME/KEY: misc_feature
<222> LOCATION: (361)..(361)
<223> OTHER INFORMATION: n is a, c, g, t or u

<400> SEQUENCE: 536
ttccctgatg actcacttac aagttagtga actccttgtt taagtattac aaactgcaca    60
ccttctccct tctcaatcta gcttcacatc aggccttcct gccaaagcgg caaacttgcc   120
acatggggca aggtactccc caagcagaca aggcccatct gtgtcatgag tgatacccaa   180
tgctaatgcc atgctctgaa atgtagtgcc caccttggct tcccaaagtg ctgggattgc   240
agacgtgagt cactgcgccc agccattcca tgtctcttaa gtctcagaat ctcccctagc   300
tncnnncnng nnncnnnagt ggttgtcccc tcaaagctgt cccacaccct cctncgagga   360 nccttgtgt atctcctcca gctaccgcag agccacaaa cccaggcatc tatcaaagtc     420
cctcattcat gagggtggtg aggacacaga ctgcgaccag aacagaaata tgaaaatgtg   480
aatgacagcg tcccccg                                                  497

<210> SEQ ID NO 537
<211> LENGTH: 340
<212> TYPE: DNA
<213> ORGANISM: Homo sapiens
<220> FEATURE:
<221> NAME/KEY: misc_feature
```

```
<222> LOCATION: (68)..(68)
<223> OTHER INFORMATION: n is a, c, g, t or u
<220> FEATURE:
<221> NAME/KEY: misc_feature
<222> LOCATION: (81)..(81)
<223> OTHER INFORMATION: n is a, c, g, t or u
<220> FEATURE:
<221> NAME/KEY: misc_feature
<222> LOCATION: (115)..(115)
<223> OTHER INFORMATION: n is a, c, g, t or u
<220> FEATURE:
<221> NAME/KEY: misc_feature
<222> LOCATION: (118)..(118)
<223> OTHER INFORMATION: n is a, c, g, t or u
<220> FEATURE:
<221> NAME/KEY: misc_feature
<222> LOCATION: (120)..(120)
<223> OTHER INFORMATION: n is a, c, g, t or u
<220> FEATURE:
<221> NAME/KEY: misc_feature
<222> LOCATION: (122)..(122)
<223> OTHER INFORMATION: n is a, c, g, t or u

<400> SEQUENCE: 537
tggagttagc aaaccttttc atgcctgtga cctcactgga gttctttgat gttgggactt     60
cataagtntg ccaaatcctg ncacttactg ctttatgacc ttgaccattt accgnttntn    120
tntggacctc agtgttctca ggatgcaaaa ggagggtcag gggtaaaata gcgactttcg    180
aactgtcagg ggtaaaatag cgactttcaa acttttcaaa cttctgggac aagggtgaag    240
ggcaggactc tgcctctctc cttcccttca ccttattcca cttaaattgt gtgattctac    300
aagcttatgt ttaaaggaat atgttcctcc attacaaaga                          340

<210> SEQ ID NO 538
<211> LENGTH: 527
<212> TYPE: DNA
<213> ORGANISM: Homo sapiens
<220> FEATURE:
<221> NAME/KEY: misc_feature
<222> LOCATION: (133)..(133)
<223> OTHER INFORMATION: n is a, c, g, t or u
<220> FEATURE:
<221> NAME/KEY: misc_feature
<222> LOCATION: (148)..(148)
<223> OTHER INFORMATION: n is a, c, g, t or u

<400> SEQUENCE: 538
tgggaccacg ggcatttttg gcatgtacaa gggtataggt gcctcctact tccgcctcgg     60
cccccacacc atcctctccc tcttcttctg ggaccagctg cgctccctct actacacaga    120
cactaaataa canccgcttt cccagtcntc caccaaatga gcactccttg gccacttgtg    180
cctccaccac tatgtcctgg tgactactga ttaggtgacc tttcatccat ccatggggga    240
cagccaaccc cactccccat ctgttctcag ggttgaatca ctacaagaga tgagtttccc    300
ttctttcctt gggtgttgct ttaaaccttc cctacccatt ccctgggtaa ctcacacccc    360
tctctcaggg ctgaacgagt catcccaaag tgtatttcct cccactcacc actgccaccc    420
ttgagtccct cctgctccca tgcacagttt taaactcctc cctccaaaac caaagggaat    480
tgagagaccc aattcccagg cgtctgggac ccaggtgtcc tgttaga                  527

<210> SEQ ID NO 539
<211> LENGTH: 532
<212> TYPE: DNA
<213> ORGANISM: Homo sapiens

<400> SEQUENCE: 539
```

```
gacatgtttt ctagccttag ttccccatct acaaaatggg cctcatggaa tggaatgtct    60
ccacttcact ccagcatcaa caagtgggga attctgatgg attcaattcg acttcttttcc  120 atgggcgtgt tctaagcagc ctctttgttc cagaagctgc cctcagccag agttggataa   180
gccaatcctc actccccagc ctcctctgga tagggatgaa gacccactg ggttggaag     240 tgcagaggca gacaggtgta tggagtcacc tgtaaattga ttcaagtgag ccaggaaagc   300
agcaaaggaa agagaaacct gagtgacgac gtggtggagg aacagggctg aaagaggct    360 gctggctgtc tggcttcgca gctctggcct cctaatcagc ctcgctcttg tctctggtgt   420
tctctggctc ttgtccatct gtctgtgttt cttttttgcca gctattgact aatctttgct  480
gaagctgagc tagaattctg gtgtttataa gcaggtaact agctgagcac ta           532
```

<210> SEQ ID NO 540
<211> LENGTH: 811
<212> TYPE: DNA
<213> ORGANISM: Homo sapiens

<400> SEQUENCE: 540

```
ctttgggagg ctgaggcagg cagatcacct aaggccagga attcgacacc agcctggcca    60
acgtggcaaa acccgtctct actaaaaata caaaaattag ccgggcgtgg tggtgtgcgc   120
ctggaatccc agctacccag gaggctgagg caggagaaat gctggaaccc gggaggcaga   180
ggctgcagtg agctgagatc atgccactac tgcactccag cctgggtgac acagcaagac   240
tccctctaaa aaagaaaaa aagaaaagaa aagaaaagaa aatgatatat ccatgatgaa    300
ttaaaatgga gtggaaccca ctgatgggaa agccacagaa ggtaccagtt atccactcac   360
tgacttaggt gcctccacta gaattctcag cacgttttttg cagaacctgg caacaagag   420 cgaaacccca tctcaaaacc acaacaacaa caacaggaca acagagatgg acgacggatc   480
gggaaagcca accagacagc gtgaggccag gacggaaaga ggcacaggga gctctgctca   540
gtgtcgctac aggggatctc tcaggctcac aacgggccac tcctctaggg aagttctggt   600
ctcatcatga tccttgtttg gtctcactcc ccatgtcctt ctctgtccct cctccaactg   660 ccatttatt atttaactga aaaagtacca atcacccaca taggcatgac atactcatcc    720
atgtacccat ttcttaaaat tgatcattgt taacatttgg tgtaatttgc tttatttatt   780
tttaatgaaa taaataaaac tttacagaaa a                                   811
```

<210> SEQ ID NO 541
<211> LENGTH: 3874
<212> TYPE: DNA
<213> ORGANISM: Homo sapiens

<400> SEQUENCE: 541

```
aaaaaggtac aactaccttg ctgatgctgt acatatggct cacttgtgcc cagagagaga    60
ataaagccat gtcgaaacta tctacgattc cttgagtgtt tttccagcta cctgccactt   120
gcccacccac tccctcaga tctcagttag aacatgacaa ttgggctcat gaacaggatc    180
ctgagtggtt gcaggtgaac aagcagttgg cacaagggca aagtgatcac atcctgattg    240
agtggctatg gacagccata cagactgtgt ggaacaacgc tggtgaaata cccaaaccat   300
ttagaagcag taatgcctca cttgcctggg actgggatgg tgtggctgag actgccttac   360
tggcagccag gtgcgctatt cagcagccac aagccctaca agtaattaac caggggcacc   420
tgtttgagct ggaggtgcat gtggccacag acgttttgg ttgaggcttg tgcaatgca    480 cagagcgcct aagaatgcca gtaggctttt ggtcccaact atggaaagga gctgaactcc   540
```

-continued

```
ggtattcatt gatagagaaa cagctagcag ctgtatatgc tggccttcgg gctcatgaga    600
gcatgacagg acaggctgca gtcatcatat ggacaactta cccaataaca ggatggatgc    660
gtctatgtgt aatgaccacc tggagtggga tagcacagat gtccactttg caaaatggg    720
gcgactcctt gcagcagtgg agtaagctga gtacaagtcc catagcagca gagttgcaag    780
aggtcttggg acgtgtagtc ctaatgcaag ataaggccat gcggcctgag caccectag    840
atcctgagtc ttcaccattt aaggaagggc atcccaggat tcctgagggg gcatggtaca    900
cagtagatga ggtgctactg ctgcctggac cactgttgca gtccaaccta gtactgacac    960
catatggttt gaaactgggt gcggacaaag tagccaatgg gctgaactca gagcagtgtg   1020
gatggtaatc accaaggagg tgacacctgt ggtaatctgt actgatagct gggcagtcta   1080
ctgaggctta accttgtggt taactacttg gaaaatacag aattggctag tgagccacag   1140
acccatttga ggccaagcca tatggcaaga cctttgggga ataggtcatc aaaaagaggt   1200
aactatttat catgtgtcag gccatatgcc tttggccacc cctagtaatg atgaggcaga   1260
tgccttggct aaggtcagat ggtcagagtc agcaccaaca caagatgtga ccttgtggct   1320
acaccggaaa ctgggacatg caggggtaa actgatgtaa caattcaata agtgttgggg   1380
tctgtccctt cccaagcaag acatttgtga ggcttgtcag aaatgcctgg catgtgttca   1440
gacatatcct aaaaagaggc agctgcccgg tgttatacaa caagtaacaa tagggtgagt   1500
gcccttgacc aggtgggaag tagactacat cgggccgccg ccaaagtcgc gagggtatac   1560
gcatgcacta acggctgtag acatggccac aggcctgttg ttcacctacc cttgcagggt   1620
ggccaaccaa cagaacacca tccaggcct gcaacactta tgttccctgt atggttgtcc    1680
tctggccatt gagagtgata ggggaacaca tttcactgga caacaggtac aatgatgggc   1740
acagcaaatg gacataaagt ggggattcca tgtgccatac agcccacaag ctgaggtatt   1800
attgaatgat ataatgggat cttgaagaat ggattacgct tgcatgtcaa acccctgtct   1860
ttgcggagct ggagttccag gctggacctg gtgctccaaa ccttaaatga atggccacag   1920
aaaggtggcc cggccccagt ggaggctttg tttcactagg ccaccacccc cattcaattg   1980
gagatacata ccaaggatga cctcctccga tcaggtatgg ggacaaatgg taacctgttg   2040
ttgcctgccc caacaaccct gaaggcaggg gaacagaaaa cctggctgtg gccatggacc   2100
ctccaagctc tccactgctg gtggttggcc atcatagctc cctgtgggga gggcctacag   2160
tatgacttgc atgtcacttt ttgagtgttc aatacatggc ttccaaggtt gactgtttgt   2220
agaggaacag ccaggaagg aaccctcctc tgagggacat atgtactatc tgatgggcct    2280
attatgagct acgctgtgac tttggcatgg atacaggatt ctaaggaacc atggagattt   2340
gagaaggtgt ggtaccatca cccagggcaa aagcccttgg tggctgcatt gttatccagg   2400
gatggaaagt tagcctatat tttgcctgag ggatgtgatt tacctctgtt agtacctgtg   2460
cctgctctgt catttcaacc gtaggttaac atgctccaat tgcattgtgg actgacccca   2520
cacctatgct gaggtgacca atgtttccaa ctgttggacc tgcactgcct ttccagcagc   2580
agctgcagac agcttgcccc gacacataca tcccgtgtct gcagagaact ggacatgcct   2640
ggagacttga gatcccatgg ctgatgcctg gaacacaatg tggcaagctt tggacaaagg   2700
acacagcaag acccatggct ggaccgtagc attcgtgatg agtggggctg gctagtaggg   2760
gaacatgtag tagcccaagc ccaggcattg cagtgcacag agcaacattg gggtaacagg   2820
atgggtacct gtcacggcct gtgcaaacat aacatgtgtc accacactga aggtatggta   2880
```

| | |
|---|---:|
| gaacaagtgg cctcaccaag gtcggacccc aatggacttt ttgcctcttg ggagcttatg | 2940 |
| ggtctatgag gacacagtag cctttcctat cagcaaactg gagtggatgt tgtatctggg | 3000 |
| ggtggcctta tgtacctgct actgttctcc ccacattgcc cagatgcctg tataactggg | 3060 |
| aggcactgtg ctctcagttt ttgcgaatgt gatgagcccc ctggtgtttc tacccttggg | 3120 |
| caatgactat ccctggagca ggtgtcaaaa ctgtagaagc acaatttact gctcttgcgg | 3180 |
| agcacaccgc tcaggctctg aattacacct gagtgtccct cctcctgtta atgaatgagg | 3240 |
| ttgatcagat caaaaagtgg tgttgcaaaa ccaagtggcc ttagacataa ctgctgccca | 3300 |
| aggagccacc tgtgcccttt taggaacaca atgttgtacc ttatccctga caatcagcag | 3360 |
| aacataacag cagccctgca aagggtgtctt ccaggagatt aaggtgactg agagcctcac | 3420 |
| tgtcaacccc ctgcagagat ggtgagcatc cctaggttct ggcgtacatt gggccctaat | 3480 |
| agtcataagt atcatagctg agatcctagt agtgagctgt tgctctctgt attgttgttg | 3540 |
| tgggttatgg actcagggct ccgccatata ggcatgtgtc cctgcctgga ggacgccctc | 3600 |
| agcctagggg gtgtagtgta agggaaatgg ctgtgcttta gtcaggagta ggctgaggca | 3660 |
| gccttctggt gcagcatgac tcagtgggtt tggagtgcaa gcacacaacc ttgctcgtta | 3720 |
| tgtaaccaca ccacatgagg cccattaggt aacaactcac atgagctcgt gtttggctca | 3780 |
| gagccactat tgtctgtaaa aggtatacct tgctgatgct gcacatatgg ctcgcttgtg | 3840 |
| cccagagaga gagtaaagcc atgttgaaac tgtc | 3874 |

<210> SEQ ID NO 542
<211> LENGTH: 177
<212> TYPE: PRT
<213> ORGANISM: Homo sapiens

<400> SEQUENCE: 542

Met Pro Val Gly Phe Trp Ser Gln Leu Trp Lys Gly Ala Glu Leu Arg
1               5                   10                  15

Tyr Ser Leu Ile Glu Lys Gln Leu Ala Ala Val Tyr Ala Gly Leu Arg
            20                  25                  30

Ala His Glu Ser Met Thr Gly Gln Ala Ala Val Ile Ile Trp Thr Thr
        35                  40                  45

Tyr Pro Ile Thr Gly Trp Met Arg Leu Cys Val Met Thr Thr Trp Ser
    50                  55                  60

Gly Ile Ala Gln Met Ser Thr Leu Ala Lys Trp Gly Asp Ser Leu Gln
65                  70                  75                  80

Gln Trp Ser Lys Leu Ser Thr Ser Pro Ile Ala Ala Glu Leu Gln Glu
                85                  90                  95

Val Leu Gly Arg Val Val Leu Met Gln Asp Lys Ala Met Arg Pro Glu
            100                 105                 110

Ala Pro Leu Asp Pro Glu Ser Ser Pro Phe Lys Glu Gly His Pro Arg
        115                 120                 125

Ile Pro Glu Gly Ala Trp Tyr Thr Val Asp Glu Val Leu Leu Leu Pro
    130                 135                 140

Gly Pro Leu Leu Gln Ser Asn Leu Val Leu Thr Pro Tyr Gly Leu Lys
145                 150                 155                 160

Leu Gly Ala Asp Lys Val Ala Asn Gly Leu Asn Ser Glu Gln Cys Gly
                165                 170                 175

Trp

<210> SEQ ID NO 543

-continued

```
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 543
catgaacagg atcctgagtg g                                              21

<210> SEQ ID NO 544
<211> LENGTH: 24
<212> TYPE: DNA
<213> ORGANISM: artificial
<220> FEATURE:
<223> OTHER INFORMATION: Description of artificial sequence:
      Oligonucleotide

<400> SEQUENCE: 544
tgaggcatta ctgcttctaa atgg                                           24

<210> SEQ ID NO 545
<211> LENGTH: 2863
<212> TYPE: DNA
<213> ORGANISM: Homo sapiens

<400> SEQUENCE: 545
cacgccaaac acgcagcccc ctcccgctgg agtgacaact ggccagcata ctctaggctg     60
ttgtcccttt aaaacttgaa tccaaggggg taatgattta tcaaacttgt attatcaaga    120
aaatgtcaaa ccaagggcac cttgctttgc actgacgcaa acccggcctt tcccaaggag    180
atatagaaag cgcctctcct gcctgagcca aacccagtct tgtcaatagc gggtttcacc    240
ctccaccagt tcagtctgtt gcctgtgtca gacatggatt gcagtgctcc caaggaaatg    300
aataaactgc cagccaacag cccggaggcg gcggcggcgc agggccaccc ggatggccca    360
tgcgctccca ggacgagccc ggagcaggag cttcccgcgg ctgccgcccc gccgccgcca    420
cgtgtgccca ggtccgcttc caccggcgcc caaactttcc agtcagcgga cgcgcgagcc    480
tgcgaggctg agcggccagg agtggggtct tgcaaactca gtagcccgcg ggcgcaggcg    540
gcctctgcag ctctgcggga cttgagagag cgcaaggcg cgcaggcctc gccccctccc     600
gggagctccg ggcccggcaa cgcgctgcac tgtaagatcc cttttctgcg aggcccggag    660
ggggatgcga acgtgagtgt gggcaagggc accctggagc ggaacaatac ccctgttgtg    720
ggctgggtga acatgagcca gagcaccgtg gtgctggcca cggatggaat cacgtccgtg    780
ctcccgggca gcgtggccac cgttgccacc caggaggacg agcaagggga tgagaataag    840
gcccgaggga actggtccag caaactggac ttcatcctgt ccatggtggg gtacgcagtg    900
gggctgggca atgtctggag gtttccctac ctggcctttcc agaacgggg aggtgctttc    960 ctcatcccctt acctgatgat gctggctctg gctggattac ccatcttctt cttggaggtg   1020
tcgctgggcc agtttgccag ccagggacca gtgtctgtgt ggaaggccat cccagctcta   1080
caaggctgtg gcatcgcgat gctgatcatc tctgtcctaa tagccatata ctacaatgtg   1140
attatttgct atacactttt ctacctgttt gcctcctttg tgtctgtact accctggggc   1200
tcctgcaaca acccttggaa tacgccagaa tgcaaagata aaccaaaact tttattagat   1260
tcctgtgtta tcagtgacca tcccaaaata cagatcaaga actcgacttt ctgcatgacc   1320
gcttatccca acgtgacaat ggttaatttc accagccagg ccaataagac atttgtcagt   1380
ggaagtgaag agtacttcaa gtactttgtg ctgaagattt ctgcagggat tgaatatcct   1440
```

-continued

```
ggcgagatca ggtggccact agctctctgc ctcttcctgg cttgggtcat tgtgtatgca    1500
tcattggcta aaggaatcaa gacttcagga aaagtggtgt acttcacggc cacgttcccg    1560
tatgtcgtac tcgtgatcct cctcatccga ggagtcaccc tgcctggagc tggagctggg    1620
atctggtact tcatcacacc caagtgggag aaactcacgg atgccacggt gtggaaagat    1680
gctgccactc agattttctt ctctttatct gctgcatggg gaggcctgat cactctctct    1740
tcttacaaca aattccacaa caactgctac agggacactc taattgtcac ctgcaccaac    1800
agtgccacaa gcatctttgc cggcttcgtc atcttctccg ttatcggctt catggccaat    1860
gaacgcaaag tcaacattga gaatgtggca gaccaagggc caggcattgc atttgtggtt    1920
tacccggaag ccttaaccag gctgcctctc tctccgttct gggccatcat cttttttcctg    1980 atgctcctca ctcttggact tgacactatg tttgccacca tcgagaccat agtgacctcc    2040
atctcagacg agtttcccaa gtacctacgc acacacaagc cagtgtttac tctgggctgc    2100
tgcatttgtt tcttcatcat gggttttcca atgatcactc agggtggaat ttacatgttt    2160
cagcttgtgg acacctatgc tgcctcctat gcccttgtca tcattgccat ttttgagctc    2220
gtggggatct cttatgtgta tggcttgcaa agattctgtg aagatataga gatgatgatt    2280
ggattccagc ctaacatctt ctggaaagtc tgctgggcat ttgtaacccc aaccattta    2340 acctttatcc tttgcttcag cttttaccag tgggagccca tgacctatgg ctcttaccgc    2400
tatcctaact ggtccatggt gctcggatgg ctaatgctcg cctgttccgt catctggatc    2460
ccaattatgt ttgtgataaa aatgcatctg gcccctggaa gatttattga gaggctgaag    2520
ttggtgtgct cgccacagcc ggactgggc ccattcttag ctcaacaccg cggggagcgt    2580
tacaagaaca tgatcgaccc cttgggaacc tcttccttgg gactcaaact gccagtgaag    2640
gatttggaac tgggcactca gtgctagtcc agtggtgtgg gatggtccag acttgatcct    2700 gttttttcctc tctgcctcct cctaatgttt tccatagctc tcctcccatt tttcttcatc    2760
tttcttccta catcttggtt cacatccacg catgagagtg attatgtaga aaagtaggca    2820
tagtgtcgca tgctgcagta aagagctaca tagaccacct gaa                     2863
```

<210> SEQ ID NO 546
<211> LENGTH: 797
<212> TYPE: PRT
<213> ORGANISM: Homo sapiens

<400> SEQUENCE: 546

Met Asp Cys Ser Ala Pro Lys Glu Met Asn Lys Leu Pro Ala Asn Ser
1               5                   10                  15

Pro Glu Ala Ala Ala Gln Gly His Pro Asp Gly Pro Cys Ala Pro
            20                  25                  30

Arg Thr Ser Pro Glu Gln Glu Leu Pro Ala Ala Ala Pro Pro Pro
        35                  40                  45

Pro Arg Val Pro Arg Ser Ala Ser Thr Gly Ala Gln Thr Phe Gln Ser
    50                  55                  60

Ala Asp Ala Arg Ala Cys Glu Ala Glu Arg Pro Gly Val Gly Ser Cys
65                  70                  75                  80

Lys Leu Ser Ser Pro Arg Ala Gln Ala Ser Ala Ala Leu Arg Asp
            85                  90                  95

Leu Arg Glu Ala Gln Gly Ala Gln Ala Ser Pro Pro Gly Ser Ser
            100                 105                 110

Gly Pro Gly Asn Ala Leu His Cys Lys Ile Pro Phe Leu Arg Gly Pro

```
            115                 120                 125
Glu Gly Asp Ala Asn Val Ser Val Gly Lys Gly Thr Leu Glu Arg Asn
            130                 135                 140
Asn Thr Pro Val Val Gly Trp Val Asn Met Ser Gln Ser Thr Val Val
145                 150                 155                 160
Leu Ala Thr Asp Gly Ile Thr Ser Val Leu Pro Gly Ser Val Ala Thr
                165                 170                 175
Val Ala Thr Gln Glu Asp Glu Gln Gly Asp Glu Asn Lys Ala Arg Gly
            180                 185                 190
Asn Trp Ser Ser Lys Leu Asp Phe Ile Leu Ser Met Val Gly Tyr Ala
            195                 200                 205
Val Gly Leu Gly Asn Val Trp Arg Phe Pro Tyr Leu Ala Phe Gln Asn
210                 215                 220
Gly Gly Gly Ala Phe Leu Ile Pro Tyr Leu Met Met Leu Ala Leu Ala
225                 230                 235                 240
Gly Leu Pro Ile Phe Phe Leu Glu Val Ser Leu Gly Gln Phe Ala Ser
                245                 250                 255
Gln Gly Pro Val Ser Val Trp Lys Ala Ile Pro Ala Leu Gln Gly Cys
            260                 265                 270
Gly Ile Ala Met Leu Ile Ile Ser Val Leu Ile Ala Ile Tyr Tyr Asn
            275                 280                 285
Val Ile Ile Cys Tyr Thr Leu Phe Tyr Leu Phe Ala Ser Phe Val Ser
            290                 295                 300
Val Leu Pro Trp Gly Ser Cys Asn Asn Pro Trp Asn Thr Pro Glu Cys
305                 310                 315                 320
Lys Asp Lys Thr Lys Leu Leu Asp Ser Cys Val Ile Ser Asp His
                325                 330                 335
Pro Lys Ile Gln Ile Lys Asn Ser Thr Phe Cys Met Thr Ala Tyr Pro
            340                 345                 350
Asn Val Thr Met Val Asn Phe Thr Ser Gln Ala Asn Lys Thr Phe Val
            355                 360                 365
Ser Gly Ser Glu Glu Tyr Phe Lys Tyr Phe Val Leu Lys Ile Ser Ala
370                 375                 380
Gly Ile Glu Tyr Pro Gly Glu Ile Arg Trp Pro Leu Ala Leu Cys Leu
385                 390                 395                 400
Phe Leu Ala Trp Val Ile Val Tyr Ala Ser Leu Ala Lys Gly Ile Lys
                405                 410                 415
Thr Ser Gly Lys Val Val Tyr Phe Thr Ala Thr Phe Pro Tyr Val Val
            420                 425                 430
Leu Val Ile Leu Leu Ile Arg Gly Val Thr Leu Pro Gly Ala Gly Ala
            435                 440                 445
Gly Ile Trp Tyr Phe Ile Thr Pro Lys Trp Glu Lys Leu Thr Asp Ala
            450                 455                 460
Thr Val Trp Lys Asp Ala Ala Thr Gln Ile Phe Phe Ser Leu Ser Ala
465                 470                 475                 480
Ala Trp Gly Gly Leu Ile Thr Leu Ser Ser Tyr Asn Lys Phe His Asn
                485                 490                 495
Asn Cys Tyr Arg Asp Thr Leu Ile Val Thr Cys Thr Asn Ser Ala Thr
            500                 505                 510
Ser Ile Phe Ala Gly Phe Val Ile Phe Ser Val Ile Gly Phe Met Ala
            515                 520                 525
Asn Glu Arg Lys Val Asn Ile Glu Asn Val Ala Asp Gln Gly Pro Gly
            530                 535                 540
```

```
Ile Ala Phe Val Val Tyr Pro Glu Ala Leu Thr Arg Leu Pro Leu Ser
545                 550                 555                 560

Pro Phe Trp Ala Ile Phe Phe Leu Met Leu Leu Thr Leu Gly Leu
            565                 570                 575

Asp Thr Met Phe Ala Thr Ile Glu Thr Ile Val Thr Ser Ile Ser Asp
            580                 585                 590

Glu Phe Pro Lys Tyr Leu Arg Thr His Lys Pro Val Phe Thr Leu Gly
                595                 600                 605

Cys Cys Ile Cys Phe Phe Ile Met Gly Phe Pro Met Ile Thr Gln Gly
            610                 615                 620

Gly Ile Tyr Met Phe Gln Leu Val Asp Thr Tyr Ala Ala Ser Tyr Ala
625                 630                 635                 640

Leu Val Ile Ile Ala Ile Phe Glu Leu Val Gly Ile Ser Tyr Val Tyr
                645                 650                 655

Gly Leu Gln Arg Phe Cys Glu Asp Ile Glu Met Met Ile Gly Phe Gln
                660                 665                 670

Pro Asn Ile Phe Trp Lys Val Cys Trp Ala Phe Val Thr Pro Thr Ile
            675                 680                 685

Leu Thr Phe Ile Leu Cys Phe Ser Phe Tyr Gln Trp Glu Pro Met Thr
690                 695                 700

Tyr Gly Ser Tyr Arg Tyr Pro Asn Trp Ser Met Val Leu Gly Trp Leu
705                 710                 715                 720

Met Leu Ala Cys Ser Val Ile Trp Ile Pro Ile Met Phe Val Ile Lys
                725                 730                 735

Met His Leu Ala Pro Gly Arg Phe Ile Glu Arg Leu Lys Leu Val Cys
            740                 745                 750

Ser Pro Gln Pro Asp Trp Gly Pro Phe Leu Ala Gln His Arg Gly Glu
            755                 760                 765

Arg Tyr Lys Asn Met Ile Asp Pro Leu Gly Thr Ser Ser Leu Gly Leu
770                 775                 780

Lys Leu Pro Val Lys Asp Leu Glu Leu Gly Thr Gln Cys
785                 790                 795

<210> SEQ ID NO 547
<211> LENGTH: 24
<212> TYPE: DNA
<213> ORGANISM: artificial
<220> FEATURE:
<223> OTHER INFORMATION: Description of artificial sequence:
      Oligonucleotide

<400> SEQUENCE: 547
ggatttgcaa gttgtgtagt gtgc                                          24

<210> SEQ ID NO 548
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 548
aagcagatgg tcatcttcca g                                             21

<210> SEQ ID NO 549
<211> LENGTH: 2426
<212> TYPE: DNA
```

<213> ORGANISM: Homo sapiens

<400> SEQUENCE: 549

```
ctctttcaac tcaagagctc agtcctgtgt ctctcatgga ggcgtctcta accaggaggc      60
tactcttta  agacaggcat tttacttgca gcaaaataat aggaaggaga ttcgcttgct     120
ttgcacagag gctgagccac aggagaaagc aaagccaatg tgatttattg aatgaaagca     180
ctggacaatt accaacaact tgttcctctg ctgcctcgaa cagcataaac tggaattgtc     240
gtgtgaaaat gacgcaacaa atgcaaaatt tacatctctg tcagtcaaaa aaacatagtg     300
ctccctcatc tcccaacgca gccaaacgcc tgtacaggaa cctctctgag aaactgaaag     360
ggagccactc ttccttcgat gaggcctatt ttaggacaag aactgatcgg ctgagtctca     420
ggaagacctc ggtgaatttc cagggcaatg aagccatgtt tgaggcagtc gaacagcagg     480
acatggatgc tgtgcagatc ctcctgtatc agtacacacc agaagaactt gacctcaaca     540
cacctaacag cgagggcttg acacccctgg atattgccat catgaccaac aatgtgccca     600
ttgcaaggat tcttctgagg acaggggccc gagaaagtcc acactttgtc agcctggaaa     660
gccgagcaat gcacctcaac acactggtcc aggaagccca ggagagggtg agtgaactgt     720
ctgcccaggt ggagaatgaa ggattcactc tggacaacac agagaaagag aagcagctga     780
aagcttggga gtggaggtat cggctctaca gacgcatgaa aacaggcttt gagcatgcca     840
gagcccctga gatgccaacc aatgtctgtc tcatggtaac cagcagcaca tcactcactg     900
tcagcttcca agagcctctt agcgtcaatg cagctgtagt aaccaggtat aaagtggaat     960
ggagtatgtc cgaagacttt tctcctttgg ctggagaaat catcatggat aatctgcaga    1020
ctctgagatg cacaatcaca ggacttacaa tgggccaaca gtattttgtt caagtctcgg    1080
cttacaatat gaaaggatgg ggacctgctc agaccacgac accggcatgt gcctctcctt    1140
ctaactggaa agactatgac gacagagagc ccagacacaa gggacagagt gaagttttgg    1200
aaggtctgct gcagcaggtc cgagcccttc atcagcatta cagttgccgg gaaagcacaa    1260
aattacaaac cacaggccgc aagcagtcag tctcaagaag cctgaaacac ctgttccatt    1320
cctcgaacaa gtttgtgaag accttaaaac ggggactcta catagccgtt atattttatt    1380
acaaagacaa tatcttagtc accaatgaag atcaagtacc aattgttgaa atagatgact    1440
ctcacaccag ttctattaca caagattttc tgtggttcac gaagctgtct tgtatgtggg    1500
aagatataag gtggctgagg caaagcatac caatatcctc atcctcatcc acagtgctgc    1560
aaactcggca agatgctc   gcagcaacag cacagctaca gaatttactt gggacacaca    1620
acttgggaag agtttactat gagcccatta agatcgaca  tggaaacata ctcatagtca    1680
ccatcaggga ggtggagatg ctttattcat ttttaatgg  caaatggatg cagatctcaa    1740
agctgcaaag ccagagaaag tctctatcaa cacctgagga gccaacagct ttagacattc    1800
tactgataac catccaggat attctatcct atcacaaaag gagtcatcag cgtctctttc    1860
ctggattata tctgggttac ctaaagctct gtagctctgt ggatcaaatc aaagttcttg    1920
ttacccaaaa gttgcccaac attctctgcc acgtgaagat ccgtgaaaac aataatattt    1980
ctagagagga atgggaatgg atccaaaagc tttctggctc tgaatctatg aaagtgtgg    2040
atcatacttc tgactgcccc atgcaattgt tcttctacga gctccagatg gcagtgaaag    2100
ctctccttca gcagatcaat ataccctac  accaggcaag gaacttccgc ctctacacac    2160
aggaggtgtt ggaaatgggt cacaatgtgt cctttcttct cctgctccct gcctcagacg    2220
acgtctgtac agccccagga cagaataatc cttacacccc acactcaggg tttcttaacc    2280
```

```
tccctcttca gatgtttgaa cttggtatag tagcttgttt cacctagaaa tattaaccca    2340
gcctccttat aataaaatca caaagttata tctgttcccc cttgtcccag tggagggtca    2400
ataaatcaca tgatggcttt ggcaac                                         2426
```

<210> SEQ ID NO 550
<211> LENGTH: 763
<212> TYPE: PRT
<213> ORGANISM: Homo sapiens

<400> SEQUENCE: 550

```
Met Glu Ala Ser Leu Thr Arg Arg Leu Leu Phe Lys Asp Arg His Phe
1               5                   10                  15

Thr Cys Ser Lys Ile Ile Gly Arg Arg Phe Ala Cys Phe Ala Gln Arg
            20                  25                  30

Leu Ser His Arg Arg Lys Gln Ser Gln Cys Asp Leu Leu Asn Glu Ser
        35                  40                  45

Thr Gly Gln Leu Pro Thr Thr Cys Ser Ser Ala Ala Ser Asn Ser Ile
    50                  55                  60

Asn Trp Asn Cys Arg Val Lys Met Thr Gln Gln Met Gln Asn Leu His
65                  70                  75                  80

Leu Cys Gln Ser Lys Lys His Ser Ala Pro Ser Ser Pro Asn Ala Ala
                85                  90                  95

Lys Arg Leu Tyr Arg Asn Leu Ser Glu Lys Leu Lys Gly Ser His Ser
            100                 105                 110

Ser Phe Asp Glu Ala Tyr Phe Arg Thr Arg Thr Asp Arg Leu Ser Leu
        115                 120                 125

Arg Lys Thr Ser Val Asn Phe Gln Gly Asn Glu Ala Met Phe Glu Ala
    130                 135                 140

Val Glu Gln Gln Asp Met Asp Ala Val Gln Ile Leu Leu Tyr Gln Tyr
145                 150                 155                 160

Thr Pro Glu Glu Leu Asp Leu Asn Thr Pro Asn Ser Glu Gly Leu Thr
                165                 170                 175

Pro Leu Asp Ile Ala Ile Met Thr Asn Asn Val Pro Ile Ala Arg Ile
            180                 185                 190

Leu Leu Arg Thr Gly Ala Arg Glu Ser Pro His Phe Val Ser Leu Glu
        195                 200                 205

Ser Arg Ala Met His Leu Asn Thr Leu Val Gln Glu Ala Gln Glu Arg
    210                 215                 220

Val Ser Glu Leu Ser Ala Gln Val Glu Asn Gly Phe Thr Leu Asp
225                 230                 235                 240

Asn Thr Glu Lys Glu Lys Gln Leu Lys Ala Trp Glu Trp Arg Tyr Arg
                245                 250                 255

Leu Tyr Arg Arg Met Lys Thr Gly Phe Glu His Ala Arg Ala Pro Glu
            260                 265                 270

Met Pro Thr Asn Val Cys Leu Met Val Thr Ser Ser Thr Ser Leu Thr
        275                 280                 285

Val Ser Phe Gln Glu Pro Leu Ser Val Asn Ala Ala Val Val Thr Arg
    290                 295                 300

Tyr Lys Val Glu Trp Ser Met Ser Glu Asp Phe Ser Pro Leu Ala Gly
305                 310                 315                 320

Glu Ile Ile Met Asp Asn Leu Gln Thr Leu Arg Cys Thr Ile Thr Gly
                325                 330                 335

Leu Thr Met Gly Gln Gln Tyr Phe Val Gln Val Ser Ala Tyr Asn Met
```

-continued

```
                340             345             350
Lys Gly Trp Gly Pro Ala Gln Thr Thr Thr Pro Ala Cys Ala Ser Pro
            355                 360                 365

Ser Asn Trp Lys Asp Tyr Asp Asp Arg Glu Pro Arg His Lys Gly Gln
        370                 375                 380

Ser Glu Val Leu Glu Gly Leu Leu Gln Gln Val Arg Ala Leu His Gln
385                 390                 395                 400

His Tyr Ser Cys Arg Glu Ser Thr Lys Leu Gln Thr Thr Gly Arg Lys
                405                 410                 415

Gln Ser Val Ser Arg Ser Leu Lys His Leu Phe His Ser Ser Asn Lys
            420                 425                 430

Phe Val Lys Thr Leu Lys Arg Gly Leu Tyr Ile Ala Val Ile Phe Tyr
        435                 440                 445

Tyr Lys Asp Asn Ile Leu Val Thr Asn Glu Asp Gln Val Pro Ile Val
    450                 455                 460

Glu Ile Asp Asp Ser His Thr Ser Ser Ile Thr Gln Asp Phe Leu Trp
465                 470                 475                 480

Phe Thr Lys Leu Ser Cys Met Trp Glu Asp Ile Arg Trp Leu Arg Gln
                485                 490                 495

Ser Ile Pro Ile Ser Ser Ser Ser Thr Val Leu Gln Thr Arg Gln
            500                 505                 510

Lys Met Leu Ala Ala Thr Ala Gln Leu Gln Asn Leu Leu Gly Thr His
        515                 520                 525

Asn Leu Gly Arg Val Tyr Tyr Glu Pro Ile Lys Asp Arg His Gly Asn
    530                 535                 540

Ile Leu Ile Val Thr Ile Arg Glu Val Glu Met Leu Tyr Ser Phe Phe
545                 550                 555                 560

Asn Gly Lys Trp Met Gln Ile Ser Lys Leu Gln Ser Gln Arg Lys Ser
                565                 570                 575

Leu Ser Thr Pro Glu Glu Pro Thr Ala Leu Asp Ile Leu Leu Ile Thr
            580                 585                 590

Ile Gln Asp Ile Leu Ser Tyr His Lys Arg Ser His Gln Arg Leu Phe
        595                 600                 605

Pro Gly Leu Tyr Leu Gly Tyr Leu Lys Leu Cys Ser Ser Val Asp Gln
    610                 615                 620

Ile Lys Val Leu Val Thr Gln Lys Leu Pro Asn Ile Leu Cys His Val
625                 630                 635                 640

Lys Ile Arg Glu Asn Asn Asn Ile Ser Arg Glu Glu Trp Glu Trp Ile
                645                 650                 655

Gln Lys Leu Ser Gly Ser Glu Ser Met Glu Ser Val Asp His Thr Ser
            660                 665                 670

Asp Cys Pro Met Gln Leu Phe Phe Tyr Glu Leu Gln Met Ala Val Lys
        675                 680                 685

Ala Leu Leu Gln Gln Ile Asn Ile Pro Leu His Gln Ala Arg Asn Phe
    690                 695                 700

Arg Leu Tyr Thr Gln Glu Val Leu Glu Met Gly His Asn Val Ser Phe
705                 710                 715                 720

Leu Leu Leu Leu Pro Ala Ser Asp Asp Val Cys Thr Ala Pro Gly Gln
                725                 730                 735

Asn Asn Pro Tyr Thr Pro His Ser Gly Phe Leu Asn Leu Pro Leu Gln
            740                 745                 750

Met Phe Glu Leu Gly Ile Val Ala Cys Phe Thr
        755                 760
```

<210> SEQ ID NO 551
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 551
agctctgtag ctctgtggat c                                            21

<210> SEQ ID NO 552
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 552
aggcggaagt tccttgcctg g                                            21

<210> SEQ ID NO 553
<211> LENGTH: 2281
<212> TYPE: DNA
<213> ORGANISM: Homo sapiens

<400> SEQUENCE: 553
gcgggccgca gccagcgcac ccagaccctg cgctgccctc ggacggccgg gcgcggagcc    60
ccagctgcgg aggccgacgg cacccggccc cgagcgcctc gacgccgagc cgcgcgcgcc   120
ttctccgcca ggcccggcgg gcgggagcgg gggcgaggga gcaggagcgg ccagtgcccc   180
cgacaccccc ggcccggcac ccccggcccg gcatcccccg ccgccgccgc cgccgcctca   240
aggccgcccg ctccccgcag gtggacgcgg ccatgggccg aggggtgcgc gtgctgctgc   300
tgctgagcct gctgcactgc gccggggggca gcgagggcag gaagacctgg cggcgccggg   360
gtcagcagcc gcctcctccc ccgcggaccg aggcggcgcc ggcggccgga cagcccgtgg   420
agagcttccc gctggacttc acggccgtgg agggtaacat ggacagcttc atggcgcaag   480
tcaagagcct ggcgcagtcc ctgtaccccc gctccgcgca gcagctcaac gaggacctgc   540
gcctgcacct cctactcaac acctcggtga cctgcaacga cggcagcccc gccggctact   600
acctgaagga gtccaggggc agccggcggt ggctcctctt cctggaaggc ggctggtact   660
gcttcaaccg cgagaactgc gactccagat acgacaccat gcggcgcctc atgagctccc   720
gggactggcc gcgcactcgc acaggcacag ggatcctgtc ctcacagccg gaggagaacc   780
cctactggtg gaacgcaaac atggtcttca tccctactg ctccagtgat gtttggagcg   840
gggcttcatc caagtctgag aagaacgagt acgccttcat gggcgccctc atcatccagg   900
aggtggtgcg ggagcttctg gcagagggc tgagcgggc caaggtgctg ctgctggccg   960
ggagcagcgc ggggggcacc ggggtgctcc tgaatgtgga ccgtgtggct gagcagctgg  1020
agaagctggg ctacccagcc atccaggtgc gaggcctggc tgactccggc tggttcctgg  1080
acaacaagca gtatcgccac acagactgcg tcgacacgat cacgtgcgcg cccacggagg  1140
ccatccgccg tggcatcagg tactggaacg gggtggtccc ggagcgctgc cgacgccagt  1200
tccaggaggg cgaggagtgg aactgcttct ttggctacaa ggtctacccg accctgcgct  1260
gccctgtgtt cgtggtgcag tggctgttg acgaggcaca gctgacggtg gacaacgtgc  1320

```
acctgacggg gcagccggtg caggagggcc tgcggctgta catccagaac ctcggccgcg    1380
agctgcgcca cacactcaag gacgtgccgg ccagctttgc ccccgcctgc ctctcccatg    1440
agatcatcat ccggagccac tggacggatg tccaggtgaa ggggacgtcg ctgccccgag    1500
cactgcactg ctgggacagg agcctccatg acagccacaa ggccagcaag accccctca     1560 agggctgccc cgtccacctg gtggacagct gcccctggcc ccactgcaac ccctcatgcc    1620
ccaccgtccg agaccagttc acggggcaag agatgaacgt ggcccagttc ctcatgcaca    1680
tgggcttcga catgcagacg gtggcccagc cgcagggact ggagcccagt gagctgctgg    1740
ggatgctgag caacggaagc taggcagact gtctggagga ggagccggca ctgaggggcc    1800
cagacacccg ctgcccagt gccacctcac ccccaccag caggccctcc cgtctcttcg       1860
ggacagggcc ccagccgtcc ccctgtctg ggtctgccca ctgccctcct gccccggctt      1920
tccctgcccc tctcccacag cccagccaga gacaagggac ctgctgtcat ccccatctgt     1980
ggcctggggg tccttcctga caacgagggg gtagccagaa gagaagcact ggattcctca    2040
gtccaccagc tcagacagca cccaccggcc ccacccatca agcccttta tattattta      2100 taaagtgact ttttattac tttaattttt taaaaaagg aaataagaa tatatgatga        2160 atgatattgt tttgtaactt tttaaaaatg attttaaaga gacaaaaag aacctcaaaa      2220 aaaaaaaaaa aaaaaaaaa aaaaaaaaa aaaaaaaaa aaaaaaaaa aaaaaaaaa          2280 a                                                                     2281

<210> SEQ ID NO 554
<211> LENGTH: 496
<212> TYPE: PRT
<213> ORGANISM: Homo sapiens

<400> SEQUENCE: 554

Met Gly Arg Gly Val Arg Val Leu Leu Leu Ser Leu Leu His Cys
1               5                   10                  15

Ala Gly Gly Ser Glu Gly Arg Lys Thr Trp Arg Arg Gly Gln Gln
                20                  25                  30

Pro Pro Pro Pro Arg Thr Glu Ala Ala Pro Ala Ala Gly Gln Pro
            35                  40                  45

Val Glu Ser Phe Pro Leu Asp Phe Thr Ala Val Glu Gly Asn Met Asp
    50                  55                  60

Ser Phe Met Ala Gln Val Lys Ser Leu Ala Gln Ser Leu Tyr Pro Cys
65                  70                  75                  80

Ser Ala Gln Gln Leu Asn Glu Asp Leu Arg Leu His Leu Leu Asn
                85                  90                  95

Thr Ser Val Thr Cys Asn Asp Gly Ser Pro Ala Gly Tyr Tyr Leu Lys
                100                 105                 110

Glu Ser Arg Gly Ser Arg Arg Trp Leu Leu Phe Leu Glu Gly Gly Trp
            115                 120                 125

Tyr Cys Phe Asn Arg Glu Asn Cys Asp Ser Arg Tyr Asp Thr Met Arg
    130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
            180                 185                 190

Ser Lys Ser Glu Lys Asn Glu Tyr Ala Phe Met Gly Ala Leu Ile Ile
```

```
                195                 200                 205
Gln Glu Val Val Arg Glu Leu Leu Gly Arg Gly Leu Ser Gly Ala Lys
    210                 215                 220

Val Leu Leu Leu Ala Gly Ser Ser Ala Gly Gly Thr Gly Val Leu Leu
225                 230                 235                 240

Asn Val Asp Arg Val Ala Glu Gln Leu Glu Lys Leu Gly Tyr Pro Ala
                245                 250                 255

Ile Gln Val Arg Gly Leu Ala Asp Ser Gly Trp Phe Leu Asp Asn Lys
            260                 265                 270

Gln Tyr Arg His Thr Asp Cys Val Asp Thr Ile Thr Cys Ala Pro Thr
        275                 280                 285

Glu Ala Ile Arg Arg Gly Ile Arg Tyr Trp Asn Gly Val Val Pro Glu
    290                 295                 300

Arg Cys Arg Arg Gln Phe Gln Glu Gly Glu Trp Asn Cys Phe Phe
305                 310                 315                 320

Gly Tyr Lys Val Tyr Pro Thr Leu Arg Cys Pro Val Phe Val Val Gln
                325                 330                 335

Trp Leu Phe Asp Glu Ala Gln Leu Thr Val Asp Asn Val His Leu Thr
            340                 345                 350

Gly Gln Pro Val Gln Glu Gly Leu Arg Leu Tyr Ile Gln Asn Leu Gly
        355                 360                 365

Arg Glu Leu Arg His Thr Leu Lys Asp Val Pro Ala Ser Phe Ala Pro
    370                 375                 380

Ala Cys Leu Ser His Glu Ile Ile Arg Ser His Trp Thr Asp Val
385                 390                 395                 400

Gln Val Lys Gly Thr Ser Leu Pro Arg Ala Leu His Cys Trp Asp Arg
                405                 410                 415

Ser Leu His Asp Ser His Lys Ala Ser Lys Thr Pro Leu Lys Gly Cys
            420                 425                 430

Pro Val His Leu Val Asp Ser Cys Pro Trp Pro His Cys Asn Pro Ser
        435                 440                 445

Cys Pro Thr Val Arg Asp Gln Phe Thr Gly Gln Glu Met Asn Val Ala
    450                 455                 460

Gln Phe Leu Met His Met Gly Phe Asp Met Gln Thr Val Ala Gln Pro
465                 470                 475                 480

Gln Gly Leu Glu Pro Ser Glu Leu Leu Gly Met Leu Ser Asn Gly Ser
                485                 490                 495

<210> SEQ ID NO 555
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 555
gagatcatca tccggagcca c                                           21

<210> SEQ ID NO 556
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 556
```
tagcttccgt tgctcagcat c                                              21

<210> SEQ ID NO 557
<211> LENGTH: 522
<212> TYPE: DNA
<213> ORGANISM: Homo sapiens

<400> SEQUENCE: 557
atgtaagcaa agtagtcatt aaaaatacac cctctacttg ggctttatac tgcatacaaa    60
tttactcatg agccttcctt tgaggaagga tgtggatctc caaataaaga tttagtgttt   120
attttgagct ctgcatctta acaagatgat ctgaacacct ctcctttgta tcaataaata   180
gccctgttat tctgaagtga gaggaccaag tatagtaaaa tgctgacatc taaaactaaa   240
taaatagaaa acaccaggcc agaactatag tcatactcac acaaagggag aaatttaaac   300
tcgaaccaag caaaaggctt cacggaaata gcatggaaaa acaatgcttc cagtggccac   360
ttcctaagga ggaacaaccc cgtctgatct cagaattggc accacgtgag cttgctaagt   420
gataatatct gtttctacta cggatttagg caacaggacc tgtacattgt cacattgcat   480
tatttttctt caagcgttaa taaaagtttt aaataaatgg ca                      522

<210> SEQ ID NO 558
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 558
actacggatt taggcaacag g                                              21

<210> SEQ ID NO 559
<211> LENGTH: 24
<212> TYPE: DNA
<213> ORGANISM: artificial
<220> FEATURE:
<223> OTHER INFORMATION: Description of artificial sequence:
      Oligonucleotide

<400> SEQUENCE: 559
gagatctcga gatctcgatc gtac                                           24

<210> SEQ ID NO 560
<211> LENGTH: 2383
<212> TYPE: DNA
<213> ORGANISM: Homo sapiens

<400> SEQUENCE: 560
cttttctctt gttgagtgca aatggagaac agctgctcac gctcgtcgtc tgacatcagc    60
tatttctcag gatgaccctg cgagacaggc cagggtcatt agacccaatt tggttctcag   120
caaatatgtg tttattcctg catgcgtggg ccacaggctg gtttcttggg tgcaatgaat   180
agctgcaggt ttattagggt gtcttttttag atggatgtat gtttcccgat gtctatagaa   240
cactccggac cccggagagt gaagactctg cctgtcggac ttgctttgag aagatccttc   300
tccacctccc catggcagaa gttgcttcac agagggaac agtttatgg atgtggctga    360 gaccttaaac ttgaggcaac ccatctgagg tggcatccag aggagactgg ctggcccctc   420
cttcaccttg gatgtagtgc tgtttctagg atctcttttc aatcagcaaa acaggggatg   480

-continued

```
ttccaagagg gtgtggattc cctgccatcc cacatggtca agtggagggg acgggaaaaa    540
gctatgaagg gtttgtgacc acacagactc tcctggcccc ctgtccttt  ggaaagaaga    600 cagggatgaa atataatcaa gcaattaacc accccccatca tcaccaagaa caacagtatc    660
aacaagaaga acagggacaa caaaacccac ggatgaaaca ttcctttctc agctcagatc    720
ttatctggtg cgttctctct ctgctctgtc ttggtgtgtg gtttagagaa acatggacaa    780
cgctgtttgg aagaacaggt gagcgagggt ggggaatttc agaggcctgg gcccaccgcc    840
tccacccctt ccccagttta acctttgaca ggatcttcac ctctctctga tcagcattgc    900
ttcttgttca aaggcctcag ccacccagct gtgtcccttt ccccagaaag caagggcaga    960
tggcagtggg tctgttgatg agagaacttt aagggcccaa tcagtccctg gcacccccct    1020
cctgggctcg ttttctccag gaggctgcat tctgatccat aaaccttctc ctcgggtttt    1080
agggtcgagc tgttcctgat gtttatcgga gactgggatc aaagctatcc aggtcataaa    1140
tctctctctg tggctgttgg gccccagggc agctgaagag ggttgacagc cctttggacc    1200
tcaaaggaaa aaatgtgctc tactccaccc actcccagct ctgccaagaa gctgtcctct    1260
gagaagccat ggctgggccg ttccattctg gggagctgct gaaaagagct gggaggccga    1320
gaagaacttg cgtgtgctgg gggagaggaa gcctggcctt gagggagggg tgcaggtgtg    1380
gctcctctgt gtgtggggc tggggacct tgtgtgcctt ttccttgtgg ctgtgaaatg    1440
ctttatgagt acttccatag gaggatggac agggagtcgg ggagataaac tcagccacaa    1500
ggccccaggg cctcaggaaa cttgcaccca accctctcat tttacagaag aaaactgtgc    1560
ctggaaggtt gaagggtttg ttcccagtca cacaaccagg gatccttagg acagccagac    1620 caggaaaacca tttccaaact gccaagccat ggcagagtat caagacctca ggaaccatcg    1680
agacaccatg gaagcattgg gaaaagcctc cttagctttt gaagctcctc attgttcttg    1740
agtgtgcatg gagcccatga ctgcggggtt ttgtagacac ctcagggatt acatgactgg    1800 taccctgac aaagtcaagg ctgctggaca aaatgagtcc gaggatttca ggggcagctg    1860
ggcgcaggag ctggtgggct gttgggagtg ccccttact gggcaggctt ccttcctcct    1920
ggtgatgggg ggttcctcag cacaaaagtg aaggggtgga ggggctggag gagcaggaat    1980
ctctcttgtt gataggtatg aggccttgaa gtccttttct ttgtcccagg attcatggac    2040
gcttcggggc tgatctttga gttttcaagc atggggtgca gagacgttta ggtaaactct    2100
taccgtcctc tctcttcgtc agggcttccc aggaatcaac aatgcccaag aaggaaggga    2160
ttgtagaaat agcttaaccc tttcatttac caacgtggaa attgaagccc agggaaggga    2220
agggaccggt cgtggaaggg agagccatca gcagaaagag accctgagat cttcgcctgg    2280
gattcccagg aagtccagcc cgagctgatt cacagaacaa atgcatgcaa accttgctat    2340
caataaatta cacatgcact tacgtaaaaa aaaaaaaaaa aaa    2383
```

<210> SEQ ID NO 561
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 561
cagagacgtt taggtaaact c    21

<210> SEQ ID NO 562

```
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 562
taccaacgtg gaaattgaag c                                              21

<210> SEQ ID NO 563
<211> LENGTH: 2336
<212> TYPE: DNA
<213> ORGANISM: Homo sapiens

<400> SEQUENCE: 563
aaaaaaacct atctaaggag gagccaagat ggccgcatag gaacagctcc agtccacagc    60
tcccagcgtg agcgacgcag aagacgggtg atttctgcat ttccatctga ggtaccgggt   120
tcttctcact agggagttcc agacagtggg cgcagcaggc ttttcttctt ggagctgaaa   180
caggcgcact ggcgagggtt gtgaggaaag gtttgcagcc ccctgccttg gtctgctata   240
gccagtgaca cgatcaatac cagggtgagc agcagaggaa gctcagggaa gattatgaag   300
atgagaattc attacctatc aaagaaaatg cgtaaactct agaagtattg cttgctcctt   360
tgccacaaag tgtacattca agagtaaatt gtttaaagcc aaagggcctt gcgccacgtc   420
cttagcctca gctttctact tgctaaaatg gaaataacaa cagtacctac cttacagacc   480
tggcgtgagg attaaattat accagcaaag tgcctggcac ctagaatttg cctgagttct   540
gatcaatgct aaaaacacca tttaacagtg ccctttcctg cctgggaagc ccacaaagat   600
ttcgcttttc acttattact catcaaactg actctggttc acagtggaaa agagaagaaa   660
agctgatgga gaaatggcag tgaagaagga gaacaaaatg tcagagcaat acttttgagc   720
gacttatcct ctgttctgca atatttgcaa aagtcagtct atagacgtga agccaacagg   780 gacccctcagg cctgtgcatc aggatggtgg gctgcctaag tcctctgggg acagcagtgc   840
cagaaggagt attggacaca gtgacccgac tgtatgagat gagaaaaaac aaaaacagga   900
ggtccgcagt actgatgaac taatctgtca ctcacaagct caggtctgca aaaaaagaa    960 acgaagcact aaacatggcc ataagagatg gaaatgcaag tcttcatttc taaatgataa  1020
tcaaaccaac gatcagaaac tgattaactg tgtaattgaa ttgaattgaa atcatccca   1080 tgaataacaa tccatcctac cttcaagggg ttaggaagct aactacaggt aattgctatc  1140
agaaatctga tttgatttcc aaaaattgtg tgaatgaacc aagtttcttc atcttgtatt  1200
actaggcagg gagtttgttc ttccaagtac tagactgctt aattgcttgc ttggggagg   1260 agaaatccta ggggaaaggc atatatgagc aatttctact ctgtgaagcc agcgctgtgt  1320
cctgagctgg atcatggcca gaaacagaaa agtctactct tccctacagt ggaagcaact  1380
gtggatattt catcctagga gtgaatgaaa aaacctaaag ctcatacttc atgggaatct  1440
ttcaatattc tgactgaaaa ctggttattt gctcctccaa cccaaagcca tctaggaaca  1500
gcactcagaa caggaaaaaa aaaagacaaa ataataatt attccaaaac gtatttgagc   1560
agaaacaaac acaacatttt gcattattaa atgggcttgt tcacacctgc tgagtagata  1620
taagacgata tttaagacaa gagctaaaaa ataaaccatc cctttctggt tttgagtgac  1680
agcagagcaa taaaaattat tttcacattc ttttccctat tgttagaagt aatcatttga  1740
gtaaatacac ttatctgtgc tgtaactatt gaatgaatc cacttcaaat atgtatacca  1800
```

```
cctttctttt ttatatttct agatatggtt tcaatataga ctttctgact tttatggtat    1860
acatatagga caatattcta ttcttctttc cttttaaata cttactgttt caatttcaaa    1920
taaaaaatca gcattctagt ttgtacattt tagcacagaa atgtttacaa ccttcagcac    1980
aattgctttt gtaatttact gacttggcat tttgaggcgt ttttaacaaa ttatgagaaa    2040
taacaccttc agaaagcatg tgactacttt gatgcaacta tttacaatgt attcataaga    2100
agtcattaac ctgtagagtt cttagacatg tggaaccttt aacaattata ctaaagagta    2160
catacaaaat acagagctat gtaataataa ctaattttaa atcctgacaa attagaagtt    2220
aagcctacta tctgtaaaaa tatgtcctga ttcattttt taagtatata cctgagcctt    2280
taaaaagtat atgcctttac aattgattc caataaacaa tactgaataa catact        2336
```

<210> SEQ ID NO 564
<211> LENGTH: 24
<212> TYPE: DNA
<213> ORGANISM: artificial
<220> FEATURE:
<223> OTHER INFORMATION: Description of artificial sequence:
      Oligonucleotide

<400> SEQUENCE: 564

```
gcaatacttt tgagcgactt atcc                                             24
```

<210> SEQ ID NO 565
<211> LENGTH: 23
<212> TYPE: DNA
<213> ORGANISM: artificial
<220> FEATURE:
<223> OTHER INFORMATION: Description of artificial sequence:
      Oligonucleotide

<400> SEQUENCE: 565

```
gatagcaatt acctgtagtt agc                                              23
```

<210> SEQ ID NO 566
<211> LENGTH: 1187
<212> TYPE: DNA
<213> ORGANISM: Homo sapiens

<400> SEQUENCE: 566

```
gaacaacatg gcttccccca gcgtgagact cgcttgtcct cccaccgcct gctctctcct      60
gatgaccagg ttccaggagt tatcaaagaa cagcctctga gctgcgtgga gaaagccatg     120
gagacagcca aagaaaacg gcaggattag attaacctgt gattcctggc tggccacgag     180
gtcacccatg gcatggagct gcccacaacg cccttctcag catgaagcat cctgaaagat     240
ccagggccag gttccccagg attggggagt tggaagctca ttggcactgt caaatttgaa     300
gaagaggcgt gctctgactg cctggacagg acccggaatc aaaccgcagg ccctgggtca     360
ccgctgccgg aaagagccag ttcctgtccg tccatgcacc caccaccaaa acccaggcct     420
tcctggaggt gctaggggag gccatgcccc ttttctgagt gcttggaagt gactgctgca     480
agtgacaagt gaccacgcct tttccccgc gggtataaat tcagaggcgc tgcgctccga     540
ttctggcagt gcagctgtgg gaacctctcc acgcgcacga actcagccaa cgatttctga     600 tagattttg ggagtttgac cagagatgca aggggtgaag gagcgcttcc taccgttagg      660
gaactctggg gacagagcgc cccggccgcc tgatggccga ggcagggtgc gacccaggac     720
ccaggacggc gtcgggaacc ataccatggc ccggatcccc aagaccctaa agttcgtcgt     780
cgtcatcgtc gcggtcctgc tgccagtgag tccccgccgc ggtcctggc tggggaagag     840
```

```
cgcacctggc gccgggaggg ggcagggaga cggggacacg gcagggatgc ctggccctgg    900
tcacctgcgg ccgggcatgt ccgggcagga cgaactcgcc gtcggagtca ggggaagaac    960
tgggtccccg ggctgggcag gagggacccg gccgcgaggg agcagagagg cggtccccct   1020
ggctgccccg agcccgcgaa gggagggaag ttccagaatc gagagaggga gggagtcaag   1080
gtggaaccca tagagtgagc ctcctgaaga cacagagcgg ttgcctctct cattaattaa   1140
ttaattagtt aataaaatta accccatgtt taaaaaaaa aaaaaaa                  1187
```

<210> SEQ ID NO 567
<211> LENGTH: 155
<212> TYPE: PRT
<213> ORGANISM: Homo sapiens

<400> SEQUENCE: 567

```
Met Gln Gly Val Lys Glu Arg Phe Leu Pro Leu Gly Asn Ser Gly Asp
1               5                   10                  15

Arg Ala Pro Arg Pro Asp Gly Arg Gly Val Arg Pro Arg Thr
            20                  25                  30

Gln Asp Gly Val Gly Asn His Thr Met Ala Arg Ile Pro Lys Thr Leu
        35                  40                  45

Lys Phe Val Val Ile Val Ala Val Leu Leu Pro Val Ser Pro Arg
    50                  55                  60

Arg Gly Pro Trp Leu Gly Lys Ser Ala Pro Ala Gly Arg Gly Gln
65                  70                  75                  80

Gly Asp Gly Asp Thr Ala Gly Met Pro Gly Pro Gly His Leu Arg Pro
                85                  90                  95

Gly Met Ser Gly Gln Asp Glu Leu Ala Val Gly Val Arg Gly Arg Thr
            100                 105                 110

Gly Ser Pro Gly Trp Ala Gly Gly Thr Arg Pro Arg Gly Ser Arg Glu
        115                 120                 125

Ala Val Pro Leu Ala Ala Pro Ser Pro Arg Arg Glu Gly Ser Ser Arg
    130                 135                 140

Ile Glu Arg Gly Arg Glu Ser Arg Trp Asn Pro
145                 150                 155
```

<210> SEQ ID NO 568
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 568

```
ggattgggga gttggaagct c                                                21
```

<210> SEQ ID NO 569
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 569

```
agaaatcgtt ggctgagttc g                                                21
```

<210> SEQ ID NO 570

```
<211> LENGTH: 857
<212> TYPE: DNA
<213> ORGANISM: Homo sapiens

<400> SEQUENCE: 570
catccctctg gctccagagc tcagagccac ccacagccgc agccatgctg tgcctcctgc      60
tcaccctggg cgtggccctg gtctgtggtg tcccggccat ggacatcccc cagaccaagc     120
aggacctgga gctcccaaag ttggcaggga cctggcactc catggccatg gcgaccaaca     180
acatctccct catggcgaca ctgaaggccc tctgagggt ccacatcacc tcactgttgc      240 ccaccccga ggacaacctg gagatcgttc tgcacagatg ggagaacaac agctgtgttg      300
agaagaaggt ccttggagag aagactgaga tccaaagaa gttcaagatc aactatacgg      360
tggcgaacga ggccacgctg ctcgatactg actacgacaa tttcctgttt ctctgcctac     420
aggacaccac cacccccatc cagagcatga tgtgccagta cctggccaga gtcctggtgg     480
aggacgatga gatcatgcag ggattcatca gggctttcag gcccctgccc aggcacctat     540
ggtacttgct ggacttgaaa cagatggaag agccgtgccg tttctaggtg agctcctgcc     600
tggtcctgcc tcctggctca cctccgcctc caggaagacc agactcccac ccttccacac     660
ctccagagca gtgggacttc ctcctgccct ttcaaagaat aaccacagct cagaagacga     720
tgacgtggtc atctgtgtcg ccatcccctt cctgctgcac acctgcacca cggccatggg     780
gaggctgctc cctgggggca gagtctctgg cagaggttat taataaaccc ttggagcatg     840
aaaaaaaaaa aaaaaaa                                                   857

<210> SEQ ID NO 571
<211> LENGTH: 180
<212> TYPE: PRT
<213> ORGANISM: Homo sapiens

<400> SEQUENCE: 571

Met Leu Cys Leu Leu Leu Thr Leu Gly Val Ala Leu Val Cys Gly Val
1               5                   10                  15

Pro Ala Met Asp Ile Pro Gln Thr Lys Gln Asp Leu Glu Leu Pro Lys
            20                  25                  30

Leu Ala Gly Thr Trp His Ser Met Ala Met Ala Thr Asn Asn Ile Ser
        35                  40                  45

Leu Met Ala Thr Leu Lys Ala Pro Leu Arg Val His Ile Thr Ser Leu
    50                  55                  60

Leu Pro Thr Pro Glu Asp Asn Leu Glu Ile Val Leu His Arg Trp Glu
65                  70                  75                  80

Asn Asn Ser Cys Val Glu Lys Lys Val Leu Gly Glu Lys Thr Glu Asn
                85                  90                  95

Pro Lys Lys Phe Lys Ile Asn Tyr Thr Val Ala Asn Glu Ala Thr Leu
            100                 105                 110

Leu Asp Thr Asp Tyr Asp Asn Phe Leu Phe Leu Cys Leu Gln Asp Thr
        115                 120                 125

Thr Thr Pro Ile Gln Ser Met Met Cys Gln Tyr Leu Ala Arg Val Leu
    130                 135                 140

Val Glu Asp Asp Glu Ile Met Gln Gly Phe Ile Arg Ala Phe Arg Pro
145                 150                 155                 160

Leu Pro Arg His Leu Trp Tyr Leu Leu Asp Leu Lys Gln Met Glu Glu
                165                 170                 175

Pro Cys Arg Phe
            180
```

<210> SEQ ID NO 572
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 572
agttcaagat caactatacg g                                           21

<210> SEQ ID NO 573
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 573
tagaaacggc acggctcttc c                                           21

<210> SEQ ID NO 574
<211> LENGTH: 4415
<212> TYPE: DNA
<213> ORGANISM: Homo sapiens

<400> SEQUENCE: 574
agagaagcaa catctttaag gtactgaggg caggagaagt taatgtagaa tactatgcca    60 gaaaaataa attcccaaaa gtggaagtga aataaggaca tttagagatg tacaaaagct   120
gaccgaattc actaccagtc aacccacact acaagaaaca tcaaatgagt cctccaagca   180
gaaggaaccc aataccagat gaaaatccag atctccacga ggaaatgaag aacaccagaa   240
atggatcggc cctttcttca aataagagca gttggaataa caaagctgtt cagttgtacc   300
cttggaatcc actgaaatcc tgggtaggga agctccagta ccaccaactg gaaagactgg   360
gaatgcctaa tagctggtac tggccattgt cgtaggcttt gtccactctg acaaactgaa   420
gatggggact cgactcacct tcgccagcca caggaggacc tccagacgag gttaggtcga   480
cttcccgata actttagatc ctgaaacctc acgggatttt tcttctcttc cctttgatct   540
ctcttccgct tgctcaacag gacaggactc gctgcctttc tttcccgtca gaagggatc    600 ccttgcggac aggacctaag tgagtagctg gtttccccta cttgtccttc cgggcctggg   660
tgtctcggga gctcaggctg acgggagacc taactaccgg cgagtgagac cagcaggagc   720
ctggaggggc gcgcaccagg gtggaggttt ggtgccgggg gttgagaaca acagtcaaac   780
cctcttcttc ccctggcacc acgcacctgc cccccgggac gccgaacgaa gtggtcccta   840
aagctcctct gcaggcccaa ccgaaacagg cctgaagctc caggatgggc gagaggatcc   900
tctttgagcg aaaccagcct tctgcctggc tggccctggt caacccctg ggaagaggcc    960 gatttggcgg acagaacgga agaaaagacc taaggtaga atctcatgat gtcgagatgt   1020
taaaacactc aaattttaag gttcgactgt gaggggggaga taggggggtct cgagcaggat  1080 cgacccctga gccttcatct gcagagtcct gtgcaccagc tcagaggaca ggactatgtg   1140
caccaatggt tctcatcagg cggcaacttc accctcacat gcctccccca tccctgctgg   1200
tacacaagac cacgactagg ggaagccggg agggagaatg ttaaccctg gcatctatct    1260 agtcagcaga ggtgagggat gctgctaaac accttacaat ccaccggagg acacccgccc   1320

```
ccaccgaccc cgaagtagcc attccctgga ggtggggaaa ctcgcctgta gatcaatgcc    1380
cacgcacttg gcggacagga aatcacgaat tggccactaa ctggatcttg gatctgagga    1440
aaaaattcca gcgtcagagg gaactctcgg agatttgccc agagcataag gaacgtactc    1500
cttccctcag tgatggatca tcacatctgg gggaaatcat agacaatttc ttttgtaggg    1560
cgaactctgc tatacagttt atgatgtcag agtgaatact ttctttgagt tgcagtcaga    1620
aactgtagat ttttaaaaat ttaaaattca ttattctctg tcagtatttc aaagtgtata    1680
cagaaagcta ttgcactgtt caggagatgg cgcctaacat tttggaaatt caaggtgatg    1740
aatgtccaga taagactatc tctcctggta caaagtttga caatgctgaa catttttaaa    1800
ggttcttttt gatatacaaa gtgcaccaat gagtgctttt taattcttac aataattctg    1860
ggtgaggtag gtattttttcc aattcccatt ttatgcttcg gtagcccttt gtatttatac    1920
ttcaaaacac ttggctctct tgtaattatt taagaaatta gttgtgatta tttgtttaat    1980
gtgcaggagt tacaaaaggc aagcgttaga acaagacaga cctggttatg attcctggct    2040
ctgaaagctg tacaccctgt gaccctagac aggtgtttta atgcctcgct gcctctgttt    2100
cttgctctgt aaaatgtgaa caataacagt attggcctca tgcttttttt gggttttaaa    2160
agtaataatg tggacaaaga tcagtggagt gcctggcatg ctgaacccat tccatgactg    2220
atagctatag ttgttatgat ttgtatcaat ccattttcac actgctataa ggaactacct    2280
gagactgggt aatctatgaa gaaagaggt ttaattgact cacagttctg catggctggg    2340
agtcctcagg aacttacaat catggcagaa ggggaagcaa gacatttctt atatggcagc    2400
aggacagaaa gagagagagt gaaggggaa gtgccacaca cttccaaaca accatatctt    2460
gtggttaatt aaaaagtact cattggtgtg ccttgtatag aaaaaaatat acactcacta    2520
tcatgagaac agcaaggagg gagtctgccc ccaaggttca atcacctccc agtagacccc    2580
tcccctgaca tgtggggatt acaattcaag atgagatttg ggtggggaaa cagagtcaaa    2640
ccatatcgtg attgttctat aataaagaga tgcccacatg tgtttcatca gggacagtgc    2700
tcattaacca gttgtcctgc cgtaattatt aatagtatcc cctttgcttt caaaagtgtc    2760
ctagtttaca aaaagtatag aaatggagga cagaatagtg gttgcccaag attggaaaag    2820
ggtaagggta aagggtgcag aggtggatgt ggttataaaa ggcaacatgg gagatcctcg    2880
tagtgaagga accgtttagt atctccactg tggtggtaga tacccgaacc taaacatgtg    2940
aaaaattgca tgaaactaaa cacacacacc aacaagtaca agttaagtta ggaaaatcca    3000
aataagattt ctacattgta tcaataggta tatcttgatt atgatattgc aagatggtac    3060
tattcaagga aactgggtag aggctacatg agactcccct gtattatttc ctataactcc    3120
atgtgaatct acaaggatct caggattaag gaagatatcc tagtttggaa gataaaaaat    3180
atatcccagt agtaatatcc actgtcccac cagggcctga ctaccttcta taaaagaag     3240 tgcctttgtt cccctcaagt tcctttattt ggttttattc ttcttcacag tacctacctc    3300
cacttggcag attacatttta ttttttcatc tttcaacagc tatttactga atgcctacta    3360
gatgccaggc ttgagatcta gcaatgaaca agatctctgt gaaacttaca ttccaggagg    3420
agaaataaat aataaaccaa aaatataatc agtaaattat ttaatatgct gggaaacaat    3480
atgtgtaatg gaagaaatat gtaaagtgat ggattagggt tctccagaga aacagaacca    3540
acaattgact catgtgatta tggaggctga gaagtctcaa gatcacagtt ggcaagcttg    3600
agacacagga gagcccatgg tgtgtttctg atttgagtcc aaaggcctga gaaccaggag    3660
agatgatggt gtgattacag ttcaaaagct ggcaggcttg aggcccagga agagccagtg    3720
```

```
ttgcagttca attccaaagg caggaaaagg ctgatatctt agctgaagca atcaggcaga    3780
aggagctctc tcttactcat gggcaggtca gacttttggt tctattcagg cctttaagtg    3840
attggatgag gatcatctac tgtggaaaga aataagcttt attcagtgta ctgattcaaa    3900
tgttaatctc atccaaaacc atgctcacag acacacccag cataatgttt gaccaagtat    3960
ctgggcacct tgtggttcag tcaaattaac acatattaac taccttagca agatgaaaag    4020
cagtgaatgc aggatggtgg ttgaaatttt aaatacgttg gttatatagt ctcattgaaa    4080
aaggaacatt tgagtgaaga cttgaagggg tggtggaata aaccatttat tgcttattg     4140 cctgtctccc tctatcagaa tgaaagcttc atgaagcgag agacttaatt tttatctgtt    4200
atatccctag tgcctggtgc agggtaagta ctcaaaaata tttgttgagt gaataagtaa    4260
tgattgagga tggggactgg tttgtatctg gttatatctc ttgtccttag cacagtacct    4320
ggcacatcct aagccatcca aaagagttgg ttatatgatt gtctttgaat tctatgactg    4380
tttataatat acagtaaact tcactgaaga cactg                               4415
```

<210> SEQ ID NO 575
<211> LENGTH: 22
<212> TYPE: DNA
<213> ORGANISM: artificial
<220> FEATURE:
<223> OTHER INFORMATION: Description of artificial sequence:
      Oligonucleotide

<400> SEQUENCE: 575

```
gaagaacacc agaaatggat cg                                               22
```

<210> SEQ ID NO 576
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 576

```
cttcagtttg tcagagtgga c                                                21
```

<210> SEQ ID NO 577
<211> LENGTH: 484
<212> TYPE: DNA
<213> ORGANISM: Homo sapiens

<400> SEQUENCE: 577

```
tgtcagcttt gtctgtgcct cgcaaatcag aggcaaggga gaggttgtta ccaggggaca      60
ctgagaatgt acatttgatc tgccccagcc acggaagtca gagtaggatg cacagtacaa    120 aggaggggg agtggaggcc tgagagggaa gtttctggag ttcagatact ctctgttggg     180
aacaggacat ctcaacagtc tcaggttcga tcagtgggtc ttttggcact ttgaaccttg    240
accacaggga ccaagaagtg gcaatgagga cacctgcagg aggggctagc ctgactccca    300
gaactttaag actttctccc cactgccttc tgctgcagcc caagcaggga gtgtcccct     360 cccagaagca tatcccagat gagtggtaca ttatataagg attttttta agttgaaaac     420 aactttctt tcttttttgta tgatggtttt ttaacccagt cattaaaaat gtttataaat     480
caaa                                                                  484
```

<210> SEQ ID NO 578

```
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 578
cagccacgga agtcagagta g                                              21

<210> SEQ ID NO 579
<211> LENGTH: 24
<212> TYPE: DNA
<213> ORGANISM: artificial
<220> FEATURE:
<223> OTHER INFORMATION: Description of artificial sequence:
      Oligonucleotide

<400> SEQUENCE: 579
ccactcatct gggatatgct tctg                                           24

<210> SEQ ID NO 580
<211> LENGTH: 592
<212> TYPE: DNA
<213> ORGANISM: Homo sapiens
<220> FEATURE:
<221> NAME/KEY: misc_feature
<222> LOCATION: (62)..(62)
<223> OTHER INFORMATION: n is a, c, g, t or u

<400> SEQUENCE: 580
ggtgcatgtt cattgggcat cttccattcg accccttttgc ccacgtggtg accgctgggg    60
anctgtgaga gtgtgagggg cacgttccag ccgtctggac tctttctctc ctactgagac   120
gcagcctata ggtccgcagg ccagtcctcc caggaactga aatagtgaaa tatgagttgg   180
cgaggaagat caacatatag gcctaggcca agaagaagtt tacagcctcc tgagctgatt   240
ggggctatgc ttgaacccac tgatgaagag cctaaagaag agaaaccacc cactaaaagt   300
cggaatccta cacctgatca aagagagaa gatgatcagg gtgcagctga gattcaagtg    360
cctgacctgg aagccgatct ccaggagcta tgtcagacaa agactgggga tggatgtgaa   420
ggtggtactg atgtcaaggg gaagattcta ccaaaagcag agcactttaa aatgccagaa   480
gcaggtgaag ggaaatcaca ggtttaaagg aagataagct gaaacaacac aaactgtttt   540
tatattagat attttacttt aaaatatctt aataaagttt taagcttttc tc            592

<210> SEQ ID NO 581
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 581
attggggcta tgcttgaacc c                                              21

<210> SEQ ID NO 582
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 582
```

```
tttcccttca cctgcttctg g                                              21
```

<210> SEQ ID NO 583
<211> LENGTH: 2514
<212> TYPE: DNA
<213> ORGANISM: Homo sapiens

<400> SEQUENCE: 583

```
actggggtct tctccatgcg gctcgggcta tgacagcctc cgtgctcctc cacccccgct      60
ggatcgagcc caccgtcatg tttctctacg acaacggcgg cggcctggtg gccgacgagc     120
tcaacaagaa catggaaggg gcggcggcgg ctgcagcagc ggctgcagcg gcggcggctg     180
ccggggccgg gggcggggc ttcccccacc cggcggctgc ggcggcaggg ggcaacttct      240
cggtggcggc ggcggccgcg gctgcggcgg cggccgcgc caaccagtgc cgcaacctga      300
tggcgcaccc ggcgcccttg gcgccaggag ccgcgtccgc ctacagcagc gccccggggg     360
aggcgccccc gtcggctgcc gccgctgctg ccgcggctgc cgctgcagcc gccgccgccg     420
ccgccgcgtc gtcctcggga ggtcccggcc cggcgggccc ggcgggcgca gaggccgcca     480
agcaatgcag cccctgctcg gcagcggcgc agagctcgtc ggggcccgcg gcgctgccct     540
atggctactt cggcagcggc tactaccgt gcgcccgcat gggcccgcac cccaacgcca      600
tcaagtcgtg cgcgcagccc gctcggccg ccgccgccgc cgccttcgcg gacaagtaca      660
tggataccgc cggcccagct gccgaggagt tcagctcccg cgctaaggag ttcgccttct     720
accaccaggg ctacgcagcc gggccttacc accaccatca gcccatgcct ggctacctgg     780
atatgccagt ggtgccgggc ctcggggggcc ccggcgagtc gcgccacgaa cccttgggtc     840
ttcccatgga aagctaccag ccctgggcgc tgcccaacgg ctggaacggc caaatgtact     900
gccccaaaga gcaggcgcag cctccccacc tctggaagtc cactctgccc gacgtggtct     960
cccatcccte ggatgccage tcctatagga ggggagaaa gaagcgcgtg ccttataccsa    1020
aggtgcaatt aaaagaactt gaacgggaat acgccacgaa taaattcatt actaaggaca    1080
aacggaggcg gatatcagcc acgacgaatc tctctgagcg gcaggtcaca atctggttcc    1140
agaacaggag ggttaaagag aaaaaagtca tcaacaaact gaaaaccact agttaatgga    1200
ttaaaaatag agcaagaagg caacttgaag aaacgcttca gaactcgttg ctttgcccag    1260
ataatgataa taatgcttaa taataattga agaatgggaa agagaaagag acagagactg    1320
gcatttccct ctcccgaagg agatctcttt ctctttaatg gaatctacaa ctgttttaaa    1380
actttaagaa aggtaaagac tgccagttct tccgccaacc ccatcagccc agcccgttaa    1440
atgtcaaacg tcaaccccca aaatacgcaa tttcagataa gttacgcagt tactgaaatc    1500
ttgtaagtat ttaagtgatc gttacatttt aggacactgc gttagatggt aataatctgg    1560
aagttggtta caaacgcaag aggccattgt aaacatctgc ttgtccttct taggtcgcca    1620
ttccctttgc atgttaagcg tctgctcagg taaatcttag tgaaattcct accgttgttg    1680
tacgttctgc aaaacatttt atgtatagat ttagagggga aacgagaagg tactgaaata    1740
atgatcttgg aatatttgct gtgaaggag aaagggagag aaaactcttc tgaggatcat      1800
ttgtcttggt agtatagtaa aaccaaccag ctgaaccttt caggctacaa gagaacccgg    1860
gtcggtaatg tcttttttaag aataattttt aattgcttat aacaagcata ttttgtggca    1920
tttgaactat atttactgct ccaatatccg ttattttcca aaggattttg tatctttttg    1980
aaaatgttta catcatcaga tgatccacag aattcacttt atgtgagatc tcccgagagt    2040
```

```
ttccatccca acataatgga ctttggtttg aacacaattc gttttttcat ttgaattggc   2100
atttcccaat atttgctaaa catttgctgg agaaatcatt tttcttttt  cttttttaga   2160 aaactcagaa tgaaaattca ttcccctgaa atatttaggt gtctatattc tatattttga   2220
tctattaagg gattagtatt tttccatgtt tattgtgtta tcagagtgca ttagaaagat   2280
tagtgattca tcttcacagc acattttaa tcaagcagtt atttcaacca gcacattcgt    2340
tttgttcata ttcactatag aatgatatct tgtaaataaa gacattcagc acactgtgaa   2400
aatgtatttg tgcacctgct ttttaaatat ttctactaaa aatgaaaaaa aaaaacccct   2460
agacctgtag atagtgatat cgtaatatta attgttaata aaatagtcac tgcc          2514
```

<210> SEQ ID NO 584
<211> LENGTH: 388
<212> TYPE: PRT
<213> ORGANISM: Homo sapiens

<400> SEQUENCE: 584

```
Met Thr Ala Ser Val Leu Leu His Pro Arg Trp Ile Glu Pro Thr Val
1               5                   10                  15

Met Phe Leu Tyr Asp Asn Gly Gly Gly Leu Val Ala Asp Glu Leu Asn
            20                  25                  30

Lys Asn Met Glu Gly Ala Ala Ala Ala Ala Ala Ala Ala Ala Ala Ala
        35                  40                  45

Ala Ala Gly Ala Gly Gly Gly Phe Pro His Pro Ala Ala Ala Ala Ala
    50                  55                  60

Ala Ala Gly Gly Asn Phe Ser Val Ala Ala Ala Ala Ala Ala Ala Ala
65                  70                  75                  80

Ala Ala Ala Ala Asn Gln Cys Arg Asn Leu Met Ala His Pro Ala Pro
                85                  90                  95

Leu Ala Pro Gly Ala Ala Ser Ala Tyr Ser Ser Ala Pro Gly Glu Ala
            100                 105                 110

Pro Pro Ser Ala Ala Ala Ala Ala Ala Ala Ala Ala Ala Ala Ala Ala
        115                 120                 125

Ala Ala Ala Ala Ala Ser Ser Ser Gly Gly Pro Gly Pro Ala Gly Pro
    130                 135                 140

Ala Gly Ala Glu Ala Ala Lys Gln Cys Ser Pro Cys Ser Ala Ala Ala
145                 150                 155                 160

Gln Ser Ser Ser Gly Pro Ala Ala Leu Pro Tyr Gly Tyr Phe Gly Ser
                165                 170                 175

Gly Tyr Tyr Pro Cys Ala Arg Met Gly Pro His Pro Asn Ala Ile Lys
            180                 185                 190

Ser Cys Ala Gln Pro Ala Ser Ala Ala Ala Ala Ala Phe Ala Asp
            195                 200                 205

Lys Tyr Met Asp Thr Ala Gly Pro Ala Ala Glu Glu Phe Ser Ser Arg
    210                 215                 220

Ala Lys Glu Phe Ala Phe Tyr His Gln Gly Tyr Ala Ala Gly Pro Tyr
225                 230                 235                 240

His His His Gln Pro Met Pro Gly Tyr Leu Asp Met Pro Val Val Pro
                245                 250                 255

Gly Leu Gly Gly Pro Gly Glu Ser Arg His Glu Pro Leu Gly Leu Pro
            260                 265                 270

Met Glu Ser Tyr Gln Pro Trp Ala Leu Pro Asn Gly Trp Asn Gly Gln
    275                 280                 285

Met Tyr Cys Pro Lys Glu Gln Ala Gln Pro Pro His Leu Trp Lys Ser
```

```
                    290                 295                 300
Thr Leu Pro Asp Val Val Ser His Pro Ser Asp Ala Ser Ser Tyr Arg
305                 310                 315                 320

Arg Gly Arg Lys Lys Arg Val Pro Tyr Thr Lys Val Gln Leu Lys Glu
                325                 330                 335

Leu Glu Arg Glu Tyr Ala Thr Asn Lys Phe Ile Thr Lys Asp Lys Arg
            340                 345                 350

Arg Arg Ile Ser Ala Thr Thr Asn Leu Ser Glu Arg Gln Val Thr Ile
        355                 360                 365

Trp Phe Gln Asn Arg Arg Val Lys Glu Lys Lys Val Ile Asn Lys Leu
    370                 375                 380

Lys Thr Thr Ser
385

<210> SEQ ID NO 585
<211> LENGTH: 24
<212> TYPE: DNA
<213> ORGANISM: artificial
<220> FEATURE:
<223> OTHER INFORMATION: Description of artificial sequence:
      Oligonucleotide

<400> SEQUENCE: 585
tctggaagtc cactctgccc gacg                                              24

<210> SEQ ID NO 586
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 586
tgtgacctgc cgctcagaga g                                                 21

<210> SEQ ID NO 587
<211> LENGTH: 8769
<212> TYPE: DNA
<213> ORGANISM: Homo sapiens

<400> SEQUENCE: 587
atttagaggc ggcgccaggg cggccgcgga gaaacgtgac acaccagccc tctcggaggg       60
gtttcggacc gaagggaaga agctgcgccg tgtcgtccgt ctccctgcgc gccgcgggca      120
cttctcctgg gctctccccg aactctcccg cgacctctgc gcgccctcag gccgccttcc      180
ccgccctggg ctcgggacaa cttctggggt ggggtgcaaa gaaagtttgc ggctcctgcc      240
gccggcctct ccgcctcttg gcctaggagg ctcgccgccc gcgcccgctc gttcggcctt      300
gcccgggacc gcgtcctgcc ccgagaccgc caccatgaac aagctttaca tcggcaacct      360
caacgagagc gtgaccccccg cggacttgga gaaagtgttt gcggagcaca gatctcctta     420
cagcggccag ttcttggtca atccggcta cgccttcgtg gactgcccgg acgagcactg      480
ggcgatgaag gccatcgaaa ctttctccgg gaaagtagaa ttacaaggaa acgcttaga      540 gattgaacat tcggtgccca aaaacaaag gagccggaaa attcaaatcc gaaatattcc      600
accccagctc cgatgggaag tactggacag cctgctggct cagtatggta cagtagagaa      660
ctgtgagcaa gtgaacaccg agagtgagac ggcagtggtg aatgtcacct attccaaccg      720
ggagcagacc aggcaagcca tcatgaagct gaatggccac cagttggaga accatgccct      780
```

```
gaaggtctcc tacatccccg atgagcagat agcacaggga cctgagaatg ggcgccgagg    840
gggctttggc tctcggggtc agcccgcca gggctcacct gtggcagcgg gggccccagc    900
caagcagcag caagtggaca tcccccttcg gctcctggtg cccacccagt atgtgggtgc    960
cattattggc aaggagggg ccaccatccg caacatcaca aaacagaccc agtccaagat   1020
agacgtgcat aggaaggaga acgcaggtgc agctgaaaaa gccatcagtg tgcactccac   1080
ccctgagggc tgctcctccg cttgtaagat gatcttggag attatgcata aagaggctaa   1140
ggacaccaaa acggctgacg aggttcccct gaagatcctg gcccataata actttgtagg   1200
gcgtctcatt ggcaaggaag gacgaacct gaagaaggta gagcaagata ccgagacaaa   1260
aatcaccatc tcctcgttgc aagaccttac cctttacaac cctgagagga ccatcactgt   1320 gaaggggggcc atcgagaatt gttgcagggc cgagcaggaa ataatgaaga aagttcggga   1380
ggcctatgag aatgatgtgg ctgccatgag cctgcagtct cacctgatcc ctggcctgaa   1440
cctggctgct gtaggtcttt tcccagcttc atccagcgca gtcccgccgc ctcccagcag   1500
cgttactggg gctgctccct atagctcctt tatgcaggct cccgagcagg agatggtgca   1560 ggtgttatc cccgcccagg cagtgggcgc catcatcggc aagaagggc agcacatcaa   1620 acagctctcc cggtttgcca gcgcctccat caagattgca ccacccgaaa cacctgactc   1680
caaagttcgt atggttatca tcactggacc gccagaggcc caattcaagg ctcagggaag   1740
aatctatggc aaactcaagg aggagaactt ctttggtccc aaggaggaag tgaagctgga   1800
gacccacata cgtgtgccag catcagcagc tggccgggtc attggcaaag gtggaaaaac   1860
ggtgaacgag ttgcagaatt tgacggcagc tgaggtggta gtaccaagag accagacccc   1920
tgatgagaac gaccaggtca tcgtgaaaat catcggacat ttctatgcca gtcagatggc   1980
tcaacggaag atccgagaca tcctggccca ggttaagcag cagcatcaga agggacagag   2040
taaccaggcc caggcacgga ggaagtgacc agcccctccc tgtcccttcg agtccaggac   2100
aacaacgggc agaaatcgag agtgtgctct ccccggcagg cctgagaatg agtgggaatc   2160
cgggacacct gggccgggct gtagatcagg tttgcccact tgattgagaa agatgttcca   2220
gtgaggaacc ctgatctctc agccccaaac acccacccaa ttggcccaac actgtctgcc   2280
cctcggggtg tcagaaattc tagcgcaagg cacttttaaa cgtggattgt ttaaagaagc   2340
tctccaggcc ccaccaagag ggtggatcac acctcagtgg gaagaaaaat aaaatttcct   2400
tcaggtttta aaacatgca gagaggtgtt ttaatcagcc ttaaaggatg gttcatttct   2460
tgaccttaat gtttttccaa tcttcttccc cctactggg taattgatta aaataccctcc   2520 atttacggcc tctttctata tttacactaa ttttttttatc tttattgcta ccagaaaaaa   2580
atgcgaacga atgcattgct ttgcttacag tattgactca agggaaaaga actgtcagta   2640
tctgtagatt aattccaatc actccctaac caataggtac aatacggaat gaagaagagg   2700
ggaaaatggg gagaaagatg gttaaaatac ataataatcc acgtttaaaa ggagcgcact   2760
tgtggctgat ctatgccaga tcaccatctt caaattggca caactgaaat ttccccactc   2820
tgttggggct tccccaccac attcatgtcc ctctcccgtg taggtttcac attatgtcca   2880
ggtgcacata ggtggtattg aatgctcagc agggtagggg ctgaccactg tccctgattc   2940
ccatcgttct caggcggatt ttatatttt ttaaagtcta ttttaatgat tggatatgag   3000
cactgggaag gggacgctaa ctccccttga taaagtctcg gttccatgga ggacttgagt   3060
ggccccaaag gctgccacgg tgccctcacc ccagcccatg tgctcccata agggctggtt   3120
```

```
cctagaggca ggggttgtgg ggcactccca gccacggcac tgttaccttg gtggtgggac    3180
ttggaaccca accctgagct cccgataaag ctaaagtcca tcatctggca aattcagtaa    3240
attggagagt acttgcttct gtttgtatct gagaggaatt tttaactgac ggcttctgtc    3300
tccatgaatc attatcagca tgatgaaagg tgtgtctaaa aaacaattca gaataccagc    3360
agcattgtac agcaaggggt aaataagctt aatttattaa tttaccaggc ttaattaaga    3420
tcccatggag tgtttagccc ttgtgggaga cagaagccat cagttaaatg aggttaggcc    3480
tctcctccta atatactgat tgacaatgca tattagccag gtaatgcact ttagctaccc    3540
tggacaatgc tatcaagtgt gctgggaagg gaggaaggcc tctctacata tggaaaagcc    3600
catgcgtgga gttcccctcc tttcaacatt gcaacaacag taacaacaag acaaccgcaa    3660
catgtgggcg tagtcaggca atgctgtgtg cgaagtaaac tacctcaagg tatgaagtta    3720
cctcagcaat tattttcctt tttgttcccc ccaaccccat taaaaaaatt ttttttttgat    3780 ttttgttttt ttgcagcttg ctgatatttt atataaaaaa gaaaagcaaa gcaaaagaga    3840
agctgatagt cttgaatatt ttatttttt aatgaaaaga aaaacaaga aagttatgtt    3900 tcataatttc ttacaacatg agccagtaac cctttaggaa ctctctatgg agaacaggcc    3960
tggtgggaaa ggctttgggg gctgccccct taggaggagg ctagtgctaa gagggaaggc    4020
ccaggtttga gagagcccag aggggcagag cccagagcct tgtttggccc tgatctctga    4080
cttctagagc cccagctgct ggcggctgct ggaatatcct acctgatagg attaaaaggc    4140
ctagtggagc tgggggctct cagtggttaa acaatgccca acaaccaacc agctggccct    4200
tggtctcctc tctttcctcc tttggttaaa gagcatctca gccagctttt cccaccagtg    4260
gtgctgttga gatattttaa aatattgcct ccgttttatc gaggagagaa ataataacta    4320
aaaaatatac ccttttaaaaa aacctatatt tctctgtcta aaaatatggg agctgagatt    4380
ccgttcgtgg aaaaaagaca aggccaccct ctcgccctca gagaggtcca cctggtttgt    4440
cattgcaatg cttttcattt tttttttttg ttattgtttc atttcagttc cgtcttgcta    4500
ttcttcctaa tctatatcca tagatctaag gggcaaacag atactagtta actgcccca    4560 cctctgtctc cctgtcttct ttagatcggt ctgattgatt ttaaaagtgg acccaaactt    4620
agggaattct tgatttaggg tggctggtgg caaggagggg caggggatat ggggacgtga    4680
ctgggacagg ttcctgcctt atcattttct ccctaggaca ttcccttgta gcccccagaa    4740
ttgtctggcc caaattgaat agaagcagaa aaacatttag ggataacatc aggccagtag    4800
aattaagcct ctccacctgt cccaaccata aaaagggtct cccagctttc catctctggc    4860
tctatatgct ttatcccaaa acaaagcaga taacgttcag acgtcggcca tttagtaatt    4920
taaagcgaat ttccagcagc aagcatgctt tgatatctgg ttcagactat catcaggaag    4980
aaaaaaaaat cccacagtac ctgaaatgtg attgttgcag tgttcagttt ccttgggggc    5040
ctgctccctt cacaccttga gcccaagtcc ttttccgttg gctgattcag ctcccagaag    5100
agacgaggaa gtgtgtggca agggactgga aaacttcact tgcttggatt aggcaaggct    5160
ccactcattg ttgatatttg cccagcagga aaatcatgta agttatacca ccagaaagca    5220
aaaggagcat ggtttggtgg ttaaggttta gtgggatgaa ggacctgtct tggtgggccg    5280
ggccctcttg tgccccgtag ctaggtctt agggcaactc cttgccctcc tgctcagcac    5340
ctccatttcc ccatccttgg tgagataaca agctatcgcg aaaagcactt gggagatttg    5400
gatgatttga gaagagtgac ttaaaaaaaa tgcttctgtg ctctaagata tatatgtgtg    5460
tgtgtgtgct acatatatat ttttaagaaa ggaccatctc tttaggatat attttaaat    5520
```

```
tctttgaaac acataaccaa aatggtttga ttcactgact gactttgaag ctgcatctgc    5580
cagttacacc ccaaatggct ttaatcccct ctcgggtctg gttgccttt gcagtttggg    5640
ttgtggactc agctcctgtg aggggtctgg ttaggagaga gccatttta aggacaggga    5700
gttttatagc ccttttctac tttcctcccc tcctcccagt ccttatcaat ctttttcct    5760
ttttcctgac cccctccttc tggaggcagt tgggagctat ccttgtttat gcctcactat    5820
tggcagaaaa gaccccattt aaaacccaga gaacactgga gggggatgct ctagttggtt    5880
ctgtgtccat tttcctctgt gccaaagaca gacagacaga ggctgagaga ggctgttcct    5940
gaatcaaagc aatagccagc tttcgacaca tacctggctg tctgaggagg aaggcctcct    6000
ggaaactggg agctaagggc gaggcccttc ccttcagagg ctcctggggg attagggtgt    6060
ggtgtttgcc aagccaaggg gtagggagcc gagaaattgg tctgtcggct cctggttgca    6120
ctttggggaa ggagaggaag tttggggctc caggtagctc cctgttgtgg gactgctctg    6180
tccctgccc ctactgcaga gatagcactg ccgagttccc ttcaggcctg gcagacgggc    6240
agtgaggagg ggcctcagtt agctctcaag ggtgccttcc cctcctccca acccagacat    6300
accctctgcc aaactgggaa ccagcagtgc tagtaactac ctcacagagc cccagagggc    6360
ctgcttgagc cttcttgctc cacaggagaa gctggtgcct ctaggcaacc ccttcctccc    6420
acctctcatc aggggtgggg gttctccttt cttcccctg aagtgttat ggggagatcc    6480
tagtggcttt gccattcaaa ccactcgact gttgcctgt ttcttgaaaa ccagtagaag    6540
ggaaacagca cagcctgtca cagtaattgc aggaagattg aagaaaaatc ctcatcaatg    6600
ccagggaca taaaagccat ttcccttcca aatactcgac aatttagatg cagaacattt    6660
ctctgtattc agacttagag taacaccagc tgaaaactgc agtttctttc ctttggatac    6720
ataaggcttc tctatcgggg tacgggacag ggaggaggcc tcatgtctga agggggattt    6780
aggggcgaga gccccagccc tgaccctcgg tcctgtgcac cgctttgggg cacagtctga    6840
tggcgccttt gctggcgcct tagtatggtt gactccggat ggacaaaaga aaaaaaattt    6900
tttttcttga atgaaatagc aggaagctcc tcgggagcat gtgttttgat taaccgcagg    6960
tgatggatgc tacgagtata aatggattaa ctacctcaat ccttacagta agattggaac    7020
taagggcagg gactcatgca taagggtatg aatcccagcc aggacaagtg agttgaggct    7080
tgtgccacaa aaggtttgtc cttggggaac aggcaggcct gccaggatcc ccccatatc    7140
gattgggctg ggagggctgg ccatgaggtc cccacttctt gctttccttg cccatgtgtc    7200
accccttgg cctccagctt gtccctctct cactttctat agcttgttg gaccagatgg    7260
tgaggaaagg aatggcctct tcccttctag agggggctgg ctggagtgag acctggggct    7320
tggcctggaa cccaccacac agccccaaag tcaggaagcc tggggaaacc agagctgaga    7380
cctcttcaac agggtttctt tgagatccta cacctccatt gggccttttt tcagtcttca    7440
atggggggccc agttggctct agaaggagaa gaggtgaagc aggatccttt gccctggggg    7500
agtctgaggg cgcggtcctt ggactcattc aggccgtctt tgtagttggg ggagttccac    7560
tgggcgatcc cagcccctcc ccacccaccc tctaatggac ctcctcatag aagccccatt    7620
tcacttttgt tttatctacc tcttagcaaa acaatagata aattaggtag tggcagctcc    7680
acttgcttag gttagggggg gaaaagatt tcttttttcca aggaaaaaaa atattacctt    7740
gagaatactt tccaaaaaat aaaattaaaa aaaaaaaac caaaaaaaaa aattttttt    7800
taaaagggag acattttcca gtgaccactg gattgtttta atttcccaag cttttttttc    7860
```

```
ccccataaat aagtttcact cttttggcgat tttcttcact tgtttaagat aacgtgctag    7920
ctattccaac aggtaacagc tttcacagtc tgccctggc ctgtctcacc ccatccccca    7980
ccctattcct gccagtgagt ccttcctgtg cttctctccc ttctcccctc ccagccagct    8040
gacttcagtc accctgtcc ccctcccct gccaataagc tcccccagga ataaaggctt    8100
tgttttgggg atgcttaaat cttgactggc acttcccggc tgtggggggct ggggagccac    8160 ttgtaacatt tctgtgcaga ttttatgtta gccactgcta tgtaaaagca cgttcaaaat    8220
gaatttcagc agattatgtg ttaccataat gaataaacgt cctctatcac catttggagt    8280
ctcccttttc tccaggatct tgatcctggt ccccaaaacc agagtgaatc aaaagagctt    8340
cctcccctga ggcaaagtgg atttgtaagc agttctgaaa catcacttac tcagaagagg    8400
gaacgatgta ttttgatgag tgcaaattgg gaagagctgg aggcctactg cttgggacag    8460 ttttttttttt ttttttttttt ttaaatatga gtgctagctt attctgtaat tgcggcaact    8520
ttgaaaattg tatttactg gaaatctgcc agccatcacc accgatttt gattgtatcc    8580 ttcctcccat cctttaatct gttcattgct ttggggaggg tgggcaget gctcacacg    8640 ttggagtttg ttctttgatg gatgaacgaa cactccagtt ttctttcccg tgaaggttgt    8700
ttcagccaca aaccacttca tttttgctgtt tcaatttcaa aataaaagga aacttatatt    8760
gaaagacaa                                                              8769
```

<210> SEQ ID NO 588
<211> LENGTH: 577
<212> TYPE: PRT
<213> ORGANISM: Homo sapiens

<400> SEQUENCE: 588

```
Met Asn Lys Leu Tyr Ile Gly Asn Leu Asn Glu Ser Val Thr Pro Ala
1               5                   10                  15

Asp Leu Glu Lys Val Phe Ala Glu His Lys Ile Ser Tyr Ser Gly Gln
            20                  25                  30

Phe Leu Val Lys Ser Gly Tyr Ala Phe Val Asp Cys Pro Asp Glu His
        35                  40                  45

Trp Ala Met Lys Ala Ile Glu Thr Phe Ser Gly Lys Val Glu Leu Gln
    50                  55                  60

Gly Lys Arg Leu Glu Ile Glu His Ser Val Pro Lys Lys Gln Arg Ser
65                  70                  75                  80

Arg Lys Ile Gln Ile Arg Asn Ile Pro Pro Gln Leu Arg Trp Glu Val
                85                  90                  95

Leu Asp Ser Leu Leu Ala Gln Tyr Gly Thr Val Glu Asn Cys Glu Gln
            100                 105                 110

Val Asn Thr Glu Ser Glu Thr Ala Val Val Asn Val Thr Tyr Ser Asn
        115                 120                 125

Arg Glu Gln Thr Arg Gln Ala Ile Met Lys Leu Asn Gly His Gln Leu
    130                 135                 140

Glu Asn His Ala Leu Lys Val Ser Tyr Ile Pro Asp Glu Gln Ile Ala
145                 150                 155                 160

Gln Gly Pro Glu Asn Gly Arg Arg Gly Gly Phe Gly Ser Arg Gly Gln
                165                 170                 175

Pro Arg Gln Gly Ser Pro Val Ala Ala Gly Ala Pro Ala Lys Gln Gln
            180                 185                 190

Gln Val Asp Ile Pro Leu Arg Leu Leu Val Pro Thr Gln Tyr Val Gly
        195                 200                 205
```

```
Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ala Ile Ser Val His Ser Thr Pro Glu Gly Cys Ser Ser Ala
                245                 250                 255

Cys Lys Met Ile Leu Glu Ile Met His Lys Glu Ala Lys Asp Thr Lys
            260                 265                 270

Thr Ala Asp Glu Val Pro Leu Lys Ile Leu Ala His Asn Asn Phe Val
        275                 280                 285

Gly Arg Leu Ile Gly Lys Glu Gly Arg Asn Leu Lys Lys Val Glu Gln
    290                 295                 300

Asp Thr Glu Thr Lys Ile Thr Ile Ser Ser Leu Gln Asp Leu Thr Leu
305                 310                 315                 320

Tyr Asn Pro Glu Arg Thr Ile Thr Val Lys Gly Ala Ile Glu Asn Cys
                325                 330                 335

Cys Arg Ala Glu Gln Glu Ile Met Lys Lys Val Arg Glu Ala Tyr Glu
            340                 345                 350

Asn Asp Val Ala Ala Met Ser Leu Gln Ser His Leu Ile Pro Gly Leu
        355                 360                 365

Asn Leu Ala Ala Val Gly Leu Phe Pro Ala Ser Ser Ala Val Pro
    370                 375                 380

Pro Pro Pro Ser Ser Val Thr Gly Ala Ala Pro Tyr Ser Ser Phe Met
385                 390                 395                 400

Gln Ala Pro Glu Gln Glu Met Val Gln Val Phe Ile Pro Ala Gln Ala
                405                 410                 415

Val Gly Ala Ile Ile Gly Lys Lys Gly Gln His Ile Lys Gln Leu Ser
            420                 425                 430

Arg Phe Ala Ser Ala Ser Ile Lys Ile Ala Pro Pro Glu Thr Pro Asp
        435                 440                 445

Ser Lys Val Arg Met Val Ile Ile Thr Gly Pro Pro Glu Ala Gln Phe
    450                 455                 460

Lys Ala Gln Gly Arg Ile Tyr Gly Lys Leu Lys Glu Glu Asn Phe Phe
465                 470                 475                 480

Gly Pro Lys Glu Glu Val Lys Leu Glu Thr His Ile Arg Val Pro Ala
                485                 490                 495

Ser Ala Ala Gly Arg Val Ile Gly Lys Gly Gly Lys Thr Val Asn Glu
            500                 505                 510

Leu Gln Asn Leu Thr Ala Ala Glu Val Val Pro Arg Asp Gln Thr
    515                 520                 525

Pro Asp Glu Asn Asp Gln Val Ile Val Lys Ile Ile Gly His Phe Tyr
530                 535                 540

Ala Ser Gln Met Ala Gln Arg Lys Ile Arg Asp Ile Leu Ala Gln Val
545                 550                 555                 560

Lys Gln Gln His Gln Lys Gly Gln Ser Asn Ala Gln Ala Arg Arg
                565                 570                 575

Lys

<210> SEQ ID NO 589
<211> LENGTH: 21
<212> TYPE: DNA
<213> ORGANISM: artificial
<220> FEATURE:
<223> OTHER INFORMATION: Description of artificial sequence:
      Oligonucleotide
```

<400> SEQUENCE: 589
atttctatgc cagtcagatg g                                    21

<210> SEQ ID NO 590
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 590
gtgggcaaac ctgatctaca g                                    21

<210> SEQ ID NO 591
<211> LENGTH: 5016
<212> TYPE: DNA
<213> ORGANISM: Homo sapiens

<400> SEQUENCE: 591
taacattctg ttcttccgcg tgatggattt tcttttggag attcgaactg aagcctgtac      60
ggaggaaatg ttgtttttaa gggaaatgaa tagaaacaat ccactttgaa gaagccatgg     120
cgaaatcaaa gacaaaacat agactttgtt ctcaggaatc ttcagtatct gccctgctgg     180
caagctgcac cctgagtggt agtaattcct ctaattctga tggctcgttt cactataaag     240
ataagctgta cagatctgct tctcaagctc tacaggctta tattgatgat tttgatctag     300
gccaaatata tcctggtgca agcactggaa aaattaacat tgatgaggat tttactaata     360
tgtcacagtt ctgcaactat atttacaaac caaacaatgc ttttgaaaac cttgatcacg     420
aaaagcactc aaacttcata tcctgtagaa gacacatcgt taatgacata gactccatga     480
gcctaacaac tgatgatcta ttaagactcc cagcagatgg atcatttttct tatacttatg     540
ttggaccgag tcaccgaacg agcaagaaaa acaagaaatg ccgtggaagg ctgggttcat     600
tggacattga aagaatcca cattttcaag gaccctacac ttccatgggc aaggataact     660
ttgttactcc tgttatacgc tcaaatataa atggaaagca atgtggtgac aaaattgaat     720
tgcttatctt gaaggccaag agaaatctag agcagtgtac tgaagaatta ccaaagtcca     780
tgaaaaagga tgacagtcct tgctcattag ataaacttga agcagacaga tcatgggaaa     840
atattcctgt tactttcaaa tctcctgttc ccgttaactc tgatgatagt cctcaacaaa     900
cttcaagggc aaagagtgct aaaggggttc ttgaagactt tctaaataat gataatcaga     960
gctgtactct ctctggaggc aaacatcatg gtcctgttga agccctgaaa caatgttat    1020
ttaaccttca agcagtacaa gaacgttta atcaaaataa gaccacagat ccaaagaag    1080
agattaaaca agtttcagaa gatgatttct ctaaattaca gttgaaggaa agtatgattc    1140
ctattactag gtcacttcag aaggctttgc accatttatc tcgcctgaga gacctggttg    1200
atgatacgaa tggagaacgg tcaccgaaaa tgtgaagagg aaaatgaaac tgtcaccacg    1260
ataaatagtc accacagaac aaataggcat tttttctatt acttaaactg acaaagtaaa    1320
tataagccat acattatttt gtggttggtt caaggattat atatttctaa aacactaaac    1380
ttgaaaatac ccataggttt tgggacctat ctttattttg tgccaacata ctagaatgtg    1440
aactgcaagg acccacaatg tatcctgaag tcttactttc gccttctggc agcaaatgt    1500
ctaatatttta aagatggatg acttctgttc ttgaagctta cctggattta accttcttca    1560
gcatcctcaa cattttatta cctggttcag gatcattaag aaacttactg gttttatcc    1620

```
aaaatcttttt acgttaaata gactttttta aagatatagt tagcatcact tttaaacagc    1680
ttaaaggaat atcaaaattg ttattgtgta tctcatctat aaggaagtct gttactttga    1740
aattttcata aatttaatat ttaagataca ttgtatttga aaattgcatt aatagtgggg    1800
tgatactgtg ttaaaaggaa cgttgtgttg tgacattcaa gagaacctcc tcatttaatt    1860
agtactttga ttctgtgtaa gataatcttg gtagtgcttg acagtttcca aaccttttt     1920 tggagagata tttaagaatt taatattttg atattagatt gtttcccaga ttttaatttt    1980
ggggttggct caaactagtg aaaactatga ctcaatggcc aattgcttta tcaaatttga    2040
taactaaaac ttaaaatgaa tatggaaaat cagaaagcaa ctctatttta gagctatttt    2100
gtaagagttg tgctttcttt aacaccatct gtagtcttaa gtttgtctct agctagaact    2160
gaacaaagct ctataatttt taccaagcac ttattattaa tacttcttat aagtagtaag    2220
catctttact aacacaactg agaattaagt cataaaacat aactaataca gcacattact    2280
gcctgacaaa attaaagagt actgtgtgta tgtataacta ctacaggtta acacttcacc    2340
caaatgatag cgttttttcct cagtagatta ttgtcaaata ggaatttcta agcacattga    2400
gtcaaagcat ttttttccagg ttaataaagt gttatttact atctttgtta gaggtgacat    2460
gtcaaacact acagtgagct ctgtggggtt tttttttttt tttttgcccg tgagtttttt    2520
accatgctgc tctgaccagt ttgagtggca attaccaata gatttgtttt ctttattcta    2580
tggagatgtt tttaccactg acactgtttt ctgattatag tctgcttcat agaaaatagc    2640
ctgcataatc aaacaaggag ttactttgaa attaaagtat gcctggctat taaaaatgca    2700
gattttaggt gggtaaacat caggtaggtc tgggtgggtc atgttctagg cctagaaaaa    2760
tacactatta gacaagttct aaagaaggca aggagataaa ggcatcaggt ggtaacttct    2820
aattgaatat tatatgttga tcatacataa tatatactat gcctggaaat tatgactgaa    2880
aagcacctat tcggttagtg ctcctattca tgagaacata tctccaatac taaatgagat    2940
aagcctgttc taaaatctta tagccagtat tttaagaaac ttgattatac ttaccaaagg    3000
aacattgttt gttttctctt gttttaaata tggagaggtt taatcccttta cataacaaag    3060 gaattaattt tagcaaaatg attcattcca accttcttat aagaaatatc taggagagtc    3120
aagtaagaaa aataacgaat ctaagtgata aacattcaag aaattctcta ataagagat     3180 ttatttataa ttttaatatc tcagggttct ttttaggttt ccaggggaaa agagcaggat    3240
aacagtgtgg agactgctaa gttgagaatt taaaacaaat gagaacataa gattttaaa     3300 attgcattgt gaatgtaaaa ttttatcaa tcctttgctc ttttagacat attgagaaaa     3360
tgttaaatag aaaaaattaa gaaatttttaa taagatgttt cagatctttg agtatgaaaa    3420
acataacaaa aaagcctaat ttcaaaaaac tatttgagat caagggacaa tggtgtgacc    3480
aatatgaagg gtcaagactg aaatgtattg tctttactat caagaactct actttcagtt    3540
gtttctcaga cagttaattt cagcttcata gagatttctg agcaaattaa gaaacactgt    3600
tttcctgggt ttgtttttggg tatatgtcat tatagttatg ttatttcttg ttgaaattta    3660
taattgtagg ttttttgtat tgttttggta tttaatggtg tataatgtgt tattacatta    3720
tatgtagtta taccaaaata ttgcctgaag agaaatcatg acaaggtccc ctgtttattc    3780
ctgtgttaca gacgcatgga attgctcctg tagatttgaa ttttttgttc atttttttct    3840
gtcccaccct tcactctctc tgtttcagaa cattttggt agaagtgcta tccagaagtg     3900
aacttgtcaa aaggcaagta gcatgaaaga agacagaaga agcaaaaggc taatacagtg    3960
```

```
gataatttct gagcacttga agtttcttca aatgtgcaag actgtgtgtc ttcctattag    4020
atgtataaat tggatatttc atgcctaatt aaatgttgcg ttggattgca gtgcctatca    4080
tacagtgatt ggagtaaatt gaggcctaat cctgaacaca tatagagcat attgttagat    4140 attttcctg tgacatttga agttattatt ctcccatttc cttttctttt ttttgtttat     4200
aatcatatgt ccctaagatt gttttccttt tttggaccaa aaaaagaaa aaaaaatct      4260 tagcttttca tcctcccagt gtattctgca ttgtccttac cctagatcag ccccttctgt    4320
gtaacagttt ttctcacaat gtagcaactt ttatccaccc ttcaggacct tcactgggac    4380
tagttcattc attttcaaat agctatttca acctttaaca tctactgtct tagtctttta    4440
cacagaagcc agagtgactg gtcttggcaa gactctgttg tgtatcacca ctctaacctt    4500
actgatttgt ttcagcaaat ttgctttagt taaattgctt tactcagatt cccccaaact    4560
ttatatgtgt attgtcatct ttgtgcatat tatttctcat gcatgaaata ctcaattttt    4620
attcttttat ctaacgctta ctcttacatt tctttaaagc tctggccaag tatttattt    4680 cgtccctaaa cattctaact atccaccaaa ctggtaagtt ggcttttctt tttcctcccc    4740
ctgtcattca tttagctgtt atatttcatt ttaatgtttt gggtggtgcc tcttatacta    4800
tgttgtattc ctagacaagg aaatgtatat caaaatatgt tagatgattg attgttttat    4860
ctccttgatg atagcacctc ttatactgct ttacagaatc aggaaaaagt aaactgcatt    4920
ttacatagtg gttttaaata ttgattgatt gatattctaa acctggtttc ctatataaag    4980
ttgtaagttc aagataaaaa aaaaaaaaa aaaaca                               5016
```

<210> SEQ ID NO 592
<211> LENGTH: 372
<212> TYPE: PRT
<213> ORGANISM: Homo sapiens

<400> SEQUENCE: 592

```
Met Ala Lys Ser Lys Thr Lys His Arg Leu Cys Ser Gln Glu Ser Ser
1               5                   10                  15

Val Ser Ala Leu Leu Ala Ser Cys Thr Leu Ser Gly Ser Asn Ser Ser
            20                  25                  30

Asn Ser Asp Gly Ser Phe His Tyr Lys Asp Lys Leu Tyr Arg Ser Ala
        35                  40                  45

Ser Gln Ala Leu Gln Ala Tyr Ile Asp Asp Phe Asp Leu Gly Gln Ile
    50                  55                  60

Tyr Pro Gly Ala Ser Thr Gly Lys Ile Asn Ile Asp Glu Asp Phe Thr
65                  70                  75                  80

Asn Met Ser Gln Phe Cys Asn Tyr Ile Tyr Lys Pro Asn Asn Ala Phe
                85                  90                  95

Glu Asn Leu Asp His Glu Lys His Ser Asn Phe Ile Ser Cys Arg Arg
            100                 105                 110

His Ile Val Asn Asp Ile Asp Ser Met Ser Leu Thr Thr Asp Leu
        115                 120                 125

Leu Arg Leu Pro Ala Asp Gly Ser Phe Ser Tyr Thr Tyr Val Gly Pro
    130                 135                 140

Ser His Arg Thr Ser Lys Lys Asn Lys Lys Cys Arg Gly Arg Leu Gly
145                 150                 155                 160

Ser Leu Asp Ile Glu Lys Asn Pro His Phe Gln Gly Pro Tyr Thr Ser
                165                 170                 175

Met Gly Lys Asp Asn Phe Val Thr Pro Val Ile Arg Ser Asn Ile Asn
            180                 185                 190
```

Gly Lys Gln Cys Gly Asp Lys Ile Glu Leu Leu Ile Leu Lys Ala Lys
                195                 200                 205

Arg Asn Leu Glu Gln Cys Thr Glu Glu Leu Pro Lys Ser Met Lys Lys
    210                 215                 220

Asp Asp Ser Pro Cys Ser Leu Asp Lys Leu Glu Ala Asp Arg Ser Trp
225                 230                 235                 240

Glu Asn Ile Pro Val Thr Phe Lys Ser Pro Val Pro Val Asn Ser Asp
                245                 250                 255

Asp Ser Pro Gln Gln Thr Ser Arg Ala Lys Ser Ala Lys Gly Val Leu
            260                 265                 270

Glu Asp Phe Leu Asn Asn Asp Asn Gln Ser Cys Thr Leu Ser Gly Gly
        275                 280                 285

Lys His His Gly Pro Val Glu Ala Leu Lys Gln Met Leu Phe Asn Leu
    290                 295                 300

Gln Ala Val Gln Glu Arg Phe Asn Gln Asn Lys Thr Thr Asp Pro Lys
305                 310                 315                 320

Glu Glu Ile Lys Gln Val Ser Glu Asp Asp Phe Ser Lys Leu Gln Leu
                325                 330                 335

Lys Glu Ser Met Ile Pro Ile Thr Arg Ser Leu Gln Lys Ala Leu His
            340                 345                 350

His Leu Ser Arg Leu Arg Asp Leu Val Asp Asp Thr Asn Gly Glu Arg
        355                 360                 365

Ser Pro Lys Met
    370

<210> SEQ ID NO 593
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 593
aatggaaagc aatgtggtga c                                           21

<210> SEQ ID NO 594
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 594
tccagagaga gtacagctct g                                           21

<210> SEQ ID NO 595
<211> LENGTH: 2061
<212> TYPE: DNA
<213> ORGANISM: Homo sapiens

<400> SEQUENCE: 595
atgaggcgga caggccccga ggaggaggcc tgcggcgtgt ggctggacgc ggcggcgctg     60
aagaggcgga aagtgcagac acatttaatc aaaccaggca ccaaaatgct aacactcctt    120
cctggagaaa gaaaggctaa tatttatttt actcaaagaa gagctccatc tacaggcatt    180
caccagagaa gcattgcttc cttcttcacc ttgcagccag gaagagacaa atggcagtgac    240

```
cagaagagtg tttcatctca tacagaaagt cagatcaaca aagagtccaa gaaaaatgcg      300
acccagctag accatttgat cccaggctta gcacacgatt gcatggcatc ccctttagcc      360
acttcaacca ctgcggacat ccaggaagct ggactctctc ctcagtccct ccagacttct      420
ggccaccaca gaatgaaaac cccatttttca actgagctat ctttgctcca gcctgatact      480
ccagactgtg ctggagatag tcataccccca ctggcttttt ccttcaccga ggacttggaa      540
agttcttgtt tgctagaccg aaaggaagaa aaagggggatt ctgccaggaa atgggaatgg     600
cttcatgagt ctaagaagaa ctatcagagt atggagaaac acaccaaact acctggggac      660
aaatgctgtc agcccttagg caagactaaa ttggaaagaa aggtgtctgc caaagaaaac      720
aggcaggccc ctgtcctcct tcaaacatac agggaatcct ggaatggaga aacatagaa       780 tcggtgaaac aaagccgtag tccagtttct gtgttttcct gggacaatga aaagaatgac      840
aaggactcct ggagtcaact tttcactgaa gattctcaag gccagcgggt cattgcccac      900
aacactagag ctccttttca agatgtaacc aataactgga attgggactt agggccgttt      960
cctaacagtc cttgggctca gtgccaggag gatgggccaa ctcaaaatct gaagcctgat     1020
ttgctcttta cccaggactc tgaaggtaat caagttatca gacaccaatt ctaaatgttt      1080
gaagctttgt ttctaaaagt accttgaaat gatagagatg taggaaaata tagttgtggg      1140
tggagagagg agtgagtttg tttaggtggg aaggtggcat gggatgaagt tgtcattact      1200
gagcatcttc tctgtgtaaa taaagggcag taccattgtt aagacagtgg gattggcatc      1260
atggctttcc ctcaggaagg tggtggctgg taaattccct gaatgagtct atgatgaaca      1320
ctgaggcagc acagtgggta tttatctcta tgaaagtgcc ttttactcag cctgcacaga      1380
gccatctctt tgcccttcca gatgtctgac tgggaccttg cttatggatg tgttttttttt      1440 tttttttttt tgagatggag tctcgctctg tcgccaggct ggagtgcagt ggtgcgacct      1500
cagctcactg caccctctgt gtcccggatt caagcgattc tcctgcctca gcctcccgaa      1560
tagcagggac tacaggcatg cgccaccacg cccagctaat ttttttttgga ttttttagtag     1620 agacgaggtt tcaccatatt agccaggatg gtctccatct cctgacctcc tgatccgccc      1680
acctcagcct cccaaagtgc tgagattaca ggcataagcc accgcgccca gccagatgtg      1740
tgagctttta atctctggct gatcttaacc cacatcagcc taagcttggg atgattactc      1800 ttgaccctttt ttttcagtg attagcaaat ctccccacaa cccaggtgtg agagaagag       1860 aggtagaatg gtgctagttt cctatttttat ttttgtggta actgtacagc actttaaagt     1920
tatatactct atgttttaaat atctcccctta aaaagcctga gctgtacaac aatctggatg    1980
tgactctgtt acccttttcc cacaagatag gagggaatcc cctttgtaaa actatgaatc     2040
caaataaatg tttacaaagt g                                                2061
```

<210> SEQ ID NO 596
<211> LENGTH: 357
<212> TYPE: PRT
<213> ORGANISM: Homo sapiens

<400> SEQUENCE: 596

```
Met Arg Arg Thr Gly Pro Glu Glu Glu Ala Cys Gly Val Trp Leu Asp
 1               5                  10                  15

Ala Ala Ala Leu Lys Arg Arg Lys Val Gln Thr His Leu Ile Lys Pro
             20                  25                  30

Gly Thr Lys Met Leu Thr Leu Leu Pro Gly Glu Arg Lys Ala Asn Ile
         35                  40                  45
```

```
Tyr Phe Thr Gln Arg Arg Ala Pro Ser Thr Gly Ile His Gln Arg Ser
 50                  55                  60
Ile Ala Ser Phe Phe Thr Leu Gln Pro Gly Lys Thr Asn Gly Ser Asp
 65                  70                  75                  80
Gln Lys Ser Val Ser Ser His Thr Glu Ser Gln Ile Asn Lys Glu Ser
                 85                  90                  95
Lys Lys Asn Ala Thr Gln Leu Asp His Leu Ile Pro Gly Leu Ala His
            100                 105                 110
Asp Cys Met Ala Ser Pro Leu Ala Thr Ser Thr Ala Asp Ile Gln
            115                 120                 125
Glu Ala Gly Leu Ser Pro Gln Ser Leu Gln Thr Ser Gly His His Arg
130                 135                 140
Met Lys Thr Pro Phe Ser Thr Glu Leu Ser Leu Leu Gln Pro Asp Thr
145                 150                 155                 160
Pro Asp Cys Ala Gly Asp Ser His Thr Pro Leu Ala Phe Ser Phe Thr
                165                 170                 175
Glu Asp Leu Glu Ser Ser Cys Leu Leu Asp Arg Lys Glu Glu Lys Gly
            180                 185                 190
Asp Ser Ala Arg Lys Trp Glu Trp Leu His Glu Ser Lys Lys Asn Tyr
            195                 200                 205
Gln Ser Met Glu Lys His Thr Lys Leu Pro Gly Asp Lys Cys Cys Gln
210                 215                 220
Pro Leu Gly Lys Thr Lys Leu Glu Arg Lys Val Ser Ala Lys Glu Asn
225                 230                 235                 240
Arg Gln Ala Pro Val Leu Leu Gln Thr Tyr Arg Glu Ser Trp Asn Gly
                245                 250                 255
Glu Asn Ile Glu Ser Val Lys Gln Ser Arg Ser Pro Val Ser Val Phe
            260                 265                 270
Ser Trp Asp Asn Glu Lys Asn Asp Lys Asp Ser Trp Ser Gln Leu Phe
            275                 280                 285
Thr Glu Asp Ser Gln Gly Gln Arg Val Ile Ala His Asn Thr Arg Ala
290                 295                 300
Pro Phe Gln Asp Val Thr Asn Asn Trp Asn Trp Asp Leu Gly Pro Phe
305                 310                 315                 320
Pro Asn Ser Pro Trp Ala Gln Cys Gln Glu Asp Gly Pro Thr Gln Asn
                325                 330                 335
Leu Lys Pro Asp Leu Leu Phe Thr Gln Asp Ser Glu Gly Asn Gln Val
            340                 345                 350
Ile Arg His Gln Phe
            355

<210> SEQ ID NO 597
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 597
caccttgcag ccaggaaaga c                                         21

<210> SEQ ID NO 598
<211> LENGTH: 21
<212> TYPE: DNA
<213> ORGANISM: artificial
<220> FEATURE:
```

<223> OTHER INFORMATION: Description of artificial sequence:
     Oligonucleotide

<400> SEQUENCE: 598
cagcacagtc tggagtatca g    21

<210> SEQ ID NO 599
<211> LENGTH: 1907
<212> TYPE: DNA
<213> ORGANISM: Homo sapiens

<400> SEQUENCE: 599

```
aatgcacacg agcagacaga gaagcaacat ctttaaggta ctgagggcag gagaagttaa      60
tgtagaatac tatgccagaa aaataaatt cccaaaagtg gaagtgaaat aaggacattt     120
agagatgtac aaaagctgac cgaattcact accagtcaac ccacactaca agaaacatca    180
aatgagtcct ccaagcagaa ggaatccaat accagatgaa aatccagatc tccacgagga    240
aatgaagaac accagaaatg ggtaactata ctagatcggc cctttcttca aataagagca    300
gttggaataa caaagctgtt cagttgtacc cttggaatcc actgaaatcc tgggtaggga    360
agctccagta ccaccaactg gaaagactgg gaatgcctaa tagctggtac tggccattgt    420
cgtaggcttt gtccactctg acaaactgaa gatggggact cgactcacct tcgccagcca    480
caggaggacc tccagacgag gacaggactc gctgcctttc tttcccgtca gaagggatc    540
ccttgcggac aggacctaag caccacgcac ctgcccccg ggatgccgaa cgaagtggtc     600
cctaaagctc ctctgcaggc ccaaccgaaa caggcctgaa gctccaggat gggcgagagg    660
atcctctttg agcgaaacca gccttctgcc tggctggccc tggtcaacac cctgggaaga    720
ggccgatttg gcggacagaa cggaagaaaa gacctaaagg tagaatctca tgatgtcgag    780
atgttaaaac actcaaattt taaggttcga ctgtgagggg gagatagggg gtctcgagct    840
ggatcgaccc ctgagccttc atctgcagag tcctgtgcac cagctcagag acaggacta    900
tgtgcaccaa tggttctcat caggcggcaa cttcaccctc acatgcctcc cccatccctg    960
ctggtacaca agaccacgac taggggaagc ccggagggag aatgttaacc cctggcatct   1020
atctagtcag cagaggtgag ggatgctgct aaacaccta caatccaccg gaggacaccc   1080
gcccccaccg accccgaagt ggccattccc tggaggtggg gaaactcgcc tgtagatcaa   1140
tgcccacgca cttggcggac aggaaatcac gaattggcca ctaactggat cttggatctg   1200
agaaaaaaat tccagcgtca gagggaactc tcggagattt gcccagagca taaggaacgt   1260
actccttccc tcagtgatgg atcctcacat ctggggggaaa tcatagacaa tttcttttgt   1320
agggcgaact ctgctataca gtttatgatg tcagagtgaa tactttcttt gagttgcagt   1380
cagaaactgt agatttttaa aaatttaaaa ttcattattc tctgtcagta ttccaaagtg   1440
tatacagaaa gctattgcac tgttcaggag atggcgctta acattttgga aattcaaggt   1500
gatgaatgtc cagataagac tatctctcct ggtacaaagt ttgacaatgc tgaacatttt   1560
taaaggttct tttttgatata caaagtgcac caatgagtgc tttttaattc ttacaataat   1620
tctgggtgag gtaggtattt ttccaattcc cattttatgc ttcggtagcc ctttgtatt   1680
atacttcaaa acacttggct ctcttgtaat tatttaagaa attagttgtg attatttgtt   1740
taatgtgcag gagttacaaa aggcaagctt tagaacaaga cagacctggt tatgattcct   1800
ggctctgaaa gctgtacacc ctgtgaccct agacaggtgt tttaatgcct cgctgcctct   1860
gtttcttgct ctgtaaaatg tgaacaataa cagtattggc ctcatgc                 1907
```

<210> SEQ ID NO 600
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 600
ttgcggacag gacctaagca c                                             21

<210> SEQ ID NO 601
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 601
tagtcctgtc ctctgagctg g                                             21

<210> SEQ ID NO 602
<211> LENGTH: 2553
<212> TYPE: DNA
<213> ORGANISM: Homo sapiens

<400> SEQUENCE: 602
tgcgtgtcgg ggtccgctcg tgcgcgcctc tccggggtct gtgcgcgtgg ccctccgctc     60
gcgccggagg gcgtgggcgt ggcctcggcg tgggtgtggc cgctcgggga ggggcctccc    120
gggggcgggg ccggcctggt ccgcgcggtg acgcgccctg cagccccgag cgagcgagcg    180
agcgagcgag ttgccgagcg cgccccgtcc ctcgcgcgcg atgctcccct ggacggcgct    240
cggcctggcc ctgagcttgc ggctggcgct ggcgcggagc ggcgcggagc gcggtccacc    300
agcatcagcc ccccgagggg acctgatgtt cctgctggac agctcagcca gcgtctctca    360
ctacgagttc tcccgggttc gggagtttgt ggggcagctg gtggctccac tgcccctggg    420
caccggggcc ctgcgtgcca gtctggtgca cgtgggcagt cggccataca ccagttccc     480 cttcggccag cacagctcgg gtgaggctgc ccaggatgcg gtgcgtgctt ctgcccagcg    540
catgggtgac acccacactg gcctggcgct ggtctatgcc aaggaacagc tgtttgctga    600
agcatcaggt gcccggccag gggtgcccaa agtgctggtg tgggtgacag atggcggctc    660
cagcgaccct gtgggccccc ccatgcagga gctcaaggac ctgggcgtca ccgtgttcat    720
tgtcagcacc ggccgaggca acttcctgga gctgtcagcc gctgcctcag cccctgccga    780
gaagcacctg cactttgtgg acgtggatga cctgcacatc attgtccaag agctgagggg    840
ctccattctc gacgcgatgc ggccgcagca gctccatgcc acggagatca cgtccagcgg    900
cttccgcctg gcctggccac ccctgctgac cgcagactcg ggctactatg tgctggagct    960
ggtgcccagc gcccagccgg gggctgcaag acgccagcag ctgccaggga cgccacgga   1020 ctggatctgg gccggcctcg acccggacac ggactacgac gtggcgctag tgcctgagtc   1080
caacgtgcgc ctcctgaggc cccagatcct gcgggtgcgc acgcggcccg gtgaggcagg   1140
gccgggggct tcgggcccgg agtcggggc tgggccggcc cccacgcagc tcgccgccct   1200
ccccgcccca gaggaggccg ggccagagcg catcgtcatc tcccacgccc ggccgcgcag   1260
cctccgcgtg agttgggccc cagcgctggg ctcagccgcg gcgctcggct accacgtgca   1320 gttcggggccg ctgcggggcg gggaggcgca gcgggtggag gtgcccgcgg gccgcaactg   1380

-continued

```
caccacgctg cagggcctgg cgccgggcac cgcctacctg gtgaccgtga ccgccgcctt    1440
ccgctcgggc cgcgagagcg cgctgtccgc caaggcctgc acgcccgacg gcccgcgccc    1500
gcgcccacgc cccgtgcccc gcgccccgac cccggggacc gccagccgtg agccgtaagc    1560
cggcgtcccc gcccagccga gagggccggc gcctacctga gggcccctgt gtcccgaacc    1620
cggagcggag gcgcccaacc cggcagacgg gtgcaggccc ggccttcccc acgcggact    1680 ccgcgcgacc ccgcccctct ccctgcggcc cagggcttc cccgcctggc gcctgccctc    1740
cagggctggg gcctcgcctg gcgggacccc gcagcagccc cggccccatc ccgcccaga    1800 gccgggcgtc gtgtgggtcc gtgggtgata attgagagcg tcagacccag gactgttcag    1860
ggaggagccc cggtcagact cccacgtgtg aagaccgggc cccaagtggc aagggctggc    1920
ctggggcggg cagcttgggt cctggacgtt gataggaagc ggaaggggaa tcgcgggaag    1980
ctggcccagg tcaggtccgc aaaggcttct gaagaagagg aagggcgagt aggggcacct    2040
ggacgctgat ggtggccagg atgctcagct ggccaggagg gcagcacctg ctggggacgg    2100
tggccctgcc ttcatgccca ggacaccagc tgggtccagc tagcagccac tgggaatcag    2160
aggaatgggg cagagctggg cattcaggac cttgaggaca cgtgaccca ccgcccacc    2220 gccactatca ggccccggga ccgcactgac aggaaacctt ccgtcgtgag ggagcacttc    2280 ccagggccg cagggacgac actctccagg gaggccccag caaccacacc atcttcttgc    2340
tgtgagaggt ctcaccccgg gctacctcct gtcactactc actgccctgg ggtccgtggg    2400
caagttgccc agggtggggg tgcctagcca ggtgcagtcc ccgccccgcc tagtcctcgg    2460
cgtcacgcaa tgctcacctc gcctcttccc cactaacatc ccagactta aaattcagta    2520 aatcagatgt acaccgaaaa aaaaaaaaaa aaa                                 2553
```

<210> SEQ ID NO 603
<211> LENGTH: 445
<212> TYPE: PRT
<213> ORGANISM: Homo sapiens

<400> SEQUENCE: 603

```
Met Leu Pro Trp Thr Ala Leu Gly Leu Ala Leu Ser Leu Arg Leu Ala
1               5                   10                  15

Leu Ala Arg Ser Gly Ala Glu Arg Gly Pro Pro Ala Ser Ala Pro Arg
            20                  25                  30

Gly Asp Leu Met Phe Leu Leu Asp Ser Ser Ala Ser Val Ser His Tyr
        35                  40                  45

Glu Phe Ser Arg Val Arg Glu Phe Val Gly Gln Leu Val Ala Pro Leu
    50                  55                  60

Pro Leu Gly Thr Gly Ala Leu Arg Ala Ser Leu Val His Val Gly Ser
65                  70                  75                  80

Arg Pro Tyr Thr Glu Phe Pro Phe Gly Gln His Ser Ser Gly Glu Ala
                85                  90                  95

Ala Gln Asp Ala Val Arg Ala Ser Ala Gln Arg Met Gly Asp Thr His
            100                 105                 110

Thr Gly Leu Ala Leu Val Tyr Ala Lys Glu Gln Leu Phe Ala Glu Ala
        115                 120                 125

Ser Gly Ala Arg Pro Gly Val Pro Lys Val Leu Val Trp Val Thr Asp
    130                 135                 140

Gly Gly Ser Ser Asp Pro Val Gly Pro Pro Met Gln Glu Leu Lys Asp
145                 150                 155                 160
```

```
Leu Gly Val Thr Val Phe Ile Val Ser Thr Gly Arg Gly Asn Phe Leu
            165                 170                 175

Glu Leu Ser Ala Ala Ser Ala Pro Ala Glu Lys His Leu His Phe
        180                 185                 190

Val Asp Val Asp Asp Leu His Ile Val Gln Glu Leu Arg Gly Ser
        195                 200                 205

Ile Leu Asp Ala Met Arg Pro Gln Gln Leu His Ala Thr Glu Ile Thr
    210                 215                 220

Ser Ser Gly Phe Arg Leu Ala Trp Pro Pro Leu Leu Thr Ala Asp Ser
225                 230                 235                 240

Gly Tyr Tyr Val Leu Glu Leu Val Pro Ser Ala Gln Pro Gly Ala Ala
                245                 250                 255

Arg Arg Gln Gln Leu Pro Gly Asn Ala Thr Asp Trp Ile Trp Ala Gly
                260                 265                 270

Leu Asp Pro Asp Thr Asp Tyr Asp Val Ala Leu Val Pro Glu Ser Asn
                275                 280                 285

Val Arg Leu Leu Arg Pro Gln Ile Leu Arg Val Arg Thr Arg Pro Gly
                290                 295                 300

Glu Ala Gly Pro Gly Ala Ser Gly Pro Glu Ser Gly Ala Gly Pro Ala
305                 310                 315                 320

Pro Thr Gln Leu Ala Ala Leu Pro Ala Pro Glu Glu Ala Gly Pro Glu
                325                 330                 335

Arg Ile Val Ile Ser His Ala Arg Pro Arg Ser Leu Arg Val Ser Trp
                340                 345                 350

Ala Pro Ala Leu Gly Ser Ala Ala Leu Gly Tyr His Val Gln Phe
                355                 360                 365

Gly Pro Leu Arg Gly Gly Glu Ala Gln Arg Val Glu Val Pro Ala Gly
                370                 375                 380

Arg Asn Cys Thr Thr Leu Gln Gly Leu Ala Pro Gly Thr Ala Tyr Leu
385                 390                 395                 400

Val Thr Val Thr Ala Ala Phe Arg Ser Gly Arg Glu Ser Ala Leu Ser
                405                 410                 415

Ala Lys Ala Cys Thr Pro Asp Gly Pro Arg Pro Arg Pro Arg Pro Val
                420                 425                 430

Pro Arg Ala Pro Thr Pro Gly Thr Ala Ser Arg Glu Pro
                435                 440                 445

<210> SEQ ID NO 604
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 604
aaccaacctg aggatttcac g                                         21

<210> SEQ ID NO 605
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 605
agacagctgt tcgtgagaag c                                         21
```

<210> SEQ ID NO 606
<211> LENGTH: 1999
<212> TYPE: DNA
<213> ORGANISM: Homo sapiens

<400> SEQUENCE: 606

```
cactctgtaa gttcaccgcc ggtcgggtcc ggccgccgcg ctgtccagct cctgagacct      60
tgctgtccgc cggtctgccg tctgcgcgcc tcacgctcct cagccctgga ccggggacaa     120
gtaaccctcg gtgacaagac caaagtgcac tgctgcccac acagttccta cctttctggc     180
ttcaattctt cagaagagtt tgccgtcctt ggggagaac gtgattttg ttatctcagc      240
ccactgactt cattgatctc taatctttt taattccttg gccaacttt gttcgtgccc      300
ccacactgta gccagaagcc cgttggcgag ctctggcacc tgcaaaccac ccgtggaac      360
gagtgtttcc tctggctgag ggttggagag gaggtgtggt ctcagcaggc ggcccgtagc     420
ctcacagcca ggcctggtgg tgaggtcacc atgtccacca aggtgcccat ctatctgaag     480
cgtggcagtc gcaagggcaa gaaggagaag cttcgggacc tgctgtcctc ggacatgatc     540
agcccaccgc tggggacttt ccgccacacc attcatattg gcagtggcgg cggcagtgac     600
atgtttggcg acatctcctt cctgcagggc aagttccacc tcctgccggg gaccatggtg     660
gaggggcctg aagaagatgg caccttcgac ctccccttcc agttcacccg caccgccacc     720
gtgtgtgggc gggagctccc ggacggccca tccctctgc tcaagaacgc catctccctc      780
ccggttatcg gtgaccccca ggctctcacc ctgcccacag cccaggctcc acccaagccc     840
cctcgcctgc acctggagac ccctcagcct tccccacagg agggagggag tgtggacatc     900
tggaggattc cagagactgg ctcccccaac agtggactga cccggagtc aggggccgag     960
gagcccttcc tgtccaatgc cagctccctg ctgtccctgc acgtggacct ggggccttcc    1020
atcctggatg atgtcctgca gatcatggat caggacctgg acagcatgca gatccccaca    1080
taggacacga ggctgcctag gctggggtcc caggtggggc ccagccagga ggtggggtgt    1140
ggacccggcc ctggcggcgg agtcaggtc ccaagatccc acctgtatgg tcgctggcca     1200
gtgattctcc ttctgagccg tgtttcccct ctccctccct ctccacgtgg gcagggcagg    1260
ccccatcgct ttcctctgat aaccacatgg acacatcctg aagtcagccc aggcgccctg    1320
agcatcttgg ggcacctgga ccccatcaca atactccttc ttccttcagg tccctgggtg    1380
aaggctttgc tgaaaccgac cccccttttc acgtcccttc tgcctctgcc ccgttggatg    1440
ccctgactgg gggcagggga agagacaggg cacagctggc cacagggctc agccactgag    1500
caggctgttc cgggcctttg gctttgcatc ctggacgggg agtgtcctgt cagggaccag    1560
atgtgtcctg cctcatccct agctccaatc ccttccccac gtgaccgggg attctggttg    1620
caataaaaca tgctgctgct ggtggcggag ctccctgtcc ctttgcccca ggtttcctcc    1680
cggaggcaga cagtctccca gagctgaggg cttgcctctg gagacccag ccccagaggg     1740
ctttgtggag acaggcctt gccctcaaga acgtcgtacc tgacgctgag cctgtcatga     1800
gaatgcaaca ggagcaaacc aagtgttgct gtgacattga ttcagatgtt tggcaagagg    1860
tggctgagca ctggggtggg cttggcactg tgccaagcct ggggccaatc cctgcccagt    1920
cagctggggt ctggtggggg acacccaaga ataaagaat aaccacaaag tgtgcaaggg     1980
aaaaaaaaaa aaaaaaaa                                                  1999
```

<210> SEQ ID NO 607

```
<211> LENGTH: 210
<212> TYPE: PRT
<213> ORGANISM: Homo sapiens

<400> SEQUENCE: 607

Met Ser Thr Lys Val Pro Ile Tyr Leu Lys Arg Gly Ser Arg Lys Gly
1               5                   10                  15

Lys Lys Glu Lys Leu Arg Asp Leu Leu Ser Ser Asp Met Ile Ser Pro
            20                  25                  30

Pro Leu Gly Asp Phe Arg His Thr Ile His Ile Gly Ser Gly Gly Gly
        35                  40                  45

Ser Asp Met Phe Gly Asp Ile Ser Phe Leu Gln Gly Lys Phe His Leu
50                  55                  60

Leu Pro Gly Thr Met Val Glu Gly Pro Glu Glu Asp Gly Thr Phe Asp
65                  70                  75                  80

Leu Pro Phe Gln Phe Thr Arg Thr Ala Thr Val Cys Gly Arg Glu Leu
                85                  90                  95

Pro Asp Gly Pro Ser Pro Leu Leu Lys Asn Ala Ile Ser Leu Pro Val
            100                 105                 110

Ile Gly Gly Pro Gln Ala Leu Thr Leu Pro Thr Ala Gln Ala Pro Pro
        115                 120                 125

Lys Pro Pro Arg Leu His Leu Glu Thr Pro Gln Pro Ser Pro Gln Glu
130                 135                 140

Gly Gly Ser Val Asp Ile Trp Arg Ile Pro Glu Thr Gly Ser Pro Asn
145                 150                 155                 160

Ser Gly Leu Thr Pro Glu Ser Gly Ala Glu Glu Pro Phe Leu Ser Asn
                165                 170                 175

Ala Ser Ser Leu Leu Ser Leu His Val Asp Leu Gly Pro Ser Ile Leu
            180                 185                 190

Asp Asp Val Leu Gln Ile Met Asp Gln Asp Leu Asp Ser Met Gln Ile
        195                 200                 205

Pro Thr
    210

<210> SEQ ID NO 608
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 608
aacgtcgtac ctgacgctga g                                         21

<210> SEQ ID NO 609
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 609
ccaagtgttg ctgtgacatt g                                         21

<210> SEQ ID NO 610
<211> LENGTH: 986
<212> TYPE: DNA
<213> ORGANISM: Homo sapiens
```

<400> SEQUENCE: 610

```
attcaagatg atgttagaga gatgacagag tctaggttag ggagggcctg agtccttgta    60
gactctgagt acggtgctga gcagggaaga gacaggctct ggcttagggt ttagaaggaa   120
cacaggctac tgcgatgagg attgtctgaa ggggaacaaa ggccaagatg ttgtttgaag   180
ccgtgagact gagtgagatc atggaggaag tgaatgtaaa tagaaaaggg aagaagtctg   240
aagacggagc cctgagacac tccattgtaa actggaagat gaggaagagc cagcaaagga   300
gactgagaag gggcagccag tgaagatgga gccagggcta gagtaagagc cccttctggg   360
atgctgtgac ccccaagttt gaagactgct gataacccca atctacgaag actagctatg   420
gaacttccta cactgagaca actccagtgg aactctgata attatcctaa ataaggagg    480
cttcttcagt agccctcgaa atatgttcaa atacatgatt acatttatgt ccttaatatt   540
gctattagtt tctgatgtta atgtaaaagt tggggaaaaa gtggaaaagt taaagcagtg   600
caggttaatt caatgccaga gtaacttctc agagggtgta tattcagtgt gaacaatttt   660
caacagagaa atgtcaactt ctggccacaa cggcaaccag taaaatgact attttactg    720
tcttatctat taatgaagag gagattgcat aatatagatg aaggagcata gtatttgcag   780
gtggaacgcc tagcagggct tgagtctcaa ctctgctgct tttactctaa ttgaccgaga   840
caagtcattt aaactaatag agcttcaatt ttctcatatc taatgtaaca taacaattca   900
cagccttta ctttgtagtt atcgtgaaga tctaatcgca gtgaaatata tttatatatc   960
tgtctgccga taaaaaaaaa aaaaaa                                       986
```

<210> SEQ ID NO 611
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 611

```
gactctgagt acggtgctga g                                             21
```

<210> SEQ ID NO 612
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 612

```
tcttactcta gccctggctc c                                             21
```

<210> SEQ ID NO 613
<211> LENGTH: 899
<212> TYPE: DNA
<213> ORGANISM: Homo sapiens

<400> SEQUENCE: 613

```
cccgagcgcc ggccgggcca tgaccccgc tgctctgtct tgcaggctcg tcgccgcggc    60
cccccgagcc cgaccgccgc cgccaccacc accagcgccc gggcgggcct cgcgcgcctc   120
gggcgcggct ccgcagtgag cccaccaaga aggaagcggc ctgcagaggt gccgacatgg   180
ggcttaagat gtcctgcctg aaaggctttc aaatgtgtgt cagcagcagc agcagcagcc   240
```

```
acgacgaggc ccccgtcctg aacgacaagc acctggacgt gcccgacatc atcatcacgc    300
cccccacccc cacgggcatg atgctgccga gggacttggg gagcacagtc tggctggatg    360
agacagggtc gtgcccagat gatggagaaa tcgacccaga agcctgagga ggtgtcctgg    420
gtttggctgg ctggctcctg ctccagcggc ccggcttcag gtgtccgggg cgtggctgc    480 ctggagcagg tgtgctgaat accctggatg ggaactgagc gaacccgggc tcccgctcag    540
agagacgtgg caggaccagc gaggaatcca gcctgtccac ttccagaaca gtgtttccca    600
ggccccgctg agtggaccgg acctctgaca cctccaggtt cttgctgact ccggcctggt    660
gaaagggagc gccatggtcc tggctgttgg ggtcccaggg agaggctctc ttctggacaa    720
acacaccctc ccagccccca gggctgtgca aacacatgcc cctgccataa gcaccaacaa    780
gaacttcttg caggtggagt ggctgttttt tataagttgt tttacagata cggaaacagt    840
ccaaaatggg atttataatt tcttttttgc attataaata aagatcctct gtaacaaaa    899
```

<210> SEQ ID NO 614
<211> LENGTH: 76
<212> TYPE: PRT
<213> ORGANISM: Homo sapiens

<400> SEQUENCE: 614

```
Met Gly Leu Lys Met Ser Cys Leu Lys Gly Phe Gln Met Cys Val Ser
1               5                   10                  15

Ser Ser Ser Ser Ser His Asp Glu Ala Pro Val Leu Asn Asp Lys His
            20                  25                  30

Leu Asp Val Pro Asp Ile Ile Ile Thr Pro Thr Pro Thr Gly Met
        35                  40                  45

Met Leu Pro Arg Asp Leu Gly Ser Thr Val Trp Leu Asp Glu Thr Gly
    50                  55                  60

Ser Cys Pro Asp Asp Gly Glu Ile Asp Pro Glu Ala
65                  70                  75
```

<210> SEQ ID NO 615
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 615
tgtcctgcct gaaaggcttt c                                               21

<210> SEQ ID NO 616
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 616
catccagggt attcagcaca c                                               21

<210> SEQ ID NO 617
<211> LENGTH: 432
<212> TYPE: DNA
<213> ORGANISM: Homo sapiens

<400> SEQUENCE: 617

```
ttatgtgcct gaagtcgcac agtgaataag ctaaaacacc tgcttttaac aatggtacca      60
tacaaccact actccattaa ctccacccac ctcctgcacc cctccccaca cacacaaaat     120
gaaccacgtt ctttgtatgg gcccaatgag ctgtcaagct gccctgtgtt catttcattt     180
ggaattgccc cctctggttc ctctgtatac tactgcttca tctctaaaga cagctcatcc     240
tcctccttca cccctgaatt tccagagcac ttcatctgct ccttcatcac aagtccagtt     300
ttctgccact agtctgaatt tcatgagaag atgccgattt ggttcctgtg ggtcctcagc     360
actattcagt acagtgcttg actcacagca ggcactcaga aaatactgga ggaaataaaa     420
caccaaagat at                                                        432
```

<210> SEQ ID NO 618
<211> LENGTH: 21
<212> TYPE: DNA
<213> ORGANISM: artificial
<220> FEATURE:
<223> OTHER INFORMATION: Description of artificial sequence:
       Oligonucleotide

<400> SEQUENCE: 618

```
ctgctccttc atcacaagtc c                                               21
```

<210> SEQ ID NO 619
<211> LENGTH: 24
<212> TYPE: DNA
<213> ORGANISM: artificial
<220> FEATURE:
<223> OTHER INFORMATION: Description of artificial sequence:
       Oligonucleotide

<400> SEQUENCE: 619

```
gagatctcga gatctcgatc gtac                                            24
```

<210> SEQ ID NO 620
<211> LENGTH: 2575
<212> TYPE: DNA
<213> ORGANISM: Homo sapiens

<400> SEQUENCE: 620

```
gagaacgggg tagcccggcg cttacacatg tcacatgtgc tttttaagac ggccgggagc      60
gcctgcgagc tggatctggt ggaggatgct gcggcaggtg cttcgcagag ggctccagtc     120
gttctgccac aggctgggtt tgtgcgtgag ccggcacccg gtcttttttcc tcaccgtgcc    180 cgcagtcctg acaatcacct tcggcctcag cgcgctcaac cgcttccagc ccagggcga     240 cctggagcgc ctggtcgctc ccagccacag cctggccaag atcgagcgca gcctggccag    300
cagccttttc cccctggacc agtccaaaag ccagctctat tcggacttac acacccctgg    360
gaggtatggc agggtgatcc tcctctcccc aaccgggac aatattttgc tccaggctga    420
ggggatcctg cagacccacc gagccgtgct ggaaatgaag gatgggagga acagttttat   480
tggacaccaa ctgggcgggg tagtggaagt gccaaacagc aaagatcagc gggtcaagtc    540
agccagagcc attcaaatca cctactacct ccagacctat ggctctgcca cccaagacct    600
cataggggag aagtgggaga atgagttctg taagcttata aggaagctcc aggaggagca    660
tcaagaactc cagctctact ctttagcatc ctttagcctc tggagggact ttcataagac    720
cagcatcctg gccagaagca aggtcctggt gagcctcgtg ctgatcctga ccacagccac    780
cctctccagc tccatgaagg actgcttgcg cagtaagccc ttcctgggcc tctgggggt     840 gctcacagta tgcatctcca tcatcacagc agcagggatc ttcttcatca ccgatggaaa    900
```

-continued

```
gtacaactcc accctgctgg gaatcccgtt cttcgccatg ggtcatggaa ctaaaggagt    960
gtttgagctt ctgtccggat ggcggagaac caaagagaac ttgcccttca agacaggat   1020
agcagatgcc tattctgatg tgatggtcac ctataccatg accagctccc tgtacttcat   1080
cactttggc atgggtgcca gcccattcac aaacatagag gctgtgaagg tcttctgtca   1140
aaacatgtgt gtctctattc tgttaaacta cttctacatt ttctccttct ttggctcctg   1200
tctggtctt gctggccaac tagagcaaaa ccgctaccac agcatctttt gctgtaagat   1260
cccttctgca gaatacctgg atcgcaaacc tgtgtggttc cagacagtga tgagtgatgg   1320
gcatcaacag acgtcccatc atgagacgaa ccccctaccag caccacttca ttcagcactt   1380
cctccgtgaa cattataatg aatggattac caatatatat gtgaagccat ttgttgtcat   1440
cctctatctc atttatgcct ccttctcctt catggggtgc ttacagatca gtgacggagc   1500
caacatcatc aatctactag ccagtgattc gccaagtgtt tcctatgcca tggttcagca   1560
gaaatatttc agcaactata gccctgtgat aggattctac gtctatgagc ccctagagta   1620
ctggaacagc agcgtccagg atgacctaag aagactctgt agtggattca ctgcagtgtc   1680
ctgggtggag cagtactacc agttcctgaa agtcagcaac gtcagtgcca ataacaaaag   1740
tgacttcatc agtgtcctgc aaagctcatt tttaaaaaag ccagaattcc agcattttcg   1800
aaatgatatc atcttctcca aggcagggga tgaaagcaat atcattgctt ctcgcttgta   1860
tctggtggcc aggactagca gagacaagca gaaagaaatc acagaagtgt tggaaaagct   1920
gaggccccta tccctctcaa agagcatccg attcatcgtg ttcaaccct cctttgtctt   1980
catggaccat tacagcttgt ctgtcacagt gcctgttctg attgcaggct ttggtgttct   2040
cctggtgtta atcctgactt ttttcctagt gatccaccct ctgggaaact tctggctaat   2100
tcttagcgtc acctcaattg agctgggcgt tctgggctta atgacattat ggaacgtcga   2160
catggattgc atttctatct tgtgccttat ctacaccttg aatttcgcca ttgaccactg   2220
tgcaccactg cttttcacat ttgtattagc aactgagcac acccgaacac aatgtataaa   2280
aagctccttg caagaccatg ggacagccat tttgcaaaat gttacttctt ttcttattgg   2340
gttagtcccc cttctatttg tgccttcgaa cctgaccttc acactgttca aatgcttgct   2400
gctcactggg ggttgcacac ttctgcactg ttttgttatt ttacctgtgt tcctaacgtt   2460
tttccccct tccaaaaagc accacaagaa aaagaaacgt gccaagcgaa aggagagaga   2520
ggaaattgaa tgcatagaaa ttcaagagaa cccggatcac gtcaccacag tatga        2575
```

<210> SEQ ID NO 621
<211> LENGTH: 829
<212> TYPE: PRT
<213> ORGANISM: Homo sapiens

<400> SEQUENCE: 621

```
Met Leu Arg Gln Val Leu Arg Arg Gly Leu Gln Ser Phe Cys His Arg
1               5                   10                  15

Leu Gly Leu Cys Val Ser Arg His Pro Val Phe Phe Leu Thr Val Pro
            20                  25                  30

Ala Val Leu Thr Ile Thr Phe Gly Leu Ser Ala Leu Asn Arg Phe Gln
        35                  40                  45

Pro Glu Gly Asp Leu Glu Arg Leu Val Ala Pro Ser His Ser Leu Ala
    50                  55                  60

Lys Ile Glu Arg Ser Leu Ala Ser Ser Leu Phe Pro Leu Asp Gln Ser
65                  70                  75                  80
```

Lys Ser Gln Leu Tyr Ser Asp Leu His Thr Pro Gly Arg Tyr Gly Arg
                85                  90                  95

Val Ile Leu Leu Ser Pro Thr Gly Asp Asn Ile Leu Leu Gln Ala Glu
            100                 105                 110

Gly Ile Leu Gln Thr His Arg Ala Val Leu Glu Met Lys Asp Gly Arg
        115                 120                 125

Asn Ser Phe Ile Gly His Gln Leu Gly Gly Val Val Glu Val Pro Asn
    130                 135                 140

Ser Lys Asp Gln Arg Val Lys Ser Ala Arg Ala Ile Gln Ile Thr Tyr
145                 150                 155                 160

Tyr Leu Gln Thr Tyr Gly Ser Ala Thr Gln Asp Leu Ile Gly Glu Lys
                165                 170                 175

Trp Glu Asn Glu Phe Cys Lys Leu Ile Arg Lys Leu Gln Glu Glu His
            180                 185                 190

Gln Glu Leu Gln Leu Tyr Ser Leu Ala Ser Phe Ser Leu Trp Arg Asp
        195                 200                 205

Phe His Lys Thr Ser Ile Leu Ala Arg Ser Lys Val Leu Val Ser Leu
    210                 215                 220

Val Leu Ile Leu Thr Thr Ala Thr Leu Ser Ser Ser Met Lys Asp Cys
225                 230                 235                 240

Leu Arg Ser Lys Pro Phe Leu Gly Leu Leu Gly Val Leu Thr Val Cys
                245                 250                 255

Ile Ser Ile Ile Thr Ala Ala Gly Ile Phe Phe Ile Thr Asp Gly Lys
            260                 265                 270

Tyr Asn Ser Thr Leu Leu Gly Ile Pro Phe Phe Ala Met Gly His Gly
        275                 280                 285

Thr Lys Gly Val Phe Glu Leu Leu Ser Gly Trp Arg Arg Thr Lys Glu
    290                 295                 300

Asn Leu Pro Phe Lys Asp Arg Ile Ala Asp Ala Tyr Ser Asp Val Met
305                 310                 315                 320

Val Thr Tyr Thr Met Thr Ser Ser Leu Tyr Phe Ile Thr Phe Gly Met
                325                 330                 335

Gly Ala Ser Pro Phe Thr Asn Ile Glu Ala Val Lys Val Phe Cys Gln
            340                 345                 350

Asn Met Cys Val Ser Ile Leu Leu Asn Tyr Phe Tyr Ile Phe Ser Phe
        355                 360                 365

Phe Gly Ser Cys Leu Val Phe Ala Gly Gln Leu Glu Gln Asn Arg Tyr
    370                 375                 380

His Ser Ile Phe Cys Cys Lys Ile Pro Ser Ala Glu Tyr Leu Asp Arg
385                 390                 395                 400

Lys Pro Val Trp Phe Gln Thr Val Met Ser Asp Gly His Gln Gln Thr
                405                 410                 415

Ser His His Glu Thr Asn Pro Tyr Gln His Phe Ile Gln His Phe
            420                 425                 430

Leu Arg Glu His Tyr Asn Glu Trp Ile Thr Asn Ile Tyr Val Lys Pro
    435                 440                 445

Phe Val Val Ile Leu Tyr Leu Ile Tyr Ala Ser Phe Ser Phe Met Gly
    450                 455                 460

Cys Leu Gln Ile Ser Asp Gly Ala Asn Ile Ile Asn Leu Leu Ala Ser
465                 470                 475                 480

Asp Ser Pro Ser Val Ser Tyr Ala Met Val Gln Gln Lys Tyr Phe Ser
                485                 490                 495

```
Asn Tyr Ser Pro Val Ile Gly Phe Tyr Val Tyr Glu Pro Leu Glu Tyr
            500                 505                 510

Trp Asn Ser Ser Val Gln Asp Asp Leu Arg Arg Leu Cys Ser Gly Phe
            515                 520                 525

Thr Ala Val Ser Trp Val Glu Gln Tyr Tyr Gln Phe Leu Lys Val Ser
            530                 535                 540

Asn Val Ser Ala Asn Asn Lys Ser Asp Phe Ile Ser Val Leu Gln Ser
545                 550                 555                 560

Ser Phe Leu Lys Lys Pro Glu Phe Gln His Phe Arg Asn Asp Ile Ile
                565                 570                 575

Phe Ser Lys Ala Gly Asp Glu Ser Asn Ile Ile Ala Ser Arg Leu Tyr
            580                 585                 590

Leu Val Ala Arg Thr Ser Arg Asp Lys Gln Lys Glu Ile Thr Glu Val
            595                 600                 605

Leu Glu Lys Leu Arg Pro Leu Ser Leu Ser Lys Ser Ile Arg Phe Ile
            610                 615                 620

Val Phe Asn Pro Ser Phe Val Phe Met Asp His Tyr Ser Leu Ser Val
625                 630                 635                 640

Thr Val Pro Val Leu Ile Ala Gly Phe Gly Val Leu Val Leu Ile
            645                 650                 655

Leu Thr Phe Phe Leu Val Ile His Pro Leu Gly Asn Phe Trp Leu Ile
            660                 665                 670

Leu Ser Val Thr Ser Ile Glu Leu Gly Val Leu Gly Leu Met Thr Leu
            675                 680                 685

Trp Asn Val Asp Met Asp Cys Ile Ser Ile Leu Cys Leu Ile Tyr Thr
            690                 695                 700

Leu Asn Phe Ala Ile Asp His Cys Ala Pro Leu Leu Phe Thr Phe Val
705                 710                 715                 720

Leu Ala Thr Glu His Thr Arg Thr Gln Cys Ile Lys Ser Ser Leu Gln
            725                 730                 735

Asp His Gly Thr Ala Ile Leu Gln Asn Val Thr Ser Phe Leu Ile Gly
            740                 745                 750

Leu Val Pro Leu Leu Phe Val Pro Ser Asn Leu Thr Phe Thr Leu Phe
            755                 760                 765

Lys Cys Leu Leu Leu Thr Gly Gly Cys Thr Leu Leu His Cys Phe Val
            770                 775                 780

Ile Leu Pro Val Phe Leu Thr Phe Phe Pro Pro Ser Lys Lys His His
785                 790                 795                 800

Lys Lys Lys Lys Arg Ala Lys Arg Lys Glu Arg Glu Ile Glu Cys
                805                 810                 815

Ile Glu Ile Gln Glu Asn Pro Asp His Val Thr Thr Val
            820                 825
```

<210> SEQ ID NO 622
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 622
cagctctact ctttagcatc c                                              21

```
<210> SEQ ID NO 623
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 623
cctttagttc catgacccat g                                              21

<210> SEQ ID NO 624
<211> LENGTH: 6035
<212> TYPE: DNA
<213> ORGANISM: Homo sapiens

<400> SEQUENCE: 624
ggcggcggcg gcggcggccc cgggcgctga gcgggtgccc ggcgcggaga gcggcgagcg      60
cagccatgcc ccaggccgcc tccggggcag cagcagcggc ggccggggcc gaggcgcggg     120
ccgggggcgc cgggggggccg gcggcggccc ggggcgggacg atgaagcggc agaacgtgcg    180
cacgctggcg ctcatcgtgt gcaccttcac ctacctgctg gtgggcgccg cggtcttcga     240
cgcgctggag tcggagcccg agctgatcga gcggcagcgg ctggagctgc ggcagcagga     300
gctgcgggcg cgctacaacc tcagccaggg cggctacgag gagctggagc gcgtcgtgct     360
gcgcctcaag ccgcacaagg ccggcgtgca gtggcgcttc gccggctcct tctacttcgc     420
catcaccgtc atcaccacca tcggctacgg gcacgcggcg cccagcacgg atggcggcaa    480
ggtgttctgc atgttctacg cgctgctggg catcccgctc acgctcgtca tgttccagag     540
cctgggcgag cgcatcaaca ccttggtgag gtacctgctg caccgcgcca agaaggggct     600
gggcatctcg tggccttcgc ttcgtctcat ccttacgggc ctcacggtca tcggcgcctt     660
cctcaacctc gtggtgctgc gcttcatgac catgaacgcc gaggacgaga gcgcgacgc     720 cgagcaccgc gcgctgctca cgcgcaacgg cgaggcgggc ggcggcggag ggagtggcag     780
cgcgcacact acggacaccg cctcatccac ggcggcagcg ggcggcggcg gcttccgcaa     840
cgtctacgcg gaggtgctgc acttccagtc catgtgctcg tgcctgtggt acaagagccg     900
cgagaagctg cagtactcca tccccatgat catcccgcgg gacctctcca cgtccgacac     960
gtgcgtggag cagagccact cgtcgccggg aggggcggc cgctacagcg acacgccctc    1020
gcgacgctgc ctgtgcagcg gggcgccacg ctccgccatc agctcggtgt ccacgggtct    1080
gcacagcctg tccaccttcc gcggactcat gaagcgcagg agctcgtgt gactgccccg    1140 agggcctgg agcacctggg ggcgcgggcg ggggacccct gctgggaggc caggagactg    1200
cccctgctgc cttctgccca gtgggacccc gcacaacatc cctcaccact ctcccccagc    1260 accccatct ccgactgtgc ctgcttgcac cagccggcag gaggccgggc tctgaggacc    1320 cctgggccc ccatcggagc cctgcaaatt ccgagaaatg tgaaacttgg tggggtcagg    1380
gaggaaaggc agaagctggg agcctccctt ccctttgaaa atctaagaag ctcccagtcc    1440
tcagagaccc tgctggtacc cagacccca ccttcggagg ggacttcatg ttccgtgtac    1500
gtttgcatct ctatttatac ctctgtcctg ctaggtctcc caccttccct tggttccaaa    1560
agccagggtg tctttgtcca agtcacccct actcagcccc actcccttc ctcatcccca    1620 gctgtgtctc ccaacctccc ttcgtgttgt tttgcatggc tttgcagtta tggagaaagt    1680
ggaaacccag cagtccctaa agctggtccc cagaaagcag acagaaaga aggagggaca    1740 ggcaggcagc aggaggggcg agctgggagg caggaggcag cggcctgtca gtctgcagaa    1800
```

```
tggtcgcact ggaggttcaa gctaactggc ctccagccac attctcatag caggtaggac    1860
ttcagccttc cagacactgc ccttagaatc tggaacagaa gacttcagac tcaccataat    1920
tgctgataat tacctactct taaatttgtc gagtgatttt tagcctctga aaactctatg    1980
ctggccactg attcctttga gtctcacaaa accctactta ggtcatcagg gcaggagttc    2040
tcactcccat tttacagatg agaatactga ggcctggaca ggtgaagtga ccagagagca    2100
aaaggcaaag gggtggggc tgggtgcagt ggctcacacc tgtattccca cacttttgg    2160 aggctgaggt tagaggattg cttgagccca ggaattcgag accagcctag gcgacatagt    2220
gagaccccat ctctacaaaa aataaaaaat ttaccaggtg tggtggcacg tgcctgggag    2280
tcccagcgac ttgggaggct gaggtgggag gattgtttga gcctgggagg tcaaggctgt    2340
agtgagccct gattcaccca ctgtactcca gcctgggtga cagggcaaga ccctgtctca    2400
aaaaaaaaaa aaaatggca aagggagaca agagcccagc ctacttgttc ctagccaaag    2460
tgttctttcc ttccagcttg gcctgctctt aaaagcaaag ctcctgcagt gtacatcctg    2520
gcattgtgtg gctacctggg ttttaaacca gaatcagaag tcccgggtca gagggcactg    2580
ctgaggctca gcctcttctc ttcttggcca ggaggcagca gctctgaatg gcccctgag    2640 gctgcacagg ggcctttgtc actggggtgc atgcttacaa acagtgcagt tcttggcacc    2700
gaggtaagca gggctgggtc tcatggcaga aaggccagga tctggggctc taggaatttg    2760
ggaattgggc agagtggcca agaaagctgg caggcatatc ctatgggaca tcacacctgg    2820
caccattgtc attgttggtg cctgtgtccc aagtagctag tgataagctg aggctgcagc    2880
aagaaacacc cttcccaggt gggggagttt ggaccagagg tgccctctgc ccaccacacc    2940
tgcaacccag aagcccagat ggaacgcagc tgatgaaggt gatgcttgag gctcactttt    3000
ggggccccac agctggagcc ggtatagtga ctgggacaac atcaagggt ggatgagggg    3060 cctctcctcc cgcaacactg ccttcccatg ctgttcccct gccagctcct taacactgcc    3120
gaccaaggcc agacctggca ttcaggaaag ttggagggca gcacccatag ggtgccagc    3180 ctcaggcccc accccagctg tgtcctctag tctctgggga cccctggggg aagaagtct    3240 accctgcttg tgagtcccgt tcagtgtgg aggaactggc tgcacgtggg acctgaaggt    3300
gccctctgtg tttatgttgg ggggggggg gcagtgctgg ctgcctctgt cctgtgtgtg    3360
accctgccct cgaagggtcc tgtcctgtca gtcccgaggg agccacaacc aaagctgcgg    3420
agagaaggtg gggaacggtg cggagtggcc gtggggcaca gcgtggcaga ctgttcagtc    3480
tctgctgggt cttttcctagg gacctggaag gccagtgttg cttccccctc actccctttc    3540
actgcaggca gcctctctcc ttccccaatg ccttatgcct gggcacactg ccacagaata    3600
tgcaatatgt gtgggtgacg atgccctcac gaccacaccc ccaccccggg cagccccgg    3660 actccaaagg tcgtggctgc cacagcctcc ctcagctctt cctgcctatc tgtcttcaca    3720
ctgagaatgg cgcccaataa atgctatcca cggagaccag gctcaggctc cagctgcctc    3780
tgtcatcgta tgcccttgct gctgccaggg agggggcatc tcccacccccc tcccctgccg    3840 gggtctacaa acatacctag ctgctgggtg ccgtggctca cacctataat cacagcacta    3900
ggcgggcaga tcacctgagg tcagaagttc aagaccagcc tggccaacat ggtaaaaccc    3960
cgtctctact aaaaatacaa aaattagctg agcgtggtgg cgcctgtctg tagtcccagc    4020
tactcggcta ctcaggaggc tgacgcacga gaatcgcttg aacccgggag gcggaggttg    4080
cagtgagctg agatcgcgcc actgcactcc agcctgagcg atagagtgag accctgtcta    4140
aaaaaaacaa taataataaa ataaaataac atacctagct gactcgccat gggctcgctg    4200
```

```
gcctgtgggc gacactggct tccctttggg gatttcccag aagatccaga ttttcttaag      4260
tccccttgga acagactaag aaagaaacac cttagaaatc acctggtcct attgtccccc      4320
cgtacatgag taactgaggc ccacagagag caaatcgcct gcctgagtca cacagcagtg      4380
agtggcagac ctaggctagg aactagaact ggggattgct attccagtgc tccccatcct      4440
cacacagcct gtggagtccg cctggacaca ccccagctga cagtggtacc tcccagtcag      4500
ccaggagaat ggattccttc tcctgcagta ggggcccccct ggctgagtgg cctgattgac      4560
taaaacatat gtcttgaag gagagtgcat cacaagcacc tttctttggg gtagatttt       4620 ctctgggtct agagggacac ctcaggcttg ggactgggcc tcagaaccta ggacagaccc      4680
tgagagcaga cccaccttat ccatctggtg ccagctcccc aggtcagcta cagcaacccc      4740
cgaacttcat agagtacaat ccacagtaat agcacacagc tctgtaccta tctagctcca      4800
tgcctatcta tctgcctacc tttcacaaaa taattcttag caaccctgct acagccaatg      4860
attctaatac gttctgttct attacatgtt ataaatgct ggtcacgatc cactaaattg       4920
atgtctctac ctgctaatgg tttaatacct gcagattgaa atatactgga gaaataaaga      4980
gagtaggagt agggacactt tctcccagtg cccacaccgc ccctcgttac ccgcataggt      5040
caactgaaag atacagagag ggaagctttg atgggggggtt cagagttcaa aggaagaaat    5100
gatggcacct gcactccctg cccccagagg caggacacag ccagccctcc tgtgacagca      5160
ctcctggcag ctccttgttg gcctgcagcc cttagttgcc attgactcac ccactcctaa      5220
ggccaccaca tcaaaatctg aggcttactg ccctggccca cctgcctctg tctttcttaa      5280
aacagctaaa tgcaacgata gcagaaatta gcttgttttt gaggttggca atgaccagtt      5340
caactcttat tttcttaagc agtgcttgca ggacataaat gtgatgacac ttgccctcct      5400
ttctttatcg cctggggcag actttacaaa cagacctggg aggagtcccc taaggggctg      5460
catttatccc catctcccta ggggtgatca gcattgtgac agctgggcag agcagtggtg      5520
aactgcaccc atgtccctgc tcacatctcc taagatctca gaattgcctg aggttctagc      5580
gtgggctcct tctctccaga tgatgccatc cccaccccccc tcatttccac acagcatctg   5640
aggcatcctg cactaaaaga tatatgtaca gcaaaacaaa aatagaaaac cagcacagca      5700
gagtggaggt ggggtataaa tatacccaga tccccgctga tttggttact cggggtgagc      5760
atcagatgga aatagaagtt tccggggggcc aagagagaaa gagggatgta acgacaattc     5820 tttttcaaaac gtgtcccatg gtatgcctcg tggaaaaaat ggttcgttgg tcaaatgaat    5880
ttgggaaaat gctgtcaata tcaccgactc atggagcttc gcaaggcatc ttagcttaat      5940
aaaggttatg aaaagtcttg cagcaaagat gctgtttacc ccacttaatc cagcactgcc      6000
caaactcatt ccaaatacca gagcctctgt ttgca                                  6035
```

<210> SEQ ID NO 625
<211> LENGTH: 323
<212> TYPE: PRT
<213> ORGANISM: Homo sapiens

<400> SEQUENCE: 625

Met Lys Arg Gln Asn Val Arg Thr Leu Ala Leu Ile Val Cys Thr Phe
1               5                   10                  15

Thr Tyr Leu Leu Val Gly Ala Ala Val Phe Asp Ala Leu Glu Ser Glu
            20                  25                  30

Pro Glu Leu Ile Glu Arg Gln Arg Leu Glu Leu Arg Gln Gln Glu Leu
        35                  40                  45

```
Arg Ala Arg Tyr Asn Leu Ser Gln Gly Gly Tyr Glu Glu Leu Glu Arg
     50                  55                  60

Val Val Leu Arg Leu Lys Pro His Lys Ala Gly Val Gln Trp Arg Phe
 65                  70                  75                  80

Ala Gly Ser Phe Tyr Phe Ala Ile Thr Val Ile Thr Thr Ile Gly Tyr
             85                  90                  95

Gly His Ala Ala Pro Ser Thr Asp Gly Gly Lys Val Phe Cys Met Phe
            100                 105                 110

Tyr Ala Leu Leu Gly Ile Pro Leu Thr Leu Val Met Phe Gln Ser Leu
            115                 120                 125

Gly Glu Arg Ile Asn Thr Leu Val Arg Tyr Leu Leu His Arg Ala Lys
130                 135                 140

Lys Gly Leu Gly Ile Ser Trp Pro Ser Leu Arg Leu Ile Leu Thr Gly
145                 150                 155                 160

Leu Thr Val Ile Gly Ala Phe Leu Asn Leu Val Val Leu Arg Phe Met
                165                 170                 175

Thr Met Asn Ala Glu Asp Glu Lys Arg Asp Ala Glu His Arg Ala Leu
            180                 185                 190

Leu Thr Arg Asn Gly Gln Ala Gly Gly Gly Gly Ser Gly Ser Ala
            195                 200                 205

His Thr Thr Asp Thr Ala Ser Ser Thr Ala Ala Gly Gly Gly Gly
210                 215                 220

Phe Arg Asn Val Tyr Ala Glu Val Leu His Phe Gln Ser Met Cys Ser
225                 230                 235                 240

Cys Leu Trp Tyr Lys Ser Arg Glu Lys Leu Gln Tyr Ser Ile Pro Met
                245                 250                 255

Ile Ile Pro Arg Asp Leu Ser Thr Ser Asp Thr Cys Val Glu Gln Ser
            260                 265                 270

His Ser Ser Pro Gly Gly Gly Arg Tyr Ser Asp Thr Pro Ser Arg
            275                 280                 285

Arg Cys Leu Cys Ser Gly Ala Pro Arg Ser Ala Ile Ser Ser Val Ser
            290                 295                 300

Thr Gly Leu His Ser Leu Ser Thr Phe Arg Gly Leu Met Lys Arg Arg
305                 310                 315                 320

Ser Ser Val

<210> SEQ ID NO 626
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 626
agactttaca aacagacctg g                                            21

<210> SEQ ID NO 627
<211> LENGTH: 23
<212> TYPE: DNA
<213> ORGANISM: artificial
<220> FEATURE:
<223> OTHER INFORMATION: Description of artificial sequence:
      Oligonucleotide

<400> SEQUENCE: 627
gcttgcagga cataaatgtg atg                                          23
```

```
<210> SEQ ID NO 628
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 628
tgacactggc aaaacaatgc a                                              21

<210> SEQ ID NO 629
<211> LENGTH: 21
<212> TYPE: DNA
<213> ORGANISM: artificial
<220> FEATURE:
<223> OTHER INFORMATION: Description of artificial sequence:
      Oligonucleotide

<400> SEQUENCE: 629
ggtccttttc accagcaagc t                                              21

<210> SEQ ID NO 630
<211> LENGTH: 21
<212> TYPE: DNA
<213> ORGANISM: artificial
<220> FEATURE:
<223> OTHER INFORMATION: Description of artificial sequence: siRNA

<400> SEQUENCE: 630
ccacagaagg uaccaguuau u                                              21

<210> SEQ ID NO 631
<211> LENGTH: 21
<212> TYPE: DNA
<213> ORGANISM: artificial
<220> FEATURE:
<223> OTHER INFORMATION: Description of artificial sequence: siRNA

<400> SEQUENCE: 631
uaacugguac cuucuguggu u                                              21

<210> SEQ ID NO 632
<211> LENGTH: 21
<212> TYPE: DNA
<213> ORGANISM: artificial
<220> FEATURE:
<223> OTHER INFORMATION: Description of artificial sequence: siRNA

<400> SEQUENCE: 632
cagcaagacu cccucuaaau u                                              21

<210> SEQ ID NO 633
<211> LENGTH: 21
<212> TYPE: DNA
<213> ORGANISM: artificial
<220> FEATURE:
<223> OTHER INFORMATION: Description of artificial sequence: siRNA

<400> SEQUENCE: 633
uuuagaggga gucuugcugu u                                              21

<210> SEQ ID NO 634
<211> LENGTH: 21
<212> TYPE: RNA
<213> ORGANISM: artificial
```

```
<220> FEATURE:
<223> OTHER INFORMATION: Description of artificial sequence: target RNA
<220> FEATURE:
<221> NAME/KEY: misc_feature
<222> LOCATION: (1)..(2)
<223> OTHER INFORMATION: n is a, c, g, t or u

<400> SEQUENCE: 634
nnccacagaa gguaccaguu a                                              21

<210> SEQ ID NO 635
<211> LENGTH: 21
<212> TYPE: RNA
<213> ORGANISM: artificial
<220> FEATURE:
<223> OTHER INFORMATION: Description of artificial sequence: target RNA
<220> FEATURE:
<221> NAME/KEY: misc_feature
<222> LOCATION: (1)..(2)
<223> OTHER INFORMATION: n is a, c, g, t or u

<400> SEQUENCE: 635
nncagcaaga cucccucuaa a                                              21

<210> SEQ ID NO 636
<211> LENGTH: 6
<212> TYPE: PRT
<213> ORGANISM: artificial
<220> FEATURE:
<223> OTHER INFORMATION: synthetic
<220> FEATURE:
<221> NAME/KEY: misc_feature
<222> LOCATION: (3)..(4)
<223> OTHER INFORMATION: Xaa is any amino acid

<400> SEQUENCE: 636

Cys Cys Xaa Xaa Cys Cys
1               5
```